US011781164B2

(12) United States Patent
Schwab et al.

(10) Patent No.: US 11,781,164 B2
(45) Date of Patent: Oct. 10, 2023

(54) DEMETHYLATION OF RETICULINE AND DERIVATIVES THEREOF WITH FUNGAL CYTOCHROME P450

(71) Applicant: River Stone Biotech LLC, Cambridge, MA (US)

(72) Inventors: Markus Schwab, Reinach (CH); Sumire Honda Malca, Reinach (CH); Philipp Friedrich Berninger, Reinach (CH); Jon Richard Heal, Reinach (CH); Joseph Michael Sheridan, Reinach (CH); Laura Tatjer Recorda, Copenhagen (DK); Rubini Maya Kannangara, Copenhagen (DK); Esben Halkjaer Hansen, Copenhagen (DK); Angela Manuela Ribeiro de Carvalho, Copenhagen (DK)

(73) Assignee: RIVER STONE BIOTECH, LLC, Cambridge, MA (US)

( * ) Notice: Subject to any disclaimer, the term of this patent is extended or adjusted under 35 U.S.C. 154(b) by 334 days.

(21) Appl. No.: 16/623,052

(22) PCT Filed: Jun. 18, 2018

(86) PCT No.: PCT/EP2018/066155
§ 371 (c)(1),
(2) Date: Dec. 16, 2019

(87) PCT Pub. No.: WO2018/229306
PCT Pub. Date: Dec. 20, 2018

(65) Prior Publication Data
US 2021/0230655 A1   Jul. 29, 2021

(30) Foreign Application Priority Data

Jun. 16, 2017  (DK) .............................. PA201770473

(51) Int. Cl.
*C12P 17/18*  (2006.01)
(52) U.S. Cl.
CPC .................................... *C12P 17/18* (2013.01)
(58) Field of Classification Search
CPC ....................................................... C12P 17/18
See application file for complete search history.

(56) References Cited

U.S. PATENT DOCUMENTS

2006/0014264 A1   1/2006  Sauer et al.

FOREIGN PATENT DOCUMENTS

| DK | WO2015/197075 A1 | 12/2015 | |
|----|------------------|---------|---|
| WO | WO-2011058446 A2 * | 5/2011 | ......... C12N 15/8243 |
| WO | WO-2015197075 A1 * | 12/2015 | ......... C07K 14/415 |

OTHER PUBLICATIONS

Madyastha K.M., et al. N-Demethylation and N-oxidation of thebaine, an isoquinoline alkaloid by Mucor piriformis. Indian Journal of Chemistry vol. 39B, pp. 377-381 (May 2000). (Year: 2000).*
Bach S.S., et al. High-Throughput Testing of Terpenoid Biosynthesis Candidate Genes Using Transient Expression in Nicotiana benthamiana. In M. Rodriguez Concepcion, ed, Plant Isoprenoids, Methods in Molecular Biology, vol. 1153. Humana Press, New York.
Bateman A, et al. Pfam 3.1: 1313 multiple alignments and profile HMMs match the majority of proteins. Nucl. Acids Res., 27(1): 260-62 (1999).
Chaudhary V, et al. Biotransformations of Morphine Alkaloids by Fungi: N-Demethylations, Oxidations, and Reductions. Collect. Czech. Chem. Commun. vol. 74, Nos. 7-8, pp. 1179-1193 (2009).
Chenna R., et al. Multiple sequence alignment with the Clustal series of programs. Nucl. Acids Res. vol. 31, No. 13, pp. 3497-3500 (2003).
Geitz R.D. and R.H. Schiestl. High-efficiency yeast transformation using the LiAc/SS carrier DNA/PEG method. Nat. Protoc. 2, 31-34 (2007).
Giaever G and C Nislow The Yeast Deletion Collection: A Decade of Functional Genomics. Genetics, vol. 197, 451-65 (2014).
Gossen M and H Bujard. Studying Gene Function in Eukaryotes by Conditional Gene Inactivation. Annu. Rev. Genet. 36:153-73 (2002).
Hansen B.G., et al. Versatile Enzyme Expreion and Characterization System for Aspergillus nidulans, with the Penicillium brevicompactum Polyketide Synthase Gene from the Mycophenolic Acid Gene Cluster as a Test Case. Appl. Environ. Microbiol. vol. 77, No. 9, pp. 3044-3051 (2011).
Hoffman K, et al. The family structure of the Mucorales: a synoptic revision based on comprehensive multigene-genealogies. Persoonia 30: 57-76 (2013).
Jensen N.B., et al. EasyClone: method for iterative chromosomal integration of multiple genes in *Saccharomyces cerevisiae*. FEMS Yeast Res. 14: 238-48 (2014).
Klein J, et al. Yeast Synthetic Biology Platform Generates Novel Chemical Structures as Scaffolds for Drug Discovery. ACS Synth. Biol. 3, 314-23 (2014).

(Continued)

*Primary Examiner* — Nancy J Leith
*Assistant Examiner* — Khaleda B Hasan
(74) *Attorney, Agent, or Firm* — McDonnell Boehnen Hulbert & Berghoff LLP

(57) ABSTRACT

The invention relates to recombinant host cells that expresses one or more genes encoding a cytochrome P450 enzyme capable of N-demethylating and/O-demethylating reticuline and/or derivatives thereof, and also methods of producing a N-demethylated and/or O-demethylated reticuline and/or derivatives thereof, comprising cultivating the recombinant host of the invention in a culture medium under conditions in which the one or more genes encoding the cytochrome P450 enzymes is/are expressed. The reticuline and derivatives thereof are useful for providing access to naturally unavailable and chemically difficult-to-produce starting materials for opioids.

16 Claims, 37 Drawing Sheets
Specification includes a Sequence Listing.

(56) References Cited

OTHER PUBLICATIONS

Kramlinger V.M., et al. Cytochome P450 3A Enzymes Catalyze the O6-Demethylation of Thebaine, a Key Step in Endogenous Mammalian Morphine Biosynthesis. J Biol.Chem. 290:20200-210 (2015).

Lewis J.C., et al. Combinatorial Alanine Substitution Enables Rapid Optimization of Cytochrome P450BM3 for Selective Hydroxylation of Large Substrates. Chembiochem. 11(18): 2502-05 (2010).

Liachko I. and M.J. Dunham An autonomously replicating sequence for use in a wide range of budding yeasts. FEMS Yeast Res. 14: 364-67 (2014).

Madyastha K.M., et al. N-Demethylation and N-oxidation of thebaine, an isoquinoline alkaloid by Mucor piriformis. Indian Journal of Chemistry vol. 39B, pp. 377-381 (May 2000).

Mumberg D, et al. Yeast vectors for the controlled expression of heterologous proteins in different genetic backgrounds. Gene, 156: 119-22 (1995).

Nicaud J-M. Yarowia lipolytica. Yeast 29: 409-18 (2012).

Nour-Eldin H.H., et al. Advancing uracil-exciion based cloning towards an ideal technique for cloning PCR fragments. Nucl. Acids Res. vol. 34, No. 18, e122 (2006).

Prelich G. Gene Overexpression: Uses, Mechanisms and Interpretation. Genetics, vol. 190, 841-54 (2012).

Sipos A., et al. First Synthesis and Utilization of Oripavidine—A Concise and Efficient Route to Important Morphinans and Apomorphines. Helvetica Chimica Acta, vol. 92, 1359-65 (2009).

Sonnhammer E.L.L., et al. Pfam: A Comprehensive Database of Protein Domain Families Based on Seed Alignments. Proteins: Structure, Function, and Genetics, 28:405-20 (1997).

Sonnhammer E.L.L., et al. Pfam: multiple sequence alignments and HMM-profiles of protein domains. Nucl. Acids Res. vol. 26, No. 1, 320-22 (1998).

* cited by examiner

Figure 29
A
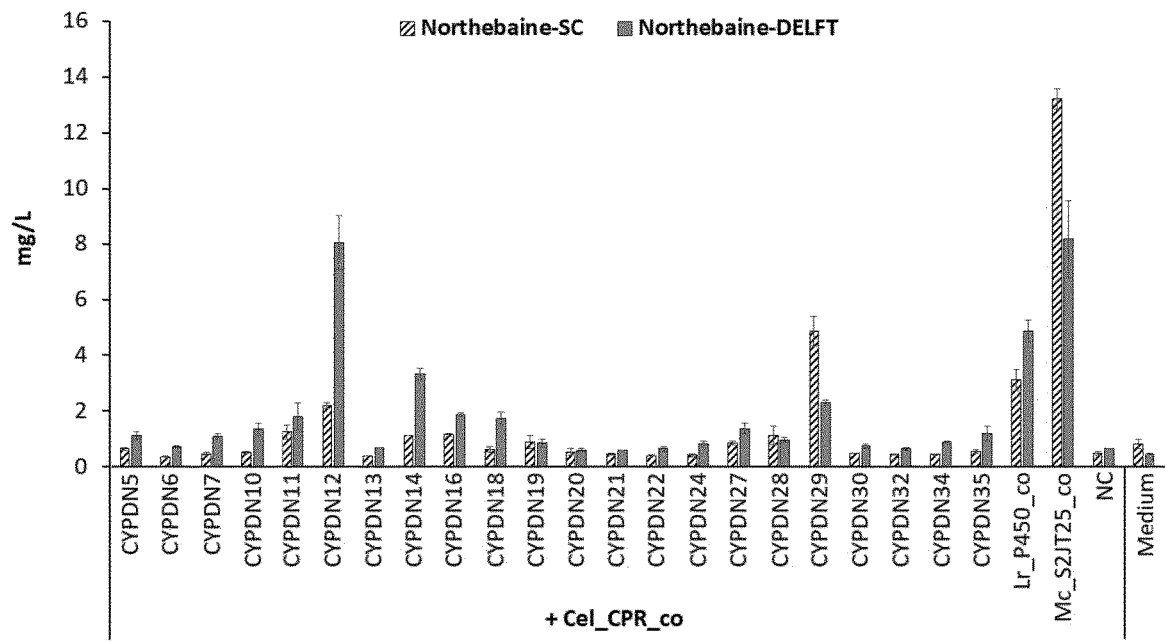
B
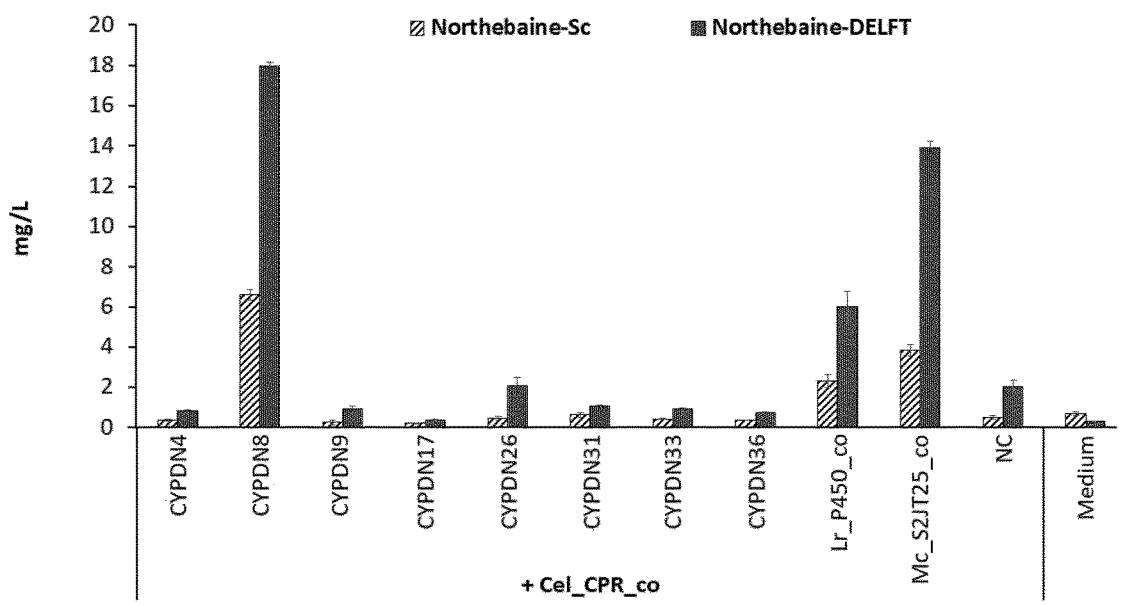

Figure 29
C
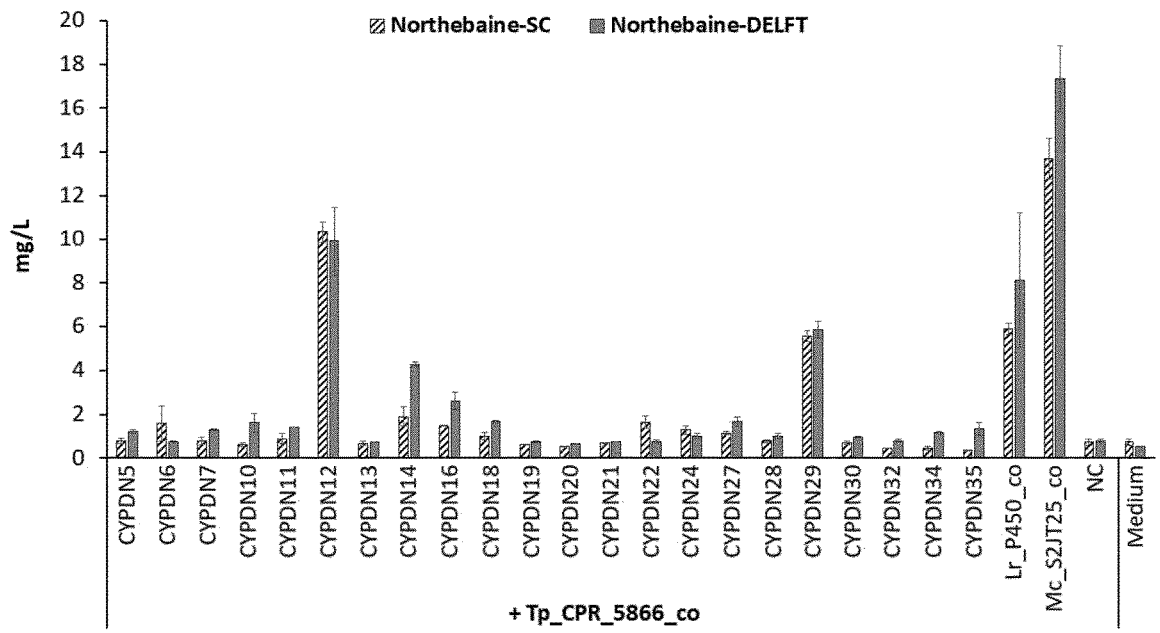
D
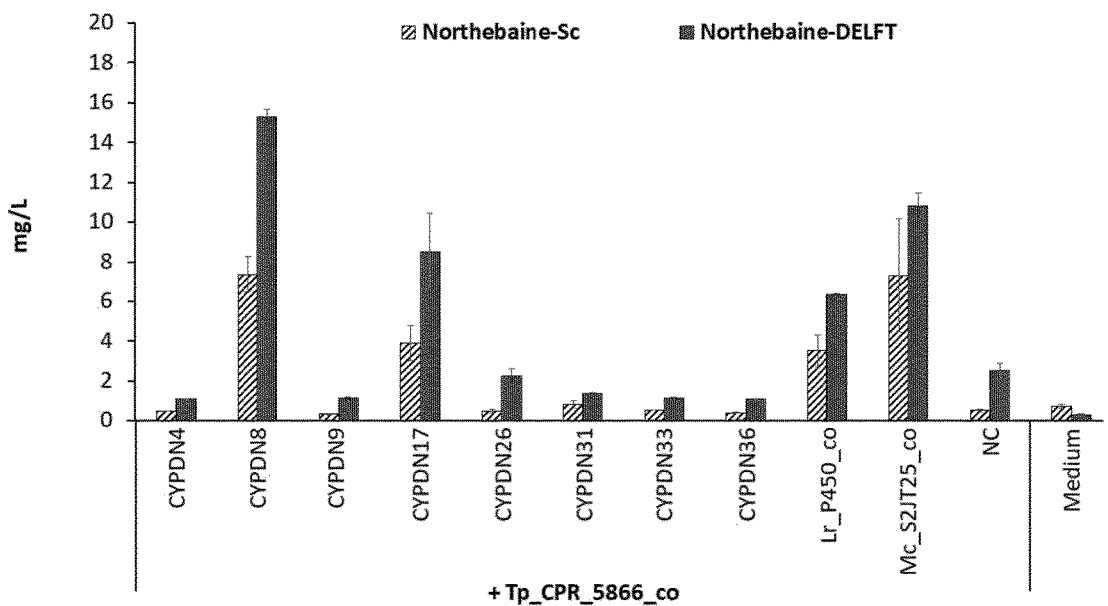

Figure 29
E
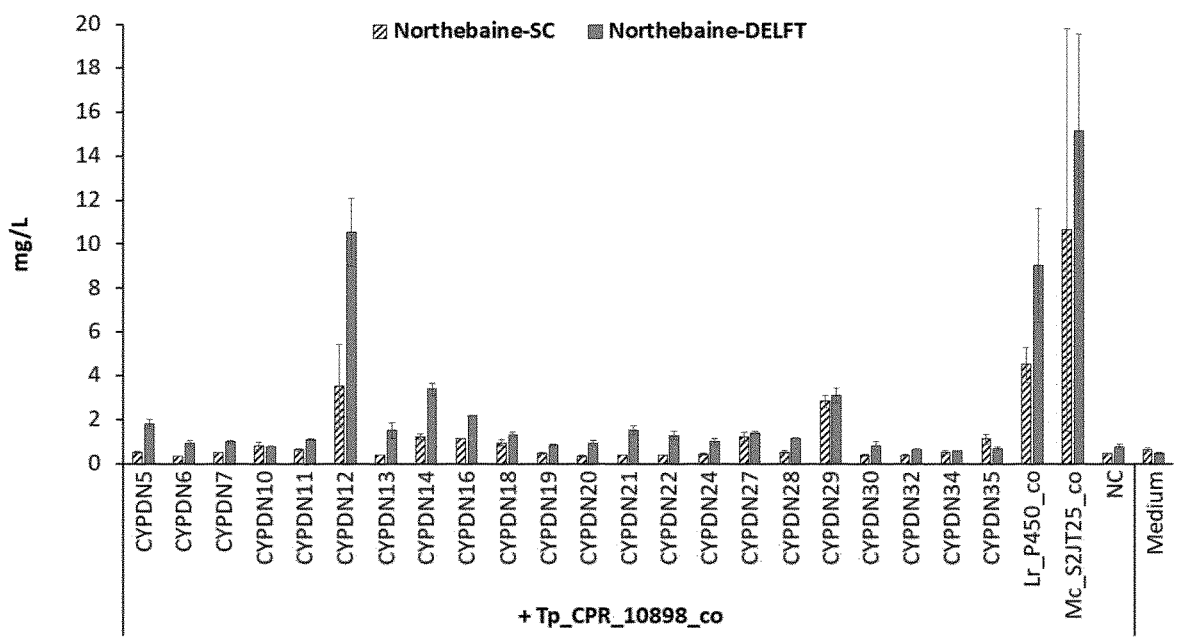
F
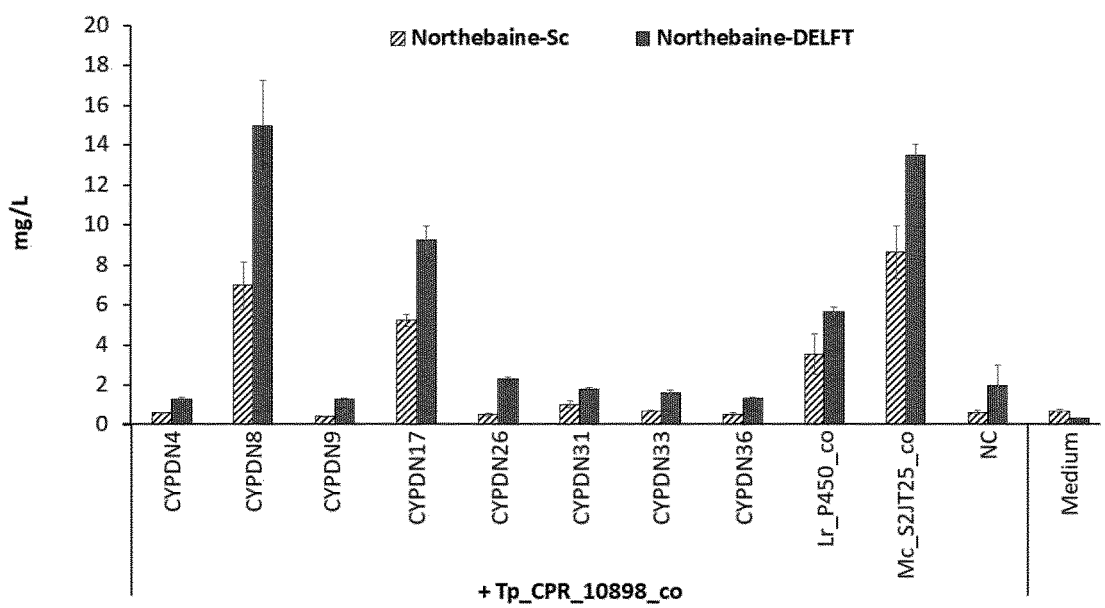

Figure 29
G
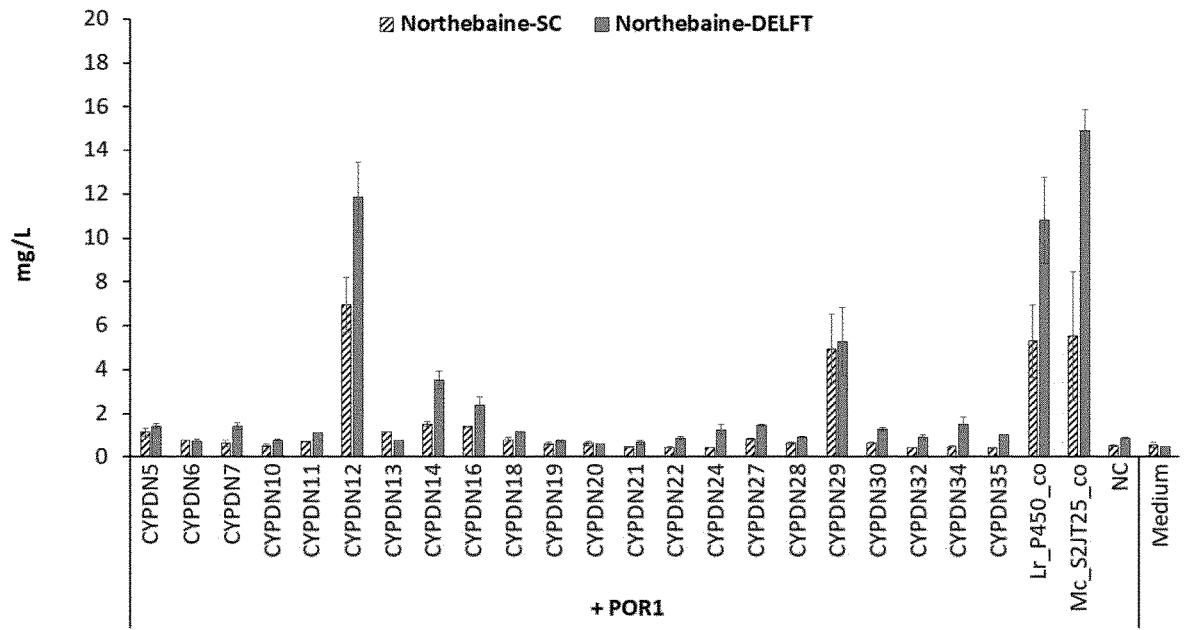
H
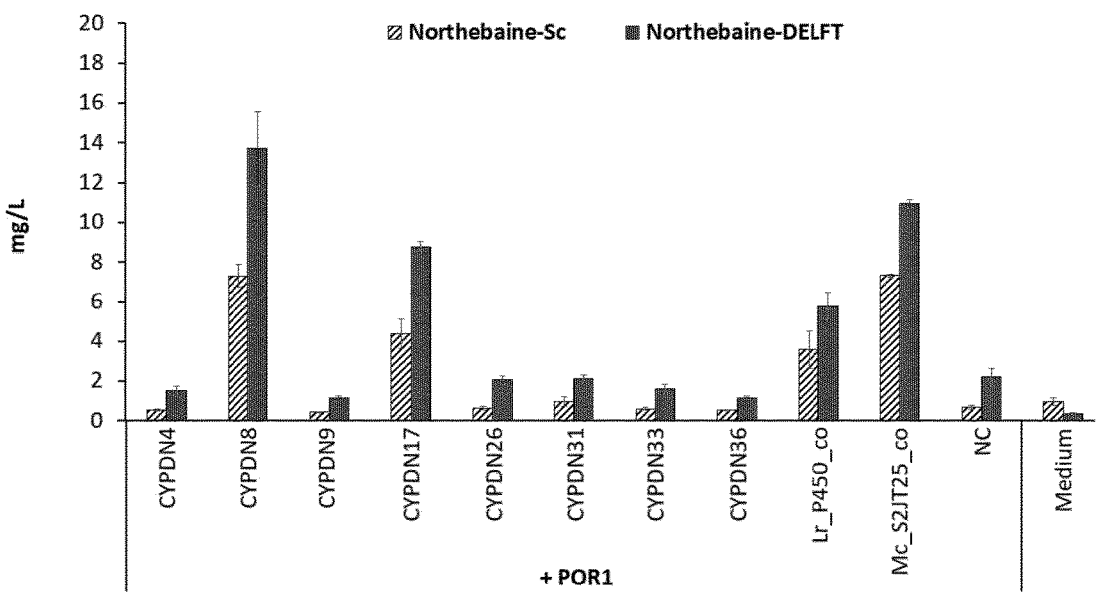

Figure 30
A
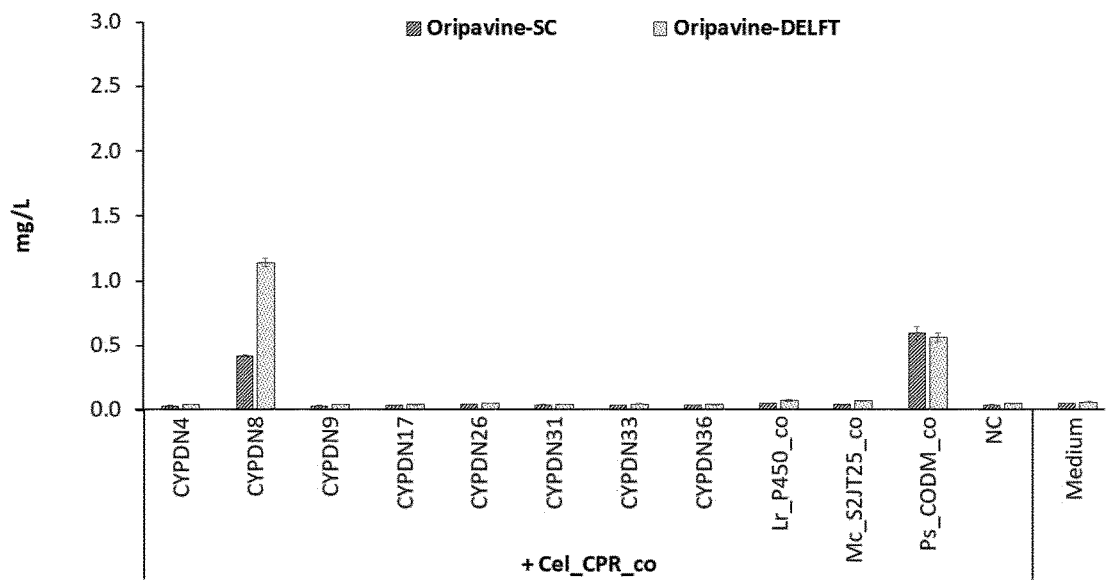
B
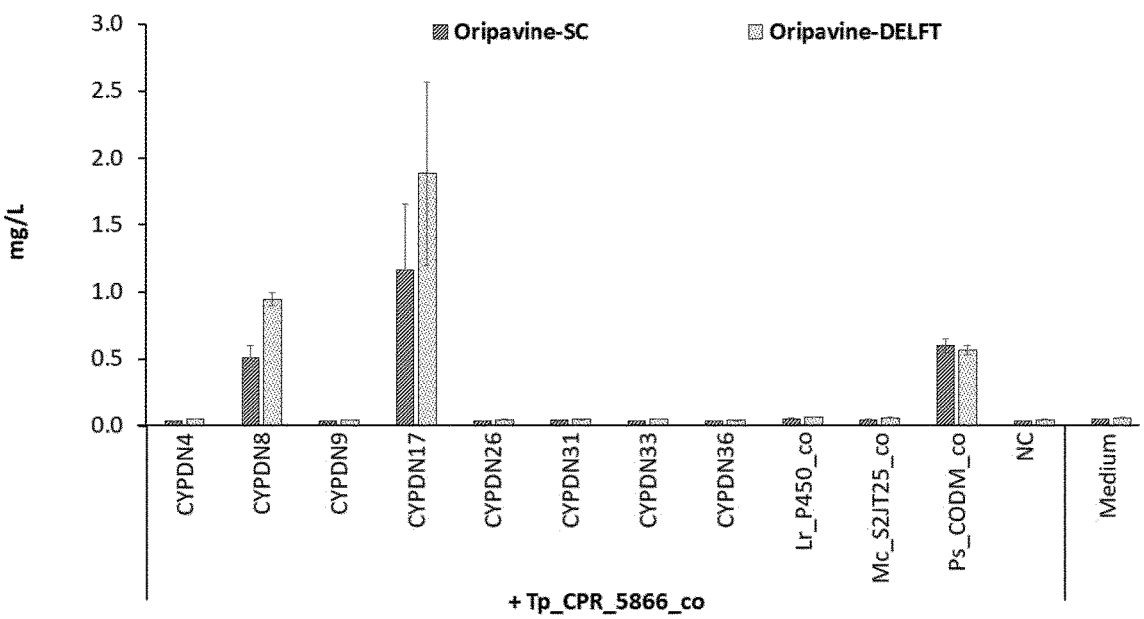

Figure 30
C
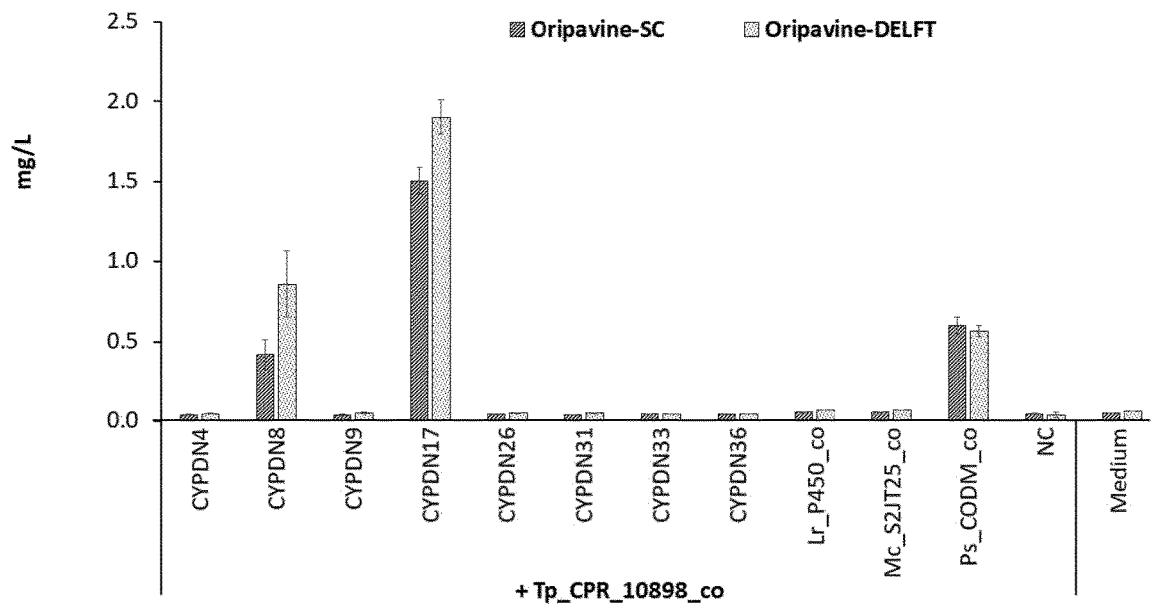
D
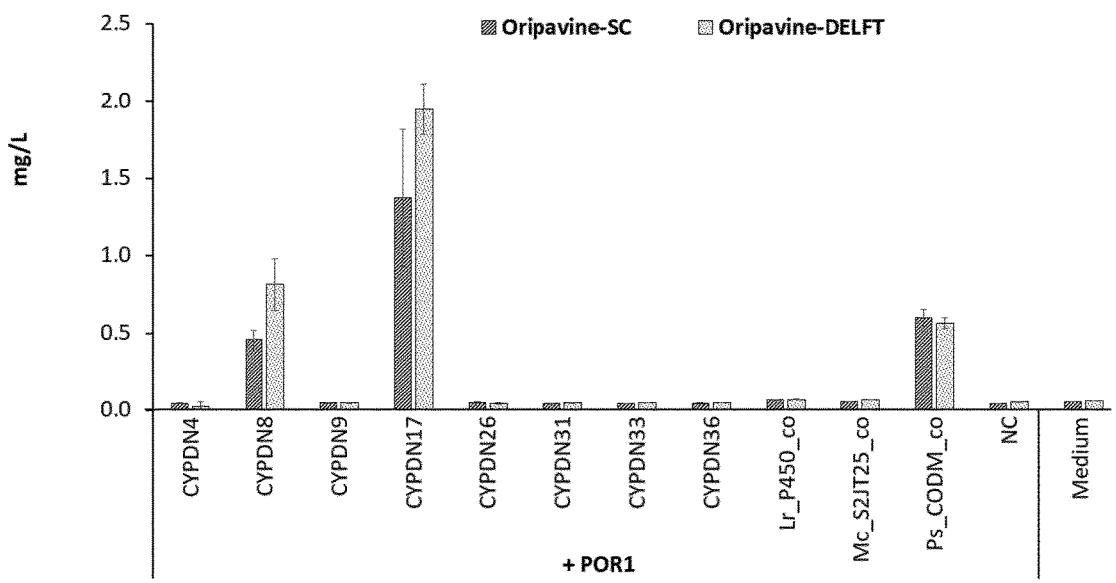

Figure 31
A
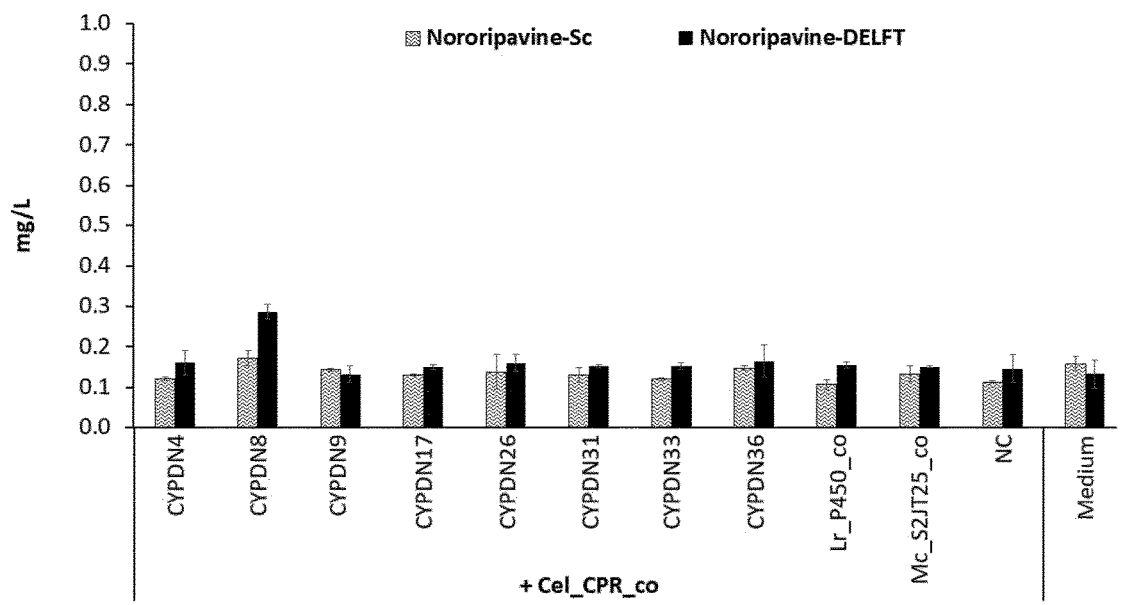
B
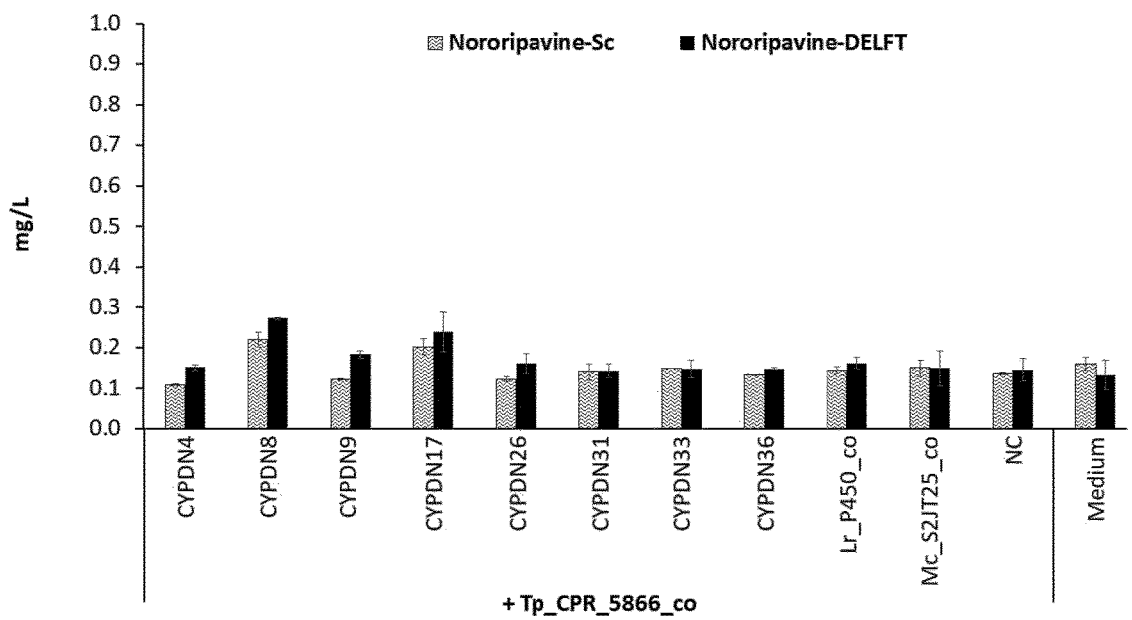

Figure 31
C
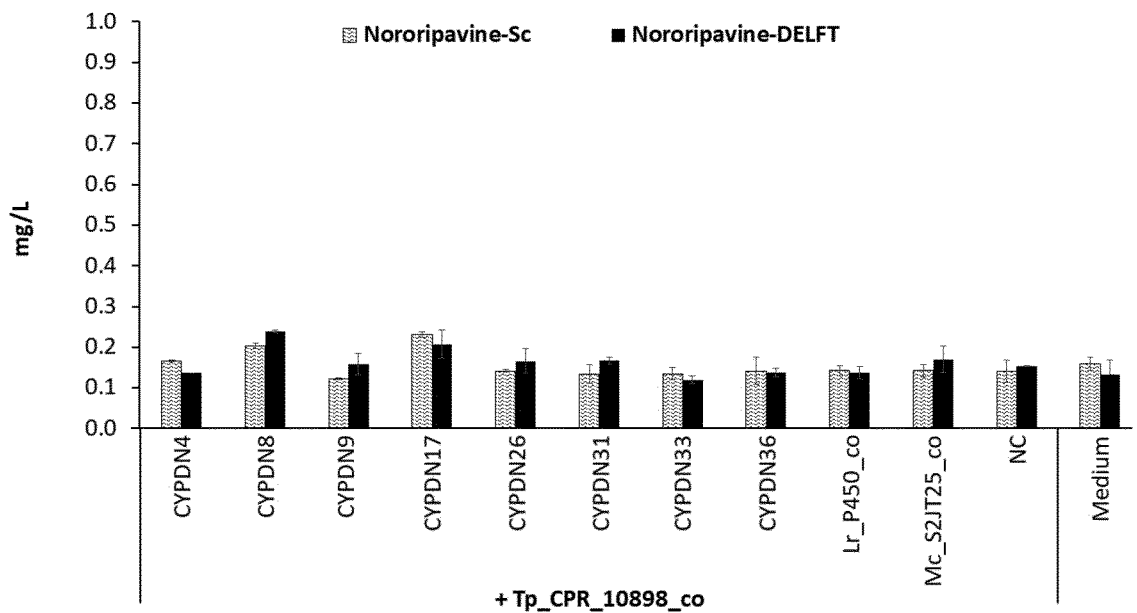
D
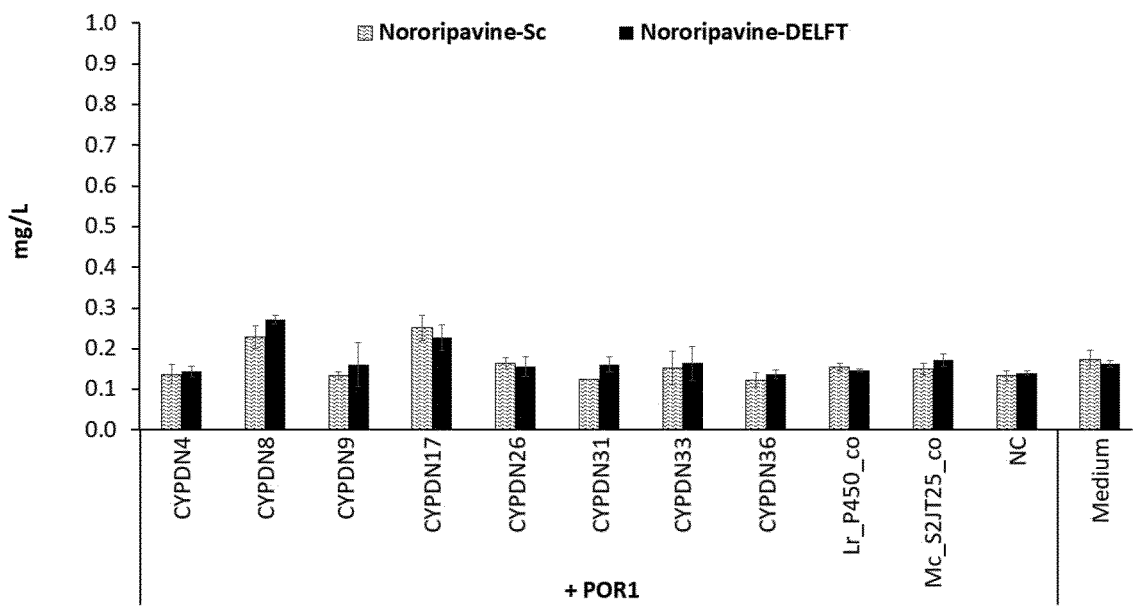

DEMETHYLATION OF RETICULINE AND DERIVATIVES THEREOF WITH FUNGAL CYTOCHROME P450

This application is a U.S. national phase application of International Patent Application No. PCT/EP2018/066155 filed on Jun. 18, 2018, which claims the benefit of Danish Patent Application PA201770473 filed on Jun. 16, 2017.

REFERENCE TO AN ELECTRONIC SEQUENCE LISTING

A computer readable form of the Sequence Listing is filed with this application by electronic submission and is hereby incorporated by reference in its entirety. The Sequence Listing is contained in the ASCII text file created on Dec. 16, 2019, having the name "19-2315-WO-US_SEQList.txt" and is 442,384 bytes in size.

FIELD OF THE INVENTION

The invention relates to recombinant host cells that express one or more genes encoding a cytochrome P450 enzyme capable of N-demethylating and/or O-demethylating reticuline and/or derivatives thereof, and also methods of producing N-demethylated and/or O-demethylated reticuline and/or derivatives thereof, comprising cultivating the recombinant host of the invention in a culture medium under conditions in which the one or more genes encoding the cytochrome P450 enzymes is/are expressed. The invention also relates to in vitro bioconversion processes that produce N-demethylated and/or O-demethylated reticuline and/or derivatives thereof. The reticuline and derivatives thereof are useful for providing access to naturally unavailable and chemically difficult-to-produce starting materials for opioids.

BACKGROUND OF THE INVENTION

Thebaine and oripavine extracted from plant material are starting materials for chemical synthesis of semisynthetic marketed opioids including buprenorphine, naltrexone, naloxone and nalbuphine.

Chemical synthesis of buprenorphine, naltrexone, naloxone and nalbuphine involves N-alkylation which is preceded by N-demethylation of thebaine or oripavine or a derivative thereof. This step is one of the most critical in the chemical synthesis of the above-mentioned compounds as it has low efficiency and produces highly toxic waste products.

N-demethylation of thebaine and oripavine or derivatives thereof by fungi belonging to the order Mucorales has been described previously by Madyastha et al. (J. Chem. Soc. Perkin. Trans., vol. 3, p. 911), by K. Madyastha, et al. (Indian J. Chem., vol. 39, pp. 377-381, 2000), and by Chaudhary et al. (Collect. Czechoslov. Chem. Commun., vol. 74, no. 7-8, pp. 1179-1193, 2009).

Furthermore, opiate demethylation including thebaine has previously been demonstrated with human CYP3A4 and CYP3A5 by Kramlinger et al. (3 Biol Chem, vol. 290, no. 33, pp. 20200-20210, 2015), and by Lalovic et al. (Drug Metab. Dispos., vol. 32, no. 4, pp. 447-454, 2004). Also, variants of the cytochrome P450 BM3 from *Bacillus megaterium* have been reported to possess similar activities (Lewis et al. (Chembiochem, vol. 11, no. 8, pp 2502-2505, 2010))

However, the activity demonstrated so far for the human/bacterial P450 enzymes and naturally active fungi are not anywhere close to being efficient enough for a commercially relevant enzymatic/biological demethylation process and there is a concrete need for isolation of more active enzymes which are suitable for expression in heterologous hosts. Without knowing the gene sequence and thereby the amino acid sequence of the enzymes responsible for the demethylation reactions such expression in heterologous hosts is not possible. Before the present invention it was not known which type of enzyme was responsible for the N-demethylation reaction in fungi of the mucorales order and sequences of the responsible enzymes not isolated. Filamentous fungi can like plants typically have more than hundred Cytochrome P450 and dioxygenase enzymes, which could all be candidates for being N-demethylases. The first isolation of the specific enzyme responsible for this reaction from a specific fungus is therefore a very complex task, and in particular when the species is not genome sequenced. Finding more homologs of the first isolated gene in related sequenced species using BLAST search is on the other hand less difficult.

An efficient setup for the production of reticuline and/or derivatives thereof is needed in order to pursue chemical synthesis of the semisynthetic marketed opioids.

Such setup would provide access to naturally unavailable and chemically difficult to produce starting materials for the opioids, such as northebaine and nororipavine, in an economic and sustainable process.

SUMMARY OF THE INVENTION

The invention relates to a recombinant host cell that expresses one or more genes encoding a cytochrome P450 enzyme capable of N-demethylating and/or O-demethylating reticuline and/or derivatives thereof, wherein at least one of the genes is a recombinant gene.

Certain embodiments of the invention relate to host cells of the invention wherein reticuline and derivatives thereof can be (S)-reticuline, 1,2 dehydroreticuline, (R)-reticuline, salutaridine, salutaridinol, thebaine, oripavine, neopinone, codeinone, codeine, morphinone, morphine, hydrocodone, 14-hydroxycodeinone, 7-O-acetyl-salutaridinol or oxycodone.

In certain embodiments of the host cells of the invention, the reticuline derivative is thebaine or oripavine.

In certain embodiments of the host cells of the invention, cytochrome P450 enzymes capable of N-demethylating and/or O-demethylating reticuline and/or derivatives thereof have at least 20% sequence identity with P450_DN15259_c0_g1_i7 (SEQ ID NO: 3), such as 30% sequence identity, such as 40% sequence identity, such as 50% sequence identity, such as 60% sequence identity, such as 70% sequence identity, such as 75% sequence identity, such as 80% sequence identity, such as 85% sequence identity, such as 90% sequence identity, such as 95% sequence identity, such as 97% sequence identity, such as 98% sequence identity, such as 99% sequence identity.

In certain embodiments of the host cells of the invention, cytochrome P450 enzymes capable of N-demethylating and/or O-demethylating reticuline and/or derivatives thereof have at least 20% sequence identity with CYPDN8 (SEQ ID NO: 72), such as 30% sequence identity, such as 40% sequence identity, such as 50% sequence identity, such as 60% sequence identity, such as 70% sequence identity, such as 75% sequence identity, such as 80% sequence identity, such as 85% sequence identity, such as 90% sequence identity, such as 95% sequence identity, such as 97% sequence identity, such as 98% sequence identity, such as 99% sequence identity.

In additional embodiments of the invention, host cells further express one or more cytochrome P450 reductase(s) (CPR(s)). This one or more reductase can be endogenous or heterologous, or there can be one or more of both.

The invention provides host cells, wherein the cell is a yeast cell including but not limited to *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., or *Rhodospiridium* sp.

The invention also relates to methods for producing reticuline or derivatives thereof, comprising cultivating the recombinant host cell of the invention in a culture medium under conditions in which the one or more genes encoding the cytochrome P450 enzymes is/are expressed and wherein at least one of the genes is recombinant.

In certain embodiments of the host cell of the invention, reticuline or derivatives thereof include but are not limited to (S)-reticuline, 1,2 dehydroreticuline, (R)-reticuline, salutaridine, salutaridinol, thebaine, oripavine, neopinone, codeinone, codeine, 7-O-acetyl-salutaridinol, morphinone, morphine, hydrocodone, 14-hydroxycodeinone or oxycodone.

In certain embodiments of the methods of the invention, the recombinant host of the invention are cultivated in a culture medium under conditions in which the one or more genes encoding the cytochrome P450 reductase is/are expressed and wherein at least one of the genes is recombinant.

The invention further relates to compositions comprising compounds that are reticuline or derivatives thereof that can be obtained from the methods according to the invention, wherein said methods further comprise elements from a fungal fermentation broth and/or at least one fungal specific metabolite Another aspect of the disclosure relates to a method of preparing buprenorphine, or a salt thereof, from Compound HO-I-H, or a salt thereof:

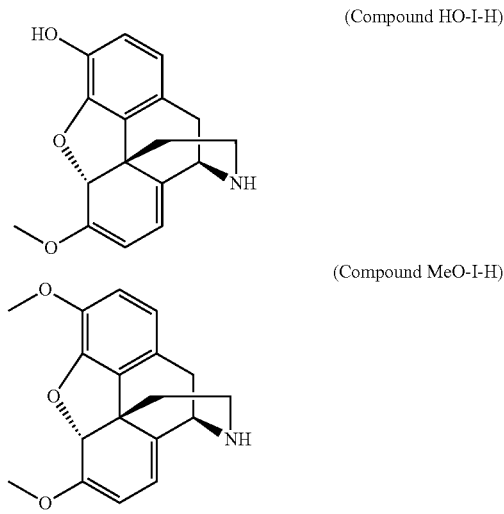

(Compound HO-I-H)

(Compound MeO-I-H)

comprising reacting compound HO-I-H (Nororipavine) or compound MeO-I-H (Northebaine) through a series of steps to provide buprenorphine.

Aspects and embodiments of the disclosure related to methods of preparing buprenorphine from Compound MeO-I-H, or HO-I-H provide improved routes to buprenorphine that can be shorter, more efficient, and/or produce less toxic waste than, e.g., current commercial routes to buprenorphine. As a result, these aspects and embodiments can be well-suited for commercial (e.g., kg-scale) production of buprenorphine. Further, in certain aspects and embodiments, the synthetic routes disclosed herein advantageously avoid the harsh conditions and/or toxic byproducts of an N-demethylation step and can accordingly be particularly well-suited for producing buprenorphine on a commercial, e.g., kg, scale.

Seven yeast codon-optimized cytochrome P450 candidates from *Cunninghamella echinulata* were co-expressed with Cel_CPR, the CPR from *C. elegans*. Cells were fed with 0.5 mM thebaine in selective medium containing 0.1 M potassium phosphate buffer pH 7 and grown at 30° C., 300 rpm for 72 h. The error bar represents the standard deviation of 4 different biological replicates. (PC, Positive control).

Figure 24:
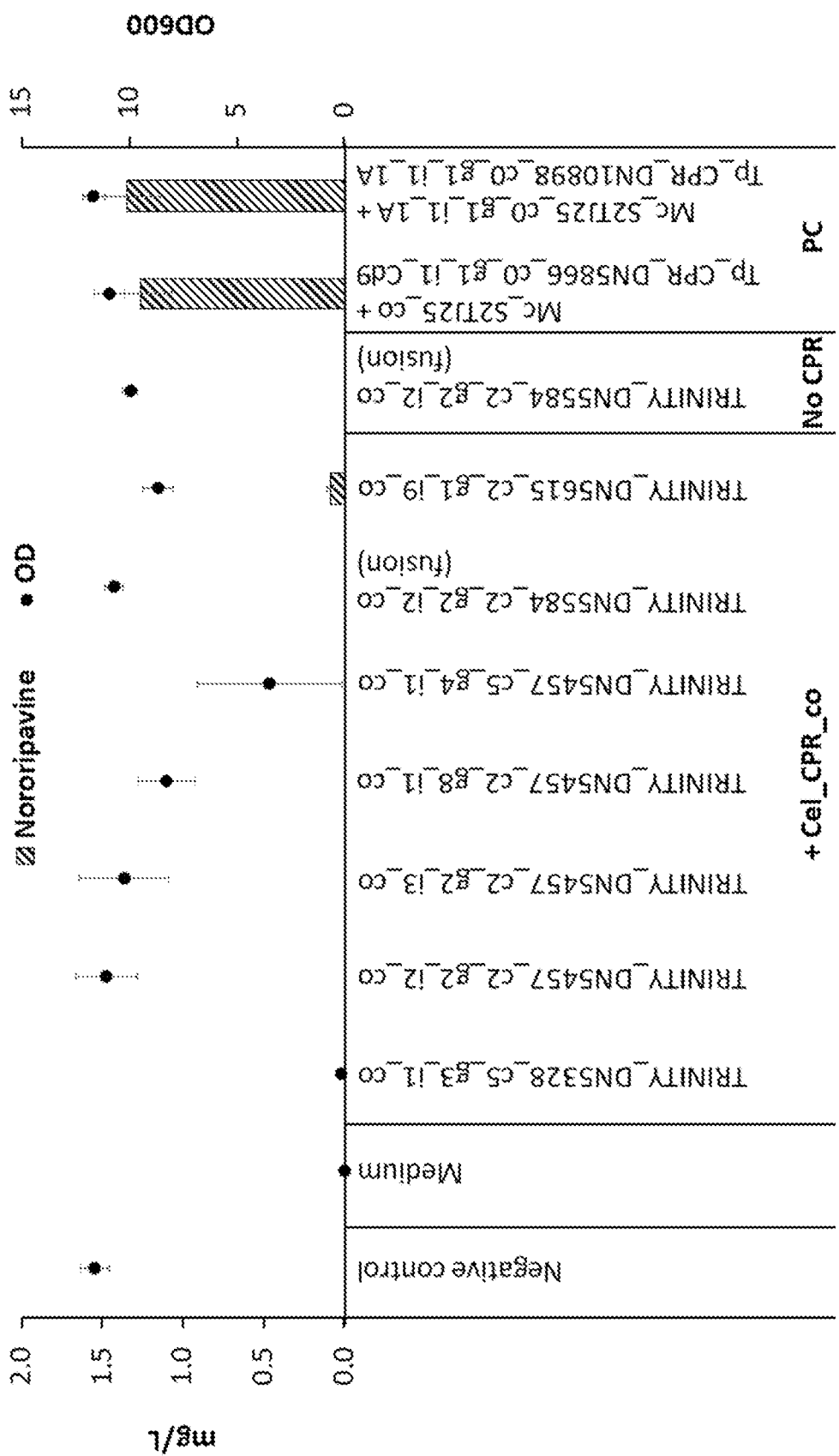

FIG. 24: Oripavine N-demethylation by codon-optimized *C. echinulata* P450 along with Cel_CPR_co. Seven yeast codon-optimized cytochrome P450 candidates from *Cunninghamella echinulata* were co-expressed with Cel_CPR, the CPR from *C. elegans*. Cells were fed with 0.5 mM oripavine in selective medium containing 0.1 M potassium phosphate buffer pH 7 and grown at 30° C., 300 rpm for 72 h. The error bar represents the standard deviation of 4 different biological replicates. (PC, Positive control).

Figure 25:
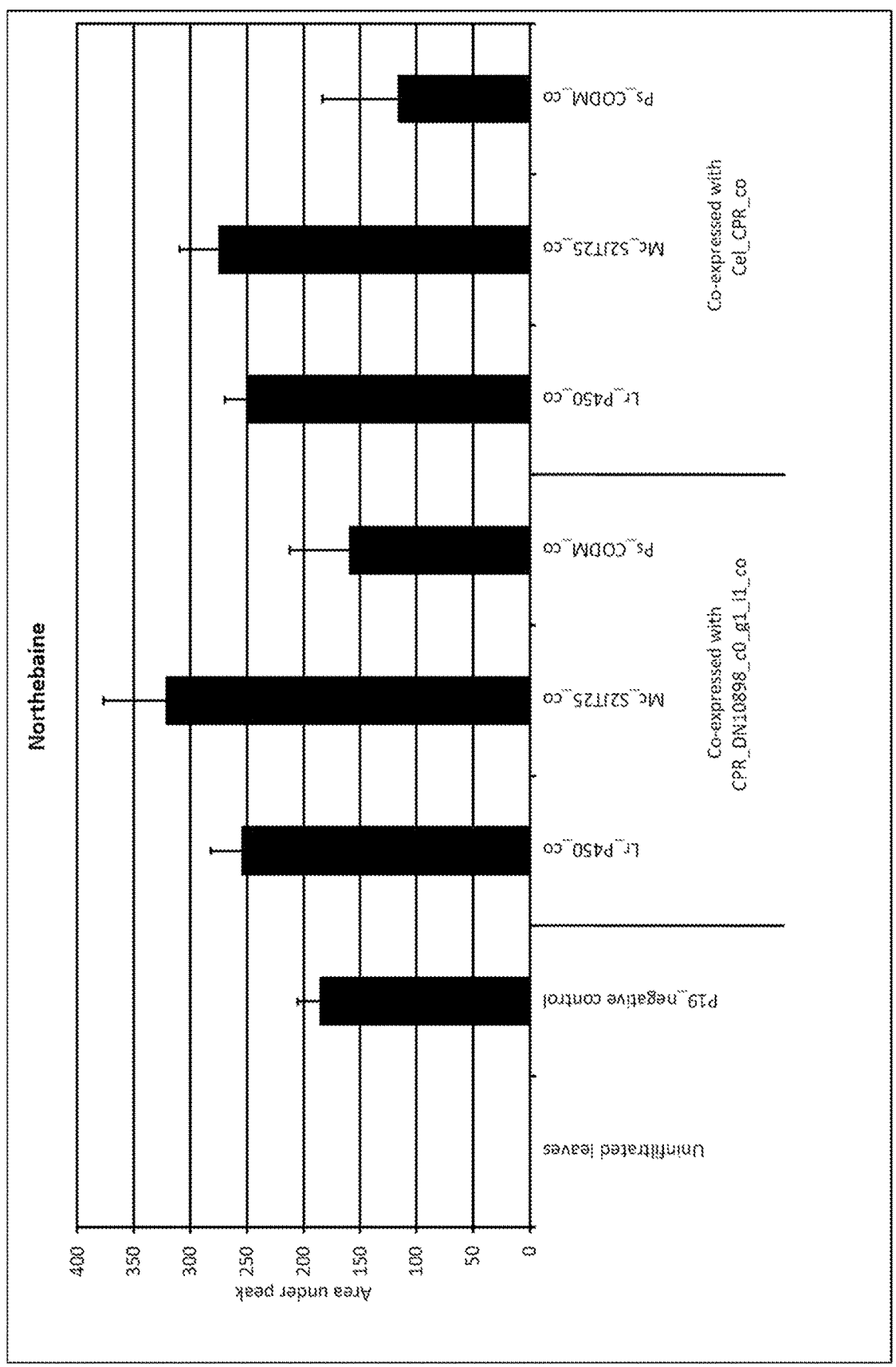

FIG. 25: Northebaine content in leaves of *N. benthamiana*. *N. benthamiana* leaves were infiltrated with a demethylase gene of *Lichtheimia ramosa* (Lr_P450_co), *Mucor circinelloides* (Mc_S2JT25_co) or *Papaver somniferum* (Ps_CODM_co) and the cytochrome P450 reductase gene of *Thamnostylum piriforme* (CPR_DN10898_c0_g1_i1_co) or *Cunninghamella elegans* (Cel_CPR_co). Leaves were then re-infiltrated with thebaine solution after 4 days and the northebaine content was measured 1 day after with LC-MS. Data shown as the mean of two individual plants, each sampled with 2 different leaf discs. Error bars represent the standard error of the mean.

Figure 26:
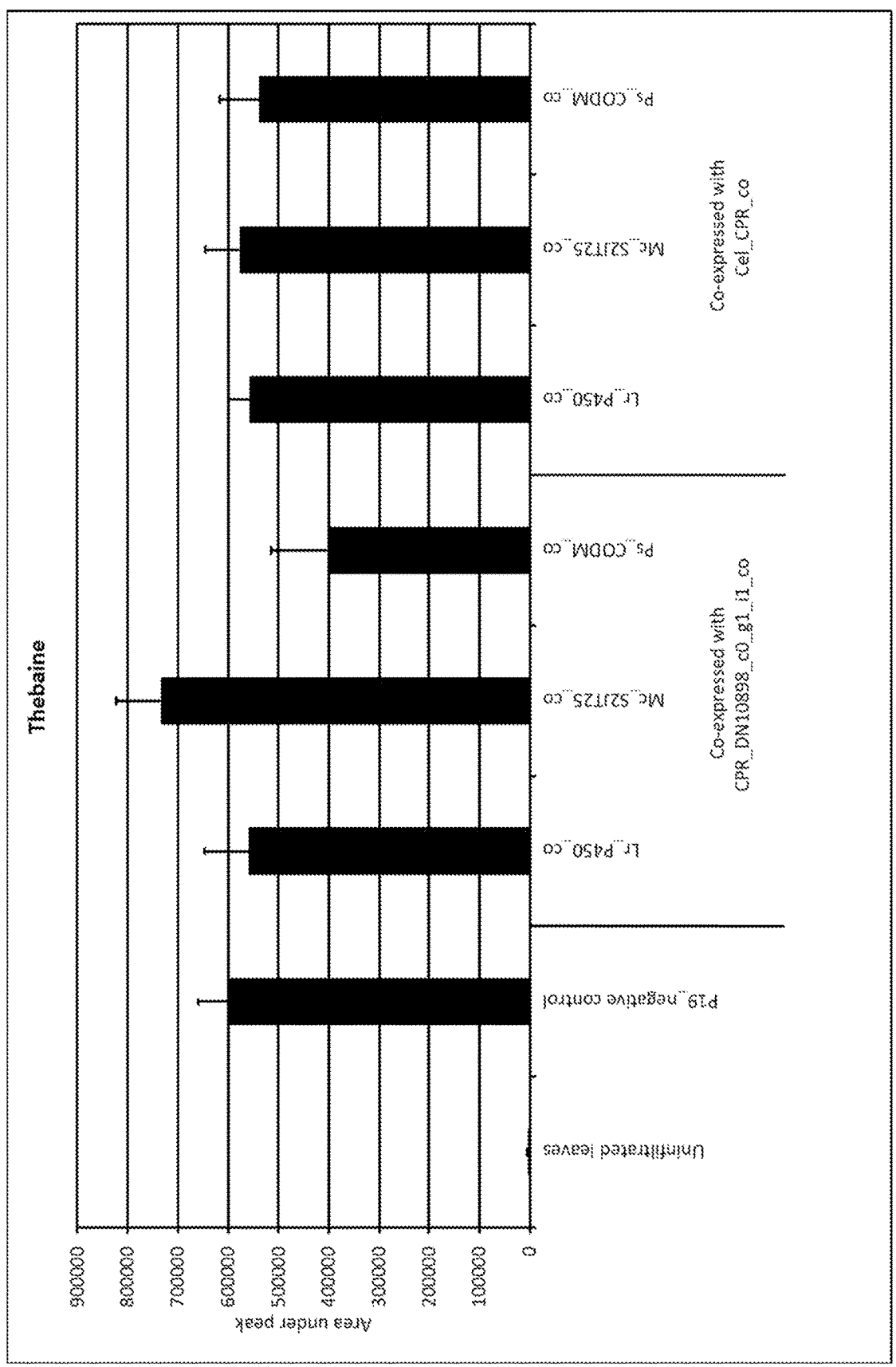

FIG. 26: Thebaine content in leaves of *N. benthamiana*.

*N. benthamiana* leaves were co-infiltrated with either a demethylase gene of *Lichtheimia ramosa* (Lr_P450_co), *Mucor circinelloides* (Mc_S2JT25_co) or *Papaver somniferum* (Ps_CODM_co) and the cytochrome P450 reductase gene of *Thamnostylum piriforme* (CPR_DN10898_c0_g1_i1_co) or *Cunninghamella elegans* (Cel_CPR_co). Leaves were re-infiltrated with thebaine solution after 4 days and the content was assessed 1 day after with LC-MS. Data shown as the mean of two individual plants, each sampled with 2 different leaf discs. Error bars represent the standard error of the mean.

Figure 27:
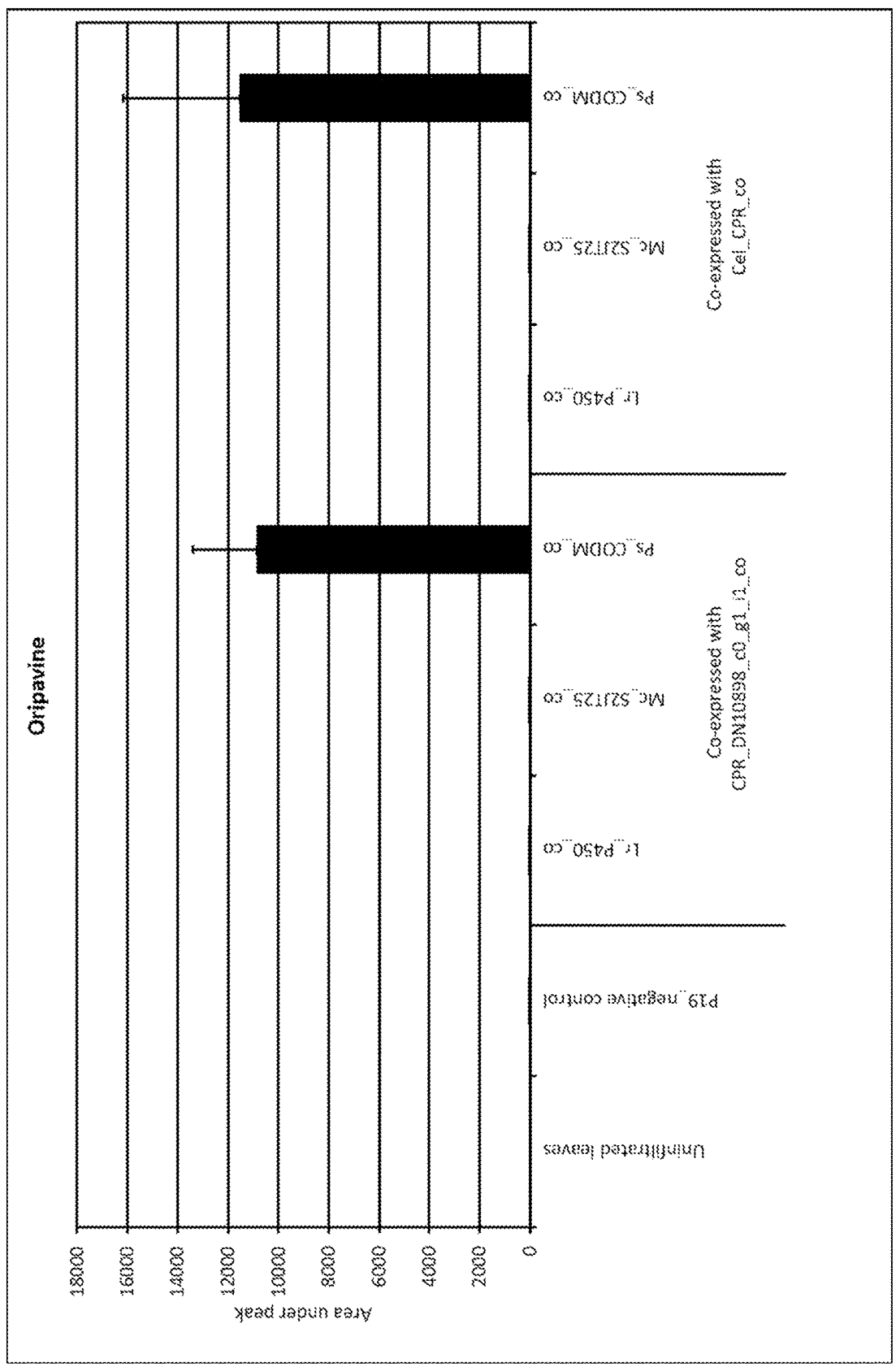

FIG. 27: Oripavine content in leaves of *N. benthamiana*.

*N. benthamiana* leaves were co-infiltrated with either a demethylase gene of *Lichtheimia ramosa* (Lr_P450_co), *Mucor circinelloides* (Mc_S2JT25_co) or *Papaver somniferum* (Ps_CODM_co) and the cytochrome P450 reductase gene of *Thamnostylum piriforme* (CPR_DN10898_c0_g1_i1_co) or *Cunninghamella elegans* (Cel_CPR_co). Leaves were re-infiltrated with thebaine after 4 days and the oripavine content was assessed 1 day after with LC-MS. Data shown as the mean of two individual plants, each sampled with 2 different leaf discs. Error bars represent the standard error of the mean.

Figure 28:
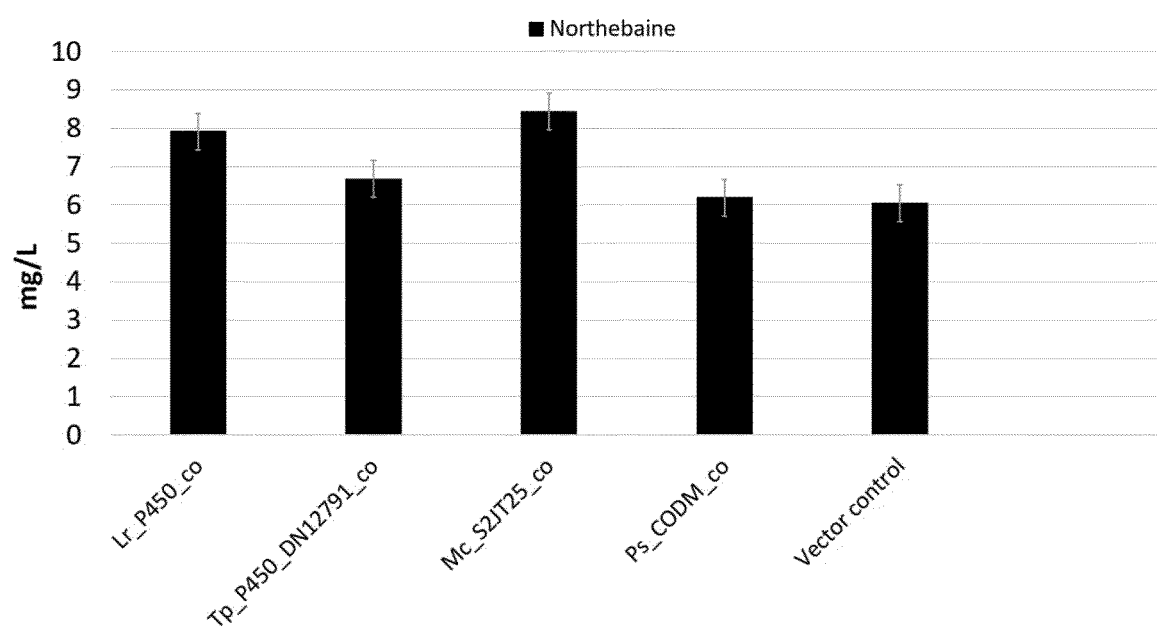

FIG. 28: Northebaine content in *Aspergillus nidulans*

Northebaine content was measured in the supernatant by LC-MS after 84 h of incubation at 30° C. Data for samples Lr_P450_co, Mc_S2JT25_co, Tp_P450_DN12791_c0_g1_i1_co and Ps_CODM_co are shown as the mean of 5 biological replicates. For the vector control, the data is shown as the mean of 3 biological replicates. A single measurement was performed for the media control. The error bars represent the standard error of the mean.

FIG. 29: Growth media effect on northebaine production by yeast strains expressing new fungal candidates. Twenty-four different cytochrome P450s from fungi belonging to the Mucorales order were co-expressed with four different CPR genes from either *T. piriforme* (Tp_CPR_10898_co and Tp_CPR_5866_co), *L. ramosa* (POR1) or *C. elegans* (Cel_CPR_co). Cells were fed with 0.5 mM thebaine in selective (Sc) or DELFT medium containing 0.1 M potassium phosphate buffer pH 7 and grown at 30° C., 300 rpm for 72 h. The error bar represents the standard deviation of 2 different biological replicates. NC: Negative control strain.

FIG. 30: Oripavine production by yeast strains expressing new fungal candidates. Ten different cytochrome P450s from fungi belonging to the Mucorales order and one cytochrome P450 from plant (Ps_CODM_co—used as a positive control) were co-expressed with four different CPR genes from either *T. piriforme* (Tp_CPR_10898_co and Tp_CPR_5866_co), *L. ramosa* (POR1) or *C. elegans* (Cel_CPR_co). Cells were fed with 0.5 mM thebaine in selective (Sc) or DELFT medium containing 0.1 M potassium phosphate buffer pH 7 and grown at 30° C., 300 rpm for 72 h. The error bar represents the standard deviation of 2 different biological replicates. NC: Negative control strain.

FIG. 31: Nororipavine production by yeast strains expressing new fungal candidates. Ten different cytochrome P450s from fungi belonging to the Mucorales order were co-expressed with four different CPR genes from either *T. piriforme* (Tp_CPR_10898_co and Tp_CPR_5866_co), *L. ramosa* (POR1) or *C. elegans* (Cel_CPR_co). Cells were fed with 0.5 mM thebaine in selective medium (Sc) or DELFT medium containing 0.1 M potassium phosphate buffer pH 7 and grown at 30° C., 300 rpm for 72 h. The error bar represents the standard deviation of 2 different biological replicates. NC: Negative control strain.

Figure 32:
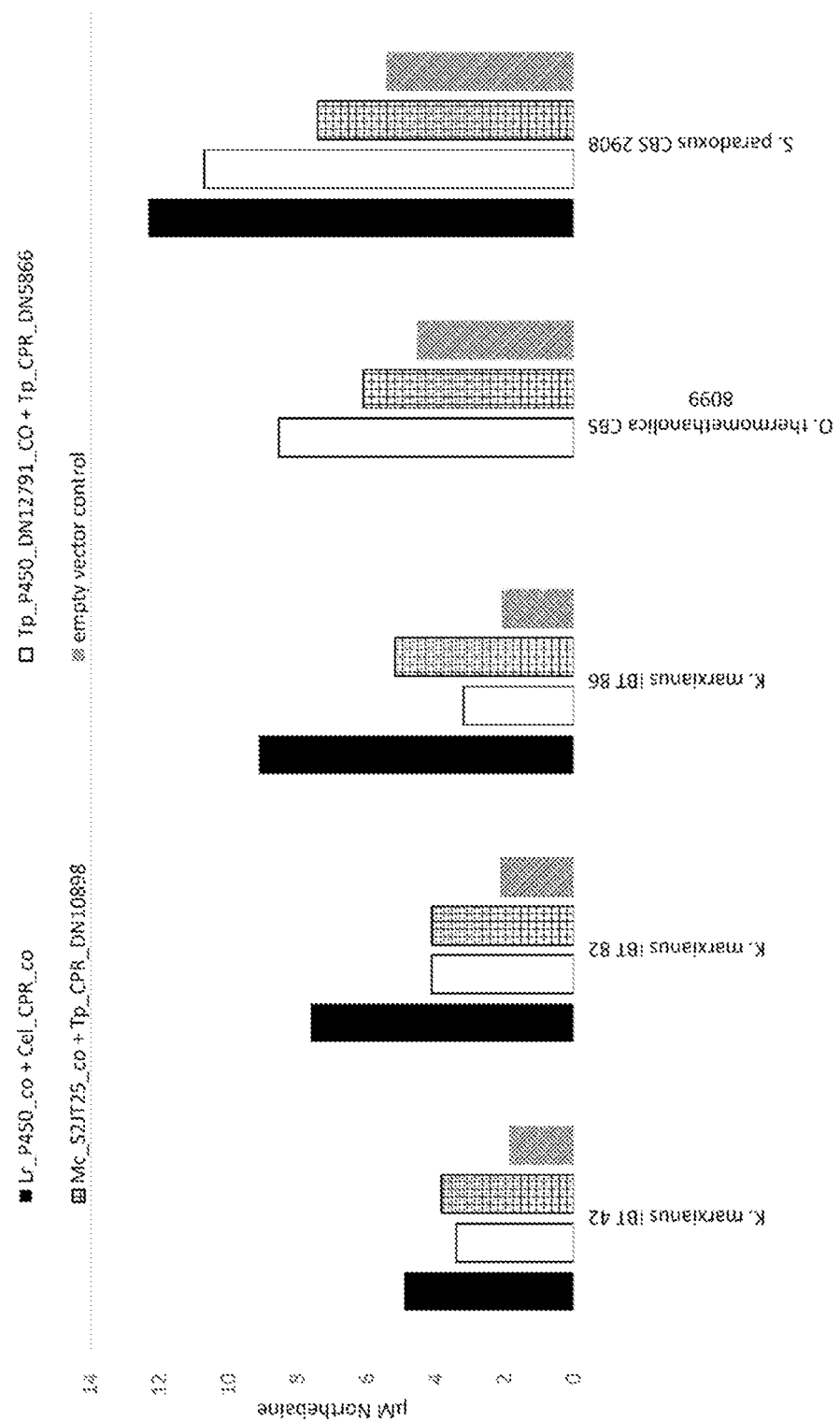

FIG. 32: Conversion of thebaine to northebaine in non-conventional yeasts. Northebaine content was measured in the supernatant by LC-MS after 4 days of incubation at 30° C. The N-demethylation of thebaine to northebaine was tested in *K. marxianus* (IBT 42, IBT82, IBT86), *O. thermomethanolica* (CBS 8099) and *S. paradoxus* (CBS 2908). The data shown was obtained from a single measurement.

DETAILED DESCRIPTION OF THE INVENTION

The invention describes a new way for N-demethylation, and optionally additionally O-demethylation, of reticuline and/or derivatives thereof, for example thebaine and oripavine, by a bioconversion process using a microbial host. This provides access to the naturally unavailable and chemically difficult-to-produce starting materials, such as northebaine and nororipavine, in an economic and sustainable process.

The invention is exemplified by identification and functional analyses of several fungal cytochrome P450 enzymes from the Mucorales order for example *Thamnostylum piriforme*, and used when produced recombinantly in *S. cerevisiae*, and plants like tobacco, for a thebaine and oripavine bioconversion process to northebaine or nororipavine, respectively. Along the same lines cytochrome P450 enzymes from human or ape have been evaluated for N-demethylation activity towards thebaine, oripavine, salutaridine, salutaridinol and codeine.

Thus, the invention relates to a recombinant host cell that expresses one or more genes encoding a cytochrome P450 enzyme capable of N-demethylating and/or O-demethylating reticuline and/or derivatives thereof, wherein at least one of the genes is a recombinant gene.

It is a unique feature of the present invention that the inventors have identified that the cytochrome P450 enzymes from the fungal Mucorales order are capable of N-demethylating recituline and derivatives hereof.

The host cell, accordingly can further express one or more cytochrome P450 reductase(s) (CPR(s)). These one or more reductases can be endogenous or heterologous, or there can be one or more of both.

General

All publications, patents and patent applications cited herein are hereby expressly incorporated by reference for all purposes.

Methods well known to those skilled in the art can be used to construct genetic expression constructs and recombinant cells according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

Before describing the invention in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the invention.

For the purposes of describing and defining the invention it is noted that the terms "substantial" or "substantially" are utilized herein to represent the inherent degree of uncertainty that can be attributed to any quantitative comparison, value, measurement, or other representation. The terms "substantial" or "substantially" are also utilized herein to represent the degree by which a quantitative representation can vary from a stated reference without resulting in a change in the basic function of the subject matter at issue.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z."

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the terms "microorganism," "microorganism host," "microorganism host cell," "host cell," "recombinant host," "recombinant microorganism host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through stable introduction of one or more recombinant genes.

Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence can already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. Said recombinant genes are particularly encoded by cDNA.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast transporter. In some embodiments, the transporter is endogenous to S. cerevisiae, including, but not limited to S. cerevisiae strain S288C. In some embodiments, an endogenous yeast transporter gene is overexpressed. As used herein, the term "overexpress" is used to refer to the expression of a gene in an organism at levels higher than the level of gene expression in a wild type organism. See, e.g., Prelich, 2012, Genetics 190:841-54. In some embodiments, an endogenous yeast transporter gene is deleted. See, e.g., Giaever & Nislow, 2014, Genetics 197 (2):451-65. As used herein, the terms "deletion," "deleted," "knockout," and "knocked out" can be used interchangeably to refer to an endogenous gene that has been manipulated to no longer be expressed in an organism, including, but not limited to, S. cerevisiae. In some embodiments, a deleted/knocked out gene is a transporter gene or a transcription factor gene that regulates expression of a transporter gene.

As used herein, the terms "heterologous sequence" and "heterologous coding sequence" are used to describe a sequence derived from a species other than the recombinant host or a sequence from the host that has been inserted into the host recombinantly. In some embodiments one or more wild type sequence is inserted to generate an overexpression of the specific gene. The overexpression can come from manipulation of for example the promoter. In some embodiments, the recombinant host is an S. cerevisiae cell, and a heterologous sequence is derived from an organism other than S. cerevisiae. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis.

Subsequent to its use in selection, a selectable marker can be removed from the genome of the host cell by, e.g., Cre-LoxP systems (see, e.g., Gossen et al., 2002, Ann. Rev. Genetics 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild type sequence of a particular protein.

Chemical terms used herein can be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety can be defined, for example, as —$B-(A)_a$, wherein a is 0 or 1. In such instances, when a is 0 the moiety is —B and when a is 1 the moiety is —B-A.

As used herein, the term "alkyl" includes a saturated hydrocarbon having a designed number of carbon atoms, such as 1 to 40 carbons (i.e., inclusive of 1 and 40), 1 to 35 carbons, 1 to 25 carbons, 1 to 20 carbons, or 1, 2, 3, 4, 5, 6, 7, 8, 9, 10, 11, 12, 13, 14, 15, 16, 17, or 18. Alkyl group can be straight or branched and depending on context, can be a monovalent radical or a divalent radical (i.e., an alkylene group). For example, the moiety "—($C_1$-$C_6$alkyl)-O—" signifies connection of an oxygen through an alkylene bridge having from 1 to 6 carbons and $C_1$-$C_3$alkyl represents methyl, ethyl, and propyl moieties. Examples of "alkyl" include, for example, methyl, ethyl, propyl, isopropyl, butyl, iso-, sec- and tert-butyl, pentyl, and hexyl. The term "alkoxy" represents an alkyl group of indicated number of carbon atoms attached to the parent molecular moiety through an oxygen bridge. Examples of "alkoxy" include, for example, methoxy, ethoxy, propoxy, and isopropoxy.

The term "alkenyl" as used herein, unsaturated hydrocarbon containing from 2 to 10 carbons (i.e., inclusive of 2 and 10), 2 to 8 carbons, 2 to 6 carbons, or 2, 3, 4, 5 or 6, unless otherwise specified, and containing at least one carbon-carbon double bond. Alkenyl group can be straight or branched and depending on context, can be a monovalent radical or a divalent radical (i.e., an alkenylene group). For example, the moiety "—($C_2$-$C_6$ alkenyl)-O—" signifies connection of an oxygen through an alkenylene bridge having from 2 to 6 carbons. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl" as used herein, unsaturated hydrocarbon containing from 2 to 10 carbons (i.e., inclusive of 2 and 10), 2 to 8 carbons, 2 to 6 carbons, or 2, 3, 4, 5 or 6 unless otherwise specified, and containing at least one carbon-carbon triple bond.

Alkynyl group can be straight or branched and depending on context, can be a monovalent radical or a divalent radical (i.e., an alkynylene group). For example, the moiety "—($C_2$-$C_6$ alkynyl)-O—" signifies connection of an oxygen through an alkynylene bridge having from 2 to 6 carbons. Representative examples of alkynyl include, but are not limited to, acetylenyl, 1-propynyl, 2-propynyl, 3-butynyl, 2-pentynyl, and 1-butynyl.

The term "aryl" represents an aromatic ring system having a single ring (e.g., phenyl) which is optionally fused to other aromatic hydrocarbon rings or non-aromatic hydrocarbon or heterocyclic rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. "Aryl" also includes ring systems having a first carbocyclic, aromatic ring fused to a nonaromatic heterocycle, for example, 1H-2,3-dihydrobenzofuranyl and tetrahydroisoquinolinyl. The aryl groups herein are unsubstituted or, when specified as "optionally substituted", can unless stated otherwise be substituted in one or more substitutable positions with various groups as indicated.

The term "heteroaryl" refers to an aromatic ring system containing at least one aromatic heteroatom selected from nitrogen, oxygen and sulfur in an aromatic ring. Most commonly, the heteroaryl groups will have 1, 2, 3, or 4 heteroatoms. The heteroaryl can be fused to one or more non-aromatic rings, for example, cycloalkyl or heterocycloalkyl rings, wherein the cycloalkyl and heterocycloalkyl rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, isoindolinyl, isobenzothienyl, benzoxazolyl, pyridopyridinyl, purinyl, benzodioxolyl, triazinyl, pteridinyl, benzothiazolyl, imidazopyridinyl, imidazothiazolyl, benzisoxazinyl, benzoxazinyl, benzopyranyl, benzothiopyranyl, chromonyl, chromanonyl, pyridinyl-N-oxide, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as indicated.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl can have 1, 2, 3 or 4 heteroatoms. The heterocycloalkyl can be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2 (1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as indicated.

The term "cycloalkyl" refers to a non-aromatic carbocyclic ring or ring system, which can be saturated (i.e., a cycloalkyl) or partially unsaturated (i.e., a cycloalkenyl). The cycloalkyl ring optionally fused to or otherwise attached (e.g., bridged systems) to other cycloalkyl rings. Certain examples of cycloalkyl groups present in the disclosed compounds have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", can be substituted in one or more substitutable positions with various groups, as indicated.

The term "ring system" encompasses monocycles, as well as fused and/or bridged polycycles.

The terms "halogen" or "halo" indicate fluorine, chlorine, bromine, and iodine. In certain embodiments of each and every embodiment described herein, the term "halogen" or "halo" refers to fluorine or chlorine. In certain embodiments of each and every embodiment described herein, the term "halogen" or "halo" refers to fluorine.

The term "halide" indicates fluoride, chloride, bromide, and iodide. In certain embodiments of each and every embodiment described herein, the term "halide" refers to bromide or chloride.

The term "substituted," when used to modify a specified group or radical, means that one or more hydrogen atoms of the specified group or radical are each, independently of one another, replaced with the same or different substituent groups as defined below, unless specified otherwise.

Specific protecting groups can be used to protect reactive functionalities of a starting material or intermediate to prepare a desired product. In general, the need for such protecting groups as well as the conditions necessary to attach and remove such groups will be apparent to those skilled in the art of organic synthesis. An authoritative account describing the many alternatives to the trained practitioner are 3. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and 3. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups can be removed at a convenient subsequent stage using methods known from the art.

Reticuline and Derivatives Thereof

Reticuline is a chemical compound found in a variety of plants including *Lindera aggregata, Annona squamosa*, and *Ocotea fasciculate*. It is based on the benzylisoquinoline structure:

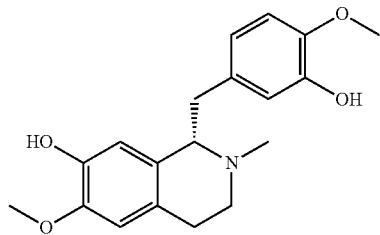

Reticuline is one of the alkaloids found in opium, and it is the precursor of morphine and many other alkaloids and opioids.

In an embodiment of the invention reticuline and/or derivatives thereof comprises (S)-reticuline, 1,2 dehydroreticuline, (R)-reticuline, salutaridine, salutaridinol, thebaine, oripavine, 7-O-acetyl-salutaridinol, neopinone, codeinone, codeine, morphinone, morphine, hydrocodone, 14-hydroxycodeinone or oxycodone.

In a further embodiment of the invention the reticuline derivative is thebaine.

In another embodiment of the invention the reticuline derivative is oripavine.

Cytochrome P450 Enzymes

Cytochromes P450 enzymes (CYPs) are proteins of the superfamily containing heme as a cofactor and, therefore, are hemoproteins. CYPs use a variety of small and large molecules as substrates in enzymatic reactions. They are, in general, the terminal oxidase enzymes in electron transfer chains, broadly categorized as P450-containing systems. The term P450 is derived from the spectrophotometric peak at the wavelength of the absorption maximum of the enzyme (450 nm) when it is in the reduced state and complexed with carbon monoxide.

Most CYPs require a protein partner to deliver one or more electrons to reduce the iron (and eventually molecular oxygen). Based on the nature of the electron transfer proteins, CYPs can be classified into several groups: Microsomal P450 systems, in which electrons are transferred from NADPH via cytochrome P450 reductase (variously CPR, POR, or CYPOR). Cytochrome b5 (cyb5) can also contribute reducing power to this system after being reduced by cytochrome b5 reductase (CYB5R). Mitochondrial P450 systems, which employ adrenodoxin reductase and adrenodoxin to transfer electrons from NADPH to P450. Bacterial P450 systems, which employ a ferredoxin reductase and a ferredoxin to transfer electrons to P450. CYB5R/cyb5/P450 systems, in which both electrons required by the CYP come from cytochrome b5. FMN/Fd/P450 systems, originally found in *Rhodococcus* species, in which a FMN-domain-containing reductase is fused to the CYP.

P450-only systems do not require external reducing power. Notable ones include thromboxane synthase (CYPS), prostacyclin synthase (CYP8), and CYP74A (allene oxide synthase).

In an embodiment of the invention the cytochrome P450 enzyme capable of N-demethylating reticuline and derivatives thereof comprises a mammalian P450 3A4 enzymes, mammalian P450 3A5 enzymes, and mammalian P450 2C8 enzymes.

In an embodiment of the invention the cytochrome P450 enzyme capable of N-demethylating reticuline and derivatives thereof comprises a fungal cytochrome P450 enzymes.

In an embodiment of the invention the cytochrome P450 enzyme capable of N-demethylating and/or O-demethylating reticuline and/or derivatives thereof comprises a fungal cytochrome P450 enzymes, mammalian P450 3A4 enzymes, mammalian P450 3A5 enzymes, and mammalian P450 2C8 enzymes.

The cytochrome P450 enzyme capable of N-demethylating and/or O-demethylating reticuline and/or derivatives thereof can originate from a fungal organism. The organism can be *Thamnostylum piriforme, Lichtheimia ramosa, Cunninghamella echinulata, Cunninghamella dalmatica, Cunninghamella polymorpha* or *Rhizopus nigricans*.

The cytochrome P450 enzyme capable of N-demethylating reticuline and derivatives thereof can originate from an organism including *Cunninghamella echinulata, Rhizopus nigricans*, and *Mucor piriformis*.

The cytochrome P450 enzyme capable of N-demethylating and/or O-demethylating reticuline and/or derivatives thereof can originate from a mammalian organism, including but not limited to *Homo sapiens, Pongo abelii, Papio anubis, Gorilla gorilla gorilla, Canis lupus familiaris, Pan troglodytes, Callithrix jacchus, Macaca fascicularis* and *Chlorocebus aethiops*.

Fungal Cytochrome P450 Enzymes

In a further embodiment of the invention the cytochrome P450 enzyme capable of N-demethylating and/or O-demethylating reticuline and/or derivatives thereof is a fungal cytochrome P450 enzyme or functional homologs or variants hereof.

In some embodiments of the invention is the cytochrome P450 enzyme capable of N-demethylating and/or O-demethylating reticuline and/or derivatives thereof from the Mucorales order. The Mucorales is the largest and best studied order of zygomycete fungi. Members of this order are sometimes called pin molds.

Being able to express the demethylases with strong promoters in a heterologous host is key for using these enzymes in a commercial process where turnover has to be fast and efficient. Without knowing the gene sequence and thereby the amino acid sequence of the enzymes responsible for the demethylation reactions such expression in heterologous hosts is not possible. Before the present invention it was not known which type of enzyme was responsible for the N-demethylation reaction in fungi of the mucorales order and sequences of the responsible enzymes not isolated. Filamentous fungi have like plants can typically have several hundred Cytochrome P450 and dioxygenase enzymes, which could all be candidates for being N-demethylases. The first isolation of the specific enzyme responsible for this reaction from a specific fungus is therefore a very complex task, and in particular when the species is not genome sequenced. Finding more homologs of the first isolated gene in related sequenced species using BLAST search is on the other hand less difficult.

It is therefore a unique feature of the present invention that the inventors have identified that the cytochrome P450 enzymes from the fungal Mucorales order are capable of N-demethylating recutiline and derivatives hereof.

The fungal cytochrome P450 enzyme can be P450_DN15259_c0_g1_i7 (SEQ ID NO: 1), P450_DN12791_c0_g1_i1 (SEQ ID NO: 4) and/or A0A077WEM0 (SEQ ID NO: 7), or functional homologs or variants hereof.

The fungal cytochrome P450 enzyme can also be P450_DN15259_c0_g1_i7 (SEQ ID NO: 1) or functional homologs or variants hereof. P450_DN15259_c0_g1_i7 is encoded by SEQ ID NO: 2 and the sequence optimized for S. cerevisiae is SEQ ID NO: 3.

The fungal cytochrome P450 enzyme can also be P450_DN12791_c0_g1_i1 (SEQ ID NO: 4) or functional homologs or variants hereof. P450_DN12791_c0_g1_i1 is encoded by SEQ ID NO: 5 and the sequence optimized for S. cerevisiae is SEQ ID NO: 6.

The fungal cytochrome P450 enzyme can also be A0A077WEM0 (SEQ ID NO: 7) or functional homologs or variants hereof. A0A077WEM0 is encoded by SEQ ID NO: 8.

The fungal Mucorales cytochrome P450 enzyme can also be selected from the group consisting of:

i) CYPDN8 (SEQ ID NO: 72), ii) Mc_S23T25 (SEQ ID NO: 52), iii) CYPDN17 (SEQ ID NO: 90), iv) CYPDN12 (SEQ ID NO: 80), v) Lr_P450 (SEQ ID NO: 8), vi) CYPDN29 (SEQ ID NO: 114), vii) CYPDN14 (SEQ ID NO: 84), vii) P450_DN15259_c0_g1_i7 (SEQ ID NO: 3), ix) LCOR_01865 (SEQ ID NO: 54), x) P450_DN5615_c2_g1_i9 (SEQ ID NO: 62), xi) P450_DN12791_c0_g1_i1 (SEQ ID NO: 5), xii) CYPDN16 (SEQ ID NO: 88), xiii) CYPDN18 (SEQ ID NO: 92), xiv) CYPDN27 (SEQ ID NO: 110), xv) CYPDN35 (SEQ ID NO: 126), xvi) CYPDN5 (SEQ ID NO: 66), xvii) CYPDN6 (SEQ ID NO: 68), xviii) CYPDN7 (SEQ ID NO: 70), xix) CYPDN10 (SEQ ID NO: 76), xx) CYPDN11 (SEQ ID NO: 78), xxi) CYPDN24 (SEQ ID NO: 104), xxii) CYPDN28 (SEQ ID NO: 112), xxiii) CYPDN13 (SEQ ID NO: 82), xxiv) CYPDN31 (SEQ ID NO: 118), xxv) CYPDN34 (SEQ ID NO: 124), xxvi) CYPDN22 (SEQ ID NO: 100), xxvii) CYPDN21 (SEQ ID NO: 98), xxviii) CYPDN30 (SEQ ID NO: 116), xxix) ArORZ22410 (SEQ ID NO: 58), xxx) CYPDN20 (SEQ ID NO: 96), xxxi) CYPDN17 (SEQ ID NO: 90), and xxxii) CYPDN8 (SEQ ID NO: 72).

Thus, the P450 enzyme can be YPDN8 (SEQ ID NO: 72). The P450 enzyme can also be Mc_S23T25 (SEQ ID NO: 52). The P450 enzyme can also be CYPDN17 (SEQ ID NO: 90). The P450 enzyme can also beCYPDN12 (SEQ ID NO: 80). The P450 enzyme can also be Lr_P450 (SEQ ID NO: 8). The P450 enzyme can also be CYPDN29 (SEQ ID NO: 114). The P450 enzyme can also be CYPDN14 (SEQ ID NO: 84). The P450 enzyme can also be P450_DN15259_c0_g1_i7 (SEQ ID NO: 3). The P450 enzyme can also beCOR_01865 (SEQ ID NO: 54). The P450 enzyme can also beP450_DN5615_c2_g1_i9 (SEQ ID NO: 62). The P450 enzyme can also beP450_DN12791_c0_g1_i1 (SEQ ID NO: 5). The P450 enzyme can also be CYPDN16 (SEQ ID NO: 88). The P450 enzyme can also be CYPDN18 (SEQ ID NO: 92). The P450 enzyme can also be CYPDN27 (SEQ ID NO: 110). The P450 enzyme can also be CYPDN35 (SEQ ID NO: 126). The P450 enzyme can also be CYPDN5 (SEQ ID NO: 66). The P450 enzyme can also be CYPDN6 (SEQ ID NO: 68). The P450 enzyme can also be CYPDN7 (SEQ ID NO: 70). The P450 enzyme can also be CYPDN10 (SEQ ID NO: 76).

The P450 enzyme can also be CYPDN11 (SEQ ID NO: 78). The P450 enzyme can also be CYPDN24 (SEQ ID NO: 104). The P450 enzyme can also be CYPDN28 (SEQ ID NO: 112). The P450 enzyme can also be CYPDN13 (SEQ ID NO: 82). The P450 enzyme can also be CYPDN31 (SEQ ID NO: 118). The P450 enzyme can also be CYPDN34 (SEQ ID NO: 124). The P450 enzyme can also be CYPDN22 (SEQ ID NO: 100). The P450 enzyme can also be CYPDN21 (SEQ ID NO: 98). The P450 enzyme can also be CYPDN30 (SEQ ID NO: 116). The P450 enzyme can also be ArORZ22410 (SEQ ID NO: 58). The P450 enzyme can also be YPDN20 (SEQ ID NO: 96), The P450 enzyme can also be CYPDN17 (SEQ ID NO: 90). The P450 enzyme can also be (SEQ ID NO: 72).

The fungal Mucorales cytochrome P450 enzyme selected from the group consisting of: i) CYPDN8 (SEQ ID NO: 72), ii) Mc_S23T25 (SEQ ID NO: 52), iii) CYPDN17 (SEQ ID NO: 90), iv) CYPDN12 (SEQ ID NO: 80), v) Lr_P450 (SEQ ID NO: 8), vi) CYPDN29 (SEQ ID NO: 114), vii) CYPDN14 (SEQ ID NO: 84), vii) P450_DN15259_c0_g1_i7 (SEQ ID NO: 3), ix) LCOR_01865 (SEQ ID NO: 54), x) P450_DN5615_c2_g1_i9 (SEQ ID NO: 62), xi) P450_DN12791_c0_g1_i1 (SEQ ID NO: 5), xii) CYPDN16 (SEQ ID NO: 88), xiii) CYPDN18 (SEQ ID NO: 92), xiv) CYPDN27 (SEQ ID NO: 110), xv) CYPDN35 (SEQ ID NO: 126), xvi) CYPDN5 (SEQ ID NO: 66), xvii) CYPDN6 (SEQ ID NO: 68), xviii) CYPDN7 (SEQ ID NO: 70), xix) CYPDN10 (SEQ ID NO: 76), xx) CYPDN11 (SEQ ID NO: 78), xxi) CYPDN24 (SEQ ID NO: 104), xxii) CYPDN28 (SEQ ID NO: 112), xxiii) CYPDN13 (SEQ ID NO: 82), xxiv) CYPDN31 (SEQ ID NO: 118), xxv) CYPDN34 (SEQ ID NO: 124), xxvi) CYPDN22 (SEQ ID NO: 100), xxvii) CYPDN21 (SEQ ID NO: 98), xxviii) CYPDN30 (SEQ ID NO: 116), xxix) Ar_ORZ22410 (SEQ ID NO: 58), and xxx) CYPDN20 (SEQ ID NO: 96)

have all been tested in the examples of the present invention, and they share the N-demethylating activity on reticuline and/or derivatives hereof.

The fungal Mcorales cytochrome P450 enzyme selected from the group consisting of: xxxi) CYPDN17 (SEQ ID NO: 90), and xxxii) CYPDN8 (SEQ ID NO: 72) share the N-demethylating and O-demethylating activity on reticuline and/or derivatives hereof.

Mammalian P450 3A4 Enzymes

In another embodiment of the invention the cytochrome P450 enzyme capable of N-demethylating reticuline and derivatives thereof is a mammalian P450 3A4 enzyme or functional homologs or variants hereof.

In certain embodiments of the invention, the mammalian P450 3A4 enzyme can be one or more of P08684 (SEQ ID NO: 22), H2PLK4 (SEQ ID NO: 24), A0A096NZ89 (SEQ ID NO: 26), G3SB46 (SEQ ID NO: 28), F1PDL2 (SEQ ID NO: 30) and functional homologs or variants hereof.

The mammalian P450 3A4 enzyme can also be P08684 (SEQ ID NO: 22) or functional homologs or variants hereof. P08684 (SEQ ID NO: 22) is encoded by SEQ ID NO: 23.

The mammalian P450 3A4 enzyme can also be H2PLK4 (SEQ ID NO: 24) or functional homologs or variants hereof. H2PLK4 (SEQ ID NO: 24) is encoded by SEQ ID NO: 25.

The mammalian P450 3A4 enzyme can also be A0A096NZ89 (SEQ ID NO: 26) or functional homologs or variants hereof. A0A096NZ89 (SEQ ID NO: 26) is encoded by SEQ ID NO: 27.

The mammalian P450 3A4 enzyme can also be G3SB46 (SEQ ID NO: 28) or functional homologs or variants hereof. G3SB46 (SEQ ID NO: 28) is encoded by SEQ ID NO: 29.

The mammalian P450 3A4 enzyme can also be F1PDL2 (SEQ ID NO: 30) or functional homologs or variants hereof. F1PDL2 (SEQ ID NO: 30) is encoded by SEQ ID NO: 31.

Mammalian P450 3A5 Enzymes

In yet another embodiment of the invention the cytochrome P450 enzyme capable of N-demethylating reticuline and derivatives thereof is a mammalian P450 3A5 enzyme or functional homologs or variants hereof.

The mammalian P450 3A5 enzyme can be one or more of Cytochrome P450 3A5 (P20815) (SEQ ID NO: 40), Cytochrome P450 3A5 (A4ZZ70) (SEQ ID NO: 42), Cytochrome P450 3A5 (A8CBR0) (SEQ ID NO: 44), and Cytochrome P450 3A5 (U3ECK3) (SEQ ID NO: 46) and functional homologs or variants hereof.

The mammalian P450 3A5 enzyme can also be Cytochrome P450 3A5 (P20815) (SEQ ID NO: 40) or functional homologs or variants hereof. Cytochrome P450 3A5 (P20815) (SEQ ID NO: 40) is encoded by SEQ ID NO: 41.

The mammalian P450 3A5 enzyme can also be Cytochrome P450 3A5 (A4ZZ70) (SEQ ID NO: 42) or functional homologs or variants hereof. Cytochrome P450 3A5 (A4ZZ70) (SEQ ID NO: 42) is encoded by SEQ ID NO: 43.

The mammalian P450 3A5 enzyme can also be Cytochrome P450 3A5 (A8CBR0) (SEQ ID NO: 44) or functional homologs or variants hereof Cytochrome P450 3A5 (A8CBR0) (SEQ ID NO: 44) is encoded by SEQ ID NO: 45.

The mammalian P450 3A5 enzyme can also be Cytochrome P450 3A5 (U3ECK3) (SEQ ID NO: 46) or functional homologs or variants hereof. Cytochrome P450 3A5 (U3ECK3) (SEQ ID NO: 46) is encoded by SEQ ID NO: 47.

Mammalian P450 2C8 Enzymes.

In another embodiment of the invention the cytochrome P450 enzyme capable of N-demethylating reticuline and derivatives thereof is a mammalian P450 2C8 enzyme.

The mammalian P450 2C8 enzyme can be one or more of P10632 (SEQ ID NO: 32), H2Q2B (SEQ ID NO: 34), H2NB34 (SEQ ID NO: 36), and Q4U0S8 (SEQ ID NO: 38) and functional homologs or variants hereof.

The mammalian P450 2C8 enzyme can also be P10632 (SEQ ID NO: 32) or functional homologs or variants hereof. P10632 (SEQ ID NO: 32) is encoded by SEQ ID NO: 33.

The mammalian P450 2C8 enzyme can also be H2Q2B (SEQ ID NO: 34) or functional homologs or variants hereof. H2Q2B (SEQ ID NO: 34) is encoded by SEQ ID NO: 35.

The mammalian P450 2C8 enzyme can also be H2NB34 (SEQ ID NO: 36) or functional homologs or variants hereof. H2NB34 (SEQ ID NO: 36) is encoded by SEQ ID NO: 37.

The mammalian P450 2C8 enzyme can also be Q4U0S8 (SEQ ID NO: 38) or functional homologs or variants hereof. Q4U0S8 (SEQ ID NO: 38) is encoded by SEQ ID NO: 39.

Cytochrome P450 Reductases

The recombinant host cell can further express one or more cytochrome P450 reductase(s) (CPR(s)).

The cytochrome P450 reductase(s) can originate from a fungal or mammalian organism. The organism can be one or more of *Mucor piriformis, Thamnostylum piriforme, Cunninghamella elegans, Gibberella fujikuroi, Saccharomyces cerevisiae, Homo sapiens, Pongo abelii, Papio anubis, Gorilla gorilla gorilla, Canis lupus familiaris, Pan troglodytes, Callithrix jacchus, Macaca fascicularis* and *Chlorocebus aethiops*

The cytochrome P450 enzyme capable of N-demethylating reticuline and derivatives thereof can also originate from an organism that is *Thamnostylum piriforme, Lichtheimia ramosa, Cunninghamella echinulata, Cunninghamella dalmatica, Cunninghamella polymorpha* and *Rhizopus nigricans*.

The cytochrome P450 reductase can originate from a fungal organism. The organism can be one or more of *Thamnostylum piriforme, Lichtheimia ramosa, Cunninghamella echinulata, Cunninghamella dalmatica, Cunninghamella polymorpha, Rhizopus nigricans, Gibberella fujikuroi,* and *Saccharomyces cerevisiae*.

The cytochrome P450 reductase can originate from a mammalian organism. The organism can be *Homo sapiens*.

The cytochrome P450 reductase can be one or more of CPR_DN2505_c0_g1_i1 (SEQ ID NO: 15), CPR_DN5866_c0_g1_i1 (SEQ ID NO: 9), CPR_DN10898_c0_g1_i1 (SEQ ID NO: 12), NADPH-dependent cytochrome P450 oxidoreductase (AAF89958) (SEQ ID NO: 16), Cytochrome P450 oxidoreductase (Q7Z8R1) (SEQ ID NO: 18), NADPH-cytochrome P450 reductase (P16603) (SEQ ID NO: 20), NADPH-cytochrome P450 reductase (BAB18572.1) (SEQ ID NO: 50), and Cytochrome b5 isoform 1 (NP_683725) (SEQ ID NO: 48) or functional homologs or variants hereof.

The cytochrome P450 reductase can also be CPR_DN2505_c0_g1_i1 (SEQ ID NO: 15) or functional homologs or variants hereof.

The cytochrome P450 reductase can also be CPR_DN5866_c0_g1_i1 (SEQ ID NO: 9) or functional homologs or variants hereof. CPR_DN5866_c0_g1_i1 is encoded by SEQ ID NO: 10 and the sequence optimized for *S. cerevisiae* is SEQ ID NO: 11.

The cytochrome P450 reductase can also be CPR_DN10898_c0_g1_i1 (SEQ ID NO: 12) or functional homologs or variants hereof. CPR_DN10898_c0_g1_i1 (SEQ ID NO: 12) is encoded by SEQ ID NO: 13 and the sequence optimized for *S. cerevisiae* is SEQ ID NO: 14.

The cytochrome P450 reductase can also be NADPH-dependent cytochrome P450 oxidoreductase (AAF89958) (SEQ ID NO: 16) or functional homologs or variants hereof. The NADPH-dependent cytochrome P450 oxidoreductase (AAF89958) (SEQ ID NO: 16) sequence optimized for *S. cerevisiae* is encoded by SEQ ID NO: 17.

The cytochrome P450 reductase can also be NADPH-cytochrome P450 reductase (P16603) (SEQ ID NO: 20) or functional homologs or variants hereof. NADPH-cytochrome P450 reductase (P16603) (SEQ ID NO: 20) is encoded by SEQ ID NO: 21.

The cytochrome P450 reductase can also be NADPH-cytochrome P450 reductase (BAB18572.1) (SEQ ID NO: 50) or functional homologs or variants hereof. NADPH-cytochrome P450 reductase (BAB18572.1) (SEQ ID NO: 50) is encoded by SEQ ID NO: 51.

The cytochrome P450 reductase can also be Cytochrome b5 isoform 1 (NP_683725) (SEQ ID NO: 48) or functional homologs or variants hereof. NADPH-cytochrome P450 reductase (BAB18572.1) (SEQ ID NO: 48) is encoded by SEQ ID NO: 49.

Combinations of Cytochrome P450 Enzymes and CPRs

Specific combinations of P450 enzyme capable of N-demethylating reticuline and derivatives thereof and cytochrome P450 reductase(s) (CPR(s)) have been experimentally shown to have advantageous effects in the examples of the present disclosure.

In an embodiment of the invention is the cytochrome P450 enzyme capable of N-demethylating reticuline and derivatives thereof P450_DN15259_c0_g1_i7 (SEQ ID NO: 3) and the cytochrome P450 reductase is one or more of AAF89958 (SEQ ID NO: 17), Q7Z8R1 (SEQ ID NO: 19) and P16603 (SEQ ID NO: 21).

In an embodiment of the invention is the cytochrome P450 enzyme capable of N-demethylating reticuline and derivatives thereof P450_DN15259_c0_g1_i7 (SEQ ID NO: 3) and the cytochrome P450 reductase is AAF89958 (SEQ ID NO: 17).

In an embodiment of the invention is the cytochrome P450 reductase CPR_DN5866_c0_g1_i1 (SEQ ID NO: 9) and/or CPR_DN10898_c0_g1_i1 (SEQ ID NO: 12).

In one embodiment of the invention is the cytochrome P450 reductase POR1 (SEQ ID NO: 131 and 132).

The reductases that are added to the P450 enzyme can be one or more of the reductases discloses herein.

In an embodiment of the invention is the P450 enzyme capable of N-demethylating reticuline and derivatives thereof P450_DN15259_c0_g1_i7 (SEQ ID NO: 3) and the cytochrome P450 reductase is CPR_DN10898_c0_g1_i1 (SEQ ID NO: 14) and/or Q7Z8R1 (SEQ ID NO: 19).

In an embodiment of the invention is the cytochrome P450 enzyme capable of N-demethylating reticuline and derivatives thereof P450_DN15259_c0_g1_i7 (SEQ ID NO: 3) and the cytochrome P450 reductase is Q7Z8R1 (SEQ ID NO: 19).

In an embodiment of the invention is the cytochrome P450 enzyme capable of N-demethylating reticuline and derivatives thereof is P450_DN15259_c0_g1_i7 (SEQ ID NO: 3) and the cytochrome P450 reductase CPR_DN5866_c0_g1_i1 (SEQ ID NO: 9) and/or CPR_DN10898_c0_g1_i1 (SEQ ID NO: 12).

In an embodiment of the invention is the derivative salutaridine and the cytochrome P450 enzyme is a P450 2C8 enzyme.

In an embodiment of the invention is the derivative salutaridine and the cytochrome P450 enzyme is one or more of P10632 (SEQ ID NO: 23), H2Q2B (SEQ ID NO: 25), H2NB34 (SEQ ID NO: 27), Q4U0S8 (SEQ ID NO: 39).

In an embodiment of the invention is the derivative salutaridinol and the cytochrome P450 enzyme is a P450 2C8 enzyme.

In an embodiment of the invention is the derivative salutaridinol and the cytochrome P450 enzyme is one or more of P10632 (SEQ ID NO: 33), H2Q2B (SEQ ID NO: 35), H2NB34 (SEQ ID NO: 37), and Q4U0S8 (SEQ ID NO: 39).

In an embodiment of the invention is the compound thebaine and the cytochrome P450 enzyme is a P450 34A enzyme.

In an embodiment of the invention is the compound thebaine and the cytochrome P450 enzyme is A4ZZ70 (SEQ ID NO: 43).

In an embodiment of the invention is the derivative oripavine and the cytochrome P450 enzyme is a P450 2C8 enzyme.

In an embodiment of the invention is the derivative oripavine and the cytochrome P450 enzyme is Q4U0S8 (SEQ ID NO: 39).

In an embodiment of the invention is the derivative morphine and the cytochrome P450 enzyme is a P450 2C8 enzyme or a P450 3A4 enzyme.

In an embodiment of the invention is the derivative morphine and the cytochrome P450 enzyme is one or more of P20815 (SEQ ID NO: 41), A4ZZ70 (SEQ ID NO: 43), P10632 (SEQ ID NO: 33), H2Q2B (SEQ ID NO: 35), H2NB34 (SEQ ID NO: 37), and Q4U0S8 (SEQ ID NO: 39).

In an embodiment of the invention is the compound thebaine and the cytochrome P450 enzyme is a P450 3A4 enzyme.

In an embodiment of the invention is the compound thebaine and the cytochrome P450 enzyme is A0A096NZ89 (SEQ ID NO: 27).

Functional Homologs and Genetic Variation

Functional homologs of the polypeptides described above are also suitable for use in producing the compounds mentioned herein in a recombinant host. A functional homolog is a polypeptide that has sequence similarity to a reference polypeptide, and that carries out one or more of the biochemical or physiological function(s) of the reference polypeptide.

A functional homolog and the reference polypeptide can be natural occurring polypeptides, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping").

Techniques for modifying genes encoding functional the polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide: polypeptide interactions in a desired manner.

Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of polypeptides described herein.

Sequence analysis can involve BLAST, Reciprocal BLAST, or PSI-BLAST analysis of nonredundant databases using the amino acid sequence of interest as the reference sequence. Amino acid sequence is, in some instances, deduced from the nucleotide sequence. Those polypeptides in the database that have greater than 40% sequence identity are candidates for further evaluation for suitability as polypeptide useful in the synthesis of compounds described herein. Amino acid sequence similarity allows for conservative amino acid substitutions, such as substitution of one hydrophobic residue for another or substitution of one polar residue for another. When desired, manual inspection of such candidates can be carried out in order to narrow the number of candidates to be further evaluated. Manual inspection can be performed by selecting those candidates that appear to have conserved functional domains.

Conserved regions can be identified by locating a region within the primary amino acid sequence of a polypeptide described herein that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/

Software/Pfam/and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some aspects, alignment of sequences from two different species can be adequate.

Typically, polypeptides that exhibit at least about 20% amino acid sequence identity are useful to identify conserved regions. Conserved regions of related polypeptides exhibit at least 25% amino acid sequence identity e.g., at least 30%, at least 40%, at least 55%, at least 50%, at least 60%, at least 70%, at least 80%, or at least 90% amino acid sequence identity. In some aspects, a conserved region exhibits at least 92%, 94%, 96%, 98%, or 99% amino acid sequence identity. The conserved region can be considered to be the entire protein or nucleic acid sequence.

An aspect of the invention relates to a functional homologue that has at least 20% sequence identity with an amino acid or nucleic acid sequence mentioned herein, such as 30% sequence identity, such as 40% sequence identity, such as 50% sequence identity, such as 60% sequence identity, such as 70% sequence identity, such as 75% sequence identity, such as 80% sequence identity, such as 85% sequence identity, such as 90% sequence identity, such as 75% sequence identity, such as 97% sequence identity, such as 98% sequence identity, such as 99% sequence identity.

In an embodiment relates to a functional homolog that has at least 30% sequence identity with an amino acid or nucleic acid sequence mentioned herein. In an embodiment relates to a functional homolog that has at least 40% sequence identity with an amino acid or nucleic acid sequence mentioned herein. In an embodiment relates to a functional homolog that has at least 50% sequence identity with an amino acid or nucleic acid sequence mentioned herein. In an embodiment relates to a functional homolog that has at least 60% sequence identity with an amino acid or nucleic acid sequence mentioned herein. In an embodiment relates to a functional homolog that has at least 70% sequence identity with an amino acid or nucleic acid sequence mentioned herein. In an embodiment relates to a functional homolog that has at least 80% sequence identity with an amino acid or nucleic acid sequence mentioned herein. In an embodiment relates to a functional homolog that has at least 90% sequence identity with an amino acid or nucleic acid sequence mentioned herein. In an embodiment relates to a functional homolog that has at least 95% sequence identity with an amino acid or nucleic acid sequence mentioned herein.

The functional homolog can have an equal or better function compared to the patent enzyme. Thus, functional variants of the cytochrome P450 enzyme capable of N-demethylating reticuline and derivatives thereof can be measured for effect by any of the methods mentioned herein. The effect can therefore be the ability to N-demethylate.

The cytochrome P450 enzyme capable of N-demethylating reticuline and derivatives thereof can be one or more of P450_DN15259_c0_g1_i7 (SEQ ID NO: 3), P450_DN12791_c0_g1_i1 (SEQ ID NO: 6), A0A077WEM0 (SEQ ID NO: 8), P08684 (SEQ ID NO: 23), H2PLK4 (SEQ ID NO: 25), A0A096NZ89 (SEQ ID NO: 27), G3SB46 (SEQ ID NO: 29), F1PDL2 (SEQ ID NO: 31), P20815 (SEQ ID NO: 41), A4ZZ70 (SEQ ID NO: 43), A8CBR0 (SEQ ID NO: 45), U3ECK3 (SEQ ID NO: 47), P10632 (SEQ ID NO: 33), H2Q2B (SEQ ID NO: 35), H2NB34 (SEQ ID NO: 37), Q4U0S8 (SEQ ID NO: 39).

The cytochrome P450 enzyme capable of N-demethylating reticuline and derivatives thereof can have at least 20% sequence identity with P450_DN15259_c0_g1_i7 (SEQ ID NO: 3), such as 30% sequence identity, such as 40% sequence identity, such as 50% sequence identity, such as 60% sequence identity, such as 70% sequence identity, such as 75% sequence identity, such as 80% sequence identity, such as 85% sequence identity, such as 90% sequence identity, such as 95% sequence identity, such as 97% sequence identity, such as 98% sequence identity, such as 99% sequence identity.

The cytochrome P450 enzyme capable of N-demethylating reticuline and derivatives thereof can have at least 40% sequence identity with P450_DN15259_c0_g1_i7 (SEQ ID NO: 3). The 40% sequence identity can also be with SEQ ID NO: 1 or SEQ ID NO: 2.

The cytochrome P450 enzyme capable of N-demethylating reticuline and derivatives thereof can have at least 50% sequence identity with P450_DN15259_c0_g1_i7 (SEQ ID NO: 3). The 50% sequence identity can also be with SEQ ID NO: 1 or SEQ ID NO: 2.

The cytochrome P450 enzyme capable of N-demethylating reticuline and derivatives thereof can have at least 60% sequence identity with P450_DN15259_c0_g1_i7 (SEQ ID NO: 3). The 60% sequence identity can also be with SEQ ID NO: 1 or SEQ ID NO: 2.

The cytochrome P450 enzyme capable of N-demethylating reticuline and derivatives thereof can have at least 70% sequence identity with P450_DN15259_c0_g1_i7 (SEQ ID NO: 3). The 70% sequence identity can also be with SEQ ID NO: 1 or SEQ ID NO: 2.

The cytochrome P450 enzyme capable of N-demethylating reticuline and derivatives thereof can have at least 80% sequence identity with P450_DN15259_c0_g1_i7 (SEQ ID NO: 3). The 80% sequence identity can also be with SEQ ID NO: 1 or SEQ ID NO: 2.

The cytochrome P450 enzyme capable of N-demethylating reticuline and derivatives thereof can have at least 90% sequence identity with P450_DN15259_c0_g1_i7 (SEQ ID NO: 3). The 90% sequence identity can also be with SEQ ID NO: 1 or SEQ ID NO: 2.

The cytochrome P450 enzyme capable of N-demethylating reticuline and derivatives thereof can have at least 95% sequence identity with P450_DN15259_c0_g1_i7 (SEQ ID NO: 3). The 95% sequence identity can also be with SEQ ID NO: 1 or SEQ ID NO: 2.

The cytochrome P450 enzyme capable of N-demethylating reticuline and derivatives thereof can have at least 98% sequence identity with P450_DN15259_c0_g1_i7 (SEQ ID NO: 3). The 98% sequence identity can also be with SEQ ID NO: 1 or SEQ ID NO: 2.

The cytochrome P450 enzyme capable of N-demethylating reticuline and derivatives thereof can have at least 99% sequence identity with P450_DN15259_c0_g1_i7 (SEQ ID NO: 3). The 99% sequence identity can also be with SEQ ID NO: 1 or SEQ ID NO: 2.

The Mucorales cytochrome P450 enzyme capable of N-demethylating reticuline and derivatives thereof can have at least 99% sequence identity with CYPDN8 (SEQ ID NO: 72. The 99% sequence identity can also be with SEQ ID NO: 72 or SEQ ID NO: 73. The sequence identity can also be at least 95%. The sequence identity can also be at least 90%. The sequence identity can also be at least 80%. The sequence identity can also be at least 70%. The sequence identity can also be at least 60%.

The fungal Mucorales cytochrome P450 enzyme capable of N-demethylating and/or 0-demethylating reticuline and/or derivatives thereof can have at least 50% sequence identity with any of the sequences selected from i) CYPDN8 (SEQ ID NO: 72), ii) Mc_S2JT125 (SEQ ID NO: 52), iii) CYPDN17 (SEQ ID NO: 90), iv) CYPDN12 (SEQ ID NO: 80), v) Lr_P450 (SEQ ID NO: 8), vi) CYPDN29 (SEQ ID NO: 114), vii) CYPDN14 (SEQ ID NO: 84), vii) P450_DN15259_c0_g1_i7 (SEQ ID NO: 3), ix) LCOR_01865 (SEQ ID NO: 54), x) P450_DN5615_c2_g1_i9 (SEQ ID NO: 62), xi) P450_DN12791_c0_g1_i1 (SEQ ID NO: 5), xii) CYPDN16 (SEQ ID NO: 88), xiii) CYPDN18 (SEQ ID NO: 92), xiv) CYPDN27 (SEQ ID NO: 110), xv) CYPDN35 (SEQ ID NO: 126), xvi) CYPDN5 (SEQ ID NO: 66), xvii) CYPDN6 (SEQ ID NO: 68), xviii) CYPDN7 (SEQ ID NO: 70), xix) CYPDN10 (SEQ ID NO: 76), xx) CYPDN11 (SEQ ID NO: 78), xxi) CYPDN24 (SEQ ID NO: 104), xxii) CYPDN28 (SEQ ID NO: 112), xxiii) CYPDN13 (SEQ ID NO: 82), xxiv) CYPDN31 (SEQ ID NO: 118), xxv) CYPDN34 (SEQ ID NO: 124), xxvi) CYPDN22 (SEQ ID NO: 100), xxvii) CYPDN21 (SEQ ID NO: 98), xxviii) CYPDN30 (SEQ ID NO: 116), xxix) Ar_ORZ22410 (SEQ ID NO: 58), xxx) CYPDN20 (SEQ ID NO: 96), xxxi) CYPDN17 (SEQ ID NO: 90), and xxxii) CYPDN8 (SEQ ID NO: 72).

such as 30% sequence identity, such as 40% sequence identity, such as 50% sequence identity, such as 60% sequence identity, such as 70% sequence identity, such as 75% sequence identity, such as 80% sequence identity, such as 85% sequence identity, such as 90% sequence identity, such as 95% sequence identity, such as 97% sequence identity, such as 98% sequence identity, such as 99% sequence identity.

The sequence identify of any one of the sequences of the present invention can be at least 50% to any one of the sequences disclosed herein. The sequence identity can also be at least 95%. The sequence identity can also be at least 90%. The sequence identity can also be at least 80%. The sequence identity can also be at least 70%. The sequence identity can also be at least 60%.

A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). See Chenna et al., Nucleic Acids Res., 31 (13):3497-500 (2003).

ClustalW calculates the best match between a reference and one or more candidate sequences, and aligns them so that identities, similarities, and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gin, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that polypeptides described herein can include additional amino acids that are not involved in other enzymatic activities carried out by the enzyme, and thus such a polypeptide can be longer than would otherwise be the case. For example, a polypeptide can include a purification tag (e.g., HIS tag or GST tag), a chloroplast transit peptide, a mitochondrial transit peptide, an amyloplast peptide, signal peptide, or a secretion tag added to the amino or carboxy terminus. In some aspects, a polypeptide includes an amino acid sequence that functions as a reporter, e.g., a green fluorescent protein or yellow fluorescent protein.

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In some aspects, the coding sequence for a polypeptide described herein is identified in a species other than the recombinant host, i.e., is a heterologous gene.

Thus, if the recombinant host is a microorganism, the coding sequence can be from other prokaryotic or eukaryotic microorganisms, from plants or from animals. In some cases, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant gene construct. In addition, stably transformed exogenous genes typically are integrated at positions other than the position where the native sequence is found.

As disclosed herein, a "regulatory region" (prokaryotic and eukaryotic) refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof.

A regulatory region typically comprises at least a core (basal) promoter. A regulatory region also can include at least one control element, such as an enhancer sequence, an upstream element, or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one skilled in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

One or more genes can be combined in a recombinant nucleic acid construct in "modules" useful for a discrete aspect of production of a compound described herein. Combining a plurality of genes in a module, particularly a polycistronic module, facilitates the use of the module in a variety of species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

Host Cells and Cultivation

At least one of the genes mentioned herein can be a recombinant gene, the particular recombinant gene(s) depending on the species or strain selected for use. Additional genes or biosynthetic modules can be included in order to increase compound yield, improve efficiency with which energy and carbon sources are used to produce the target compounds mentioned herein, and/or to enhance productivity from the cell culture or plant.

The cytochrome P450 reductase can originate from an organism that is *Thamnostylum piriforme, Cunninghamella elegans, Lichtheimia ramosa, Gibberella fujikuroi, Saccharomyces cerevisiae, Mucor piriformis, Aspergillus* sp., *Homo sapiens, Pongo abelii, Papio anubis, Gorilla gorilla gorilla, Canis lupus familiaris, Pan troglodytes, Callithrix jacchus, Macaca fascicuiaris* or *Chlorocebus aethiops*.

The cytochrome P450 enzyme capable of N-demethylating reticuline and derivatives thereof can also originate from an organism that is *Thamnostylum piriforme, Lichtheimia ramosa, Cunninghamella echinulata, Cunninghamella dalmatica, Cunninghamella polymorpha, Rhizopus nigricans, Gibberella fujikuroi,* or *Saccharomyces cerevisiae.*

In certain aspects of this invention, the recombinant host comprises a yeast cell, a plant cell, a mammalian cell, an insect cell, a fungal cell, an algal cell, a cyanobacteria or a bacterial cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., or *Rhodospiridium* sp.

In some aspects, the yeast cell is a Saccharomycete.

In some aspects, the yeast cell is a *Saccharomyces cerevisiae* cell.

In some aspects, the algal cell is a cell from *Blakeslea trispora, Dunaliella salina, Haematococcus pluvialis, Chlorella* sp., *Undaria pinnatifida, Sargassum, Laminaria japonica, Scenedesmus almeriensis* species.

In some aspects, the cyanobacerial cell is a cell from *Phormidium laminosum, Microcystis* sp., *Synechococcus* sp., *Pantoea* sp., *Flavobacterium* sp.

In certain aspects of this invention, the recombinant host cell is a plant cell, a filamentous fungus, or a yeast cell. The host cell can also be a fungus cell.

In some aspects, the cell is a plant cell. The plant cell can be a *Papaver* sp. (e.g. *Papaver somniferum* or *Papaver bracteatum* cells), *Nicotiana* sp. (e.g. *Nicotiana benthamiana* cells), *Arabidopsis* sp., *Physcomitrella* sp., *Thalictrum* sp. (e.g. *Thalictrum flavum*), *Coptis* sp. (e.g. *Coptis japonica*), *Lindera* sp. (*Lindera aggregate*), *Annona* sp. (e.g. *Annona squamosa* or *Annona muricata*), *Ocotea* sp. (e.g. *Ocotea fasciculate*), *Duguetia* sp., *Sinomenium* sp., *Berberis* sp., *Corydalis* sp., *Ceratocapnos palaestinus, Anomianthus dulcis, Dicentra spectabilis, Glaucium flavum, Eschscholzia californica, Caulophyllum thalicroides, Chelidonium majus, Cocculus laurifolius, Delphinium pentagynum, Cinnamomum camphora, Clematis parviloba, Phylica rogersii, Phellodendron chinensis, Hypecoum lactiflorum, Fumaria officinalis, Croton celtidifolius, Mahonia aquifolium, Illigera parviflora, Aniba canelilla, Cryptocarya odorata, Litsea* sp., *Machilus thunbergii, Nectandra salicifolia, Neolitsea* sp., *Phoebe minutiflora, Strychnos holstii, Tinospora cordifolia,* or *Siparuna tonduziana* cell.

The recombinant host cell can be a *Nicotiana* sp. cell. In certain aspects of this invention, the *Nicotiana* sp. cell is a *Nicotiana benthamiana* cell.

In some aspects, the recombinant host cell is a *Physcomitrella* sp. cell.

In certain aspects of this invention, the recombinant host cell is a filamentous fungus cell. The filamentous fungus cell can be *Aspergillus nidulans, Aspergillus sydowii, Aspergillus terreus, Aspergillus oryzae, Aspergillus caelatus, Aspergillus chevalieri, Aspergillus longivesica, Aspergillus parvulus, Aspergillus amylovorus, Aspergillus niger, Aspergillus niger, Aspergillus aculeatus, Aspergillus ellipticus, Aspergillus violaceofuscus, Aspergillus brunneoviolaceus, Aspergillus japonicus, Aspergillus brasiliensis, Aspergillus brasiliensis, Aspergillus aculeatinus, Aspergillus thermomutatus, Aspergillus implicatus, Aspergillus acristatus, Penicillium bilaiae, Penicillium rubens, Penicillium chrysogenum, Peni-*

*cillium expansum, Penicillium antarcticum, Trichoderma reesei, Talaromyces atroroseus, Asteromyces cruciatus,* or *Neurospora crassa.*

In certain aspects of this invention, the recombinant host cell is a yeast cell comprising *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., *Schwanniomyces occidentalis, Sporidiobolus salmonicolor, Starmerella bacillaris, Sugiyamaella americana, Talaromyces atroroseus, Torulaspora delbrueckii, Trichoderma reesei, Wickerhamia fluorescens, Wickerhamiella sorbophila, Wickerhamiella versatilis, Zygosaccharomyces rouxii, Zygotorulaspora Florentina, Saccharomyces cerevisiae* var. *ellipsoideus, Saccharomyces paradoxus, Saccharomyces pastorianus, Saccharomyces uvarum, Saccharomycodes ludwigii* var. *ludwigii, Saitoella complicate, Schizosaccharomyces japonicus, Schizosaccharomyces octosporus, Asteromyces cruciatus, Aureobasidium pullulans, Candida cylindracea, Candida albicans, Cutaneotrichosporon curvatus, Cyberlindnera jadinii, Debaromyces hansenii, Dekkera bruxellensis, Diutina rugosa, Eremothecium gossypii, Galactomyces candidus, Geotrichum candidum, Geotrichum fermentans, Hanseniaspora uvarum, Hanseniaspora vineae, Issatchenkia orientalis, Kazachstania exigua, Kazachstania servazzii, Kluyveromyces lactis, Kluyveromyces marxianus, Komagataella phaffii, Lachancea thermotolerans, Lipomyces starkeyi, Moesziomyces antarcticus, Naumovozyma castellii, Naumovozyma dairenensis, Ogataea polymorpha, Ogataea thermomethanolica, Pachysolen tannophilus, Papiliotrema laurentii, Penicillium arizonense, Pichia fermentans, Rhodotorula mucilaginosa, Saccharomyces bayanus* or *Rhodospiridium* sp.

In certain aspects of this invention, microorganisms can include, but are not limited to, *S. cerevisiae* and *E. coli*. The constructed and genetically engineered microorganisms provided by the invention can be cultivated using conventional fermentation processes, including, inter alia, chemostat, batch, fed-batch cultivations, continuous perfusion fermentation, and continuous perfusion cell culture.

The constructed and genetically engineered microorganisms provided by the invention can be cultivated using conventional fermentation processes, including, inter alia, chemostat, batch, fed-batch cultivations, continuous perfusion fermentation, and continuous perfusion cell culture.

A number of prokaryotes and eukaryotes are suitable for use in constructing the recombinant microorganisms described herein, e.g., gram-negative bacteria, yeast and fungi. A species and strain selected for use as a strain for production of the compounds described herein is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species can be suitable. For example, suitable species can be *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* and *Yarrowia*. Exemplary species from such genera include *Lentinus tigrinus, Laetiporus sulphureus, Phanerochaete chrysosporium, Pichia pastoris, Physcomitrella patens, Rhodoturula glutinis 32, Rhodoturula mucilaginosa, Phaffia rhodozyma* UBV-AX, *Xanthophyllomyces dendrorhous, Fusarium fujikuroi, Gibberella fujikuroi, Candida utilis* and *Yarrowia lipolytics*. In some aspects, a microorganism can be an Ascomycete such as *Gibberella fujikuroi, Kluyveromyces lactis, Schizosaccharomyces pombe, Aspergillus niger*, or *Saccharomyces cerevisiae*.

In some aspects, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of the compounds described herein.

In other aspects, the recombinant host cell can be a plant cell, a filamentous fungus, or a yeast cell.

The recombinant host cell of the present invention can be a plant cell. For example, suitable plant species can be *Papaver*sp. (e.g. *Papaver somniferum* or *Papaver bracteatum* cells), *Nicotiana* sp. (e.g. *Nicotiana benthamiana* cells), *Arabidopsis* sp., *Physcomitrella* sp., *Thalictrum* sp. (e.g. *Thalictrum flavum*), *Coptis* sp. (e.g. *Coptis japonica*), *Lindera* sp. (*Lindera* aggregate), *Annona* sp. (e.g. *Annona squamosa* or *Annona muricata*), *Ocotea* sp. (e.g. *Ocotea fasciculate*), *Duguetia* sp., *Sinomenium* sp., *Berberis* sp., *Corydalis* sp., *Ceratocapnos palaestinus, Anomianthus dulcis, Dicentra spectabilis, Glaucium flavum, Eschscholzia californica, Caulophyllum thalicroides, Chelidonium majus, Cocculus laurifolius, Delphinium pentagynum, Cinnamomum camphora, Clematis parviloba, Phylica rogersii, Phellodendron chinensis, Hypecoum lactiflorum, Fumaria officinalis, Croton celtidifolius, Mahonia aquifolium, Illigera parviflora, Aniba canelilla, Cryptocarya odorata, Litsea* sp., *Machilus thunbergii, Nectandra salicifolia, Neolitsea* sp., *Phoebe minutiflora, Strychnos holstii, Tinospora cordifolia*, or *Siparuna tonduziana,*

In some aspects, the cell can be a *Papaver*sp. cell. The *Papaver* sp. cell can be a *Papaver somniferum* or a *Papaver bracteatum* cell.

In other aspects, the recombinant host cell can be a *Nicotiana* sp. cell. The *Nicotiana* sp. cell can be a *Nicotiana benthamiana* cell.

The recombinant host cell can also be an *Arabidopsis* sp. cell.

In some aspects, the cell can be a *Physcomitrella* sp. cell. *Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

The recombinant host cell of the present invention can be a filamentous fungus cell. For example, suitable filamentous fungus cell species can be *Aspergillus nidulans, Aspergillus sydowii, Aspergillus terreus, Aspergillus oryzae, Aspergillus caelatus, Aspergillus chevalieri, Aspergillus longivesica, Aspergillus parvulus, Aspergillus amylovorus, Aspergillus niger, Aspergillus niger, Aspergillus aculeatus, Aspergillus ellipticus, Aspergillus violaceofuscus, Aspergillus brunneoviolaceus, Aspergillus japonicus, Aspergillus brasiliensis, Aspergillus brasiliensis, Aspergillus aculeatinus, Aspergillus thermomutatus, Aspergillus implicatus, Aspergillus acristatus, Penicillium bilaiae, Penicillium rubens, Penicil-* lium chrysogenum, Penicillium expansum, Penicillium antarcticum, Trichoderma reesei, Talaromyces atroroseus, Asteromyces cruciatus, or Neurospora crassa.

The recombinant host cell of the present invention can be a yeast cell. For example, suitable yeast cell species can be Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula sp., Schwanniomyces occidentalis, Sporidiobolus salmonicolor, Starmerella bacillaris, Sugiyamaella americana, Talaromyces atroroseus, Torulaspora delbrueckii, Trichoderma reesei, Wickerhamia fluorescens, Wickerhamiella sorbophila, Wickerhamiella versatilis, Zygosaccharomyces rouxii, Zygotorulaspora Florentina, Saccharomyces cerevisiae var. ellipsoideus, Saccharomyces paradoxus, Saccharomyces pastorianus, Saccharomyces uvarum, Saccharomycodes ludwigii var. ludwigii, Saitoella complicate, Schizosaccharomyces japonicus, Schizosaccharomyces octosporus, Asteromyces cruciatus, Aureobasidium pullulans, Candida cylindracea, Candida albicans, Cutaneotrichosporon curvatus, Cyberlindnera jadinii, Debaromyces hansenii, Dekkera bruxellensis, Diutina rugosa, Eremothecium gossypii, Galactomyces candidus, Geotrichum candidum, Geotrichum fermentans, Hanseniaspora uvarum, Hanseniaspora vineae, Issatchenkia orientalis, Kazachstania exigua, Kazachstania servazzii, Kluyveromyces lactis, Kluyveromyces marxianus, Komagataella phaffii, Lachancea thermotolerans, Lipomyces starkeyi, Moesziomyces antarcticus, Naumovozyma castellii, Naumovozyma dairenensis, Ogataea polymorpha, Ogataea thermomethanolica, Pachysolen tannophilus, Papiliotrema laurentii, Penicillium arizonense, Pichia fermentans, Rhodotorula mucilaginosa, Saccharomyces bayanus or Rhodospiridium sp.

*Saccharomyces cerevisiae*

*Saccharomyces cerevisiae* is a widely used organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

The genes described herein can be expressed in yeast using any of a number of known promoters. Strains that overproduce terpenes are known and can be used to increase the amount of geranylgeranyl diphosphate available for production of the compounds described herein.

In some aspects, auxotrophic markers for cloning include, but are not limited to, HIS3, URA3, TRP1, LEU2, LYS2, ADE2, and GAL, which allow for selection of recombinant strains with an inserted gene of interest. For example, one or more of the auxotrophic markers of strains EYS583-7a (MAT alpha lys2 ADE8 his3 ura3 leu2 trpl), EFSC1772 (MAT alpha ura3 (x2) his3 leu2), EYS4853 (MATalpha his3Δ0 leu2Δ0 ura3Δ0 ho GAL2 CAT5(J91M) MIP1 (A661T) SAL1(G403L) YORWΔ22::npBIO1nt-npBIO6nt) or EVST25898 (MATalpha his3Δ0 leu2Δ0 ura3Δ0 aro3Δ:: pTEF1-ARO4(K229L)-tCYC1::pPGK1-ARO7(T266L)-tADH1::KI CAT5-91Met GAL2 ho MIP1-661Thr SAL1-1 YORWΔ22::npBIO1nt-npBIO6nt) can be used during cloning. Auxotrophic markers can be optionally removed from the yeast genome using methods not limited to Cre-Lox recombination or negative selection with 5-fluoroorotic acid (5-FOA). In other aspects, antibiotic resistance, such as kanamycin, can be used as selection marker for construction of recombinant strains.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Arxula adeninivorans (Blastobotrys adeninivorans)*

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorgamism.

*Yarrowia lipolyptica* can accumulate lipid content to approximately 40% of its dry cell weight and is a model organism for lipid accumulation and remobilization. See e.g., Nicaud, 2012, Yeast 29(10):409-18; Beopoulos et al., 2009, Biochimie 91(6):692-6; Bankar et al., 2009, Appl Microbiol Biotechnol. 84(5):847-65.

*Rhodotorula sp.*

*Rhodotorula* is unicellular, pigmented yeast. The oleaginous red yeast, *Rhodotorula glutinis*, has been shown to produce lipids and carotenoids from crude glycerol (Saenge et al., 2011, Process Biochemistry 46(1):210-8). *Rhodotorula toruloides* strains have been shown to be an efficient fed-batch fermentation system for improved biomass and lipid productivity (Li et al., 2007, Enzyme and Microbial Technology 41:312-7).

*Rhodosporidium toruloides*

*Rhodosporidium toruloides* is oleaginous yeast and useful for engineering lipid-production pathways (See e.g. Zhu et al., 2013, Nature Commun. 3:1112; Ageitos et al., 2011, Applied Microbiology and Biotechnology 90(4): 1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, Methods Mol Biol. 824:329-58; Khoury et al., 2009, Protein Sci. 18(10):2125-38.

*Hansenula polymorpha (Pichia angusta)*

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, Virol Sin. 29(6):403-9.

Kluyveromyces lactis

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, FEMS Yeast Res. 6(3):381-92.

Pichia pastoris

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al, 2014, N Biotechnol. 31 (6):532-7.

Methods for Production

The N-demethylated reticuline and derivatives thereof can be produced though methods comprising cultivation of the host cells of the invention in presence of a reticuline and derivative substrate. Thus, an aspect of the invention relates to a method of producing a N-demethylated and/or O-demethylated reticuline and/or derivatives thereof, comprising cultivating the recombinant host of the invention in a culture medium under conditions in which the one or more genes encoding the cytochrome P450 enzymes of the invention is/are expressed.

The N-demethylated compounds mentioned herein are also known as nor-compounds. N-demethylated thebaine is therefore also known as northebaine.

The reticuline and/or derivatives thereof can be one or more of (S)-reticuline, 1,2 dehydroreticuline, (R)-reticuline, salutaridine, salutaridinol, thebaine, 7-O-acetyl-salutaridinol, oripavine, neopinone, codeinone, codeine, morphinone, morphine, hydrocodone, 14-hydroxycodeinone and oxycodone.

The reticuline and/or derivatives thereof can be (S)-reticuline. The reticuline and derivatives thereof can be 1,2 dehydroreticuline. The reticuline and derivatives thereof can be (R)-reticuline. The reticuline and derivatives thereof can be salutaridine. The reticuline and derivatives thereof can be salutaridinol or 7-O-acetyl-salutaridinol. The reticuline and derivatives thereof can be thebaine. The reticuline and derivatives thereof can be oripavine. The reticuline and derivatives thereof can be neopinone. The reticuline and derivatives thereof can be codeinone. The reticuline and derivatives thereof can be codeine. The reticuline and derivatives thereof can be morphinone. The reticuline and derivatives thereof can be morphine. The reticuline and derivatives thereof can be hydrocodone. The reticuline and derivatives thereof can be 14-hydroxycodeinone. The reticuline and derivatives thereof can be oxycodone.

The method can further comprise cultivating the recombinant host of the invention in presence of reticuline or derivatives thereof in a culture medium under conditions in which the one or more genes encoding the cytochrome P450 reductase of the invention is/are expressed.

The reticuline or derivatives thereof can be added to the culture.

Another embodiment of the invention relates to an in vitro method for converting reticuline or derivatives thereof into its nor-version comprising contacting a crude cell extract, microsomal fraction or lysate of one or more host cells of the invention with reticuline or derivatives thereof to produce an N-demethylated nor-version of reticuline or derivatives thereof.

A further embodiment of the invention relates to an in vitro method for converting reticuline or derivatives thereof into its nor-version comprising purifying the one or more enzymes of the invention from a naturally producing or recombinant host and adding reticuline or derivatives thereof to a suitable reaction mixture containing NADPH or an NADPH regenerating system for N-demethylating and/or O-demethylated reticuline or derivatives thereof.

Another embodiment of the invention relates to purification of one or more of the enzymes of the current invention from a natural or a recombinant host, coupling them to a solid support and using them for N-demethylation of reticuline or derivatives thereof in presence of a suitable buffer system, an NADPH regenerating system.

An aspect of the invention relates to an in vitro method for N-demethylating and/or 0-demethylated a reticuline or a derivative thereof, comprising contacting reticuline or a derivative thereof with a recombinant P450 enzyme capable of N-demethylating reticuline or a derivative thereof.

The method can further comprise cultivating a recombinant host cell of the invention in a culture medium in presence of reticuline or a derivative thereof, under conditions in which the one or more genes encoding the cytochrome P450 enzymes is/are expressed.

The method can further comprise cultivating the recombinant host cell of the invention in a culture medium under conditions in which the one or more genes encoding the cytochrome P450 reductase is/are expressed.

An embodiment of the invention relates to a composition comprising a compound selected from the group consisting of reticuline and derivatives thereof obtainable from the methods according to the invention, and further comprising elements from a fungal fermentation broth and/or at least one fungal specific metabolite.

A further embodiment of the invention relates to a composition comprising a N-demethylated reticuline or a derivative thereof, and a recombinant P450 enzyme capable of N-demethylating thebaine or oripavine.

DNA Molecules

The enzymes mentioned herein can be encoded by a DNA molecule. Thus, an aspect of the invention relates to a DNA molecule comprising a nucleic acid encoding one or more of the recombinant genes of the invention.

The DNA molecule can be an expression vector comprising the DNA molecule according to the invention, and a promoter suitable for expression of the DNA molecule in a cell.

The DNA molecule can be introduced into a host cell using techniques that are well-known to the person skilled in the art. Thus, an embodiment of the invention relates to a host cell comprising the DNA molecule of the invention.

Chemical Synthesis of Buprenorphine

Aspects and embodiments of the disclosure related to methods of preparing buprenorphine from Compound MeO-I-H, or HO-I-H (as defined below) provide improved routes to buprenorphine that can be shorter, more efficient, and/or produce less toxic waste than, e.g., current commercial routes to buprenorphine. As a result, these aspects and embodiments can be well-suited for commercial (e.g., kg-scale) production of buprenorphine. Further, in certain aspects and embodiments, the synthetic routes disclosed herein advantageously avoid the harsh conditions and/or toxic byproducts of an N-demethylation step and can accordingly be particularly well-suited for producing buprenorphine on a commercial, e.g., kg, scale.

An aspect of the present invention relates to a method of preparing buprenorphine, or a salt thereof, from Compound HO-I-H, or a salt thereof, comprising contacting thebaine and/or oripavine with the recombinant host of the present invention to produce the Compound MeO-I-H or the Compound HO-I-H, and prepare buprenorphine by any one or more of the below chemical synthesis pathways.

The disclosure relates to methods for preparing buprenorphine:

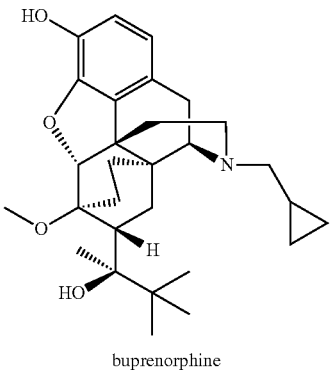 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

buprenorphine

In various aspects and embodiments, the methods comprise a series of reaction steps to prepare buprenorphine from a compound of Formula I-H:

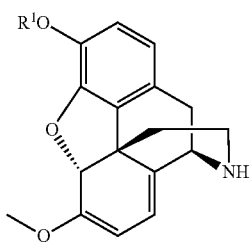

Formula I-H wherein $R^1$ is H (Compound HO-I-H; nororipavine), methyl (Compound MeO-I-H; northebaine). In certain embodiments, the compound of Formula I-H (e.g., nororipavine or northebaine) is produced by a method as otherwise described herein (e.g., a method comprising cultivating a recombinant host in a culture medium under conditions in which one or more genes encoding cytochrome P450 enzymes is/are expressed). Such methods provide an improved route to buprenorphine that can be shorter, more efficient, and/or produce less toxic waste than, e.g., current commercial routes to buprenorphine. As a result, these aspects and embodiments can be well-suited for commercial (e.g., kg-scale) production of buprenorphine. Further, such methods advantageously avoid the harsh conditions and/or toxic byproducts of an N-demethylation step and can accordingly be particularly well-suited for producing buprenorphine on a commercial, e.g., kg, scale.

As used herein, the term "benzyl" ("Bn") includes unsubstituted (i.e., $(C_6H_5)$—$CH_2$—) and substituted benzyl (i.e., benzyl substituted at the 2-, 3-, and/or 4-position with $C_1$-$C_8$ alkyl or halide). The person of ordinary skill in the art will appreciate that oxygen protecting groups include alkoxycarbonyl, acyl, acetal, ether, ester, silyl ether, alkylsulfonyl, and arylsulfonyl. Exemplary oxygen protecting groups include allyl, triphenylmethyl (trityl or Tr), benzyl, methanesulfonyl, p-toluenesulfonyl, p-methoxybenzyl (PMB), p-methoxyphenyl (PMP), methoxymethyl (MOM), p-methoxyethoxymethyl (MEM), tetrahydropyranyl (THP), ethoxyethyl (EE), methylthiomethyl (MTM), 2-methoxy-2-propyl (MOP), 2-trimethylsilylethoxymethyl (SEM), benzoate (BZ), allyl carbonate, 2.2.2-trichloroethyl carbonate (Troc), 2-trimethylsilylethyl carbonate, trimethylsilyl (TMS), triethylsilyl (TES), triisopropylsilyl (TIPS), triphenylsilyl (TPS), t-butyldimethylsilyl (TBDMS), and t-butyldiphenylsilyl (TBDPS). A variety of protecting groups for the oxygen and the synthesis thereof can be found in "Protective Groups in Organic Synthesis" by T. W. Greene and P. G. M. Wuts, John Wiley & Sons, 1999. In certain embodiments, an appropriate oxygen protecting group can be used in place of benzyl.

In some embodiments, the methods comprise reacting a compound of Formula I-H with cyclopropane carboxaldehyde followed by a hydride source; or reacting a compound of Formula I-H with cyclopropanecarboxylic acid halide followed by a reducing agent; or reacting a compound of Formula I-H with cyclopropylmethyl halide or activated cyclopropane methanol; to provide a compound of Formula I-MCP:

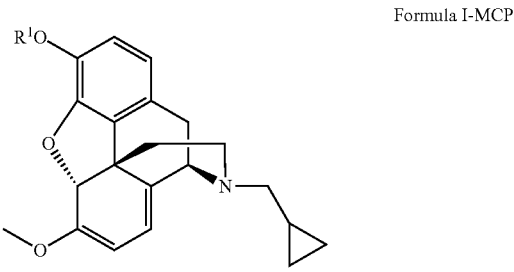

Formula I-MCP wherein $R^1$ is H (Compound HO-I-MCP), methyl (Compound MeO-I-MCP), In some embodiments, the methods comprise reacting a compound of Formula I-H with benzyl halide, benzyl sulfonate, or activated benzyl alcohol to provide a compound of Formula I-Bn:

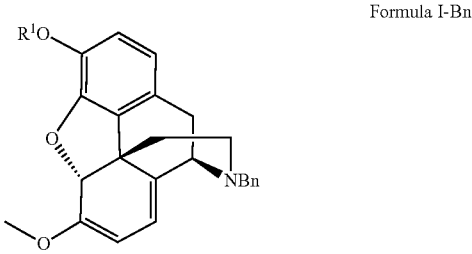

Formula I-Bn wherein $R^1$ is benzyl (Compound BnO-I-Bn). A preparation of Compound BnO-I-Bn, as an intermediate towards noroxymorphone and ultimately towards naltrexone and naloxone, was described in Helv. Chim. Acta 92:1359-65 (2009).

In some embodiments, the methods comprise reacting a compound of Formula I-H with acyl halide to provide a compound of Formula I-Ac:

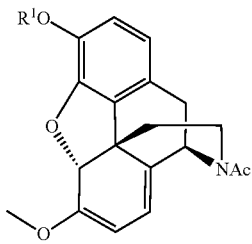

Formula I-Ac wherein $R^1$ is H (Compound HO-I-Ac), benzyl (Compound BnO-I-Ac), or acyl (Compound AcO-I-Ac).

As used herein, the term "acyl" includes $C_1$-$C_8$ aliphatic acyl groups (e.g., acetyl, ethanoyl, cyclopropanecarbonyl, etc.) and optionally substituted $C_6$-$C_{13}$ aromatic acyl groups (e.g., optionally substituted benzoyl ("Bz"), e.g., benzoyl, 4-methylbenzoyl, 4-fluorobenzoyl, etc.). For example, in certain embodiments, the methods comprise reacting a compound of Formula I-H with benzoyl chloride to provide a compound of Formula I-Ac.

In some embodiments, the methods comprise reacting a compound of Formula I-Ac (e.g., Compound HO-I-Ac) with benzyl halide, benzyl sulfonate, or activated benzyl alcohol to provide another compound of Formula I-Ac (e.g., Compound BnO-I-Ac).

In some embodiments, the methods comprise reacting a compound of Formula I-Ac (e.g., Compound AcO-I-Ac) with lithium aluminum hydride (LAH) to provide a compound of Formula I-Bn (e.g., Compound BnO-I-Bn).

In some embodiments, the methods comprise reacting a compound of Formula I-MCP (e.g., Compound HO-I-MCP) with benzyl halide, benzyl sulfonate, or activated benzyl alcohol to provide another compound of Formula I-MCP (e.g., Compound BnO-I-MCP).

In some embodiments, the methods comprise reacting a compound of Formula I-MCP with methyl vinyl ketone to provide a compound of Formula II-MCP:

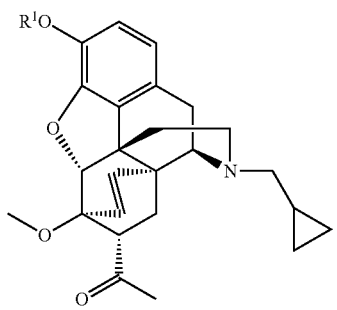

Formula II-MCP wherein $R^1$ is H (Compound HO-II-MCP), methyl (Compound MeO-II-MCP), or benzyl (Compound BnO-II-MCP).

In some embodiments, the methods comprise reacting a compound of Formula I-Bn with methyl vinyl ketone to provide a compound of Formula II-Bn:

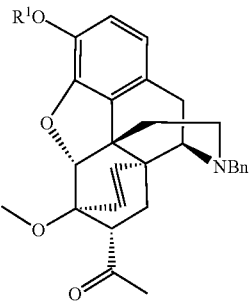

Formula II-Bn wherein $R^1$ is benzyl (Compound BnO-II-Bn).

In some embodiments, the methods comprise reacting a compound of Formula II-MCP (e.g., Compound HO-II-MCP) with benzyl halide, benzyl sulfonate, or activated benzyl alcohol to provide another compound of Formula II-MCP (e.g., Compound BnO-II-MCP).

In some embodiments, the methods comprise reacting a compound of Formula I-Ac with methyl vinyl ketone to provide a compound of Formula II-Ac:

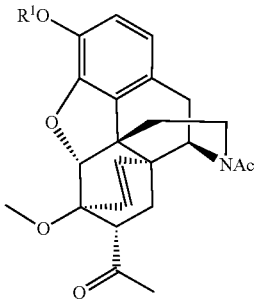

Formula II-Ac wherein $R^1$ is acyl (Compound AcO-II-Ac).

In some embodiments, the methods comprise reacting a compound of Formula II-MCP with $H_2$ in the presence of a hydrogenation catalyst to provide a compound of Formula IIIB-MCP:

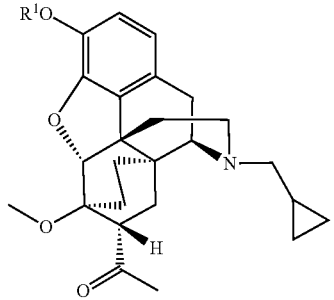

Formula IIIB-MCP wherein $R^1$ is H (Compound HO-IIIB-MCP) or methyl (Compound MeO-IIIB-MCP).

In some embodiments, the methods comprise reacting a compound of Formula II-Ac with $H_2$ in the presence of a hydrogenation catalyst to provide a compound of Formula IIIB-Ac:

Formula IIIB-Ac

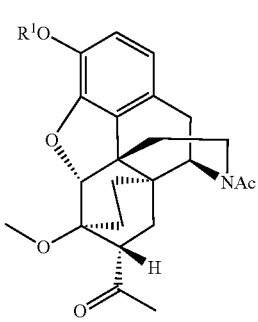

wherein R¹ is Ac (Compound AcO-IIIB-Ac).

In some embodiments, the methods comprise reacting a compound of Formula II-MCP with tert-butylmagnesium halide to provide a compound of Formula IIIA-MCP:

Formula IIIA-MCP

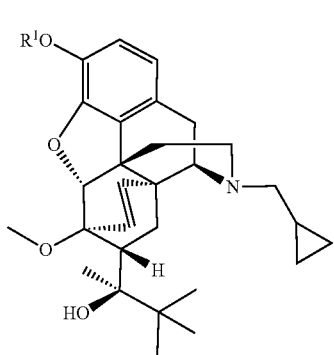

wherein R¹ is H (Compound HO-IIIA-MCP), methyl (Compound MeO-IIIA-MCP), or benzyl (Compound BnO-IIIA-MCP).

In some embodiments, the methods comprise reacting a compound of formula IIIA-MCP (e.g., Compound Me-IIIA-MCP) with a demethylating agent to provide another compound of IIIA-MCP (e.g., Compound HO-IIIA-MCP).

In some embodiments, the methods comprise reacting a compound of Formula II-Bn with tert-butylmagnesium halide to provide a compound of Formula IIIA-Bn:

Formula IIIA-Bn

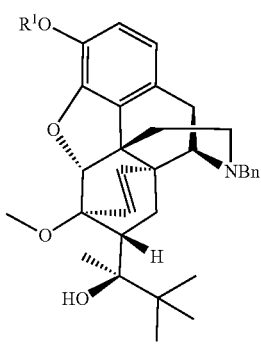

wherein R¹ is benzyl (Compound BnO-IIIA-Bn).

In some embodiments, the methods comprise reacting a compound of Formula II-Ac with tert-butylmagnesium halide to provide a compound of Formula IIIA-Ac:

Formula IIIA-Ac

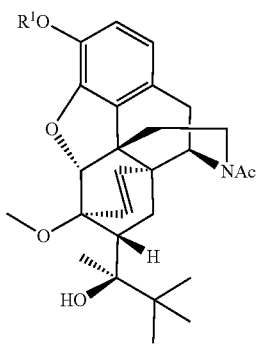

wherein R¹ is H (Compound HO-IIIA-Ac).

In some embodiments, the methods comprise reacting a compound of Formula IIIA-Ac (e.g., Compound HO-IIIA-Ac), wherein Ac is optionally substituted benzoyl, with lithium aluminum hydride (LAH) to provide a compound of Formula IIIA-Bn (e.g., Compound HO-IIIA-Bn).

In some embodiments, the methods comprise reacting a compound of Formula IIIB-MCP with tert-butylmagnesium halide to provide a compound of Formula IV-MCP:

Formula IV-MCP

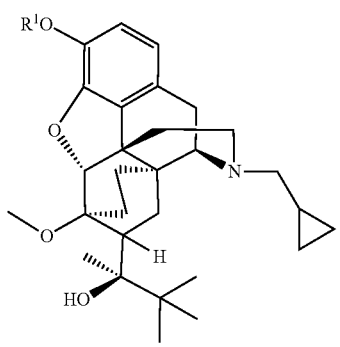

wherein R¹ is H (Compound HO-IV-MCP; buprenorphine) or methyl (Compound Me0-IV-MCP).

In some embodiments, the methods comprise reacting a compound of Formula IIIB-Ac with tert-butylmagnesium halide to provide a compound of Formula IV-Ac:

Formula IV-Ac

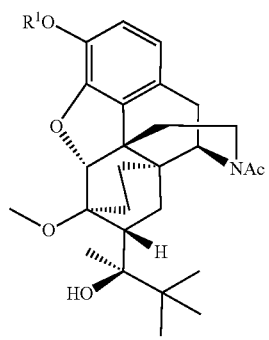

wherein R¹ is H (Compound HO-IV-Ac).

In some embodiments, the methods comprise reacting a compound of Formula IIIA-MCP with H₂ in the presence of a hydrogenation catalyst to provide a compound of Formula IV-MCP (see above), wherein R₁ is H (Compound HO-IV-MCP; buprenorphine) or methyl (Compound MeO-IV-MCP).

In some embodiments, the methods comprise reacting a compound of Formula IIIA-Ac with H₂ in the presence of a hydrogenation catalyst to provide a compound of Formula IV-Ac (see above), wherein R₁ is H (Compound HO-IV-Ac).

In some embodiments, the methods comprise reacting a compound of Formula IIIA-Bn with H₂ in the presence of a hydrogenation catalyst to provide a compound of Formula IV-H:

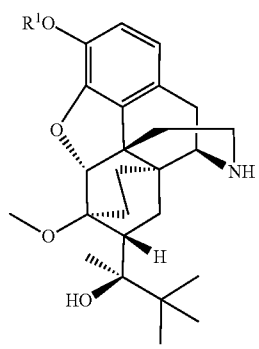

Formula IV-H wherein $R^1$ is H (Compound HO-IV-H; norbuprenorphine).

In some embodiments, the methods comprise reacting a compound of Formula IV-Ac (e.g., compound HO-IV-Ac) with Schwartz's reagent (zirconocene hydrochloride) or base to provide a compound of Formula IV-H (e.g., compound HO-IV-H).

In some embodiments, the methods comprise reacting a compound of Formula IV-MCP (e.g., Compound Me-IV-MCP) with a demethylating agent to provide buprenorphine.

In some embodiments, the methods comprise reacting a compound of Formula IV-H (e.g., Compound HO-IV-H) with cyclopropane carboxaldehyde followed by a hydride source; or reacting a compound of Formula IV-H (e.g., Compound HO-IV-H) with cyclopropanecarboxylic acid halide followed by a reducing agent; or reacting a compound of Formula IV-H (e.g., Compound HO-IV-H) with cyclopropylmethyl halide or activated cyclopropane methanol; to provide buprenorphine.

Formula I-H→Formula I-MCP

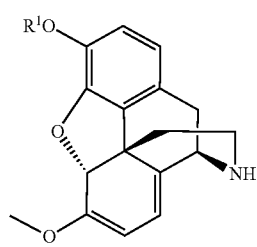

Formula I-H

| $R^1$ of Formula I-H | Compound |
|---|---|
| H | Compound HO-I-H |
| Me | Compound MeO-I-H |

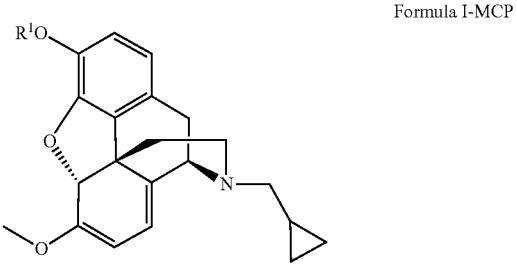

Formula I-MCP

| $R^1$ of Formula I-MCP | Compound |
|---|---|
| H | Compound HO-I-MCP |
| Me | Compound MeO-I-MCP |
| Bn | Compound BnO-I-MCP |

Step (i)(A1)

In some embodiments, reacting a compound of Formula I-H with cyclopropane carboxaldehyde followed by a hydride source provides a compound of Formula I-MCP. In certain embodiments, reacting Compound HO-I-H with cyclopropane carboxaldehyde followed by a hydride source provides Compound HO-I-MCP. In certain embodiments, reacting Compound MeO-I-H with cyclopropane carboxaldehyde followed by a hydride source provides Compound MeO-I-MCP. In certain embodiments, reacting See Examples 12 and 23.

In some embodiments, the hydride source is formic acid, hydrogen, sodium cyanoborohydride, sodium borohydride, or sodium triacetoxy borohydride. In some embodiments, the hydride source is formic acid. In some embodiments, the reaction is catalyzed by a ruthenium(I) complex or a ruthenium(II) complex, e.g., a dichloro(p-cymene)ruthenium(II) dimer. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof. In some embodiments, the reaction is performed in the presence of a trialkylamine, e.g., triethylamine, diisopropylethylamine, 4-methyl-morpholine, or N-methyl-piperidine.

In some embodiments, the cyclopropane carboxaldehyde is reacted at a temperature within the range of about 30° C. to about 90° C., e.g., about 35° C. to about 90° C., or about 40° C. to about 90° C., or about 45° C. to about 90° C., or about 50° C. to about 90° C., or about 55° C. to about 90° C., or about 60° C. to about 90° C., or about 65° C. to about 90° C., or about 70° C. to about 90° C., or about 30° C. to about 85° C., or about 30° C. to about 80° C., or about 30° C. to about 75° C., or about 30° C. to about 70° C., or about 30° C. to about 65° C., or about 30° C. to about 60° C., or about 30° C. to about 55° C., or about 30° C. to about 50° C., or about 35° C. to about 85° C., or about 40° C. to about 80° C., or about 45° C. to about 75° C., or about 50° C. to about 70° C., or about 55° C. to about 65° C. In some embodiments, the cyclopropane carboxaldehyde is reacted for a period of time within the range of about 30 minutes to about 5 hours, e.g., about 1 hour to about 5 hours, or about 1.5 hours to about 5 hours, or about 2 hours to about 5 hours, or about 2.5 hours to about 5 hours, or about 3 hours to about 5 hours, or about 3.5 hours to about 5 hours, or about 4 hours to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 30 minutes to about 2 hours, or about 30 minutes to about 1.5 hours.

Step (i)(A2)

In some embodiments, reacting a compound of Formula I-H with cyclopropanecarboxylic acid halide followed by a reducing agent provides a compound of Formula I-MCP. In certain embodiments, reacting Compound HO-I-H with cyclopropanecarboxylic acid halide followed by a reducing agent provides Compound HO-I-MCP. In certain embodiments, reacting Compound MeO-I-H with cyclopropanecarboxylic acid halide followed by a reducing agent provides Compound MeO-I-MCP. In certain embodiments, reacting Compound BnO-I-H with cyclopropanecarboxylic acid halide followed by a reducing agent provides Compound BnO-I-MCP. See Examples 13 and 24.

In some embodiments, the cyclopropanecarboxylic acid halide is cyclopropanecarboxylic acid chloride, cyclopropanecarboxylic acid anhydride, cyclopropanecarboxylic acid bromide, or an activated cyclopropanecarboxylic acid (e.g., an activated cyclopropanecarboxylic acid formed by reaction with an alcohol such as pentafluorophenol, 4-nitrophenol, N-hydroxysuccinimide, N-hydroxymaleimide, 1-Hydroxybenzotriazole, or 1-hydroxy-7-azabenzotriazole). In some embodiments, the reducing agent is $LiAlH_4$ or $NaBH_4$. In some embodiments, the reaction with cyclopropanecarboxylic acid halide is performed in a solvent comprising a nonpolar solvent, e.g., dichloromethane, chloroform, toluene, 1,4-dioxane, diethyl ether, benzene, or a mixture thereof. In some embodiments, the reaction with a reducing agent is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the cyclopropanecarboxylic acid halide is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the cyclopropanecarboxylic acid halide is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days. In some embodiments, the reducing agent is reacted at a temperature within the range of about 35° C. to about 85° C., e.g., about 40° C. to about 85° C., or about 45° C. to about 85° C., or about 50° C. to about 85° C., or about 55° C. to about 85° C., or about 60° C. to about 85° C., or about 65° C. to about 85° C., or about 35° C. to about 80° C., or about 35° C. to about 75° C., or about 35° C. to about 70° C., or about 35° C. to about 65° C., or about 35° C. to about 60° C., or about 35° C. to about 55° C., or about 40° C. to about 80° C., or about 45° C. to about 75° C., or about 50° C. to about 70° C., or about 55° C. to about 65° C. In some embodiments, the reducing agent is reacted for a period of time within the range of about 5 minutes to about 3 hours, e.g., or about 10 minutes to about 3 hours, or about 15 minutes to about 3 hours, or about 30 minutes to about 3 hours, or about 45 minutes to about 3 hours, or about 1 hour to about 3 hours, or about 1.25 hours to about 3 hours, or about 1.5 hours to about 3 hours, or about 1.75 hours to about 3 hours, or about 2 hours to about 3 hours, or about 5 minutes to about 2.75 hours, or about 5 minutes to about 2.5 hours, or about 5 minutes to about 2.25 hours, or about 5 minutes to about 2 hours, or about 5 minutes to about 1.75 hours, or about 5 minutes to about 1.5 hours, or about 5 minutes to about 1.25 hours, or about 5 minutes to about 1 hour, or about 10 minutes to about 2.75 hours, or about 15 minutes to about 2.5 hours, or about 30 minutes to about 2.25 hours, or about 45 minutes to about 2 hours, or about 1 hour to about 1.75 hours.

Step (i)(A3)

In some embodiments, reacting a compound of Formula I-H with cyclopropylmethyl halide or activated cyclopropane methanol (e.g., activated with a sulfonate group such as a p-toluene sulfonyl group or a methyl sulfonyl group, or with triphenylphosphine) provides a compound of Formula I-MCP. In certain embodiments, reacting Compound HO-I-H with cyclopropylmethyl halide or activated cyclopropane methanol provides Compound HO-I-MCP. In certain embodiments, reacting Compound MeO-I-H with cyclopropylmethyl halide or activated cyclopropane methanol provides Compound MeO-I-MCP. In certain embodiments, reacting Compound BnO-I-H with cyclopropylmethyl halide or activated cyclopropane methanol provides Compound BnO-I-MCP. See Examples 14, 25, and 34.

In some embodiments, the cyclopropylmethyl halide is cyclopropylmethyl chloride or cyclopropylmethyl bromide. In some embodiments, the reaction is performed in the presence of a trialkylamine, e.g., triethylamine, diisopropylethylamine, 4-methyl-morpholine, or N-methyl-piperidine. In some embodiments, the reaction is performed in a solvent comprising a polar protic solvent, e.g., n-butanol, isopropanol, ethanol, methanol, water, or a mixture thereof.

In some embodiments, the cyclopropylmethyl halide or activated cyclopropane methanol is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the cyclopropylmethyl halide or activated cyclopropane methanol is reacted for a period of time within the range of about 30 minutes to about 6 hours, e.g., about 1 hours to about 6 hours, or about 1.5 hours to about 6 hours, or about 2 hours to about 6 hours, or about 2.5 hours to about 6 hours, or about 3 hours to about 6 hours, or about 3.5 hours to about 6 hours, or about 4 hours to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 1 hours to about 5.5 hours, or about 1.5 hours to about 5 hours, or about 2 hours to about 4.5 hours, or about 2.5 hours to about 4 hours.

Formula I-H→Formula I-Bn

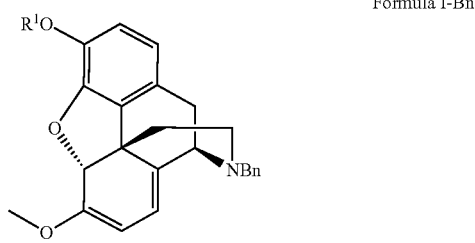

Formula I-Bn

| $R^1$ of Formula I-Bn | Compound |
|---|---|
| Bn | Compound BnO-I-Bn |

Step (i)(F)

In some embodiments, reacting a compound of Formula I-H with benzyl halide, benzyl sulfonate, or activated benzyl alcohol (e.g., activated with a sulfonate group such as a p-toluene sulfonyl group or a methyl sulfonyl group, or with triphenylphosphine) provides a compound of Formula I-Bn. In certain embodiments, reacting Compound HO-I-H with benzyl halide, benzyl sulfonate, or activated benzyl alcohol provides Compound BnO-I-Bn. See Example 40.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula I-H→Formula I-Ac

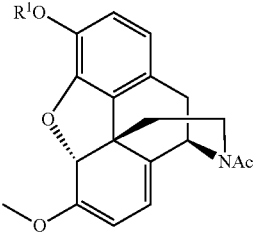

Formula I-Ac

| $R^1$ of Formula I-Ac | Compound |
|---|---|
| H | Compound HO-I-Ac |
| Ac | Compound AcO-I-Ac |
| Bn | Compound BnO-I-Ac |

Step (i)(G)

In some embodiments, reacting a compound of Formula I-H with acyl halide provides a compound of Formula I-Ac. In certain embodiments, reacting Compound HO-I-H with acyl halide provides Compound HO-I-Ac. See Example 45. In certain embodiments, reacting Compound HO-I-H with acyl halide provides Compound AcO-I-Ac. See Example 48.

In some embodiments, the acyl halide is optionally substituted $C_6$-$C_{13}$ aromatic acyl halide, e.g., optionally substituted benzoyl halide. In some embodiments, the acyl halide is aliphatic acylc halide, e.g., acetyl chloride. In some embodiments, the reaction is performed in the presence of a trialkylamine, e.g., triethylamine, diisopropylethylamine, 4-methyl-morpholine, or N-methyl-piperidine. In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the acyl halide is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 40° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the acyl halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 1.5 hours to about 6.5 hours, or about 1.5 hours to about 6 hours, or about 1.5 hours to about 5.5 hours.

Formula I-Ac→Formula I-Ac

Step (ii)(F)

In some embodiments, reacting a compound of Formula I-Ac with benzyl halide, benzyl sulfonate, or activated benzyl alcohol (e.g., activated with a sulfonate group such as a p-toluene sulfonyl group or a methyl sulfonyl group, or with triphenylphosphine) provides another compound of Formula I-Ac. In certain embodiments, reacting Compound HO-I-Ac with benzyl halide, benzyl sulfonate, or activated benzyl alcohol provides Compound BnO-I-Ac. See Example 46.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula I-Ac→Formula I-Bn

Step (iii)(H)

In some embodiments, reacting a compound of Formula I-Ac with lithium aluminum hydride provides a compound of Formula I-Bn. In certain embodiments, reacting Compound BnO-I-Ac with lithium aluminum hydride provides Compound BnO-I-Bn. See Example 47.

In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the lithium aluminum hydride is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to about 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the lithium aluminum hydride is reacted for a period of time within the range of about 10 minutes to about 8 hours, e.g., about 20 minutes to about 8 hours, about 30 minutes to about 8 hours, about 1 hour to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours.

Formula I-MCP→Formula I-MCP

Step (ii)(F)

In some embodiments, reacting a compound of Formula I-MCP with benzyl halide, benzyl sulfonate, or activated benzyl alcohol (e.g., activated with a sulfonate group such as a p-toluene sulfonyl group or a methyl sulfonyl group, or with triphenylphosphine) provides another compound of Formula I-MCP. In certain embodiments, reacting Compound HO-I-MCP with benzyl halide, benzyl sulfonate, or activated benzyl alcohol provides Compound BnO-I-MCP. See Example 33.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 40° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula I-MCP→Formula II-MCP

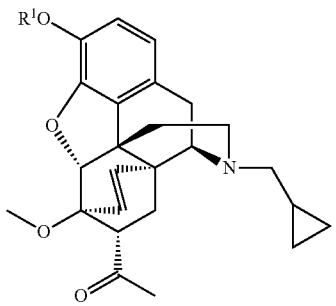

Formula II-MCP

| R¹ of Formula II-MCP | Compound |
|---|---|
| H | Compound HO-II-MCP |
| Me | Compound MeO-II-MCP |
| Bn | Compound BnO-II-MCP |

Step (ii)(B)

In some embodiments, reacting a compound of Formula I-MCP with methyl vinyl ketone provides a compound of Formula II-MCP. In certain embodiments, reacting Compound HO-I-MCP with methyl vinyl ketone provides Compound HO-II-MCP. In certain embodiments, reacting Compound MeO-I-MCP with methyl vinyl ketone provides Compound MeO-II-MCP. See Examples 15 and 26.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Step (iii)(B)

In some embodiments, reacting a compound of Formula I-MCP with methyl vinyl ketone provides a compound of Formula II-MCP. In certain embodiments, reacting Compound BnO-I-MCP with methyl vinyl ketone provides Compound BnO-II-MCP. See Example 36.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Formula I-Bn→Formula II-Bn

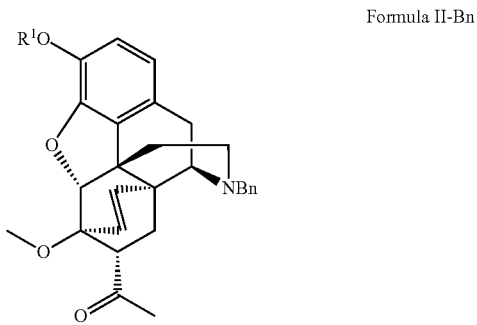

Formula II-Bn

| $R^1$ of Formula II-Bn | Compound |
|---|---|
| Bn | Compound BnO-II-Bn |

Step (ii)(B), Step (iv)(B)

In some embodiments, reacting a compound of Formula I-Bn with methyl vinyl ketone provides a compound of Formula II-Bn. In certain embodiments, reacting Compound BnO-I-Bn with methyl vinyl ketone provides Compound BnO-II-Bn. See Example 41.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Formula I-Ac→Formula II-Ac

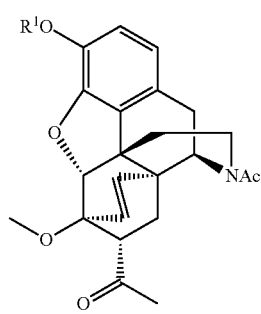

Formula II-Ac

| $R^1$ of Formula II-Ac | Compound |
|---|---|
| Ac | Compound AcO-II-Ac |

Step (ii)(B)

In some embodiments, reacting a compound of Formula I-Ac with methyl vinyl ketone provides a compound of Formula II-Ac. In certain embodiments, reacting Compound AcO-I-Ac with methyl vinyl ketone provides Compound AcO-II-Ac. See Example 49.

In some embodiments, the reaction is performed in a solvent comprising a nonpolar solvent, e.g., dichloromethane, chloroform, toluene, 1,4-dioxane, diethyl ether, benzene, or a mixture thereof.

In some embodiments, the methyl vinyl ketone is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the methyl vinyl ketone is reacted for a period of time within the range of about 2 hours to about 2 days, e.g., about 4 hours to about 2 days, or about 6 hours to about 2 days, or about 12 hours to about 2 days, or about 18 hours to about 2 days, or about 1 days to about 2 days, or about 1.25 days to about 2 days, or about 1.5 days to about 2 days, or about 2 hours to about 1.75 days, or about 2 hours to about 1.5 days, or about 2 hours to about 1.25 days, or about 2 hours to about 1 day, or about 2 hours to about 18 hours, or about 2 hours to about 12 hours, or about 4 hours to about 1.75 days, or about 6 hours to about 1.5 days, or about 12 hours to about 1.25 days, or about 18 hours to about 1 day.

Formula II-MCP→Formula II-MCP

Step (iii)(F)

In some embodiments, reacting a compound of Formula II-MCP with benzyl halide, benzyl sulfonate, or activated benzyl alcohol provides another compound of Formula II-MCP. In certain embodiments, reacting Compound HO-II-MCP with benzyl halide, benzyl sulfonate, or activated benzyl alcohol provides Compound BnO-II-MCP. See Example 35.

In some embodiments, the benzyl halide is benzyl chloride or benzyl bromide. In some embodiments, the reaction is performed in the presence of a strong base, e.g., an alkali metal hydride. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the benzyl halide, benzyl sulfonate, or activated benzyl alcohol is reacted at a temperature within the range of about −20° C. to about 40° C., e.g., about −20° C. to about 35° C., or about −20° C. to about 30° C., or about −20° C. to about 25° C., or about −20° C. to about 20° C., or about −20° C. to about 15° C., or about −20° C. to about 10° C., or about −20° C. to about 5° C., or about −20° C. to about 0° C., or about −15° C. to about 40° C., or about −10° C. to about 40° C., or about −5° C. to about 40° C., or about 0° C. to about 40° C., or about 5° C. to about 20° C., or about 10° C. to about 40° C., or about 15° C. to about 40° C., or about 20° C. to about 40° C., or about −15° C. to about 35° C., or about −10° C. to about 30° C., or about −5° C. to about 25° C., or about 0° C. to about 20° C., or about 5° C. to about 15° C. In some embodiments, the benzyl halide, benzyl sulfonate, or activated benzyl alcohol is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days.

Formula II-MCP→Formula IIIB-MCP

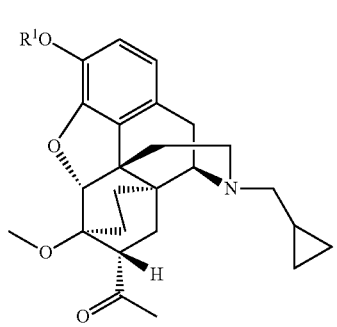

Formula IIIB-MCP

| R¹ of Formula IIIB-MCP | Compound |
|---|---|
| H | Compound HO-IIIB-MCP |
| Me | Compound MeO-IIIB-MCP |

Step (iii)(C)

In some embodiments, reacting a compound of Formula II-MCP with $H_2$ in the presence of a hydrogenation catalyst provides a compound of Formula IIIB-MCP. In certain embodiments, reacting Compound HO-II-MCP with $H_2$ in the presence of a hydrogenation catalyst provides Compound HO-IIIB-MCP. In certain embodiments, reacting Compound MeO-II-MCP with $H_2$ in the presence of a hydrogenation catalyst provides Compound MeO-IIIB-MCP. See Examples 16, 27, and 28.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula II-Ac→Formula IIIB-Ac

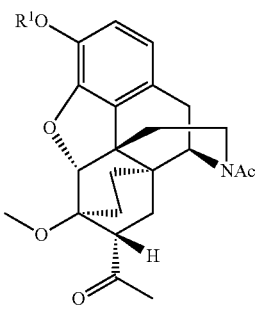

Formula III-Ac

| R¹ of Formula IIIB-Ac | Compound |
|---|---|
| Ac | Compound AcO-IIIB-Ac |

Step (iii)(C)

In some embodiments, reacting a compound of Formula II-Ac with $H_2$ in the presence of a hydrogenation catalyst provides a compound of Formula IIIB-Ac. In certain embodiments, reacting Compound AcO-II-Ac with $H_2$ in the presence of a hydrogenation catalyst provides Compound AcO-IIIB-Ac. See, Example 53.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula II-MCP→Formula IIIA-MCP

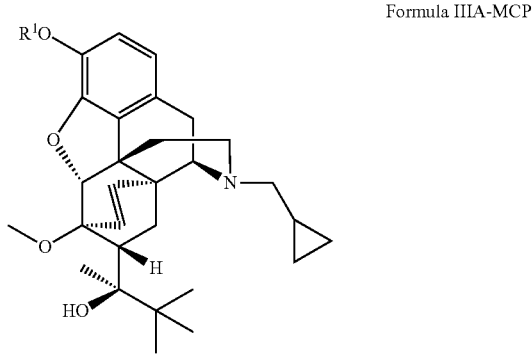

Formula IIIA-MCP

| R¹ of Formula IIIA-MCP | Compound |
|---|---|
| H | Compound HO-IIIA-MCP |
| Me | Compound MeO-IIIA-MCP |
| Bn | Compound BnO-IIIA-MCP |

Step (iii)(D)

In some embodiments, reacting a compound of Formula II-MCP with tert-butylmagnesium halide provides a compound of Formula IIIA-MCP. In certain embodiments, reacting Compound HO-II-MCP with tert-butylmagnesium halide provides Compound HO-IIIA-MCP. In certain embodiments, reacting Compound MeO-II-MCP with tert-butylmagnesium halide provides Compound MeO-IIIA-MCP. In certain embodiments, reacting Compound BnO-II-MCP with tert-butylmagnesium halide provides Compound BnO-IIIA-MCP. See Examples 17 and 29.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula II-Bn→Formula IIIA-Bn

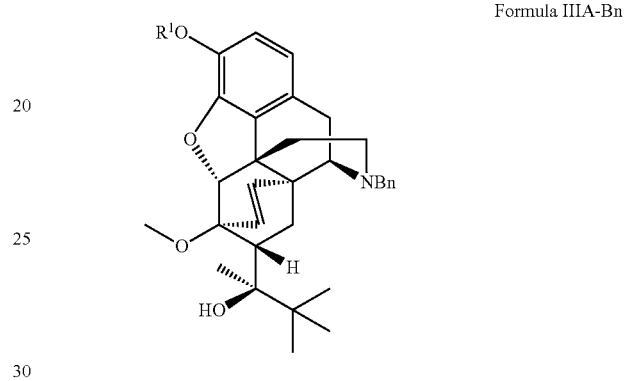

Formula IIIA-Bn

| R¹ of Formula IIIA-Bn | Compound |
|---|---|
| Bn | Compound BnO-IIIA-Bn |
| H | Compound HO-IIIA-Bn |

Step (iii)(D), Step (v)(D)

In some embodiments, reacting a compound of Formula II-Bn with tert-butylmagnesium halide provides a compound of Formula IIIA-Bn. In certain embodiments, reacting Compound BnO-II-Bn with tert-butylmagnesium halide provides Compound BnO-IIIA-Bn. See Example 42.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 100° C., e.g., about 20° C. to about 100° C., or about 25° C. to about 100° C., or about 30° C. to about 100° C., or about 15° C. to about 95° C., or about 15° C. to about 90° C., or about 15° C. to about 85° C., or about 20° C. to about 95° C., or about 25° C. to about 90° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula II-Ac→Formula IIIA-Ac

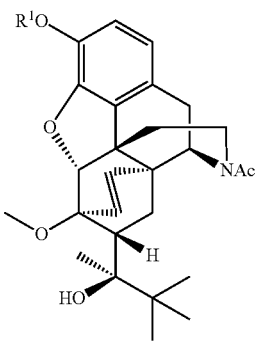

Formula IIIA-Ac

| R¹ of Formula IIIA-Bn | Compound |
|---|---|
| H | Compound HO-IIIA-Ac |

Step (iii)(D)

In some embodiments, reacting a compound of Formula II-Ac with tert-butylmagnesium halide provides a compound of Formula IIIA-Ac. In certain embodiments, reacting Compound AcO-II-Ac with tert-butylmagnesium halide provides Compound HO-IIIA-Ac. See Example 50.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 100° C., e.g., about 20° C. to about 100° C., or about 25° C. to about 100° C., or about 30° C. to about 100° C., or about 15° C. to about 95° C., or about 15° C. to about 90° C., or about 15° C. to about 85° C., or about 20° C. to about 95° C., or about 25° C. to about 90° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula IIIA-Ac→Formula IIIA-Bn

Step (iv)(H)

In some embodiments, reacting a compound of Formula IIIA-Ac with lithium aluminum hydride provides a compound of Formula IIIA-Bn. In certain embodiments, reacting Compound HO-IIIA-Ac with lithium aluminum hydride provides Compound HO-IIIA-Bn. See Example 51.

In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the lithium aluminum hydride is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the lithium aluminum hydride is reacted for a period of time within the range of about 10 minutes to about 8 hours, e.g., about 20 minutes to about 8 hours, about 30 minutes to about 8 hours, about 1 hour to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours.

Formula IIIA-MCP→Formula IIIA-MCP

Step (iv)(E)

In some embodiments, reacting a compound of Formula IIIA-MCP with a demethylating agent provides another compound of Formula IIIA-MCP. In certain embodiments, reacting Compound MeO-IIIA-MCP with a demethylating agent provides Compound HO-IIIA-MCP. See Example 20.

In some embodiments, the demethylating agent is a thiolate, e.g., a dodecane thiolate. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the demethylating agent is reacted at a temperature within the range of about 50° C. to about 190° C., e.g., about 60° C. to about 190° C., or about 70° C. to about 190° C., or about 80° C. to about 190° C., or about 90° C. to about 190° C., or about 100° C. to about 190° C., or about 110° C. to about 190° C., or about 120° C. to about 190° C., or about 130° C. to about 190° C., or about 140° C. to about 190° C., or about 150° C. to about 190° C., or about 50° C. to about 180° C., or about 50° C. to about 170° C., or about 50° C. to about 160° C., or about 50° C. to about 150° C., or about 50° C. to about 140° C., or about 50° C.

to about 130° C., or about 50° C. to about 120° C., or about 50° C. to about 110° C., or about 50° C. to about 100° C., or about 50° C. to about 90° C., or about 60° C. to about 180° C., or about 70° C. to about 170° C., or about 80° C. to about 160° C., or about 90° C. to about 150° C., or about 100° C. to about 140° C. In some embodiments, the demethylating agent is reacted for a period of time within the range of about 4 hours to about 2 days, e.g., about 8 hours to about 2 days, or about 12 hours to about 2 days, or about 16 hours to about 2 days, or about 20 hours to about 2 days, or about 1 day to about 2 days, or about 1.25 days to about 2 days, or about 1.5 days to about 2 days, or about 4 hours to about 1.75 days, or about 4 hours to about 1.5 days, or about 4 hours to about 1.25 days, or about 4 hours to about 1 day, or about 4 hours to about 20 hours, or about 4 hours to about 16 hours, or about 4 hours to about 12 hours, or about 8 hours to about 1.75 days, or about 12 hours to about 1.5 days, or about 16 hours to about 1.25 days.

Formula IIIB-MCP→Formula IV-MCP

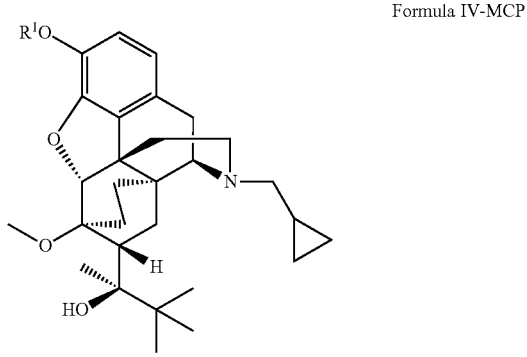

Formula IV-MCP

| $R^1$ of Formula IV-MCP | Compound |
|---|---|
| H | buprenorphine |
| Me | Compound MeO-IV-MCP |

Step (iv)(D)

In some embodiments, reacting a compound of Formula IIIB-MCP with tert-butylmagnesium halide provides a compound of Formula IV-MCP. In certain embodiments, reacting Compound HO-IIIB-MCP with tert-butylmagnesium halide provides buprenorphine. In certain embodiments, reacting Compound MeO-IIIB-MCP with tert-butylmagnesium halide provides Compound MeO-IV-MCP. See Examples 18, 30, 31, and 37.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula IIIA-MCP→Formula IV-MCP

Step (iv)(C), Step (v)(C)

In some embodiments, reacting a compound of Formula IIIA-MCP with $H_2$ in the presence of a hydrogenation catalyst provides a compound of Formula IV-MCP. In certain embodiments, reacting Compound HO-IIIA-MCP with $H_2$ in the presence of a hydrogenation catalyst provides buprenorphine. In certain embodiments, reacting Compound MeO-IIIA-MCP with $H_2$ in the presence of a hydrogenation catalyst provides Compound MeO-IV-MCP. In certain embodiments, reacting Compound BnO-IIIA-MCP with $H_2$ in the presence of a hydrogenation catalyst provides buprenorphine. See Examples 19, 22, 32, and 38.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula IIIB-Ac→Formula IV-Ac

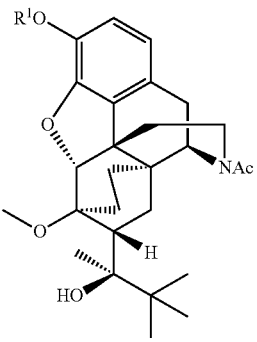

Formula IV-Ac

| $R^1$ of Formula IV-Ac | Compound |
|---|---|
| H | Compound HO-IV-Ac |

Step (iv)(D)

In some embodiments, reacting a compound of Formula IIIB-Ac with tert-butylmagnesium halide provides a compound of Formula IV-Ac. In certain embodiments, reacting Compound AcO-IIIB-Ac with tert-butylmagnesium halide provides Compound HO-IV-Ac. See, Example 54.

In some embodiments, the tert-butylmagnesium halide is tert-butylmagnesium chloride or tert-butylmagnesium bromide. In some embodiments, the reaction is performed in a solvent comprising a nonpolar solvent, e.g., tert-butylmethyl ether, 2-methyl-tetrahydrofuran, diethyl ether, dimethoxymethane, benzene, toluene, or a mixture of thereof.

In some embodiments, the tert-butylmagnesium halide is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the tert-butylmagnesium halide is reacted for a period of time within the range of about 30 minutes to about 8 hours, e.g., about 1 hours to about 8 hours, or about 1.5 hours to about 8 hours, or about 2 hours to about 8 hours, or about 2.5 hours to about 8 hours, or about 3 hours to about 8 hours, or about 3.5 hours to about 8 hours, or about 4 hours to about 8 hours, or about 4.5 hours to about 8 hours, or about 5 hours to about 8 hours, or about 30 minutes to about 7.5 hours, or about 30 minutes to about 7 hours, or about 30 minutes to about 6.5 hours, or about 30 minutes to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 1 hour to about 7.5 hours, or about 1.5 hours to about 7 hours, or about 2 hours to about 6.5 hours, or about 2.5 hours to about 6 hours, or about 3 hours to about 5.5 hours.

Formula IIIA-MCP→Formula IV-Ac

Step (iv)(C)

In some embodiments, reacting a compound of Formula IIIA-Ac with $H_2$ in the presence of a hydrogenation catalyst provides a compound of Formula IV-Ac. In certain embodiments, reacting Compound HO-IIIA-Ac with $H_2$ in the presence of a hydrogenation catalyst provides Compound HO-IV-Ac. See, Example 55.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula IIIA-Bn→Formula IV-H

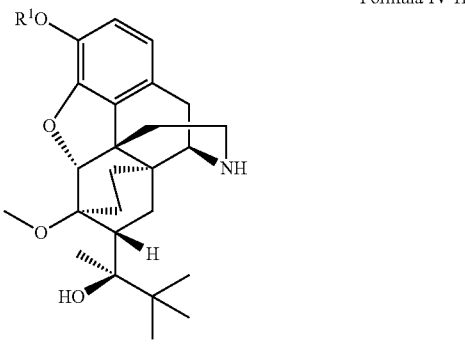

Formula IV-H

| $R^1$ of Formula IV-H | Compound |
|---|---|
| H | HO-IV-H |

Step (iv)(C), Step (v)(C), Step (vi)(C)

In some embodiments, reacting a compound of Formula IIIA-Bn with $H_2$ in the presence of a hydrogenation catalyst provides a compound of Formula IV-Bn. In certain embodiments, reacting Compound BnO-IIIA-Bn with $H_2$ in the presence of a hydrogenation catalyst provides Compound HO-IV-H. See Example 43. In certain embodiments, reacting Compound HO-IIIA-Bn with $H_2$ in the presence of a hydrogenation catalyst provides Compound HO-IV-H. See Examples 43 and 52.

In some embodiments, the hydrogenation catalyst comprises nickel, palladium, platinum, rhodium, or ruthenium. In some embodiments, the hydrogenation catalyst comprises platinum or palladium, supported on carbon. In some embodiments, the reaction is performed in a solvent comprising a polar protic or aprotic solvent, e.g., n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

In some embodiments, the hydrogen is reacted at a temperature within the range of about 15° C. to about 120° C., e.g., about 20° C. to about 120° C., or about 30° C. to about 120° C., or about 40° C. to about 120° C., or about 15° C. to about 115° C., or about 20° C. to about 110° C., or about 30° C. to about 105° C., or about 40° C. to about 115° C., or about 50° C. to about 110° C. In some embodiments, the hydrogen is reacted for a period of time within the range of about 6 hours to about 3 days, e.g., about 12 hours to about 3 days, or about 18 hours to about 3 days, or about 1 day to about 3 days, or about 1.25 days to about 3 days, or about 1.5 days to about 3 days, or about 6 hours to about 2.75 days, or about 6 hours to about 2.5 days, or about 6 hours to about 2.25 days, or about 6 hours to about 2 day, or about 6 hours to about 36 hours, or about 12 hours to about 2.5 days, or about 24 hours to about 2 days. In some embodiments, the hydrogen is reacted at a pressure within the range of about 1 atm to about 3 atm, e.g., about 1.25 atm to about 3 atm, or about 1.5 atm to about 3 atm, or about 1.75 atm to about 3 atm, or about 2 atm to about 3 atm, or about 1 atm to about 2.75 atm, or about 1 atm to about 2.5 atm, or about 1 atm to about 2.25 atm, or about 1 atm to about 2 atm, or about 1.25 atm to about 2.75 atm, or about 1.5 atm to about 2.5 atm, or about 1.75 atm to about 2.25 atm.

Formula IV-Ac→Formula IV-H

Step (v)(I)

In some embodiments, reacting a compound of Formula IV-Ac with Schwartz's reagent (zirconocene hydrochloride) or base provides a compound of Formula IV-H. In certain embodiments, reacting Compound HO-IV-Ac with Schwartz's reagent or base provides Compound HO-IV-H. See Examples 56 and 57.

In some embodiments, the reaction with Schwartz's reagent is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the Schwartz's reagent is reacted at a temperature within the range of about 15° C. to about 40° C., e.g., about 20° C. to about 40° C., or about 25° C. to about 40° C., or about 30° C. to about 40° C., or about 15° C. to about 35° C., or about 15° C. to about 30° C., or about 15° C. to about 25° C., or about 20° C. to about 35° C., or about 25° C. to about 30° C. In some embodiments, the Schwartz's reagent is reacted for a period of time within the range of about 5 minutes to about 3 hours, e.g., or about 10 minutes to about 3 hours, or about 15 minutes to about 3 hours, or about 30 minutes to about 3 hours, or about 45 minutes to about 3 hours, or about 1 hour to about 3 hours, or about 1.25 hours to about 3 hours, or about 1.5 hours to about 3 hours, or about 1.75 hours to about 3 hours, or about 2 hours to about 3 hours, or about 5 minutes to about 2.75 hours, or about 5 minutes to about 2.5 hours, or about 5 minutes to about 2.25 hours, or about 5 minutes to about 2 hours, or about 5 minutes to about 1.75 hours, or about 5 minutes to about 1.5 hours, or about 5 minutes to about 1.25 hours, or about 5 minutes to about 1 hour, or about 10 minutes to about 2.75 hours, or about 15 minutes to about 2.5 hours, or about 30 minutes to about 2.25 hours, or about 45 minutes to about 2 hours, or about 1 hour to about 1.75 hours.

In some embodiments, the base is an inorganic base, e.g., potassium hydroxide or sodium hydroxide. In some embodiments, the reaction with base is performed in a solvent comprising a high-boiling-point polar protic or aprotic solvent, e.g., ethylene glycol, diethylene glycol, N-methylpyrrolidone, dimethylformamide, or dimethylsulfoxide.

In some embodiments, the base is reacted at a temperature within the range of about 50° C. to about 240° C., e.g., about 60° C. to about 240° C., or about 70° C. to about 240° C., or about 80° C. to about 240° C., or about 90° C. to about 240° C., or about 100° C. to about 240° C., or about 110° C. to about 240° C., or about 120° C. to about 240° C., or about 130° C. to about 240° C., or about 140° C. to about 240° C., or about 150° C. to about 240° C., or about 50° C. to about 230° C., or about 50° C. to about 220° C., or about 50° C. to about 2100° C., or about 50° C. to about 2000° C., or about 50° C. to about 190° C., or about 50° C. to about 180° C., or about 90° C. to about 210° C., or about 100° C. to about 200° C. In some embodiments, the base is reacted for a period of time within the range of about 4 hours to about 2 days, e.g., about 8 hours to about 2 days, or about 12 hours to about 2 days, or about 16 hours to about 2 days, or about 20 hours to about 2 days, or about 1 day to about 2 days, or about 1.25 days to about 2 days, or about 1.5 days to about 2 days, or about 4 hours to about 1.75 days, or about 4 hours to about 1.5 days, or about 4 hours to about 1.25 days, or about 4 hours to about 1 day, or about 4 hours to about 20 hours, or about 4 hours to about 16 hours, or about 4 hours to about 12 hours, or about 8 hours to about 1.75 days, or about 12 hours to about 1.5 days, or about 16 hours to about 1.25 days.

Formula IV-H→Formula IV-MCP

Step (v)(A1), Step (vi)(A1)

In some embodiments, reacting a compound of Formula IV-H with cyclopropane carboxaldehyde followed by a hydride source provides a compound of Formula IV-MCP. In certain embodiments, reacting Compound HO-IV-H with cyclopropane carboxaldehyde followed by a hydride source provides buprenoprhine. See Example 44.

In some embodiments, the hydride source is formic acid, hydrogen, sodium cyanoborohydride, sodium borohydride, or sodium triacetoxy borohydride. In some embodiments, the hydride source is formic acid. In some embodiments, the reaction is catalyzed by a ruthenium(I) complex or a ruthenium(II) complex, e.g., a dichloro(p-cymene)ruthenium(II) dimer. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof. In some embodiments, the reaction is performed in the presence of a trialkylamine, e.g., triethylamine, diisopropylethylamine, 4-methyl-morpholine, or N-methyl-piperidine.

In some embodiments, the cyclopropane carboxaldehyde is reacted at a temperature within the range of about 30° C. to about 90° C., e.g., about 35° C. to about 90° C., or about 40° C. to about 90° C., or about 45° C. to about 90° C., or about 50° C. to about 90° C., or about 55° C. to about 90° C., or about 60° C. to about 90° C., or about 65° C. to about 90° C., or about 70° C. to about 90° C., or about 30° C. to about 85° C., or about 30° C. to about 80° C., or about 30° C. to about 75° C., or about 30° C. to about 70° C., or about 30° C. to about 65° C., or about 30° C. to about 60° C., or about 30° C. to about 55° C., or about 30° C. to about 50° C., or about 35° C. to about 85° C., or about 40° C. to about 80° C., or about 45° C. to about 75° C., or about 50° C. to about 70° C., or about 55° C. to about 65° C. In some embodiments, the cyclopropane carboxaldehyde is reacted for a period of time within the range of about 30 minutes to about 5 hours, e.g., about 1 hour to about 5 hours, or about 1.5 hours to about 5 hours, or about 2 hours to about 5 hours, or about 2.5 hours to about 5 hours, or about 3 hours to about 5 hours, or about 3.5 hours to about 5 hours, or about 4 hours to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 30 minutes to about 2 hours, or about 30 minutes to about 1.5 hours.

Step (v)(A2), Step (vi)(A2)

In some embodiments, reacting a compound of Formula IV-H with cyclopropanecarboxylic acid halide followed by a reducing agent provides a compound of Formula IV-MCP. In certain embodiments, reacting Compound HO-IV-H with cyclopropanecarboxylic acid halide followed by a reducing agent provides buprenorphine.

In some embodiments, the cyclopropanecarboxylic acid halide is cyclopropanecarboxylic acid chloride, cyclopropanecarboxylic acid anhydride, cyclopropanecarboxylic acid bromide, or an activated cyclopropanecarboxylic acid (e.g., an activated cyclopropanecarboxylic acid formed by reaction with an alcohol such as pentafluorophenol, 4-nitrophenol, N-hydroxysuccinimide, N-hydroxymaleimide, 1-Hydroxybenzotriazole, or 1-hydroxy-7-azabenzotriazole). In some embodiments, the reducing agent is LiAlH$_4$ or NaBH$_4$. In some embodiments, the reaction with cyclopropanecarboxylic acid halide is performed in a solvent comprising a nonpolar solvent, e.g., dichloromethane, chloroform, toluene, 1,4-dioxane, diethyl ether, benzene, or a mixture thereof. In some embodiments, the reaction with a reducing agent is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the cyclopropanecarboxylic acid halide is reacted at a temperature within the range of about –20° C. to about 40° C., e.g., about –20° C. to about 35° C., or about –20° C. to about 30° C., or about –20° C. to about 25° C., or about –20° C. to about 20° C., or about –20° C. to about 15° C., or about –20° C. to about 10° C., or about –20° C. to about 5° C., or about –20° C. to about 0° C., or about –15° C. to about 40° C., or about –10° C. to about 40° C., or about –5° C. to about 40° C., or about 0° C. to about 40° C., or about 5° C. to about 20° C., or about 10° C. to about 40° C., or about 15° C. to about 40° C., or about 20° C. to about 40° C., or about –15° C. to about 35° C., or about –10° C. to about 30° C., or about –5° C. to about 25° C., or about 0° C. to about 20° C., or about 5° C. to about 15° C. In some embodiments, the cyclopropanecarboxylic acid halide is reacted for a period of time within the range of about 6 hours to about 2 days, e.g., about 12 hours to about 2 days, or about 18 hours to about 2 days, or about 1 day to about 2 days, or about 1.25 days to about 2 days, or about 1.5 days to about 2 days, or about 6 hours to about 1.75 days, or about 6 hours to about 1.5 days, or about 6 hours to about 1.25 days, or about 6 hours to about 1 day, or about 6 hours to about 18 hours, or about 12 hours to about 1.75 days, or about 18 hours to about 1.5 days. In some embodiments, the reducing agent is reacted at a temperature within the range of about 35° C. to about 85° C., e.g., about 40° C. to about 85° C., or about 45° C. to about 85° C., or about 50° C. to about 85° C., or about 55° C. to about 85° C., or about 60° C. to about 85° C., or about 65° C. to about 85° C., or about 35° C. to about 80° C., or about 35° C. to about 75° C., or about 35° C. to about 70° C., or about 35° C. to about 65° C., or about 35° C. to about 60° C., or about 35° C. to about 55° C., or about 40° C. to about 80° C., or about 45° C. to about 75° C., or about 50° C. to about 70° C., or about 55° C. to about 65° C. In some embodiments, the reducing agent is reacted for a period of time within the range of about 5 minutes to about 3 hours, e.g., or about 10 minutes to about 3 hours, or about 15 minutes to about 3 hours, or about 30 minutes to about 3 hours, or about 45 minutes to about 3 hours, or about 1 hour to about 3 hours, or about 1.25 hours to about 3 hours, or about 1.5 hours to about 3 hours, or about 1.75 hours to about 3 hours, or about 2 hours to about 3 hours, or about 5 minutes to about 2.75 hours, or about 5 minutes to about 2.5 hours, or about 5 minutes to about 2.25 hours, or about 5 minutes to about 2 hours, or about 5 minutes to about 1.75 hours, or about 5 minutes to about 1.5 hours, or about 5 minutes to about 1.25 hours, or about 5 minutes to about 1 hour, or about 10 minutes to about 2.75 hours, or about 15 minutes to about 2.5 hours, or about 30 minutes to about 2.25 hours, or about 45 minutes to about 2 hours, or about 1 hour to about 1.75 hours.

Step (v)(A3), Step (vi)(A3)

In some embodiments, reacting a compound of Formula IV-H with cyclopropylmethyl halide or activated cyclopropane methanol (e.g., activated with a sulfonate group such as a p-toluene sulfonyl group or a methyl sulfonyl group, or with triphenylphosphine) provides a compound of Formula IV-MCP. In certain embodiments, reacting Compound HO-IV-H with cyclopropylmethyl halide or activated cyclopropane methanol provides buprenorphine.

In some embodiments, the cyclopropylmethyl halide is cyclopropylmethyl chloride or cyclopropylmethyl bromide. In some embodiments, the reaction is performed in the presence of a trialkylamine, e.g., triethylamine, diisopropylethylamine, 4-methyl-morpholine, or N-methyl-piperidine. In some embodiments, the reaction is performed in a solvent comprising a polar protic solvent, e.g., n-butanol, isopropanol, ethanol, methanol, water, or a mixture thereof.

In some embodiments, the cyclopropylmethyl halide or activated cyclopropane methanol is reacted at a temperature within the range of about 40° C. to about 120° C., e.g., about 45° C. to about 120° C., or about 50° C. to about 120° C., or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to about 120° C., or about 90° C. to about 120° C., or about 40° C. to about 115° C., or about 40° C. to about 110° C., or about 40° C. to about 105° C., or about 40° C. to about 100° C., or about 40° C. to about 95° C., or about 40° C. to about 90° C., or about 40° C. to about 85° C., or about 40° C. to about 80° C., or about 40° C. to about 75° C., or about 40° C. to about 70° C., or about 45° C. to about 115° C., or about 50° C. to about 110° C., or about 55° C. to about 105° C., or about 60° C. to about 100° C., or about 65° C. to about 95° C., or about 70° C. to about 90° C. In some embodiments, the cyclopropylmethyl halide or activated cyclopropane methanol is reacted for a period of time within the range of about 30 minutes to about 6 hours, e.g., about 1 hours to about 6 hours, or about 1.5 hours to about 6 hours, or about 2 hours to about 6 hours, or about 2.5 hours to about 6 hours, or about 3 hours to about 6 hours, or about 3.5 hours to about 6 hours, or about 4 hours to about 6 hours, or about 30 minutes to about 5.5 hours, or about 30 minutes to about 5 hours, or about 30 minutes to about 4.5 hours, or about 30 minutes to about 4 hours, or about 30 minutes to about 3.5 hours, or about 30 minutes to about 3 hours, or about 30 minutes to about 2.5 hours, or about 1 hours to about 5.5 hours, or about 1.5 hours to about 5 hours, or about 2 hours to about 4.5 hours, or about 2.5 hours to about 4 hours.

Formula IV-MCP→Formula IV-MCP

Step (v)(E)

In some embodiments, reacting a compound of Formula IV-MCP with a demethylating agent provides another compound of Formula IV-MCP. In certain embodiments, reacting Compound MeO-IV-MCP with a demethylating agent provides buprenorphine. See Example 21.

In some embodiments, the demethylating agent is a thiolate, e.g., a dodecane thiolate. In some embodiments, the reaction is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

In some embodiments, the demethylating agent is reacted at a temperature within the range of about 50° C. to about 190° C., e.g., about 60° C. to about 190° C., or about 70° C. to about 190° C., or about 80° C. to about 190° C., or about 90° C. to about 190° C., or about 100° C. to about 190° C., or about 110° C. to about 190° C., or about 120° C. to about 190° C., or about 130° C. to about 190° C., or about 140° C. to about 190° C., or about 150° C. to about 190° C., or about 50° C. to about 180° C., or about 50° C. to about 170° C., or about 50° C. to about 160° C., or about 50° C. to about 150° C., or about 50° C. to about 140° C., or about 50° C. to about 130° C., or about 50° C. to about 120° C., or about 50° C. to about 110° C., or about 50° C. to about 100° C., or about 50° C. to about 90° C., or about 60° C. to about 180° C., or about 70° C. to about 170° C., or about 80° C. to about 160° C., or about 90° C. to about 150° C., or about 100° C. to about 140° C. In some embodiments, the demethylating agent is reacted for a period of time within the range of about 4 hours to about 2 days, e.g., about 8 hours to about 2 days, or about 12 hours to about 2 days, or about 16 hours to about 2 days, or about 20 hours to about 2 days, or about 1 day to about 2 days, or about 1.25 days to about 2 days, or about 1.5 days to about 2 days, or about 4 hours to about 1.75 days, or about 4 hours to about 1.5 days, or about 4 hours to about 1.25 days, or about 4 hours to about 1 day, or about 4 hours to about 20 hours, or about 4 hours to about 16 hours, or about 4 hours to about 12 hours, or about 8 hours to about 1.75 days, or about 12 hours to about 1.5 days, or about 16 hours to about 1.25 days.

Formula I-H→Buprenorphine

In one aspect, the method of preparing buprenorphine comprises the series of steps provided in Table 17:

TABLE 17

| 4-step buprenorphine route | | | |
|---|---|---|---|
| No. | Substrate | Step | Product |
| i | Compound HO-I-H | (A1), (A2), or (A3) | Compound HO-I-MCP |
| ii | Compound HO-I-MCP | (B) | Compound HO-II-MCP |
| iii | Compound HO-II-MCP | (C) | Compound HO-IIIB-MCP |
| iv | Compound HO-IIIB-MCP | (D) | buprenorphine |

In another aspect, the method of preparing buprenorphine comprises the series of steps provided in Table 18:

TABLE 18

| 4-step buprenorphine route | | | |
|---|---|---|---|
| No. | Substrate | Step | Product |
| i | Compound HO-I-H | (A1), (A2), or (A3) | Compound HO-I-MCP |
| ii | Compound HO-I-MCP | (B) | Compound HO-II-MCP |
| iii | Compound HO-II-MCP | (D) | Compound HO-IIIA-MCP |
| iv | Compound HO-IIIA-MCP | (C) | buprenorphine |

In another aspect, the method of preparing buprenorphine comprises the series of steps provided in Table 20:

TABLE 20

| 5-step buprenorphine route | | | |
|---|---|---|---|
| No. | Substrate | Step | Product |
| i | Compound MeO-I-H | (A1), (A2), or (A3) | Compound MeO-I-MCP |
| ii | Compound MeO-I-MCP | (B) | Compound MeO-II-MCP |
| iii | Compound MeO-II-MCP | (C) | Compound MeO-IIIB-MCP |
| iv | Compound MeO-IIIB-MCP | (D) | Compound MeO-IV-MCP |
| v | Compound MeO-IV-MCP | (E) | buprenorphine |

In another aspect, the method of preparing buprenorphine comprises the series of steps provided in Table 21:

TABLE 21

| 5-step buprenorphine route | | | |
|---|---|---|---|
| No. | Substrate | Step | Product |
| i | Compound MeO-I-H | (A1), (A2), or (A3) | Compound MeO-I-MCP |
| ii | Compound MeO-I-MCP | (B) | Compound MeO-II-MCP |
| iii | Compound MeO-II-MCP | (D) | Compound MeO-IIIA-MCP |
| iv | Compound MeO-IIIA-MCP | (C) | Compound MeO-IV-MCP |
| v | Compound MeO-IV-MCP | (E) | buprenorphine |

In another aspect, the method of preparing buprenorphine comprises the series of steps provided in Table 22:

TABLE 22

| 5-step buprenorphine route | | | |
|---|---|---|---|
| No. | Substrate | Step | Product |
| i | Compound MeO-I-H | (A1), (A2), or (A3) | Compound MeO-I-MCP |
| ii | Compound MeO-I-MCP | (B) | Compound MeO-II-MCP |
| iii | Compound MeO-II-MCP | (D) | Compound MeO-IIIA-MCP |
| iv | Compound MeO-IIIA-MCP | (E) | Compound HO-IIIA-MCP |
| v | Compound HO-IIIA-MCP | (C) | buprenorphine |

In another aspect, the method of preparing buprenorphine comprises the series of steps provided in Table 23:

TABLE 23

5-step buprenorphine route

| No. | Substrate | Step | Product |
|---|---|---|---|
| i | Compound HO-I-H | (A1), (A2), or (A3) | Compound HO-I-MCP |
| ii | Compound HO-I-MCP | (B) | Compound HO-II-MCP |
| iii | Compound HO-II-MCP | (F) | Compound BnO-II-MCP |
| iv | Compound BnO-II-MCP | (D) | Compound BnO-IIIA-MCP |
| v | Compound BnO-IIIA-MCP | (C) | buprenorphine |

In another aspect, the method of preparing buprenorphine comprises the series of steps provided in Table 24:

TABLE 24

5-step buprenorphine route

| No. | Substrate | Step | Product |
|---|---|---|---|
| i | Compound HO-I-H | (A1), (A2), or (A3) | Compound HO-I-MCP |
| ii | Compound HO-I-MCP | (F) | Compound BnO-I-MCP |
| iii | Compound BnO-I-MCP | (B) | Compound BnO-II-MCP |
| iv | Compound BnO-II-MCP | (D) | Compound BnO-IIIA-MCP |
| v | Compound BnO-IIIA-MCP | (C) | buprenorphine |

In another aspect, the method of preparing buprenorphine comprises the series of steps provided in Table 25:

TABLE 25

5-step buprenorphine route

| No. | Substrate | Step | Product |
|---|---|---|---|
| i | Compound HO-I-H | (F) | Compound BnO-I-Bn |
| ii | Compound BnO-I-Bn | (B) | Compound BnO-II-Bn |
| iii | Compound BnO-II-Bn | (D) | Compound BnO-IIIA-Bn |
| iv | Compound BnO-IIIA-Bn | (C) | Compound HO-IV-H |
| v | Compound HO-IV-H | (A1), (A2), or (A3) | buprenorphine |

In another aspect, the method of preparing buprenorphine comprises the series of steps provided in Table 26:

TABLE 26

7-step buprenorphine route

| No. | Substrate | Step | Product |
|---|---|---|---|
| i | Compound HO-I-H | (G) | Compound HO-I-Ac |
| ii | Compound HO-I-Ac | (F) | Compound BnO-I-Ac |
| iii | Compound BnO-I-Ac | (H) | Compound BnO-I-Bn |
| iv | Compound BnO-I-Bn | (B) | Compound BnO-II-Bn |
| v | Compound BnO-II-Bn | (D) | Compound BnO-IIIA-Bn |
| vi | Compound BnO-IIIA-Bn | (C) | Compound HO-IV-H |
| vii | Compound HO-IV-H | (A1), (A2), or (A3) | buprenorphine |

In another aspect, the method of preparing buprenorphine comprises the series of steps provided in Table 27:

TABLE 27

6-step buprenorphine route

| No. | Substrate | Step | Product |
|---|---|---|---|
| i | Compound HO-I-H | (G) | Compound AcO-I-Ac |
| ii | Compound AcO-I-Ac | (B) | Compound AcO-II-Ac |
| iii | Compound AcO-II-Ac | (D) | Compound HO-IIIA-Ac |
| iv | Compound HO-IIIA-Ac | (H) | Compound HO-IIIA-Bn |
| v | Compound HO-IIIA-Bn | (C) | Compound HO-IV-H |
| vi | Compound HO-IV-H | (A1), (A2), or (A3) | Buprenorphine |

In another aspect, the method of preparing buprenorphine comprises the series of steps provided in Table 28:

TABLE 28

6-step buprenorphine route

| No. | Substrate | Step | Product |
|---|---|---|---|
| i | Compound HO-I-H | (G) | Compound AcO-I-Ac |
| ii | Compound AcO-I-Ac | (B) | Compound AcO-II-Ac |
| iii | Compound AcO-II-Ac | (D) | Compound HO-IIIA-Ac |
| iv | Compound HO-IIIA-Ac | (C) | Compound HO-IV-Ac |
| v | Compound HO-IV-Ac | (I) | Compound HO-IV-H |
| vi | Compound HO-IV-H | (A1), (A2), or (A3) | Buprenorphine |

In another aspect, the method of preparing buprenorphine comprises the series of steps provided in Table 29:

TABLE 29

6-step buprenorphine route

| No. | Substrate | Step | Product |
|---|---|---|---|
| i | Compound HO-I-H | (G) | Compound AcO-I-Ac |
| ii | Compound AcO-I-Ac | (B) | Compound AcO-II-Ac |
| iii | Compound AcO-II-Ac | (C) | Compound AcO-IIIB-Ac |
| iv | Compound AcO-IIIB-Ac | (D) | Compound HO-IV-Ac |
| v | Compound HO-IV-Ac | (I) | Compound HO-IV-H |
| vi | Compound HO-IV-H | (A1), (A2), or (A3) | Buprenorphine |

Product-by-Process

The methods described herein all have favourable characteristics. The same goes for the products produced by the methods.

This, one aspect of the present invention relates to a product obtainable from a method of the present invention.

One embodiment of the present invention relates to an N-demethylated compound obtainable from a method of the present invention. These compounds can be any N-demethylated retiduline derivative described herein.

Another embodiment of the present invention relates to an N- and O-demethylated compounds obtainable from a method of the present invention.

A further embodiment of the present invention relates to buprenorphine obtainable from a method disclosed herein.

Additional Steps

The methods of the present invention can optionally comprise one or more additional steps. These steps can for example be directed toward isolation and/or purification of the compounds from the host cells before the chemical synthesis.

A number of different methods can be used to isolate and purify Northebaine and Nororipavine produced by the methods disclosed herein. For example, the isolating steps may comprise: (a) contacting the cell culture comprising the Nor-compounds (Oripavine/Thebaine) with: (i) one or more adsorbent resins in a packed column in order to bind at least a portion of the Nor-alkaloid compounds to the resin, thereby isolating the nor compound; or (ii) one or more ion exchange or reversed-phase chromatography columns in order to bind at least a portion of the nor compound in the column, thereby isolating the nor-alkaloid compound; or (b) crystallizing and/or organic solvent extracting the Nor-alkaloid compounds from the cell culture, thereby isolating the northebaine and nororipavine compound; (i) contacting the cell culture with an organic solvent immiscible with water and separating the organic phase enriched in nor-alkaloids (c) separating the cell culture into a solid phase and a liquid phase, wherein the liquid phase comprises of the Nor-alkaloids; and (i) contacting the liquid phase with one or more adsorbent resins in order to bind at least a portion of the nor compound to the resin, thereby isolating the products; (ii) contacting the liquid phase with one or more ion exchange or reversed-phase chromatography columns in order to bind at least a portion of the Nor-alkaloid compound in the column, thereby isolating the pure products; or (iii) crystallizing and/or extracting the nor-alkaloids from the liquid phase, thereby isolating the Nororipavine and Northebaine in pure form.

The isolating step can comprise, separating the solid phase from the liquid phase using a process comprising tangential flow filtration with diafiltration membranes to generate a permeate stream comprising the nor-alkaloid compounds (Northebaine/Nororipavine), wherein the membranes used in the tangential flow filtration are ultrafiltration or nanofiltration membranes. In an embodiment, the permeate stream is extracted by an organic solvent which phase-separates from the aqueous phase to generate an extracted nor-alkaloid product (Northebaine or Nororipavine) in the organic solvent.

Optionally the permeate stream containing the nor-alkaloids product could be concentrated by some evaporation to produce a crystallized Nor-alkaloid compound.

The aqueous permeate or the concentrate can be extracted by an organic solvent which phase-separates from the aqueous phase. The solvent extraction could be performed in a counter-current extraction centrifuge such as a Podbelniak extractor, or in a counter-current extraction column such as a Karr or Scheibel column. This yields the Northebaine or Nororipavine products in an organic solvent suitable for subsequent purification processing.

It will be understood that organic solvent extraction can be replaced with a series of process operations which yield a similar organic solution of nor-alkaloid. The series of process operations would include (a) precipitation of nor-alkaloid from the aqueous concentrate produced by addition of acid until acidic pH; (b) filtration and optionally water-washing of the resulting solids; and (c) dissolution of the filtered nor-alkaloid containing solids into an organic solvent suitable for further purification. Optionally the organic extract can be contacted with carbon to adsorb impurities and color bodies. Optionally the carbon contacting can be done by mixing carbon in the organic extract and filtering the carbon out of the resulting suspension, or by feeding the organic extract to a column or filter containing a fixed bed of carbon and collecting a purified effluent stream. The organic extract can be crystallized by concentrating the solution evaporatively. The resulting nor-alkaloid products crystals can be filtered, washed, and dried to yield a high-purity Northebaine or Nororipavine product. The reaction mixture can be filtered in order to remove the solid in the media (cell debris etc.). The resulting aqueous solution can be extracted repeatedly with an organic solvent not miscible with water (This can be Chloroform, Toluene, Dichloromethane, Ethyl acetate, etc.). The resulting organic phase can be concentrated into small quantity (resulting into a syrup). The aqueous phase can be discarded. The resulting residue (Nor crude material) can be then crystallized from any short chain alcohol, such as methanol or it can be purified with other suitable purification technique such as Chromatography or other standard techniques. Another possible procedure to extract the alkaloids from the poppy straw, can be a caustic wash of the poppy straw followed by a filtration in order to remove the plant material. The alkaloids can then be precipitated from the basic solution as salt after adjusting the pH to acidic with addition of acid (f. ex. Sulphuric acid or hydrochloric acid, etc.). The nor-alkaloids can be extracted from the poppy straw trough percolation via an organic solvent. The resulting organics can be concentrated into small quantity. The resulting residue can be purified with other suitable purification technique such as crystallization and/or chromatography or other standard techniques.

EXAMPLES

Example 1. Fungal Bioconversion of Thebaine

*Cunninghamella echinulata* ATCC 9244 was propagated on potato dextrose agar at room temperature. Mature cultures on plates (7-10 days) were used for the preparation of concentrated spore suspensions. Spores were harvested by flooding the lawn culture with a sterile solution containing 0.9% sodium chloride and 0.01% Tween 80 (10 ml/plate), scratching them from the hyphae with the aid of a sterile loop and filtering the suspension through sterile cotton to remove hyphal fragments. *Thamnostylum piriforme* ATCC 8992 was propagated on malt extract agar (CM0059) at room temperature and spore suspensions were prepared as indicated above. *C. echinulata* and *T. piriforme* were cultivated in 0.25 L baffled flasks containing 25 ml of modified media based on Chaudhary et al., 2009 (For *C. echinulata*: 20 g/l glucose, 8 g/l Difco nutrient broth, 2 g/L yeast extract, pH 6.0 and for *T. piriforme*: 30 g/L glucose, 8 g/L Difco nutrient broth, 2 g/L yeast extract, 2 g/L potassium phosphate dibasic, 1 g/L potassium phosphate monobasic, 2 g/L sodium nitrate, 0.5 g/L potassium chloride, 0.5 g/L magnesium sulfate heptahydrate 0.02 g/L iron (II) sulfate heptahydrate, pH 6.0). Cultures were incubated at 28° C. with vigorous aeration (200 rpm on an orbital shaker).

Figure 1:
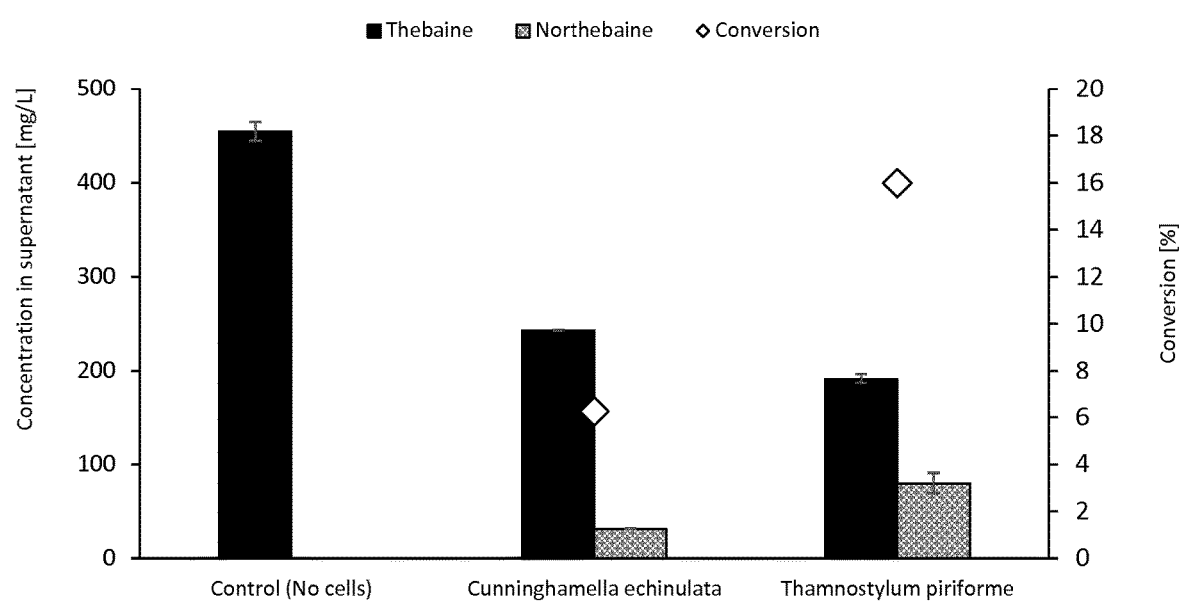
FIG. 1: Bioconversion of thebaine to northebaine by *Cunninghamella echinulata* and *Thamnostylum piriforme*. Thebaine in a final concentration of 0.5 mg/mL was added after 48 h of growth. Samples were taken 11 days after thebaine addition.
Figure 2:
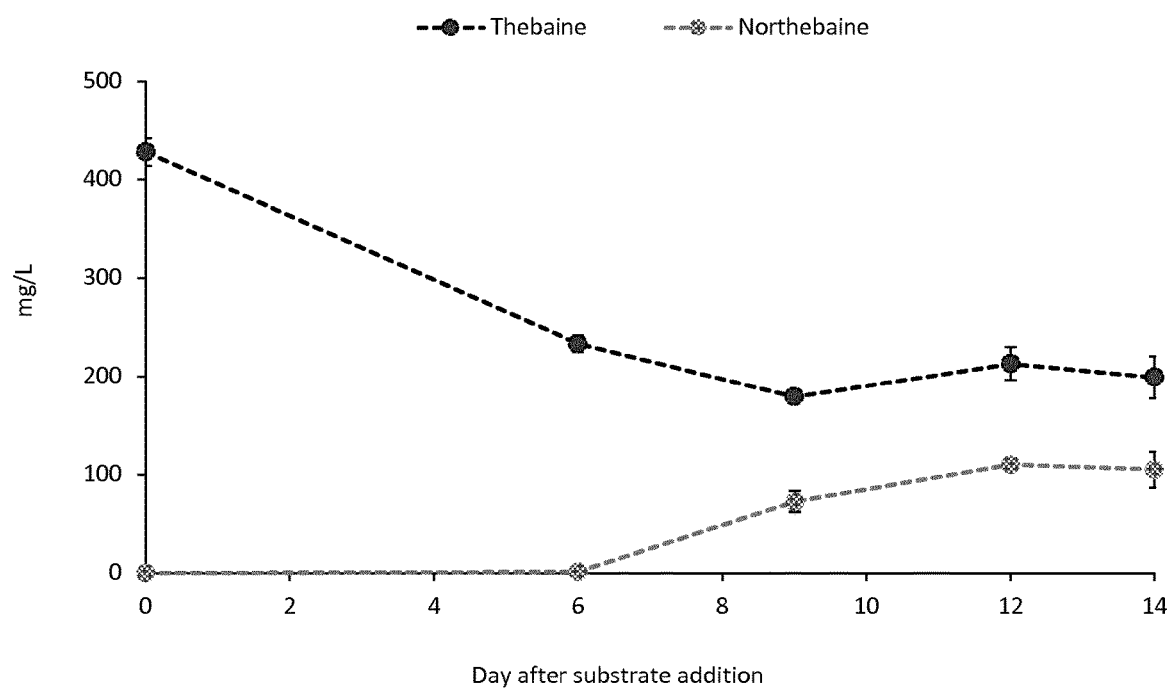
FIG. 2: Bioconversion of thebaine to northebaine by *Thamnostylum piriforme*. Thebaine in a final concentration of 0.5 mg/mL was added after 48 h of growth. Total RNA was extracted from biomass sampled on day 0, 6 and 9 after thebaine addition.

Media was inoculated with 0.25 ml of freshly-prepared spore suspensions. After 48 h of growth, thebaine was added to the cultures in a final concentration of 0.5 mg/ml from a 50 mg/ml stock solution prepared in methanol-1 M HCl (1:1). Eleven days after thebaine addition, supernatants were collected and analyzed by LC-MS. Thebaine was N-demethylated to northebaine by both *C. echinulata* and *T. piriforme*, reaching 6% and 16% conversion, respectively (FIG. 1). New *T. piriforme* cultures were set up in duplicates including negative controls for the purpose of inducing thebaine conversion activity and harvesting the biomass for RNA extraction and differential transcriptome analysis. Supernatant and biomass samples of induced and non-induced cultures were withdrawn from the flasks at time point 0 and on days 6 and 9 after thebaine addition. Thebaine and northebaine were monitored in the supernatants, reaching a conversion level of 25% on day 12 after substrate addition (FIG. 2).

Example 2. mRNA Preparation from Fungi and Sequencing

Total RNA was isolated from *T. piriforme* biomass samples according to a standard protocol using the RNeasy Plant Mini Kit (Qiagen), taking care that all materials, buffers and solutions were RNAse-free. Around 100 mg of biomass were harvested in screw-cap microcentrifuge tubes containing Zirconia beads with the aid of a sterile spatula, flash-frozen with liquid nitrogen and lysed using a Precellys homogenizer (3×15 s) keeping the temperature at 4° C. Total RNA was eluted in 50 µl RNAse-free water. RNA purity and integrity were verified by using the Qubit® BR RNA kit, NanoDrop spectroscopy and 1% agarose gel electrophoresis. Five RNA-seq samples, corresponding to day 0, day 6 (non-induced), day 6 (induced), day 9 (non-induced) and day 9 (induced), were sent to GATC Biotech AG (Konstanz, Germany) for sequencing.

Example 3. Bioinformatic Transcriptome Analysis

After Illumina sequencing, fastq files from all 5 RNA-Seq libraries were clipped and quality filtered with Trimmomatic (version 0.33, paramteres: SLIDINGWINDOW:4:28, MINLEN:75 LEADING:28 TRAILING:28), Bolger et al, 2014, Bioinformatics 30(15):2114-20).

Transcriptome was afterwards assembled with Trinity (version 2.2.0 parameters: —KMER_SIZE 31, —normalize_reads, —SS_lib_type, —min_kmer_cov 2, Grabherr et al, 2011, Nat Biotechnol., 29(7):644-52). Obtained transcripts were annotated via Trinotate (version 3, https://trinotate.github.io/) and transcripts containing either PFAM domain code PF00067 or COG2124 were considered as putative p450 enzymes. Similarly, CPRs were identified from the Trinotate annotation in case the closest hit was a fungal P450 reductase.

Expression levels (transcripts per million, TPM) of all transcripts were estimated with RSEM Li and Dewey, 2011, BMC Bioinformatics 4; 12:323) with default parameters, and afterwards a shortlist of P450 candidates was created by selecting those P450 candidates which had a minimal expression of 10 transcripts per million and showed at least 20% upregulation in the thebaine samples at day points 6 and 9 when compared to the non-induced samples, resulting in a list of 17 P450 candidates. Other 6 candidates were handpicked and checked afterwards for completeness by blasting the sequences against NCBI non-redundant database.

Example 4. Cloning of Fungal CYP450 Enzymes and CPRs cDNA Synthesis cDNA was obtained according to a standard protocol using the Mint-2 cDNA synthesis kit (Evrogen). For *T. piriforme*, RNA samples from days 6 and 9 after induction were heated at 65° C. for 1-2 min and utilized for cDNA synthesis. One microgram total RNA was combined with 10 µM primer EV2424 (CDS-4M Adapter: 5'-AAGCAGTGGTAT-CAACGCAGAGTGGCCAGAATGGCCTTTGTTTTTTC TTTTTTTTTTTTTVN-3') and 10 µM primer EV2425 (Short Oligo-Adapter: 5'-AGTGGCCTGCAGGGCCGGGGG-3'), incubated in a thermocycler at 70° C. for 2 min and then at 42° C. for 3 min. Five microliter of reverse transcriptase mix made of 2 µl 5× First-strand buffer, 1 µl DTT (20 mM), 1 µl dNTP (10 mM each), 0.5 µl RNase inhibitor and 1 µl Mint reverse transcriptase, was added to each RNA sample at 42° C. without removing them from the thermocycler. After incubation at 42° C. for 30 min, 5 µl of IP-solution was added and incubated at the same temperature for 1.5 h.

First-strand cDNA samples were amplified using 10 µM PCR primer-M1 (5'-AAGCAGTGGTATCAACGCAGAGT-3') and adequate volumes of dNTPs, 10× Encyclo buffer and Encyclo polymerase mix, following the cycling program and temperatures described in the protocol. Optimal cycling conditions were determined by 1% agarose gel electrophoresis. Full-scale preparation of ds cDNA was performed using 18 and 21 cycles for RNA samples from days 6 and 9 after induction, respectively. Ds cDNA was column-purified and stored at −20° C.

Cloning of Target Genes into *S. cerevisiae* Expression Vectors

Twenty-six transcript sequences putatively encoding 20 cytochrome P450s (23 individual sequences, 3 isoforms with different N-termini) and 3 CPRs (Table 1) were amplified from *T. piriforme* ds cDNA and cloned into vectors for episomal yeast expression. The cytochrome P450 genes were inserted by In-Fusion Cloning (Takara Bio, USA) into pEVE2120 (URA3) and all CPRs were cloned similarly into pEVE3307 (HIS3) or pEVE3308 (LEU2). Forward and reverse primers for amplification of cytochrome P450 genes contained SfiI and SacII sites, with the exception of the reverse primer for amplification of transcript Tp_P450_6 (P450_DN9560_c0_g1_i1), which contained a BamHI site instead. Forward and reverse primers for amplification of CPR genes contained PmeI and PacI sites. To ensure cytochrome P450 oxidation activity, CPR from *S. cerevisiae* (Sc_CPR) and other yeast codon-optimized CPR genes from *Cunninghamella elegans* (Cel_CPR_co) and *Gibberella fujikuroi* (Gf_CPR_co) (Table 1) were synthesized (GeneArt, Thermo Fisher Scientific) to be cloned alone or in combination with the CPRs from *T. piriforme*. Constructs containing Sc_CPR, Cel_CPR and Gf_CPR were obtained by standard restriction site digestion and ligation (Table 2). Oligonucleotide sequences used for the amplification of all target genes are shown in Table 3.

Amplification of gene candidates was performed using Q5 High-Fidelity DNA polymerase and the primers from table B. Thermocycler programs were set according to the user manual (annealing temperatures ranging from 54 to 61° C., extension: 60 s for cytochrome P450s and 75 s for CPRs). Following agarose gel and column purification, 1 µl (50-200 ng) of each PCR-amplified fragment was mixed with 1 µl linearized vector (50 ng), 1 µl In-Fusion Enzyme and 1 µl millipore water. Samples were incubated at 50° C. for 15 min. Competent *E. coli* cells (50 µl) were transformed with 2.5 µl of the reaction mix and plated on LB-Amp. Finally, 3-4 clones were picked from each plate, assigned letters A to D, grown in LB-Amp for plasmid isolation and sent out for DNA sequencing (Microsynth). The resulting plasmids are indicated in Table 4.

Selection of Cytochrome P450 Homolog and Cloning of Codon-Optimized Cytochrome P450 Genes A putative cytochrome P450 gene from *Lichtheimia ramosa* (SEQ ID NO: 7) was identified by protein similarity to P450_DN15259_c0_g1_i7 (60%). Two cytochrome P450 sequences from *T. piriforme*, P450_DN15259_c0_g1_i7 and P450_DN12791_c0_g1_i1, as well as the cytochrome P450 from *L. ramosa* (Table 5) were codon-optimized for *S.* cerevisiae, synthesized (GeneArt, Thermo Fisher Scientific) and cloned by restriction site digestion with HindIII/SacII into pEVE3306 (URA3) for expression under the control of the PGK1 promoter (Table 6).

Example 5. Expression of Fungal CYP450 Enzymes and CPRs in Yeast

Expression of *T. piriforme* Cytochrome P450 Genes Along with CPRs from *C. elegans, G. fujikuroi* and *S. cerevisiae*.

Yeast strain EVST25898 was transformed with plasmids containing each cytochrome P450 gene (pEV31493-31564) along with two other plasmids containing three CPRs: pEV31215 (Cel_CPR_co) and pEV31308 (Sc_CPR/Gf_CPR_co). A negative control strain containing pEV31215, pEV31308 and pEVE2120 (empty URA) was also created. Cells were grown in SC-His-Leu-Ura medium at 30° C. with shaking at 300 rpm for 20-24 h and utilized as pre-cultures for in vivo bioconversion assays.

Expression of P450_DN15259_c0_g1_i7 in Combination with CPRs from *T. piriforme*

Yeast strain EVST25898 was transformed with pEV31541 (P450_DN15259_c0_g1_i7_A) along with plasmids containing a CPR alone or in combination (Table 7). Eight constructs based on the three CPRs from *T. piriforme* were selected due to their match with the corresponding sequences obtained from the transcriptome analysis (low number or complete absence of SNPs). Plasmids pEVE3307 (empty HIS) or pEVE3308 (empty LEU) were used to replace the absence of one CPR gene. Cells were grown in SC-His-Leu-Ura medium at 30° C. with shaking at 300 rpm for 20-24 h and utilized as pre-cultures for in vivo bioconversion assays.

Expression of P450_DN12791_c0_g1_i1 in Combination with CPR from *C. elegans*

Yeast strain EVST25898 was transformed with pEV31522 (P450_DN12791_c0_g1_i1_C) together with pEV31215 (Cel_CPR_co). Cells were grown in SC-His-Leu-Ura medium at 30° C., 300 rpm for 20-24 h and utilized as pre-cultures for in vivo bioconversion assays.

Expression of Codon Optimized P450s in Combination with CPR from *C. elegans*

Yeast strain EVST25898 was transformed with either pEV32226 (P450_DN15259_co), pEV32227 (P450_DN12791_co) or pEV32228 (Lr_P450_co) together with pEV31215 (Cel_CPR_co) and pEVE3308 (empty LEU) to yield strains EVST29159, EVST29160 and EVST29161, respectively. A negative control strain containing pEV3306 (empty URA), pEVE3308 (empty LEU) and pEV31215 was also created (EVST29162). Cells were grown in SC-His-Leu-Ura medium at 30° C., 300 rpm for 20-24 h and utilized as pre-cultures for in vivo bioconversion assays.

Example 6. Bioconversion Assay with Thebaine or Oripavine

Bioconversion of Thebaine by *S. cerevisiae* Harboring *T. piriforme* Cytochrome P450 Candidates and CPRs from *C. elegans, G. Fujikuroi* and *S. cerevisiae*.

Figure 3:
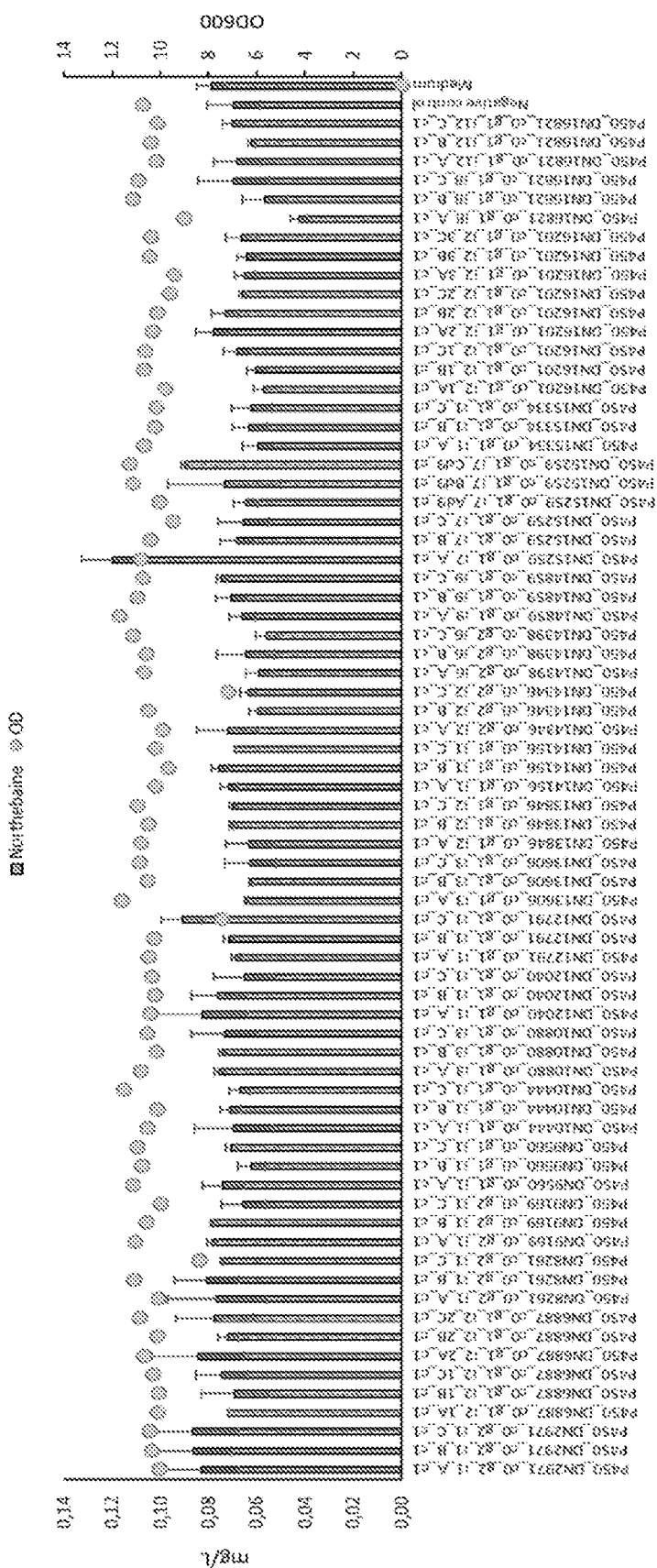
FIG. 3: Screening of thebaine N-demethylation by *S. cerevisiae* strains expressing cytochrome P450 candidates from *Thamnostylum piriforme* in combination with CPRs from *Cunninghamella elegans, Gibberella fujikuroi* and *S. cerevisiae*. Cells were fed with 0.1 mM (31 mg/L) thebaine in non-buffered selective medium and grown at 30° C. with shaking at 300 rpm for 72 h.

Yeast strain EVST25898 expressing *T. piriforme* cytochrome P450 gene candidates together with the CPRs from *C. elegans, G. fujikuroi* and *S. cerevisiae* as well as a negative control strain lacking P450 were assayed in a 96-deep-well-plate (DWP) format. Cells were grown in 0.5 ml SC-His-Leu-Ura medium containing 0.1 mM thebaine added from a 25 mM stock solution in DMSO. After 72 h of growth at 30° C. with shaking at 300 rpm, 100 µl-supernatants were harvested and spiked with 1 mg/l caffeine as internal standard. Northebaine was analyzed by LC-MS. Cytochrome P450 DN_15259_c0_g1_i7_A was identified as a thebaine N-demethylase (FIG. 3) and thus further investigated under optimized culture conditions.

Bioconversion of Thebaine and Oripavine by *S. cerevisiae* Harboring P450_DN15259_c0_g1_i7_A in Combination with CPRs from *T. piriforme*

Figure 4:
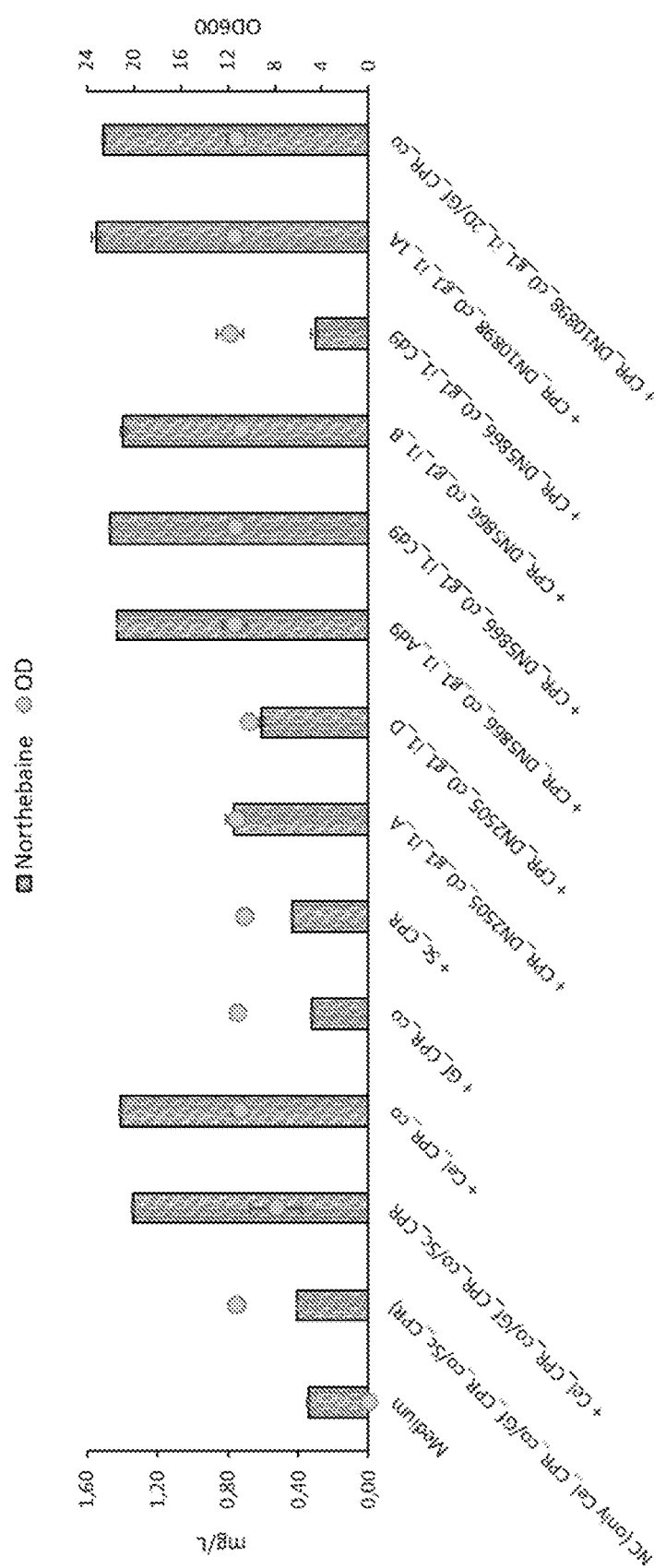
FIG. 4: N-demethylation of thebaine by *S. cerevisiae* strains expressing *Thamnostylum piriforme* P450_DN15259_c0_g1_i7_A in combination with codon-optimized CPRs from *Cunninghamella elegans* and *Gibberella fujikuroi* or native CPRs from *S. cerevisiae* and *T. piriforme* (CPR_DN2505_c0_g1_i1, CPR_DN5866_c0_g1_i1 and CPR_DN10898_c0_g1_i1). NC: Negative control strain. Cells were fed with 0.1 mM (31 mg/L) thebaine in selective medium containing 0.1 M potassium phosphate buffer pH 7 and grown at 30° C. with shaking at 300 rpm for 72 h.

Yeast strain EVST25898 expressing P450_DN15259_c0_g1_i7_A along with the CPRs evaluated in the previous section or the native CPR candidates from *T. piriforme* were assayed in a 96-DWP format. Cells were grown in 0.5 ml SC-His-Leu-Ura medium containing 0.1 M potassium phosphate buffer pH 7 and 0.1 mM thebaine. After 72 h of growth at 30° C. with shaking at 300 rpm, 100 µl-supernatants were harvested, spiked with 1 mg/l caffeine as internal standard and analyzed by LC-MS. *Cunninghamella elegans* CPR (Cel_CPR_co) was found to support N-demethylase activity of P450_DN15259_c0_g1_i7_A. In addition, strains harboring CPR_DN5866_c0_g1_Cd9 and CPR_DN10898_c0_g1_1A yielded more northebaine compared to those containing CPR_DN2505_c0_g1_i1_A (FIG. 4).

Figure 5:
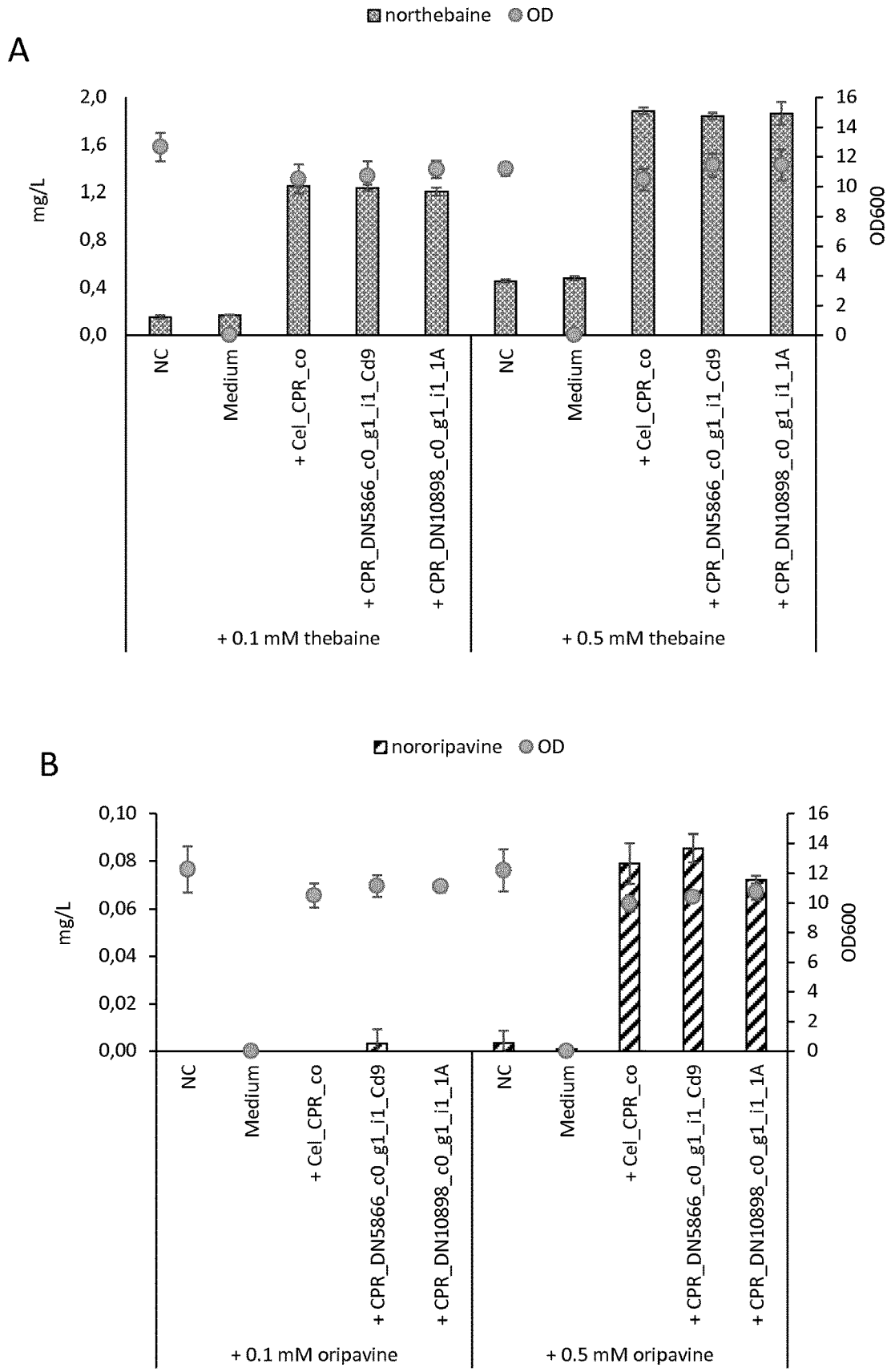
FIG. 5: N-demethylation of thebaine and oripavine by *S. cerevisiae* strains expressing *Thamnostylum piriforme* P450_DN15259_c0_g1_i7_A in combination with the codon-optimized CPR from *Cunninghamella elegans* or native CPRs from *T. piriforme*. NC: Negative control strain. Cells were fed with 0.1 mM or 0.5 mM thebaine (A) or oripavine (B) in selective medium containing 0.1 M potassium phosphate buffer pH 7 and grown at 30° C. with shaking at 300 rpm for 72 h.

Yeast strain EVST25898 containing P450_DN15259_c0_g1_i7_A and separately co-expressing Cel_CPR_co, CPR_DN5866_c0_g1_Cd9 and CPR_DN10898_c0_g1_1A were grown in 0.5 ml SC-His-Leu-Ura medium containing 0.1 M potassium phosphate buffer pH 7 and either 0.1 or 0.5 mM thebaine or oripavine. After 72 h of growth at 30° C. with shaking at 300 rpm, 100 µl-supernatants were treated as described above and subjected to LC-MS analysis. Northebaine and nororipavine titers are shown in FIGS. 5A and 5B, respectively. The three CPRs performed similarly and increasing thebaine concentration to 0.5 mM caused a 50% increase in northebaine titers (FIG. 5A). P450_DN15259_c0_g1_i7_A was able to N-demethylate oripavine, though this activity was detected only when feeding cells with 0.5 mM oripavine (FIG. 5B). Nororipavine titers were lower than those of northebaine by 20-fold.

Bioconversion of Oripavine by *S. cerevisiae* Harboring *T. piriforme* Cytochrome P450 Candidates in Combination with the CPR from *C. elegans*

Figure 6:
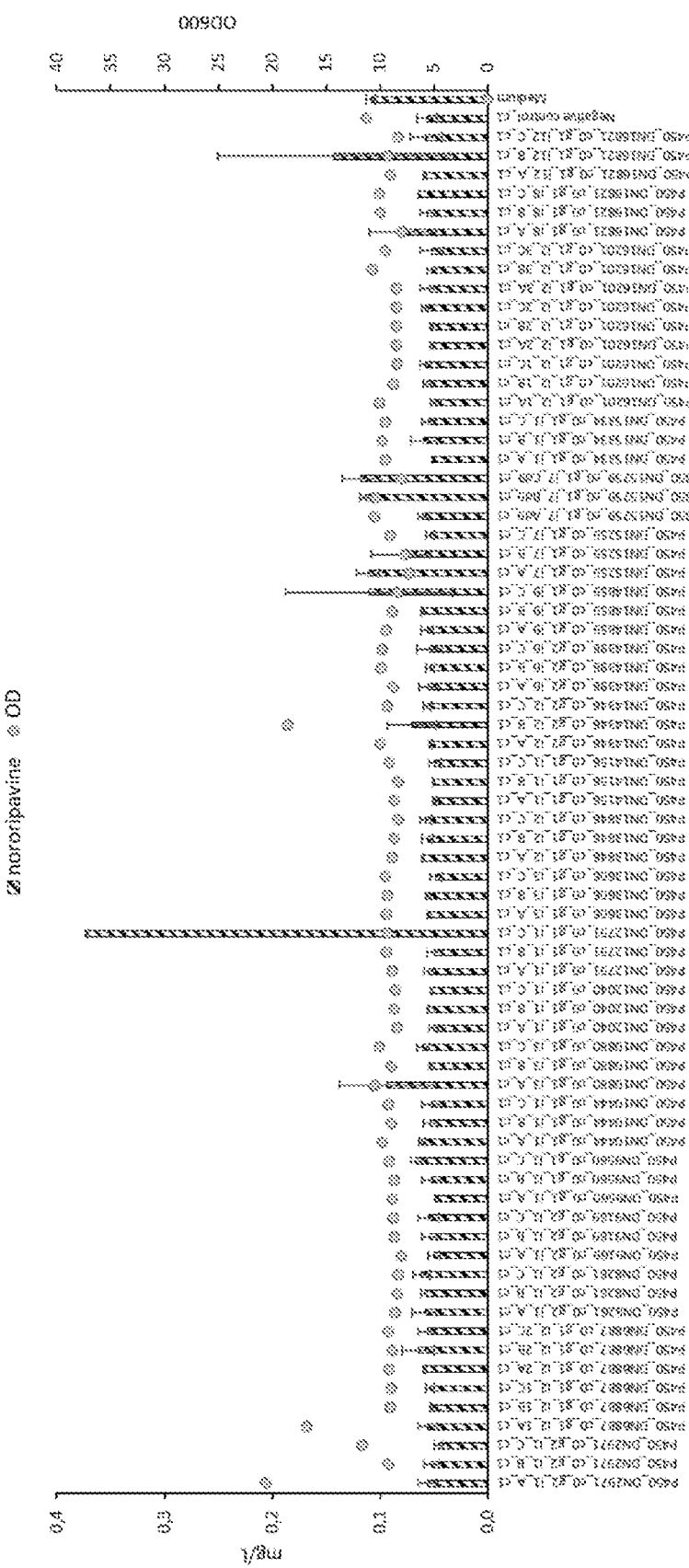
FIG. 6: Screening of oripavine N-demethylation by *S. cerevisiae* strains expressing cytochrome P450 candidates from *Thamnostylum piriforme* in combination with CPRs from *Cunninghamella elegans, Gibberella fujikuroi* and *S. cerevisiae*. Cells were fed with 0.5 mM oripavine in selective medium containing 0.1 M potassium phosphate pH 7 and grown at 30° C. with shaking at 300 rpm for 72 h.

Yeast strain EVST25898 expressing *T. piriforme* cytochrome P450 gene candidates together with the CPRs from *C. elegans, G. fujikuroi* and *S. cerevisiae* were grown in 0.5 ml SC-His-Leu-Ura medium containing 0.1 M potassium phosphate buffer pH 7 and 0.5 mM oripavine. After 72 h of growth at 30° C. with shaking at 300 rpm, 100 µl-supernatants were harvested, treated as described above and subjected to LC-MS analysis of nororipavine. P450_DN12791_c0_g1_C was identified as an oripavine N-demethylase (FIG. 6). Other potential candidates such as P450_DN10880_c0_g1_i3_A, P450_DN14346_c0_g2_i2_B, P450_DN14859_c0_g1_i9_C and P450_DN16821_c0_g1_i12_B were re-tested for oripavine N-demethylation and found not to perform better than the negative control strain under the conditions used (data not shown).

Bioconversion of Thebaine and Oripavine by *S. cerevisiae* Harboring Native and Codon Optimized Fungal N-Demethylase Candidates in Combination with the CPR from *C. elegans*

Figure 7:
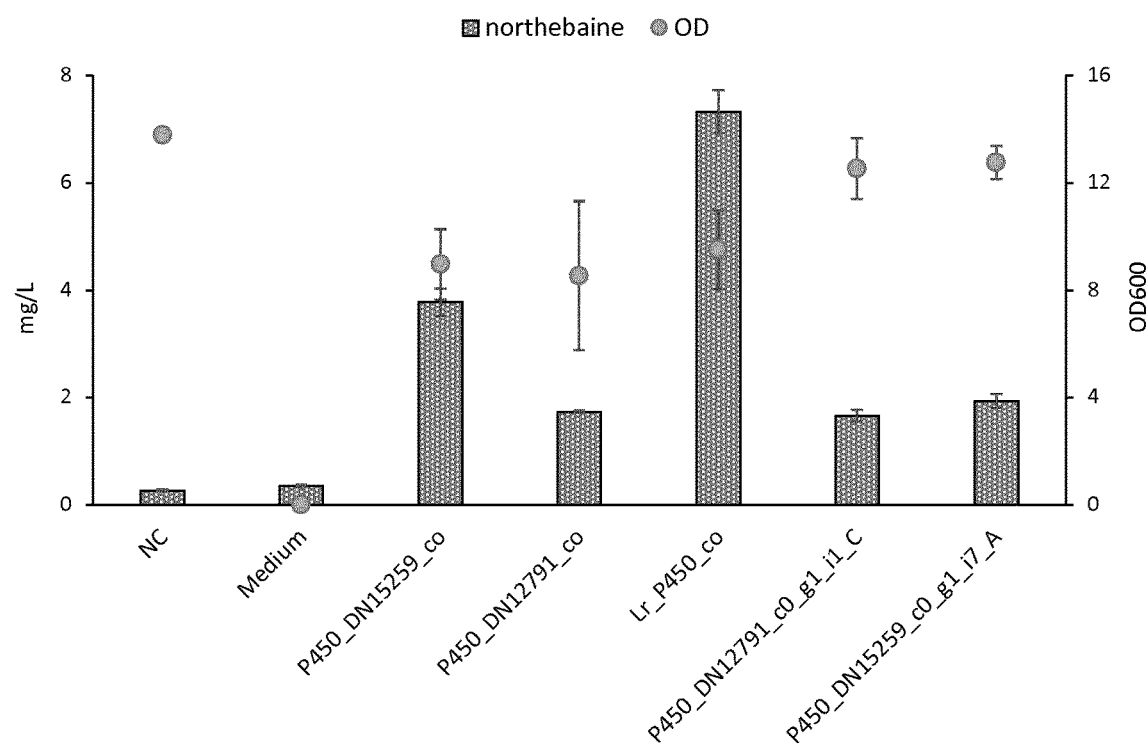
FIG. 7: N-demethylation of thebaine by *S. cerevisiae* strains expressing either native *Thamnostylum piriforme* P450_DN15259_c0_g1_i7_A, P450_DN12791_c0_g1_i1_C or codon-optimized P450_DN15259_co, P450_DN12791_co, Lr_P450_co (from *Lichtheimia ramosa*) in combination with the CPR from *Cunninghamella elegans*. Cells were fed with 0.5 mM thebaine in selective medium containing 0.1 M potassium phosphate buffer pH 7 and grown at 30° C. with shaking at 300 rpm for 72 h.
Figure 8:
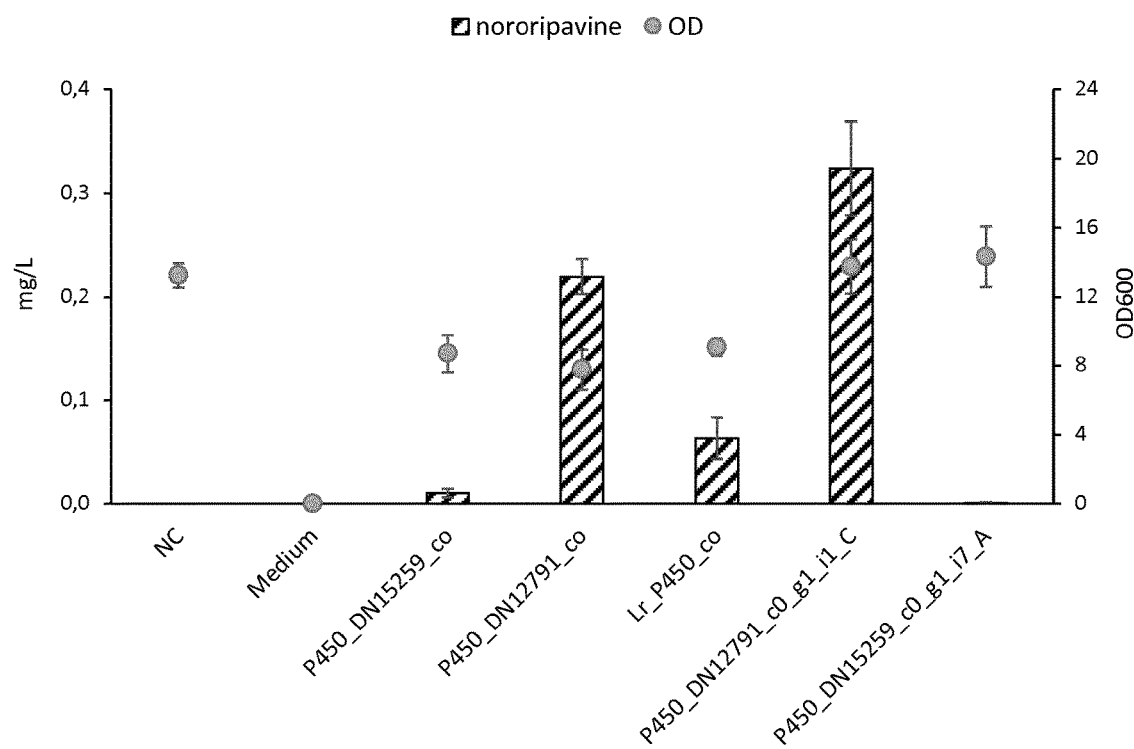
FIG. 8: N-demethylation of oripavine by *S. cerevisiae* strains expressing either native *Thamnostylum piriforme* P450_DN15259_c0_g1_i7_A, P450_DN12791_c0_g1_i1_C or codon-optimized P450_DN15259_co, P450_DN12791_co, Lr_P450_co (from *Lichtheimia ramosa*) in combination with the CPR from *Cunninghamella elegans*. NC: Negative control strain. Cells were fed with 0.5 mM oripavine in selective medium containing 0.1 M potassium phosphate buffer pH 7 and grown at 30° C. with shaking at 300 rpm for 72 h.

Yeast strain EVST25898_co-expressing Cel_CPR_co and five cytochrome P450 genes separately, namely P450_DN15259_c0_g1_i7_A, P450_DN12791_c0_g1_C, P450_DN15259_co, P450_DN12791_co or P450 from *Lichtheimia ramosa* (Lr_P450_co), were grown in SC-His-Leu-Ura medium containing 0.1 M potassium phosphate buffer pH 7 and either 0.5 mM thebaine or oripavine. After 72 h of growth at 30° C. with shaking at 300 rpm, 100 µl-supernatants were harvested, treated as described above and subjected to LC-MS analysis. Northebaine and nororipavine titers are shown in FIGS. 7 and 8, respectively. Yeast codon-optimized P450_DN15259_co yielded 2-fold higher northebaine titers than the native P450_DN15259_c0_g1_i7_A. Lr_P450_co yielded more than 7 mg/L northebaine, equivalent to 2-fold higher northebaine titers compared to P450_DN15259_co. Thebaine N-demethylation activity of P450_DN12791_co was lower, with no significant difference between the codon optimized and non-codon optimized versions (FIG. 7). N-demethylase activity of the five tested P450 candidates towards oripavine was about 20-fold lower compared to that towards thebaine, with the highest nororipavine titers being obtained from yeast strains harboring P450_DN12791_c0_g1_C and P450_DN12791_co (FIG. 8).

Example 7. Bioinformatic Identification of Mammalian CYP450 Enzymes

Human CYP3A4, CYP3A5 and CYP2C8 have been reported as having opioid N-demethylation activity in studies with liver microsomes. Initially a set of immediate homologs of the human sequences were explored for sequence activity relationships.

BLAST searches were conducted with human CYP3A4, CYP3A5 and CYP2C8. The top 250 sequences in each case were aligned with Clustal Omega and a phylogenetic tree generated. Genes were then selected based on phylogeny positions.

To this end, 5 CYP3A4, 4 CYP3A5 and 4 CYP2C8 gene sequences have been selected for evaluation as a first part in this project.

Example 8. Sourcing of Mammalian CYP450 Enzymes, Cloning and Expression in Yeast The mammalian cytochrome P450s belonging to families 3A4 and 2C8 identified above (Tables 8, 10) were codon optimized for *Saccharomyces cerevisiae* and synthesized by TWIST Bioscience. The mammalian cytochrome P450s belonging to family 3A5 (Table 9) were codon optimized for *Saccharomyces cerevisiae* and synthesized by GeneArt® Gene Synthesis (ThermoFischer Scientific). Each cytochrome P450 enzyme was co-expressed with a human NADPH cytochrome P450 reductase (Table 1) and with the cytochrome b5 isoform 1 from *Homo sapiens* (Table 11), both codon optimized for *Saccharomyces cerevisiae* and synthesized by GeneArt® Gene Synthesis (ThermoFischer Scientific).

Each of the cytochrome P450 genes and the human NADPH cytochrome P450 reductase (CPR) were cloned into the replicative plasmid pEVE3307 containing a chromosomal replication origin for yeast (ARS), a centromere (CEN) of a yeast chromosome, a HIS3 yeast selection marker, an expression cassette consisting of the constitutive promoter PGK1 and CYC1 terminator, and an expression cassette consisting of the TEF1 promoter and ADH1 terminator. More specifically, the human CPR was PCR amplified with primers EVPR18206 and EVPR18207 (Table 12) containing the restriction sites HindIII and SacII, respectively. The PCR fragment was subsequently digested with SacII, followed by treatment with DNA Polymerase I, Large (Klenow) Fragment to generate blunt ends, followed by digestion with HindIII.

The obtained fragment was then cloned into pEVE3307 previously digested with AarI and PmeI, placing the human CPR between TEF1 promoter and CYC1 terminator, and generating plasmid pEV30967.

The cytochrome P450 genes were provided flanked by HindIII and SacII restriction sites by the synthesis companies. The fragments were digested with HindIII/SacII and cloned into pEV30967 previously digested with the same restriction enzymes, placing the human CPR between PGK1 promoter and ADH1 terminator, and originating plasmids pEV31021, pEV31022, pEV31023, pEV31024, pEV31025, pEV31026, pEV31027, pEV31028, pEV31029, pEV32390, pEV32391, pEV32392, pEV32393. The human cytochrome b5 was cloned into the replicative plasmid pEVE2120 containing a chromosomal replication origin for yeast (ARS), a centromere (CEN) of a yeast chromosome, a URA3 yeast selection marker and an expression cassette consisting of the constitutive promoter PGK1 and ADH2 terminator. More specifically, a HindIII/SacII digested cytochrome b5 was cloned into pEVE2120 previously digested with the same restriction enzymes, generating plasmid pEV31030.

Plasmids were transformed into strain background EVST25898 (genotype MATalpha his3Δ0 leu2Δ0 ura3Δ0 aro3Δ::pTEF1-ARO4(K229L)-tCYC1::pPGK1-ARO7(T266L)-tADH1::KI CAT5-91Met GAL2 ho MIP1-661Thr SAL1-1 YORWΔ22::npBIO1nt-npBIO6nt) using the lithium acetate method (Gietz et al. 2002. Methods Enzymol. Vol 350, p 87-96). Transformants were selected in synthetic complete (SC) medium lacking histidine and uracil.

Example 9. Cultivation of Yeast Strains

Yeast cells expressing the mammalian cytochrome P450s (Tables 8, 9, 10), the human CPR (Table 1) and the human cytochrome b5 (Table 11) were grown in Erlenmeyer shake flasks containing 20 mL SC medium lacking histidine and uracil. After approximately 20 hours at 30° C. with shaking at 160 rpm, an OD600 of 15-17 was reached. A number of cells equivalent to 220-240 OD units was harvested by centrifugation at 3000 g for 5 minutes, washed and resuspended in 3 mL water. The cell suspension was divided in three screw-cap-tubes (each containing approximately 75-80 OD units), centrifuged at 8000 g for 3 minutes and the supernatant removed. Cells were kept on ice to continue with in vitro assays, or frozen at −80° C. for further experiments.

Example 10. In Vitro Assays for Bioconversion of Several Substrates

Approximately 75-80 OD units of cell pellets kept on ice were disrupted in 0.8 mL lysis buffer (100 mM potassium phosphate buffer pH 7.5, 1.2 M sorbitol, 100 mM NaCl, 0.5 mM fresh PMSF, 1 mM DTT, 1 tablet protease cocktail inhibitor and water to final 50 mL) and 0.5 mL glass beads. Cells were disrupted in a Precellys homogenizer for 3×25s keeping the temperature at 5-10° C.

The in vitro reactions were done in a final volume of 0.2 mL with 0.096 mL reaction buffer (100 mM potassium phosphate buffer pH 7, 5 mM NADP+, 25 mM glucose-6-phosphate, 5 µg/mL G6P dehydrogenase, 1 mM MgCl₂) and 0.1 mL crude cell extract. The reactions were initiated by addition of 0.2 mM substrate in DMSO, and incubated for approximately 20 hours at 30° C. The substrates tested for N-demethylation include: salutaridine, salutaridinol, thebaine, oripavine, morphine and codeine. The assays were terminated by addition of 0.2 mL methanol with 1% acetic acid, followed by centrifugation at 20000 g for 2 minutes. A volume of 0.1 mL of supernatant was analysed by LC-MS for the respective N-demethylated compounds.

Figure 9:
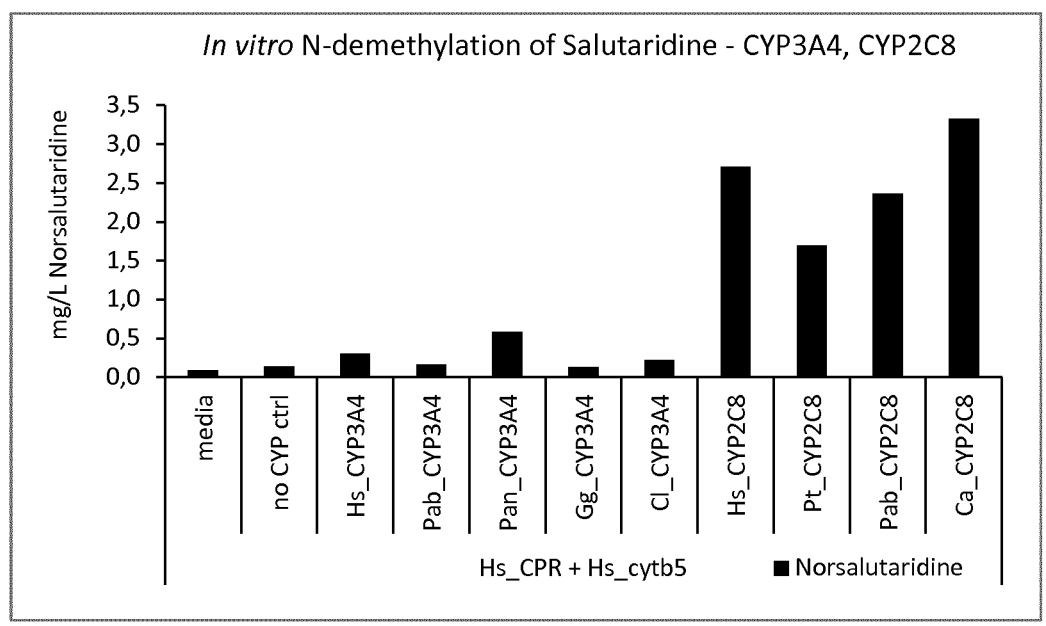
FIG. 9: In vitro N-demethylation of salutaridine by mammalian cytochrome P450s of families 3A4 and 2C8. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM salutaridine, for 48 h at 30° C. The control strain lacked cytochrome P450.
Figure 14:
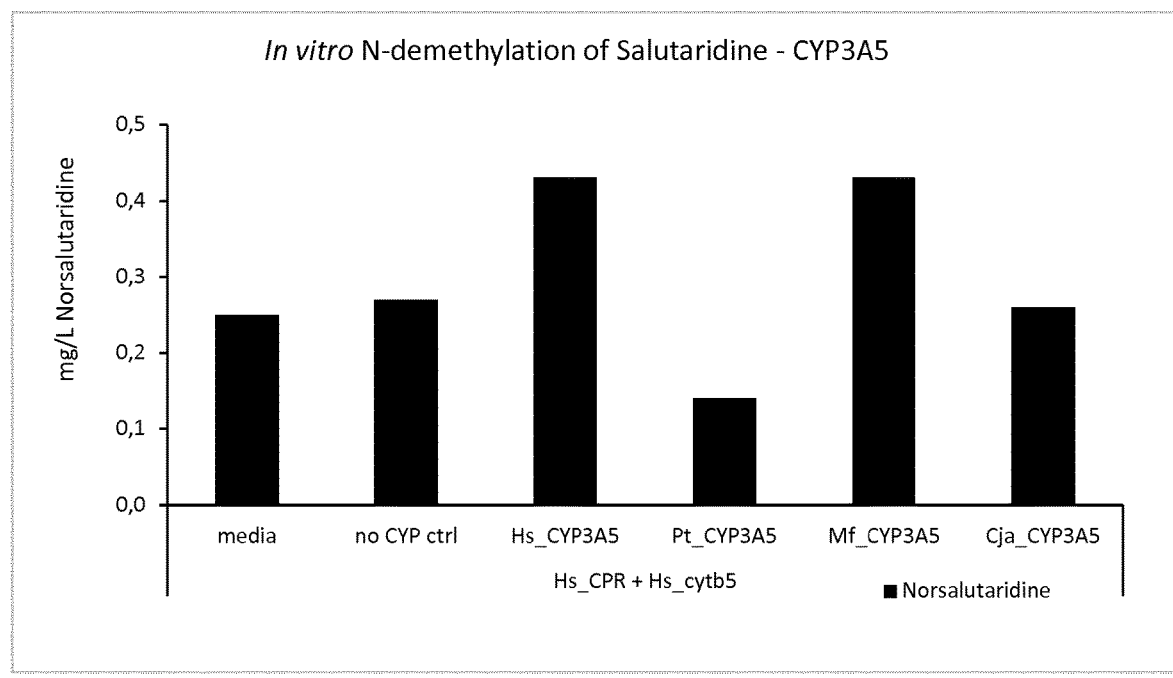
FIG. 14: In vitro N-demethylation of salutaridine by mammalian cytochrome P450s of family 3A5. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM salutaridine, for 48 h at 30° C. The control strain lacked cytochrome P450.
Figure 15:
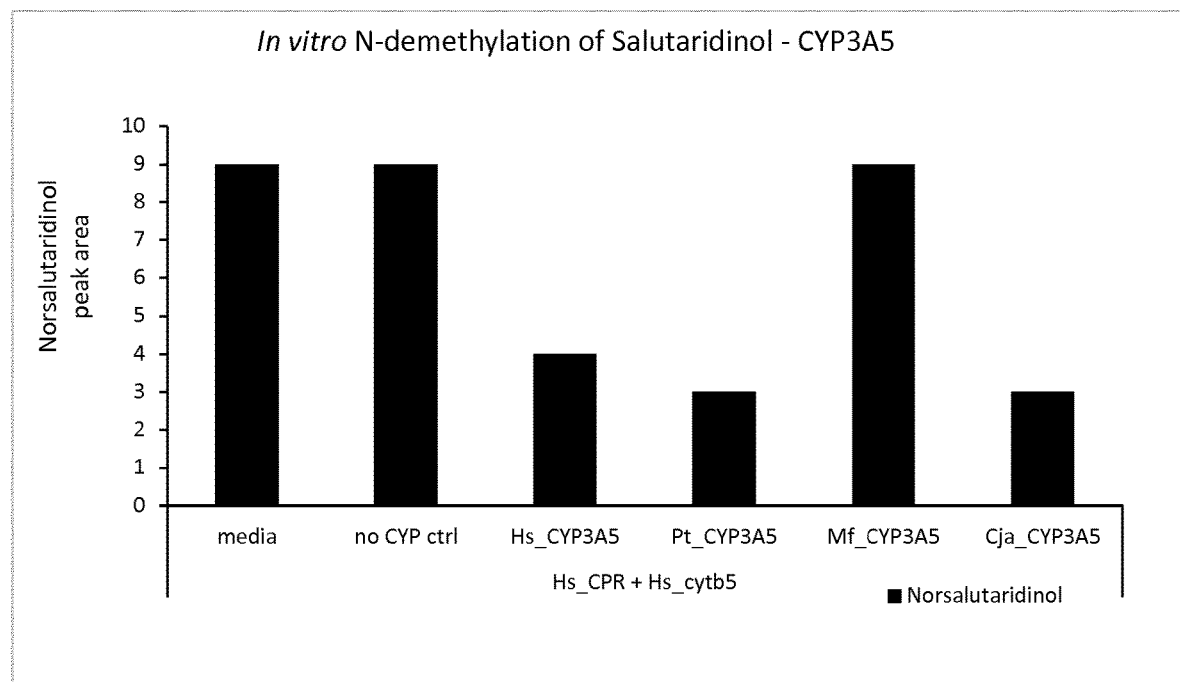
FIG. 15: In vitro N-demethylation of salutaridinol by mammalian cytochrome P450s of family 3A5. Crude cell lysates were prepared from yeast strains overexpressing a mammalian cytochrome P450 together with a human NADPH cytochrome P450 reductase, and a human cytochrome b5. The reactions occurred at pH7 in the presence of 200 μM salutaridinol, for 48 h at 30° C. The control strain lacked cytochrome P450.

In vitro N-demethylation activity of the tested mammalian cytochrome P450s on salutaridine was detected for Hs_CYP3A4, Pan_CYP3A4, Hs_CYP2C8, Pt_CYP2C8, Pab_CYP2C8, Ca_CYP2C8 (FIG. 9), Hs_CYP3A5, Mf_CYP3A5 (FIG. 14) compared to the negative control strain without cytochrome P450s.

Figure 10:
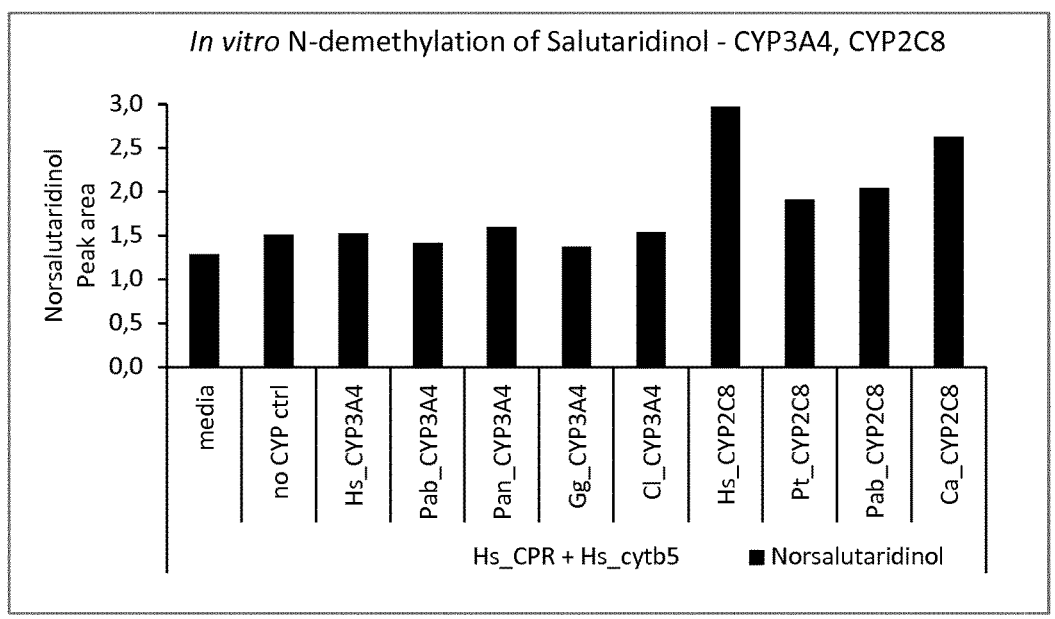
FIG. 10: In vitro N-demethylation of salutaridinol by mammalian cytochrome P450s of families 3A4 and 2C8. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM salutaridinol, for 48 h at 30° C. The control strain lacked cytochrome P450.

In vitro N-demethylation activity of the tested mammalian cytochrome P450s on salutaridinol was detected for Hs_CYP2C8, Ca_CYP2C8 (FIG. 10) compared to the negative control strain without cytochrome P450s.

Figure 11:
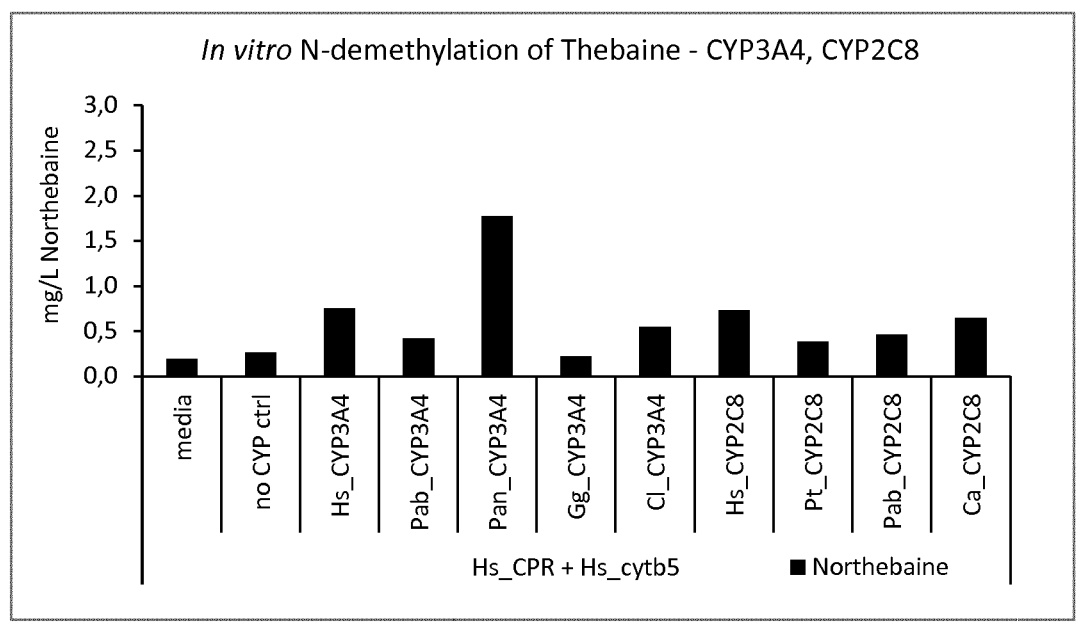
FIG. 11: In vitro N-demethylation of thebaine by mammalian cytochrome P450s of families 3A4 and 2C8. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM thebaine, for 48 h at 30° C. The control strain lacked cytochrome P450.
Figure 16:
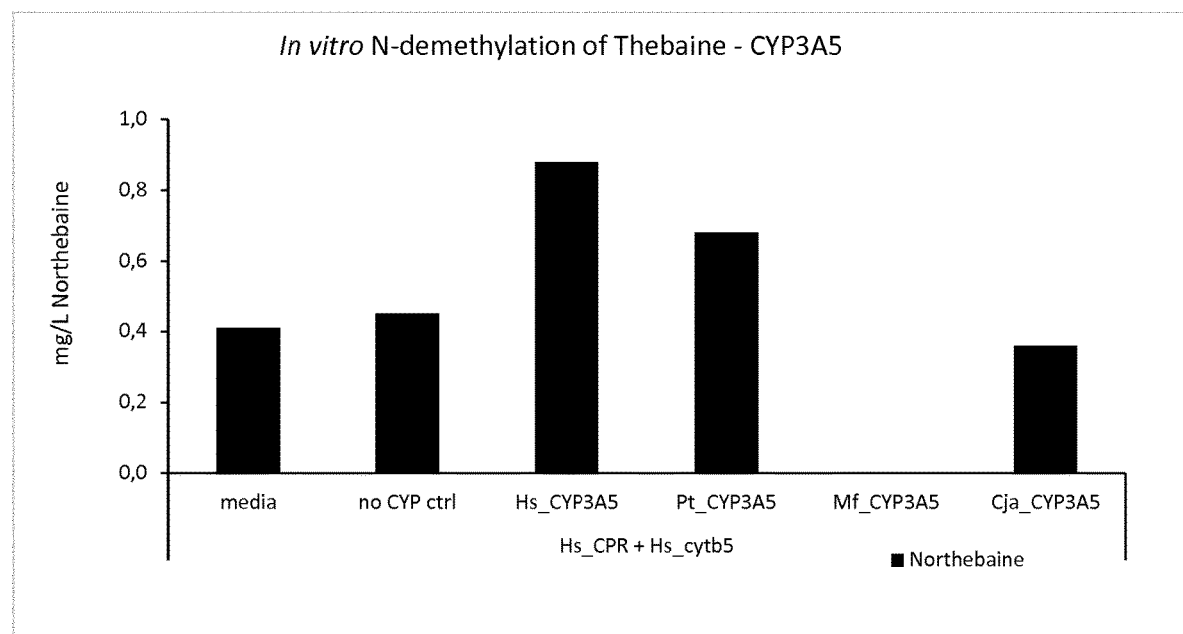
FIG. 16: In vitro N-demethylation of thebaine by mammalian cytochrome P450s of family 3A5. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM thebaine, for 48 h at 30° C. The control strain lacked cytochrome P450.

In vitro N-demethylation activity of the tested mammalian P450s on Thebaine was detected for Hs_CYP3A4, Pab_CYP3A4, Pan_CYP3A4, Cl_CYP3A4, Hs_CYP2C8, Pab_CYP2C8, Ca_CYP2C8 (FIG. 11), Hs_CYP3A5, Pt_CYP3A5 (FIG. 16) compared to the negative control strain without P450s.

Figure 12:
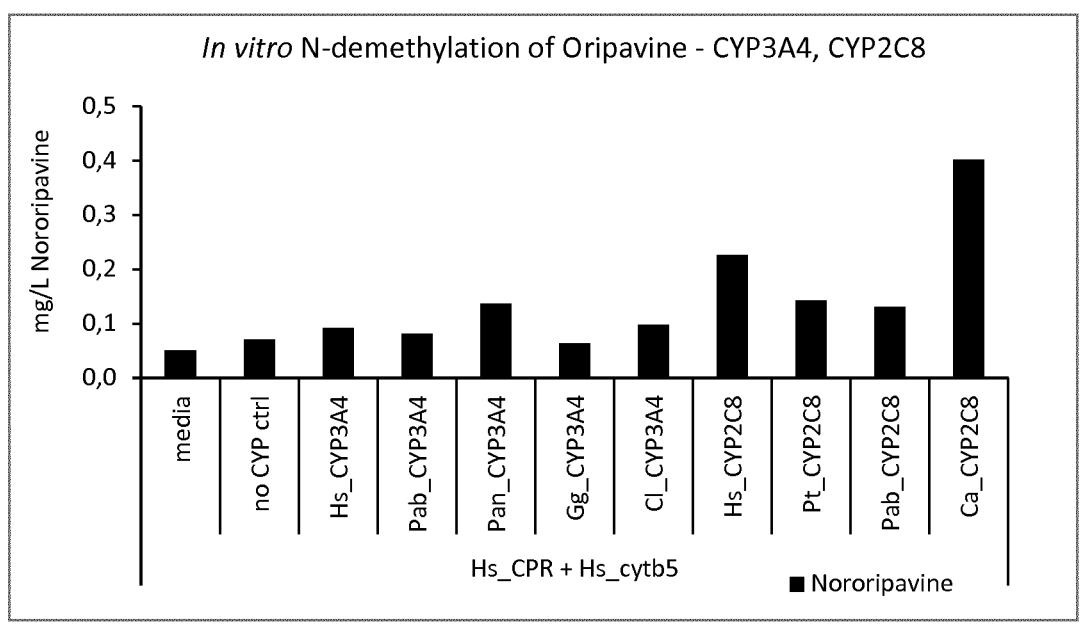
FIG. 12: In vitro N-demethylation of oripavine by mammalian cytochrome P450s of families 3A4 and 2C8. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM oripavine, for 48 h at 30° C. The control strain lacked cytochrome P450.
Figure 17:
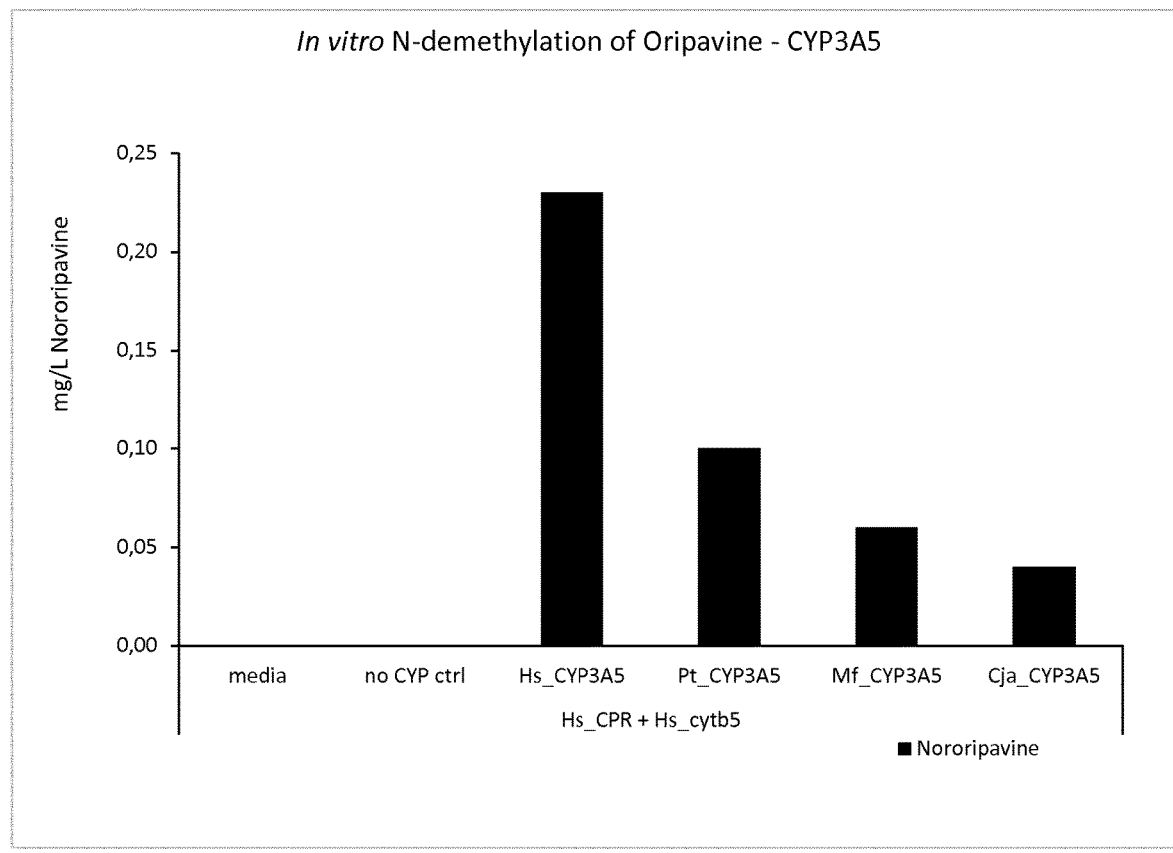
FIG. 17: In vitro N-demethylation of oripavine by mammalian cytochrome P450s of family 3A5. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM oripavine, for 48 h at 30° C. The control strain lacked cytochrome P450.

In vitro N-demethylation activity of the tested mammalian cytochrome P450s on oripavine was detected for Hs_CYP3A4, Pan_CYP3A4, Cl_CYP3A4, Hs_CYP2C8, Pt_CYP2C8, Pab_CYP2C8, Ca_CYP2C8 (FIG. 12), Hs_CYP3A5, Pt_CYP3A5, Mf_CYP3A5, Cja_CYP3A5 (FIG. 17) compared to the negative control strain without cytochrome P450s.

Figure 13:
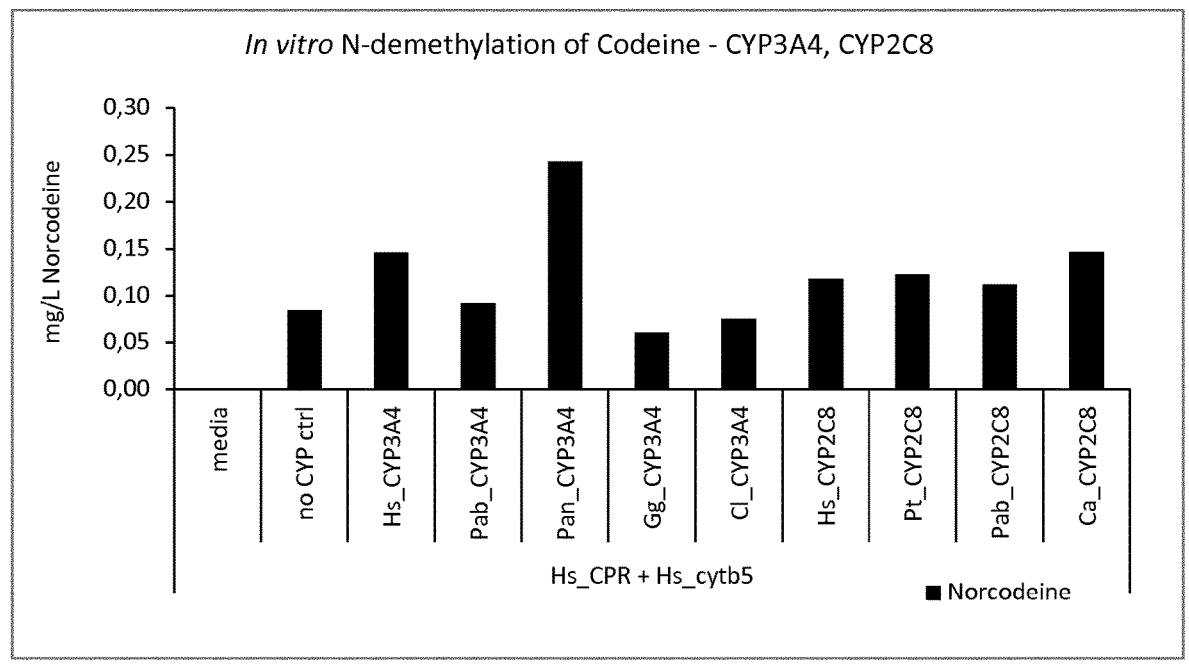
FIG. 13: In vitro N-demethylation of codeine by mammalian cytochrome P450s of families 3A4 and 2C8. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM codeine, for 48 h at 30° C. The control strain lacked cytochrome P450.
Figure 18:
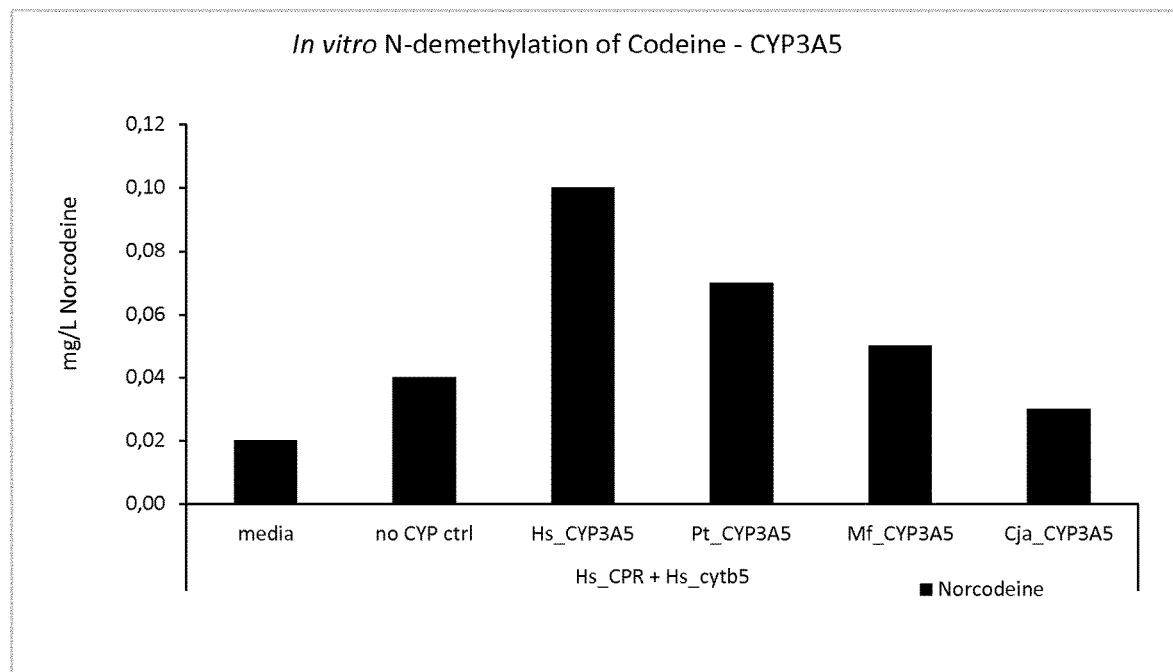
FIG. 18: In vitro N-demethylation of codeine by mammalian cytochrome P450s of family 3A5. Crude cell lysates were prepared from yeast strains overexpressing a mammalian cytochrome P450 together with a human NADPH cytochrome P450 reductase, and a human cytochrome b5. The reactions occurred at pH 7 in the presence of 200 μM codeine, for 48 h at 30° C. The control strain lacked cytochrome P450.

In vitro N-demethylation activity of the tested mammalian cytochrome P450s on codeine was detected for Hs_CYP3A4, Pan_CYP3A4, Hs_CYP2C8, Pt_CYP2C8, Pab_CYP2C8, Ca_CYP2C8 (FIG. 13), Hs_CYP3A5, Pt_CYP3A5, Mf_CYP3A5 (FIG. 18) compared to the negative control strain without cytochrome P450s.

Example 11. Measurements of Bioconversion Substrates and Products by LC/MS LC-MS/MS Analysis of Nor-Compounds Stock solutions for all compounds were prepared in DMSO at 1 g/L. A series of calibration solutions at 4 mg/L, 2 mg/L, 1 mg/L, 0.5 mg/L, 0.25 mg/L, 0.125 mg/L, 62.5 µg/L and 31.25 µg/L in the culture medium was prepared from this stock solution. Caffeine (Sigma) was added as internal standard to a concentration of 1 mg/L and samples were injected into the UPLC-TQD (Waters).

The LC-MS method was as follows: Mobile Phase A: water+0.1% formic acid; Mobile Phase B: acetonitrile+0.1% formic acid; Column: Aquity BEH C18100×2.1 mm (Waters).

The elution gradient is shown in Table 3 and the LC-MS conditions are given in Table 14.

Table 15 shows the mass spectrometer source and detector parameters.

Table 16 shows the target compounds, their parent ion, daughter ion (MRM) as well as dwell times, cone voltages and collision energies used.

Example 12. Preparation of Compound MeO-I-MCP (Step A1)

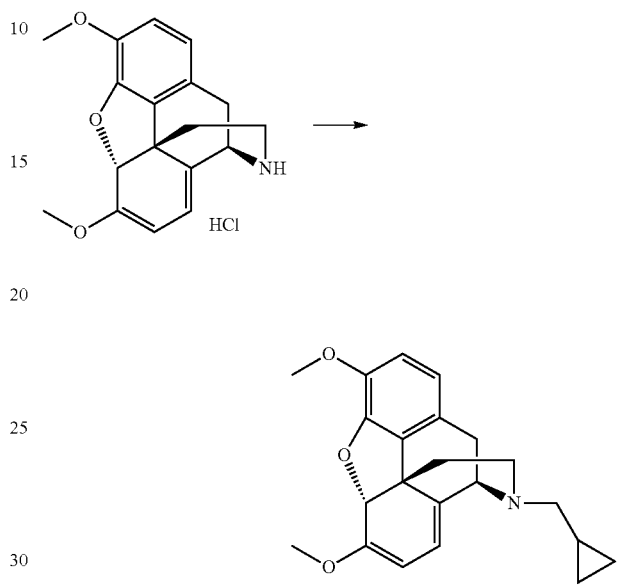

A 100 mL 3-necked flask was charged with Compound MeO-I-H (5.5 g, 16.5 mmol), cyclopropane carboxaldehyde (2.5 mL, 33 mmol), dichloro(p-cymene)ruthenium(II) dimer (100 mg, 0.165 mmol), triethylamine (13.75 mL, 99 mmol), and acetonitrile (50 mL) under a nitrogen atmosphere. The suspension was stirred at room temperature. Formic acid (7.78 mL, 206 mmol) was added slowly. The resulting mixture was heated at 60° C. for 2.5 h. The mixture was cooled to room temperature and concentrated under vacuum. The residue was partitioned between toluene and a 1 N NaOH aqueous solution. The aqueous layer was extracted twice with toluene. The combined organic layers were washed twice with water and then concentrated under vacuum to afford quantitatively Compound MeO-I-MCP (6.2 g).

N-Cyclopropylmethyl-Northebaine

HPLC 92.5% at 215 nm.

MS (ES-API pos) m/z 352.2 (M+H).

$^1$H NMR (300 MHz, CDCl$_3$) δ [ppm] 6.64 (d, J=8.2 Hz, 1H), 6.57 (d, J=8.2 Hz, 1H), 5.54 (d, J=6.5 Hz, 1H), 5.27 (s, 1H), 5.02 (d, J=6.5 Hz, 1H), 3.91 (d, J=6.4 Hz, 1H), 3.83 (s, 3H), 3.58 (s, 3H), 3.24 (d, J=18H, 1H), 2.65-2.87 (m, 3H), 2.47 (d, J=6.0 Hz, 2H), 2.19 (dt, J=5.8 and 12.3 Hz, 1H), 1.70 (d, J=12 Hz, 1H), 0.90 (m, 1H), 0.54 (m, 2H), 0.15 (m, 2H).

$^{13}$C NMR (75 MHz, CDCl$_3$) δ [ppm] 152.5, 142.8, 133.6, 132.6, 127.8, 119.2, 112.8, 111.7, 96.0, 89.2, 59.1, 58.6, 56.4, 54.9, 46.6, 44.3, 36.8, 30.6, 9.5, 3.9, 3.7.

Example 13. Preparation of Compound MeO-I-MCP (step A2)

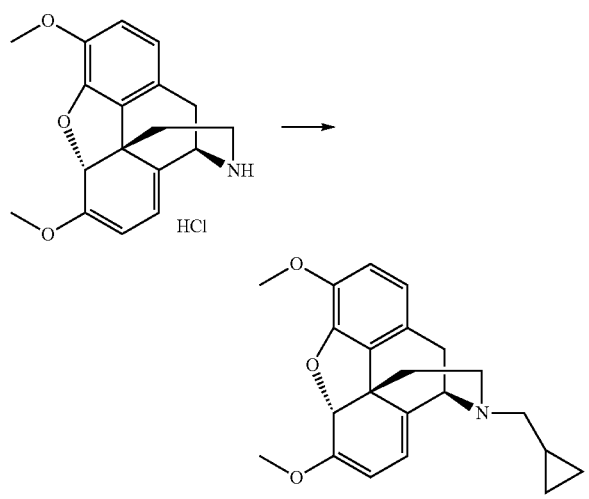

Triethylamine (1.6 mL, 12 mmol) was added to a suspension of Compound MeO-I-H (1.0 g, 3 mmol) in dichloromethane (25 mL). The mixture was cooled in an ice-water bath and cyclopropanecarboxylic acid chloride (0.35 mL, 3.6 mmol) was added dropwise. The cooling bath was removed and the mixture was stirred at room temperature overnight. The mixture was washed with a 1 N HCl aqueous solution, then with brine, dried with sodium sulfate and concentrated to a brown solid. The residue was dissolved in dry THF (10 mL) and slowly added to a stirred slurry of LiAlH$_4$ (0.20 g, 5.4 mmol) in anhydrous THF. The reaction mixture was heated at 60° C. for 1 h and then cooled in an ice-water bath. Wet diethyl ether was added to the mixture until there was no more bubbling. The mixture was filtered and the precipitate was washed several times with THF. The filtrate was concentrated under vacuum to give Compound MeO-I-MCP (0.80 g, 76%).

N-Cyclopropylmethyl-Northebaine

HPLC 89.8% at 215 nm.

NMR and MS data were in agreement with those obtained from Example 12.

Example 14. Preparation of Compound MeO-I-MCP (Step A3)

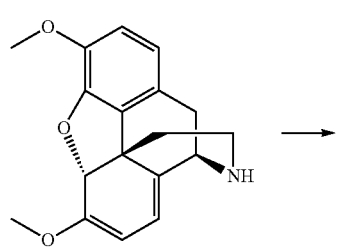

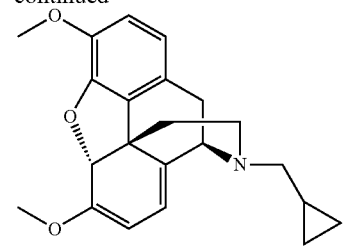

A 50 mL 3-necked flask was charged with Compound MeO-I-H (0.59 g, 2 mmol), cyclopropylmethylbromide (0.54 g, 4 mmol), triethylamine (0.5 g, 5 mmol) and ethanol (15 mL). The mixture was heated to reflux for 3 h. The ethanol was removed under vacuum and the residue was partitioned between dichloromethane and water. The organic layer was dried with sodium sulfate and concentrated under vacuum to obtain Compound MeO-I-MCP as light brown solid (0.60 g, 85% yield).

N-Cyclopropylmethyl-Northebaine

HPLC purity 97% at 215 nm.

MS (ES-API pos) m/z 352.3 (M+H).

NMR data was in agreement with those obtained from Example 12.

Example 15. Preparation of Compound MeO-II-MCP (Step B)

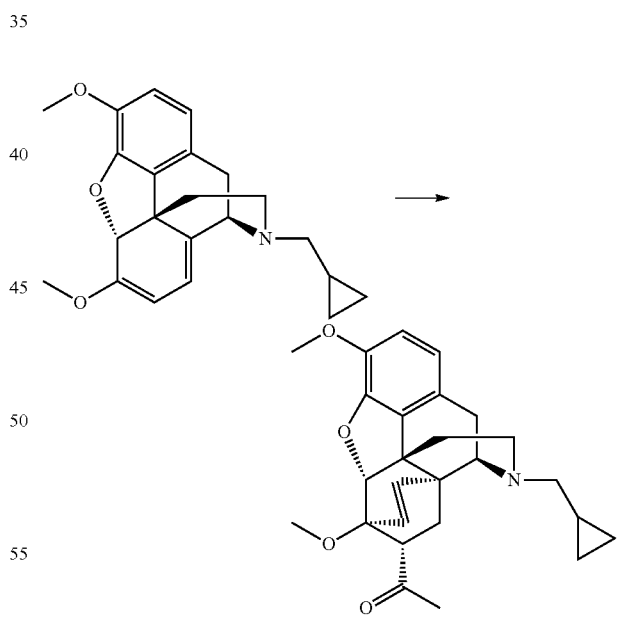

A solution of Compound MeO-I-MCP (5.8 g, 16.5 mmol) and methyl vinyl ketone (12 mL, 144 mmol) in toluene (100 mL) was heated at 80° C. for 16 h. After cooling to room temperature the mixture was concentrated under vacuum to give a brown oily residue (6.5 g), which was purified by column chromatography (120 g SiO$_2$, elution with 0-20% EtOAc in heptane, R$_f$ 0.3) to afford Compound MeO-II-MCP as a colorless solid (6.2 g, 89% yield).

7α-Acetyl-17-cyclopropylmethyl-6,14-endo(etheno) tetrahydro-northebaine

HPLC-purity 92.3% at 215 nm.
MS (ES-API pos) m/z 422.2 (M+H).
$^1$H NMR (300 MHz, CDCl$_3$) δ [ppm] 6.61 (d, J=8.2 Hz, 1H), 6.50 (d, J=8.2 Hz, 1H), 5.89 (d, J=8.8 Hz, 1H), 5.58 (d, J=8.8 Hz, 1H), 4.57 (s, 1H), 3.80 (s, 3H), 3.59 (s, 3H), 3.54 (d, J=6.4 Hz, 1H), 3.10 (d, J=18H, 1H), 2.89-3.03 (m, 2H), 2.66-2.72 (dd, J=4.7 and 11.8 Hz, 1H), 2.29-2.46 (m, 4H), 2.13 (s, 3H), 1.95 (dt, J=5.0 and 12.0 Hz, 1H), 1.83 (dd, J=2.3 and 12.9 Hz, 1H), 1.35 (dd, J=5.9 and 12.3 Hz, 1H), 0.81 (m, 1H), 0.51 (m, 2H), 0.12 (m, 2H).
$^{13}$C NMR (75 MHz, CDCl$_3$) δ [ppm] 209.2, 148.0, 141.7, 136.2 (−), 134.3, 128.3, 125.8 (−), 119.3 (−), 113.5 (−), 95.4 (−), 81.3, 59.8, 57.0 (−), 56.6 (−), 53.5 (−), 50.7 (−), 48.2, 44.0, 43.2, 33.6, 30.5 (−), 30.0, 23.2, 9.5 (−), 4.1, 3.4.

Example 16. Preparation of Compound MeO-IIIB-MCP (step C)

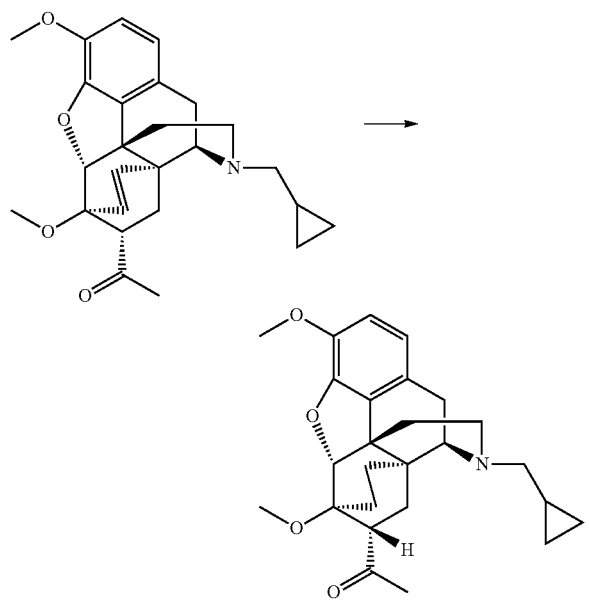

A vigorously stirred mixture of Compound MeO-II-MCP (1.1 g, 2.61 mmol) and Pd/C (10%, 50 mg) in iPrOH (20 mL) was hydrogenated at 80° C. for 16 h under 1 atm. H$_2$ using a hydrogen-filled balloon. The mixture was filtered over Celite and the solid washed with iPrOH. The filtrate was concentrated to 1.1 g oil, which was purified by column chromatography (40 g SiO$_2$, elution 0-25% EtOAc in heptane) to yield Compound MeO-IIIB-MCP (1.0 g, 90% yield).

7α-Acetyl-17-cyclopropylmethyl-6,14-endo(ethano) tetrahydro-northebaine

HPLC-purity 89.3% at 215 nm.
MS (ES-API pos) m/z 424.2 (M+H).
$^1$H NMR (300 MHz, CDCl$_3$) δ [ppm] 6.70 (d, J=7.8 Hz, 1H), 6.56 (d, J=7.8 Hz, 1H), 4.48 (s, 1H), 3.87 (s, 3H), 3.43 (s, 3H), 2.95-3.07 (m, 3H), 2.59-2.78 (m, 2H), 2.21-2.36 (m, 3H), 2.26 (s, 3H), 2.19 (dt, J=5.8 and 12.3 Hz, 1H), 1.51-1.76 (m, 4H), 1.25-1.35 (m, 2H), 0.65-0.85 (m, 2H), 0.48 (m, 2H), 0.09 (m, 2H).
$^{13}$C NMR (75 MHz, CDCl$_3$) δ [ppm] 210.9, 146.8, 141.7, 132.7, 128.8, 119.1, 114.0, 94.7, 77.5, 59.8, 58.4, 56.7, 52.2, 49.7, 46.4, 43.7, 35.4, 35.3, 33.8, 30.3, 28.7, 22.8, 17.4, 9.5, 4.0, 3.4.

Example 17. Preparation of Compound MeO-IIIA-MCP (step D)

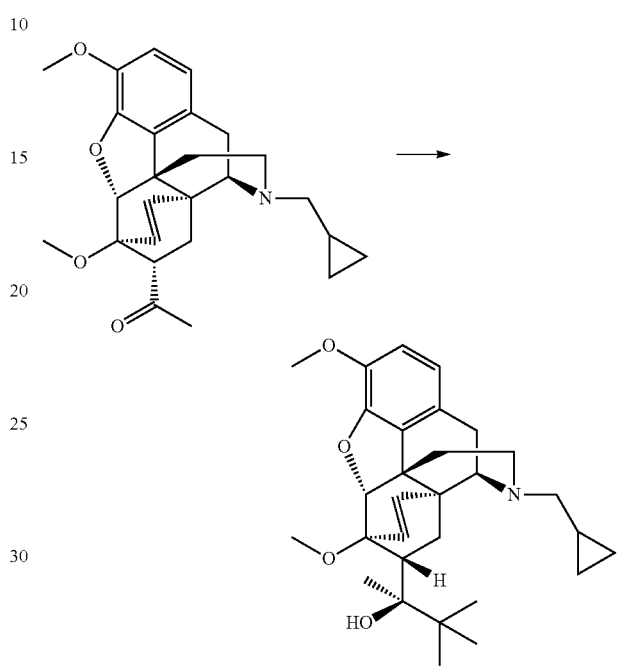

To a magnetically stirred solution of Compound MeO-II-MCP (2.1 g, 5 mmol) in toluene (50 mL) at room temperature was added a solution of tert-butylmagnesium chloride (1.7 M in THF, 20 mL, 34 mmol) over 5 min. The brown solution was stirred at room temperature for 4 h. The mixture was poured in a 10% ammonium chloride aqueous solution (100 mL) and the mixture was extracted with toluene. The extract was dried with sodium sulfate and concentrated to give a waxy solid. Purification by column chromatography (80 g SiO$_2$, 25% EtOAc in Heptane) gave Compound MeO-IIIA-MCP (1 g, 42% yield, R$_f$ 0.6) as a solid. Some starting material (0.32 g, 15%, R$_f$ 0.2) and reduced starting material (0.4 g, 18%, R$_f$ 0.1) were also recovered.

7α-(2-(5)-hydroxy-3,3-dimethyl-2-butyl)-17-cyclopropylmethyl-6,14-endo(etheno)tetrahydro-northebaine HPLC-purity 97.4% at 215 nm.
MS (ES-API pos) m/z 480.3 (M+H).
$^1$H NMR (300 MHz, CDCl$_3$) δ [ppm] 6.61 (d, J=8.2 Hz, 1H), 6.48 (d, J=8.2 Hz, 1H), 5.98 (d, J=8.8 Hz, 1H), 5.64 (s, 1H), 5.43 (d, J=8.8 Hz, 1H), 4.55 (s, 1H), 3.81 (s, 3H), 3.77 (s, 3H), 3.49 (d, J=6.4H, 1H), 3.09 (d, J=18 Hz, 1H), 2.97 (dd, J=12.3 and 8.8 Hz, 1H), 2.64 (m, 1H), 2.35-2.43 (m, 4H), 2.14 (t, J=8.8 Hz, 1H), 1.80-2.0 (m, 2H), 1.00 (s, 9H), 0.80-1.0 (m, 3H), 0.51 (m, 2H), 0.15 (m, 2H).
$^{13}$C NMR (75 MHz, CDCl$_3$) δ [ppm] 148.1, 141.7, 135.5, 134.7, 128.5, 124.8, 119.2, 113.7, 99.0, 84.5, 78.4, 59.5, 56.7, 55.2, 47.1, 45.8, 44.1, 43.1, 39.7, 34.0, 32.2, 26.6, 23.1, 19.6, 9.5, 4.3, 3.2.

Example 18. Preparation of Compound MeO-IV-MCP (Step D)

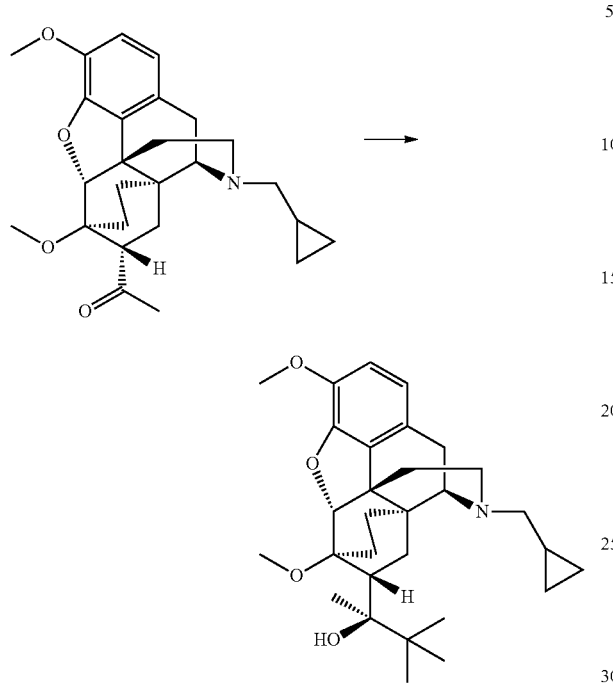

To a magnetically stirred solution of Compound MeO-IIIB-MCP (0.90 g, 2.1 mmol) in dry toluene (25 mL) at room temperature was added dropwise a solution of tert-butyl-magnesium chloride (1.7 M solution in THF, 7.5 mL, 12.75 mmol). The reaction was quenched after 4 h by pouring the mixture into an aqueous solution made of 10% ammonium chloride (50 mL) and ice-water (50 mL). The layers were separated and the aqueous layer was extracted with toluene (3×25 mL). The combined organic layers were washed with brine, dried with sodium sulfate, and concentrated to an oil. Purification by column chromatography (80 g SiO$_2$, elution with 0-20% EtOAc in heptane, R$_f$ 0.5) to yield Compound MeO-IV-MCP as a waxy solid (0.60 g, 60% yield).

7α-(2-(5)-hydroxy-3,3-dimethyl-2-butyl)-17-cyclo-propylmethyl-6,14-endo(ethano)tetrahydro-nor-thebaine HPLC-purity 95.6% at 215 nm.

MS (ES-API pos) m/z 482.4 (M+H).

$^1$H NMR (300 MHz, CDCl$_3$) δ [ppm] 6.69 (d, J=8.2 Hz, 1H), 6.54 (d, J=8.2 Hz, 1H), 5.91 (s, 1H), 4.43 (s, 1H), 3.87 (s, 3H), 3.54 (s, 3H), 2.82-3.02 (m, 3H), 2.60 (dd, J=11.7 and 5.3H, 1H), 2.11-2.38 (m, 5H), 1.97 (dt, J=5.8 and 12.3 Hz, 1H), 1.60-1.85 (m, 3H), 1.36 (s, 3H), 1.25-1.30 (m, 1H), 1.00-1.12 (m, 1H), 1.03 (s, 9H), 0.70-0.83 (m, 2H), 0.48 (m, 2H), 0.10 (m, 2H).

$^{13}$C NMR (75 MHz, CDCl$_3$) δ [ppm] 146.9, 141.6, 132.9, 128.9, 119.1, 114.0, 96.7, 80.7, 79.3, 59.5, 58.3, 56.9, 52.6, 46.2, 43.9, 43.7, 40.4, 35.9, 35.8, 33.4, 29.7, 26.4, 22.8, 20.0, 18.2, 9.5, 4.2, 3.2.

Example 19. Preparation of Compound MeO-IV-MCP (Step C)

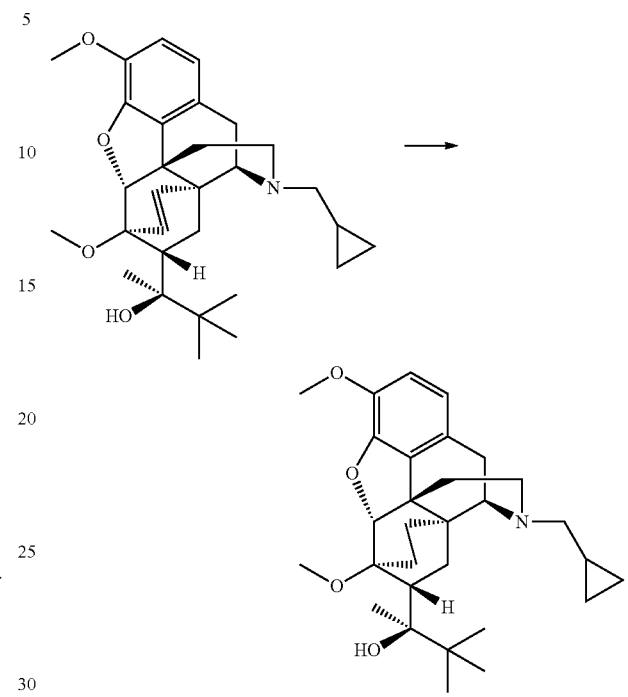

A vigorously stirred mixture of Compound MeO-IIIA-MCP (40 mg, 0.75 mmol), and Pd/C (10%, 10 mg) in iPrOH (10 mL) was hydrogenated at 80° C. for 16 h under 1 atmosphere of hydrogen. The mixture was filtered over Celite. The filtrate was concentrated to give Compound MeO-IV-MCP as a wax (40 mg, 100%).

7α-(2-(S)-hydroxy-3,3-dimethyl-2-butyl)-17-cyclo-propylmethyl-6,14-endo(ethano)tetrahydro-nor-thebaine HPLC-purity 83% at 254 nm.

MS (ES-API pos) m/z 482.3 (M+H).

The NMR data were in agreement with those obtained for Example 18.

Example 20. Preparation of Compound HO-IIIA-MCP (step E)

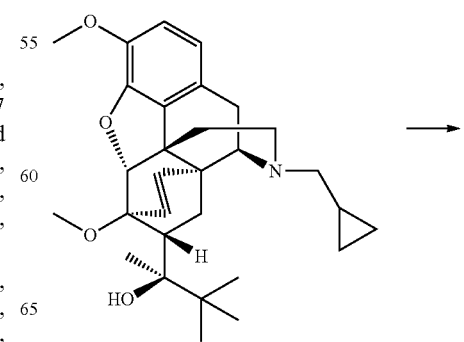

Example 21. Preparation of Buprenorphine (Step E)

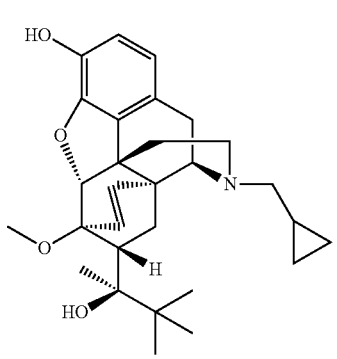

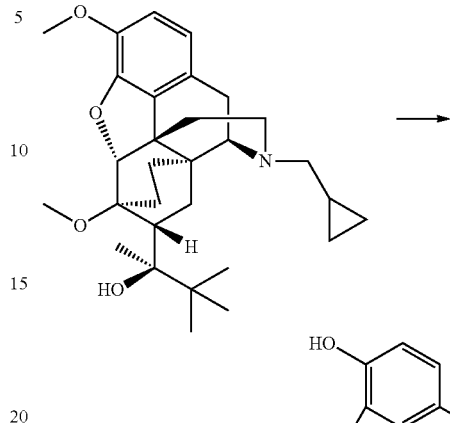

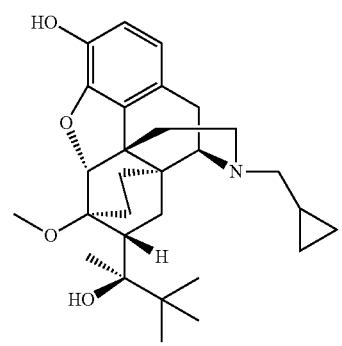

To a magnetically stirred solution of KOtBu (1.12 g, 10 mmol) and DMSO (10 mL) was added 1-dodecanethiol (2.03 g, 10 mmol). The resulting suspension was heated to 70° C. and a solution of Compound MeO-IIIA-MCP (0.90 g, 1.87 mmol) in DMSO (12 mL) was added. The resulting solution was heated at 110° C. for 16 h. The mixture was cooled to room temperature. Heptane (40 mL), EtOAc (10 mL) and a 1 N NH$_4$Cl aqueous solution (50 mL) were added. The layers were separated. The aqueous layer was washed twice with a heptane/EtOAc (4/1) mixture. The acidic aqueous layer was neutralized to pH 7-8 by careful addition of solid NaHCO$_3$ and extracted with EtOAc. The extract was washed with brine, dried with sodium sulfate and concentrated to an oil. Crystallization in MeOH and filtration afforded Compound HO-IIIA-MCP (240 mg, 28%) after drying. The mother liquor was concentrated and the residue purified by column chromatography to afford additional Compound HO-IIIA-MCP (270 mg, 31%), hence a total Compound HO-IIIA-MCP (510 mg, 59%) was obtained.

7α-(2-(S)-hydroxy-3,3-dimethyl-2-butyl)-17-cyclopropylmethyl-6,14-endo(etheno)tetrahydro-nororipavine HPLC-purity 94.1% at 215 nm.
MS (ES-API pos) m/z 466.2 (M+1).
$^1$H NMR (300 MHz, CDCl$_3$) δ [ppm] 6.58 (d, J=8.2 Hz, 1H), 6.44 (d, J=8.2 Hz, 1H), 5.96 (d, J=8.8 Hz, 1H), 5.64 (s, 1H), 5.43 (d, J=8.8 Hz, 1H), 4.89 (br s, 1H), 4.58 (s, 1H), 3.75 (s, 3H), 3.49 (d, J=6.0H, 1H), 3.08 (d, J=18 Hz, 1H), 2.97 (dd, J=12.3 and 8.8 Hz, 1H), 2.65 (m, 1H), 2.31-2.43 (m, 4H), 2.15 (t, J=8.8 Hz, 1H), 1.80-2.0 (m, 2H), 1.00 (s, 9H), 0.80-1.0 (m, 3H), 0.51 (m, 2H), 0.15 (m, 2H).
$^{13}$C NMR (75 MHz, CDCl$_3$) δ [ppm] 146.6, 137.2, 135.7, 134.5, 128.0, 124.4, 119.7, 116.0, 99.4, 84.5, 78.6, 59.5, 56.7, 55.2, 47.4, 45.8, 44.1, 43.1, 39.7, 33.9, 32.1, 26.6, 23.1, 19.6, 9.5, 4.3, 3.2

A 100 mL 3-necked flask was charged with KOtBu (200 mg, 1.8 mmol) and DMF (10 mL) under a nitrogen atmosphere, and the mixture was heated to 50° C. After the addition of 1-dodecanethiol (0.43 mL, 0.364 mg, 1.8 mmol) a white suspension was formed. Then a solution of Compound MeO-IV-MCP (600 mg, 1.28 mmol) in DMF (10 mL) was added and the resulting solution was heated at 120° C. for 16 h. The mixture was quenched by addition of 50 mL of a 10% citric acid solution to reach pH 4. The mixture was poured in water (50 mL) and washed with toluene (3×25 mL). The aqueous layer was neutralized to pH 7 by the addition of NaOH and extracted with EtOAc (3×25 mL). The combined extracts were dried with sodium sulfate and concentrated to an oil (0.35 g, 59% yield, HPLC 79% purity). Crystallization from wet MeOH (10 mL) gave crystalline buprenorphine (50 mg). The mother liquor was purified by column chromatography (12 g SiO$_2$, elution with 0-25% EtOAc in heptane) and provided additional buprenorphine as white solid (190 mg). A total of 240 mg of buprenorphine (40% yield) was obtained. Analytical data were in agreement with the literature.

Buprenorphine

HPLC-purity 98.8% at 215 nm.
DSC-Melting point 216.7° C. (Lit. 216-218).
MS (ES-API pos) m/z 468.4 (M+H).
$^1$H NMR (300 MHz, CDCl$_3$) δ [ppm] 6.68 (d, J=8.2 Hz, 1H), 6.51 (d, J=8.2 Hz, 1H), 5.88 (s, 1H), 4.88 (br s, 1H), 4.45 (s, 1H), 3.53 (s, 3H), 2.82-3.02 (m, 3H), 2.60 (dd, J=11.8 and 4.7H, 1H), 2.12-2.36 (m, 5H), 1.97 (dt, J=5.3 and 12.3 Hz, 1H), 1.60-1.85 (m, 3H), 1.36 (s, 3H), 1.26-1.36 (m, 1H), 1.03-1.11 (m, 1H), 1.03 (s, 9H), 0.69-0.82 (m, 2H), 0.48 (m, 2H), 0.10 (m, 2H). $^{13}$C NMR (75 MHz, CDCl$_3$) δ [ppm] 145.4, 137.2, 132.6, 128.4, 119.6, 116.3, 97.1, 80.8, 79.5, 59.5, 58.3, 52.5, 46.5, 43.7, 43.7, 40.4, 36.0, 35.8, 33.4, 29.6, 26.4, 22.9, 20.1, 18.2, 9.5, 4.1, 3.2.

Example 22. Preparation of Buprenorphine (Step C)

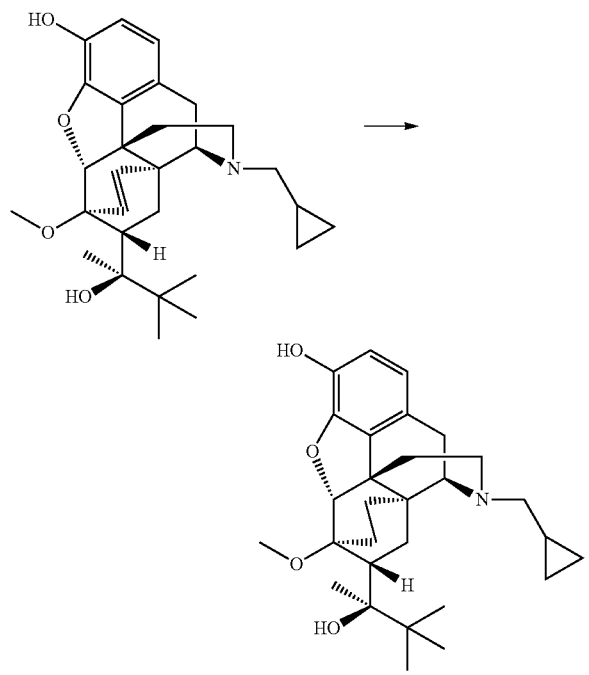

A vigorously stirred mixture of Compound HO-IIIA-MCP (350 mg, 0.75 mmol) and Pd/C (10%, 80 mg, 10 mol % Pd) in iPrOH (20 mL) and water (1 mL) was hydrogenated at 80° C. for 16 h under 1 atm. H$_2$ using a hydrogen-filled balloon. The mixture was filtered over Celite. The filtrate was concentrated to a white foam, which was taken up in MeOH (5 mL) and stirred for 1 h. The solid was collected by filtration and dried under vacuum to give buprenorphine as solid (165 mg, 47%). The mother liquor was concentrated to give more buprenorphine as a solid (180 mg, 51%). A total of 345 mg of buprenorphine (98% yield) was obtained.

Buprenorphine

HPLC-purity 86%.
MS and NMR data were in agreement with those obtained for Example 21.

Example 23. Preparation of Compound HO-I-MCP (Step A1)

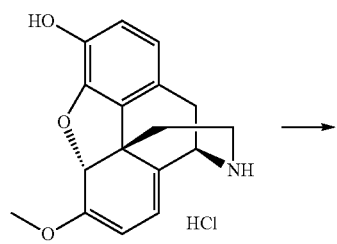

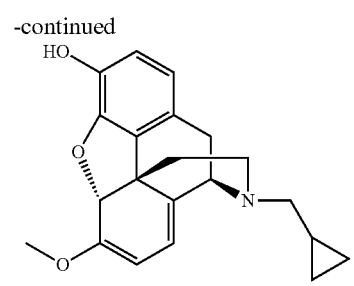

A 50 mL 3-neck round bottom flask was charged with Compound HO-I-H (910 mg, 3.21 mmol), cyclopropane carboxaldehyde (455 mg, 6.49 mmol), triethylamine (1.64 g, 16.22 mmol) and acetonitrile (9 mL), at room temperature and under a nitrogen atmosphere. To the stirred solution was added formic acid (2.4 mL) dropwise, over 10-15 min. After 10 min, di-p-chlorobis[(p-cymene)chlororuthenium(II)] (5 mg, 0.0082 mmol) was added and the mixture was stirred at 50° C. overnight. The volatiles were removed under vacuum and water (50 mL) was added to the resulting mixture. A 25% NH$_4$OH aqueous solution (10 mL) was added and the aqueous mixture was extracted with CHCl$_3$ (3×50 mL). The combined organic layers were washed with brine (100 mL), dried over sodium sulfate, filtered off and the solvent was removed under vacuum. The crude product was purified by flash chromatography (0 to 10% MeOH in DCM) to afford Compound HO-I-MCP (1.07 g, 98%) was obtained as an off white solid.

(4R,7aR,12bS)-3-(Cyclopropylmethyl)-7-methoxy-2,3,4,7a-tetrahydro-1H-4,12-methanobenzofuro[3,2-e]isoquinolin-9-ol HPLC-purity 98.6% at 215 nm.
MS (ES-API pos) m/z 338.2 (M+H).
$^1$H NMR (300 MHz, CDCl$_3$) δ [ppm] 6.65 (d, J=8.4 Hz, 1H), 6.55 (d, J=8.4 Hz, 1H), 5.59 (d, J=6.6 Hz, 1H), 5.31 (s, 1H), 5.09 (d, J=6.6 Hz, 1H), 3.95 (d, J=6.6 Hz, 1H), 3.63 (s, 3H), 3.26 (d, J=18.0 Hz, 1H), 2.95 (dd, J=12.6, 4.2 Hz, 1H), 2.83 (m, 1H), 2.72 (dd, J=18.0, 7.2 Hz, 1H), 2.52 (m, 2H), 2.22 (dt, 1H), 1.75 (d, J=11.4 Hz, 1H), 0.93 (m, 1H), 0.56 (d, J=8.4 Hz, 2H), 0.18 (d, J=8.4 Hz, 2H).
$^{13}$C NMR (75 MHz, CDCl$_3$) δ [ppm] 151.9, 142.9, 138.3, 133.2, 132.9, 127.3, 119.7, 116.0, 111.5, 96.5, 89.7, 59.0, 58.5, 55.0, 46.9, 44.2, 36.7, 30.6, 9.4, 3.9, 3.8.

Example 24. Preparation of Compound HO-I-MCP (Step A2)

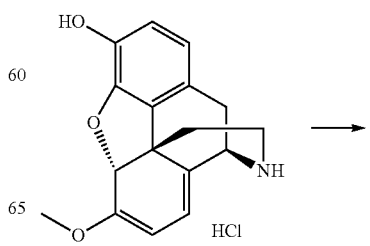

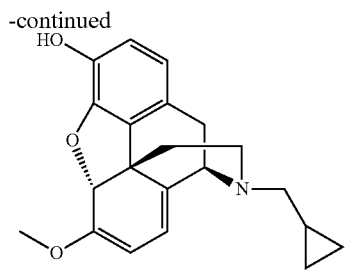

To a suspension of Compound HO-I-H (505 mg, 1.78 mmol) in CHCl₃ (14 mL) was added triethylamine (0.65 mL, 4.63 mmol) at room temperature and under a nitrogen atmosphere. The mixture was cooled to 0° C. with an ice/water bath and cyclopropane carboxylic acid chloride (440 mg, 4.12 mmol) dropwise. The mixture was stirred for 3h at room temperature. The mixture was washed with a 1M HCl aqueous solution (30 mL), water (30 mL), dried over sodium sulfate and filtered off. The solvents were removed under vacuum. The brown residue was dissolved in THF (8 mL) then added dropwise to a slurry of LiAlH₄ (203 mg, 5.35 mmol) in THF (8 mL), at room temperature and under a nitrogen atmosphere. The mixture was then refluxed for 1.5h. The mixture was cooled to 0° C. with an ice/water bath and carefully quenched with an ammonium chloride saturated aqueous solution. The mixture was diluted with THF (20 mL) and filtered off. The solid was washed with THF and the filtrate was concentrated under vacuum. The crude product Compound HO-I-MCP (500 mg, 83%) was obtained as an off white solid.

(4R,7aR,12bS)-3-(Cyclopropylmethyl)-7-methoxy-2,3,4,7a-tetrahydro-1H-4,12-methanobenzofuro[3,2-e]isoquinolin-9-ol HPLC-purity 94% at 215 nm.
NMR and MS data were in agreement with those obtained from Example 23.

Example 25. Preparation of Compound HO-I-MCP (Step A3)

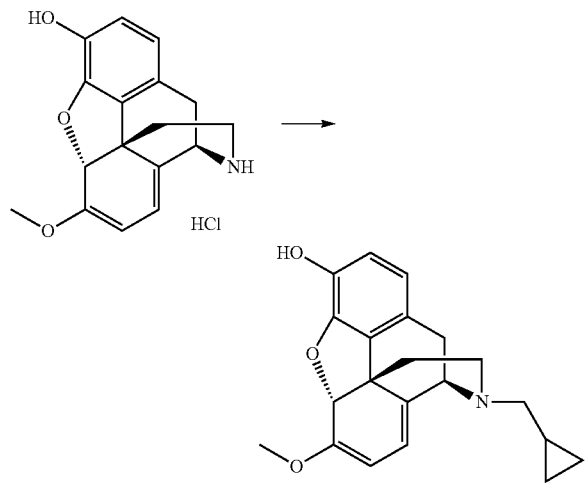

To a suspension of Compound HO-I-H (495 mg, 1.747 mmol) in EtOH (15 mL) were added triethylamine (0.61 mL, 4.37 mmol) and (bromomethyl)cyclopropane (0.35 mL, 3.494 mmol) at room temperature and under a nitrogen atmosphere. The mixture was refluxed overnight. The volatiles were removed under vacuum. Water (50 mL) and CHCl₃ (50 mL) were added. The aqueous phase was extracted with CHCl₃ (2×50 mL). The combined organic layers were dried over sodium sulfate, filtered off and the solvent was removed under vacuum. The crude product (510 mg) was purified by flash chromatography (0 to 10% MeOH in DCM) to afford Compound HO-I-MCP (370 mg, 63%) was obtained as an off white solid.

(4R,7aR,12bS)-3-(Cyclopropylmethyl)-7-methoxy-2,3,4,7a-tetrahydro-1H-4,12-methanobenzofuro[3,2-e]isoquinolin-9-ol HPLC-purity 94% at 215 nm.
NMR and MS data were in agreement with those obtained from Example 23.

Example 26. Preparation of Compound HO-II-MCP (Step B)

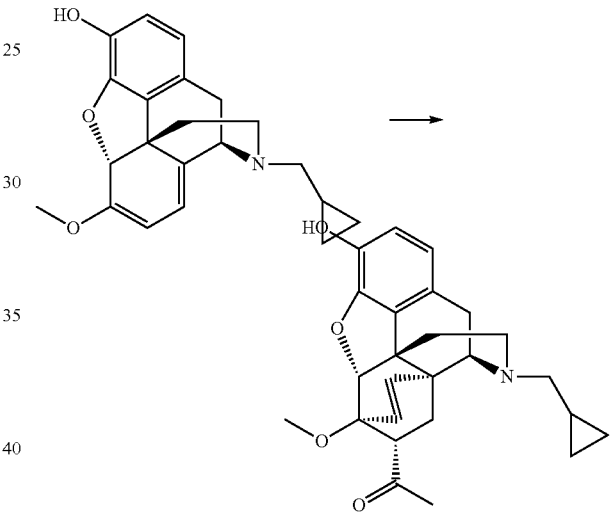

To a suspension of Compound HO-I-MCP (2.51 mg, 6.7 mmol) in toluene (50 mL) was added methyl vinyl ketone (12.2 mL, 139.1 mmol), at room temperature and under a nitrogen atmosphere. The reaction mixture was stirred at 80° C. overnight. The volatiles were removed under vacuum and the obtained crude material was triturated in hot EtOH, filtered off and washed with EtOH. Isolated Compound HO-II-MCP (1.88 g, 67%) was obtained as a beige solid. The mother liquor was concentrated under vacuum and the residue was purified by flash chromatography (0 to 5% MeOH in DCM). The obtained material was further triturated in hot EtOH and the solid was washed 3 times with EtOH prior to being isolated as additional Compoound III-A (270 mg, 11%) as a beige solid (total amount: 2.15 g, 78%).

1-((4R,4aI,7I,7aI,12bI)-3-(Cyclopropylmethyl)-9-hydroxy-7-methoxy-1,2,3,4,7,7a-hexahydro-4a,7-ethano-4,12-methanobenzofuro[3,2-e]isoquinolin-14-yl)ethan-1-one HPLC-purity at 215 nm: 95.9% (1.88 g batch); 97.1% (270 mg batch).
MS (ES-API pos) m/z 408.2 (M+H).
¹H NMR (300 MHz, CDCl₃) δ [ppm] 6.6 (d, J=7.8 Hz, 1H), 6.46 (d, J=7.8 Hz, 1H), 5.83 (d, J=9.0 Hz, 1H), 5.57 (d, J=9.0 Hz, 1H), 4.58 (s, 1H), 3.6-3.53 (m, 4H), 3.09 (d, J=18.6 Hz, 1H), 3.08-2.87 (m, 2H), 2.76-2.62 (dd, J=12.0, 4.8 Hz, 1H), 2.5-2.24 (m, 4H), 2.12 (s, 3H), 1.95 (dt, J=13.2, 5.4 Hz, 1H), 1.83 (dd, J=12.6, 2.4 Hz, 1H), 1.34 (dd, J=12.6, 6.6 Hz, 1H), 0.9-0.72 (m, 1H), 0.6-0.42 (m, 2H), 0.22-0.06 (m, 2H).

$^{13}$C NMR (75 MHz, CDCl$_3$) δ [ppm] 209.3, 146.5, 137.6, 134.0, 127.5, 125.7, 119.9, 116.5, 94.8, 81.3, 59.7, 57.0, 52.9, 50.6, 48.4, 44.0, 43.2, 33.5, 30.1, 30.0, 23.2, 9.4, 4.1, 3.4.

Example 27. Preparation of Compound HO-IIIB-MCP (Step C)

3.11-3.01 (m, 2H), 2.96 (d, J=18.3 Hz, 1H), 2.74 (dt, 3=13.5, 11.4, 3.9 Hz, 1H), 2.64 (dd, J=12.0, 5.1 Hz, 1H), 2.56-2.28 (m, 7H), 2.04 (dt, 3=12.6, 5.7 Hz, 1H), 1.76-1.4 (m, 4H), 1.38-1.21 (m, 1H), 0.96-0.62 (m, 2H), 0.56-0.41 (m, 2H), 0.15-0.05 (m, 2H).

$^{13}$C NMR (75 MHz, CDCl$_3$) δ [ppm] 210.9, 145.2, 137.4, 132.3, 128.1, 119.6, 116.6, 94.7, 77.8, 59.8, 58.3, 52.1, 49.5, 46.7, 43.7, 35.5, 35.1, 33.6, 30.4, 28.5, 22.8, 17.6, 9.4, 4.1, 3.3.

Example 28. Preparation of Compound HO-IIIB-MCP (Step C)

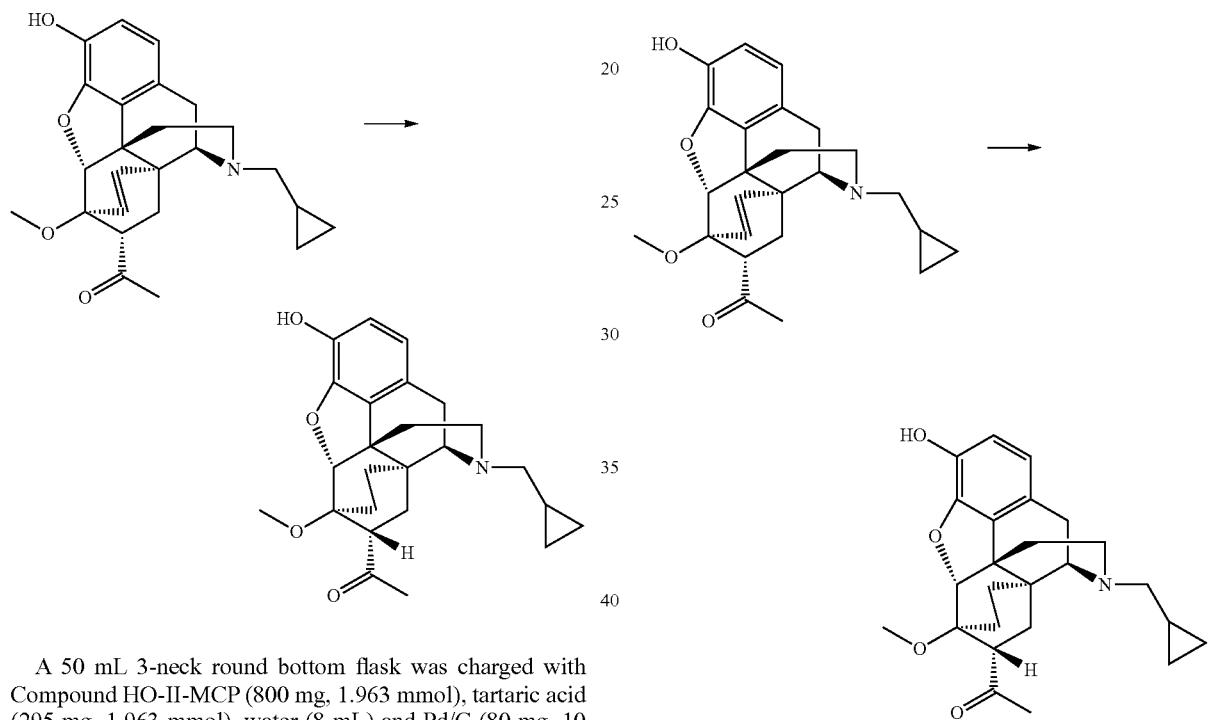

A 50 mL 3-neck round bottom flask was charged with Compound HO-II-MCP (800 mg, 1.963 mmol), tartaric acid (295 mg, 1.963 mmol), water (8 mL) and Pd/C (80 mg, 10 w/w). The mixture was then hydrogenated under 1 atmosphere of hydrogen at 80° C. for 12 h. The reaction mixture was filtered through Celite, while hot, and Celite was rinsed with some hot water. After cooling to room temperature, the pH of the aqueous solution was adjusted to 6.6-6.7 with 10% KOH. The aqueous solution was extracted with CHCl$_3$ (3×50 mL). The combined organic layers were dried over sodium sulfate, filtered off, and the solvent was removed under vacuum. Purification by flash chromatography (0 to 20% ethyl acetate in heptane) yielded Compound HO-IIIB-MCP (570 mg, 71%) as a white solid.

1-((4R,4aS,7R,7aR,12bS)-3-(Cyclopropylmethyl)-9-hydroxy-7-methoxy-1,2,3,4,5,6,7,7a-octahydro-4a,7-ethano-4,12-methanobenzofuro[3,2-e]isoquinolin-6-yl)ethan-1-one HPLC-purity 92.5% at 215 nm.

MS (ES-API pos) m/z 410.2 (M+H).

$^1$H NMR (300 MHz, CDCl$_3$) δ [ppm] 6.7 (d, J=8.1 Hz, 1H), 6.52 (d, J=8.1 Hz, 1H), 4.49 (s, 1H), 3.41 (s, 3H), To a suspension of Compound HO-II-MCP (270 mg, 0.662 mmol) in a mixture of iPrOH (4.6 mL) and water (0.4 mL) was added Pd/C (30 mg, 10% w/w), at room temperature and under a nitrogen atmosphere. The mixture was then hydrogenated under 1 atmosphere of hydrogen at 80° C. overnight and was filtered off through Celite. Celite was rinsed with DCM. The filtrate was concentrated under vacuum and purification by flash chromatography (0 to 50% ethyl acetate in heptane) yielded Compound HO-IIIB-MCP (215 mg, 79%) as an off white solid.

1-((4R,4aS,7R,7aR,12bS)-3-(Cyclopropylmethyl)-9-hydroxy-7-methoxy-1,2,3,4,5,6,7,7a-octahydro-4a,7-ethano-4,12-methanobenzofuro[3,2-e]isoquinolin-6-yl)ethan-1-one HPLC-purity 92.5% at 215 nm.

NMR and MS data were in agreement with those obtained with Example 27.

Example 29. Preparation of Compound HO-MA-MCP (Step D)

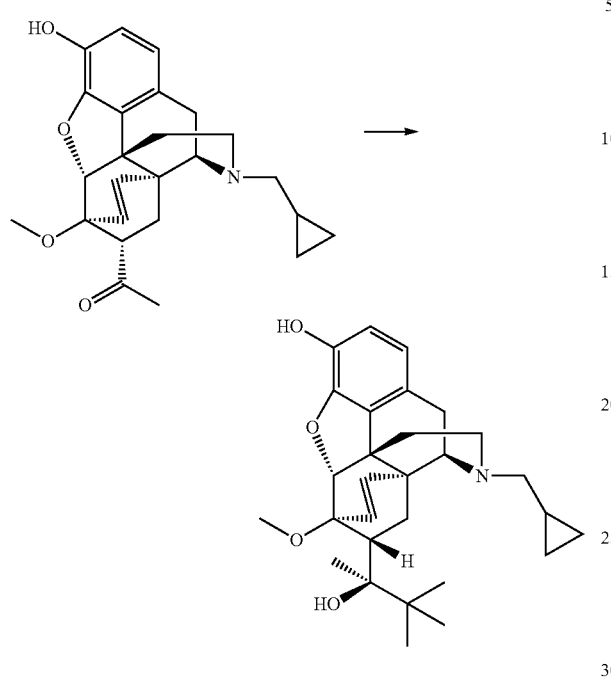

Compound HO-II-MCP (750 mg, 1.84 mmol) dissolved in dioxane (8 mL) was added to a 2.0 M solution of tert-butylmagnesium chloride in ether (11 mL, 22 mmol) and TMEDA (3.31 mL, 22 mmol) dropwise, over 10 min, at room temperature and under a nitrogen atmosphere. Once the addition was complete the mixture was stirred at 60° C. for 4h under a nitrogen atmosphere. The mixture was then cooled to 0° C. with an ice/water bath and carefully quenched with a saturated aqueous ammonium chloride solution over 15 min. Ethyl acetate (15 mL) was added. After separation the aqueous phase was extracted with ethyl acetate (2×15 mL). The combined organic layers were dried over sodium sulfate, filtered off and the solvents were removed under vacuum. Purification by flash chromatography (0 to 100% ethyl acetate in heptane) yielded Compound HO-IIIA-MCP (200 mg, 23%) as a white solid.

(4R,4aR,7R,7aR,12bS)-3-(cyclopropylmethyl)-14-((S)-2-hydroxy-3,3-dimethylbutan-2-yl)-7-methoxy-1,2,3,4,7,7a-hexahydro-4a,7-ethano-4,12-methano-benzofuro[3,2-e]isoquinolin-9-ol HPLC-purity 99.4% at 215 nm.

MS (ES-API pos) m/z 466.2 (M+1).

$^1$H NMR (300 MHz, CDCl$_3$) δ [ppm] 6.59 (d, 1H), 6.44 (d, 1H), 5.96 (d, 1H), 5.71 (s, 1H), 5.44 (d, 1H), 4.58 (s, 1H), 3.74 (s, 3H), 3.49 (d, 1H), 3.08 (d, 1H), 2.96 (dd, 1H), 2.66 (dd, 1H), 2.48-2.26 (m, 4H), 2.2-2.09 (t, 1H), 1.98-1.78 (m, 2H), 0.99 (s, 12H), 0.91-0.86 (m, 1H), 0.6-0.53 (m, 2H), 0.2-0.09 (m, 2H).

$^{13}$C NMR (75 MHz, CDCl$_3$) δ [ppm] 146.6, 137.3, 135.6, 134.4, 127.8, 124.4, 119.7, 116.1, 99.3, 84.5, 78.7, 59.5, 56.7, 55.2, 47.4, 45.7, 44.1, 43.1, 39.6, 33.8, 32.1, 26.6, 23.1, 19.6, 9.4, 4.3, 3.1.

Example 30. Preparation of Buprenorphine (Step D)

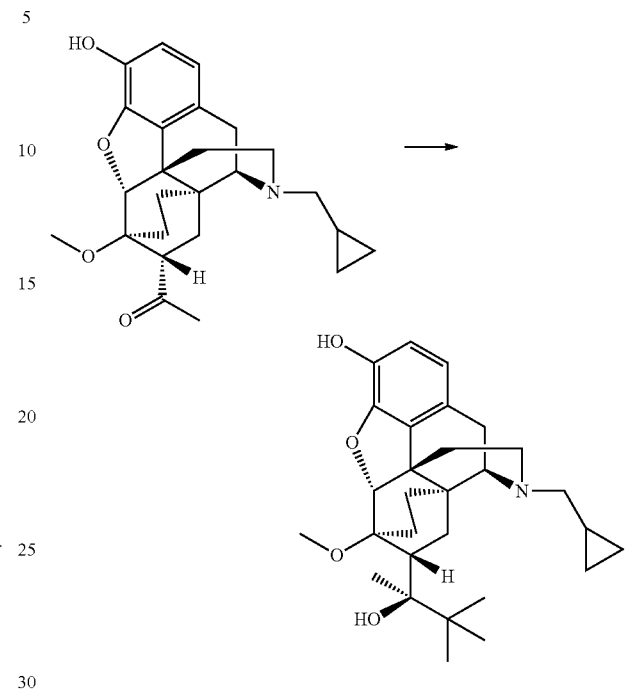

To a stirred solution of Compound HO-IIIB-MCP (130 mg, 0.317 mmol) in a mixture of ether (11 mL) and toluene (5 mL), cooled to 0° C. with an ice/water bath and under a nitrogen atmosphere, was added a 2.0 M solution of tert-butylmagnesium chloride in ether (3.08 mL, 6.153 mmol) containing TMEDA (0.92 mL, 6.153 mmol) dropwise. After completion of the addition, the mixture was allowed to warm up to room temperature and was stirred for 1.5h. The mixture was then poured into a mixture of ice/water (25 mL) and a saturated aqueous solution of ammonium chloride (25 mL). The aqueous phase was extracted with ethyl acetate (3×50 mL). The combined organic phases were dried over sodium sulfate, filtered off and the solvent was removed under vacuum. Purification by flash chromatography (0 to 100% ethyl acetate in heptane) yielded buprenorphine (99 mg, 41%) as a white solid.

Buprenorphine

HPLC-purity 98.9% at 215 nm.

MS (ES-API pos) m/z 468.3 (M+H).

$^1$H NMR (300 MHz, CDCl$_3$) δ [ppm] 6.67 (d, J=8.0 Hz, 1H), 6.49 (d, J=8.0 Hz, 1H), 6.02 (s, 1H), 5.78 (br, 1H), 4.43 (d, J=1.2 Hz, 1H), 3.51 (s, 3H), 3.01-2.82 (m, 3H), 2.6 (dd, J=11.9, 5.1 Hz, 1H), 2.38-2.21 (m, 3H), 2.20-2.10 (m, 2H), 1.97 (dt, 3=12.6, 5.6 Hz, 1H), 1.9-1.7 (m, 2H), 1.65 (dd, J=12.8, 2.5 Hz, 1H), 1.36 (s, 3H), 1.29 (m, 1H), 1.12-0.96 (m, 10H), 0.9-0.63 (m, 2H), 0.56-0.4 (m, 2H), 0.2-0.07 (m, 2H).

$^{13}$C NMR (75 MHz, CDCl$_3$) δ [ppm] 145.5, 137.4, 132.5, 128.1, 119.5, 116.5, 96.8, 80.8, 79.7, 59.5, 58.3, 52.5, 46.4, 43.7, 43.5, 40.3, 35.9, 35.6, 33.4, 29.6, 26.4, 22.8, 20.1, 18.2, 9.4, 4.1, 3.2.

Example 31. Preparation of Buprenorphine (Step D)

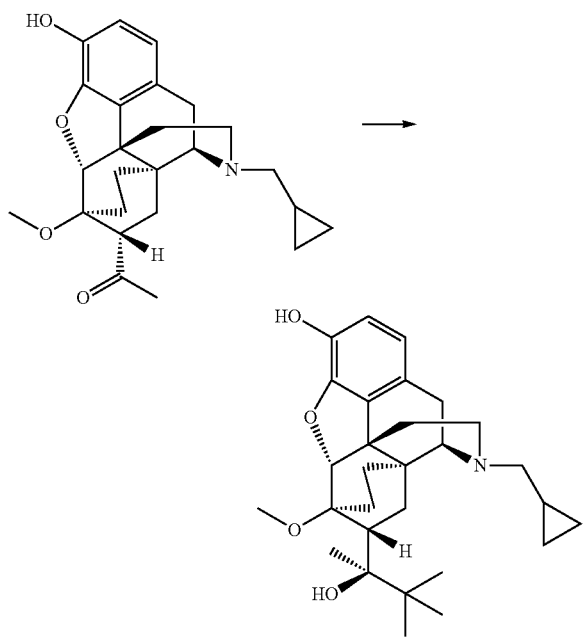

To a stirred solution of Compound HO-IIIB-MCP (130 mg, 0.317 mmol) in a mixture of ether and toluene (3:2, 10 mL), cooled to 0° C. with an ice/water bath and under a nitrogen atmosphere, was added a 2.0 M solution of tert-butylmagnesium chloride in ether (2 mL, 4 mmol) dropwise. A white precipitate was obtained. The reaction mixture was allowed to warm to room temperature and the mixture was agitated for 15 h at room temperature. Water (10 mL) was carefully added to the reaction mixture, previously cooled to 0° C. with an ice/water bath, followed by the addition of a saturated aqueous solution of ammonium chloride (10 mL). The aqueous phase was extracted with ethyl acetate (3×50 mL). The combined organic phases were dried over sodium sulfate, filtered off and the solvent was removed under vacuum. Purification by flash chromatography (0 to 100% ethyl acetate in heptane) yielded buprenorphine (47 mg, 32%) as a white solid.

Buprenorphine

HPLC-purity 99.0% at 215 nm.
NMR and MS data were in agreement with those obtained from Example 30.

Example 32. Preparation of Buprenorphine (Step C)

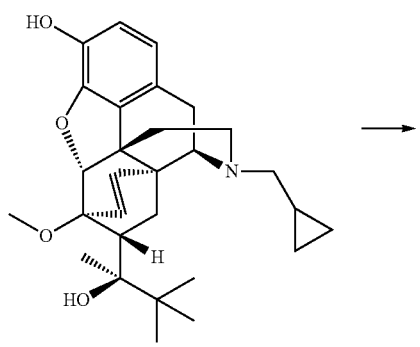

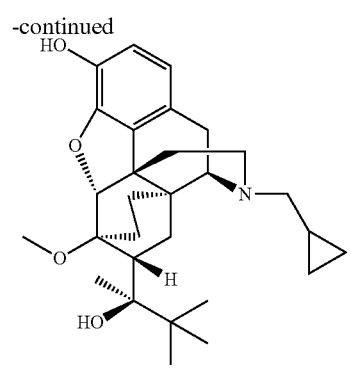

To a suspension of Compound HO-IIIA-MCP (250 mg, 0.537 mmol) in a mixture of isopropanol (4.6 mL) and water (0.4 mL) was added Pd/C (25 mg, 10% w/w) at room temperature. The mixture was then hydrogenated under 1 atmosphere of hydrogen at 80° C. overnight. The mixture was filtered through a plug of Celite and Celite was rinsed with CHCl$_3$. The mother liquor was concentrated under vacuum. Purification by flash chromatography (0 to 80% ethyl acetate in heptane) yielded intermediate buprenorphine (200 mg, 80%) was obtained as a white solid.

Buprenorphine

HPLC-purity 99.1% at 215 nm.
NMR and MS data were in agreement with those obtained for buprenorphine with method A and B previously reported

Example 33. Preparation of Compound BnO-I-MCP (Step F)

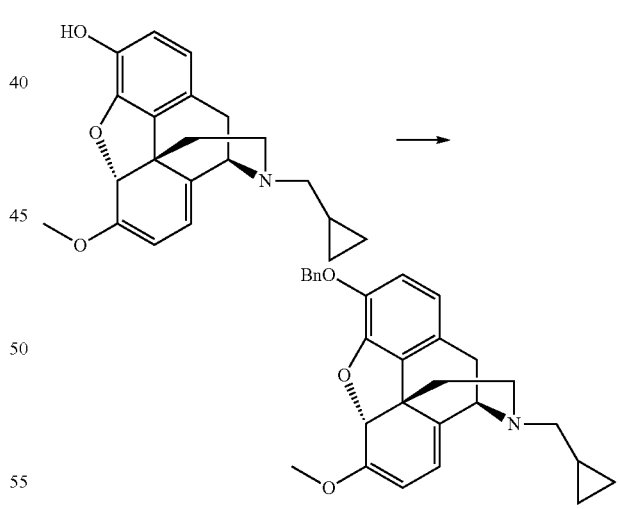

To a solution of intermediate Compound HO-I-MCP (200 mg, 0.59 mmol) in DMF (5 mL) was added sodium hydride (36 mg, 0.89 mmol) at 0° C. and under a nitrogen atmosphere. The mixture was then stirred at 45° C. for 20 min and was cooled to 0° C. Benzyl bromide (130 mg, 0.741 mmol) was added and the mixture was stirred overnight at room temperature. The mixture was cooled to 0° C. with an ice/water bath and water (25 mL) was carefully added. The aqueous mixture was extracted with CHCl$_3$ (3×25 mL). The combined organic layers were washed with water (25 mL), brine (50 mL), dried over sodium sulfate, filtered off and the solvents were removed under vacuum. Purification by flash chromatography (0 to 5% MeOH in DCM) yielded Compound BnO-I-MCP (190 mg, 68%) as an orange/brownish oil.

(4R,7aR,12bS)-9-(Benzyloxy)-3-(cyclopropylmethyl)-7-methoxy-2,3,4,7a-tetrahydro-1H-4,12-methanobenzofuro[3,2-e]isoquinoline HPLC-purity 96.8% at 215 nm.
MS (ES-API pos) m/z 428.2 (M+H).
$^1$H NMR (300 MHz, CDCl$_3$) δ [ppm] 7.95 (br, 1H from DMF), 7.4 (d, 2H), 7.35-7.2 (m, 3H), 6.65 (d, 1H), 6.5 (d, 1H), 5.54 (d, 1H), 5.27 (s, 1H), 5.13 (dd, 2H), 5.02 (d, 1H), 3.94 (d, 1H), 3.55 (s, 3H), 3.26 (d, 1H), 2.95-2.77 (m, 2H+DMF), 2.7 (dd, 1H), 2.5 (d, 2H), 2.18 (dt, 1H), 1.7 (d, 1H), 1.00-0.8 (m, 1H), 0.6-0.47 (m, 2H), 0.2-0.1 (m, 2H).
$^{13}$C NMR (75 MHz, CDCl$_3$) δ [ppm] 152.6, 145.1, 141.6, 137.5, 133.7, 131.7, 128.3, 128.0, 127.7, 127.6, 119.3, 115.8, 112.4, 95.9, 89.0, 71.6, 58.8, 58.6, 54.9, 46.3, 44.1, 36.4, 36.3, 30.8, 9.2, 4.0, 3.8.

(4R,7aR,12bS)-9-(Benzyloxy)-3-(cyclopropylmethyl)-7-methoxy-2,3,4,7a-tetrahydro-1H-4,12-methanobenzofuro[3,2-e]isoquinoline HPLC-purity 96.4% at 215 nm.
NMR and MS data were in agreement with those obtained for Example 33.

Example 35. Preparation of Compound BnO-II-MCP (Step F)

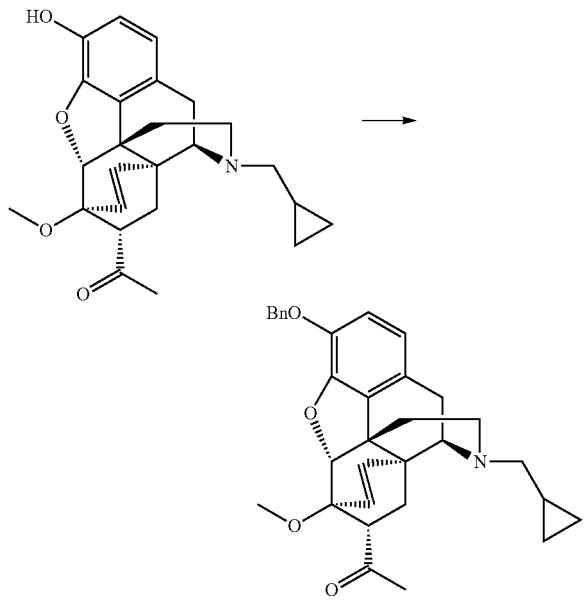

To a suspension of Compound BnO-I-MCP (240 mg, 0.59 mmol) in CHCl$_3$ (3 mL) were added benzyl bromide (0.093 mL, 0.78 mmol) and potassium carbonate (450 mg, 3.26 mmol) at room temperature under a nitrogen atmosphere. The reaction mixture was then refluxed for 15 h. The mixture was cooled down to room temperature and filtered off. The solid was washed with DCM and the filtrate was concentrated under vacuum. Purification by flash chromatography (0 to 50% ethyl acetate in heptane) yielded Compound BnO-II-MCP (270 mg, 92%) as a colorless oil.

1-((4R,4aR,7R,7aR,12bS)-9-(Benzyloxy)-3-(cyclopropylmethyl)-7-methoxy-1,2,3,4,7,7a-hexahydro-4a,7-ethano-4,12-methanobenzofuro[3,2-e]isoquinolin-14-yl)ethan-1-one HPLC-purity 96.4% at 215 nm.
MS (ES-API pos) m/z 498.4 (M+H).
$^1$H NMR (300 MHz, CDCl$_3$) δ [ppm] 7.45-7.23 (m, 5H), 6.65 (d, 1H), 6.47 (d, 1H), 5.91 (d, 1H), 5.59 (d, 1H), 5.19-5.05 (dd, 2H), 4.59 (s, 1H), 3.61 (s, 3H), 3.55 (d, 1H), 3.15-2.86 (m, 3H), 2.75-2.65 (dd, 1H), 2.47-2.28 (m, 4H), 2.15 (s, 3H), 2.05-1.91 (dt, 1H), 1.89-1.8 (dd, 1H), 1.71-1.58 (m, 1H), 1.4-1.31 (dd, 1H), 0.91-0.75 (m, 3H), 0.58-0.42 (m, 2H), 0.18-0.08 (m, 2H).
$^{13}$C NMR (75 MHz, CDCl$_3$) δ [ppm] 209.3, 148.8, 140.6, 137.5, 136.5, 134.6, 129.0, 128.3, 127.7, 127.5, 125.5, 119.4, 116.7, 95.8, 81.4, 72.0, 59.8, 57.0, 53.7, 53.7, 50.8, 48.1, 43.9, 43.2, 33.6, 30.6, 29.9, 23.3, 9.4, 4.1, 3.4.

Example 36. Preparation of Compound BnO-II-MCP (Step B)

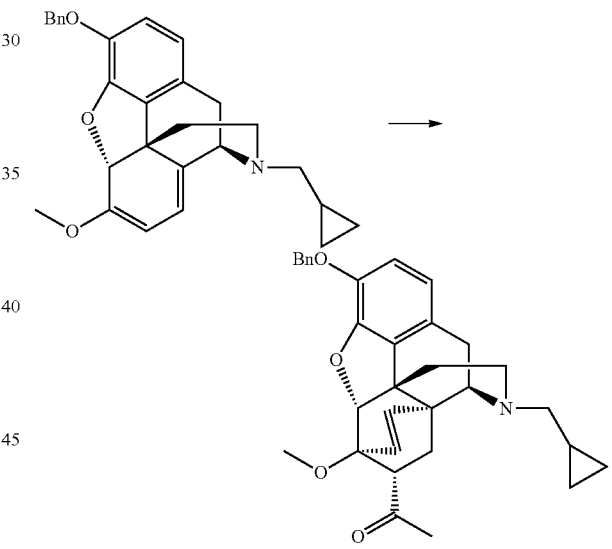

To a solution of Compound BnO-I-MCP (190 mg, 0.415 mmol) in toluene (3 mL) was added methyl vinyl ketone (0.73 mL, 8.35 mmol) at room temperature and under a nitrogen atmosphere. The mixture was stirred at 80° C. for 15 h and the volatiles were removed under vacuum. Purification by flash chromatography (0 to 60% ethyl acetate in heptane) yielded Compound BnO-II-MCP (170 mg, 82%) as a colorless oil.

1-((4R,4aR,7R,7aR,12bS)-9-(Benzyloxy)-3-(cyclopropylmethyl)-7-methoxy-1,2,3,4,7,7a-hexahydro-4a,7-ethano-4,12-methanobenzofuro[3,2-e]isoquinolin-14-yl)ethan-1-one HPLC-purity 92.9% at 215 nm.
NMR and MS data were in agreement with those obtained for Example 35.

Example 37. Preparation of Compound BnO-IIIA-MCP (Step D)

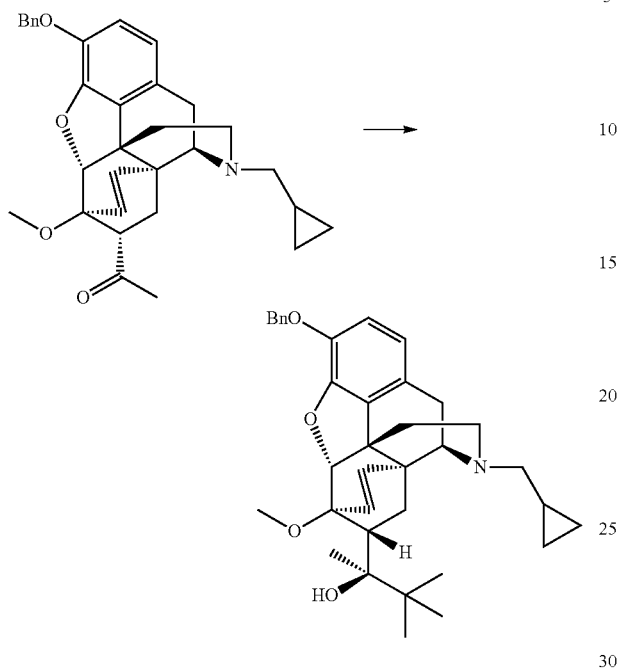

To a solution of Compound BnO-II-MCP (250 mg, 0.5 mmol) in dry toluene (6 mL) at room temperature and under a nitrogen atmosphere, was added a 1.7 M tert-butylmagnesium chloride solution in THF (1.77 mL, 3 mmol) dropwise. The mixture was stirred at room temperature for 18 h prior to further dropwise addition of a 1.7 M tert-butylmagnesium chloride solution in THF (1.77 mL, 3 mmol). The reaction mixture was stirred for 5 h and was poured into a mixture made of ice/water (50 mL) and of an ammonium chloride saturated aqueous solution (50 mL). The mixture was extracted with toluene (3×50 mL). The combined organic layers were washed with brine (50 mL), dried over sodium sulfate, filtered off and the solvents were removed under vacuum. Purification by flash chromatography (0 to 20% ethyl acetate in heptane) yielded Compound BnO-IIIA-MCP (107 mg, 38%) as a colorless oil.

(2S)-2-((4R,4aR,7R,7aR,12bS)-9-(Benzyloxy)-3-(cyclopropylmethyl)-7-methoxy-1,2,3,4,7,7a-hexahydro-4a,7-ethano-4,12-methanobenzofuro[3,2-e]isoquinolin-14-yl)-3,3-dimethylbutan-2-ol HPLC-purity 97.2% at 215 nm.
MS (ES-API pos) m/z 556.4 (M+H).
$^1$H NMR (300 MHz, CDCl$_3$) δ [ppm] 7.43-7.3 (m, 5H), 6.65 (d, 1H), 6.46 (d, 1H), 6.00 (d, 1H), 5.65 (s, 1H), 5.43 (d, 1H), 5.19-5.04 (dd, 2H), 4.58 (s, 1H), 3.79 (s, 3H), 3.5 (d, 1H), 3.1 (d, 1H), 2.9 (dd, 1H), 2.69 (dd, 1H), 2.47-2.3 (m, 4H), 2.21-2.12 (t, 1H), 2.01-1.82 (m, 2H), 1.55 (s, 3H), 1.01 (s, 9H), 0.99-0.8 (m, 2H), 0.62-0.43 (m, 2H), 0.22-0.12 (m, 2H).
$^{13}$C NMR (75 MHz, CDCl$_3$) δ [ppm] 148.9, 140.6, 137.8, 137.6, 135.1, 129.2, 129.0, 128.4, 128.2, 127.7, 127.5, 125.3, 124.7, 119.4, 116.7, 99.0, 84.5, 78.4, 72.1, 67.9, 59.5, 56.7, 55.2, 47.1, 45.9, 44.1, 43.1, 39.7, 34.0, 32.2, 26.7, 25.6, 23.2, 19.6, 9.5, 4.3, 3.2.

Example 38. Preparation of Buprenorphine (Step C)

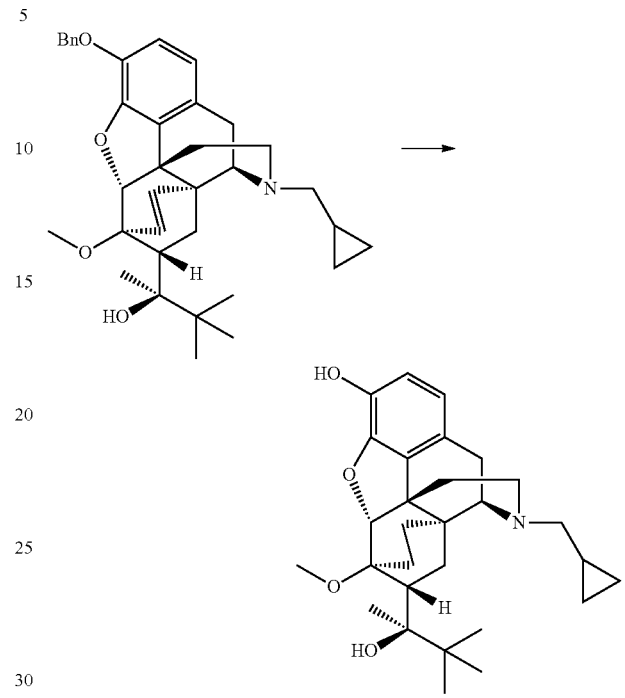

To a solution of Compound BnO-IIIA-MCP (194 mg, 0.349 mmol) in a mixture of isopropanol (4.6 mL) and water (0.4 mL) was added Pd/C (20 mg, 10% w/w) at room temperature and under a nitrogen atmosphere. The mixture was then hydrogenated under 1 atmosphere of hydrogen at 80° C. for 15 min. The mixture was filtered through Celite with isopropanol and CHCl$_3$ used as eluents. The solvents were removed under vacuum. Purification by flash chromatography (0 to 60% ethyl acetate in heptane) yielded buprenorphine (115 mg, 70%) as a white solid.

Buprenorphine

HPLC-purity 96.3% at 215 nm.
NMR and MS data were in agreement with those obtained for Examples 21-22 and 30-32.

Example 39. Preparation of Buprenorphine-HCl from Buprenorphine

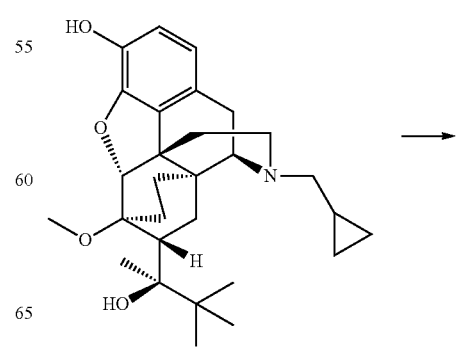

-continued

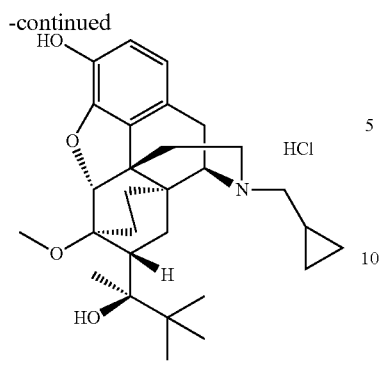

Buprenorphine (100 mg, 0.21 mmol) was taken in EtOH (2 mL) and the mixture was heated until all solid had dissolved. To the warm solution was added 0.5 mL of a mixture of 95 mL EtOH and 5 mL 37% hydrochloric acid (approx. 0.3 mmol). The solution was cooled in the fridge overnight during which time crystals were formed. The crystals were collected and dried under vacuum at 50° C. to yield buprenorphine hydrochloride (102 mg, 96%).

Buprenorphine-HCl

HPLC-purity 99.4% at 215 nm.
DSC-Melting point 267.84-275.26° C.
MS (ES-API pos) m/z 468.2 (M free base+H).
$^1$H NMR (300 MHz, CDCl$_3$/CD$_3$OD) δ [ppm] 6.68 (d, J=8.2 Hz, 1H), 6.50 (d, J=8.2 Hz, 1H), 4.44 (s, 1H), 3.82 (d, J=6.5 Hz, 1H), 3.47 (s, 3H), 3.18-3.35 (m, 4H), 3.0 (d, J=9.5 Hz, 1H), 2.70-2.88 (m, 3H), 2.40 (dt, J=5 and 14 Hz, 1H), 2.22 (t, J=8.8 Hz, 1H), 1.63-1.90 (m, 3H), 1.50 (dd, J=8 and 14 Hz, 1H), 1.29 (s, 3H), 1.20-1.25 (m, 1H), 1.03-1.18 (m, 1H), 1.00 (s, 9H), 0.60-0.85 (m, 4H), 0.38 (m, 1H).

Example 40. Preparation of Compound BnO-I-Bn (Step F)

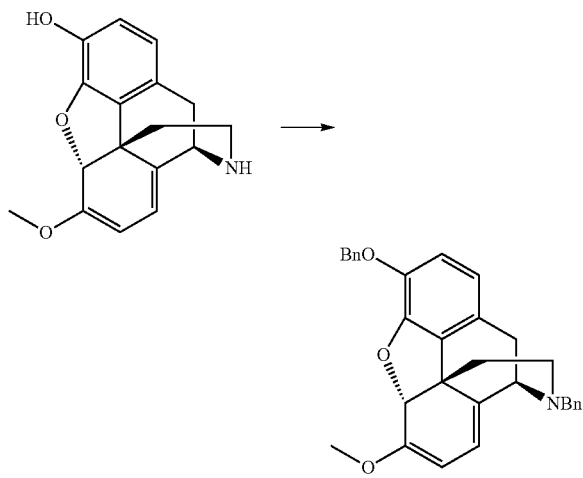

A 500 mL flask was charged with nororipavine (5.66 g, 20 mmol), MeOH (100 mL), and water (50 mL). The suspension was stirred at room temperature and NaOH-pellets (2.50 g, 60 mmol, 3 equiv) were added. After 10 min a light brown solution was obtained and benzyl bromide (8.50 g, 50 mmol, 2.5 equiv) was added over a period of 1 min. A slight exotherm was observed and after 10 min a precipitate was formed. After 2 h the mixture was rotary evaporated to remove most of the MeOH (65 mL). The residue (approximately 100 mL) was cooled in ice-water for 15 min and then filtered. The solid was washed with water (2×10 mL), then with MeOH (10 mL), and dried under vacuum to afford Compound BnO-I-Bn (8.6 g, 93%).

N,O-Dibenzyl-Nororipavine

HPLC-purity 95.7% at 254 nm.
MS (ES-API pos) m/z 464.4 (M+H).
$^1$H NMR (300 MHz, CDCl$_3$) δ [ppm] 7.49-7.24 (m, 10H), 6.68 (d, J=8.1 Hz, 1H), 6.54 (d, J=8.2 Hz, 1H), 5.49 (d, J=6.4 Hz, 1H), 5.32 (s, 1H), 5.22 (d, J=12.2 Hz, 1H), 5.15 (d, J=12.1 Hz, 1H), 5.06 (d, J=6.4 Hz, 1H), 3.77 (d, J=2.9 Hz, 2H), 3.63 (s, 4H), 3.33 (d, J=18.0 Hz, 1H), 2.96 (td, J=13.0, 3.5 Hz, 1H), 2.72 (m, 2H), 2.26 (td, J=12.6, 4.9 Hz, 1H), 1.70 (dd, J=12.6, 3.0 Hz, 1H).
$^{13}$C NMR (75 MHz, CDCl$_3$) δ [ppm] 152.6, 145.7, 141.7, 138.7, 137.6, 132.9, 132.5, 129.0, 128.4, 127.7, 127.6, 127.1, 119.3, 115.9, 111.8, 96.0, 89.2, 71.7, 58.3, 58.2, 55.0, 46.6, 44.1, 36.5, 31.7.

Example 41. Preparation of Compound BnO-II-Bn (step B)

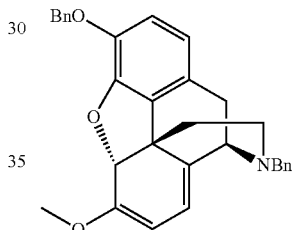

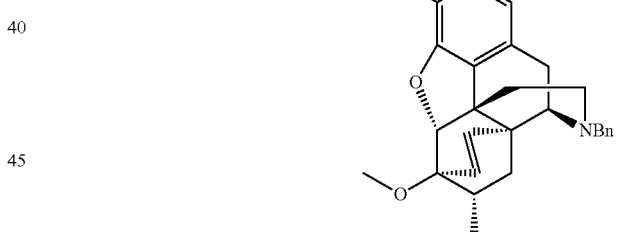

A solution of Compound BnO-I-Bn (4.63 g, 10.0 mmol) and methyl vinyl ketone (8 mL, 100 mmol) in toluene (50 mL) was heated at 80° C. for 16 h. After cooling to room temperature the mixture was concentrated under vacuum to give a brown oily residue (5.5 g), which was purified by column chromatography (120 g SiO$_2$, elution with 0-20% EtOAc in heptane, R$_f$ 0.3) to afford Compound BnO-II-Bn as a colorless solid (4.25 g, 77% yield).

7α-Acetyl-N,O-dibenzyl-6,14-endo(etheno)tetra-hydro-nororipavine

HPLC-purity 97.3% at 215 nm.
MS (ES-API pos) m/z 534.4 (M+H).
$^1$H NMR (300 MHz, CDCl$_3$) δ [ppm] 7.45-7.20 (m, 10H), 6.68 (d, J=8.1 Hz, 1H), 6.51 (d, J=8.2 Hz, 1H), 5.89 (dt, J=8.9, 1.2 Hz, 1H), 5.53 (d, J=8.8 Hz, 1H), 5.13 (d, J=5.4

Hz, 2H), 4.60 (d, J=1.5 Hz, 1H), 3.66 (s, 2H), 3.62 (s, 3H), 3.27 (dd, J=12.5, 6.0 Hz, 2H), 3.09 (dd, J=12.6, 9.4 Hz, 1H), 2.95 (dd, J=9.4, 6.5 Hz, 1H), 2.67-2.38 (m, 3H), 2.16 (s, 3H), 2.00 (td, J=12.5, 5.9 Hz, 1H), 1.87 (ddd, J=13.1, 4.0, 1.8 Hz, 1H), 1.35 (dd, J=12.6, 6.5 Hz, 1H).

$^{13}$C NMR (75 MHz, CDCl$_3$) δ [ppm] 209.35, 148.84, 140.76, 139.09, 137.57, 136.20, 134.56, 128.86, 128.65, 128.38, 127.77, 127.53, 127.10, 125.62, 119.54, 116.84, 95.69, 81.33, 72.08, 59.50, 57.04, 53.70, 50.98, 48.09, 43.81, 43.35, 33.60, 30.56, 29.89, 23.53.

Example 42. Preparation of Compound BnO-IIIA-Bn (Step D)

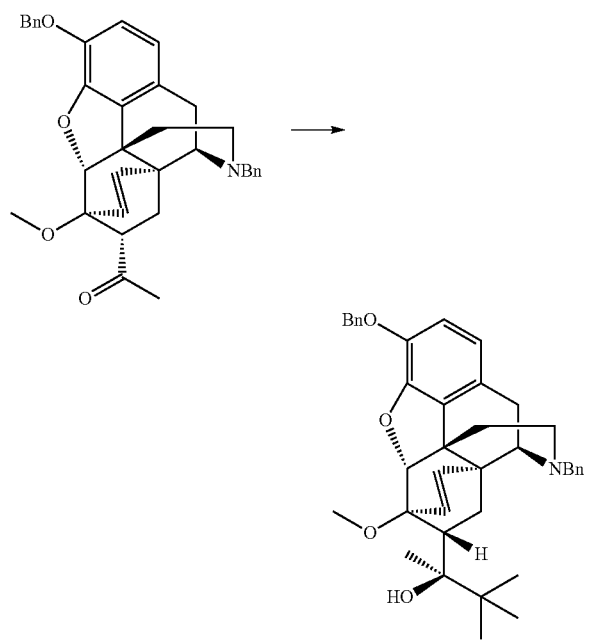

A 50 mL flask was charged with a solution of tert-butylmagnesium chloride (1.7 M solution in THF, 5 mL, 8.5 mmol) and toluene (8 mL). The THF was evaporated in vacuo and to the residual Grignard solution in toluene (approximately 10 mL) was added a solution of Compound BnO-II-Bn (0.70 g, 1.3 mmol) in dry toluene (8 mL). The reaction mixture was heated to 60° C. for 2 h and then cooled in an ice-water bath and quenched by addition of 10% aqueous ammonium chloride (25 mL). The layers were separated and the aqueous layer was extracted with toluene (3×25 mL). The combined organic layers were washed with brine, dried with sodium sulfate, and concentrated to an oil. Purification by column chromatography (120 g SiO$_2$, elution with 0-20% EtOAc in heptane, Rf 0.6) afforded Compound BnO-III-Bn as white solid (0.38 g, 50%).

N,O-Dibenzyl-7α-(2-(S)-hydroxy-3,3-dimethyl-2-butyl)-6,14-endo(etheno)tetrahydro-nororipavine (3)

HPLC-purity 95.6% at 215 nm.
MS (ES-API pos) m/z 492.4 (M+H).
$^1$H NMR (300 MHz, CDCl$_3$) δ [ppm] 7.43-7.30 (m, 10H), 6.66 (d, J=8.1 Hz, 1H), 6.48 (d, J=8.2 Hz, 1H), 5.95 (d, J=8.9 Hz, 1H), 5.60 (s, 1H), 5.34 (d, J=8.9 Hz, 1H), 5.14 (d, J=12.0 Hz, 1H), 5.07 (d, J=12.0 Hz, 1H), 4.58 (d, J=1.4 Hz, 1H), 3.76 (s, 3H), 3.68 (d, J=2.7 Hz, 2H), 3.22 (d, J=12 Hz, 1H), 3.17-3.01 (m, 2H), 2.70-2.52 (m, 2H), 2.39 (dd, J=18.5, 6.6 Hz, 1H), 2.17 (t, J=8.6 Hz, 1H), 1.99 (td, J=12.1, 11.3, 6.1 Hz, 1H), 1.89 (d, J=12.6 Hz, 1H), 1.04 (s, 9H), 0.98 (s, 3H), 1.01-0.82 (m, 1H).

$^{13}$C NMR (75 MHz, CDCl$_3$) δ [ppm] 148.89, 140.64, 139.37, 137.56, 135.31, 135.00, 128.93, 128.61, 128.38, 128.32, 127.78, 127.46, 127.06, 124.71, 119.44, 116.71, 98.94, 84.46, 78.34, 72.11, 59.10, 56.04, 55.21, 47.00, 45.92, 44.28, 43.14, 39.70, 34.08, 32.22, 26.64, 23.39, 19.57

Example 43. Preparation of Compound HO-IV-H (Step C)

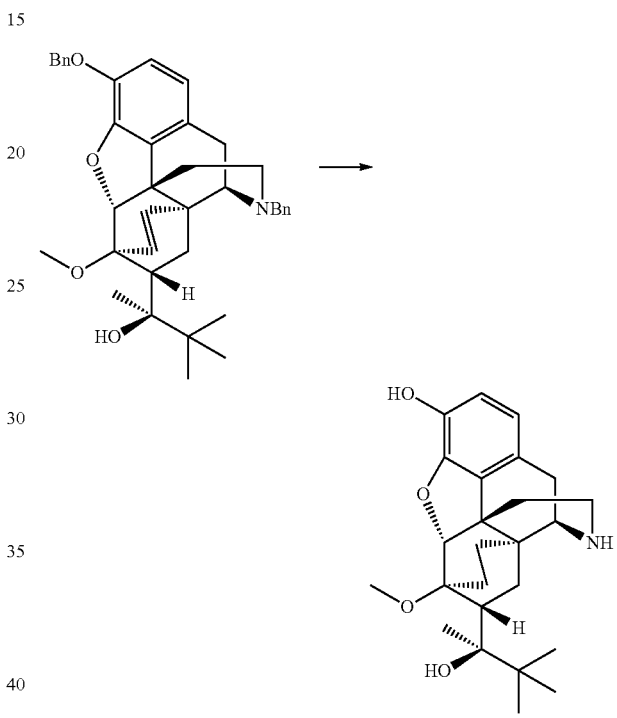

A vigorously stirred mixture of Compound BnO-III-Bn (355 mg, 0.6 mmol), and Pd/C (10%, 30 mg) in iPrOH (10 mL), water (0.2 mL), and acetic acid (0.1 mL) was hydrogenated at 60° C. for 16 h under 1 atmosphere of hydrogen. IPC NMR showed that both benzyl groups were removed and the double bond was only partly reduced. The catalyst was refreshed and hydrogenation was continued at 80° C. for 60 h. ICP NMR showed no more double bond signals. The mixture was filtered over Celite. The filter was flushed with iPrOH and DCM. The filtrate was concentrated to give Compound HO-IV-H as acetate salt (300 mg, 100%).

Norbuprenorphine

HPLC-purity 89% at 215 nm.
MS (ES-API pos) m/z 414.3 (M+H).
$^1$H NMR (300 MHz, CDCl$_3$) δ [ppm] 7.64 (br s, 2H), 6.76 (d, J=8.0 Hz, 1H), 6.49 (d, J=8.1 Hz, 1H), 5.80 (br s, 1H), 4.40 (s, 1H), 3.59 (d, J=6.4 Hz, 1H), 3.51 (s, 3H), 3.35-3.25 (m, 2H), 3.04 (t, J=13.5 Hz, 1H), 2.88 (dd, J=19.2, 6.4 Hz, 1H), 2.75 (t, J=13.5 Hz, 1H), 2.22-2.07 (m, 2H), 2.01 (s, 3H), 1.90-1.70 (m, 3H), 1.52 (dd, J=13.1, 9.0 Hz, 1H), 1.33 (s, 3H), 1.18 (m, 1H), 1.03 (s, 9H), 0.76 (t, J=12.3 Hz, 1H).

$^{13}$C NMR (75 MHz, CDCl$_3$) δ [ppm] 145.91, 139.04, 129.99, 123.75, 120.29, 118.23, 95.53, 79.85, 79.62, 53.66, 52.69, 45.00, 42.97, 40.34, 34.40, 32.1, 31.8, 29.9, 29.1, 26.23, 22.9, 20.13, 17.8.

Example 44. Preparation of Buprenorphine (Step A1)

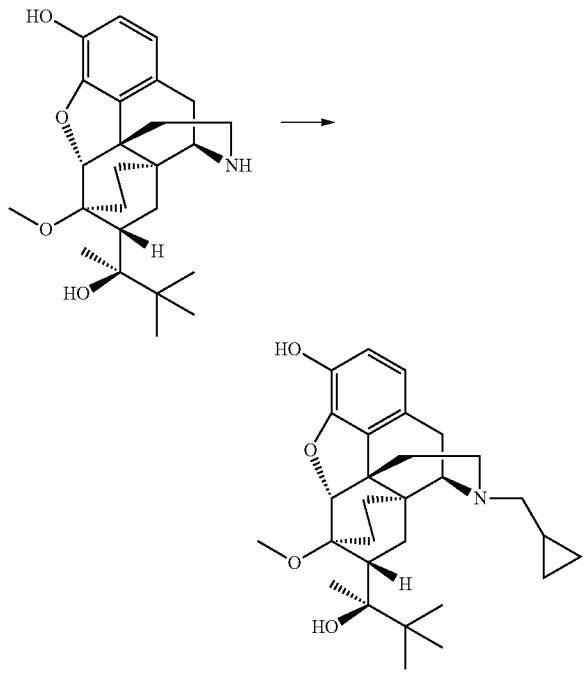

A 50 mL flask was charged with Compound HO-I-H (210 mg, 0.44 mmol), cyclopropane carboxaldehyde (80 μL, 1 mmol), dichloro(p-cymene)ruthenium(II) dimer (10 mg, 0.016 mmol), triethylamine (0.42 mL, 3.1 mmol), and acetonitrile (5 mL). The mixture was stirred under nitrogen at room temperature and formic acid (0.24 mL, 6.2 mmol) was added dropwise. The resulting mixture was heated at 60° C. for 1 h. The mixture was cooled to room temperature and concentrated under vacuum. The residue was partitioned between toluene and 1 N aqueous NaOH. The aqueous layer was extracted twice with toluene. The combined organic layers were washed with brine, dried on sodium sulfate, and concentrated under vacuum to afford buprenorphine (160 mg, 78%).

Buprenorphine

HPLC-purity 85.6% at 215 nm.
MS and NMR data were in agreement with those obtained in previous examples Example 45. Preparation of Compound HO-I-Ac (Step G)

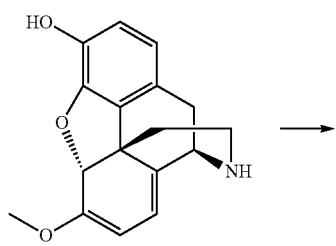

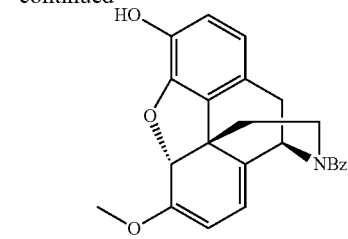

Under a nitrogen atmosphere benzoyl chloride (0.45 mL, 3.88 mmol) was added slowly to a stirred mixture of nororipavine (1.00 g, 3.53 mmol) and triethylamine (0.59 mL) in dichloromethane (10 mL). The resulting mixture was stirred for 50 minutes at room temperature. Dichloromethane (20 mL) was added. The mixture was extracted with water (2×10 mL). The organic layer was dried over Na$_2$SO$_4$, filtered and concentrated under reduced pressure. The residue was purified by column chromatography (4 g of silica, 0-60% EtOAc in heptanes) to afford Compound HO-I-Ac (0.82 g, 60%).

((12bS)-9-hydroxy-7-methoxy-1,2,4,7a-tetrahydro-3H-4,12-methanobenzofuro[3,2-e]isoquinolin-3-yl)(phenyl)methanone MS (ES-API pos) m/z 388.3 (M+H).
$^1$H NMR (300 MHz, CDCl$_3$) δ [ppm] 7.44 and 7.40 (2×s, 5H), 6.69 (d, J=8.2 Hz, 1H), 6.59 and 6.54 (2×d, J=8.2 Hz, 1H), 5.76 (m, 1H), 5.54 (s, 1H), 5.33 (d, J=7.6 Hz, 1H), 5.11 (d, J=5.9 Hz, 0.5H), 5.02 (d, J=6.5 Hz, 0.5H), 4.69 (m, 1H), 3.70-3.51 (m, 1H), 3.62 (s, 3H), 3.28-2.95 (m, 3H), 2.25-1.60 (m, 2H).

Example 46. Preparation of Compound BnO-I-Ac (Step F)

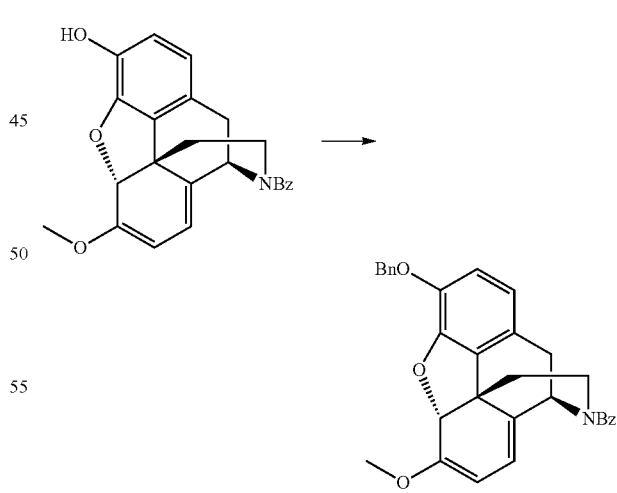

Under a nitrogen atmosphere a mixture of Compound BnO-I-Ac (826 mg, 2.13 mmol), benzyl bromide (0.38 mL, 3.20 mmol) and potassium carbonate (589 mg, 4.26 mmol) in acetone (6 mL) was heated to reflux for 18 h. The solvent was removed under reduced pressure. Water (20 mL) was added and the mixture was extracted with EtOAc (2×20 mL). The combined extracts were dried over Na$_2$SO$_4$, filtered and concentrated under reduced pressure. The residue was stirred with heptanes. The solvent was decanted and the residue was dried under reduced pressure at 50° C. to afford Compound BnO-I-Ac (1.13 g, quantitative yield).

((12bS)-9-(benzyloxy)-7-methoxy-1,2,4,7a-tetrahydro-3H-4,12-methanobenzofuro[3,2-e]isoquinolin-3-yl)(phenyl)methanone MS (ES-API pos) m/z 478.3 (M+H).
$^1$H NMR (300 MHz, CDCl$_3$) δ [ppm] 8.22-7.28 (m, 10H), 6.71 (d, J=8.2 Hz, 1H), 6.58 and 6.52 (2×d, J=8.2 Hz, 1H), 5.77 (m, 1H), 5.34 (d, J=8.8 Hz, 1H), 5.19 (m, 2H), 5.10 (d, J=5.9 Hz, 0.5H), 5.01 (d, J=6.5 Hz, 0.5H), 4.69 (m, 1H), 3.70-3.46 (m, 1H), 3.64 (s, 3H), 3.31-2.95 (m, 3H), 2.21-1.65 (m, 2H).

Example 47. Preparation of Compound BnO-I-Bn (step H)

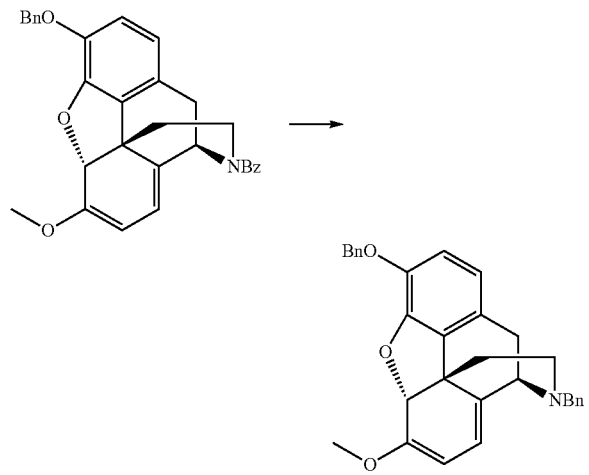

Under a nitrogen atmosphere lithium aluminium hydride (162 mg, 4.26 mmol) was added to a stirred solution of Compound BnO-I-Ac (1.02 g, 2.13 mmol) in THF (15 mL). The mixture was heated at 60° C. for 1.5 h. Water (0.16 mL), 15% aqueous NaOH (0.16 mL) and water (0.48 mL) were added. After stirring for 15 minutes EtOAc was added and the mixture was filtered over a pad of Celite. The filtrate was concentrated under reduced pressure and the residue was purified by column chromatography (25 g of silica, 0-90% EtOAc in heptanes to afford Compound BnO-I-Bn (694 mg, 70%) as an off-white solid.

(12bS)-3-benzyl-9-(benzyloxy)-7-methoxy-2,3,4,7a-tetrahydro-1H-4,12-methanobenzofuro[3,2-e]isoquinoline MS (ES-API pos) m/z 464.3 (M+H).
$^1$H NMR (300 MHz, CDCl$_3$) δ [ppm] 7.58-7.16 (m, 10H), 6.68 (d, J=8.1 Hz, 1H), 6.54 (d, J=8.2 Hz, 1H), 5.49 (d, J=6.4 Hz, 1H), 5.32 (s, 1H), 5.26-5.10 (m, 2H), 5.06 (d, J=6.4 Hz, 1H), 3.76 (m, 2H), 3.63 (s, 3H+m, 1H), 3.32 (d, J=17.9 Hz, 1H), 2.95 (td, J=13.0, 3.5 Hz, 1H), 2.76-2.66 (m, 2H), 2.26 (td, J=12.6, 5.0 Hz, 1H), 1.69 (d, J=12.3 Hz, 1H).
MS and NMR data were in agreement with those obtained in previous examples Example 48. Preparation of Compound AcO-I-Ac (step G)

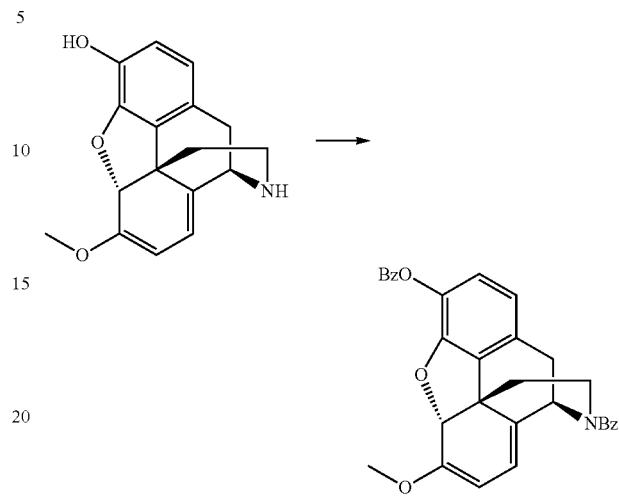

Under a nitrogen atmosphere benzoyl chloride (1.8 mL, 15.5 mmol) was added slowly to a stirred mixture of nor-oripavine (2.00 g, 7.06 mmol) and triethylamine (2.3 mL, 16.9 mmol) in dichloromethane (10 mL), while cooling in an ice-bath. The cooling bath was removed and the mixture was stirred at room temperature for 1.5 h. Dichloromethane (65 mL) was added and the mixture was extracted with water (2×30 mL). The organic layer was dried over Na$_2$SO$_4$, filtered and concentrated under reduced pressure. The residue was purified by column chromatography (40 g of silica, 0-85% EtOAc in heptanes) to afford Compound AcO-I-Ac (2.93 g, 84%).

(12bS)-3-benzoyl-7-methoxy-2,3,4,7a-tetrahydro-1H-4,12-methanobenzofuro[3,2-e]isoquinolin-9-yl benzoate MS (ES-API pos) m/z 492.2 (M+H).
$^1$H NMR (300 MHz, CDCl$_3$) δ [ppm] 8.20 (d, J=7.1 Hz, 2H), 7.62 (m, 1H), 7.51-7.42 (m, 7H), 6.94 (d, J=8.2 Hz, 1H), 6.73 and 6.68 (2×d, J=8.2 Hz, 1H), 5.80 (m, 1H), 5.36 (m, 1H), 5.11 (d, J=5.9 Hz, 0.5H), 5.02 (d, J=5.3 Hz, 0.5H), 4.73 (m, 1H), 3.73-3.49 (m, 1H), 3.61 (s, 3H), 3.37-3.03 (m, 3H), 2.26-1.82 (m, 2H).

Example 49. Preparation of Compound AcO-II-Ac (Step B)

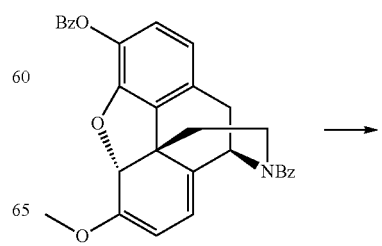

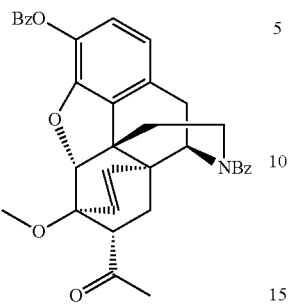

Under a nitrogen atmosphere a mixture of Compound AcO-I-Ac (2.93 g, 5.96 mmol) and methyl vinyl ketone (3.9 mL, 47.7 mmol) in toluene (25 mL) was heated at 80° C. for 16 h. After standing for 2 days at room temperature methyl vinyl ketone (3.9 mL, 47.7 mmol) was added. The mixture was heated at 80° C. for 16 h. The solvent was removed by evaporation under reduced pressure. The residue was purified by column chromatography (120 g of silica, 0-50% EtOAc in heptanes) to afford Compound AcO-II-Ac (2.89 g, 86%).

(4R,4aR,7R,7aR,12bS,14S)-14-acetyl-3-benzoyl-7-methoxy-1,2,3,4,7,7a-hexahydro-7,4a-ethano-4,12-methanobenzofuro[3,2-e]isoquinolin-9-yl benzoate MS (ES-API pos) m/z 562.2 (M+H).

$^1$H NMR (300 MHz, CDCl$_3$) δ [ppm] 8.15 (d, J=7.6 Hz, 2H), 7.62 (m, 1H), 7.52-7.39 (m, 7H), 6.91 (d, J=8.2 Hz, 1H), 6.70 and 6.66 (2×d, J=8.2 Hz, 1H), 6.10 (d, J=8.8 Hz, 0.5H), 5.97 (d, J=8.8 Hz, 0.5H), 5.73 (d, J=8.8 Hz, 0.5H), 5.52 (d, J=6.4 Hz, 0.5H), 5.43 (d, J=8.8 Hz, 0.5H), 4.75 (d, J=10.0 Hz, 0.5H), 4.60 (s, 1H), 4.40 (d, J=4.7 Hz, 0.5H), 3.71 (d, J=14.7 Hz, 0.5H), 3.55-3.26 (m, 1H), 3.50 (s, 3H), 3.20-3.03 (m, 2H), 2.93-2.84 (m, 1H), 2.38 (dd, J=12.9, 9.4 Hz, 1H), 2.18-2.02 (m, 4H), 1.91 (m, 1H), 1.71-1.56 (m, 1H).

Example 50. Preparation of Compound HO-IIIA-Ac (step D)

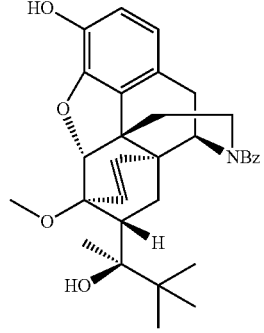

Dry toluene (120 mL) was added to a solution of tert-butylmagnesium chloride (1.7 M in THF, 27 mL). Part of the solvent was evaporated under reduced pressure at 50° C., leaving around 30 mL. Under a nitrogen atmosphere a solution of Compound AcO-II-Ac (1.69 g, 3.01 mmol) in dry toluene (12 mL) was added slowly by means of a syringe. The mixture was stirred at 60° C. for 3 h. After cooling to room temperature diethyl ether (50 mL) and water (75 mL) were added. The mixture was acidified with 1N aqueous HCl. Both layers were separated. The aqueous layer was extracted with EtOAc (2×50 mL). The combined organic layers were dried over Na$_2$SO$_4$, filtered and concentrated under reduced. The residue was purified by column chromatography (40 g of silica, 0-50% EtOAc in heptanes) to afford Compound HO-IIIA-Ac (1.10 g, 71%).

((4R,4aR,7R,7aR,12bS,14R)-9-hydroxy-14-(2-hydroxy-3,3-dimethylbutan-2-yl)-7-methoxy-1,2,7,7a-tetrahydro-7,4a-ethano-4,12-methanobenzofuro[3,2-e]isoquinolin-3(4H)-yl)(phenyl)methanone MS (ES-API pos) m/z 516.3 (M+H).

$^1$H NMR (300 MHz, CDCl$_3$) δ [ppm] 7.44-7.40 (m, 5H), 6.65 (d, J=8.2 Hz, 1H), 6.54 and 6.49 (2×d, J=8.2 Hz, 1H), 6.07 and 5.99 (2×d, J=9.4 Hz, 1H), 5.54-5.42 (m, 2H), 5.23 (d, J=8.8 Hz, 0.5H), 4.90-4.71 (m, 1.5H), 4.60 (d, J=10.6 Hz, 1H), 4.28 (d, J=6.5 Hz, 0.5H), 3.76 and 3.74 (2×s, 3H), 3.70-3.65 (m, 0.5H), 3.44-3.33 (m, 0.5H), 3.26-2.94 (m, 2.5H), 2.39-2.27 (m, 1H), 2.20-2.11 (m, 1H), 2.08-1.88 (m, 1H), 1.88-1.78 (m, 1H), 1.38-1.20 (m, 1H), 1.01 (s, 9H), 0.92 (s, 3H).

Example 51. Preparation of Compound HO-IIIA-Bn (Step H)

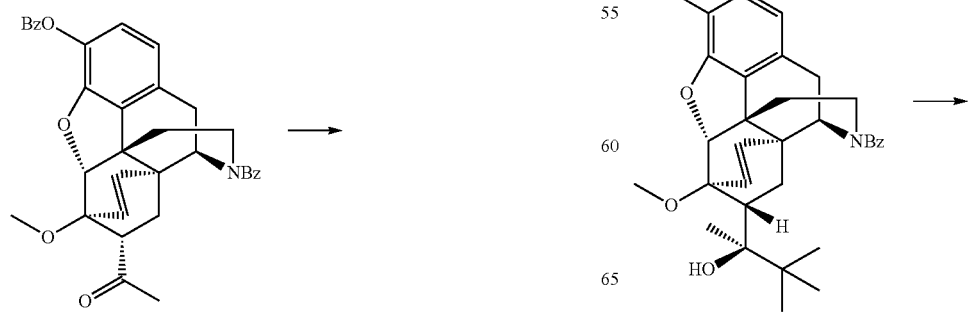

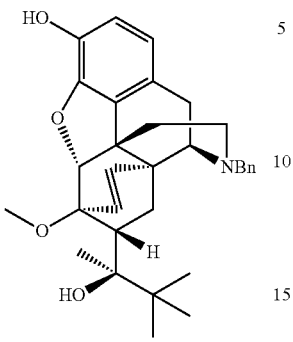

Under a nitrogen atmosphere Compound HO-II-Ac (1.01 g, 1.96 mmol) was dissolved in THF (25 mL). Lithium aluminum hydride (149 mg, 3.92 mmol) was added and the mixture was heated at 70° C. for 3 h. After standing for 18 h at room temperature water (70 mL) was added and the mixture was extracted with EtOAc (3×70 mL). The combined extracts were dried over Na₂SO₄, filtered and concentrated under reduced pressure. The residue was purified by column chromatography (24 g of silica, 0-30% EtOAc in heptanes) to afford Compound HO-IIIA-Bn (564 mg, 57%).

(4R,4aR,7R,7aR,12bS,14R)-3-benzyl-14-(2-hydroxy-3,3-dimethylbutan-2-yl)-7-methoxy-1,2,3,4,7,7a-hexahydro-7,4a-ethano-4,12-methanobenzofuro[3,2-e]isoquinolin-9-ol MS (ES-API pos) m/z 502.3 (M+H).
¹H NMR (300 MHz, CDCl₃) δ [ppm] 7.46-7.21 (m, 5H), 6.62 (d, J=8.0 Hz, 1H), 6.49 (d, J=8.1 Hz, 1H), 5.95 (d, J=8.9 Hz, 1H), 5.67 (s, 1H), 5.35 (d, J=8.9 Hz, 1H), 5.29 (s, 1H), 4.61 (s, 1H), 3.75 (s, 3H), 3.69 (s, 2H), 3.24 (d, J=18.4 Hz, 1H), 3.18-3.03 (m, 2H), 2.74-2.49 (m, 2H), 2.40 (dd, J=18.4, 6.7 Hz, 1H), 2.19 (t, J=8.6 Hz, 1H), 2.12-1.81 (m, 2H), 1.06 (s, 9H), 0.99 (s, 3H), 0.93 (dd, J=12.3, 8.8 Hz, 1H).

Example 52. Preparation of Compound HO-IV-H (Step C)

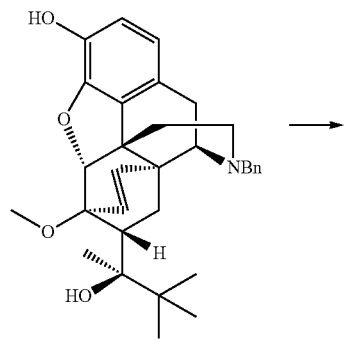

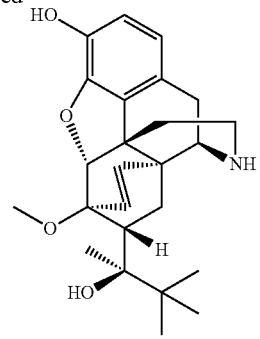

Compound HO-IIIA-Bn (560 mg, 1.12 mmol) was dissolved in 2-propanol (20 mL), followed by the addition of water (1 mL), 10% Pd/C (280 mg) and glacial acetic acid (0.2 mL). The mixture was reduced at 1 atmosphere of hydrogen pressure for 3 days. The reaction mixture was filtered over a pad of Celite and the filtrate was concentrated under reduced pressure. The residue was dissolved in a mixture of methanol (20 mL), water (1 mL) and glacial acetic acid (0.2 mL). After the addition of 10% Pd/C (280 mg) the mixture was reduced at 1 atmosphere of hydrogen pressure at 60° C. for 3 days. After cooling to room temperature the reaction mixture was filtered over a pad of Celite and the filtrate was concentrated under reduced pressure. The residue was purified by column chromatography (24 g of silica, 0-10% methanol in dichloromethane) to afford Compound HO-IV-H (228 mg, 49%).

Norbuprenorphine

MS and NMR data were in agreement with those obtained in previous examples.

Example 53. Preparation of Compound AcO-IIIB-Ac (Step C)

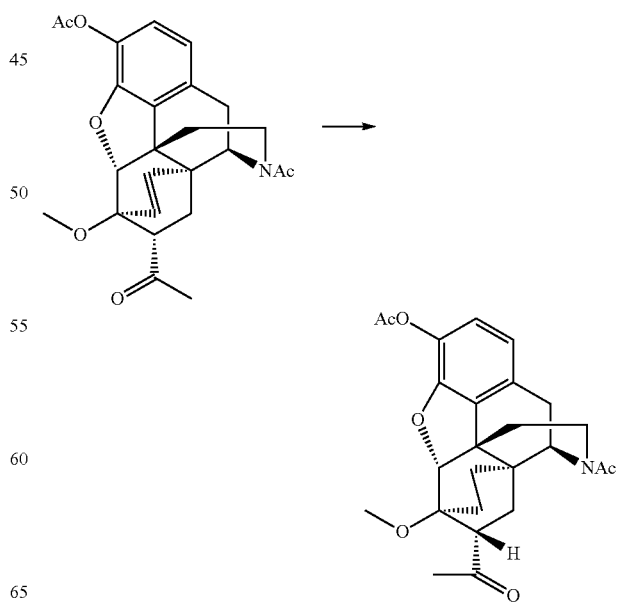

Compound AcO-II-Ac is dissolved in 2-propanol, followed by the addition of water, 10% Pd/C (10%) and glacial acetic acid. The mixture is reduced at 1 atmosphere of hydrogen pressure for 3 days at 80° C. After cooling to room temperature the reaction mixture is filtered over a pad of Celite and the filtrate is concentrated under reduced pressure. The residue is purified by column chromatography.

Example 54. Preparation of Compound HO-IV-Ac (Step D)

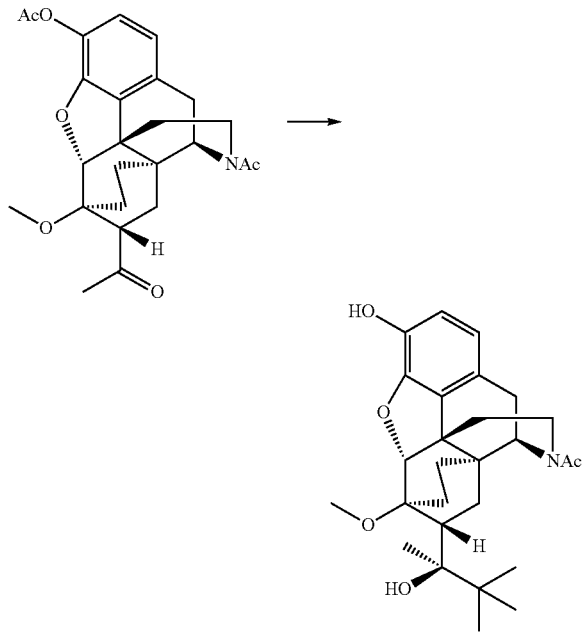

Dry toluene is added to a solution of tert-butylmagnesium chloride (1.7 M in THF). Under a nitrogen atmosphere a solution of Compound AcO-IIIB-Ac in dry toluene is added to the Grignard solution slowly by means of a syringe. The mixture is stirred at 60° C. for 3 h. After cooling to room temperature diethyl ether and water are added. The mixture is acidified with 1N aqueous HCl. Both layers are separated. The aqueous layer is extracted with EtOAc. The combined organic layers are dried over $Na_2SO_4$, filtered and concentrated under reduced. The residue is purified by column chromatography.

Example 55. Preparation of Compound HO-IV-Ac (Step C)

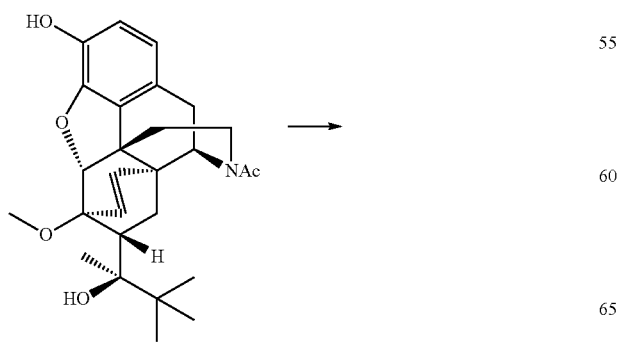

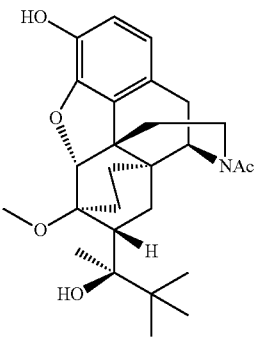

Compound HO-IIIA-Ac is dissolved in 2-propanol, followed by the addition of water, 10% Pd/C (10%) and glacial acetic acid). The mixture is reduced at 1 atmosphere of hydrogen pressure for 3 days at 80° C. After cooling to room temperature the reaction mixture is filtered over a pad of Celite and the filtrate is concentrated under reduced pressure. The residue is purified by column chromatography.

Example 56. Preparation of Compound HO-IV-H (Step I)

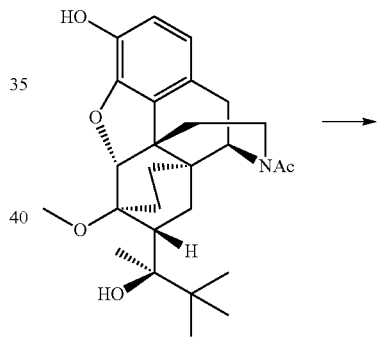

To a solution of HO-IV-Ac in THF at room temperature is added Schwartzs reagent in one portion. The resulting suspension is stirred under an argon atmosphere for 40 min, when the suspension turns pale red. The reaction mixture is evaporated to a thick oil, which is purified by column chromatography.

Example 57. Preparation of Compound HO-IV-H (Step I)

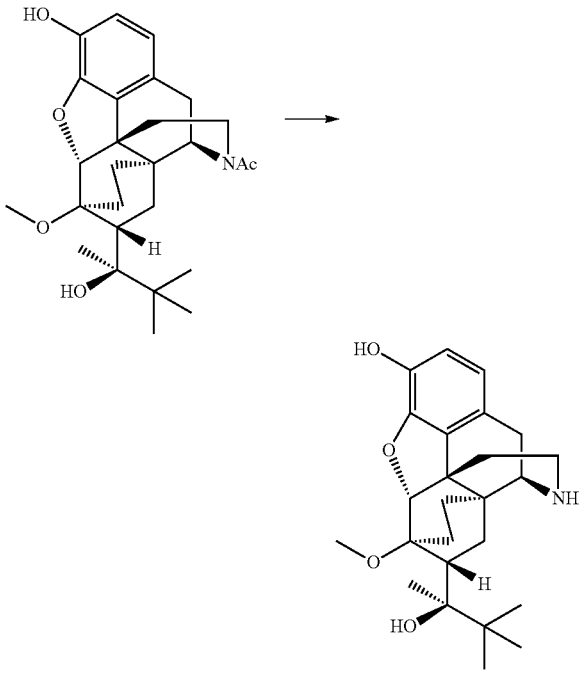

A mixture of HO-IV-Ac, KOH and diethylene glycol is stirred under an inert atmosphere at 170-180° C. for 7 h. The reaction mixture is then quenched with water (10 mL) and the products are extracted with dichloromethane. The combined organic layers are washed with water, brine, dried over Na2SO4 and concentrated. The product is isolated by column chromatography.

Example 58. Thebaine and Oripavine N-Demethylation by New Fungal Candidates

Figure 19:
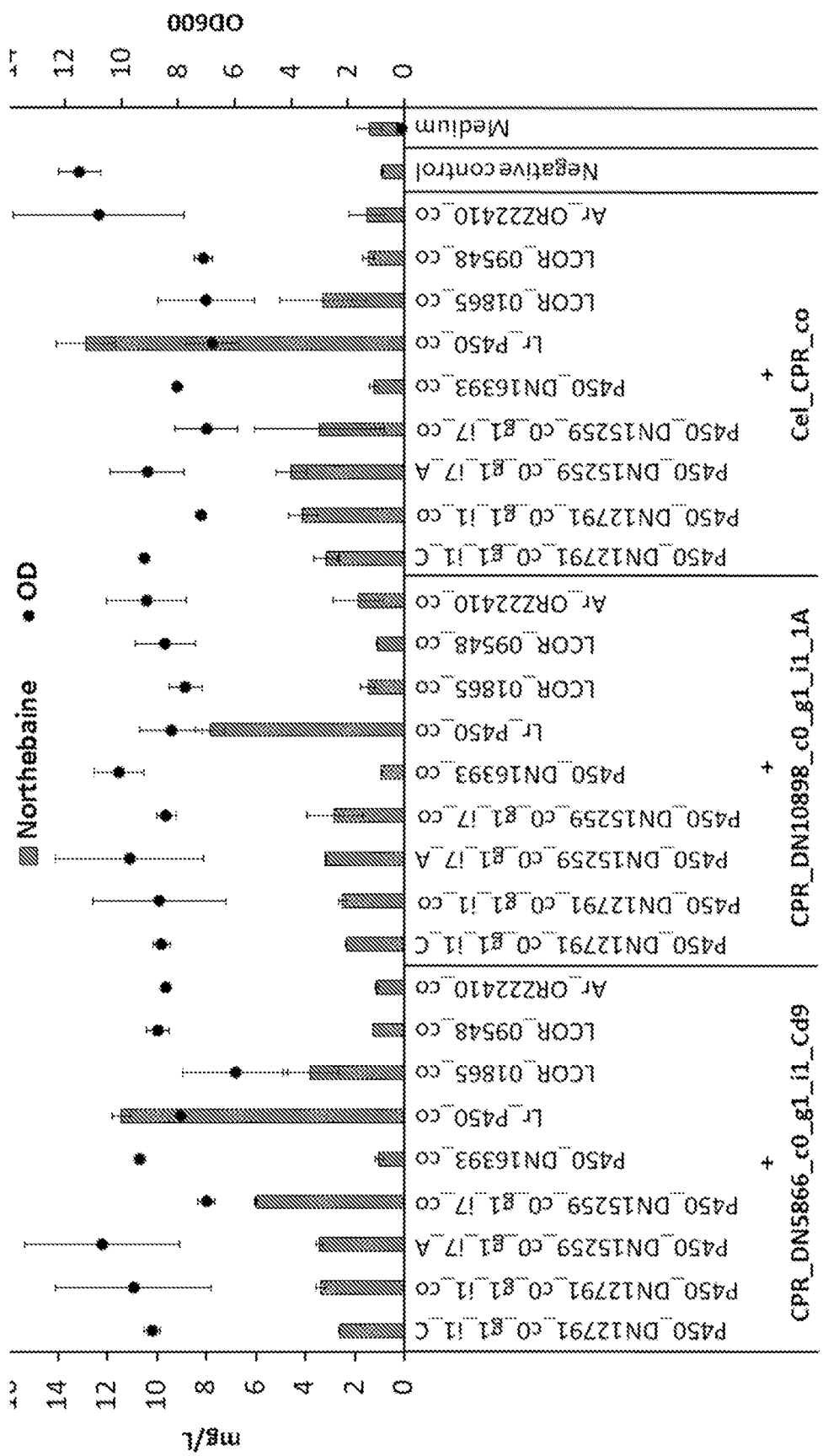
FIG. 19: Thebaine N-demethylation by new fungal candidates. Four new fungal cythochrome P450 candidates (P450_DN16393_co, LCOR_01865_co, LCOR_09548_co and Ar_ORZ22410_co) were co-expressed with three different CPRs in *S. cerevisiae*. Cells were fed with 0.5 mM thebaine in selective medium containing 0.1 M potassium phosphate buffer pH 7 and grown at 30° C. with shaking at 300 rpm for 72 h. The error bar represents the standard deviation of 4 different biological replicates.

The yeast codon-optimized putative cytochrome P450 genes from *Thamnostylum piriforme* (P450_DN16393_co (SEQ ID NO: 60)), *Lichtheimia corymbifera* (LCOR_01865_co (SEQ ID NO: 54) and LCOR_09548_co (SEQ ID NO: 56)) and *Absidia repens* (Ar_ORZ22410_co (SEQ ID NO: 58)) (see Table 6 shown in Example 4) were expressed in *S. cerevisiae* strains in combination with the CPRs, CPR_DN5866_c0_g1_i1_Cd9 (SEQ ID NO: 10) and CPR_DN10898_c0_g1_i1_1A (SEQ ID NO: 13) from *Thamnostylum piriforme* (Table 4 shown in Example 4) or the yeast codon-optimized CPR from *Cunninghamella elegans* Cel_CPR_co (SEQ ID NO. 17). The *Thamnostylum piriforme* P450_DN15259_c0_g1_i7_A (SEQ ID NO: 3) and P450_DN12791_c0_g1_i1_C (SEQ ID NO: 5), together with their yeast codon-optimized versions (P450_DN15259_c0_g1_i7_co (SEQ ID NO: 3) and P450_DN12791_c0_g1_i1_co (SEQ ID NO: 6)) and the *Lichtheimia ramosa* cytochrome P450 (Lr_P450_co) were used as positive controls. Cells were fed with either 0.5 mM thebaine or oripavine which were both prepared from a 25 mM stock dissolved in DMSO. Yeast cell incubation was performed in selective medium containing 0.1 M potassium phosphate buffer pH 7. After 72 h of growth at 30° C. with shaking at 300 rpm, 100 µl-supernatants were harvested, spiked with 1 mg/l caffeine as internal standard and analyzed by LC-MS (as described in Example 11). As seen in FIG. 19, both LCOR_01865_co (SEQ ID NO: 54) and Ar_ORZ22410_co (SEQ ID NO: 58) displayed activity towards thebaine, converting it to northebaine when co-expressed with at least one of the tested CPRs. In this study it appeared that Lr_P450_co (SEQ ID NO: 8) was performing the best conversion of thebaine into northebaine. This was not the case for P450_DN16393_co (SEQ ID NO: 60) and LCOR_09548_co (SEQ ID NO: 56) when compared to the controls.

Figure 20:
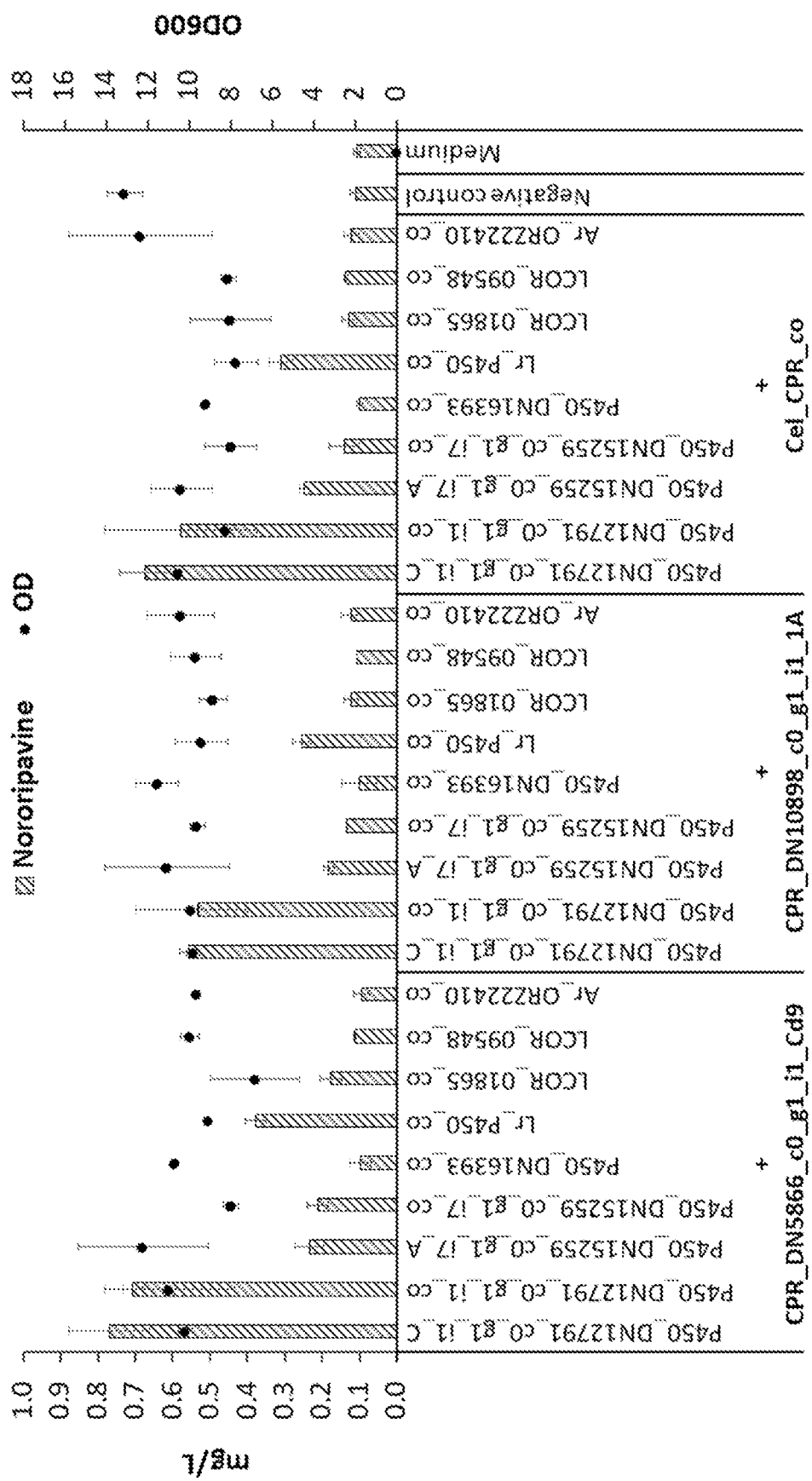
FIG. 20: Oripavine N-demethylation by new fungal candidates. Four new fungal cythochrome P450 candidates (P450_DN16393_co, LCOR_01865_co, LCOR_09548_co and Ar_ORZ22410_co) were co-expressed with three different CPRs in *S. cerevisiae*. Cells were fed with 0.5 mM oripavine in selective medium containing 0.1 M potassium phosphate buffer pH 7 and grown at 30° C. with shaking at 300 rpm for 72 h. The error bar represents the standard deviation of 4 different biological replicates.

Furthermore, it was shown that both LCOR_01865_co (SEQ ID NO: 54), Ar_ORZ22410_co (SEQ ID NO: 58) and LCOR_09548_co (SEQ ID NO: 56) were capable of producing nororipavine when oripavine was administered (FIG. 20).

Example 59. Thebaine or Oripavine N-Demethylation by Codon-Optimized Lr_P450 and Mc_S2JT25 Co-Expressed with CPRs Codon-optimized cytochrome P450 genes from *Lichteimia ramosa* (Lr_P450_co (SEQ ID NO: 8)) and the candidate homolog Mc_S2JT25_co (SEQ ID NO: 52) from *Mucor circinelloides* were co-expressed with two CPRs from *Thamnostylum piriforme*, that were either native or codon-optimized and one codon-optimized CPR, Cel_CPR from *Cunninghamella elegans*.

Figure 21:
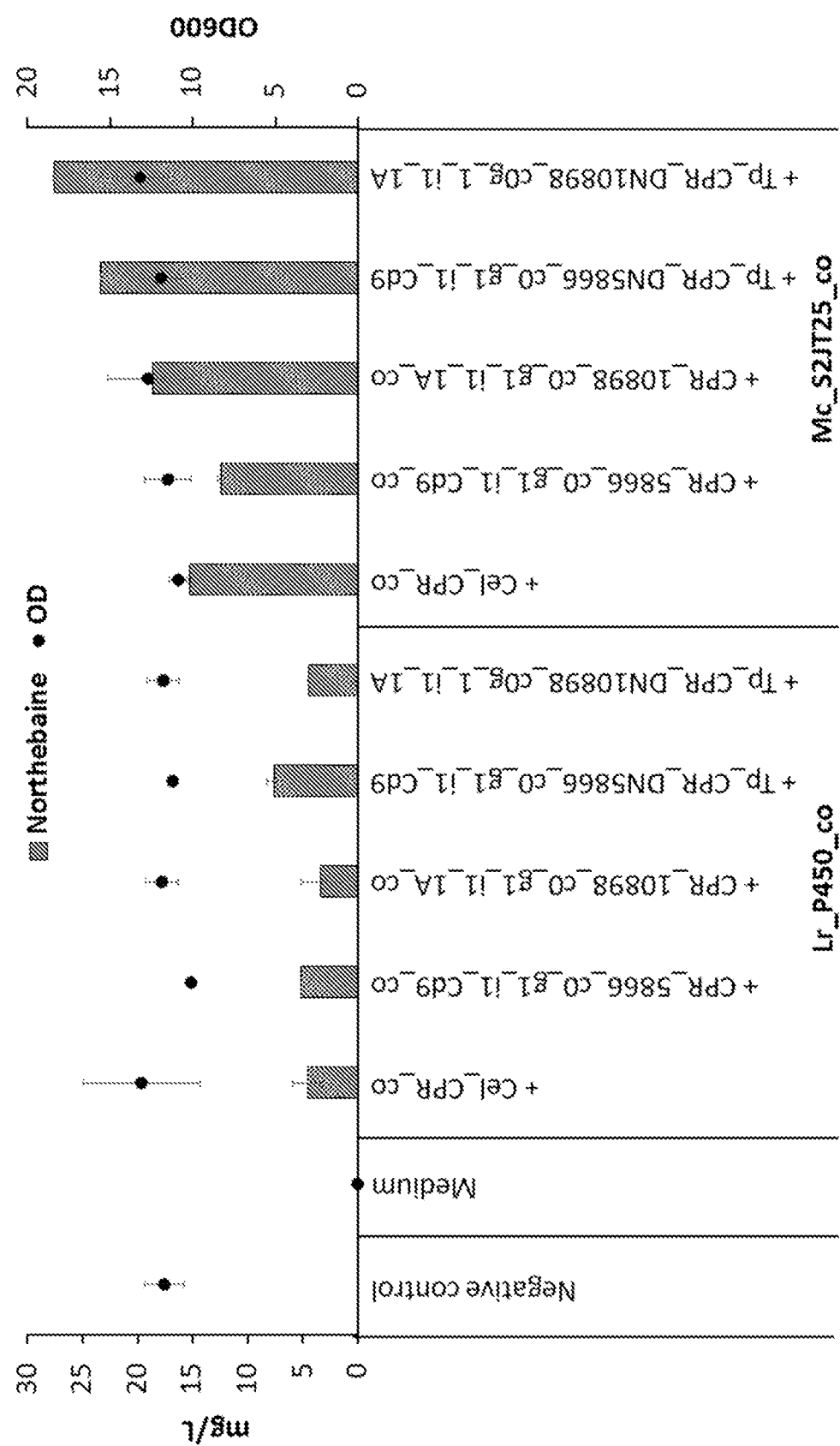
FIG. 21: Thebaine N-demethylation by codon-optimized Lr_P450 and Mc_S2JT125. The cytochrome P450 candidate Mc_S2J125_co from *Mucor circinelloides* and the cytochrome P450_Lr_P450_co from *L. ramosa* (used as positive control) were co-expressed with different CPRs. Cells were fed with 0.5 mM thebaine in selective medium containing 0.1 M potassium phosphate buffer pH 7 and grown at 30° C., 300 rpm for 72 h. The error bar represents the standard deviation of 4 different biological replicates.
Figure 22:
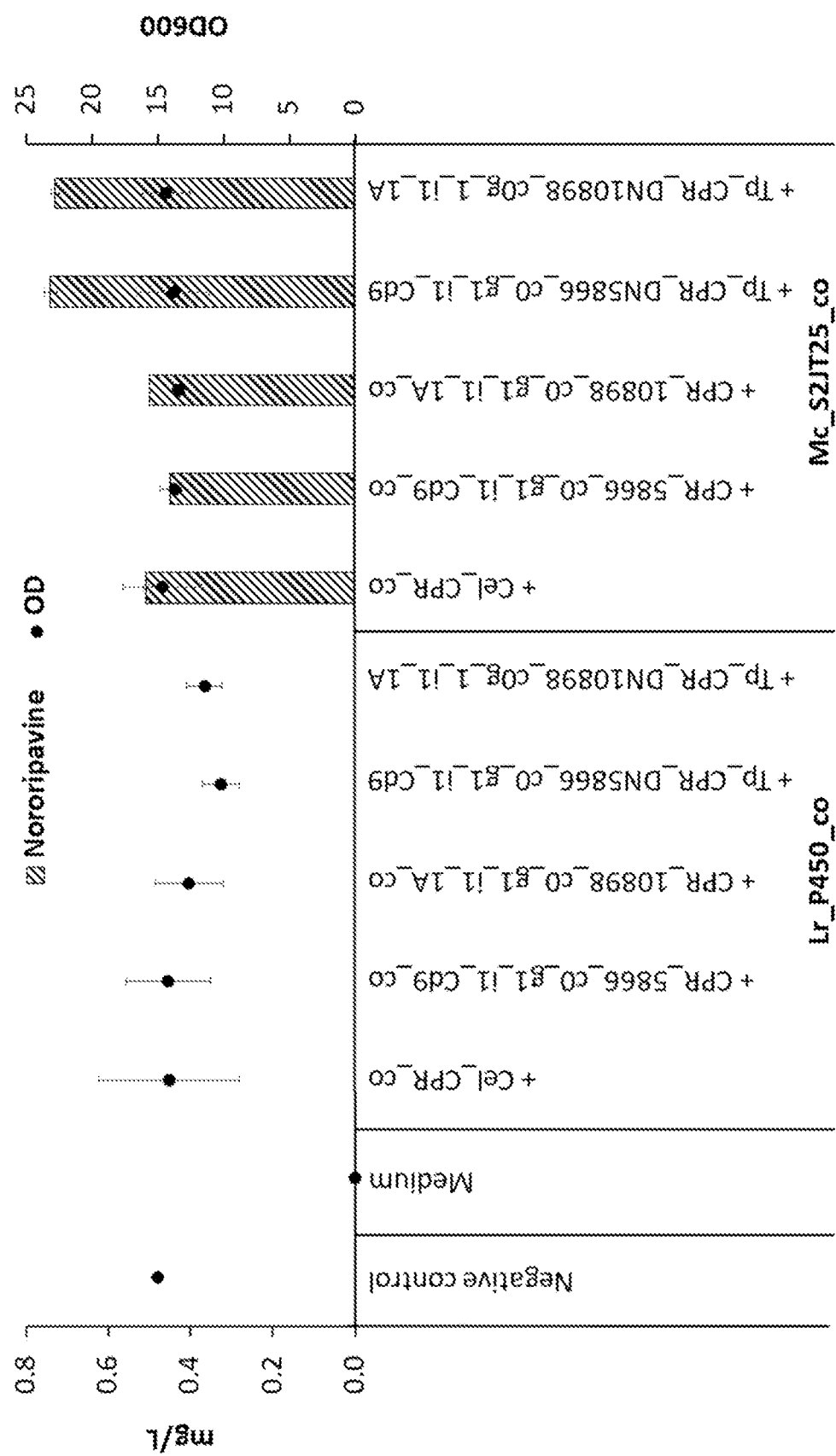
FIG. 22: Oripavine N-demethylation by codon-optimized Lr_P450 and Mc_S2JT125. The cytochrome P450 candidate Mc_S2JT25_co from *Mucor circinelloides* and the cytochrome P450 Lr_P450_co from *L. ramosa* (used as positive control) were co-expressed with different CPRs. Cells were fed with 0.5 mM oripavine in selective medium containing 0.1 M potassium phosphate buffer pH 7 and grown at 30° C., 300 rpm for 72 h. The error bar represents the standard deviation of 4 different biological replicates.

Cells were fed with either 0.5 mM thebaine or oripavine which were both prepared from a 25 mM stock dissolved in DMSO. Yeast cell incubation was performed in selective medium containing 0.1 M potassium phosphate buffer pH 7. After 72 h of growth at 30° C. with shaking at 300 rpm, 100 µl-supernatants were harvested, spiked with 1 mg/l caffeine as internal standard and analyzed by LC-MS (as described in Example 11). As seen in FIG. 21, the candidate homolog Mc_S2JT25_co (SEQ ID NO: 52) yielded the highest northebaine amount compared to Lr_P450_co (SEQ ID NO: 8), which previously was shown to have high thebaine conversion to northebaine. It was also shown that the codon usage of the CPR has an effect on northebaine production. Similarly, Mc_S2JT25_co (SEQ ID NO: 52) resulted in the highest amount of nororipavine compared to Lr_P450_co (SEQ ID NO: 8) when oripavine was administered (FIG. 22).

Figure 23:
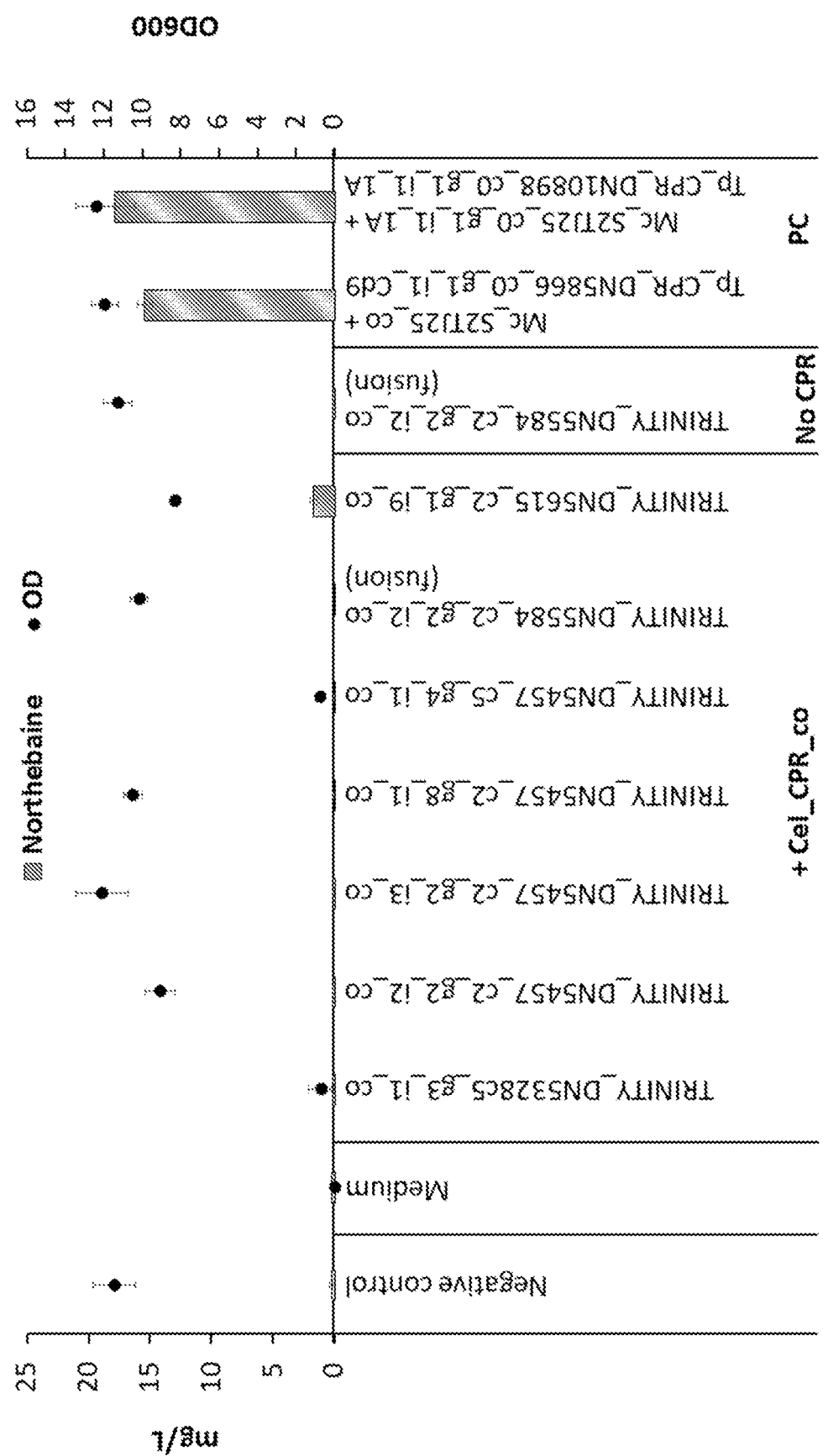
FIG. 23: Thebaine N-demethylation by codon-optimized *C. echinulata* cytochrome P450s along with Cel_CPR_co.

Example 60. Thebaine or Oripavine N-Demethylation by Codon-Optimized C. echinulata Cytochrome P450 Co-Expressed with Cel_CPR_Co Seven yeast-codon optimized cytochrome P450 candidates from *Cunninghamella echinulata* (Table 6 shown in example 4) were co-expressed with the CPR, Cel_CPR (SEQ ID NO: 17) from *Cunninghamella elegans* in *S. cerevisiae*. Cells were fed with either 0.5 mM thebaine or oripavine which were both prepared from a 25 mM stock dissolved in DMSO. Yeast cell incubation was performed in selective medium containing 0.1 M potassium phosphate buffer pH 7. After 72 h of growth at 30° C. with shaking at 300 rpm, 100 µl-supernatants were harvested, spiked with 1 mg/l caffeine as internal standard and analyzed by LC-MS (as described in Example 11). As seen in FIGS. 23 and 24, only one of the tested candidates, P450_DN5615_c2_g1_i9_co (SEQ ID NO: 62), displayed demethylase activity towards thebaine and oripavine, producing northebaine and nororipavine, respectively. Although the activity was substantially below the in vivo demethylation activity observed for Mc_S2JT25_co (SEQ ID NO: 52).

Example 61. In Planta Production of Either Northebaine or Oripavine by Heterologous Expression of Genes Encoding N-Demethylases and O-Demethylases, Respectively Transient expression of gene constructs in *Nicotiana benthamiana* Synthetic DNA fragments, codon optimized for *Saccharomyces cerevisiae* expression and encoding the demethylase enzymes Lr_P450_co (SEQ ID NO: 8), Mc_S2JT25_co (SEQ ID NO: 52) and Ps_CODM_co (SEQ ID NO: 132) and the cytochrome P450 reductase enzymes CPR_DN10898_c0_g1_i1_co (SEQ ID NO: 14) and Cel_CPR_co (SEQ ID NO: 17) were PCR amplified using standard deoxyuracil(dU)-containing primers. All amplified fragments were cloned into a modified version of the pCAMBIA130035Su plasmid under the control of the doubled enhancer element from CaMV 35S promoter, by using Uracil-Specific Excision Reagent (USER) cloning technology (Nour-Eldin et al., 2006). The modified pCAMBIA130035Su plasmid was generated by PCR amplifying the pCAMBIA130035Su plasmid using a standard deoxyuracil(dU)-containing primer pairand the amplified plasmid backbone was hereafter treated with DpnI (New England BioLabs). A synthetic DNA fragment encoding the OCS (Octapine Synthase) terminator from *Agrobacterium tumefaciens* (Genbank accession no. CP011249.1) was purchased from Integrated DNA Technologies and PCR amplified using a set of standard deoxyuracil(dU)-containing primers. The amplified OCS terminator was cloned in the DpnI-treated plasmid backbone with USER technology, yielding the modified pCAMBIA130035Su plasmid, pCAMBIA130035Su_MOD which was verified by DNA sequencing.

All plasmid-gene constructs along with a pCAMBIA130035Su_MOD plasmid containing the tomato p19 viral supressor gene (Baulcombe and Molnar, 2004) were transformed into the *Agrobacterium tumefaciens* strain, AGL-1 and infiltrated into leaves of *Nicotiana benthamiana* plants as described in (Bach et al., 2014). After 4 days, agroinfiltrated leaves were re-infiltrated with 0.5 mM thebaine which was prepared from a 110 mM thebaine stock dissolved in DMSO and diluted in water. Plants were hereafter left to grow for another 1 day in the green house.

Metabolite Extraction and LC-MS-MS Analysis

Metabolites were extracted from discs (Ø=3 cm) of agroinfiltrated *N. benthamiana* leaves. Leaf discs, excised with a cork borer, were flash frozen in liquid nitrogen. 0.5 ml of extraction buffer (60% (v/v) methanol, 0.1% (v/v) formic acid), equilibrated to 50° C., were added to each frozen leaf disc followed by incubation for 1 hour at 50° C., agitating at 600 rpm. The supernatant was isolated and passed through a Multiscreen$_{HTS}$ HV 0.45 µm filter plate (Merck Milipore) before analysis by LC-MS-MS.

For all compounds (thebaine, northebaine and oripavine) stock solutions were prepared in DMSO at a concentration of 10 mM. Standard solutions were prepared at concentrations of 6 µM, 4 µM, 2 µM, 1 µM, 500 nM, 200 nM, 100 nM, 50 nM, 20 nM and 10 nM from the stock solutions. Samples were injected into the Agilent 1290 UPLC coupled to an Ultivo Triple Quadrupole. The LC-MS method was as follows: Mobile Phase A. $H_2O$+0.1% Formic acid; Mobile Phase B: Acetonitrile+0.1% Formic acid; Column: Phenomenex Kinetex 1.7 µm XB-C18 100 Å, 2.1×100 mm. The elution gradient is shown in Table 2 and the LC-MS conditions are given in Table 3. Table 4 shows the mass spectrometer source and detector parameters and Table 5 shows the target compounds, their retention times, their parent ion, transition ions (MRM) as well as dwell times, cone voltages and collision energies used.

TABLE 2

| Gradient for LC-MS | |
|---|---|
| Time (min) | % B |
| 0 | 2 |
| 0.30 | 2 |
| 4.00 | 30 |
| 4.40 | 100 |
| 4.90 | 100 |
| 5 | 2 |
| 6 | 2 |

TABLE 3

| LC-MS conditions | |
|---|---|
| Parameter | Value |
| Injection volume | 2 µl |
| Column Temperature | 30° C. ± 4° C. |
| Injection method | Flow through needle |
| Flow | 0.4 ml/min |
| Auto sampler temperature | 10° C. ± 2° C. |
| Reconditioning wash | 2% Acetonitrile (in $H_2O$), 5 sec |
| Weak wash | 20% Methanol (in $H_2O$), 5 sec |
| Strong wash | 30% Acetonitrile, 30% Methanol, 30% 2-Propanol, 10% $H_2O$, 10 sec |
| Seal wash | 20% 2-Propanol (in $H_2O$) |

TABLE 4

| Mass spectrometer source and detector parameters (Ultivo Triple Quadrupole) | |
|---|---|
| Source Parameter | Value |
| Ion Source | Electrospray Positive Mode (ESI+) |
| Capillary Voltage | 3.5 kV |
| Nozzle Voltage | 500 V |
| Source Gas Temperature | 290° C. |
| Source Gas Flow | 12 L/min |
| Source Sheath Gas Temperature | 380° C. |
| Source Sheath Gas Flow | 12 L/min |
| Nebulizer | 30 psi |
| Mode | MS/MS |
| Collision | See Table 4 |

TABLE 5

Multiple reaction monitoring targets and conditions (ESI +)

| Target compound | Retention time (min) | Parent ion (m/z) | Daughter ion (m/z) | Dwell time (ms) | Fragment or voltage (V) | Collision energy (V) |
|---|---|---|---|---|---|---|
| Oripavine | 2.59 | 298 | 237 | 64.05 | 110 | 5 |
| Northebaine | 3.53 | 298 | 249 | 55.03 | 100 | 20 |
| Thebaine | 3.6 | 312 | 58 | 61.53 | 110 | 10 |

As seen in FIG. 25, a clear increase in northebaine is achieved upon transient co-expression of the N-demethylase genes, Lr_P450_co (SEQ ID NO: 8) or Mc_S2JT25_co (SEQ ID NO: 52) together with either the reductase genes, CPR_DN10898_c0_g1_i1_co (SEQ ID NO: 15) or Cel_CPR_co (SEQ ID NO: 17), in *N. benthamiana* leaves after thebaine infiltration (FIG. 26). This increase appears to be significantly above the levels detected in the negative P19 control. Such an increase in northebaine levels was however not apparent upon transiently co-expressing the O-demethylase gene, Ps_CODM_co (SEQ ID NO: 132) with either CPR_DN10898_c0_g1_i1_co (SEQ ID NO: 15) or Cel_CPR_co (SEQ ID NO: 17) in *N. benthamiana* (FIG. 25). The accumulation of small amounts of northebaine in the negative P19 control could point to one or more endogenous *N. benthamiana* enzymes which are capable of performing some conversion of the thebaine into northebaine.

In contrast, but as expected, the Ps_CODM_co (SEQ ID NO: 132) was the only enzyme of the tested demethylases that was capable of converting thebaine into oripavine when compared to the negative control (FIG. 27).

REFERENCES

1: Nour-Eldin H. H., Hansen B. G., Nørholm M. H., Jensen J. K., Halkier B. A. (2006). Advancing uracil-excision based cloning towards an ideal technique for cloning PCR fragments. Nucleic Acids Res. 34:e122.
2: Baulcombe D. C., Molnár A. (2004). Crystal structure of p19—a universal suppressor of RNA silencing. Trends Biochem Sci. 29: 279-81.
3: Bach, S. S., Bassard, J. E., Andersen-Ranberg, J., Moldrup, M. E., Simonsen, H. T., Hamberger, B. (2014). High-Throughput Testing of Terpenoid Biosynthesis Candidate Genes Using Transient Expression in *Nicotiana benthamiana*. In M Rodriguez Concepcion, ed, Plant Isoprenoids, Methods in Molecular Biology, Vol. 1153. Humana Press, New York.

Example 62. Production of Northebaine and Oripavine from Thebaine by Heterologous Expression of Genes Encoding Demethylases in *Aspergillus nidulans*

A selection of cytochrome P450 enzymes and the *P. somiferum* CODM (SEQ ID NO: 132) were tested in *Aspergillus nidulans* strain NID1 (argB2, pyrG89, veA1, nkuAΔ) (Nielsen et al 2008), in order to evaluate their demethylation capacity of thebaine to either northebaine (N-demethylation) or oripavine (O-demethylation).

A combination of N-demethylases (Lr_P450_co (SEQ ID NO: 8, Mc_S2JT25_co (SEQ ID NO: 52), P450_DN12791_c0_g1_i1_co (SEQ ID NO: 4)) and cytochrome P450 reductase enzymes were tested for demethylation of thebaine to northebaine. The 0-demethylase enzyme Ps_CODM_co (SEQ ID NO: 132), was also tested for the conversion of thebaine to oripavine.

All tested gene sequences were codon optimized for *Saccharomyces cerevisiae* expression and PCR amplified with standard deoxyuracil(dU)-containing primers. The PCR amplified fragments were cloned using the Uracil-Specific Excision Reagent (USER) cloning system (Nour-Eldin et al., 2006) and introduced into a vector system designed for expression and genomic integration in *A. nidulans* integration site 1 (IS1) (Hansen et al. 2011). The vector used in this study was pU1111-1, together with the gpdA promoter and trpC terminator as described by Hansen et al. 2011. Transformants were selected using the auxotrophic argB marker in the pU1111-1 plasmid. Correct genomic insertion of the expression cassettes were verified by PCR on fungal colonies, as described by Hansen et al. 2011. Five colonies from each transformation were inoculated in Minimal Medium (MM) containing uridine and uracil at pH 7 and 0.5 mM thebaine which was prepared from a 110 mM thebaine stock dissolved in DMSO. The cultures were incubated at 37° C. with 130 rpm agitation for 84 hours.

Metabolite Extraction and LC-MS-MS Analysis

Metabolites were extracted from 0.5 ml of culture supernatant with 0.5 ml of extraction buffer (80% (v/v) ethanol, 0.1% (v/v) formic acid), equilibrated to 50° C. by incubation for 1 hour at 50° C. with agitation at 600 rpm. The supernatant was isolated and passed through a MultiscreenHTS HV 0.45 μm filter plate (Merck Milipore) before analysis by LC-MS-MS as described in Example 64.

The production of northebaine was achieved upon heterologous expression of the N-demethylase genes Mc_S2JT25_co (SEQ ID NO: 52) and Tp_P450_DN12791_c0_g1_i1_co (SEQ ID NO: 5) (FIG. 28). This production appears to be significantly above the levels detected in the vector control (FIG. 28). Such an increase in northebaine levels was however not apparent upon heterologous expression of Lr_P450_co (SEQ ID NO: 8) (FIG. 28). The accumulation of northebaine in the vector control could point to one or more endogenous *A. nidulans* enzymes, which are capable of performing some conversion of the thebaine into northebaine. The bioconversion rate of thebaine to northebaine could likely be improved by the combination of the N-demethylase enzymes tested in this study with CPR enzymes, as it was done in the examples with *Saccharomyces cerevisiae*.

REFERENCES

Nour-Eldin H. H., Hansen B. G., Nørholm M. H., Jensen J. K., Halkier B. A. (2006). Advancing uracil-excision based cloning towards an ideal technique for cloning PCR fragments. Nucleic Acids Res. 34:e122.
Hansen B. G. et al (2011). Versatile enzyme expression and characterization system for *Aspergillus nidulans*, with the *Penicillium* brevicompactum polyketide synthase gene from the mycophenolic acid gene cluster as a test case. App. and Environmental Microbiology. 77(9):3044-3051
Nielsen, 3. B., M. L. Nielsen, and U. H. Mortensen. (2008). Transient disruption of non-homologous end-joining facilitates targeted genome manipulation in the filamentous fungus *Aspergillus nidulans*. Fungal Genet. Biol. 45:165-170.

Example 63. N-Demethylation Activity of New Cytochrome P450 Fungal and Plant Homologs Expression of cytochrome P450 fungal and plant homologs in *S. cerevisiae* Synthetic DNA fragments, codon-optimized for *Saccharomyces cerevisiae* expression and encoding different cytochrome P450 fungal and plant homologs together with a codon-optimized CPR from *Lichtheimia ramosa* (POR1) (Tablet) were synthesized by TWIST Bioscience or Integrated DNA technologies. The codon optimized-sequences Cel_CPR_co (SEQ ID NO: 17), CPR_5866_c0_g1_i1_co (SEQ ID NO: 11), CPR_DN10898_c0_g1_i1_co (SEQ ID NO: 12), Lr_P450_co (SEQ ID NO: 8), Mc_S2JT25_co (SEQ ID NO: 52) and the 0-demethylase enzyme Ps_CODM_co (SEQ ID NO: 132) were PCR amplified with standard primer sets, containing a SpeI (in the forward primer) and XhoI (in the reverse primer) restriction site. All cytochrome P450 genes were cloned into the SpeI and XhoI restriction sites of the P415-TEF vector and controlled by the TEF1 promoter (Mumberg et al., 1995)) (Table 6 shown in Example 4) and all cytochrome P450 reductase gene candidates and the Ps_CODM were cloned into the P413-TEF plasmid under the control of the TEF1 promoter (Mumberg, 1995) (Table 2)

Finally, all generated plasmid-construct were verified by DNA sequencing.

All plasmids containing cytochrome P450 homologs were co-expressed in *S. cerevisiae* together with each of the following CPRs: Cel_CPR_co (SEQ ID NO: 17), Tp_CPR_5866_c0_g1_i1_co (SEQ ID NO: 11), Tp_CPR_DN10898_c0_g1_i1_co (SEQ ID NO: 14) and POR1 (SEQ ID NO: 130). Cells were fed with 0.5 mM thebaine prepared from a 25 mM stock dissolved in DMSO and incubated in Synthetic Complete (SC) or DELFT media containing 0.1 M potassium phosphate buffer pH 7. Cells were grown at 30° C. with shaking at 300 rpm for 72 h.

Metabolite Detection

Metabolites were analyzed by harvesting the media supernatant and detected directly by LC-MS-MS. LC-MS-MS were as Example 64.

TABLE 1

Different tested gene sequences

| Name | Accession number | ORGANISM |
|---|---|---|
| Mc_S2JT25_co (SEQ ID NO: 52 and 53) | S2JT25 | *Mucor circinelloides* |
| LCOR_01865_co (SEQ ID NO: 54 and 55) | A0A068RKI7 | *Lichtheimia corymbifera* |
| LCOR_09548_co(SEQ ID NO: 56 and 57) | A0A068S8J3 | *Lichtheimia corymbifera* |
| Ar_ORZ22410_co(SEQ ID NO: 58 and 59) | A0A1X2IUG5 | *Absidia repens* |
| P450_DN16393_co (SEQ ID NO: 60 and 61) | | *Thamnostylum piriforme* |
| P450_DN5615_c2_g1_i9 (SEQ ID NO: 62 and 63) | TRINITY_DN5615_c2_g1_i9 | *Cunninghamella echinulata* |
| CYPDN4 (SEQ ID NO: 64 and 65) | I1CCX6 | *Rhizopus delemar* |
| CYPDN5 (SEQ ID NO: 66 and 67) | A0A1X0RYU8 | *Rhizopus microsporus* |
| CYPDN6 (SEQ ID NO: 68 and 69) | A0A0B7NKC0 | *Parasitella parasitica* |
| CYPDN7 (SEQ ID NO: 70 and 71) | I1CBZ0 | *Rhizopus delemar* |
| CYPDN8 (SEQ ID NO: 72 and 73) | A0A0C7AZL4 | *Rhizopus microsporus* |
| CYPDN9 (SEQ ID NO: 74 and 75) | A0A1X2HQ99 | *Syncephalastrum racemosum* |
| CYPDN10 (SEQ ID NO: 76 and 77) | A0A0B7NB52 | *Parasitella parasitica* |
| CYPDN11 (SEQ ID NO: 78 and 79) | A0A068SB73 | *Lichtheimia corymbifera* |
| CYPDN12 (SEQ ID NO: 80 and 81) | A0A1C7N669 | *Choanephora cucurbitarum* |
| CYPDN13 (SEQ ID NO: 82 and 83) | A0A1X2HZE4 | *Absidia repens* |
| CYPDN14 (SEQ ID NO: 84 and 85) | A0A168T1R5 | *Absidia glauca* |
| CYPDN15 (SEQ ID NO: 86 and 87) | XM_023607540 | *Rhizopus microsporus* |
| CYPDN16 (SEQ ID NO: 88 and 89) | A0A1X2HFU1 | *Syncephalastrum racemosum* |
| CYPDN17 (SEQ ID NO: 90 and 91) | A0A2G4SQ34 | *Rhizopus microsporus* |
| CYPDN18 (SEQ ID NO: 92 and 93) | A0A0C9MNJ6 | *Mucor ambiguus* |
| CYPDN19 (SEQ ID NO: 94 and 95) | A0A163B0W9 | *Phycomyces blakesleeanus* |
| CYPDN20 (SEQ ID NO: 96 and 97) | A0A163A6R1 | *Phycomyces blakesleeanus* |
| CYPDN21 (SEQ ID NO: 98 and 99) | XM_018432503 | *Phycomyces blakesleeanus* |
| CYPDN22 (SEQ ID NO: 100 and 101) | XM_023609077 | *Rhizopus microsporus* |
| CYPDN23 (SEQ ID NO: 102 and 103) | A0A162U6J3 | *Phycomyces blakesleeanus* |
| CYPDN24 (SEQ ID NO: 104 and 105) | A0A077WFB8 | *Lichtheimia ramosa* |
| CYPDN25 (SEQ ID NO: 106 and 107) | A0A1X2GSN6 | *Hesseltinella vesiculosa* |
| CYPDN26 (SEQ ID NO: 108 and 109) | A0A162N972 | *Phycomyces blakesleeanus* |
| CYPDN27 (SEQ ID NO: 110 and 111) | A0A077WLY1 | *Lichtheimia ramosa* |
| CYPDN28 (SEQ ID NO: 112 and 113) | A0A1X2HYB6 | *Absidia repens* |

TABLE 1-continued

Different tested gene sequences

| Name | Accession number | ORGANISM |
|---|---|---|
| CYPDN29 (SEQ ID NO: 114 and 115) | A0A068SBU5 | Lichtheimia corymbifera |
| CYPDN30 (SEQ ID NO: 116 and 117) | A0A1X2H4N2 | Syncephalastrum racemosum |
| CYPDN31 (SEQ ID NO: 118 and 119) | A0A291C3B2 | Absidia caerulea |
| CYPDN32 (SEQ ID NO: 120 and 121) | A0A173GQ95 | Absidia caerulea |
| CYPDN33 (SEQ ID NO: 122 and 123) | A0A162UUM5 | Phycomyces blakesleeanus |
| CYPDN34 (SEQ ID NO: 124 and 125) | A0A068SBP8 | Lichtheimia corymbifera |
| CYPDN35 (SEQ ID NO: 126 and 127) | A0A1X2GSL0 | Hesseltinella vesiculosa |
| CYPDN36 (SEQ ID NO: 128 and 129) | E5KY66 | Nicotiana sylvestris |
| POR1 (SEQ ID NO: 130 and 131) | A0A077WBH1 | Lichtheimia ramosa |
| Tp_CPR_DN5866_co (SEQ ID NO: 11 and 9) | | Thamnostylum piriforme |
| Tp_CPR_DN10898_co (SEQ ID NO: 14 and 12) | | Thamnostylum piriforme |
| Ps_CODM (SEQ ID NO: 132 and 133) | D4N502 | Papaver somniferum |

TABLE 2

Description of plasmids containing codon-optimized CPR genes.

| Vector name | Backbone | Promoter-Gene-Terminator | Description |
|---|---|---|---|
| pOD11 | P413-TEF | pTEF1-Tp_CPR_DN 10898 -tCYC1 | CPR_DN10898_c0_g1_i1 (co) from T. piriforme |
| pOD12 | P413-TEF | pTEF1- Tp_CPR_DN5866-tCYC1 | CPR_DN5866_c0_g1_i1 (co) from T. piriforme |
| pOD13 | P413-TEF | pTEF1- Cel_CPR_CO-tCYC1 | Cel_CPR (co) from Cunninghamella elegans |
| pOD14 | P413-TEF | pTEFl- POR1-tCYC1 | A0A077WBH1 (co) from Lichtheimia ramosa |

Thebaine N-Demethylation by New Fungal and Plant Candidates

As seen in FIG. 29a-29h, most of the new cytochrome P450 homologs tested show N-demethylation activity towards thebaine when they are expressed together with at least one of the tested CPRs (see Table 3). This activity seemed to markedly increased, in most cases, when the yeast cells were grown in DELFT media when compared to synthetic complete medium.

Thebaine O-Demethylation by New Cytochrome P450 Fungal Homologs

As seen in FIG. 30a-30d, CYPDN8 (SEQ ID NO: 72) and CYPDN17 (SEQ ID NO: 90) homologs display 0-demethylation activity and are capable of converting thebaine to oripavine. This 0-demethylation activity is apparently substantially higher than the one detected for the positive control Ps_CODM_co. Similarly, we also observed a positive effect on the oripavine production when cells were cultured in DELFT medium compared to synthetic complete medium.

Nororipavine Production by New Cytochrome P450 Fungal Homologs

As seen in FIG. 31a-31d, nororipavine production was detected when S. cerevisiae strains expressing cytochrome P450s CYPDN8 (SEQ ID NO: 72) or CYPDN17 (SEQ ID NO: 90) were grown in the presence of thebaine. Based on the previous observations with N- and O-demethylation of thebaine and the detection of nororipavine production, CYPDN8 (SEQ ID NO: 72) or CYPDN17 (SEQ ID NO: 90) appear to possess both N- and O-demethylation activity.

REFERENCES

Mumberg D., Müller R., Funk M. (1995). Yeast vectors for the controlled expression of heterologous proteins in different genetic backgrounds. Gene. 156(1):119-22.

TABLE 3

Northebaine production by fungal P450 and a N. sylvestris P450.

| Name | Northebaine production |
|---|---|
| CYPDN4 | − |
| CYPDN5 | + |
| CYPDN6 | + |
| CYPDN7 | + |
| CYPDN8 | + |
| CYPDN9 | − |
| CYPDN10 | + |
| CYPDN11 | + |
| CYPDN12 | + |
| CYPDN13 | + |
| CYPDN14 | + |

TABLE 3-continued

Northebaine production by fungal P450 and a *N. sylvestris* P450.

| Name | Northebaine production |
|---|---|
| CYPDN16 | + |
| CYPDN17 | + |
| CYPDN18 | + |
| CYPDN19 | − |
| CYPDN20 | + |
| CYPDN21 | + |
| CYPDN22 | + |
| CYPDN24 | + |
| CYPDN26 | − |
| CYPDN27 | + |
| CYPDN28 | + |
| CYPDN29 | + |
| CYPDN30 | + |
| CYPDN31 | + |
| CYPDN32 | − |
| CYPDN33 | − |
| CYPDN34 | + |
| CYPDN35 | + |
| CYPDN36 | − |

−: same or lower northebaine titers than negative control;
+: northebaine titers higher than negative control.

Example 64. Production of Northebaine from Thebaine by Heterologous Expression of Genes Encoding N-Demethylases in Non-Conventional Yeasts Example: Cloning of fungal CYP450/CPRs and enzymes in non-conventional yeasts A combination of CYP450/CPRs were tested in a set of non-conventional yeasts in order to evaluate the N-demethylation of thebaine to northebaine. The tested CYP450 candidates were Lr_P450_co (SEQ ID NO: 8), Mc_S2JT25_co (SEQ ID NO: 52), P450_DN12791_c0_g1_i1_co (SEQ ID NO: 4) and the tested CPR enzymes were CPR_10898_c0_g1_i1_co (SEQ ID NO: 12), Cel_CPR_co (SEQ ID NO: 16) and CPR_5866_c0_g1_i1_co (SEQ ID NO: 9).

All gene sequences were codon-optimized for *Saccharomyces cerevisiae* expression and cloned in between the *S. cerevisiae* promoters (TEF1 or PGK1) and terminators (CYC1 or ADH1)) (see Table 1). DNA constructs containing promoter-gene-terminator were PCR amplified from plasmid templates (see Table 1) with standard primer sets containing deoxyuracil (dU). The PCR amplified fragments were cloned using the Uracil-Specific Excision Reagent (USER) based vector system (Jensen et al., 2014; Nour-Eldin et al., 2006) with some modifications. In order to express these genes in various non-conventional yeasts, a self-replicating vector containing a pangenomic optimized yeast replication origin panARS that allows stable plasmid expression in different yeast species, was used (Liachko and Dunham 2014). Nourseothricin/clonNat (natMX) dominant marker was used for selection in the different yeast species. Different combinations of plasmids containing CPRs/P450s were constructed (see Table 2). PanARS plasmids, containing the different promoter-gene-terminator fragments were transformed into different yeast strains (see Table 3) using the lithium acetate method (Gietz and Woods 2007) with some minor modifications. The heat shock step was performed at 40° C. for 1 h and cultures were grown at 30° C. on YPD media for 4 hours before plating to allow cells to acquire antibiotic resistance. The transformed strains expressing the genes of interest were grown in 0.5 ml of YEPD media at pH 7 with 50 mg/L of clonNat and 0.5 mM of thebaine added as a 110 mM stock solution in DMSO. The cultures were incubated at 30° C. with shaking at 300 rpm for 96 hours.

Metabolite Detection

Metabolites were analyzed by harvesting the media supernatant and detected directly by LC-MS-MS. LC-MS-MS were as Example 64.

TABLE 1

Amplified DNA fragments

| promoter-gene-terminator | DNA template |
|---|---|
| pTEF1 - Cel_CPR_co - tADH1 | pEV31215 |
| pTEF1 - CPR_5866_c0_g1_i1 _co - tADH1 | pEV32634 |
| pTEF1 - CPR_10898_c0_g1_i1_co - tADH1 | pEV32635 |
| pPGK1 - Lr_P450_co - tCYC1 | pEV32228 |
| pPGK1 -P450_DN12791_c0_g1_i1_co - tCYC1 | PEV32227 |
| pPGK1 - Mc_S2JT25_co - tCYC1 | pEV33161 |

TABLE 2

List of plasmids constructs

| Name | DNA constructs | Plasmid Backbone | Bacterial Selection Marker | Selection Marker |
|---|---|---|---|---|
| pOD73 | [pTEF1 - Cel_CPR_co - tADH1] + [pPGK1 - Lr_P450_co - tCYC1] | pDIV19 | Amp | clonNat |
| pOD74 | [pTEF1 - CPR_5866_c0_g1_i1_co - tADH1] + [pPGK1 - P450_DN12791_c0_g1_i1_co - tCYC1] | pDIV19 | Amp | clonNat |
| pOD75 | [pTEF1- CPR_10898_c0_g1_i1_co - tADH1] + [pPGK1 - Mc_S2JT25_co - tCYC1] | pDIV19 | Amp | clonNat |

TABLE 3

List of yeasts strains tested in this study

| Specie name | Genotype | Collection Ids |
|---|---|---|
| *Saccharomyces paradoxus* | WT | CBS 2908 |
| *Kluyveromyces marxianus* | WT | IBT 42; CBS 1574 |
| *Kluyveromyces marxianus* | WT | IBT 82 |
| *Kluyveromyces marxianus* | WT | IBT 86 |
| *Ogataea thermomethanolica* | WT | CBS 8099 |

The bioconversion of thebaine to northebaine was achieved upon heterologous co-expression of N-demethylase genes together with cytochrome P450 reductase genes in 3 different strains of *K. marxianus* and one strain of *O. thermomethanolica* and one strain of *S. paradoxus* (FIG. 32). The formation of northebaine is clearly increased above the levels detected in the control strains containing the empty vector. The accumulation of northebaine in the vector control, especially for *O. thermomethanolica* and *S. paradoxus*, could point to one or more endogenous enzymes, which are capable of performing some conversion of thebaine into northebaine.

REFERENCES

Nour-Eldin H. H., Hansen B. G., Nørholm M. H., Jensen J. K., Halkier B. A. (2006). Advancing uracil-excision based cloning towards an ideal technique for cloning PCR fragments. Nucleic Acids Res. 34:e122.

Jensen, N. B. et al (2014). EasyClone: Method for iterative chromosomal integration of multiple genes in *Saccharomyces cerevisiae*. FEMS Yeast Res. 14, 238-248.

Gietz, R. D. & Schiestl, R. H. (2007). High-efficiency yeast transformation using the LiAc/SS carrier DNA/PEG method. Nat Protoc 2(1), 31-4.

Liachko and Dunham (2014). An Autonomously Replicating Sequence for use in a wide range of budding yeasts. FEMS Yeast Res. 14(2): 364-367.

Tables

TABLE 1

Cytochrome P450 reductases

| Transcript/protein (Accession Number) | Species/Strain |
|---|---|
| CPR_DN2505_c0_g1_i1 (n.a.) (nucleotide sequence SEQ ID NO: 15) | *Thamnostylum piriforme* ATCC 8992 |
| CPR_DN5866_c0_g1_i1 (n.a.) (SEQ ID NO: 9) | *Thamnostylum piriforme* ATCC 8992 |
| CPR_DN10898_c0_g1_i1 (n.a.) (SEQ ID NO: 12) | *Thamnostylum piriforme* ATCC 8992 |
| NADPH-dependent cytochrome P450 oxidoreductase (AAF89958) (SEQ ID NO: 16) | *Cunninghamella elegans* |
| Cytochrome P450 oxidoreductase (Q7Z8R1) (SEQ ID NO: 18) | *Gibberella fujikuroi* |
| NADPH-cytochrome P450 reductase (P16603) (SEQ ID NO: 20) | *Saccharomyces cerevisiae* |
| NADPH-cytochrome P450 reductase (BAB18572.1) (SEQ ID NO: 50) | *Homo sapiens* |

TABLE 3

Oligonucleotides used for PCR amplification of target genes from *Thamnostylum piriforme*.

| No. | Transcript name | Primer name | |
|---|---|---|---|
| | P450 gene candidates | | |
| 1 | P450_DN2971_c0_g2_i1 | EVPR18235_39D2 | fw |
| | | EVPR18236_39D3 | rev |
| 2 | P450_DN6887_c0_g1_i2_1 | EVPR18237_39D4 | fw |
| | | EVPR18239_39D6 | rev |
| 3 | P450_DN6887_c0_g1_i2_2 | EVPR18238_39D5 | fw |
| | | EVPR18239_39D6 | rev |
| 4 | P450_DN8261_c0_g2_i1 | EVPR18240_39D7 | fw |
| | | EVPR18241_39D8 | rev |
| 5 | P450_DN9169_c0_g2_i1 | EVPR18242_39D9 | fw |
| | | EVPR18243_39E1 | rev |
| 6 | P450_DN9560_c0_g1_i1 | EVPR18244_39E2 | fw |
| | | EVPR18245_39E3 | rev |
| 7 | P450_DN10444_c0_g1_i1 | EVPR18246_39E4 | fw |
| | | EVPR18247_39E5 | rev |
| 8 | P450_DN10880_c0_g1_i3 | EVPR18248_39E6 | fw |
| | | EVPR18249_39E7 | rev |
| 9 | P450_DN12040_c0_g1_i1 | EVPR18250_39E8 | fw |
| | | EVPR18251_39E9 | rev |
| 10 | P450_DN12791_c0_g1_i1 | EVPR18252_39F1 | fw |
| | | EVPR18253_39F2 | rev |
| 11 | P450_DN13606_c0_g1_i3 | EVPR18254_39F3 | fw |
| | | EVPR18255_39F4 | rev |
| 12 | P450_DN13846_c0_g1_i2 | EVPR18256_39F5 | fw |
| | | EVPR18257_39F6 | rev |
| 13 | P450_DN14156_c0_g1_i1 | EVPR18258_39F7 | fw |
| | | EVPR18259_39F8 | rev |
| 14 | P450_DN14346_c0_g2_i2 | EVPR18260_39F9 | fw |
| | | EVPR18261_39G1 | rev |
| 15 | P450_DN14398_c0_g2_i6 | EVPR18262_39G2 | fw |
| | | EVPR18263_39G3 | rev |
| 16 | P450_DN14859_c0_g1_i9 | EVPR18264_39G4 | fw |
| | | EVPR18265_39G5 | rev |
| 17 | P450_DN15259_c0_g1_i7 | EVPR18266_39G6 | fw |
| | | EVPR18267_39G7 | rev |
| 18 | P450_DN15334_c0_g1_i1 | EVPR18268_39G8 | fw |
| | | EVPR18269_39G9 | rev |

TABLE 2

Cloning strategy of target genes into yeast expression vectors.

| Parent backbone and description | Promoter-Gene-Terminator | Gene Description | Restriction sites used | Final construct |
|---|---|---|---|---|
| PEVE2120, single expression vector [ARS-CEN/pPGK1-tADH2/URA3], Amp$^R$ | pPGK1-Tp_P450 (_1 to _23)-tADH2, except Tp_P450_6 | P450s from *T. piriforme* (22 ORFs) | SfiI/SacII | PEV31493-31564, excluding PEV31508-3150 |
| | pPGK1-Tp_P450_6-tADH2 | P450_DN9560_c0_g1_i1 from *T. piriforme* | SfiI/BamHI | PEV31508-31510 |
| PEVE3307, double expression vector [ARS-CEN/pTEF1-tADH1/pPGK1-tCYC1/HIS3], Amp$^R$ | pTEF1-Tp_CPR_1-tADH1 | CPR_DN2505_c0_g1_i1 from *T. piriforme* | PmeI/PacI | PEV31719-31722 |
| | pTEF1-Cel_CPR_co-tADH1 | CPR from *Cunninghamella elegans* (co) | PmeI/PacI | PEV31215 |
| | pTEF1-Sc_CPR-tADH1 | CPR from *S. cerevisiae* | PmeI/PacI | pEV28686 |
| pEVE3308, double expression vector [ARS-CEN/PTEF1-tADH1/pPGK1-tCYC1/LEU2], Amp$^R$ | pTEF1-Tp_CPR_2-tADH1 | CPR_DN5866_c0_g1_i1 from *T. piriforme* | PmeI/PacI | pEV31723-31729 |
| | pTEF1-Tp_CPR_3-tADH1 | CPR_DN10898_c0_g1_i1 from *T. piriforme* | PmeI/PacI | pEV31730-31733 |
| | pPGK1-Gf_CPR_co-tCYC1 | CPR from *Gibberella fujikuroi* (co) | HindIII/SacII | PEV31104 |
| PEV31104 | pTEF1-Sc_CPR-tADH1/pPGK1-Gf_CPR_co-tCYC1 | CPR from *S. cerevisiae* and CPR from *Gibberella fujikuroi* (co) | PmeI/PacI | PEV31308 |
| | pTEF1-Tp_CPR_3-tADH1/pPGK1-Gf_CPR_co-tCYC1 | CPR_DN10898_c0_g1_i1 from *T. piriforme* and CPR from *Gibberella fujikuroi* (co) | PmeI/PacI | pEV31734-31737 |

Abbreviations: co, codon optimized for *S. cerevisiae*.

TABLE 3-continued

Oligonucleotides used for PCR amplification of target genes from *Thamnostylum piriforme*.

| No. | Transcript name | Primer name | |
|---|---|---|---|
| 19 | P450_DN16201_c0_g1_i2_1 | EVPR18270_39H1 | fw |
| | | EVPR18273_39H4 | rev |
| 20 | P450_DN16201_c0_g1_i2_2 | EVPR18271_39H2 | fw |
| | | EVPR18273_39H4 | rev |
| 21 | P450_DN16201_c0_g1_i2_3 | EVPR18272_39H3 | fw |
| | | EVPR18273_39H4 | rev |
| 22 | P450_DN16821_c0_g1_i8 | EVPR18274_39H5 | fw |
| | | EVPR18275_39H6 | rev |
| 23 | P450_DN16821_c0_g1_i12 | EVPR18276_39H7 | fw |
| | | EVPR18277_39H8 | rev |
| CPR gene candidates | | | |
| 1 | CPR_DN2505_c0_g1_i1 | EVPR18278_39H9 | fw |
| | | EVPR18279_39I1 | rev |
| 2 | CPR_DN5866_c0_g1_i1 | EVPR18280_39I2 | fw |
| | | EVPR18281_39I3 | rev |
| 3 | CPR_DN10898_c0_g1_i1 | EVPR18282_39I4 | fw |
| | | EVPR18283_39I5 | rev |

Abbreviations: fw: forward primer; rev: reverse primer.

TABLE 4

Description of plasmids containing target genes from *T. piriforme*. Unless otherwise specified, all clones originated from cDNA obtained on day 6 after induction.

| Vector name | Backbone | Promoter-Gene-Terminator |
|---|---|---|
| pEV31493 | pEVE2120 | pPGK1-P450_DN2971_c0_g2_i1_A-tADH2 |
| pEV31494 | pEVE2120 | pPGK1-P450_DN2971_c0_g2_i1_B-tADH2 |
| pEV31495 | pEVE2120 | pPGK1-P450_DN2971_c0_g2_i1_C-tADH2 |
| pEV31496 | pEVE2120 | pPGK1-P450_DN6887_c0_g1_i2_1A-tADH2 |
| PEV31497 | pEVE2120 | pPGK1-P450_DN6887_c0_g1_i2_1B-tADH2 |
| PEV31498 | pEVE2120 | pPGK1-P450_DN6887_c0_g1_i2_1C-tADH2 |
| pEV31499 | pEVE2120 | pPGK1-P450_DN6887_c0_g1_i2_2A-tADH2 |
| pEV31500 | pEVE2120 | pPGK1-P450_DN6887_c0_g1_i2_2B-tADH2 |
| PEV31501 | pEVE2120 | pPGK1-P450_DN6887_c0_g1_i2_2C-tADH2 |
| pEV31502 | pEVE2120 | pPGK1-P450_DN8261_c0_g2_i1_A-tADH2 |
| pEV31503 | pEVE2120 | pPGK1-P450_DN8261_c0_g2_i1_B-tADH2 |
| pEV31504 | pEVE2120 | pPGK1-P450_DN8261_c0_g2_i1_C-tADH2 |
| pEV31505 | pEVE2120 | pPGK1-P450_DN9169_c0_g2_i1_A-tADH2 |
| PEV31506 | pEVE2120 | pPGK1-P450_DN9169_c0_g2_i1_B-tADH2 |
| pEV31507 | pEVE2120 | pPGK1-P450_DN9169_c0_g2_i1_C-tADH2 |
| pEV31508 | pEVE2120 | pPGK1-P450_DN9560_c0_g1_i1_A-tADH2 |
| pEV31509 | pEVE2120 | pPGK1-P450_DN9560_c0_g1_i1_B-tADH2 |
| pEV31510 | pEVE2120 | pPGK1-P450_DN9560_c0_g1_i1_C-tADH2 |
| pEV31511 | pEVE2120 | pPGK1-P450_DN10444_c0_g1_i1_A-tADH2 |
| pEV31512 | pEVE2120 | pPGK1-P450_DN10444_c0_g1_i1_B-tADH2 |
| pEV31513 | pEVE2120 | pPGK1-P450_DN10444_c0_g1_i1_C-tADH2 |
| pEV31514 | pEVE2120 | pPGK1-P450_DN10880_c0_g1_i3_A-tADH2 |
| pEV31515 | pEVE2120 | pPGK1-P450_DN10880_c0_g1_i3_B-tADH2 |
| pEV31516 | pEVE2120 | pPGK1-P450_DN10880_c0_g1_i3_C-tADH2 |
| pEV31517 | pEVE2120 | pPGK1-P450_DN12040_c0_g1_i1_A-tADH2 |
| pEV31518 | pEVE2120 | pPGK1-P450_DN12040_c0_g1_i1_B-tADH2 |
| pEV31519 | pEVE2120 | pPGK1-P450_DN12040_c0_g1_i1_C-tADH2 |
| pEV31520 | pEVE2120 | pPGK1-P450_DN12791_c0_g1_i1_A-tADH2 |
| PEV31521 | pEVE2120 | pPGK1-P450_DN12791_c0_g1_i1_B-tADH2 |
| pEV31522 | pEVE2120 | pPGK1-P450_DN12791_c0_g1_i1_C-tADH2 |
| pEV31523 | pEVE2120 | pPGK1-P450_DN13606_c0_g1_i3_A-tADH2 |
| pEV31524 | pEVE2120 | pPGK1-P450_DN13606_c0_g1_i3_B-tADH2 |
| pEV31525 | pEVE2120 | pPGK1-P450_DN13606_c0_g1_i3_C-tADH2 |
| PEV31526 | pEVE2120 | pPGK1-P450_DN13846_c0_g1_i2_A-tADH2 |
| PEV31527 | pEVE2120 | PPGK1-P450_DN13846_c0_g1_i2_B-tADH2 |
| PEV31528 | pEVE2120 | pPGK1-P450_DN13846_c0_g1_i2_C-tADH2 |
| PEV31529 | pEVE2120 | pPGK1-P450_DN14156_c0_g1_i1_A-tADH2 |
| pEV31530 | pEVE2120 | pPGK1-P450_DN14156_c0_g1_i1_B-tADH2 |
| PEV31531 | pEVE2120 | pPGK1-P450_DN14156_c0_g1_i1_C-tADH2 |
| pEV31532 | pEVE2120 | pPGK1-P450_DN14346_c0_g2_i2_A-tADH2 |
| pEV31533 | pEVE2120 | pPGK1-P450_DN14346_c0_g2_i2_B-tADH2 |
| pEV31534 | pEVE2120 | pPGK1-P45O_DN14346_c0_g2_i2_C-tADH2 |
| pEV31535 | pEVE2120 | pPGK1-P450_DN14398_c0_g2_i6_A-tADH2 |
| pEV31536 | pEVE2120 | pPGK1-P450_DN14398_c0_g2_i6_B-tADH2 |

TABLE 4-continued

Description of plasmids containing target genes from *T. piriforme*. Unless otherwise specified, all clones originated from cDNA obtained on day 6 after induction.

| Vector name | Backbone | Promoter-Gene-Terminator |
|---|---|---|
| pEV31537 | pEVE2120 | pPGK1-P450_DN14398_c0_g2_i6_C-tADH2 |
| pEV31538 | pEVE2120 | pPGK1-P450_DN14859_c0_g1_i9_A-tADH2 |
| pEV31539 | pEVE2120 | pPGK1-P450_DN14859_c0_g1_i9_B-tADH2 |
| PEV31540 | pEVE2120 | pPGK1-P450_DN14859_c0_g1_i9_C-tADH2 |
| pEV31541 | pEVE2120 | pPGK1-P450_DN15259_c0_g1_i7_A-tADH2 |
| PEV31542 | pEVE2120 | pPGK1-P450_DN15259_c0_g1_i7_B-tADH2 |
| pEV31543 | pEVE2120 | pPGK1-P450_DN15259_c0_g1_i7_C-tADH2 |
| pEV31544 | pEVE2120 | pPGK1-P450_DN15259_c0_g1_i7_Ad9-tADH2 |
| pEV31545 | pEVE2120 | pPGK1-P450_DN15259_c0_g1_i7_Bd9-tADH2 |
| PEV31546 | pEVE2120 | pPGK1-P450_DN15259_c0_g1_i7_Cd9-tADH2 |
| PEV31547 | pEVE2120 | pPGK1-P450_DN15334_c0_g1_i1_A-tADH2 |
| PEV31548 | pEVE2120 | pPGK1-P450_DN15334_c0_g1_i1_B-tADH2 |
| PEV31549 | pEVE2120 | pPGK1-P450_DN15334_c0_g1_i1_C-tADH2 |
| pEV31550 | pEVE2120 | pPGK1-P450_DN16201_c0_g1_i2_1A-tADH2 |
| pEV31551 | pEVE2120 | pPGK1-P450_DN16201_c0_g1_i2_1B-tADH2 |
| pEV31552 | pEVE2120 | pPGK1-P450_DN16201_c0_g1_i2_1C-tADH2 |
| pEV31553 | pEVE2120 | pPGK1-P450_DN16201_c0_g1_i2_2A-tADH2 |
| pEV31554 | pEVE2120 | pPGK1-P450_DN16201_c0_g1_i2_2B-tADH2 |
| pEV31555 | pEVE2120 | pPGK1-P450_DN16201_c0_g1_i2_2C-tADH2 |
| pEV31556 | pEVE2120 | pPGK1-P450_DN16201_c0_g1_i2_3A-tADH2 |
| pEV31557 | pEVE2120 | pPGK1-P450_DN16201_c0_g1_i2_3B-tADH2 |
| pEV31558 | pEVE2120 | pPGK1-P450_DN16201_c0_g1_i2_3C-tADH2 |
| pEV31559 | pEVE2120 | pPGK1-P450_DN16821_c0_g1_i8_A-tADH2 |
| PEV31560 | pEVE2120 | pPGK1-P450_DN16821_c0_g1_i8_B-tADH2 |
| pEV31561 | pEVE2120 | pPGK1-P450_DN16821_c0_g1_i8_C-tADH2 |
| PEV31562 | pEVE2120 | pPGK1-P450_DN16821_c0_g1_i12_A-tADH2 |
| pEV31563 | pEVE2120 | pPGK1-P450_DN16821_c0_g1_i12_B-tADH2 |
| PEV31564 | pEVE2120 | pPGK1-P450_DN16821_c0_g1_i12_C-tADH2 |
| pEV31719 | PEVE3307 | pTEF1-CPR_DN2505_c0_g1_i1_A-tADH1 |
| PEV31720 | PEVE3307 | pTEF1-CPR_DN2505_c0_g1_i1_B-tADH1 |
| PEV31721 | PEVE3307 | pTEF1-CPR_DN2505_c0_g1_i1_C-tADH1 |
| pEV31722 | pEVE3307 | pTEF1-CPR_DN2505_c0_g1_i1_D-tADH1 |
| pEV31723 | pEVE3308 | pTEF1-CPR_DN5866_c0_g1_i1_Ad9-tADH1 |
| PEV31724 | pEVE3308 | pTEF1-CPR_DN5866_c0_g1_i1_Bd9-tADH1 |
| pEV31725 | pEVE3308 | pTEF1-CPR_DN5866_c0_g1_i1_Cd9-tADH1 |
| PEV31726 | pEVE3308 | pTEF1-CPR_DN5866_c0_g1_i1_A-tADH1 |
| pEV31727 | pEVE3308 | pTEF1-CPR_DN5866_c0_g1_i1_B-tADH1 |
| pEV31728 | pEVE3308 | pTEF1-P450_DN5866_c0_g1_i1_C-tADH1 |
| PEV31729 | pEVE3308 | pTEF1-CPR_DN5866_c0_g1_i1_D-tADH1 |
| pEV31730 | pEVE3308 | pTEF1-CPR_DN10898_c0_g1_1_1A-tADH1 |
| PEV31731 | pEVE3308 | pTEF1-CPR_DN10898_c0_g1_1_1B-tADH1 |
| pEV31732 | pEVE3308 | pTEF1-CPR_DN10898_c0_g1_1_1C-tADH1 |
| pEV31733 | pEVE3308 | pTEF1-CPR_DN10898_c0_g1_1_1D-tADH1 |
| pEV31734 | pEV31104 | pTEF1-CPR_DN10898_c0_g1_1_2A-tADH1/ PPGK1-Gf_CPR_coSc-tCYC1 |
| pEV31735 | PEV31104 | pTEF1-CPR_DN10898_c0_g1_1_2B-tADH1/ pPGK1-Gf_CPR_coSc-tCYC1 |
| pEV31736 | pEV31104 | pTEF1-CPR_DN10898_c0_g1_1_2C-tADH1/ pPGK1-Gf_CPR_coSc-tCYC1 |
| PEV31737 | PEV31104 | pTEF1-CPR_DN10898_c0_g1_i1_2D-tADH1/ pPGK1-Gf_CPR_coSc-tCYC1 |

"d9" stands for day 9 after induction.

TABLE 5

Fungal Cytochrome P450 enzymes

| Transcript/protein | Species/Strain |
|---|---|
| DN15259_c0_g1_17 (n.a.) (SEQ ID NO: 1) | *Thamnostylum piriforme* ATCC 8992 |
| DN12791_c0_g1_i1 (n.a.) (SEQ ID NO: 4) | *Thamnostylum piriforme* ATCC 8992 |
| hypothetical protein LRAMOSA08132 (A0A077WEM0) (SEQ ID NO: 7) | *Lichtheimia ramosa* |

TABLE 6

Description of plasmids containing codon-optimized P450 genes.

| Vector name | Backbone | Promoter-Gene-Terminator | Description |
| --- | --- | --- | --- |
| PEV32226 | pEVE3306 | pPGK1-P450_DN15259_c0_g1_i7_co-tADH2 | P450_DN_15259 (co) from *T. piriforme* |
| pEV32227 | pEVE3306 | pPGK1-P450_DN12791_c0_g1_i1_co-tADH2 | P450_DN_12791 (co) from *T. piriforme* |
| pEV32228 | pEVE3306 | pPGK1-Lr_P450_co-tADH2 | P450 from *Lichtheimia ramosa* (co) |
| PEV32640 | pEVE3306 | pPGK1-P450_DN_16393_co-tCYC1 | P450_DN16393 (co) from *T. piriforme* |
| PEV32641 | PEVE3306 | pPGK1-LCOR_01865_co-tCYC1 | LCOR_01865 (co) from *Lichtheimia corymbifera* |
| pEV32642 | pEVE3306 | pPGK1-LCOR_09548_co-tCYC1 | LCOR_09548 (co) from *Lichtheimia corymbifera* |
| pEV32643 | pEVE3306 | pPGK1-Ar_ORZ22410_co-tCYC1 | ORZ22410 (co) from *Absidia repens* |
| pEV33161 | pEVE3306 | pPGK1-Mc_S2JT25_co-tCYC1 | S2JT25 (co) from *Mucor circinelloides* |
| pOD8 | P415-TEF | pTEF1-Lr_P450_co-tCYC1 | P450 from *Lichtheimia ramosa* (co) |
| pOD10 | P415-TEF | pTEF1-Mc_S2JT25_co-tCYC1 | S2JT25 (co) from *Mucor circinelloides* |
| pOD36 | P415-TEF | pTEF1-CYPDN5-tCYC1 | A0A1X0RYU8 (co) from *Rhizopus microsporus* |
| pOD37 | P415-TEF | pTEF1-CYPDN6-tCYC1 | A0A0B7NKC0 (co) from *Parasitella parasitica* |
| pOD38 | P415-TEF | pTEF1-CYPDN7-tCYC1 | HCBZ0 (co) from *Rhizopus delemar* |
| pOD39 | P415-TEF | pTEF1-CYPDN10-tCYC1 | A0A0B7NB52 (co) from *Parasitella parasitica* |
| pOD40 | P415-TEF | pTEF1-CYPDN11-tCYC1 | A0A068SB73 (co) from *Lichtheimia corymbifera* |
| pOD41 | P415-TEF | pTEF1-CYPDN12-tCYC1 | A0A1C7N669 (co) from *Choanephora cucurbitarum* |
| pOD42 | P415-TEF | pTEF1-CYPDN13-tCYC1 | A0A1X2HZE4 (co) from *Absidia repens* |
| pOD43 | P415-TEF | pTEF1-CYPDN14-tCYC1 | A0A168T1R5 (co) from *Absidia glauca* |
| pOD44 | P415-TEF | pTEF1-CYPDN16-tCYC1 | A0A1X2HFU1 (co) from *Syncephalastrum racemosum* |
| pOD45 | P415-TEF | pTEF1-CYPDN18-tCYC1 | A0A0C9MNJ6 (co) from *Mucor ambiguus* |
| pOD46 | P415-TEF | pTEF1-CYPDN19-tCYC1 | A0A163B0W9 (co) from *Phycomyces blakesleeanus* |
| pOD47 | P415-TEF | pTEF1-CYPDN20-tCYC1 | A0A163A6R1 (co) from *Phycomyces blakesleeanus* |
| pOD48 | P415-TEF | pTEF1-CYPDN21-tCYC1 | XM_018432503 (co) from *Phycomyces blakesleeanus* |
| pOD49 | P415-TEF | pTEF1-CYPDN22-tCYC1 | XM_023609077 (co) from *Rhizopus microsporus* |
| pOD50 | P415-TEF | pTEF1-CYPDN24-tCYC1 | A0A077WFB8 (co) from *Lichtheimia ramosa* |
| pOD51 | P415-TEF | pTEF1-CYPDN27-tCYC1 | A0A077WLY1 (co) from *Lichtheimia ramosa* |
| pOD52 | P415-TEF | pTEF1-CYPDN28-tCYC1 | A0A1X2HYB6 (co) from *Absidia repens* |
| pOD53 | P415-TEF | pTEF1-CYPDN29-tCYC1 | A0A068SBU5 (co) from *Lichtheimia corymbifera* |
| pOD54 | P415-TEF | pTEF1-CYPDN30-tCYC1 | A0A1X2H4N2 (co) from *Syncephalastrum racemosum* |
| pOD55 | P415-TEF | pTEF1-CYPDN32-tCYC1 | A0A173GQ95 (co) from *Absidia caerulea* |
| pOD56 | P415-TEF | pTEF1-CYPDN34-tCYC1 | A0A068SBP8 (co) from *Lichtheimia corymbifera* |
| pOD57 | P415-TEF | pTEF1-CYPDN35-tCYC1 | A0A1X2GSL0 (co) from *Hesseltinella vesiculosa* |
| pOD75 | P415-TEF | pTEF1-CYPDN8-tCYC1 | A0A0C7AZL4 (co) from *Rhizopus microsporus* |
| pOD79 | P415-TEF | pTEF1-CYPDN4-tCYC1 | I1CCX6 (co) from *Rhizopus delemar* |
| pOD80 | P415-TEF | pTEF1-CYPDN9-tCYC1 | A0A1X2HQ99 (co) from *Syncephalastrum racemosum* |
| pOD82 | P415-TEF | pTEF1-CYPDN17-tCYC1 | A0A2G4SQ34 (co) from *Rhizopus microsporus* |
| pOD85 | P415-TEF | pTEF1-CYPDN26-tCYC1 | A0A162N972 (co) from *Phycomyces blakesleeanus* |
| pOD86 | P415-TEF | pTEF1-CYPDN31-tCYC1 | A0A291C3B2 (co) from *Absidia caerulea* |
| pOD87 | P415-TEF | pTEF1-CYPDN33-tCYC1 | A0A162UUM5 (co) from *Phycomyces blakesleeanus* |
| pOD88 | P415-TEF | pTEF1-CYPDN36-tCYC1 | E5KY66 (co) from *Nicotiana sylvestris* |
| pEV33313 | PEVE3306 | pPGK1-P450_DN5328_c5_g3_i1_coSc-tCYC1 | P450_DN5328_c5_g3_i1 (co) from *Cunninghamella echinulata* |
| pEV33314 | PEVE3306 | pPGK1-P450_DN5457_c2_g2_i2_coSc-tCYC1 | P450_DN5457_c2_g2_i2 (co) from *Cunninghamella echinulata* |
| pEV33315 | PEVE3306 | pPGK1-P450_DN5457_c2_g2_i3_coSc-tCYC1 | P450_DN5457_c2_g2_i3 (co) from *Cunninghamella echinulata* |

TABLE 6-continued

Description of plasmids containing codon-optimized P450 genes.

| Vector name | Backbone | Promoter-Gene-Terminator | Description |
|---|---|---|---|
| pEV33316 | PEVE3306 | pPGK1-P450_DN5457_c2_g8_i1_coSc-tCYC1 | P450_DN5457_c2_g8_i1 (co) from *Cunninghamella echinulata* |
| pEV33317 | PEVE3306 | pPGK1-P450_DN5458_c5_g4_i1_coSc-tCYC1 | P450_DN5458_c5_g4_i1 (co) from *Cunninghamella echinulata* |
| pEV33318 | PEVE3306 | pPGK1-P450_DN5584_c2_g2_i2_coSc-tCYC1 | P450_DN5584_c2_g2_i2 (co) from *Cunninghamella echinulata* |
| pEV33319 | PEVE3306 | pPGK1-P450_DN5615_c2_g1_i9_coSc-tCYC1 | P450_DN5615_c2_g1_i9 (co) from *Cunninghamella echinulata* |

Abbreviations: co, codon optimized for *S. cerevisiae*.

TABLE 7

Transformation of EVST25898 with cytochrome P450 P450_DN15259_c0_g1_i7_A and CPR genes

| Genes in EVST25898 | HIS | LEU | URA |
|---|---|---|---|
| P450_DN15259_c0_g1_i7_A/Cel_CPR_co/Sc_CPR/Gf_CPR_co | pEV31215 | pEV31308 | pEV31541 |
| P450_DN15259_c0_g1_i7_A/Cel_CPR_co | pEV31215 | pEVE3308 | pEV31541 |
| P450_DN15259_c0_g1_i7_A/Gf_CPR_co | pEVE3307 | PEV31104 | pEV31541 |
| P450_DN15259_c0_g1_i7_A/Sc_CPR | pEV28686 | pEVE3308 | pEV31541 |
| P450_DN15259_c0_g1_i7_A/CPR_DN2505_c0_g1_i1_A | pEV31719 | pEVE3308 | pEV31541 |
| P450_DN15259_c0_g1_i7_A/CPR_DN2505_c0_g1_i1_D | pEV31722 | pEVE3308 | pEV31541 |
| P450_DN15259_c0_g1_i7_A/CPR_DN5866_c0_g1_i1_Ad9 | pEVE3307 | pEV31723 | pEV31541 |
| P450_DN15259_c0_g1_i7_A/CPR_DN5866_c0_g1_i1_Cd9 | pEVE3307 | pEV31725 | pEV31541 |
| P450_DN15259_c0_g1_i7_A/CPR_DN5866_c0_g1_i1_B | pEVE3307 | pEV31727 | pEV31541 |
| P450_DN15259_c0_g1_i7_A/CPR_DN5866_c0_g1_i1_Cd9 | pEVE3307 | pEV31728 | pEV31541 |
| P450_DN15259_c0_g1_i7_A/CPR_DN10898_c0_g1_i_1A | pEVE3307 | pEV31730 | pEV31541 |
| P450_DN15259_c0_g1_i7_A/CPR_DN10898_c0_g1_i_2D | pEVE3307 | pEV31737 | pEV31541 |

TABLE 8

Mammalian Cytochrome P450 3A4

| Transcript/protein (Accession Number) | Species/Strain |
|---|---|
| Cytochrome P450 3A4 (P08684) (SEQ ID NO: 22) | *Homo sapiens* |
| Uncharacterized protein (H2PLK4) (SEQ ID NO: 24) | *Pongo abelii* |
| Uncharacterized protein (A0A096NZ89) (SEQ ID NO: 26) | *Papio anubis* |
| Uncharacterized protein (G3SB46) (SEQ ID NO: 28) | *Gorilla gorilla gorilla* |
| Uncharacterized protein (F1PDL2) (SEQ ID NO: 30) | *Canis lupus familiaris* |

TABLE 9

Mammalian Cytochrome P450 3A5

| Transcript/protein (Accession Number) | Species/Strain |
|---|---|
| Cytochrome P450 3A5 (P20815) (SEQ ID NO: 40) | *Homo sapiens* |
| Cytochrome P450 3A5 (A4ZZ70) (SEQ ID NO: 42) | *Pan troglodytes* |
| Cytochrome P450 3A5 (A8CBR0) (SEQ ID NO: 44) | *Macaca fascicularis* |
| Cytochrome P450 3A5 (U3ECK3) (SEQ ID NO: 46) | *Callithrix jacchus* |

TABLE 10

Mammalian Cytochrome P450 2C8

| Transcript/protein (Accession Number) | Species/Strain |
|---|---|
| Cytochrome P450 2C8 (P10632) (SEQ ID NO: 32) | *Homo sapiens* |
| Uncharacterized protein (H2Q2B) (SEQ ID NO: 34) | *Pan troglodytes* |
| Uncharacterized protein (H2NB34) (SEQ ID NO: 36) | *Pongo abelii* |
| Cytochrome P450 2C8 (Q4U0S8) (SEQ ID NO: 38) | *Chlorocebus aethiops* |

TABLE 11

Cytochrome b5

| Transcript/protein (Accession Number) | Species/Strain |
|---|---|
| Cytochrome b5 isoform 1 (NP_683725) (SEQ ID NO: 48) | *Homo sapiens* |

TABLE 13

Gradient for chiral separation

| Time (min) | % B |
|---|---|
| 0 | 2 |
| 5 | 35 |
| 6 | 100 |
| 7 | 100 |

TABLE 13-continued

Gradient for chiral separation

| Time (min) | % B |
| --- | --- |
| 7.1 | 1 |
| 8 | 1 |

TABLE 2

LC-MS conditions

| Parameter | Value |
| --- | --- |
| Injection volume | 2 μl |
| Column Temperature | 30° C. ± 4° C. |
| Injection method | Partial loop |
| Flow | 0.4 ml/min |
| Auto sampler temperature | 10° C. ± 2° C. |
| Weak wash | 800 μl water/acetonitrile 8:2 |
| Strong wash | 300 μl MeOH |
| Seal wash | 5 min with water/acetonitrile 9:1 |

Table 14: LC-MS conditions

TABLE 3

Mass spectrometer source and detector parameters (TQD)

| Source Parameter | Value |
| --- | --- |
| Ion Source | Electrospray Positive Mode (ESI+) |
| Capillary Voltage | 3.5 kV |
| Cone Voltage | 16 V |
| Extractor | 3 V |
| RF lens | 0.1 V |
| Source Temperature | 150° C. |
| Desolvation temperature | 350° C. |
| LM resolution 1 | 14 |
| HM resolution 1 | 14 |
| Ion Energy | 0.5 eV |
| Mode | MS/MS |
| Entrance | 50 eV |
| Collision | See Table 4 |
| Exit | 50 eV |
| LM resolution2 | 14 |
| HM resolution2 | 14 |
| Ion Energy2 | 0.5 |
| Desolvation gas | 500 L/hour |
| Cone gas | 50 L/hour |

Table 15: Mass spectrometer source and detector parameters (TQD)

TABLE 4

Multiple reaction monitoring targets and conditions (ESI +)

| Target compound | Retention time (min) | Parent ion (m/z) | Daughter ion (m/z) | Dwell time (s) | Cone voltage (V) | Collision energy (V) |
| --- | --- | --- | --- | --- | --- | --- |
| Caffeine | 2.85 | 195 | 138 | 0.222 | 30 | 24 |
| Normorphine | 1.54 | 272 | 152 | 0.222 | 50 | 60 |
| Norcodeine | 2.36 | 286 | 152 | 0.222 | 44 | 56 |
| Nororipavine | 2.54 | 284 | 218 | 0.222 | 20 | 20 |
| Northebaine | 3.79 | 298 | 251 | 0.222 | 18 | 28 |
| Norsalutaridine | 3.16 | 314 | 165 | 0.222 | 34 | 52 |
| Norsalutaridinol | 2.57 | 316 | 178 | 0.222 | 30 | 18 |

Table 16. Multiple reaction monitoring targets and conditions (ESI +)

Items

Exemplary cells, methods and other embodiments of the invention are set out in the following items:

1. A recombinant host cell that expresses one or more genes encoding a cytochrome P450 enzyme capable of N-demethylating and/or O-demethylating reticuline and/or derivatives thereof,
   wherein at least one of the genes is a recombinant gene.

2. The recombinant host cell according to item 1, wherein reticuline and/or derivatives thereof are selected from the group consisting of (S)-reticuline, 1,2 dehydroreticuline, (R)-reticuline, salutaridine, salutaridinol, thebaine, oripavine, 7-O-acetyl-salutaridinol, neopinone, codeinone, codeine, morphinone, morphine, hydrocodone, 14-hydroxycodeinone and oxycodone.

3. The recombinant host cell according to any one of items 1-2, wherein the reticuline derivative is thebaine.

4. The recombinant host cell according to any one of items 1-3, wherein the reticuline derivative is oripavine.

5. The recombinant host cell according to any one of items 1-4, wherein the cytochrome P450 enzyme capable of N-demethylating reticuline and derivatives thereof is selected from the group consisting of fungal cytochrome P450 enzymes, mammalian P450 3A4 enzymes, mammalian P450 3A5 enzymes, and mammalian P450 2C8 enzymes.

6. The recombinant host cell according to any one of items 1-5, wherein the cytochrome P450 enzyme capable of N-demethylating and/or O-demethylating reticuline and derivatives thereof has at least 20% sequence identity with a protein sequence selected from the group consisting of A0A077WEM0 (SEQ ID NO: 7), P450_DN15259_c0_g1_i7 (SEQ ID NO: 1), and DN12791_c0_g1_i1 (n.a.) (SEQ ID NO: 4) such as 30% sequence identity, such as 40% sequence identity, such as 50% sequence identity, such as 60% sequence identity, such as 70% sequence identity, such as 75% sequence identity, such as 80% sequence identity, such as 85% sequence identity, such as 90% sequence identity, such as 95% sequence identity, such as 97% sequence identity, such as 98% sequence identity, such as 99% sequence identity.

7. The recombinant host cell according to any one of items 1-6, wherein the cytochrome P450 enzyme capable of N-demethylating reticuline and derivatives thereof is selected from the group consisting of P450_DN15259_c0_g1_i7 (SEQ ID NO: 1), P450_DN12791_c0_g1_i1 (SEQ ID NO: 4), A0A077WEM0 (SEQ ID NO: 7), P08684 (SEQ ID NO: 22), H2PLK4 (SEQ ID NO: 24), A0A096NZ89 (SEQ ID NO: 26), G3SB46 (SEQ ID NO: 28), F1PDL2 (SEQ ID NO: 30), P20815 (SEQ ID NO: 40), A4ZZ70 (SEQ ID NO: 42), A8CBR0 (SEQ ID NO: 44), U3ECK3 (SEQ ID NO: 46), P10632 (SEQ ID NO: 32), H2Q2B (SEQ ID NO: 34), H2NB34 (SEQ ID NO: 36), Q4U0S8 (SEQ ID NO: 38), i) CYPDN8 (SEQ ID NO: 72),
   ii) Mc_SZT125 (SEQ ID NO: 52),
   iii) CYPDN17 (SEQ ID NO: 90),
   iv) CYPDN12 (SEQ ID NO: 80),
   v) Lr_P450 (SEQ ID NO: 8),
   vi) CYPDN29 (SEQ ID NO: 114),
   vii) CYPDN14 (SEQ ID NO: 84),
   vii) P450_DN15259_c0_g1_i7 (SEQ ID NO: 3),
   ix) LCOR_01865 (SEQ ID NO: 54),
   x) P450_DN5615_c2 g1_i9 (SEQ ID NO: 62),
   xi) P450_DN12791_c0_g1_i1 (SEQ ID NO: 5),
   xii) CYPDN16 (SEQ ID NO: 88),
   xiii) CYPDN18 (SEQ ID NO: 92), xiv) CYPDN27 (SEQ ID NO: 110),
xv) CYPDN35 (SEQ ID NO: 126),
xvi) CYPDN5 (SEQ ID NO: 66),
xvii) CYPDN6 (SEQ ID NO: 68),
xviii) CYPDN7 (SEQ ID NO: 70),
xix) CYPDN10 (SEQ ID NO: 76),
xx) CYPDN11 (SEQ ID NO: 78),
xxi) CYPDN24 (SEQ ID NO: 104),
xxii) CYPDN28 (SEQ ID NO: 112),
xxiii) CYPDN13 (SEQ ID NO: 82),
xxiv) CYPDN31 (SEQ ID NO: 118),
xxv) CYPDN34 (SEQ ID NO: 124),
xxvi) CYPDN22 (SEQ ID NO: 100),
xxvii) CYPDN21 (SEQ ID NO: 98),
xxviii) CYPDN30 (SEQ ID NO: 116),
xxix) Ar_ORZ22410 (SEQ ID NO: 58),
xxx) CYPDN20 (SEQ ID NO: 96),
xxxi) CYPDN17 (SEQ ID NO: 90), and
xxxii) CYPDN8 (SEQ ID NO: 72).

8. The recombinant host cell according to any one of items 1-7, wherein the cytochrome P450 enzyme capable of N-demethylating reticuline and derivatives thereof is P450_DN15259_c0_g1_i7 (SEQ ID NO: 3).

9. The recombinant host cell according to any one of items 1-6, wherein the cytochrome P450 enzyme capable of N-demethylating reticuline and derivatives thereof is P450_DN12791_c0_g1_i1 (SEQ ID NO: 6).

10. The recombinant host cell according to any one of items 1-7, wherein the cytochrome P450 enzyme capable of N-demethylating reticuline and derivatives thereof is P450_DN15259_c0_g1_i7 (SEQ ID NO: 3).

11. The recombinant host cell according to any one of items 1-6 wherein the cytochrome P450 enzyme capable of N-demethylating reticuline and derivatives thereof is P450_DN12791_c0_g1_i1 (SEQ ID NO: 6).

12. The recombinant host cell according to any one of items 1-7, wherein the cytochrome P450 enzyme capable of N-demethylating reticuline and derivatives thereof is P450_DN15259_c0_g1_i7 (SEQ ID NO: 3).

13. The recombinant host cell according to any one of items 1-6, wherein the cytochrome P450 enzyme capable of N-demethylating reticuline and derivatives thereof is P450_DN12791_c0_g1_i1 (SEQ ID NO: 6).

14. The recombinant host cell according to any one of items 1-13, wherein the cytochrome P450 enzyme capable of N-demethylating reticuline and derivatives thereof originates from a fungal organism.

15. The recombinant host cell according to any one of items 1-14, wherein the cytochrome P450 enzyme capable of N-demethylating reticuline and derivatives thereof originates from a fungal organism selected from the group consisting of *Thamnostylum piriforme* and *Lichtheimia ramosa*.

16. The recombinant host cell according to any one of items 1-7, wherein the cytochrome P450 enzyme capable of N-demethylating reticuline and derivatives thereof originates from a mammalian organism.

17. The recombinant host cell according to claim 16, items the cytochrome P450 enzyme capable of N-demethylating reticuline and derivatives thereof originates mammalian organism selected from the group consisting of *Homo sapiens, Pongo abelii, Papio anubis, Gorilla gorilla gorilla, Canis lupus familiaris, Pan troglodytes, Callithrix jacchus*, and *Chlorocebus aethiops*.

18. The recombinant host cell according to any one of items 1-7, further expressing one or more cytochrome P450 reductase(s) (CPR(s)).

19. The recombinant host cell according to item 18, wherein the cytochrome P450 reductase originates from a fungal or mammalian organism.

20. The recombinant host cell according to any one of items 18-19, wherein the cytochrome P450 reductase originates from an organism selected from the group consisting of *Thamnostylum piriforme, Cunninghamella elegans, Gibberella fujikuroi, Saccharomyces cerevisiae*, and *Homo sapiens*.

21. The recombinant host cell according to any one of items 18-20, wherein the cytochrome P450 reductase originates from a fungal organism.

22. The recombinant host cell according to any one of items 1-21, wherein the cytochrome P450 reductase originates from a fungal organism selected from the group consisting of *Thamnostylum piriforme, Cunninghamella elegans, Gibberella fujikuroi*, and *Saccharomyces cerevisiae*.

23. The recombinant host cell according to any one of items 18-20, wherein the cytochrome P450 reductase originates from a mammalian organism.

24. The recombinant host cell according to item 23, wherein the cytochrome P450 reductase originates from a mammalian organism which is *Homo sapiens*.

25. The recombinant host cell according to any one of items 18-22, wherein the cytochrome P450 reductase is selected from the group consisting of cytochrome P450 reductase is selected from the group consisting of DN5866_c0_g1_i1 (SEQ ID NO: 11), DN10898_c0_g1_i1 (SEQ ID NO: 14), AAF89958 (SEQ ID NO: 17), Q7Z8R1 (SEQ ID NO: 19), P16603 (SEQ ID NO: 21), POR1 (SEQ ID NO: 131), and BAB18572.1 (SEQ ID NO: 50).

26. The recombinant host cell according to any one of items 18-21, and 25 wherein the cytochrome P450 reductase is cytochrome P450 reductase is AAF89958 (SEQ ID NO: 17).

27. The recombinant host cell according to any one of items 18-21, and 25, wherein the cytochrome P450 reductase is cytochrome P450 reductase is P16603 (SEQ ID NO: 21).

28. The recombinant host cell according to any one of items 18-21, and 25, wherein the cytochrome P450 reductase is cytochrome P450 reductase is Q7Z8R1 (SEQ ID NO: 19).

29. The recombinant host cell according to any one of items 18-21, and 25, wherein the cytochrome P450 reductase is cytochrome P450 reductase is DN5866_c0_g1_i1 (SEQ ID NO: 11) or POR1 (SEQ ID NO: 131).

30. The recombinant host cell according to any one of items 18-21, and 25, wherein the cytochrome P450 reductase is cytochrome P450 reductase is DN10898_c0_g1_i1 (SEQ ID NO: 14).

31. The recombinant host cell according to any one of items 18-21, and 25, wherein the cytochrome P450 reductase is cytochrome P450 reductase is BAB18572.1 (SEQ ID NO: 50).

32. The recombinant host cell according to any one of items 1-15 and 18-21, wherein the cytochrome P450 enzyme capable of N-demethylating reticuline and derivatives thereof is P450_DN15259_c0_g1_i7 (SEQ ID NO: 3) and the cytochrome P450 reductase is selected from one or more from the list consisting of AAF89958 (SEQ ID NO: 17), Q7Z8R1 (SEQ ID NO: 19) and P16603 (SEQ ID NO: 21).

33. The recombinant host cell according to any one of items 1-15, 18-21, 23-25 and 32, wherein the cytochrome P450 enzyme capable of N-demethylating reticuline and derivatives thereof is P450_DN15259_c0_g1_i7 (SEQ ID NO: 3) and the cytochrome P450 reductase is AAF89958 (SEQ ID NO: 16).

34. The recombinant host cell according to any one of items 1-15 and 18-21, wherein the cytochrome P450 reductase is DN5866_c0_g1_i1 (SEQ ID NO: 11), POR1 (SEQ ID NO.: 131 and/or DN10898_c0_g1_i1 (SEQ ID NO: 14).

35. The recombinant host cell according to any one of items 1-15 and 18-21, wherein the P450 enzyme capable of N-demethylating reticuline and derivatives thereof is P450_DN15259_c0_g1_i7 (SEQ ID NO: 3) and the cytochrome P450 reductase is DN10898_c0_g1_i1 (SEQ ID NO: 14) and/or Q7Z8R1 (SEQ ID NO: 19).

36. The recombinant host cell according to any one of items 1-15 and 18-21, 25 and 28, wherein the cytochrome P450 enzyme capable of N-demethylating reticuline and derivatives thereof is P450_DN15259_c0_g1_i7 (SEQ ID NO: 3) and the cytochrome P450 reductase is Q7Z8R1 (SEQ ID NO: 19).

37. The recombinant host cell according to any one of items 1-15 and 18-21, and 25, wherein the cytochrome P450 enzyme capable of N-demethylating reticuline and derivatives thereof is P450_DN15259_c0_g1_i7 (SEQ ID NO: 3) and the cytochrome P450 reductase is DN5866_c0_g1_i1 (SEQ ID NO: 11) and/or DN10898_c0_g1_i1 (SEQ ID NO: 14).

38. The recombinant host cell according to any one of items 1-25, wherein the derivative is salutaridine and the cytochrome P450 enzyme is a P450 2C8 enzyme.

39. The recombinant host cell according to any one of items 1-25 and 38, wherein the derivative is salutaridine and the cytochrome P450 enzyme is selected from one or more from the group consisting of P10632 (SEQ ID NO: 23), H2Q2B (SEQ ID NO: 25), H2NB34 (SEQ ID NO: 27), Q4U0S8 (SEQ ID NO: 39).

40. The recombinant host cell according to any one of items 1-25, wherein the derivative is salutaridinol and the cytochrome P450 enzyme is a P450 2C8 enzyme.

41. The recombinant host cell according to any one of items 1-25 and 40, wherein the derivative is salutaridinol and the cytochrome P450 enzyme is selected from one or more from the group consisting of P10632 (SEQ ID NO: 33), H2Q2B (SEQ ID NO: 35), H2NB34 (SEQ ID NO: 37), and Q4U0S8 (SEQ ID NO: 39).

42. The recombinant host cell according to any one of items 1-25, wherein the compound is thebaine and the cytochrome P450 enzyme is a P450 34A enzyme.

43. The recombinant host cell according to any one of items 1-25 and 41, wherein the compound is thebaine and the cytochrome P450 enzyme is A4ZZ70 (SEQ ID NO: 43).

44. The recombinant host cell according to any one of items 1-25, wherein the derivative is oripavine and the cytochrome P450 enzyme is a P450 2C8 enzyme.

45. The recombinant host cell according to any one of items 1-25 and 44, wherein the derivative is oripavine and the cytochrome P450 enzyme is Q4U0S8 (SEQ ID NO: 39).

46. The recombinant host cell according to any one of items 1-25, wherein the derivative is morphine and the cytochrome P450 enzyme is a P450 2C8 enzyme or a P450 3A4 enzyme.

47. The recombinant host cell according to any one of items 1-25 and 46, wherein the derivative is morphine and the cytochrome P450 enzyme is selected from one or more from the group consisting of P20815 (SEQ ID NO: 41), A4ZZ70 (SEQ ID NO: 43), P10632 (SEQ ID NO: 33), H2Q2B (SEQ ID NO: 35), H2NB34 (SEQ ID NO: 37), and Q4U0S8 (SEQ ID NO: 39).

48. The recombinant host cell according to any one of items 1-25, wherein the compound is thebaine and the cytochrome P450 enzyme is a P450 3A4 enzyme.

49. The recombinant host cell according to any one of items 1-25, wherein the compound is thebaine and the cytochrome P450 enzyme is A0A096NZ89 (SEQ ID NO: 27).

50. The recombinant host cell according to any one of items 1-46, wherein the cell is a yeast cell, a plant cell, a mammalian cell, an insect cell, a fungal cell, a bacterial cell, an algal cell, or a cyanobacterial cell.

51. The recombinant host cell according to any one of items 1-50, wherein the cell is that originates from a fungal or mammalian organism.

52. The recombinant host cell according to any one of items 1-51, wherein the cytochrome P450 reductase originates from an organism selected from the group consisting of *Thamnostylum piriforme, Cunninghamella elegans, Gibberella fujikuroi, Saccharomyces cerevisiae, Mucor piriformis, Aspergillus* sp., and *Homo sapiens*.

53. The recombinant host cell according to any one of items 1-51, wherein the cell is a yeast cell selected from the group consisting of *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., or *Rhodospiridium* sp.

54. The recombinant host cell according to any one of items 1-53, wherein the host cell is a Saccharomycete.

55. The recombinant host cell according to any one of items 1-54, wherein the host cell is a yeast cell that is a *Saccharomyces cerevisiae* cell.

56. An in vitro method for N-demethylating a reticuline or a derivative thereof, comprising contacting reticuline or a derivative thereof with a recombinant P450 enzyme capable of N-demethylating reticuline or a derivative thereof.

57. The method according to item 56, further comprising cultivating a recombinant host cell of any one of items 1-55, in a culture medium in presence of reticuline or a derivative thereof, under conditions in which the one or more genes encoding the cytochrome P450 enzymes is/are expressed.

58. The method according to any one of items 56-57, further comprising cultivating the recombinant host of any one of items 1-55 in a culture medium under conditions in which the one or more genes encoding the cytochrome P450 reductase is/are expressed.

59. A method of producing a N-demethylated reticuline (norreticuline) and derivatives thereof, comprising cultivating the recombinant host of any one of items 1-55 in a culture medium under conditions in which the one or more genes encoding the cytochrome P450 enzymes is/are expressed in presence of reticuline or derivatives thereof.

60. The method according to any one of items 56-60, wherein reticuline and derivatives thereof are selected from the group consisting of (S)-reticuline, 1,2 dehydroreticuline, (R)-reticuline, salutaridine, salutaridinol, thebaine, oripavine, neopinone, 7-O-acetyl-salutaridinol, codeinone, codeine, morphinone, morphine, hydrocodone, 14-hydroxy-codeinone and oxycodone.

61. The method according to any one of items 56-60, further comprising cultivating the recombinant host of any one of claims 1-55 in a culture medium under conditions in which the one or more genes encoding the cytochrome P450 reductase is/are expressed.

62. A composition comprising a compound selected from the group consisting of N-demethylated reticuline and derivatives thereof obtainable from the methods according to any one of items 56-61, and further comprising elements from a fungal fermentation broth and/or at least one fungal specific metabolite.

63. A composition comprising a N-demethylated reticuline or a derivative thereof, and a recombinant P450 enzyme capable of N-demethylating reticuline or a derivative thereof.

64. A DNA molecule comprising a nucleic acid encoding one or more of the recombinant genes according to any one of items 1-55.

65. An expression vector comprising the DNA molecule according to item 60 and a promoter suitable for expression of the DNA molecule in a cell.

66. A host cell comprising the expression vector of item 65.

67. A method of preparing buprenorphine, or a salt thereof, from Compound HO-I-H (Nororipavine), or a salt thereof:

(Compound HO-I-H)

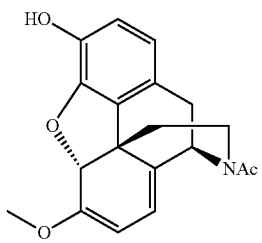

comprising:

(i)(A1) reacting Compound HO-I-H with cyclopropane carboxaldehyde followed by a hydride source; or (i)(A2) reacting Compound HO-I-H with cyclopropanecarboxylic acid halide followed by a reducing agent; or (i)(A3) reacting Compound HO-I-H with cyclopropylmethyl halide or activated cyclopropane methanol;

to provide Compound HO-I-MCP:

(Compound HO-I-MCP)

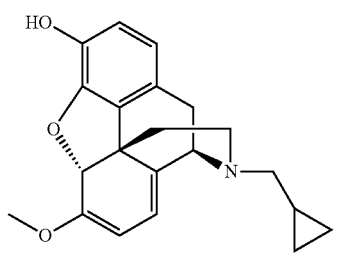

(ii)(B) reacting Compound HO-I-MCP with methyl vinyl ketone to provide Compound HO-II-MCP:

(Compound HO-II-MCP)

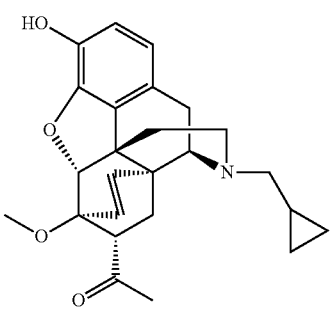

(iii)(C) reacting Compound HO-II-MCP with $H_2$ in the presence of a hydrogenation catalyst to provide Compound HO-IIIB-MCP:

(Compound HO-IIIB-MCP)

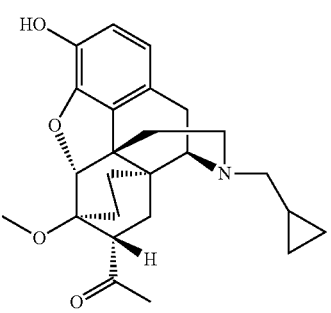

(iv)(D) reacting Compound HO-IIIB-MCP with tert-butylmagnesium halide to provide buprenorphine.

Another aspect of the disclosure relates to a method of preparing buprenorphine, or a salt thereof, from Compound HO-II-MCP (iii)(D) reacting Compound HO-II-MCP with tert-butylmagnesium halide to provide Compound HO-IIIA-MCP:

(Compound HO-IIIA-MCP)

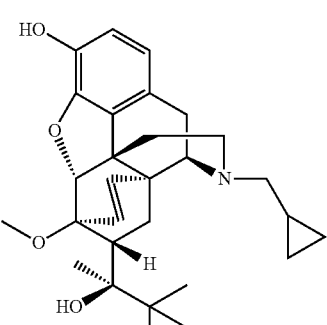

(iv)(C) reacting Compound HO-IIIA-MCP with $H_2$ in the presence of a hydrogenation catalyst to provide buprenorphine.

Another aspect of the disclosure relates to a method of preparing buprenorphine, or a salt thereof, from Compound HO-II-MCP (iii)(F) reacting Compound HO-II-MCP with benzyl halide, benzyl sulfonate, or activated benzyl alcohol to provide Compound BnO-II-MCP:

(Compound BnO-II-MCP)

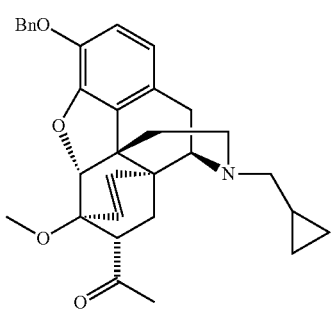

(iv)(D) reacting Compound BnO-II-MCP with tert-butylmagnesium halide to provide Compound BnO-IIIA-MCP:

(Compound BnO-IIIA-MCP)

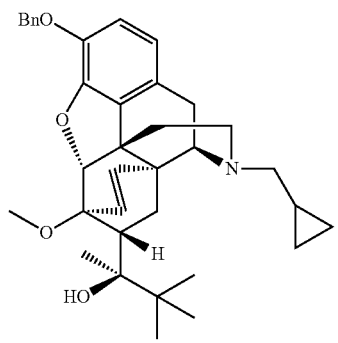

(v)(C) reacting Compound BnO-IIIA-MCP with $H_2$ in the presence of a hydrogenation catalyst to provide buprenorphine Another aspect of the disclosure relates to a method of preparing buprenorphine, or a salt thereof, from Compound HO-I-MCP (ii)(F) reacting Compound HO-I-MCP with benzyl halide, benzyl sulfonate, or activated benzyl alcohol to provide Compound BnO-I-MCP:

(Compound BnO-I-MCP)

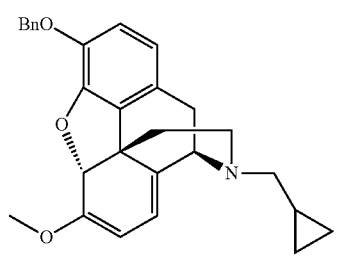

(iii)(B) reacting Compound BnO-I-MCP with methyl vinyl ketone to provide Compound BnO-II-MCP:

(Compound BnO-II-MCP)

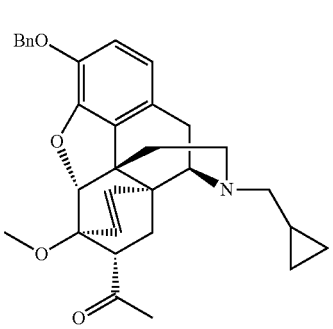

(iv)(D) reacting Compound BnO-II-MCP with tert-butylmagnesium halide to provide Compound BnO-IIIA-MCP:

(Compound BnO-IIIA-MCP)

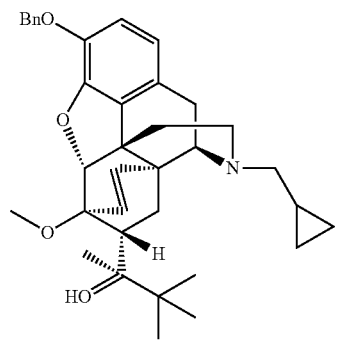

(v)(C) reacting Compound BnO-IIIA-MCP with $H_2$ in the presence of a hydrogenation catalyst to provide buprenorphine.

Another aspect of the disclosure relates to a method of preparing buprenorphine, or a salt thereof, from Compound MeO-I-H (Northebaine), or a salt thereof:

(Compound MeO-I-H)

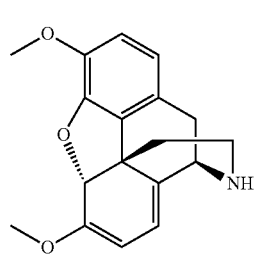

comprising:
(i)(A1) reacting Compound MeO-I-H with cyclopropane carboxaldehyde followed by a hydride source; or
(i)(A2) reacting Compound MeO-I-H with cyclopropanecarboxylic acid halide followed by a reducing agent; or
(i)(A3) reacting Compound MeO-I-H with cyclopropylmethyl halide or activated cyclopropane methanol;

to provide Compound MeO-I-MCP:

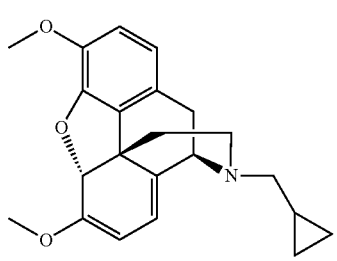
(Compound MeO-I-MCP)

(ii)(B) reacting Compound MeO-I-MCP with methyl vinyl ketone to provide Compound MeO-II-MCP:

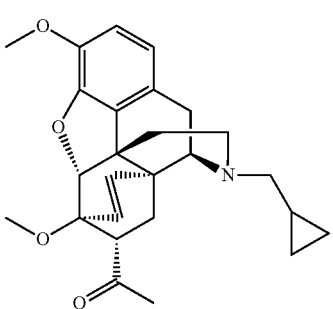
(Compound MeO-II-MCP)

(iii)(C) reacting Compound MeO-II-MCP with $H_2$ in the presence of a hydrogenation catalyst to provide Compound MeO-IIIB-MCP:

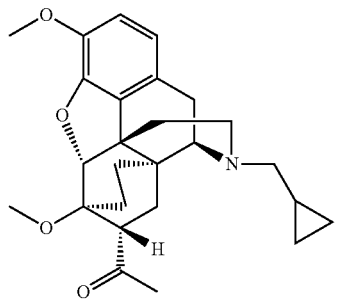
(Compound MeO-IIIB-MCP)

(iv)(D) reacting Compound MeO-IIIB-MCP with tert-butylmagnesium halide to provide Compound MeO-IV-MCP:

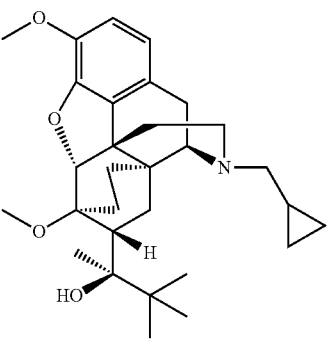
(Compound MeO-IV-MCP)

(v)(E) reacting a compound of Compound MeO-IV-MCP with a demethylating agent to provide buprenorphine.

Another aspect of the disclosure relates to a method of preparing buprenorphine, or a salt thereof, from Compound MeO-II-MCP, or a salt thereof (iii)(D) reacting Compound MeO-II-MCP with tert-butylmagnesium halide to provide Compound MeO-IIIA-MCP:

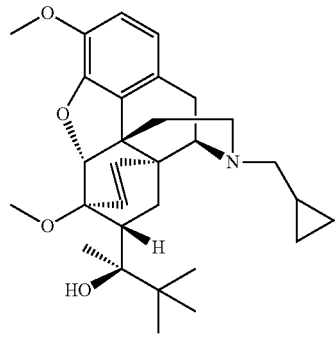
(Compound MeO-IIIA-MCP)

(iv)(C) reacting Compound MeO-IIIA-MCP with $H_2$ in the presence of a hydrogenation catalyst to provide a compound of Compound MeO-IV-MCP:

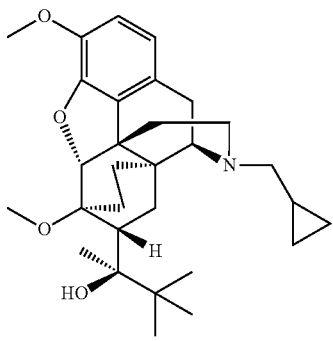
(Compound MeO-IV-MCP)

(v)(E) reacting a compound of Compound MeO-IV-MCP with a demethylating agent to provide buprenorphine.

Another aspect of the disclosure relates to a method of preparing buprenorphine, or a salt thereof, from Compound MeO-IIIA-MCP, or a salt thereof iv)(E) reacting Compound MeO-IIIA-MCP with a demethylating agent to provide Compound HO-IIIA-MCP:

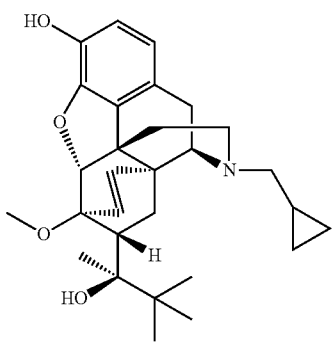
(Compound HO-IIIA-MCP)

(v)(C) reacting Compound HO-IIIA-MCP with $H_2$ in the presence of a hydrogenation catalyst to provide buprenorphine.

80. A method according to any of items 67-72, wherein the demethylating agent of step (E) is a thiolate.

81. A method according to any of items 67-72, wherein the demethylating agent of step (E) is a dodecane thiolate.

82. A method according to any of items 67-72 and 80-81, wherein step (E) is performed in a solvent comprising a polar aprotic solvent.

83. A method according to any of items 67-72 and 80-81, wherein step (E) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

84. A method according to any of items 67-72 and 80-81, wherein the demethylating agent of step (E) is reacted at a temperature within the range of about 50° C. to about 190° C., for a period of time within the range of about 4 hours to about 2 days.

85. A method according to any of items 73-76, wherein the benzyl halide of step (F) is benzyl chloride or benzyl bromide.

86. A method according to any of items 73-76 and 85, wherein step (F) is performed in the presence of a strong base.

87. A method according to any of items 73-76 and 85, wherein step (F) is performed in the presence of an alkali metal hydride.

88. A method according to any of items 73-76 and 85-87, wherein step (F) is performed in a solvent comprising a polar aprotic solvent.

89. A method according to any of items 73-76 and 85-87, wherein step (F) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

90. A method according to any of items 73-76 and 85-897, wherein the benzyl halide, benzyl sulfonate, or activated benzyl alcohol of step (F) is reacted at one or more temperatures within the range of about of about −20° C. to about 40° C., for a period of time within the range of about 6 hours to about 2 days.

91. A method according to any of items 76-77, wherein step (H) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

92. A method according to any of items 76-77 and 91, wherein the lithium aluminum hydride of step (H) is reacted at a temperature within the range of about 40° C. to about 120° C.

93. A method according to any of items 76-79 and 91-92, wherein step (G) is performed in the presence of a trialkylamine, e.g., triethylamine, diisopropylethylamine, 4-methyl-morpholine, or N-methyl-piperidine.

94. A method according to any of items 76-79 and 91-93, wherein step (G) is performed in a solvent comprising dichloromethane, chloroform, toluene, 1,4-dioxane, diethyl ether, benzene, or a mixture thereof.

95. A method according to any of items 76-79 and 91-94, wherein the acyl halide of step (G) is reacted at one or more temperatures within the range of about of about −20° C. to about 40° C., for a period of time within the range of about 30 minutes to about 8 hours.

96. A method according to item 78 or 79, wherein step (I) comprises reacting Compound HO-IV-Ac with Schwartz's reagent.

97. A method according to item 96, wherein step (I) is performed in a solvent comprising a polar aprotic solvent, e.g., N-methylpyrrolidone, tetrahydrofuran, ethyl acetate, acetone, dimethylformamide, acetonitrile, dimethylsulfoxide, propylene carbonate, or a mixture thereof.

98. A method according to item 96 or 97, wherein the Schwartz's reagent is reacted at a temperature within the range of about 15° C. to about 40° C., for a period of time within the range of about 5 minutes to about 3 hours.

99. A method according to item 78 or 79, wherein step (I) comprises reacting Compound HO-IV-Ac with base, e.g., KOH.

100. A method according to item 99, wherein step (I) is performed in a solvent comprising a high-boiling-point polar protic or aprotic solvent, e.g., ethylene glycol, diethylene glycol, N-methylpyrrolidone, dimethylformamide, or dimethylsulfoxide.

101. A method according to item 99 or 100, wherein the base is reacted at a temperature within the range of about 50° C. to about 240° C., for a period of time within the range of about 4 hours to about 2 days.

102. A method according to any of items 1-101, comprising step (A1).

103. A method according to item 102, wherein the hydride source of step (A1) is formic acid or sodium cyanoborohydride.

104. A method according to item 102, wherein the hydride source of step (A1) is formic acid.

105. A method according to any of items 102-1049, wherein step (A1) is catalyzed by a ruthenium(II) complex.

106. A method according to any of items 102-104, wherein step (A1) is catalyzed by dichloro(p-cymene)ruthenium(II) dimer.

107. A method according to any of items 102-106, wherein step (A1) is performed in a solvent comprising a polar aprotic solvent.

108. A method according to any of items 102-106, wherein step (A1) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

109. A method according to any of items 102-108, wherein step (A1) is performed in the presence of a trialkylamine.

110. A method according to any of items 102-108, wherein step (A1) is performed in the presence of triethylamine, diisopropylethylamine, 4-methyl-morpholine, or N-methyl-piperidine.

111. A method according to any of items 102-110, wherein the cyclopropane carboxaldehyde of step (A1) is reacted at a temperature within the range of about 30° C. to about 90° C., for a period of time within the range of about 30 minutes to about 5 hours.

112. A method according to any of items 1-101, comprising step (A2).

113. A method according to item 112, wherein the cyclopropanecarboxylic acid halide is cyclopropanecarboxylic acid chloride or cyclopropanecarboxylic acid bromide.

114. A method according to item 112 or 113, wherein the reducing agent is $LiAlH_4$ or $NaBH_4$.

115. A method according to any of items 112-114, wherein the reaction with cyclopropanecarboxylic acid halide of step (A2) is performed in a solvent comprising a nonpolar solvent.

116. A method according to any of items 112-114, wherein the reaction with cyclopropanecarboxylic acid halide of step (A2) is performed in a solvent comprising dichloromethane, chloroform, toluene, 1,4-dioxane, diethyl ether, benzene, or a mixture thereof.

117. A method according to any of items 112-116, wherein the reaction with a reducing agent of step (A2) is performed in a solvent comprising a polar aprotic solvent.

118. A method according to any of items 112-116, wherein the reaction with a reducing agent of step (A2) is performed in a solvent comprising N-methylpyrrolidone, tetrahydrofuran, ethyl acetate, acetone, dimethylformamide, acetonitrile, dimethylsulfoxide, propylene carbonate, or a mixture thereof.

119. A method according to any of items 112-118, wherein the cyclopropanecarboxylic acid halide of step (A2) is reacted at one or more temperatures within the range of about −20° C. to about 40° C., for a period of time within the range of about 6 hours to about 2 days.

120. A method according to any of items 112-119, wherein the reducing agent of step (A2) is reacted at a temperature within the range of about 35° C. to about 85° C., for a period of time within the range of about 5 minutes to about 3 hours.

121. A method according to any of items 1-101, comprising step (A3).

122. A method according to item 121, wherein the cyclopropylmethyl halide is cyclopropylmethyl chloride or cyclopropylmethyl bromide.

123. A method according to item 121 or 122, wherein step (A3) is performed in a solvent comprising a polar protic solvent.

124. A method according to item 121 or 122, wherein step (A3) is performed in a solvent comprising n-butanol, isopropanol, ethanol, methanol, water, or a mixture thereof.

125. A method according to any of items 121-124, wherein step (A3) is performed in the presence of a trialkylamine.

126. A method according to any of items 121-124, wherein step (A3) is performed in the presence of triethylamine, diisopropylethylamine, 4-methyl-morpholine, or N-methyl-piperidine.

127. A method according to any of items 121-124, wherein the cyclopropylmethyl halide or activated cyclopropane methanol of step (A3) is reacted a temperature within the range of about 40° C. to about 120° C., for a period of time within the range of about 30 minutes to about 6 hours.

128. A method according to any of items 67-127, wherein step (B) is performed in a solvent comprising a nonpolar solvent.

129. A method according to any of items 67-127, wherein step (B) is performed in a solvent comprising dichloromethane, chloroform, toluene, 1,4-dioxane, diethyl ether, benzene, or a mixture thereof.

130. A method according to any of items 67-129, wherein the methyl vinyl ketone of step (B) is reacted at a temperature within the range of about 40° C. to about 120° C. for a period of time within the range of about 2 hours to about 2 days.

131. A method according to any of items 67-130, wherein the hydrogenation catalyst of step (C) comprises nickel, palladium, platinum, rhodium, or ruthenium.

132. A method according to any of items 67-130, wherein the hydrogenation catalyst of step (C) comprises platinum or palladium supported on carbon.

133. A method according to any of items 67-132, wherein step (C) is performed in a solvent comprising a polar protic or aprotic solvent.

134. A method according to any of items 67-132, wherein step (C) is performed in a solvent comprising n-butanol, isopropanol, ethanol, methanol, N-methylpyrrolidone, tetrahydrofuran, ethyl acetate, acetone, dimethylformamide, acetonitrile, dimethylsulfoxide, propylene carbonate, or a mixture thereof.

135. A method according to any of items 67-134, wherein the hydrogen of step (C) is reacted at a temperature within the range of about 15° C. to about 120° C., for a period of time within the range of about 6 hours to about 3 days.

136. A method according to any of items 67-135, wherein the hydrogen of step (C) is reacted at a pressure within the range of about 1 atm. to about 3 atm.

137. A method according to any of items 67-136, wherein the tert-butylmagnesium halide of step (D) is tert-butylmagnesium chloride or tert-butylmagnesium bromide.

138. A method according to any of items 67-137, wherein step (D) is performed in a solvent comprising a nonpolar solvent.

139. A method according to any of items 67-138, wherein step (D) is performed in a solvent comprising tert-butylmethyl ether, 2-methyl-tetrahydrofuran, diethyl ether, dimethoxymethane, benzene, toluene, or a mixture of thereof.

140. A method according to any of items 1-139, wherein the tert-butylmagnesium halide of step (D) is reacted at a temperature within the range of about 15° C. to about 100° C. for a period of time within the range of about 30 minutes to about 8 hours.

141. A method according to any of items 67-140, further comprising contacting thebaine and/or oripavine with the recombinant host of any of items 1-55 to produce the Compound MeO-I-H or the Compound HO-I-H.

142. A method according to any of items 67-140, wherein the Compound MeO-I-H or the Compound HO-I-H is produced by a method according to any of items 56-61.

143. The recombinant host cell according to any one of items 1-55, wherein the cell is a plant cell, a filamentous fungus, or a yeast cell.

144. The recombinant host cell according to any one of items 1-55 or 143, wherein the cell is a plant cell.

145. The recombinant host cell according to any one of items 1-55 or 143-144, wherein the cell is a plant cell comprising *Papaver* sp. (e.g. *Papaver somniferum* or *Papaver bracteatum* cells), *Nicotiana* sp. (e.g. *Nicotiana benthamiana* cells), *Arabidopsis* sp., *Physcomitrella* sp., *Thalictrum* sp. (e.g. *Thalictrum flavum*), *Coptis* sp. (e.g. *Coptis japonica*), *Lindera* sp. (*Lindera aggregate*), *Annona* sp. (e.g. *Annona squamosa* or *Annona muricata*), *Ocotea* sp. (e.g. *Ocotea fasciculate*), *Duguetia* sp., *Sinomenium* sp., *Berberis* sp., *Corydalis* sp., *Ceratocapnos palaestinus*, *Anomianthus dulcis*, *Dicentra spectabilis*, *Glaucium flavum*, *Eschscholzia californica*, *Caulophyllum thalicroides*, *Chelidonium majus*, *Cocculus laurifolius*, *Delphinium pentagynum*, *Cinnamomum camphora*, *Clematis parviloba*, *Phylica rogersii*, *Phellodendron chinensis*, *Hypecoum lactiflorum*, *Fumaria officinalis*, *Croton celtidifolius*, *Mahonia aquifolium*, *Illigera parviflora*, *Aniba canelilla*, *Cryptocarya odorata*, *Litsea* sp., *Machilus thunbergii*, *Nectandra salicifolia*, *Neolitsea* sp., *Phoebe minutiflora*, *Strychnos holstii*, *Tinospora cordifolia*, or *Siparuna tonduziana*, 146. The recombinant host cell according to any one of items 1-55 or 143-145, wherein the cell is a *Papaver* sp. cell.

147. The recombinant host cell according to item 146, wherein the *Papaver* sp. cell is a *Papaver somniferum* or a *Papaver bracteatum* cell.

148. The recombinant host cell according to any one of items 1-55 or 143-146, wherein the cell is a *Nicotiana* sp. cell.

149. The recombinant host cell according to item 148, wherein the *Nicotiana* sp. cell is a *Nicotiana benthamiana* cell.

150. The recombinant host cell according to any one of items 1-55 or 143-146, wherein the cell is an *Arabidopsis* sp. cell.

151. The recombinant host cell according to any one of items 1-55 or 143-146, wherein the cell is a *Physcomitrella* sp. cell.

152. The recombinant host cell according to any one of items 1-55 or 143-143, wherein the cell is a filamentous fungus cell.

153. The recombinant host cell according to item 152, wherein the cell is a filamentous fungus cell comprising *Aspergillus nidulans, Aspergillus sydowii, Aspergillus terreus, Aspergillus oryzae, Aspergillus caelatus, Aspergillus chevalieri, Aspergillus longi vesica, Aspergillus parvulus, Aspergillus amylovorus, Aspergillus niger, Aspergillus niger, Aspergillus aculeatus, Aspergillus ellipticus, Aspergillus violaceofuscus, Aspergillus brunneoviolaceus, Aspergillus japonicus, Aspergillus brasiliensis, Aspergillus brasiliensis, Aspergillus aculeatinus, Aspergillus thermomutatus, Aspergillus implicatus, Aspergillus acristatus, Penicillium bilaiae, Penicillium rubens, Penicillium chrysogenum, Penicillium expansum, Penicillium antarcticum, Trichoderma reesei, Talaromyces atroroseus, Asteromyces cruciatus*, or *Neurospora crassa*.

154. The recombinant host cell according to any one of items 1-55 or 143-143, wherein the cell is a yeast cell comprising *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., *Schwanniomyces occidentalis, Sporidiobolus salmonicolor, Starmerella bacillaris, Sugiyamaella americana, Talaromyces atroroseus, Torulaspora delbrueckii, Trichoderma reesei, Wickerhamia fluorescens, Wickerhamiella sorbophila, Wickerhamiella versatilis, Zygosaccharomyces rouxii, Zygotorulaspora Florentina, Saccharomyces cerevisiae* var. *ellipsoideus, Saccharomyces paradoxus, Saccharomyces pastorianus, Saccharomyces uvarum, Saccharomycodes ludwigii* var. *ludwigii, Saitoella complicate, Schizosaccharomyces japonicus, Schizosaccharomyces octosporus, Asteromyces cruciatus, Aureobasidium pullulans, Candida cylindracea, Candida albicans, Cutaneotrichosporon curvatus, Cyberlindnera jadinii, Debaromyces hansenii, Dekkera bruxellensis, Diutina rugosa, Eremothecium gossypii, Galactomyces candidus, Geotrichum candidum, Geotrichum fermentans, Hanseniaspora uvarum, Hanseniaspora vineae, Issatchenkia orientalis, Kazachstania exigua, Kazachstania servazzii, Kluyveromyces lactis, Kluyveromyces marxianus, Komagataella phaffii, Lachancea thermotolerans, Lipomyces starkeyi, Moesziomyces antarcticus, Naumovozyma castellii, Naumovozyma dairenensis, Ogataea polymorpha, Ogataea thermomethanolica, Pachysolen tannophilus, Papiliotrema laurentii, Penicillium arizonense, Pichia fermentans, Rhodotorula mucilaginosa, Saccharomyces bayanus* or *Rhodospiridium* sp.

155. A method of preparing buprenorphine, or a salt thereof, from Compound HO-I-H, or a salt thereof, comprising:
contacting thebaine and/or oripavine with the recombinant host of any of claims 1-55 to produce the Compound MeO-I-H or the Compound HO-I-H, wherein buprenorphine is produced by a method according to any of items 67-140.

156. The method according to item 155, wherein the Compound MeO-I-H or the Compound HO-I-H produced from the recombinant host undergoes one or more purification steps before buprenorphine is produced by a method according to any of items 67-140.

157. A product obtainable from a method according to any one or more of items 56-61, 67-141 or 155-156.

158. Buprenorphine obtainable from a method according to any one or more of items 67-141 or 155-156.

The invention claimed is:

1. A recombinant host cell that expresses one or more genes encoding a Mucorales cytochrome P450 enzyme capable of N-demethylating a reticuline derivative, wherein at least one of the genes is a recombinant gene, and wherein the Mucorales cytochrome P450 enzyme capable of N-demethylating a reticuline derivative has at least 80% sequence identity with a sequence selected from the group consisting of:
   i) CYPDN8 (SEQ ID NO: 73),
   ii) Mc_S2JT25 (SEQ ID NO: 53),
   iii) CYPDN17 (SEQ ID NO: 91),
   iv) CYPDN12 (SEQ ID NO: 81),
   v) Lr_P450 (SEQ ID NO: 7),
   vi) CYPDN29 (SEQ ID NO: 115),
   vii) CYPDN14 (SEQ ID NO: 85),
   viii) P450_DN15259_c0_g1_i7 (SEQ ID NO: 1),
   ix) LCOR_01865 (SEQ ID NO: 55),
   x) P450_DN5615_c2_g1_i9 (SEQ ID NO: 63),
   xi) P450_DN12791_c0_g1_i1 (SEQ ID NO: 4),
   xii) CYPDN16 (SEQ ID NO: 89),
   xiii) CYPDN18 (SEQ ID NO: 93),
   xiv) CYPDN27 (SEQ ID NO: 111),
   xv) CYPDN35 (SEQ ID NO: 127),
   xvi) CYPDN5 (SEQ ID NO: 67),
   xvii) CYPDN6 (SEQ ID NO: 69),
   xviii) CYPDN7 (SEQ ID NO: 71),
   xix) CYPDN10 (SEQ ID NO: 77),
   xx) CYPDN11 (SEQ ID NO: 79),
   xxi) CYPDN24 (SEQ ID NO: 105),
   xxii) CYPDN28 (SEQ ID NO: 113),
   xxiii) CYPDN13 (SEQ ID NO: 83),
   xxiv) CYPDN31 (SEQ ID NO: 119),
   xxv) CYPDN34 (SEQ ID NO: 125),
   xxvi) CYPDN22 (SEQ ID NO: 101),
   xxvii) CYPDN21 (SEQ ID NO: 99),
   xxviii) CYPDN30 (SEQ ID NO: 117),
   xxix) Ar_ORZ22410 (SEQ ID NO: 59), and
   xxx) CYPDN20 (SEQ ID NO: 97).

2. The recombinant host cell according to claim 1, wherein the reticuline derivative is selected from the group consisting of thebaine, oripavine, (S)-reticuline, 1,2 dehydroreticuline, (R)-reticuline, salutaridine, salutaridinol, neopinone, codeinone, codeine, morphinone, morphine, hydrocodone, 14-hydroxycodeinone, 7-O-acetyl-salutaridinol and oxycodone.

3. The recombinant host cell according to claim 1, wherein the Mucorales cytochrome P450 enzyme capable of N-demethylating a reticuline derivative further is capable of O-demethylating the reticuline derivative.

4. The recombinant host cell according to claim 3, wherein the Mucorales cytochrome P450 enzyme capable of N-demethylating a reticuline derivative and O-demethylating the reticuline derivative has at least 80% sequence identity with a sequence selected from the group consisting of:
   i) CYPDN17 (SEQ ID NO: 91), and
   ii) CYPDN8 (SEQ ID NO: 73).

5. The recombinant host cell according to claim 1, further expressing one or more cytochrome P450 reductase(s) (CPR(s)), wherein the one or more reductase(s) is endogenous or heterologous.

6. The recombinant host cell according to claim 1, wherein the cell is a plant cell or a fungal cell.

7. The recombinant host cell according to claim 1, wherein the cell is a plant cell.

8. The recombinant host cell according to claim 1, wherein the cell is a *Papaver* sp. cell.

9. The recombinant host cell according to claim 1, wherein the cell is a *Nicotiana* sp. cell.

10. The recombinant host cell according to claim 1, wherein the cell is a filamentous fungus cell.

11. The recombinant host cell according to claim 1, wherein the cell is a *Saccharomyces cerevisiae* cell.

12. A method for N-demethylating a reticuline derivative, comprising contacting the reticuline derivative with a recombinant Mucorales cytochrome P450 enzyme capable of N-demethylating the reticuline derivative, wherein the Mucorales cytochrome P450 enzyme capable of N-demethylating the reticuline derivative has at least 80% sequence identity with a sequence selected from the group consisting of:
   i) CYPDN8 (SEQ ID NO: 73),
   ii) Mc S2JT25 (SEQ ID NO: 53),
   iii) CYPDN17 (SEQ ID NO: 91),
   iv) CYPDN12 (SEQ ID NO: 81),
   v) Lr P450 (SEQ ID NO: 7),
   vi) CYPDN29 (SEQ ID NO: 115),
   vii) CYPDN14 (SEQ ID NO: 85),
   viii) P450 DN15259 c0 g1 i7 (SEQ ID NO: 1),
   ix) LCOR 01865 (SEQ ID NO: 55),
   x) P450 DN5615 c2 g1 i9 (SEQ ID NO: 63), xi) P450 DN12791 c0 q1 i1 (SEQ ID NO: 4),
xii) CYPDN16 (SEQ ID NO: 89),
xiii) CYPDN18 (SEQ ID NO: 93),
xiv) CYPDN27 (SEQ ID NO: 111),
xv) CYPDN35 (SEQ ID NO: 127),
xvi) CYPDN5 (SEQ ID NO: 67),
xvii) CYPDN6 (SEQ ID NO: 69),
xviii) CYPDN7 (SEQ ID NO: 71),
xix) CYPDN10 (SEQ ID NO: 77),
xx) CYPDN11 (SEQ ID NO: 79),
xxi) CYPDN24 (SEQ ID NO: 105),
xxii) CYPDN28 (SEQ ID NO: 113),
xxiii) CYPDN13 (SEQ ID NO: 83),
xxiv) CYPDN31 (SEQ ID NO: 119),
xxv) CYPDN34 (SEQ ID NO: 125),
xxvi) CYPDN22 (SEQ ID NO: 101),
xxvii) CYPDN21 (SEQ ID NO: 99),
xxviii) CYPDN30 (SEQ ID NO: 117),
xxix) Ar ORZ22410 (SEQ ID NO: 59), and
xxx) CYPDN20 (SEQ ID NO: 97).

13. The method according to claim 12, further comprising cultivating a recombinant host cell in presence of the reticuline derivative, under conditions in which the recombinant Mucorales cytochrome P450 enzyme is expressed.

14. The method according to claim 13, further comprising cultivating the recombinant host cell under conditions in which the recombinant Mucorales cytochrome P450 enzyme is expressed.

15. The method according to claim 12, which is performed in vitro.

16. A composition comprising an N-demethylated reticuline derivative obtainable from the method of claim 12, and further comprising elements from:
   a) a fungal fermentation broth and/or at least one fungal specific metabolite, if the host cell is a fungus cell, or
   b) at least one plant specific metabolite, if the host cell is a plant cell.

* * * * *

SEQUENCE LISTING

```
<160> NUMBER OF SEQ ID NOS: 133

<210> SEQ ID NO 1
<211> LENGTH: 519
<212> TYPE: PRT
<213> ORGANISM: Thamnostylum piriforme

<400> SEQUENCE: 1

Met Asp Asn Lys Ala Ile Leu Arg Gln Ala Val Tyr Ser Tyr Arg Tyr
1               5                   10                  15

His Ile Gly Ile Ala Ala Ala Val Ala Ile Val Cys Gln Gln Ile Tyr
            20                  25                  30

Ser Arg Val Phe Arg Val Pro Lys Asn Leu Arg His Ile Pro Ala Ile
        35                  40                  45

Ser Tyr Trp Ser Gln Met Lys Ala Leu Leu Lys Lys Glu Ala Ile Thr
    50                  55                  60

Pro Arg Thr Lys Arg Leu Val Tyr Pro Leu Leu Ser Lys Ala Asn Gly
65                  70                  75                  80

Leu Tyr Leu Asn Arg Met Pro Phe Asp Trp Thr Val Tyr Val Ala Asn
```

```
            85              90              95
Pro Met Ile Ala Lys Thr Val Leu Phe Lys Pro Glu Phe Ala Thr Lys
            100             105             110

Met Ser Leu Ile Gly Ser Phe Ser Asp Asp Ser Ala Val Leu Gln Phe
            115             120             125

Val Gly Lys Asp Asn Ile Ala Val Ser Asn Gly His Gln Trp Lys Lys
130             135             140

Gln Arg Lys Ile Met Asn Pro Ala Phe His Arg Ser Met Pro Val Ala
145             150             155             160

Leu Phe Ala Ser Leu Met Pro Lys Val Phe Cys Met Ile Asp Glu Thr
                165             170             175

Gln Glu Asn Gly Asp Ser Val Gly Ala Ile Gln Leu Met Gln Ala Leu
                180             185             190

Thr Leu Glu Ala Leu Gly Lys Ala Val Phe Gly Phe Asp Phe Gly Gly
                195             200             205

Leu Asp Asp Lys Asn Ser Val Trp Val Lys Thr Tyr Asn Glu Val Phe
            210             215             220

Lys Ala Phe Thr Asp Phe Thr Val Phe Leu Pro Arg Leu Asn Ala Phe
225             230             235             240

Leu Arg Arg Val Ser Pro Pro His Arg Ser Arg His Arg Glu Met Leu
                245             250             255

Lys Leu Ile Gly Leu Leu Asp Glu Met Val Asp Lys Lys Arg Gln Ala
                260             265             270

Leu Leu Asp Ala Lys Asn Lys Ser Val Glu Lys Val Pro Glu His Glu
                275             280             285

Lys Asp Leu Leu Thr Leu Met Leu Glu Ala Glu Met Asp Gly Glu Gly
            290             295             300

Val Trp Glu Lys Glu Leu Arg His Asn Ile Gly Ile Leu Phe Val
305             310             315             320

Ala Gly His Asp Thr Thr Ala Asn Ser Leu Ala Phe Ala Val Tyr Asn
                325             330             335

Leu Ala Val Asn Lys Asp Val Gln Asp Lys Ala Arg Lys Glu Ile Ile
                340             345             350

Asp Leu Leu Gly Asp Glu Pro Lys Asp Val Ala Pro Thr Leu Asp Asp
            355             360             365

Cys Lys His Met Asp Tyr Ile Asp Met Ile Ile Lys Glu Thr Leu Arg
            370             375             380

Met Asn Ala Pro Ala Asn Asp Leu Leu Ala Arg Ile Ala Ser Glu Asp
385             390             395             400

Leu Glu Leu Gly Gly Val Leu Ile Pro Lys Gly Thr Met Val Ser Val
                405             410             415

Asp Phe His Ala Leu His Leu His Pro Asp Leu Trp Glu Asp Ser Glu
                420             425             430

Arg Phe Asn Pro Gln Arg Phe Gln Asp Asn Gly Glu His Ser Lys His
                435             440             445

Glu Gly Val Thr Trp Val Pro Phe Ser Gly Gly Ser Arg Gln Cys Ile
            450             455             460

Gly Ile Asn Phe Ser Met Met Glu Gln Arg Val Ala Leu Ser Thr Leu
465             470             475             480

Leu Arg Lys Tyr Glu Trp Glu Leu Pro Ala Asp Ser Ile His Arg Asn
                485             490             495

Gly Leu Val Met Asp Gln Pro Phe Ser Phe Ala Pro Ser Ser Leu Lys
            500             505             510
```

Ile Lys Phe Lys Lys Arg Tyr
    515

<210> SEQ ID NO 2
<211> LENGTH: 1560
<212> TYPE: DNA
<213> ORGANISM: Thamnostylum piriforme

<400> SEQUENCE: 2

| | | | | | |
|---|---|---|---|---|---|
| atggacaaca | aagcaatttt | acgacaagcc | gtttactcgt | atcgttacca | catcgggatc | 60 |
| gcggcggctg | tagctatcgt | ttgccagcaa | atatacagtc | gcgtctttcg | tgttcccaaa | 120 |
| aatttgcgtc | atattccagc | aattagctat | tggagtcaaa | tgaaagcact | tttgaaaaag | 180 |
| gaggcaatca | ctccacgtac | gaagaggcta | gtttacccgc | tgctttcaaa | agcgaatgga | 240 |
| ctctacctga | atcgaatgcc | atttgactgg | acagtttatg | tcgcgaatcc | aatgattgcg | 300 |
| aagactgtct | tgtttaagcc | agagtttgca | accaaaatgt | cattaatagg | ctcattcagc | 360 |
| gatgatagtg | cagttttgca | atttgttgga | aaggataata | ttgcggtatc | aaacggtcac | 420 |
| cagtggaaaa | agcaaagaaa | gattatgaac | cctgctttcc | atcgatcaat | gccggtagct | 480 |
| ctctttgcaa | gtctcatgcc | aaaggttttt | tgtatgattg | atgaaacaca | agagaacggt | 540 |
| gattctgttg | gtgccataca | acttatgcag | gcccttactc | ttgaagcgct | tggaaaagca | 600 |
| gttttcggtt | ttgattttgg | aggattggac | gataaaaatt | ctgtttgggt | caagacatac | 660 |
| aacgaagtat | tcaaggcatt | tacagacttc | acggtattcc | ttccacgact | taatgctttt | 720 |
| cttcggcggg | taagcccacc | gcatcgaagt | cgtcatagag | aaatgctcaa | gttgatcggc | 780 |
| cttctggatg | aaatggtgga | caaaaagaga | caagcgctct | ggatgccaa | gaataaatcc | 840 |
| gtcgagaaag | tgcctgagca | tgaaaaggat | ctacttactc | tcatgctcga | ggctgaaatg | 900 |
| gatggtgaag | gtgtttggga | aaaagaagaa | ttacggcaca | atatcgggat | attattcgtg | 960 |
| gcagggcatg | atacaaccgc | caattcattg | gcatttgcgg | tttacaatct | agccgtcaac | 1020 |
| aaagacgtac | aagataaggc | ccgcaaagaa | attatcgact | tactaggaga | cgagcctaag | 1080 |
| gatgttgcgc | ccaccttgga | tgactgcaaa | catatggatt | atatcgatat | gattatcaaa | 1140 |
| gagacgctcc | gcatgaatgc | tcctgcaaat | gacttgcttg | ctcgaatagc | atcggaagac | 1200 |
| ttggaactag | gaggggtttt | aatacccaag | gggacaatgg | tctcggtcga | ctttcacgca | 1260 |
| ctgcaccttc | accctgattt | atgggaggat | tcagagcgtt | tcaacccgca | gcgatttcaa | 1320 |
| gataatggag | agcatagcaa | acacgaagga | gtaacatggg | ttccttttag | tggaggctca | 1380 |
| agacaatgca | ttggaatcaa | ttttagtatg | atggagcaac | gggtggccct | atcgacgcta | 1440 |
| ttgagaaaat | atgaatggga | gctacctgct | gattctatcc | accgtaatgg | acttgtgatg | 1500 |
| gatcaacctt | ttagttttgc | accaagctct | ctcaaaatta | agtttaaaaa | acgttattga | 1560 |

<210> SEQ ID NO 3
<211> LENGTH: 1560
<212> TYPE: DNA
<213> ORGANISM: Thamnostylum piriforme

<400> SEQUENCE: 3

| | | | | | |
|---|---|---|---|---|---|
| atggataata | aagctatttt | gagacaagct | gtttattctt | atagatacca | tattggtatt | 60 |
| gctgctgctg | ttgctattgt | ttgtcaacaa | atttattcta | gagtttttag | agttccaaaa | 120 |
| aatttgagac | atattccagc | tatttcttat | tggtctcaaa | tgaaagcatt | gttgaaaaaa | 180 |
| gaagctatta | ctccaagaac | taaaagattg | gtttatccat | tgttgtctaa | agctaatggt | 240 |

```
ttgtatttga atagaatgcc atttgattgg actgtttatg ttgctaatcc aatgattgct    300
aaaactgttt tgtttaaacc agaatttgct actaaaatgt ctttgattgg ttcttttttct   360
gatgattctg ctgttttgca atttgttggt aaagataata ttgctgtttc taatggtcat    420
caatggaaaa aacaaagaaa aattatgaat ccagcttttc atagatctat gccagttgct    480
ttgtttgctt ctttgatgcc aaaagttttt tgtatgattg atgaaactca agaaaatggt    540
gattctgttg gtgctattca attgatgcaa gcattgactt tggaagcatt gggtaaagct    600
gttttggtt ttgattttgg tggtttggat gataaaaatt ctgtttgggt taaaacttat     660
aatgaagttt ttaaagcatt tactgatttt actgtttttt tgccaagatt gaatgctttt    720
ttgagaagag tttctccacc acatagatct agacatagag aaatgttgaa attgattggt    780
ttgttggatg aaatggttga taaaaaaaga caagcattgt tggatgctaa aaataaatct    840
gttgaaaaag ttccagaaca tgaaaaagat ttgttgactt tgatgttgga agctgaaatg    900
gatggtgaag tgtttggga aaaagaagaa ttgagacata atattggtat tttgtttgtt    960
gctggtcatg atactactgc taattctttg gcttttgctg tttataattt ggctgttaat   1020
aaagatgttc aagataaagc tagaaaagaa attattgatt tgttgggtga tgaaccaaaa   1080
gatgttgctc aactttggca tgattgtaaa catatggatt atattgatat gattattaaa   1140
gaaactttga atgaatgc tccagctaat gatttgttgg ctagaattgc ttctgaagat    1200
ttggaattgg gtggtgtttt gattccaaaa ggtactatgg tttctgttga ttttcatgct   1260
ttgcatttgc atccagattt gtgggaagat tctgaaagat ttaatccaca aagatttcaa   1320
gataatggtg aacattctaa acatgaaggt gttacttggg ttccattttc tggtggttct   1380
agacaatgta ttggtattaa ttttttctatg atggaacaaa gagttgcttt gtctactttg   1440
ttgagaaaat atgaatggga attgccagct gattctattc atagaaatgg tttggttatg   1500
gatcaaccat tttctttttgc tccatcttct ttgaaaatta aatttaaaaa aagatattga  1560
```

<210> SEQ ID NO 4
<211> LENGTH: 509
<212> TYPE: PRT
<213> ORGANISM: Thamnostylum piriforme

<400> SEQUENCE: 4

Met Ala Ile Leu Gln Asn Leu Val Leu Gln Ser Asp Gln Arg His Leu
1               5                   10                  15

Gly Val Val Thr Ala Ala Val Phe Leu Ser Ala Tyr Ala Leu Tyr Arg
            20                  25                  30

His Glu Ser Lys Lys Glu Leu Gly Asn Glu Cys Pro Thr Val Pro Tyr
        35                  40                  45

Thr Asn Pro Met Phe Gly Ser Thr Asp Glu Tyr Arg Lys Asn Pro Ala
    50                  55                  60

Ala Phe Val Glu Lys Trp Ser Ala Ala Leu Gly Pro Val Phe Arg Val
65                  70                  75                  80

His Ile Phe Gly Arg Met Gln Thr Val Val Ser Gly Arg Tyr Val Arg
                85                  90                  95

Glu Val Leu Phe Asn Asp Asn Phe Ser Phe Val Glu Gly Ile Arg Thr
            100                 105                 110

Arg Phe Asp Leu Arg Leu Leu Thr Gly Ile Pro Asn Ser His Leu Asn
        115                 120                 125

Asp Lys Asp Val Arg Glu Val Val Lys Ser Leu Thr Ala Gln Met
    130                 135                 140

```
Lys Lys Tyr Thr Pro Arg Ala Val His Tyr Leu Ser Val Gly Leu Gln
145                 150                 155                 160

Glu Ala Leu Gly Asp Leu Lys Asp Pro Arg Thr Leu Asp Asn Leu Phe
                165                 170                 175

Leu Thr Val Gln Asn Met Val Ala Lys Ala Ser Ala Ser Ile Phe Val
            180                 185                 190

Gly Glu Glu Leu Cys Asn Asn Ile Glu Leu Val Asp Thr Phe Lys His
        195                 200                 205

Val Thr Ser Asp Ile Gly Ser Glu Ile Arg Leu Asp Asn Thr Trp Leu
    210                 215                 220

Glu Phe Phe Lys Thr Ile Asn Gln Ile Arg Met Trp Tyr Val Gly Lys
225                 230                 235                 240

His Ser Pro Arg Val Thr Lys His Arg Arg Gln Leu Ile Gln Ala Met
                245                 250                 255

Ala Pro Glu Ile Asp Arg Arg Leu Gln Gly Leu Ala Gly Asn Asp Pro
                260                 265                 270

Ser Trp Thr Arg Pro Glu Asp Ile Leu Gln Glu Ile Met Glu Asn Tyr
            275                 280                 285

Pro Ser Pro Ser Thr Val Pro Ala Asp Ile Tyr Thr Tyr Tyr Ala Asn
        290                 295                 300

Trp Met Ile Val Leu Ile Phe Ala Ser Val His Thr Thr Thr Glu His
305                 310                 315                 320

Ala Thr Ile Val Leu Tyr Arg Leu Leu Gln Gln Pro Glu Leu Ile Asp
                325                 330                 335

Glu Leu Leu Gln Gln Lys Glu Ala Leu Gly Gln Gly Thr Val Phe
                340                 345                 350

Thr Gly Glu Val Ile Arg Lys Leu Val Lys Leu Asp Ser Val Cys Arg
            355                 360                 365

Glu Ser Leu Arg Ile Lys Asn Glu Tyr Phe Gly Leu Pro His Arg Asn
        370                 375                 380

Met Ser His Glu Asn Ile Ser Leu Ser Asn Gly Val Val Ile Lys Pro
385                 390                 395                 400

Gly Asp Asn Val Met Leu Asn Val Trp Thr Asn His Asp Ser Asp
                405                 410                 415

Leu Gln Lys Asp Val His Gly Asn His Asp Lys Phe Glu Pro Phe Arg
                420                 425                 430

Tyr Val Asn Ala Asp Arg Pro Ala Thr Lys Ile Gly Asp Asp Tyr Leu
            435                 440                 445

Ile Phe Gly Glu Gly Lys His Ala Cys Pro Gly Arg Trp Phe Ala Leu
        450                 455                 460

Gln Glu Ile Lys Thr Ile Val Ser Val Leu Ile Arg Asp Tyr Thr Leu
465                 470                 475                 480

Thr Pro Cys Gly Pro Ile Val Phe Pro Ser Gly Thr Ser Thr Gly Ile
                485                 490                 495

Pro Ser Gly Glu Val Thr Ile Gln Arg Lys Ser Glu Val
            500                 505
```

<210> SEQ ID NO 5
<211> LENGTH: 1530
<212> TYPE: DNA
<213> ORGANISM: Thamnostylum piriforme

<400> SEQUENCE: 5
atggcaattc ttcaaaacct tgtcctacaa tctgatcagc gacaccttgg tgtcgttaca    60

```
gctgctgttt ttttgtcagc gtacgcgctc tatcgacatg agtcgaaaaa ggaactgggg      120
aatgagtgtc ctactgtacc ctataccaat ccaatgttcg gttccactga cgaatatcgc      180
aagaatccag ccgcatttgt tgaaaaatgg agcgctgcac ttggcccagt atttcgcgtt      240
catatctttg gcagaatgca gacggtagtt tcgggccgtt atgtccgcga agttttgttc      300
aacgacaact ttagttttgt ggaaggaatc cggacacggt ttgaccttcg attgctcacc      360
ggtataccta acagtcacct caatgacaaa gatgttcgag aggttgttgt caagtcgttg      420
actgcgcaaa tgaagaagta cacccgcgc gcagtacact acctcagcgt tggcttgcaa      480
gaggcactag gagatttgaa agatcctcga actcttgaca acctattctt gactgttcaa      540
aacatggtcg ccaaagctag cgcctccatc ttcgtcggtg aagaactttg taacaatatt      600
gagttggttg acacattcaa gcacgttaca agcgacattg gttcggagat acgtctcgac      660
aacacctggc tggaattctt taaaacaata aaccaaattc gaatgtggta cgttggcaag      720
cattctccca gagtgacaaa gcacagacga cagctcatac aggcgatggc acctgaaatc      780
gacagacggc tgcaaggtct tgcagggaat gatccttctt ggaccagacc agaagacatt      840
ttgcaagaga ttatggaaaa ctatccttcc ccgtccactg taccagcaga tatttacacc      900
tattatgcca attggatgat tgtgttgata tttgcatccg ttcacacgac cactgagcat      960
gcaacaattg tcctttaccg tttactccaa cagcccgagc ttatcgacga gcttcttcaa      1020
gaacaaaagg aggcccttgg ccaaggcact gtatttacag gcgaggtcat tcgcaaactg      1080
gtgaaactgg atagcgtgtg tcgtgagtct ttgcggatca aaaacgagta ctttggtctt      1140
ccacacagga atatgtctca tgaaaatatt tctttgagca atggagttgt tatcaaacca      1200
ggcgacaatg tcatgctgaa tgtttggaca aaccatcatg acagtgactt gcaaaaggat      1260
gtacacggca accatgacaa gtttgaacct ttccgttacg ttaatgctga tcgccctgca      1320
acgaagattg gtgatgatta cttgatattt ggggagggaa agcacgcttg ccccggtcga      1380
tggtttgctt tacaagaaat taagacgatt gtatcagtac taattcgaga ttacacgcta      1440
acaccatgtg gtccaattgt gtttccatcc ggcacaagta ctggtattcc aagtggagaa      1500
gtgacaattc aacgaaagtc agaagtgtaa                                        1530
```

<210> SEQ ID NO 6
<211> LENGTH: 1530
<212> TYPE: DNA
<213> ORGANISM: Thamnostylum piriforme

<400> SEQUENCE: 6

```
atggctattt tgcaaaattt ggttttgcaa tctgatcaaa gacatttggg tgttgttact       60
gctgctgttt ttttgtctgc ttatgctttg tatagacatg aatctaaaaa agaattgggt      120
aatgaatgtc caactgttcc atatactaat ccaatgtttg gttctactga tgaatataga      180
aaaaatccag cagcttttgt tgaaaaatgg tctgctgctt gggtccagt ttttagagtt      240 catattttg gtagaatgca aactgttgtt tctggtagat atgttagaga agttttgttt      300
aatgataatt tttcttttgt tgaaggtatt agaactagat ttgatttgag attgttgact      360
ggtattccaa attctcattt gaatgataaa gatgttagag aagttgttgt taaatctttg      420
actgctcaaa tgaaaaaata ctccaagga gctgttcatt attgtctgt tggtttgcaa      480 gaagcattgg gtgatttgaa agatccaaga acttggata atttgttttt gactgttcaa      540
aatatggttg ctaaagcatc tgcttctatt tttgttggtg aagaattgtg taataatatt      600
```

```
gaattggttg atacttttaa acatgttact tctgatattg gttctgaaat tagattggat      660
aatacttggt tggaattttt taaaactatt aatcaaatta gaatgtgtta tgttggtaaa      720
cattctccaa gagttactaa acatagaaga caattgattc aagctatggc tccagaaatt      780
gatagaagat tgcaaggttt ggctggtaat gatccatctt ggactagacc agaagatatt      840
ttgcaagaaa ttatggaaaa ttatccatct ccatctactg ttccagcaga tatttatact      900
tattatgcta attggatgat tgttttgatt tttgcttctg ttcatactac tactgaacat      960
gctactattg ttttgtatag attgttgcaa caaccagaat tgattgatga attgttgcaa     1020
gaacaaaaag aagcattggg tcaaggtact gtttttactg gtgaagttat tagaaaattg     1080
gttaaattgg attctgtttg tagagaatct ttgagaatta aaaatgaata ttttggtttg     1140
ccacatagaa atatgtctca tgaaaatatt tctttgtcta atggtgttgt tattaaacca     1200
ggtgataatg ttatgttgaa tgtttggact aatcatcatg attctgattt gcaaaaagat     1260
gttcatggta atcatgataa atttgaacca tttagatatg ttaatgctga tagaccagct     1320
actaaaattg gtgatgatta tttgattttt ggtgaaggta acatgcttg tccaggtaga      1380 tggtttgctt tgcaagaaat taaaactatt gtttctgttt tgattagaga ttatactttg     1440
actccatgtg tccaattgt ttttccatct ggtacttcta ctggtattcc atctggtgaa      1500
gttactattc aaagaaaatc tgaagtttaa                                      1530
```

<210> SEQ ID NO 7
<211> LENGTH: 514
<212> TYPE: PRT
<213> ORGANISM: Lichtheimia ramosa
<400> SEQUENCE: 7

```
Met Thr Glu Ile Lys Glu His Ile Tyr Arg Tyr Arg His Tyr Ile Gly
1               5                   10                  15

Val Ala Ala Val Ala Leu Val Cys Gln Gln Val Tyr Tyr Arg Ile
            20                  25                  30

Phe Arg Ile Pro Lys Asn Leu Arg His Ile Pro Ala Ile Pro Tyr Gly
        35                  40                  45

Gln Gln Leu Lys Ala Leu Arg Ser Asp Glu Ala Leu Thr Ser Arg Thr
    50                  55                  60

Lys Arg Leu Val Phe Pro Leu Leu Ser Lys Cys Asn Gly Val Tyr Leu
65                  70                  75                  80

Asn Arg Met Pro Phe Lys Trp Thr Ile Tyr Val Ala Asp Pro Glu Ile
                85                  90                  95

Ala Arg Ala Ile Leu Phe Lys Pro Glu Phe Gly His Lys Thr Arg Ser
            100                 105                 110

Val Thr Asp Ser Leu Asp Lys Asn Ser Ser Leu Phe Glu Phe Val Gly
        115                 120                 125

Asp Asp Asn Ile Ala Ile Val Asn Gly His Glu Trp Lys Glu Gln Arg
    130                 135                 140

Lys Ile Met Asn Pro Ala Phe His Arg Ala Thr Pro Val Gly Met Phe
145                 150                 155                 160

Gly Ser Leu Met Pro Lys Val Phe Arg Leu Val Glu Glu Gln Pro Thr
                165                 170                 175

Leu Pro Ala Leu Asp Leu Met Gln Lys Leu Thr Leu Asp Ala Leu Gly
            180                 185                 190

Lys Ser Val Phe Gly Phe Glu Phe Gly Ala Leu Asp Asp Pro Asp Ser
        195                 200                 205
```

```
Val Trp Val Lys Thr Tyr Arg Gln Val Phe Asp Ser Phe Thr Asp Val
210                 215                 220

Phe Ser Leu Val Phe Pro Arg Leu Asp Pro Ile Tyr Arg Tyr Phe Ser
225                 230                 235                 240

Ala Lys His Arg Glu Gln Tyr Asn Ala Val Tyr Lys Leu Ile Asp Leu
                245                 250                 255

Leu Asp Gly Met Ala Asp Lys Lys Arg Ser Met Leu Gln Asp Ala Ser
            260                 265                 270

Asn Ser Asp Ile Lys Asp Val Pro Asp His Glu Lys Asp Leu Leu Gln
        275                 280                 285

Leu Met Leu Glu Ala Glu Leu Arg Gly Glu Gly Ser Trp Thr Lys Arg
290                 295                 300

Glu Leu Arg His Asn Met Ala Ile Phe Phe Val Ala Gly Gln Asp Thr
305                 310                 315                 320

Thr Ser His Ala Leu Thr Phe Cys Leu Tyr Leu Leu Ala Lys Asn Gln
                325                 330                 335

Asp Ile Gln Lys Lys Ala Arg Glu Glu Ile Leu Asn Val Phe Gly Asp
            340                 345                 350

Glu Pro Lys Asp Val Phe Pro Thr Leu Glu Asp Cys Lys Lys Leu Asn
        355                 360                 365

Tyr Leu Asp Met Val Ile Lys Glu Ser Met Arg Ile Tyr Pro Pro Ala
370                 375                 380

Asn Asp Val Leu Ala Arg Asp Val Asn Glu Asp Leu Asn Val Lys Gly
385                 390                 395                 400

Val Phe Ile Pro Lys Gly Ser Met Val Ser Val Asp Ile His Ala Leu
                405                 410                 415

His His Arg Pro Asp Leu Trp His Glu Pro Asp Lys Phe Asn Pro Asp
            420                 425                 430

Arg Phe Leu Pro Gly Gly Glu His Asp Ser His Val Gly Val Thr Tyr
        435                 440                 445

Ala Pro Phe Ser Ser Gly Ser Arg Gln Cys Ile Ala Leu Lys Phe Ala
450                 455                 460

Thr Met Gln Gln Arg Val Val Leu Ser Met Leu Leu Arg Lys Tyr Glu
465                 470                 475                 480

Trp Glu Leu Pro Lys Asp Ser Lys His Lys Asp Ser Ile Gln Phe Gln
                485                 490                 495

Ile Pro Phe Asn Ile Ala Pro Lys Asp Leu Glu Leu Thr Phe His Lys
            500                 505                 510

Arg Tyr

<210> SEQ ID NO 8
<211> LENGTH: 1545
<212> TYPE: DNA
<213> ORGANISM: Lichtheimia ramosa

<400> SEQUENCE: 8
atgactgaaa ttaaagaaca tatttataga tatagacatt atattggtgt tgctgctgct    60
gttgctttgg tttgtcaaca agtttattat agaattttta gaataccaaa aaatttgaga   120
catattccag ctattccata tggtcaacaa ttgaaagcat tgagatctga tgaagcattg   180
acttctagaa ctaaaagatt ggttttttcca ttgttgtcta atgtaatgg tgtttatttg   240 aatagaatgc catttaaatg gactatttat gttgctgatc cagaaattgc tagagctatt   300
ttgtttaaac cagaatttgg tcataaaact agatctgtta ctgattcttt ggataaaaat   360
```

```
tcttctttgt ttgaatttgt tggtgatgat aatattgcta ttgttaatgg tcatgaatgg      420
aaagaacaaa gaaaaattat gaatccagct tttcatagag ctactccagt tggtatgttt      480
ggttctttga tgccaaaagt ttttagattg gttgaagaac aaccaacttt gccagctttg      540
gatttgatgc aaaaattgac tttgatgct ttgggtaaat ctgttttttgg ttttgaattt      600 ggtgctttgg atgatccaga ttctgtttgg gttaaaactt atagacaagt ttttgattct      660
tttactgatg ttttttcttt ggttttttcca agattggacc caatttatag atatttttct      720
gctaaacata gagaacaata taatgctgtt tataaattga ttgatttgtt ggatggtatg      780
gctgataaaa aagatctat gttgcaagat gcttctaatt ctgatattaa agatgttcca      840
gatcatgaaa aagatttgtt gcaattgatg ttggaagctg aattgagagg tgaaggttct      900
tggactaaaa gagaattgag acataatatg gctatttttt ttgttgctgg tcaagatact      960
acttctcatg ctttgacttt ttgtttgtat ttgttggcta aaaatcaaga tattcaaaaa     1020
aaagctagag aagaaatttt gaatgttttt ggtgatgaac caaagatgt ttttccaact     1080 ttggaagatt gtaaaaaatt gaattatttg gatatggtta ttaaagaatc tatgagaatt     1140
tatccaccag ctaatgatgt tttggctaga gatgttaatg aagatttgaa tgttaaaggt     1200
gtttttattc caaaaggttc tatggtttct gttgatattc atgctttgca tcatagacca     1260
gatttgtggc atgaaccaga taaatttaat ccagatagat ttttgccagg tggtgaacat     1320
gattctcatg ttggtgttac ttatgctcca ttttcttctg gttctagaca atgtattgct     1380
ttgaaatttg ctactatgca acaaagagtt gttttgtcta tgttgttgag aaaatatgaa     1440
tgggaattgc caaagattc taaacataaa gattctattc aatttcaaat tccatttaat     1500
attgctccaa aagatttgga attgactttt cataaaagat attaa                     1545
```

<210> SEQ ID NO 9
<211> LENGTH: 701
<212> TYPE: PRT
<213> ORGANISM: Thamnostylum piriforme

<400> SEQUENCE: 9

Met Ala Gln Ser Ser Pro Ala Leu Leu Asp Ser Leu Asp Ile Val Phe
1               5                   10                  15

Leu Gly Thr Ile Gly Leu Gly Thr Ile Ala Trp Phe Ala Arg Arg Gln
            20                  25                  30

Ile Ala Glu Arg Ile Phe Gly Ser Lys Asp Asp Ala Asn Lys Asn Val
        35                  40                  45

Gly Asn Gly Asn Ala Pro Thr Ala Pro Lys Arg Glu Arg Asn Phe Val
    50                  55                  60

Lys Val Met Gln Glu Gln Gly Arg Lys Val Ile Phe Phe Tyr Gly Ser
65                  70                  75                  80

Gln Thr Gly Thr Ala Glu Asp Tyr Ala Ser Arg Leu Ala Lys Glu Cys
                85                  90                  95

Ser Gln Lys Tyr Gly Val Ser Cys Met Thr Ala Asp Ile Glu Leu Tyr
            100                 105                 110

Asp Leu Thr Tyr Leu Asp Thr Val Pro Glu Asp Phe Leu Val Phe Phe
        115                 120                 125

Ile Met Ala Thr Tyr Gly Glu Gly Glu Pro Thr Asp Asn Ala Val Asp
    130                 135                 140

Phe Trp Glu Gln Leu Thr Glu Glu Pro Gln Phe Ser Glu Gly Asp
145                 150                 155                 160

Thr Leu Gly Asn Leu Arg Tyr Val Val Phe Gly Leu Gly Asn Lys Thr

```
            165                 170                 175
Tyr Glu His Tyr Asn Glu Val Ala Arg Arg Met Asp Lys Leu Leu Thr
            180                 185                 190
Lys Leu Gly Ala Lys Arg Ile Gly Glu Arg Gly Glu Gly Asp Asp Asp
            195                 200                 205
Ala Ser Leu Glu Glu Asp Phe Leu Ala Trp Gln Asp Ser Met Trp Pro
            210                 215                 220
Ala Phe Cys Asp Ala Leu Gly Val Asp Glu Ser Asn Gly Ser Ser Gly
225                 230                 235                 240
Pro Arg Gln Ala Met Tyr Ala Val Glu Glu Leu Glu Gly Gln Glu Ala
            245                 250                 255
Val Tyr Leu Gly Glu Leu Gly Glu Lys Pro Lys Glu Gly Val Lys Val
            260                 265                 270
Val Tyr Asp Ala Lys Arg Pro Tyr Asn Ala Pro Leu Val Ser Gln Asp
            275                 280                 285
Leu Phe Lys Asn Thr Asp Arg His Cys Leu His Ile Asp Ile Asp Val
            290                 295                 300
Ser Asp Ser Asn Leu Ser Tyr Gln Thr Gly Asp His Ile Ala Ile Trp
305                 310                 315                 320
Pro Thr Asn Ser Asp Asp Glu Val Ala Arg Leu Ala Ser Leu Leu Gly
                    325                 330                 335
Leu Thr Asp Lys Leu Asp Thr Ser Val Met Val Lys Ala Ile Asp Ser
            340                 345                 350
Thr Ala Ser Lys Gln Tyr Pro Phe Pro Val Pro Ala Thr Tyr Arg Ser
            355                 360                 365
Ile Phe Arg His Tyr Leu Asp Ile Cys Ala Pro Ala Ser Arg Gln Thr
            370                 375                 380
Leu Met Ser Leu Val Glu Tyr Ala Pro Thr Glu Ala Ser Lys Glu Ala
385                 390                 395                 400
Leu Arg Leu Leu Ser Lys Asp Lys Asp Glu Tyr Arg Leu Lys Val Gly
                    405                 410                 415
Glu Ala Val Arg Asn Leu Gly Glu Val Leu Glu Leu Ala Ala Gly Ala
            420                 425                 430
Asp Ala Arg Pro Gly Leu Phe Ser Thr Val Pro Phe Asp Leu Ile Val
            435                 440                 445
Glu Ser Val Ser Arg Leu Gln Pro Arg Tyr Tyr Ser Ile Ser Ser Ser
            450                 455                 460
Ala Lys Glu Ser Pro Lys Val Ile Ala Val Thr Ala Val Thr Leu Thr
465                 470                 475                 480
Tyr Asn Pro Asp Pro Thr Pro Glu Arg Thr Val Tyr Gly Val Asn Thr
                    485                 490                 495
Asn Tyr Leu Trp Gln Ile His Ala Ala Lys His Asn Val Asn Asp Gly
            500                 505                 510
Gln Arg Tyr Pro Thr Tyr Asp Leu Ala Gly Pro Arg Asn Ala Leu Gln
            515                 520                 525
Gly Ala Lys Val Pro Val His Ile Arg Arg Ser Gln Phe Lys Leu Pro
            530                 535                 540
Arg Asn Pro Thr Val Pro Val Ile Met Val Gly Pro Gly Thr Gly Val
545                 550                 555                 560
Ala Pro Phe Arg Gly Phe Val Arg Glu Arg Ala Ala Gln Lys Thr Asp
                    565                 570                 575
Gly Lys Pro Val Gly Pro Thr Leu Leu Phe Phe Gly Cys Arg Asn Ser
            580                 585                 590
```

```
Gln Gln Asp Phe Leu Tyr Lys Asp Glu Trp Pro Glu Leu Phe Ala Thr
        595                 600                 605
Leu Gly Asp Glu Ser Arg Ile Val Thr Ala Phe Ser Arg Glu Thr Pro
    610                 615                 620
Gln Lys Val Tyr Val Gln His Arg Leu Gln Glu Asn Gly Glu Glu Leu
625                 630                 635                 640
Trp Asn Leu Leu Gln Lys Gly Ala Tyr Ile Tyr Val Cys Gly Asp Ala
            645                 650                 655
Lys Asn Met Ala Arg Asp Val Asn Gln Thr Phe Val Asn Phe Ala Ile
            660                 665                 670
Glu Phe Gly Gly Gln Thr Glu Glu Lys Ala His Asp Tyr Val Lys Asn
            675                 680                 685
Leu Arg Asn Ser Gly Arg Tyr Gln Glu Asp Val Trp Ser
    690                 695                 700

<210> SEQ ID NO 10
<211> LENGTH: 2106
<212> TYPE: DNA
<213> ORGANISM: Thamnostylum piriforme

<400> SEQUENCE: 10
```

| | | | | | |
|---|---|---|---|---|---|
| atggcgcaat | cgtcacctgc | tcttctcgac | tctttggaca | ttgtgttcct | cggaacgatt    60 |
| ggtcttggca | ccattgcctg | gtttgcacgt | cgacagattg | cagaacgaat | ctttggatcc   120 |
| aaggatgatg | caaacaaaaa | cgtcggcaat | ggcaacgctc | ctactgcgcc | gaagcgagag   180 |
| cgcaactttg | tcaaagtgat | gcaagaacag | ggtcgcaaag | tcatcttctt | ttacggttcg   240 |
| cagaccggca | cggctgaaga | ctacgcttct | cggctagcca | aggaatgctc | gcaaaagtac   300 |
| ggtgtgagct | gtatgacagc | cgatatcgag | ctgtacgatc | tgacctatct | ggacactgtg   360 |
| cctgaagact | tcttggtgtt | cttcatcatg | gcgacgtacg | gcgagggtga | gcccaccgac   420 |
| aacgccgtcg | acttctggga | gcaattgacg | gaggaggagc | cccagttctc | ggaaggcgac   480 |
| actttgggta | acttgcgcta | tgtggtgttt | ggcctgggca | caagacgta  | cgagcattac   540 |
| aacgaggtgg | ctcgtcggat | ggacaagctg | ctgacgaagc | tgggtgccaa | gcgcattggc   600 |
| gagcggggcg | aaggcgacga | cgatgcttcg | ttggaagagg | acttttttggc | gtggcaagat   660 |
| agcatgtggc | ccgcgttctg | cgacgctctg | gcgtggacg  | agagcaacgg | atccagcggg   720 |
| ccccgccagg | ccatgtacgc | ggtggaggag | cttgagggcc | aagaggccgt | gtatctcggc   780 |
| gagctcggag | agaagcccaa | ggagggcgtt | aaggttgtgt | acgacgccaa | gcgcccctac   840 |
| aacgcgccgc | tcgtctcgca | ggacctcttc | aaaaacacag | accgccattg | cctgcacatc   900 |
| gacatcgacg | tctcggactc | caacctgtcg | taccagaccg | cgaccacat  | cgcgatctgg   960 |
| cccaccaaca | gcgatgacga | agtggcgcgt | ctcgcttccc | tgctcggcct | gaccgacaag  1020 |
| ctcgacacca | cgtcatggt  | caaggccatc | gactccaccg | cctccaagca | gtacccattc  1080 |
| cccgtgcccg | ccacctaccg | gtccatttttc | cgccactacc | tcgacatctg | cgcgcccgcg  1140 |
| tcgcgccaga | cgctcatgtc | gctggtcgag | tacgcgccca | cggaggcgtc | caaagaggcc  1200 |
| ttgcgtctgc | tgtccaagga | caaggacgag | taccgcctca | aggtcggcga | ggctgtccgc  1260 |
| aacctgggcg | aggtgcttga | gctggctgcc | ggagcggatg | cccgaccggg | cctgttctcc  1320 |
| accgtgccct | ttgacctgat | cgtcgagagc | gtgtcgcgcc | tgcagccccg | ctactactcc  1380 |
| atctcctcat | cggccaagga | gtcgcccaag | gtcattgccg | tcaccgccgt | cacccttgaca  1440 |
| tacaacccag | accccacgcc | cgagcgcacc | gtgtatggcg | tcaacaccaa | ctatttgtgg  1500 |

```
caaatccacg ccgccaagca caacgtcaac gacggccagc gctacgccac ctacgacctg    1560
gctggcccgc gcaacgccct gcaaggcgcc aaggtccccg tccacatccg ccgctcgcag    1620
ttcaagctgc cgcgcaaccc caccgtccct gtcatcatgg tcggcccagg caccggtgtc    1680
gcgcccttcc gtggctttgt tcgcgagcgt gccgcccaaa agaccgacgg caagcccgtc    1740
ggccccaccc tgctcttctt cggctgccgc aactcgcaac aggacttctt gtacaaggac    1800
gagtggcccg agctgttcgc caccctgggc gacgagtcgc gtatcgtgac tgcattctcg    1860
cgcgagactc cccagaaggt ctacgtccag caccggctcc aggagaacgg cgaggagctg    1920
tggaatctgc tgcaaaaggg agcctacatt tacgtgtgcg gtgacgcaaa gaacatggca    1980
cgcgatgtca accagacctt cgtcaacttt gcgatcgagt ttggcggcca gaccgaagag    2040
aaggcgcatg actacgtcaa gaacctcaga acagcggtc gataccagga ggatgtgtgg     2100
agctaa                                                               2106

<210> SEQ ID NO 11
<211> LENGTH: 2106
<212> TYPE: DNA
<213> ORGANISM: Thamnostylum piriforme

<400> SEQUENCE: 11
atggctcaat cttctccagc tttgttggat tctttggata ttgtttttt gggtactatt      60 ggtttgggta ctattgcttg gtttgctaga agacaaattg ctgaaagaat ttttggttct    120
aaagatgatg ctaataaaaa tgttggtaat ggtaatgctc caactgctcc aaaaagagaa    180
agaaattttg ttaaagttat gcaagaacaa ggtagaaaag ttattttttt ttatggttct    240
caaactggta ctgctgaaga ttatgcttct agattggcta agaatgttc tcaaaaatat    300 ggtgtttctt gtatgactgc tgatattgaa ttgtatgatt tgacttattt ggatactgtt    360
ccagaagatt ttttggtttt ttttattatg ctacttatg gtgaaggtga accaactgat    420
aatgctgttg atttttggga caattgact gaagaagaac cacaattttc tgaaggtgat    480
actttgggta atttgagata tgttgttttt ggtttgggta ataaaactta tgaacattat    540
aatgaagttg ctagaagaat ggataaaattg ttgactaaat tgggtgctaa agaattggt    600 gaaagaggtg aaggtgatga tgatgcttct ttggaagaag attttttggc ttggcaagat    660
tctatgtggc cagcttttttg tgatgctttg ggtgttgatg aatctaatgg ttcttctggt    720
ccaagacaag ctatgtatgc tgttgaagaa ttggaaggtc aagaagctgt ttatttgggt    780 gaattggggtg aaaaaaccaaa agaaggtgtt aagttgtttt atgatgctaa aagaccatat    840
aatgctccat tggtttctca agatttgttt aaaaatactg atagacattg tttgcatatt    900
gatattgatg tttctgattc taatttgtct tatcaaactg gtgatcatat tgctatttgg    960
ccaactaatt ctgatgatga agttgctaga ttggcttctt tgttgggttt gactgataaa    1020
ttggatactg ctgttatggt taaagctatt gattctactg cttctaaaca atatccattt    1080
ccagttccag ctacttatag atctattttt agacattatt tggatatttg tgctccagct    1140
tctagacaaa ctttgatgtc tttggttgaa tatgctccaa ctgaagcatc taaagaagca    1200
ttgagattgt tgtctaaaga taaagatgaa tatagattga agttggtga agctgttaga    1260 aatttgggtg aagttttgga attggctgct ggtgctgatg ctagaccagg ttttgttttct    1320 actgttccat tgatttgat tgttgaatct gtttctagat gcaaccaag atattattct    1380 atttcttctt ctgctaaaga atctccaaaa gttattgctg ttactgctgt tactttgact    1440
```

```
tataatccag atccaactcc agaaagaact gtttatggtg ttaatactaa ttatttgtgg    1500
caaattcatg ctgctaaaca taatgttaat gatggtcaaa gatacccaac ttatgatttg    1560
gctggtccaa gaaatgcttt gcaaggtgct aaagttccag ttcatattag aagatctcaa    1620
tttaaattgc caagaaatcc aactgttcca gttattatgg ttggtccagg tactggtgtt    1680
gctccattta gaggttttgt tagagaaaga gctgctcaaa aaactgatgg taaaccagtt    1740
ggtccaactt tgttgttttt tggttgtaga aattctcaac aagatttttt gtataaagat    1800
gaatggccag aattgtttgc tactttgggt gatgaatcta gaattgttac tgcttttttct   1860 agagaaactc cacaaaaagt ttatgttcaa catagattgc aagaaaatgg tgaagaattg    1920
tggaatttgt tgcaaaaagg tgcttatatt tatgtttgtg gtgatgctaa aaatatggct    1980
agagatgtta atcaaacttt tgttaatttt gctattgaat tggtggtca aactgaagaa      2040 aaagctcatg attatgttaa aaatttgaga aattctggta gataccaaga agatgtttgg    2100
tcttag                                                                2106

<210> SEQ ID NO 12
<211> LENGTH: 707
<212> TYPE: PRT
<213> ORGANISM: Thamnostylum piriforme

<400> SEQUENCE: 12

Met Ser Lys Lys Pro Thr Thr Phe Ala Ile Ser Pro Leu Asp Leu Leu
1               5                   10                  15

Leu Leu Gly Thr Leu Gly Ile Gly Ala Leu Leu Tyr Ile Thr Arg Lys
            20                  25                  30

Leu Arg Ala Ala Pro Pro Ala Ala Gly Asp Ala Ala Arg Pro Ser
        35                  40                  45

Asp Lys Ala Pro Ser Asn Lys Pro Glu Arg Asn Phe Val Lys Leu Met
    50                  55                  60

Glu Gln Gln Lys Arg Arg Val Ile Phe Phe Tyr Gly Ser Gln Thr Gly
65                  70                  75                  80

Thr Ala Glu Asp Tyr Ala Ser Arg Leu Ala Lys Glu Ser Ser Gln Lys
                85                  90                  95

Tyr Gly Val Ser Ser Met Ala Ala Asp Ile Glu Leu Tyr Asp Leu Ser
            100                 105                 110

Tyr Leu Asp Thr Val Pro Glu Asp Lys Leu Val Val Phe Val Met Ala
        115                 120                 125

Thr Tyr Gly Glu Gly Glu Pro Thr Asp Asn Ala Val Asp Phe Trp Glu
    130                 135                 140

Thr Leu Thr Asp Glu Ala Pro Met Phe Ser Leu Gly Glu Glu Leu Ala
145                 150                 155                 160

Pro Leu Arg Asn Leu Asn Tyr Ile Val Phe Gly Leu Gly Asn Lys Thr
                165                 170                 175

Tyr Glu His Tyr Asn Glu Val Ala Arg Val Leu Asp Lys Arg Leu Ala
            180                 185                 190

Ala Leu Gly Ala Thr Arg His Gly Val Arg Gly Glu Gly Asp Asp Asp
        195                 200                 205

Ala Ser Leu Glu Glu Asp Phe Leu Ala Trp Gln Glu Asp Met Trp Pro
    210                 215                 220

Ala Phe Cys Ala Ala Leu Asn Val Asp Glu Ser Asn Ala Gln Ala Gly
225                 230                 235                 240

Pro Arg Gln Ala Met Tyr Gly Val Lys Glu Leu Glu Gly His Asp Glu
                245                 250                 255
```

```
Asn Gly Leu Phe Leu Gly Glu Leu Gly Glu Trp Leu Gln Pro Glu Gln
            260                 265                 270

Leu Gln Lys Gln Thr Ala Val His Asp Ala Lys His Pro Tyr Leu Ala
        275                 280                 285

Pro Ile Ala Ala Ser Arg Asp Leu Phe Ser His Ala Ala Asp Arg His
    290                 295                 300

Cys Leu His Leu Glu Val Asp Ile Ala Ser Ser Asn Leu Thr Tyr Gln
305                 310                 315                 320

Thr Gly Asp His Ile Ala Ile Trp Pro Thr Asn Asn Asp Val Glu Val
                325                 330                 335

Leu Arg Leu Ala Thr Val Leu Gly Leu Ala Asp Lys Leu Asp Thr Ala
            340                 345                 350

Ile Met Val Lys Ala Leu Asp Ser Ala Ala Ser Lys Lys Tyr Pro Phe
        355                 360                 365

Pro Val Pro Thr Thr Tyr Arg Ala Ala Phe Lys His Tyr Leu Asp Ile
    370                 375                 380

Cys Ser Pro Ala Ser Arg Gln Thr Leu Ile Ser Leu Val Asp Tyr Ala
385                 390                 395                 400

Pro Thr Ala Ser Ser Lys Asp Ala Leu His Lys Leu Ala Thr Asp Lys
                405                 410                 415

Asp Ala Tyr Lys Thr Gln Val Ser Glu Ala Ala Arg Asn Leu Ala Glu
            420                 425                 430

Val Leu Glu Leu Cys Gln Asp Asp Glu Gly Thr Thr Ala Ala Pro Gly
        435                 440                 445

Phe Phe Ser Thr Val Pro Phe Asp Leu Ile Val Glu Ser Val Ser Arg
    450                 455                 460

Leu Gln Pro Arg Tyr Tyr Ser Ile Ser Ser Ser Ser Leu Thr Ser Pro
465                 470                 475                 480

Lys Ser Val Ala Val Thr Ala Val Thr Leu Ser Tyr Gln Pro Ser Thr
                485                 490                 495

Thr Lys Ser Arg Thr Val Tyr Gly Val Asn Thr Asn Tyr Leu Trp Arg
            500                 505                 510

Ile His Ala Pro His Asp Ala Ser Val Pro Ala Tyr Asp Leu Asp Gly
        515                 520                 525

Pro Arg Asn Thr Leu Gln Gly Lys Lys Val Pro Val His Ile Arg Arg
    530                 535                 540

Ser Thr Phe Lys Leu Pro Arg Asn Thr Lys Leu Pro Val Ile Met Val
545                 550                 555                 560

Gly Pro Gly Thr Gly Val Ala Pro Phe Arg Gly Phe Ile His Asp Arg
                565                 570                 575

Val His Gln Lys Gln Ser Gly Lys Glu Val Gly Pro Thr Val Leu Phe
            580                 585                 590

Tyr Gly Cys Arg His Ser Lys Gln Asp Phe Leu Tyr Ala Glu Glu Trp
        595                 600                 605

Pro Ala Leu Phe Glu Ala Leu Gly Glu Gly Ser Gln Leu Ile Thr Ala
    610                 615                 620

Phe Ser Arg Glu Ser Ala Gln Lys Val Tyr Val Gln His Arg Leu Lys
625                 630                 635                 640

Glu His Gly Glu Gln Met Trp Lys Tyr Ile Glu Gln Gly Ala Tyr Ile
                645                 650                 655

Tyr Val Cys Gly Asp Ala Lys Asn Met Ala Arg Asp Val Gln Gln Thr
            660                 665                 670
```

Phe Ile Glu Phe Ala Gln Ala Leu Gly Asn Lys Thr Glu Ser Gln Ala
675                 680                 685

Gln Asp Tyr Val Lys Asn Leu Arg Asn Thr Gly Arg Tyr Gln Glu Asp
690                 695                 700

Val Trp Ser
705

<210> SEQ ID NO 13
<211> LENGTH: 2124
<212> TYPE: DNA
<213> ORGANISM: Thamnostylum piriforme

<400> SEQUENCE: 13

| | | | | | |
|---|---|---|---|---|---|
| atgtcaaaaa | agcctactac | gtttgccatc | agtccgcttg | acctgctgct | gctgggcacg | 60 |
| ctggggattg | gcgccctcct | ctacataacg | agaaagctca | gggcagcgcc | tccacccgcg | 120 |
| gctggcgacg | cagcacgccc | atccgataaa | gcgccgagca | acaagcctga | acggaacttc | 180 |
| gtcaagctga | tggagcagca | gaaacggcgc | gtcattttct | tttacggatc | tcagacaggc | 240 |
| actgcagagg | attacgcctc | acggctggcc | aaggaaagct | cccagaaata | tggcgtgagc | 300 |
| agcatggcgg | ccgacattga | gctgtacgac | ctcagctacc | tggacaccgt | acccgaggac | 360 |
| aagctggtgg | tgtttgtcat | ggccacctac | ggcgagggcg | agccgaccga | caacgccgtc | 420 |
| gacttctggg | aaacgctgac | cgacgaagcg | cccatgttct | cgctgggaga | gagttagcg | 480 |
| ccgctgcgaa | acctgaacta | cattgtgttt | ggactgggca | caagaccta | cgagcattac | 540 |
| aacgaagtgg | cccgtgtcct | tgacaagcgc | cttgcggctc | tgggcgccac | gcggcacggc | 600 |
| gtgcggggcg | aaggcgacga | cgacgcttct | ctggaagagg | actttctggc | atggcaggag | 660 |
| gatatgtggc | ctgcgttctg | cgctgcgttg | aatgtcgacg | agagcaatgc | gcaggcgggt | 720 |
| ccgcggcagg | cgatgtacgg | cgtgaaggag | ctcgagggcc | acgacgaaaa | cggtctgttt | 780 |
| ttgggagagc | tgggcgagtg | gctgcagcct | gaacagctgc | agaagcagac | agccgtgcat | 840 |
| gacgccaaac | atccgtacct | ggcccccatc | gctgcctcgc | gtgatctgtt | cagccacgcc | 900 |
| gccgaccgcc | actgcctgca | cctggaagtc | gacatcgcca | gcagcaacct | cacctaccag | 960 |
| accggcgacc | acatcgccat | ctggcccacc | aacaacgacg | tcgaggtgct | cgcgcctggcc | 1020 |
| accgtgctgg | gtctggcgga | caagctggac | accgccatca | tggtcaaggc | tttggacagc | 1080 |
| gccgcctcca | aaaagtaccc | cttccctgtc | ccaccacgt | accgcgccgc | attcaaacac | 1140 |
| tacctcgata | tctgctctcc | tgcatctcgc | cagacgctga | tctcgttggt | cgactacgcg | 1200 |
| cccaccgcgt | cgtccaagga | cgcgctgcac | aaactggcaa | ccgacaagga | cgcctataaa | 1260 |
| acgcaggtca | gcgaggccgc | gcgcaacctg | gccgaggtgc | tggagctgtg | ccaggacgac | 1320 |
| gagggcacga | cagccgcgcc | tggcttctt | tccaccgtgc | ccttcgacct | gattgtcgaa | 1380 |
| agcgtgtcgc | gtctccagcc | acggtactac | tccatctcgt | catcctcgct | cacctctccg | 1440 |
| aaatccgtcg | ctgtcaccgc | cgtcacgctg | tcctaccagc | catccaccac | caaaagccgc | 1500 |
| accgtctacg | gcgtcaacac | caactacctg | tggcgcatcc | atgcaccgca | cgacgcgtcc | 1560 |
| gtcccagcct | acgatctcga | cggtccgcgc | aacactctcc | aaggcaaaaa | ggtgccggtg | 1620 |
| catatccgcc | gatcgacctt | caaactgccg | cgcaacacca | agcttcccgt | catcatggtg | 1680 |
| gggcctggca | cgggcgtcgc | gccgttccgc | gggttcatcc | atgatcgcgt | gcatcagaag | 1740 |
| caaagtggca | aggaggtggg | gcccacgtg | ctgttctatg | gatgccgcca | ttccaaacag | 1800 |
| gacttttgt | atgcggaaga | atggccggcg | ctctttgagg | cgttgggcga | aggatcgcag | 1860 |

```
ttgatcaccg cgttttcgcg agaatcagcg caaaaggtct atgttcagca ccggttaaag    1920
gagcacggcg agcagatgtg gaagtatatc gagcagggag cgtatatcta cgtttgcggt    1980
gacgccaaaa acatggccag ggacgtgcag cagacgttca ttgagtttgc acaggctctg    2040
ggaaacaaaa cggaaagcca ggcacaggac tacgtcaaga atctgcgaaa caccggacgc    2100
taccaggagg acgtgtggtc gtag                                           2124

<210> SEQ ID NO 14
<211> LENGTH: 2124
<212> TYPE: DNA
<213> ORGANISM: Thamnostylum piriforme

<400> SEQUENCE: 14
atgtctaaaa aaccaactac ttttgctatt tctccattgg atttgttgtt gttgggtact      60
ttgggtattg gtgctttgtt gtatattact agaaaattga gagctgctcc accaccagct     120
gctggtgatg ctgctagacc atctgataaa gctccatcta ataaaccaga aagaaatttt     180
gttaaattga tggaacaaca aaaaagaaga gttatttttt tttatggttc tcaaactggt     240
actgctgaag attatgcttc tagattggct aaagaatctt ctcaaaaata tggtgtttct     300
tctatggctg ctgatattga attgtatgat ttgtcttatt ggatactgt tccagaagat     360 aaattggttg tttttgttat ggctacttat ggtgaaggtg aaccaactga taatgctgtt     420
gattttgggg aaactttgac tgatgaagct ccaatgtttt ctttgggtga gaattggct     480 ccattgagaa atttgaatta tattgttttt ggtttgggta taaaacttta tgaacattat     540
aatgaagttg ctagagtttt ggataaaaga ttggctgctt gggtgctac tagacatggt     600 gttagaggtg aaggtgatga tgatgcttct ttggaagaag attttttggc ttggcaagaa     660
gatatgtggc cagcttttg tgctgctttg aatgttgatg aatctaatgc tcaagctggt     720
ccaagacaag ctatgtatgg tgttaaagaa ttggaaggtc atgatgaaaa tggtttgttt     780
ttgggtgaat tgggtgaatg gttgcaacca gaacaattgc aaaaacaaac tgctgttcat     840
gatgctaaac atccatattt ggctccaatt gctgcttcta gagatttgtt ttctcatgct     900
gctgatagac attgttttgca tttgaagtt gatattgctt cttctaattt gacttatcaa     960
actggtgatc atattgctat ttggccaact aataatgatg ttgaagtttt gagattggct    1020
actgttttgg gttggctga taaattggat actgctatta tggttaaagc attggattct    1080
gctgcttcta aaaatatcc atttccagtt ccaactactt atagagctgc ttttaaacat    1140
tatttggata tttgttctcc agcttctaga caaactttga tttctttggt tgattatgct    1200
ccaactgctt cttctaaaga tgctttgcat aaattggcta ctgataaaga tgcttataaa    1260
actcaagttt ctgaagctgc tagaaatttg gctgaagttt tggaattgtg tcaagatgat    1320
gaaggtacta ctgctgctcc aggtttttttt tctactgttc catttgattt gattgttgaa    1380
tctgtttcta gattgcaacc aagatattat tctatttctt cttcttcttt gacttctcca    1440
aaatctgttg ctgttactgc tgttactttg tcttatcaac catctactac taaatctaga    1500
actgtttatg gtgttaatac taattatttg tggagaatcc atgctccaca tgatgcttct    1560
gttccagctt atgatttgga tggtccaaga aatactttgc aaggtaaaaa agttccagtt    1620
catattagaa gatctacttt taaattgcca agaaatacta aattgccagt tattatggtt    1680
ggtccaggta ctggtgttgc tccatttaga ggttttattc atgatagagt tcatcaaaaa    1740
caatctggta agaagttgg tccaactgtt ttgttttatg gttgtagaca ttctaaacaa    1800
gattttttgt atgctgaaga atggccagct ttgtttgaag cattgggtga aggttctcaa    1860
```

| | |
|---|---|
| ttgattactg cttttttctag agaatctgct caaaaagttt atgttcaaca tagattgaaa | 1920 |
| gaacatggtg aacaaatgtg gaaatatatt gaacaaggtg cttatattta tgtttgtggt | 1980 |
| gatgctaaaa atatggctag agatgttcaa caaacttttta ttgaatttgc tcaagcattg | 2040 |
| ggtaataaaa ctgaatctca agctcaagat tatgttaaaa atttgagaaa tactggtaga | 2100 |
| taccaagaag atgtttggtc ttag | 2124 |

<210> SEQ ID NO 15
<211> LENGTH: 2085
<212> TYPE: DNA
<213> ORGANISM: Thamnostylum piriforme

<400> SEQUENCE: 15

| | |
|---|---|
| atggcaaaaa atactacatt aaacaagcaa gtggtgcttc tcatcagtgc cctgggcctg | 60 |
| agcgctgttg cctacatggc cagccgatac tttttttggaa acagcgcaag caccccctgaa | 120 |
| caatcgaaaa agcccattca accagaagaa aaagaagacg aatcaaactt tgtgcaaacc | 180 |
| atgaagaagc agaatcgtaa agtagtgatc ttttatggtt cgcaaacagg cacggctgaa | 240 |
| gattgtgcgc agcgacttgg caagcagtgc aaaaagcaat tcggcgttcc tgctttggtt | 300 |
| cttgatatcg aacaatgcaa catgtcgtac ttggatcaga ttcccgagga ctgtgttgcg | 360 |
| atatttgtca tggcaactta tggcgaaggt gaacccactg acaacgccac tgacttttgg | 420 |
| gaaatgcttg aagcccatcc tgaattttcc caaagcgaca acctcaagaa tctccgatac | 480 |
| ttcatcttcg gacttggcaa cagctcctat acctattaca actgggtctc caaaactgtc | 540 |
| gacaagaaac tcactgaatt aggcgcgaca cgacttggca aacttggctt gggcgacgac | 600 |
| gaaaagtcgc tcgaagacga ctttgaagca tggcaggaag gcatgtggcc tatttttgga | 660 |
| gaagctgtgg aaacggacgc cgccagcaat atcagcggcg gacacgagcc cacataccat | 720 |
| gtggtggagc taaccgaaca tgacggccac gtgtattctg gtgaattggg agacaaaatcg | 780 |
| caagctctct atagcggcaa gaagccttac ccagcaccta ttaccacgcg cgatttgttg | 840 |
| aacggatcgg atcgccactg tctacacctg gaagtcgata tcagtggatc aggcatgagc | 900 |
| tataccactg gcgatcatat tgccatctgg cccacaaaca gcgaagacga ggtcttgagc | 960 |
| ttggcacgcg ccattggtct cgaaaacaag ctggataccg tcatttgcgt tactgctgcg | 1020 |
| gatgagacgt ccgccaagca atcaccgttc cctcagccaa caacataccg tgccatgctg | 1080 |
| cgacactact tggatatttg ccaaatgcca tcacggcaga cactggagat gctcgtacct | 1140 |
| tttgcaccgt cgcccgaagc tgcagagact ctagaaaagc tggcaaagga caaggatgag | 1200 |
| catcgtcgag tggttctggg accagttcgt aacttggctg ctgtgctgag ttatgcgtcg | 1260 |
| tcgggcgctg catacaagat cccatccgat gtgctgcttg agtgccttgg tcgactacag | 1320 |
| ccccgatatt actcgatttc ctcctctgcc ttggagagcc caaacagtgt cagtgtcact | 1380 |
| gccgttacac tcaaattcaa ccccgaacca acgcctgagc gcactgtctt tggcgtcaat | 1440 |
| accaactacc tgtgggccgt ccataccgcg ctcaacgatg acgacgaggc aatccaagtt | 1500 |
| gaaaccgagt attccatcgg tggacctaac ggtcaatact ttgacgagaa gctcaaaact | 1560 |
| gcaagattgc ctgttcacat ccgccaatca aacttcaagc tgccagcaga cacaactaag | 1620 |
| ccagtgatca tgattggccc cggcaccggt gtcgctcctt tccgagcctt cgttcgcgag | 1680 |
| cgtgcctatc aaaagaagca ccttggcaaa tccatcggtc caactattct gtactttggc | 1740 |
| tgccgacgtt ccaacgagga cttttttgtat caggaagagt ggccagagct ctttaacgaa | 1800 |

```
ttgggcggct cctctcgatt gatcactgca ttctcccggg aaacggatcg aaaagtatac    1860
gtccaagaca agctcaacga gaacggccca gagacttggg atttgattaa taacaagggc    1920
gcctatgtct atgtttgtgg cgacgctaag cgtatggcca agacgtcca gtccgcactt    1980 gttagttttg caaagcagta tggcagctat gacgacgctg gtgcagctga ctacatcagc    2040
aagttaagag atgccggacg atatcaagaa gacgtctggg cataa                   2085
```

<210> SEQ ID NO 16
<211> LENGTH: 710
<212> TYPE: PRT
<213> ORGANISM: Cunninghamella elegans

<400> SEQUENCE: 16

Met Ala Gln Gln Thr Pro Ala Val Ile Asp Thr Leu Asp Leu Ile Leu
1               5                   10                  15

Leu Gly Ser Ile Gly Leu Gly Thr Ile Ala Trp Phe Thr Arg Arg Gln
            20                  25                  30

Leu Ser Glu Arg Leu Phe Gly Thr Gly Gln Ser Asn Ala Thr Pro Lys
        35                  40                  45

Pro Thr Thr Pro Gln Ala Pro Lys Arg Glu Arg Asn Phe Val Lys Val
    50                  55                  60

Met Glu Gln Gln Gly Arg Lys Val Ile Phe Phe Tyr Gly Ser Gln Thr
65                  70                  75                  80

Gly Thr Ala Glu Asp Phe Ala Ser Arg Leu Ala Lys Gln Cys Ser Gln
                85                  90                  95

Lys Tyr Gly Val Ser Cys Met Thr Ala Asp Ile Glu Met Tyr Asp Leu
            100                 105                 110

Ser Tyr Leu Asp Thr Leu Ser Glu Asp Ser Leu Val Cys Phe Val Met
        115                 120                 125

Ala Thr Tyr Gly Glu Gly Glu Pro Thr Asp Asn Ala Val Asp Phe Trp
    130                 135                 140

Glu Gln Phe Ile Thr Asp Glu Ser Pro Val Phe Ser Glu Gly Gly Glu
145                 150                 155                 160

Thr Leu Glu Asn Leu Arg Tyr Leu Met Phe Gly Leu Gly Asn Lys Thr
                165                 170                 175

Tyr Glu His Tyr Asn Ala Val Ala Arg Ile Leu Asp Lys Lys Leu Thr
            180                 185                 190

Gly Leu Gly Ala Lys Arg Ile Gly Glu Arg Gly Glu Gly Asp Asp Asp
        195                 200                 205

Gly Ser Leu Glu Glu Asp Phe Leu Ala Trp Gln Glu Ser Met Trp Pro
    210                 215                 220

Thr Phe Cys Asp Ala Leu Gly Val Asp Glu Asn Asn Ala Gln Gln Gly
225                 230                 235                 240

Pro Arg Gln Ala Ser Tyr Ser Val Asp Glu Leu Lys Glu Glu Tyr Lys
                245                 250                 255

Asn Asp Asp Val Tyr Phe Gly Glu Leu Gly Thr Lys Ser Lys Asp Ser
            260                 265                 270

Ser Arg Val Val Tyr Asp Ala Lys Arg Pro Tyr Asn Ala Pro Ile Thr
        275                 280                 285

Thr Arg Glu Leu Phe Asn Ser Ser Glu Arg His Cys Leu His Val Asp
    290                 295                 300

Ile Asp Ile Ser Gly Thr Asn Leu Ser Tyr Gln Thr Gly Asp His Val
305                 310                 315                 320

Ala Met Trp Pro Thr Asn Asn Glu Asp Glu Val Leu Arg Leu Ala Asn

```
                    325                 330                 335
Ile Leu Gly Leu Gln Asp Lys Leu Asp Asn Val Ile Ser Val Lys Ala
            340                 345                 350
Ile Asp Pro Ala Ala Pro Lys Gln His Pro Phe Pro Val Pro Thr Thr
        355                 360                 365
Tyr Arg Ala Ile Phe Arg His Tyr Ile Asp Ile Cys Ala Pro Ala Ser
    370                 375                 380
Arg Gln Ser Leu Met Ser Phe Val Glu Phe Ala Pro Thr Asp Ser Ala
385                 390                 395                 400
Lys Asp Leu Leu Lys Leu Leu Ala Thr Asp Lys Asp Glu Tyr Arg Leu
            405                 410                 415
Lys Val Gly Glu Ala Val Arg Asn Leu Gly Glu Val Leu Glu Leu Val
        420                 425                 430
Ser Gly Asn Asp Lys Asp Thr Gln Pro Gly Ser Phe Ser Val Pro
    435                 440                 445
Phe Asp Leu Ile Val Glu Thr Ile Pro Arg Leu Gln Pro Arg Tyr Tyr
450                 455                 460
Ser Ile Ser Ser Ser Ser Lys Glu Asn Ser Ser Ile Ile Ser Ala Thr
465                 470                 475                 480
Cys Val Thr Leu Ala Tyr Gln Pro Asp Pro Thr Pro Asp Arg Thr Val
            485                 490                 495
Tyr Gly Val Asn Thr Asn Phe Leu Tyr Arg Ile His Thr Gln Ser Ser
        500                 505                 510
Asp Asn Asp Ile Gln Gly Leu Pro Lys Tyr Asp Leu Ala Gly Pro Arg
    515                 520                 525
Lys Ala Phe Leu Asn Glu Gln Gly Gln Ser His Lys Leu Pro Ile His
    530                 535                 540
Ile Arg Arg Ser Gln Phe Lys Leu Pro Arg Asn Thr Ser Cys Pro Val
545                 550                 555                 560
Ile Met Ile Gly Pro Gly Thr Gly Val Ala Pro Phe Arg Gly Phe Val
            565                 570                 575
Arg Glu Arg Ala Leu Gln Lys Lys Glu Gly Lys Ser Val Gly Pro Thr
        580                 585                 590
Val Leu Phe Phe Gly Asn Arg His Ser Glu His Asp Phe Leu Tyr Ser
    595                 600                 605
Asp Glu Trp Pro Glu Leu Phe Asn Thr Leu Gly Asp Asp Ser Lys Leu
    610                 615                 620
Ile Thr Ala Phe Ser Arg Glu Thr Glu His Lys Val Tyr Val Gln His
625                 630                 635                 640
Arg Leu Glu Glu Asn Gly Lys Asp Ile Trp Gln Leu Leu Glu Lys Gly
            645                 650                 655
Ala Tyr Ile Tyr Val Cys Gly Asp Ala Arg Asn Met Ala Arg Asp Val
        660                 665                 670
Asn Gln Thr Phe Val Asn Leu Ala Met Glu Tyr Gly Glu Lys Thr Glu
    675                 680                 685
Gln Lys Ala Leu Asp Tyr Val Lys Ser Leu Arg Asn Thr Gly Arg Tyr
    690                 695                 700
Gln Glu Asp Val Trp Ser
705                 710

<210> SEQ ID NO 17
<211> LENGTH: 2133
<212> TYPE: DNA
<213> ORGANISM: Cunninghamella elegans
```

<400> SEQUENCE: 17

```
atggctcaac aaactccagc tgttattgat actttggatt tgattttgtt gggttctatt        60
ggtttgggta ctattgcttg gtttactaga agacaattgt ctgaaagatt gtttggtact       120
ggtcaatcta atgctactcc aaaaccaact actccacaag ctccaaaaag agaaagaaat       180
tttgttaaag ttatggaaca acaaggtaga aaagttattt tttttatgg ttctcaaact        240
ggtactgcta agattttgc ttctagattg gctaaacaat gttctcaaaa atatggtgtt        300
tcttgtatga ctgctgatat tgaaatgtat gatttgtctt atttggatac tttgtctgaa       360
gattctttgg tttgttttgt tatggctact tatggtgaag gtgaaccaac tgataatgct       420
gttgattttt gggaacaatt tattactgat gaatctccag ttttttctga aggtggtgaa       480
actttggaaa atttgagata tttgatgttt ggtttgggta ataaaactta tgaacattat       540
aatgctgttg ctagaatttt ggataaaaaa ttgactggtt tgggtgctaa agaattggt        600
gaaagaggtg aaggtgatga tgatggttct ttggaagaag attttttggc ttggcaagaa       660
tctatgtggc aacttttttg tgatgctttg ggtgttgatg aaaataatgc tcaacaaggt       720
ccaagacaag catcttattc tgttgatgaa ttgaaagaag aatataaaaa tgatgatgtt       780
tattttggtg aattgggtac taaatctaaa gattcttcta gagttgttta tgatgctaaa       840
agaccatata atgctccaat tactactaga gaattgttta attcttctga aagacattgt       900
ttgcatgttg atattgatat ttctggtact aatttgtctt atcaaactgg tgatcatgtt       960
gctatgtggc caactaataa tgaagatgaa gttttgagat ggctaatat  tttgggtttg      1020
caagataaat tggataatgt tatttctgtt aaagctattg atccagctgc tccaaaacaa      1080
catccatttc cagttccaac tacttataga gctatttta gacattatat tgatatttgt        1140
gctccagctt ctagacaatc tttgatgtct tttgttgaat ttgctccaac tgattctgct      1200
aaagatttgt tgaaattgtt ggctactgat aaagatgaat atagattgaa agttggtgaa      1260
gctgttagaa atttgggtga agttttggaa ttggtttctg gtaatgataa agatactcaa      1320
ccaggttctt ttacttctgt tccatttgat ttgattgttg aaactattcc aagattgcaa      1380
ccaagatatt attctatttc ttcttcttct aaagaaaatt cttctattat ttctgctact      1440
tgtgttactt tggcttatca accagatcca actccagata aactgtttta tggtgttaat      1500
actaattttt tgtatagaat ccatactcaa tcttctgata tgatattca aggttttgcca      1560
aaatatgatt tggctggtcc aagaaaagca ttttttgaatg aacaaggtca atctcataaa      1620
ttgccaattc atattagaag atctcaattt aaattgccaa gaaatacttc ttgtccagtt      1680
attatgattg gtccaggtac tggtgttgct ccatttagag ttttgttag agaaagagct      1740
ttgcaaaaaa agaaggtaa atctgttggt ccaactgttt tgtttttgg taatagacat        1800
tctgaacatg attttttgta ttctgatgaa tggccagaat tgtttaatac tttgggtgat      1860
gattctaaat tgattactgc ttttttctaga gaaactgaac ataagtttta tgttcaacat      1920
agattggaag aaaatggtaa agatatttgg caattgttgg aaaaaggtgc ttatatttat      1980
gtttgtggtg atgctagaaa tatggctaga gatgttaatc aaactttgt taatttggct      2040
atggaatatg tgaaaaaac tgaacaaaaa gcattggatt atgttaaatc tttgagaaat      2100
actggtagat accaagaaga tgtttggtct tag                                   2133
```

<210> SEQ ID NO 18
<211> LENGTH: 713
<212> TYPE: PRT

<213> ORGANISM: Gibberella fujikuroi

<400> SEQUENCE: 18

```
Met Ala Glu Leu Asp Thr Leu Asp Ile Val Val Gly Val Ile Phe
1               5                   10                  15

Leu Gly Thr Val Ala Tyr Phe Thr Lys Gly Lys Leu Trp Gly Val Thr
                20                  25                  30

Lys Asp Pro Tyr Ala Asn Gly Phe Ala Ala Gly Gly Ala Ser Lys Pro
            35                  40                  45

Gly Arg Thr Arg Asn Ile Val Glu Ala Met Glu Glu Ser Gly Lys Asn
        50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
            100                 105                 110

Ser Asp Asn Ile Val Met Phe Val Leu Ala Thr Tyr Gly Glu Gly Glu
        115                 120                 125

Pro Thr Asp Asn Ala Val Asp Phe Tyr Glu Phe Ile Thr Gly Glu Asp
    130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
            180                 185                 190

Gly Glu Ala Gly Glu Gly Asp Asp Gly Ala Gly Thr Met Glu Glu Asp
        195                 200                 205

Phe Leu Ala Trp Lys Asp Pro Met Trp Glu Ala Leu Ala Lys Lys Met
210                 215                 220

Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Glu Val Tyr Leu Gly Glu
                245                 250                 255

Pro Asn Lys Leu His Leu Glu Gly Thr Ala Lys Gly Pro Phe Asn Ser
            260                 265                 270

His Asn Pro Tyr Ile Ala Pro Ile Ala Glu Ser Tyr Glu Leu Phe Ser
        275                 280                 285

Ala Lys Asp Arg Asn Cys Leu His Met Glu Ile Asp Ile Ser Gly Ser
    290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335

Lys Gln His Ser Val Val Thr Val Lys Ala Leu Glu Pro Thr Ala Lys
            340                 345                 350

Val Pro Phe Pro Asn Pro Thr Thr Tyr Asp Ala Ile Leu Arg Tyr His
        355                 360                 365

Leu Glu Ile Cys Ala Pro Val Ser Arg Gln Phe Val Ser Thr Leu Ala
    370                 375                 380

Ala Phe Ala Pro Asn Asp Asp Ile Lys Ala Glu Met Asn Arg Leu Gly
385                 390                 395                 400
```

Ser Asp Lys Asp Tyr Phe His Glu Lys Thr Gly Pro His Tyr Tyr Asn
            405                 410                 415

Ile Ala Arg Phe Leu Ala Ser Val Ser Lys Gly Glu Lys Trp Thr Lys
        420                 425                 430

Ile Pro Phe Ser Ala Phe Ile Glu Gly Leu Thr Lys Leu Gln Pro Arg
    435                 440                 445

Tyr Tyr Ser Ile Ser Ser Ser Leu Val Gln Pro Lys Lys Ile Ser
450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
            500                 505                 510

Gly Pro Arg Asn Lys Tyr Asp Gly Ile His Val Pro His Val Arg
        515                 520                 525

His Ser Asn Phe Lys Leu Pro Ser Asp Pro Gly Lys Pro Ile Ile Met
    530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
            580                 585                 590

Trp Gln Glu Tyr Lys Glu Ala Leu Gly Asp Lys Phe Glu Met Ile Thr
        595                 600                 605

Ala Phe Ser Arg Glu Gly Ser Lys Lys Val Tyr Val Gln His Arg Leu
    610                 615                 620

Lys Glu Arg Ser Lys Glu Val Ser Asp Leu Leu Ser Gln Lys Ala Tyr
625                 630                 635                 640

Phe Tyr Val Cys Gly Asp Ala Ala His Met Ala Arg Glu Val Asn Thr
                645                 650                 655

Val Leu Ala Gln Ile Ile Ala Glu Gly Arg Gly Val Ser Glu Ala Lys
            660                 665                 670

Gly Glu Glu Ile Val Lys Asn Met Arg Ser Ala Asn Gln Tyr Gln Val
        675                 680                 685

Cys Ser Asp Phe Val Thr Leu His Cys Lys Glu Thr Thr Tyr Ala Asn
    690                 695                 700

Ser Glu Leu Gln Glu Asp Val Trp Ser
705                 710

<210> SEQ ID NO 19
<211> LENGTH: 2142
<212> TYPE: DNA
<213> ORGANISM: Gibberella fujikuroi

<400> SEQUENCE: 19
atggcagaat tagatacact tgatatagta gtattaggtg ttatcttttt gggtactgtg     60
gcatacttta ctaagggtaa attgtggggt gttaccaagg atccatacgc taacggattc    120
gctgcaggtg gtgcttccaa gcctggcaga actagaaaca tcgtcgaagc tatggaggaa    180
tcaggtaaaa actgtgttgt tttctacggc agtcaaacag gtacagcgga ggattacgca    240
tcaagacttg caaaggaagg aaagtccaga ttcggtttga acactatgat cgccgatcta    300
gaagattatg acttcgataa cttagacact gttccatctg ataacatcgt tatgtttgta    360

```
ttggctactt acggtgaagg cgaaccaaca gataacgccg tggatttcta tgagttcatt    420
actggcgaag atgcctcttt caatgagggc aacgatcctc cactaggtaa cttgaattac    480
gttgcgttcg gtctgggcaa caatacctac gaacactaca actcaatggt caggaacgtt    540
aacaaggctc tagaaaagtt aggagctcat agaattggag aagcaggtga gggtgacgac    600
ggagctggaa ctatggaaga ggactttta gcttggaaag atccaatgtg gaagccttg     660 gctaaaaaga tgggcttgga ggaaagaaa gctgtatatg aacctatttt cgctatcaat    720
gagagagatg atttgacccc tgaagcgaat gaggtatact gggagaacc taataagcta    780 cacttggaag gtacagcgaa aggtccattc aactcccaca acccatatat cgcaccaatt    840
gcagaatcat acgaactttt ctcagctaag gatagaaatt gtctgcatat ggaaattgat    900
atttctggta gtaatctaaa gtatgaaaca ggcgaccata tcgcgatctg gcctaccaac    960
ccaggtgaag aggtcaacaa atttcttgac attctagatc tgtctggtaa gcaacattcc   1020
gtcgtaacag tgaaagcctt agaacctaca gccaaagttc cttttccaaa tccaactacc   1080
tacgatgcta tattgagata ccatctggaa atatgcgctc cagtttctag acagtttgtc   1140
tcaactttag cagcattcgc ccctaatgat gatatcaaag ctgagatgaa ccgtttggga   1200
tcagacaaag attacttcca cgaaaagaca ggaccacatt actacaatat cgctagattt   1260
ttggcctcag tctctaaagg tgaaaaatgg acaaagatac cattttctgc tttcatagaa   1320
ggccttacaa aactacaacc aagatactat tctatctctt cctctagttt agttcagcct   1380
aaaaagatta gtattactgc tgttgtcgaa tctcagcaaa ttccaggtag agatgaccca   1440
ttcagaggtg tagcgactaa ctacttgttc gctttgaagc agaaacaaaa cggtgatcca   1500
aatccagctc cttttggcca atcatacgag ttgacaggac caggaataa gtatgatggt    1560 atacatgttc cagtccatgt aagacattct aactttaagc taccatctga tccaggcaaa   1620
cctattatca tgatcggtcc aggtaccggt gttgcccctt ttagaggctt cgtccaagag   1680
agggcaaaac aagccagaga tggtgtagaa gttggtaaaa cactgctgtt ctttggatgt   1740
agaaagagta cagaagattt catgtatcaa aagagtggc aagagtacaa ggaagctctt    1800
ggcgacaaat tcgaaatgat tacagctttt tcaagagaag gatctaaaaa ggtttatgtt   1860
caacacagac tgaaggaaag atcaaaggaa gtttctgatc ttctatccca aaaagcatac   1920
ttctacgttt gcggagacgc cgcacatatg gcacgtgaag tgaacactgt gttagcacag   1980
atcatagcag aaggccgtgg tgtatcagaa gccaagggtg aggaaattgt caaaaacatg   2040
agatcagcaa atcaatacca agtgtgttct gatttcgtaa ctttacactg taaagagaca   2100
acatacgcga attcagaatt gcaagaggat gtctggagtt aa                      2142
```

<210> SEQ ID NO 20  
<211> LENGTH: 691  
<212> TYPE: PRT  
<213> ORGANISM: Saccharomyces cerevisiae

<400> SEQUENCE: 20

Met Pro Phe Gly Ile Asp Asn Thr Asp Phe Thr Val Leu Ala Gly Leu  
1               5                   10                  15

Val Leu Ala Val Leu Leu Tyr Val Lys Arg Asn Ser Ile Lys Glu Leu  
            20                  25                  30

Leu Met Ser Asp Asp Gly Asp Ile Thr Ala Val Ser Ser Gly Asn Arg  
        35                  40                  45

Asp Ile Ala Gln Val Val Thr Glu Asn Asn Lys Asn Tyr Leu Val Leu

```
             50                  55                  60
Tyr Ala Ser Gln Thr Gly Thr Ala Glu Asp Tyr Ala Lys Lys Phe Ser
 65                  70                  75                  80

Lys Glu Leu Val Ala Lys Phe Asn Leu Asn Val Met Cys Ala Asp Val
                 85                  90                  95

Glu Asn Tyr Asp Phe Glu Ser Leu Asn Asp Val Pro Val Ile Val Ser
                100                 105                 110

Ile Phe Ile Ser Thr Tyr Gly Glu Gly Asp Phe Pro Asp Gly Ala Val
                115                 120                 125

Asn Phe Glu Asp Phe Ile Cys Asn Ala Glu Ala Gly Ala Leu Ser Asn
130                 135                 140

Leu Arg Tyr Asn Met Phe Gly Leu Gly Asn Ser Thr Tyr Glu Phe Phe
145                 150                 155                 160

Asn Gly Ala Ala Lys Lys Ala Glu Lys His Leu Ser Ala Ala Gly Ala
                165                 170                 175

Ile Arg Leu Gly Lys Leu Gly Glu Ala Asp Asp Gly Ala Gly Thr Thr
                180                 185                 190

Asp Glu Asp Tyr Met Ala Trp Lys Asp Ser Ile Leu Glu Val Leu Lys
                195                 200                 205

Asp Glu Leu His Leu Asp Glu Gln Glu Ala Lys Phe Thr Ser Gln Phe
210                 215                 220

Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
                260                 265                 270

Ile Val Lys Ser Arg Glu Leu Phe Ser Ser Asn Asp Arg Asn Cys Ile
                275                 280                 285

His Ser Glu Phe Asp Leu Ser Gly Ser Asn Ile Lys Tyr Ser Thr Gly
                290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
                340                 345                 350

Gly Ala Ala Ile Lys His Tyr Leu Glu Ile Thr Gly Pro Val Ser Arg
                355                 360                 365

Gln Leu Phe Ser Ser Leu Ile Gln Phe Ala Pro Asn Ala Asp Val Lys
370                 375                 380

Glu Lys Leu Thr Leu Leu Ser Lys Asp Lys Asp Gln Phe Ala Val Glu
385                 390                 395                 400

Ile Thr Ser Lys Tyr Phe Asn Ile Ala Asp Ala Leu Lys Tyr Leu Ser
                405                 410                 415

Asp Gly Ala Lys Trp Asp Thr Val Pro Met Gln Phe Leu Val Glu Ser
                420                 425                 430

Val Pro Gln Met Thr Pro Arg Tyr Tyr Ser Ile Ser Ser Ser Ser Leu
                435                 440                 445

Ser Glu Lys Gln Thr Val His Val Thr Ser Ile Val Glu Asn Phe Pro
450                 455                 460

Asn Pro Glu Leu Pro Asp Ala Pro Pro Val Val Gly Val Thr Thr Asn
465                 470                 475                 480
```

```
Leu Leu Arg Asn Ile Gln Leu Ala Gln Asn Asn Val Asn Ile Ala Glu
            485                 490                 495

Thr Asn Leu Pro Val His Tyr Asp Leu Asn Gly Pro Arg Lys Leu Phe
        500                 505                 510

Ala Asn Tyr Lys Leu Pro Val His Val Arg Arg Ser Asn Phe Arg Leu
            515                 520                 525

Pro Ser Asn Pro Ser Thr Pro Val Ile Met Ile Gly Pro Gly Thr Gly
        530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
            580                 585                 590

Pro Glu Tyr Ala Lys Lys Leu Asp Gly Ser Phe Glu Met Val Val Ala
        595                 600                 605

His Ser Arg Leu Pro Asn Thr Lys Lys Val Tyr Val Gln Asp Lys Leu
    610                 615                 620

Lys Asp Tyr Glu Asp Gln Val Phe Glu Met Ile Asn Asn Gly Ala Phe
625                 630                 635                 640

Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
        675                 680                 685

Asp Val Trp
    690

<210> SEQ ID NO 21
<211> LENGTH: 2076
<212> TYPE: DNA
<213> ORGANISM: Saccharomyces cerevisiae

<400> SEQUENCE: 21
atgccgtttg aatagacaa caccgacttc actgtcctgg cggggctagt gcttgccgtg      60
ctactgtacg taaagagaaa ctccatcaag aactgctga tgtccgatga cggagatatc     120
acagctgtca gctcgggcaa cagagacatt gctcaggtgg tgaccgaaaa caacaagaac     180
tacttggtgt tgtatgcgtc gcagactggg actgccgagg attacgccaa aaagttttcc     240
aaggagctgg tggccaagtt caacctaaac gtgatgtgcg cagatgttga gaactacgac     300
tttgagtcgc taaacgatgt gcccgtcata gtctcgattt ttatctctac atatggtgaa     360
ggagacttcc ccgacggggc ggtcaacttt gaagacttta tttgtaatgc ggaagcgggt     420
gcactatcga acctgaggta taatatgttt ggtctgggaa attctactta tgaattcttt     480
aatggtgccg ccaagaaggc cgagaagcat ctctccgctg cgggcgctat cagactaggc     540
aagctcggtg aagctgatga tggtgcagga actacagacg aagattacat ggcctggaag     600
gactccatcc tggaggtttt gaagacgaa ctgcatttgg acgaacagga agccaagttc     660
acctctcaat tccagtacac tgtgttgaac gaaatcactg actccatgtc gcttggtgaa     720
ccctctgctc actatttgcc ctcgcatcag ttgaaccgca acgcagacgg catccaattg     780
ggtcccttcg atttgtctca accgtatatt gcacccatcg tgaaatctcg cgaactgttc     840
```

-continued

```
tcttccaatg accgtaattg catccactct gaatttgact tgtccggctc taacatcaag      900
tactccactg tgaccatct tgctgtttgg ccttccaacc cattggaaaa ggtcgaacag       960
ttcttatcca tattcaacct ggaccctgaa accattttg acttgaagcc cctggatccc      1020
accgtcaaag tgcccttccc aacgccaact actattggcg ctgctattaa acactatttg    1080
gaaattacag acctgtctc cagacaattg ttttcatctt tgattcagtt cgccccaac      1140 gctgacgtca aggaaaaatt gactctgctt tcgaaagaca aggaccaatt cgccgtcgag    1200
ataacctcca atatttcaa catcgcagat gctctgaaat atttgtctga tggcgccaaa    1260
tgggacaccg tacccatgca attcttggtc gaatcagttc cccaaatgac tcctcgttac    1320
tactctatct cttcctcttc tctgtctgaa aagcaaaccg tccatgtcac ctccattgtg    1380
gaaaactttc ctaacccaga attgcctgat gctcctccag ttgttggtgt tacgactaac    1440
ttgttaagaa acattcaatt ggctcaaaac aatgttaaca ttgccgaaac taacctacct    1500
gttcactacg atttaaatgg cccacgtaaa cttttcgcca attacaaatt gcccgtccac    1560
gttcgtcgtt ctaacttcag attgccttcc aaccctcca ccccagttat catgatcggt    1620
ccaggtaccg tgttgcccc attccgtggg tttatcagag agcgtgtcgc gttcctcgaa    1680
tcacaaaaga agggcggtaa caacgtttcg ctaggtaagc atatactgtt ttatggatcc    1740
cgtaacactg atgatttctt gtaccaggac gaatggccag aatacgccaa aaaattggat    1800
ggttcgttcg aaatggtcgt ggcccattcc aggttgccaa acaccaaaaa agtttatgtt    1860
caagataaat taaaggatta cgaagaccaa gtatttgaaa tgattaacaa cggtgcattt    1920
atctacgtct gtggtgatgc aaagggtatg gccaagggtg tgtcaaccgc attggttggc    1980
atcttatccc gtggtaaatc cattaccact gatgaagcaa cagagctaat caagatgctc    2040
aagacttcag gtagatacca agaagatgtc tggtag                              2076
```

<210> SEQ ID NO 22
<211> LENGTH: 503
<212> TYPE: PRT
<213> ORGANISM: Homo sapiens
<400> SEQUENCE: 22

```
Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Leu Ser Tyr His Lys Gly Phe Cys Met Phe Asp Met Glu Cys
    50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160
```

Arg Arg Glu Ala Glu Thr Gly Lys Pro Val Thr Leu Lys Asp Val Phe
            165                 170                 175
Gly Ala Tyr Ser Met Asp Val Ile Thr Ser Thr Ser Phe Gly Val Asn
            180                 185                 190
Ile Asp Ser Leu Asn Asn Pro Gln Asp Pro Phe Val Glu Asn Thr Lys
            195                 200                 205
Lys Leu Leu Arg Phe Asp Phe Leu Asp Pro Phe Leu Ser Ile Thr
        210                 215                 220
Val Phe Pro Phe Leu Ile Pro Ile Leu Glu Val Leu Asn Ile Cys Val
225                 230                 235                 240
Phe Pro Arg Glu Val Thr Asn Phe Leu Arg Lys Ser Val Lys Arg Met
            245                 250                 255
Lys Glu Ser Arg Leu Glu Asp Thr Gln Lys His Arg Val Asp Phe Leu
            260                 265                 270
Gln Leu Met Ile Asp Ser Gln Asn Ser Lys Glu Thr Glu Ser His Lys
        275                 280                 285
Ala Leu Ser Asp Leu Glu Leu Val Ala Gln Ser Ile Ile Phe Ile Phe
        290                 295                 300
Ala Gly Tyr Glu Thr Thr Ser Ser Val Leu Ser Phe Ile Met Tyr Glu
305                 310                 315                 320
Leu Ala Thr His Pro Asp Val Gln Gln Lys Leu Gln Glu Glu Ile Asp
            325                 330                 335
Ala Val Leu Pro Asn Lys Ala Pro Pro Thr Tyr Asp Thr Val Leu Gln
            340                 345                 350
Met Glu Tyr Leu Asp Met Val Val Asn Glu Thr Leu Arg Leu Phe Pro
            355                 360                 365
Ile Ala Met Arg Leu Glu Arg Val Cys Lys Lys Asp Val Glu Ile Asn
        370                 375                 380
Gly Met Phe Ile Pro Lys Gly Val Val Met Ile Pro Ser Tyr Ala
385                 390                 395                 400
Leu His Arg Asp Pro Lys Tyr Trp Thr Glu Pro Glu Lys Phe Leu Pro
            405                 410                 415
Glu Arg Phe Ser Lys Lys Asn Lys Asp Asn Ile Asp Pro Tyr Ile Tyr
            420                 425                 430
Thr Pro Phe Gly Ser Gly Pro Arg Asn Cys Ile Gly Met Arg Phe Ala
        435                 440                 445
Leu Met Asn Met Lys Leu Ala Leu Ile Arg Val Leu Gln Asn Phe Ser
        450                 455                 460
Phe Lys Pro Cys Lys Glu Thr Gln Ile Pro Leu Lys Leu Ser Leu Gly
465                 470                 475                 480
Gly Leu Leu Gln Pro Glu Lys Pro Val Val Leu Lys Val Glu Ser Arg
            485                 490                 495
Asp Gly Thr Val Ser Gly Ala
            500

<210> SEQ ID NO 23
<211> LENGTH: 1533
<212> TYPE: DNA
<213> ORGANISM: Homo sapiens

<400> SEQUENCE: 23
aagcttaaaa tggcactgat tcccgattta gcaatggaga cttggttgtt gcttgccgta      60
agtctcgtct tactgtattt gtacggaacg cactcgcacg gattatttaa gaaattgggc     120

```
attcccgggc ccactccact accattccta ggtaatatac ttagttatca caagggtttc    180
tgcatgttcg acatggaatg tcacaagaag tatggtaagg tatggggatt ctacgacggc    240
caacaacctg tgttggcgat caccgaccca gacatgatca aaactgtcct cgtaaaagaa    300
tgttactctg ttttcactaa tagaagacca tttggacctg taggattcat gaagagtgct    360
atatccattg cagaggacga agaatggaag aggcttagaa gccttctgtc acctacattc    420
acaagcggca agttgaagga gatggtccct atcatcgccc agtatggcga tgtcttagtg    480
agaaatttac gtagggaagc tgaaactggt aagcctgtga cgctgaagga tgtctttgga    540
gcttatagca tggacgtgat cacttcgact cctttggcg taaatatcga ttcgcttaac    600
aacccacagg atccctttgt tgagaacacg aagaaactgt tgagatttga ctttctcgat    660
ccgttcttcc tttccattac cgtcttccct ttcctcatac ccattctgga agtcctgaat    720
atatgcgtat tcccaagaga ggtgacgaac ttcttaagga aatcggtaaa gaggatgaag    780
gaatcccgtc ttgaggacac ccagaagcac agggtcgact ttctacagtt aatgatagat    840
tcacagaatt cgaaagagac ggagagccat aaggctttaa gtgatcttga gcttgtagca    900
cagagtatca tcttcatttt cgccggctac gagacgacga gcagtgtgtt gtcgttcatc    960
atgtacgagt tggcgacaca tcccgacgtg cagcagaagt acaggaaga aatcgatgct   1020
gttttaccaa ataaagcccc acccacttat gatacagttt tgcagatgga gtacttagac   1080
atggtggtta acgaaacact aagactgttt ccgattgcta tgcgattgga acgagtgtgt   1140
aagaaggacg tagaaattaa cggcatgttt ataccaaagg gcgtagttgt catgatacct   1200
tcttatgctt tgcatcgaga ccctaagtac tggaccgaac tgaaaagtt tctcccagag   1260
cgctttagca agaagaataa ggataacata gaccctaca tttatacgcc attcggatcc   1320
ggtccacgta actgtatagg catgcgtttc gctctgatga acatgaagct ggcgttaatc   1380
agggtattac agaacttttc attcaaacca tgcaaagaga cacagatacc gttgaagctc   1440
tctttaggtg gacttctgca gcccgagaag ccagtggttc tcaaagttga gagcagggac   1500
ggtacagttt caggcgctta gaagactccg cgg                                1533
```

<210> SEQ ID NO 24
<211> LENGTH: 503
<212> TYPE: PRT
<213> ORGANISM: Pongo abelii

<400> SEQUENCE: 24

```
Met Asp Leu Ile Pro Asp Leu Ala Met Glu Thr Trp Ile Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Leu Leu Gly
        35                  40                  45

Asn Val Phe Ser Tyr Arg Lys Gly Phe Trp Arg Phe Asp Met Glu Cys
    50                  55                  60

His Lys Lys Tyr Gly Lys Val Trp Gly Phe Tyr Asp Gly Arg Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125
```

```
Ile Arg Ser Leu Leu Ser Pro Thr Phe Thr Ser Gly Lys Leu Lys Glu
    130                 135                 140

Met Val Pro Ile Ile Ala Arg Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Leu Ser Ile Ile
    210                 215                 220

Val Phe Pro Phe Leu Thr Pro Ile Leu Glu Ile Leu Asn Ile Ser Val
225                 230                 235                 240

Phe Pro Arg Glu Val Thr Ser Phe Leu Arg Lys Ser Val Lys Arg Met
                245                 250                 255

Lys Glu Ser Arg Leu Lys Asp Thr Gln Lys His Arg Val Asp Phe Leu
            260                 265                 270

Gln Leu Met Ile Asp Ser Gln Asn Ser Lys Glu Thr Glu Ser His Lys
        275                 280                 285

Ala Leu Ser Asp Leu Glu Leu Val Ala Gln Ser Ile Ile Phe Ile Phe
    290                 295                 300

Ala Gly Tyr Glu Thr Thr Ser Ser Val Leu Ser Phe Ile Met Tyr Glu
305                 310                 315                 320

Leu Ala Thr His Pro Asp Val Gln Arg Lys Leu Gln Glu Glu Ile Asp
                325                 330                 335

Ala Val Leu Pro Asn Lys Ala Pro Pro Thr Tyr Asp Thr Val Leu Gln
            340                 345                 350

Met Glu Tyr Leu Asp Met Val Val Asn Glu Thr Leu Arg Leu Phe Pro
        355                 360                 365

Ile Ala Met Arg Leu Glu Arg Val Cys Lys Lys Asp Val Glu Ile Asn
    370                 375                 380

Gly Met Phe Ile Pro Lys Gly Val Val Met Ile Pro Ser Tyr Ala
385                 390                 395                 400

Leu His His Asp Pro Lys Tyr Trp Thr Glu Pro Gly Lys Phe Leu Pro
                405                 410                 415

Glu Arg Phe Ser Lys Lys Asn Lys Asp Asn Ile Glu Pro Tyr Val Tyr
            420                 425                 430

Thr Pro Phe Gly Thr Gly Pro Arg Asn Cys Ile Gly Met Arg Phe Ala
        435                 440                 445

Leu Met Asn Met Lys Leu Ala Val Ile Arg Val Leu Gln Asn Phe Ser
    450                 455                 460

Phe Lys Pro Cys Lys Glu Thr Gln Ile Pro Leu Lys Leu Arg Leu Gly
465                 470                 475                 480

Gly Leu Leu Gln Thr Glu Lys Pro Ile Val Leu Lys Val Glu Ser Arg
                485                 490                 495

Asp Gly Thr Leu Ser Gly Ala
            500

<210> SEQ ID NO 25
<211> LENGTH: 1533
<212> TYPE: DNA
<213> ORGANISM: Pongo abelii
```

<400> SEQUENCE: 25

```
aagcttaaaa tggaccttat ccctgacctc gctatggaga cttggatctt acttgcggtt      60
tctctagtgc tgttatactt gtatggaaca cactcccatg gattgtttaa gaaattaggt     120
atcccaggac caacaccgtt gcctttgcta ggaaacgtct tcagttatcg aaagggcttc     180
tggagatttg atatggaatg tcacaagaag tacggcaagg tgtggggctt ctacgatggc     240
aggcagcctg tcctcgcaat aacagatccg gatatgataa agacggtttt agtaaaagaa     300
tgctactctg tatttactaa caggcgccct ttcgggccag tggggttcat gaagagcgcc     360
atctctatcg ccgaagatga ggagtggaag cgtatccgat ccttattatc tcctacgttt     420
acaagcggga agttaaaaga gatggtgcca ataatagcca ggtatggaga cgttctggtt     480
aggaatttga agagagaggc tgagacgggg aagcctgtta ccttaaagga cgtcttcggc     540
gcctacagca tggacgtaat aaccagtact tcatttggcg tcaacatcga cagtctaaac     600
aaccctcagg atccatttgt cgagaatacc aagaaactct taaggttcga ctttctagac     660
ccattcttcc tgagcattat tgtgttccct ttccttaccc ctattctcga gatactaaat     720
atctctgttt tcccaagaga ggtaacgtcg ttcttacgca aatctgtaaa gagaatgaaa     780
gagagtagat tgaaggatac acaaaagcac agagtagact tccttcagct aatgattgat     840
tctcagaatt caaaggagac cgagagccac aaggcccttt ctgacctgga attagtagca     900
cagtcaatta tcttcatttt cgccggatac gaaacaacta gttctgtgtt atcatttatt     960
atgtacgagt tagcaactca cccggacgta cagaggaaat tacaggaaga gatagatgca    1020
gttcttccaa acaaggcccc accaacttat gacaccgtcc tacaaatgga gtatttggat    1080
atggttgtga acgagacact gagattgttt cctatagcaa tgagacttga gcgtgtgtgt    1140
aagaaagatg tcgagataaa tggaatgttc atccctaagg gcgtagtcgt gatgattccg    1200
tcctacgcac tccaccacga ccctaagtat tggacggagc cgggtaagtt cttacctgag    1260
aggttcagta gaagaacaa agacaacata gaaccttatg tatacacgcc ctttggaacc    1320
gggccacgta actgcattgg gatgcgtttc gcactcatga acatgaaact tgcggtcata    1380
cgagtgcttc aaaacttttc ctttaagcca tgcaaggaga cacaaatacc gctaaagttg    1440
agattgggtg gattgttgca gacagagaag ccgattgtcc ttaaggtcga atcgcgcgac    1500
ggcacattat ctggcgccta gaagactccg cgg                                  1533
```

<210> SEQ ID NO 26
<211> LENGTH: 503
<212> TYPE: PRT
<213> ORGANISM: Papio anubis

<400> SEQUENCE: 26

```
Met Asp Leu Ile Pro Asp Leu Ala Val Glu Thr Trp Leu Leu Leu Ala
1               5                   10                  15

Val Thr Leu Val Leu Leu Tyr Leu Tyr Gly Thr His Ser His Gly Leu
            20                  25                  30

Phe Lys Lys Leu Gly Ile Pro Gly Pro Thr Pro Leu Pro Leu Leu Gly
        35                  40                  45

Asn Val Leu Ser Tyr Arg Lys Gly Phe Trp Thr Phe Asp Met Glu Cys
    50                  55                  60

Tyr Lys Lys Tyr Gly Lys Val Trp Gly Phe Tyr Asp Gly Arg Gln Pro
65                  70                  75                  80

Val Leu Ala Ile Thr Asp Pro Asn Met Ile Lys Thr Val Leu Val Lys
                85                  90                  95
```

-continued

Glu Cys Tyr Ser Val Phe Thr Asn Arg Arg Pro Phe Gly Pro Val Gly
              100                 105                 110

Phe Met Lys Ser Ala Ile Ser Ile Ala Glu Asp Glu Trp Lys Arg
        115                 120                 125

Ile Arg Ser Leu Leu Ser Pro Thr Phe Thr Ser Gly Lys Leu Lys Glu
    130                 135                 140

Met Val Pro Ile Ile Ala Lys Tyr Gly Asp Val Leu Val Arg Asn Leu
145                 150                 155                 160

Arg Arg Glu Thr Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
                180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Phe Leu Ser Ile Thr
    210                 215                 220

Ile Phe Pro Phe Leu Ile Pro Ile Leu Glu Val Leu Asn Ile Ser Ile
225                 230                 235                 240

Phe Pro Arg Glu Val Thr Ser Phe Leu Arg Lys Ser Val Lys Arg Ile
                245                 250                 255

Lys Glu Ser Arg Leu Lys Asp Thr Gln Lys His Arg Val Asp Phe Leu
                260                 265                 270

Gln Leu Met Ile Asp Ser Gln Asn Ser Lys Glu Thr Glu Ser His Lys
        275                 280                 285

Ala Leu Ser Asp Leu Glu Leu Val Ala Gln Ser Ile Ile Phe Ile Phe
    290                 295                 300

Ala Gly Tyr Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
                340                 345                 350

Met Glu Tyr Leu Asp Met Val Val Asn Glu Thr Leu Arg Leu Phe Pro
        355                 360                 365

Ile Ala Met Arg Leu Glu Arg Val Cys Lys Lys Asp Val Glu Ile Asn
        370                 375                 380

Gly Ile Phe Ile Pro Lys Gly Val Val Met Ile Pro Thr Tyr Ala
385                 390                 395                 400

Leu His His Asp Ser Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
                420                 425                 430

Thr Pro Phe Gly Ser Gly Pro Arg Asn Cys Ile Gly Met Arg Phe Ala
        435                 440                 445

Leu Met Asn Met Lys Leu Ala Leu Ile Arg Val Leu Gln Asn Phe Ser
        450                 455                 460

Phe Lys Pro Cys Lys Glu Thr Gln Ile Pro Leu Lys Leu Arg Leu Gly
465                 470                 475                 480

Gly Leu Leu Gln Thr Glu Lys Pro Ile Val Leu Lys Ile Glu Ser Arg
                485                 490                 495

Asp Gly Thr Val Ser Gly Ala
                500

<210> SEQ ID NO 27
<211> LENGTH: 1533
<212> TYPE: DNA
<213> ORGANISM: Papio anubis

<400> SEQUENCE: 27

```
aagcttaaaa tggatcttat tcctgacctc gctgttgaga catggctgct tttggcagtt      60
acactagtac tactttacct gtacggaacc cactcccacg gcctatttaa gaagttggga     120
atcccaggac ctactccgct acctctacta gggaatgtat tatcataccg taaaggtttc     180
tggactttcg acatggagtg ttataagaag tacggaaagg tctggggctt ttatgatgga     240
cgccaaccgg tcctagccat tacagatcca aacatgataa agaccgtttt ggtaaaagag     300
tgctactctg ttttcacgaa tagaagaccc tttggaccag ttggcttcat gaagagtgcg     360
atctctatcg ccgaggatga ggagtggaag agaatcagat ccctgttatc gccaaccttc     420
acttcaggca agctcaaaga gatggtgcca ataattgcga aatacggtga cgtacttgtc     480
cgtaatctgc gtagagagac agagaccgga aagccagtta cattaaagga cgtctttggt     540
gcatactcta tggacgtgat cacaagtact tctttcggtg tgaatattga ttctttgaat     600
aacccacagg atccttttgt ggagaacact aagaaattgc tgaggtttga cttcttggat     660
cccttcttcc tgagcataac catctttcct tttctaattc caatcttgga gttttaaat     720
atcagtatct ttcccaggga agtcacttct ttcctacgaa agtcggtgaa gcgtataaaa     780
gagagcagat tgaaggatac gcaaaagcat cgcgtcgact ttctccaact catgatagac     840
agccagaatt cgaaagaaac agaatcacac aaggcgctct ctgacttgga gttggtggcc     900
caatcgataa tattcatatt cgcaggatat gagacaacat cgtccgtgtt gagctttatt     960
atgtacgagt tggccaccca ccccgacgta cagcagaagt tgcaggaaga gatcgacgcc    1020
gttttgccga caaagctccg cccacttat gataccgtgc tacagatgga ataactagac    1080
atggtagtta atgagacgtt gaggttattc ccaatagcaa tgaggttgga aagagtttgt    1140
aagaaggatg tagagataaa tggtatcttt attccaaaag gggtcgtagt gatgatcccc    1200
acatacgcct acaccacga ttctaaatat tggacagagc cggagaaatt cttgccggaa    1260
cgcttctcaa agaagaacaa agataacatc gacccgtaca tctacactcc atttggatcg    1320
ggcccgagga actgtattgg tatgaggttc gcgcttatga acatgaagct agccttgatt    1380
agggtattac agaacttcag ctttaagcca tgtaaagaga cccagatacc gctgaaactg    1440
aggttgggtg gctgttgca gaccgagaag cccatagttt tgaagattga atcgagggac    1500
gggaccgtat caggtgcgta gaagactccg cgg                                 1533
```

<210> SEQ ID NO 28
<211> LENGTH: 504
<212> TYPE: PRT
<213> ORGANISM: Gorilla gorilla gorilla

<400> SEQUENCE: 28

```
Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Trp Ser Tyr Arg Lys Gly Phe Cys Met Phe Asp Met Glu Cys
    50                  55                  60
```

```
His Lys Lys Tyr Gly Lys Val Trp Gly Phe Tyr Asp Gly Arg Gln Pro
 65                  70                  75                  80

Val Leu Ala Ile Thr Asp Pro Asp Met Ile Lys Thr Val Leu Val Lys
                 85                  90                  95

Glu Cys Tyr Ser Val Phe Thr Asn Arg Arg Pro Phe Gly Pro Val Gly
                100                 105                 110

Phe Met Lys Ser Ala Ile Ser Ile Ala Glu Asp Glu Glu Trp Lys Arg
            115                 120                 125

Leu Arg Ser Leu Leu Ser Pro Thr Phe Thr Ser Gly Lys Leu Lys Glu
        130                 135                 140

Met Val Pro Leu Ile Ala Gln Tyr Gly Asp Val Leu Val Arg Asn Leu
145                 150                 155                 160

Ser Arg Glu Ala Glu Thr Gly Lys Pro Val Thr Met Lys Asp Leu Phe
                165                 170                 175

Asn Thr Phe Ser Thr Thr Met Glu Ile Ser Thr Thr Asp Ala Gly Gln
                180                 185                 190

Asn Ile Asp Ser Leu Asn Asn Pro Gln Asp Pro Phe Val Glu Asn Thr
            195                 200                 205

Lys Lys Leu Leu Arg Phe Asp Phe Leu Asp Pro Phe Leu Ser Ile
        210                 215                 220

Ile Val Phe Pro Phe Leu Thr Pro Ile Leu Glu Val Leu Asn Ile Ser
225                 230                 235                 240

Val Phe Pro Arg Ala Val Thr Ser Phe Leu Arg Lys Ser Val Lys Arg
                245                 250                 255

Met Lys Glu Ser Arg Leu Glu Asp Thr Gln Lys His Arg Val Asp Phe
                260                 265                 270

Leu Gln Leu Met Ile Asp Ser Gln Asn Ser Lys Glu Thr Glu Ser His
            275                 280                 285

Lys Ala Leu Ser Asp Leu Glu Leu Val Ala Gln Ser Ile Ile Phe Ile
        290                 295                 300

Phe Ala Gly Tyr Glu Thr Thr Ser Ser Val Leu Ser Phe Ile Thr Tyr
305                 310                 315                 320

Glu Leu Ala Thr His Pro Asp Val Gln Gln Lys Leu Gln Glu Glu Ile
                325                 330                 335

Asp Ala Val Leu Pro Asn Lys Ala Pro Pro Thr Tyr Asp Thr Val Leu
                340                 345                 350

Gln Met Glu Tyr Leu Asp Met Val Val Asn Glu Thr Leu Arg Leu Phe
            355                 360                 365

Pro Ile Ala Met Arg Leu Glu Arg Val Cys Lys Lys Asp Val Glu Ile
        370                 375                 380

Asn Gly Met Phe Ile Pro Lys Gly Val Val Met Ile Pro Ser Tyr
385                 390                 395                 400

Ala Leu His His Asp Pro Lys Tyr Trp Thr Glu Pro Glu Lys Phe Leu
                405                 410                 415

Pro Glu Arg Phe Ser Lys Lys Asn Lys Asp Asn Ile Asp Pro Tyr Ile
                420                 425                 430

Tyr Thr Pro Phe Gly Ser Gly Pro Arg Asn Cys Ile Gly Met Arg Phe
            435                 440                 445

Ala Leu Met Asn Met Lys Leu Ala Leu Ile Arg Val Leu Gln Asn Phe
        450                 455                 460

Ser Phe Lys Pro Cys Lys Glu Thr Gln Ile Pro Leu Lys Leu Arg Leu
465                 470                 475                 480
```

Gly Gly Leu Leu Gln Pro Glu Lys Pro Ile Val Leu Lys Val Glu Ser
                485                 490                 495

Arg Asp Gly Thr Val Ser Gly Ala
            500

<210> SEQ ID NO 29
<211> LENGTH: 1536
<212> TYPE: DNA
<213> ORGANISM: Gorilla gorilla gorilla

<400> SEQUENCE: 29

| | | | | | |
|---|---|---|---|---|---|
| aagcttaaaa | tggctttaat | tcccgacttg | gccatggaga | cctggttgtt | gttagctgtt | 60 |
| agcctagtct | tgttgtactt | gtacgggacc | cattctcacg | gcttatttaa | gaaactcggt | 120 |
| ataccagggc | ctactccatt | accattctta | gggaacattt | ggtcatatag | aaagggattt | 180 |
| tgcatgttcg | acatggagtg | tcacaagaaa | tacgggaagg | tatggggatt | ctatgacggt | 240 |
| cgtcaacccg | tgttggccat | aaccgaccct | gatatgatta | agactgtctt | agtcaaggag | 300 |
| tgttattctg | ttttcacgaa | caggcgtcct | ttcggtccag | tcggcttcat | gaaatcagca | 360 |
| atatccattg | cagaggacga | ggagtggaaa | cgattacgtt | ctttgttgtc | tcctactttt | 420 |
| acatcaggga | aacttaaaga | gatggtcccg | ttaatcgctc | agtacggcga | cgtgttagtt | 480 |
| aggaacctgt | ccagagaggc | agaaactgga | aaacctgtca | ccatgaaaga | cttattcaac | 540 |
| accttctcga | ccacgatgga | gattagtacc | actgatgcag | gccagaacat | cgattccctc | 600 |
| aacaatccgc | aagacccttt | cgtagagaac | accaagaagt | tacttagatt | tgatttccta | 660 |
| gacccgttct | ttctttcgat | aatcgtgttc | ccttttctaa | caccaatcct | agaggtattg | 720 |
| aatatatcgg | tcttcccccg | cgctgtaaca | tcttttcctta | gaaaatcagt | aaagcgtatg | 780 |
| aaagaatcta | gattggaaga | tacacaaaag | caccgtgtcg | acttcttaca | attaatgatc | 840 |
| gacagtcaaa | actcgaaaga | gacggaatca | cacaaagcac | tttcggacct | ggagttagtt | 900 |
| gcgcaaagca | taattttcat | ctttgcgggg | tacgagacta | catcctcagt | tttgtcattc | 960 |
| ataacctacg | agctggccac | tcatccggat | gtgcagcaaa | agctgcagga | agaaattgac | 1020 |
| gcagtcttac | ccaacaaggc | tcccccaacc | tacgacactg | ttcttcagat | ggagtacctc | 1080 |
| gacatggtag | tgaatgagac | attgagattg | tttcccatcg | ccatgaggtt | agaaagggta | 1140 |
| tgcaagaagg | acgtcgagat | aaacggcatg | ttcatcccta | agggcgtggt | tgtaatgatc | 1200 |
| ccctcttacg | cgctccacca | tgatccaaaa | tactggacag | agcccgaaaa | gttccttccg | 1260 |
| gagagattca | gcaagaagaa | caaggacaac | atagacccctt | acatatatac | cccattcggt | 1320 |
| agtggaccac | gtaactgcat | cggcatgagg | tttgctttaa | tgaacatgaa | acttgcattg | 1380 |
| atcagagttc | tgcaaaaactt | ttccttcaag | ccctgtaaag | agacgcagat | tccgttaaag | 1440 |
| ctaaggttag | gtggcctact | gcaaccagag | aagccgattg | tactcaaagt | cgagagtagg | 1500 |
| gatggtactg | tctctggcgc | ttagaagact | ccgcgg | | | 1536 |

<210> SEQ ID NO 30
<211> LENGTH: 503
<212> TYPE: PRT
<213> ORGANISM: Canis lupus familiaris

<400> SEQUENCE: 30

Met Asp Leu Ile Pro Ser Phe Ser Met Glu Thr Trp Leu Leu Leu Ala
1               5                   10                  15

Thr Ser Leu Val Leu Leu Tyr Leu Tyr Gly Thr Tyr Thr His Gly Val
            20                  25                  30

-continued

Phe Lys Lys Leu Gly Ile Pro Gly Pro Thr Pro Leu Pro Phe Val Gly
            35                  40                  45

Thr Ala Leu Gly Tyr Arg Lys Gly Phe Ser Val Phe Asp Glu Asn Cys
    50                  55                  60

Phe Arg Lys Tyr Gly Arg Met Trp Gly Phe Tyr Asp Gly Arg Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Ser Phe Gly Pro Val Gly
                100                 105                 110

Phe Met Lys Ser Ala Ile Ser Leu Ser Glu Asp Glu Trp Lys Arg
        115                 120                 125

Ile Arg Thr Leu Leu Ser Pro Thr Phe Thr Ser Gly Lys Leu Lys Glu
        130                 135                 140

Met Phe Pro Ile Ile Gly Gln Tyr Gly Asp Val Leu Val Arg Asn Leu
145                 150                 155                 160

Arg Lys Glu Ala Glu Lys Gly Lys Ser Ile Asn Leu Lys Asp Ile Phe
                165                 170                 175

Gly Ala Tyr Ser Met Asp Val Ile Thr Ser Thr Ser Phe Gly Val Asn
                180                 185                 190

Ile Asp Ser Leu Asn Asn Pro Gln Asp Pro Phe Val Glu Asn Ile Lys
        195                 200                 205

Lys Leu Leu Lys Phe Asp Phe Leu Asp Pro Phe Phe Phe Ser Ile Leu
        210                 215                 220

Leu Phe Pro Phe Leu Thr Pro Val Phe Glu Val Leu Asn Ile Trp Leu
225                 230                 235                 240

Phe Pro Lys Ser Val Thr Asp Phe Phe Thr Lys Ser Val Lys Arg Met
                245                 250                 255

Lys Glu Asn Arg Leu Lys Asp Lys Gln Lys His Arg Val Asp Phe Leu
                260                 265                 270

Gln Leu Met Ile Asn Ser Gln Asn Ser Lys Glu Thr Asp Thr His Lys
        275                 280                 285

Ala Leu Ser Asp Leu Glu Leu Val Ala Gln Ser Ile Ile Phe Ile Phe
        290                 295                 300

Ala Gly Tyr Glu Thr Thr Ser Thr Ser Leu Ser Phe Leu Met Tyr Glu
305                 310                 315                 320

Leu Ala Thr His Pro Asp Val Gln Gln Lys Leu Gln Glu Glu Ile Asp
                325                 330                 335

Ala Thr Phe Pro Asn Lys Ala Leu Pro Thr Tyr Asp Ala Leu Val Gln
                340                 345                 350

Met Glu Tyr Leu Asp Met Val Leu Asn Glu Thr Leu Arg Leu Tyr Pro
        355                 360                 365

Ile Ala Gly Arg Leu Glu Arg Val Cys Lys Lys Asp Val Glu Ile Ser
        370                 375                 380

Gly Val Phe Ile Pro Lys Gly Thr Val Val Met Val Pro Thr Phe Thr
385                 390                 395                 400

Leu His Arg Asp Gln Ser Leu Trp Pro Glu Pro Glu Glu Phe Arg Pro
                405                 410                 415

Glu Arg Phe Ser Arg Lys Asn Lys Asp Ser Ile Asn Pro Tyr Thr Tyr
                420                 425                 430

Leu Pro Phe Gly Thr Gly Pro Arg Asn Cys Ile Gly Met Arg Phe Ala
        435                 440                 445

Ile Met Asn Met Lys Leu Ala Leu Val Arg Val Leu Gln Asn Phe Ser
450                 455                 460

Phe Lys Pro Cys Lys Glu Thr Gln Ile Pro Leu Lys Leu Asn Ala Gln
465                 470                 475                 480

Gly Ile Ile Gln Pro Glu Lys Pro Ile Val Leu Lys Val Glu Pro Arg
                485                 490                 495

Asp Gly Ser Val Asn Gly Ala
            500

<210> SEQ ID NO 31
<211> LENGTH: 1533
<212> TYPE: DNA
<213> ORGANISM: Canis lupus familiaris

<400> SEQUENCE: 31

| | | | | | |
|---|---|---|---|---|---|
| aagcttaaaa | tggacttgat | ccctagcttc | agtatggaaa | catggctact | gctcgcgaca | 60 |
| tcccttgtat | tgctttatct | ctacggcaca | tacactcatg | gcgtgtttaa | gaagttgggt | 120 |
| atcccaggac | ctacacctct | tcctttcgtc | ggcactgcgt | taggatatag | gaagggcttc | 180 |
| tcagtctttg | acgagaattg | cttccgtaag | tacggaagaa | tgtggggttt | ctatgacgga | 240 |
| aggcagcctg | tgttggcgat | cacgatcca | gacatgatta | gaccgtatt | agtcaaagag | 300 |
| tgctatagcg | tattcacgaa | cagacgttcc | tttgggcccg | tcggtttcat | gaagtcagcc | 360 |
| atctcgttga | gcgaagacga | ggagtggaaa | agaattagga | cacttctgtc | tccaacattt | 420 |
| acttcaggca | aactcaagga | aatgtttcct | atcataggac | agtacgggga | cgtccttgtt | 480 |
| cgtaacctca | ggaaggaagc | cgagaaaggg | aagtccataa | acttaaagga | catcttcgga | 540 |
| gcttattcta | tggacgtcat | cacttccacg | tccttcggcg | ttaatattga | tagtttaaac | 600 |
| aaccccaag | acccgttcgt | ggagaacatc | aagaaattat | tgaagttcga | tttcctggac | 660 |
| cctttcttct | tctcaattct | actgttcccc | ttcttaacac | ctgttttcga | ggttttgaat | 720 |
| atatggttgt | ttccgaagag | cgttacggat | ttctttacaa | agtcggtaaa | gcgtatgaaa | 780 |
| gagaaccgcc | taaaagacaa | gcagaaacat | agagtagact | tcttgcagct | tatgataaac | 840 |
| tcacaaaatt | ctaaagagac | tgacacccac | aaagccctgt | ccgacttgga | gttggttgct | 900 |
| cagtcgataa | tcttcatatt | cgccggctat | gagacgacca | gtacttcgct | gtccttctta | 960 |
| atgtatgaat | tagcgaccca | ccccgatgtc | cagcagaagt | tacaagagga | aattgacgcc | 1020 |
| acgttcccaa | ataaagcgtt | acccacttac | gatgctctgg | tgcagatgga | gtacttggat | 1080 |
| atggttttaa | acgaaactct | ccgtttatac | ccaatcgccg | ggagattgga | gagagtatgc | 1140 |
| aagaaagacg | ttgagattag | tggagtattc | atccccaagg | gaactgtcgt | gatggttcca | 1200 |
| actttcaccc | tacatcgtga | tcagagcttg | tggccggagc | ctgaggaatt | tagacccgag | 1260 |
| aggttctcaa | gaaagaataa | ggattccatc | aacccatata | cttaccttcc | gttcggtact | 1320 |
| ggacctagaa | actgtattgg | aatgcgcttc | gccataatga | acatgaagct | agctctagtt | 1380 |
| cgcgtattgc | agaacttctc | atttaagccg | tgtaaagaga | cacaaatccc | attaaagctg | 1440 |
| aatgctcagg | gtatcataca | gccagagaag | ccaattgttt | taaaggttga | gcctagggac | 1500 |
| ggtagtgtga | acggggctta | gaagactccg | cgg | | | 1533 |

<210> SEQ ID NO 32
<211> LENGTH: 490
<212> TYPE: PRT
<213> ORGANISM: Homo sapiens

<400> SEQUENCE: 32

-continued

```
Met Glu Pro Phe Val Val Leu Val Leu Cys Leu Ser Phe Met Leu Leu
1               5                   10                  15

Phe Ser Leu Trp Arg Gln Ser Cys Arg Arg Lys Leu Pro Pro Gly
            20                  25                  30

Pro Thr Pro Leu Pro Ile Ile Gly Asn Met Leu Gln Ile Asp Val Lys
        35                  40                  45

Asp Ile Cys Lys Ser Phe Thr Asn Phe Ser Lys Val Tyr Gly Pro Val
    50                  55                  60

Phe Thr Val Tyr Phe Gly Met Asn Pro Ile Val Val Phe His Gly Tyr
65                  70                  75                  80

Glu Ala Val Lys Glu Ala Leu Ile Asp Asn Gly Glu Glu Phe Ser Gly
                85                  90                  95

Arg Gly Asn Ser Pro Ile Ser Gln Arg Ile Thr Lys Gly Leu Gly Ile
            100                 105                 110

Ile Ser Ser Asn Gly Lys Arg Trp Lys Glu Ile Arg Arg Phe Ser Leu
        115                 120                 125

Thr Thr Leu Arg Asn Phe Gly Met Gly Lys Arg Ser Ile Glu Asp Arg
130                 135                 140

Val Gln Glu Glu Ala His Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Val Val Phe Gln Lys Arg Phe Asp Tyr Lys Asp Gln
            180                 185                 190

Asn Phe Leu Thr Leu Met Lys Arg Phe Asn Glu Asn Phe Arg Ile Leu
        195                 200                 205

Asn Ser Pro Trp Ile Gln Val Cys Asn Asn Phe Pro Leu Leu Ile Asp
    210                 215                 220

Cys Phe Pro Gly Thr His Asn Lys Val Leu Lys Asn Val Ala Leu Thr
225                 230                 235                 240

Arg Ser Tyr Ile Arg Glu Lys Val Lys Glu His Gln Ala Ser Leu Asp
                245                 250                 255

Val Asn Asn Pro Arg Asp Phe Ile Asp Cys Phe Leu Ile Lys Met Glu
            260                 265                 270

Gln Glu Lys Asp Asn Gln Lys Ser Glu Phe Asn Ile Glu Asn Leu Val
        275                 280                 285

Gly Thr Val Ala Asp Leu Phe Val Ala Gly Thr Glu Thr Thr Ser Thr
    290                 295                 300

Thr Leu Arg Tyr Gly Leu Leu Leu Leu Leu Lys His Pro Glu Val Thr
305                 310                 315                 320

Ala Lys Val Gln Glu Glu Ile Asp His Val Ile Gly Arg His Arg Ser
                325                 330                 335

Pro Cys Met Gln Asp Arg Ser His Met Pro Tyr Thr Asp Ala Val Val
            340                 345                 350

His Glu Ile Gln Arg Tyr Ser Asp Leu Val Pro Thr Gly Val Pro His
        355                 360                 365

Ala Val Thr Thr Asp Thr Lys Phe Arg Asn Tyr Leu Ile Pro Lys Gly
    370                 375                 380

Thr Thr Ile Met Ala Leu Leu Thr Ser Val Leu His Asp Asp Lys Glu
385                 390                 395                 400

Phe Pro Asn Pro Asn Ile Phe Asp Pro Gly His Phe Leu Asp Lys Asn
                405                 410                 415
```

-continued

Gly Asn Phe Lys Lys Ser Asp Tyr Phe Met Pro Phe Ser Ala Gly Lys
                420                 425                 430

Arg Ile Cys Ala Gly Glu Gly Leu Ala Arg Met Glu Leu Phe Leu Phe
            435                 440                 445

Leu Thr Thr Ile Leu Gln Asn Phe Asn Leu Lys Ser Val Asp Asp Leu
        450                 455                 460

Lys Asn Leu Asn Thr Thr Ala Val Thr Lys Gly Ile Val Ser Leu Pro
465                 470                 475                 480

Pro Ser Tyr Gln Ile Cys Phe Ile Pro Val
                485                 490

<210> SEQ ID NO 33
<211> LENGTH: 1494
<212> TYPE: DNA
<213> ORGANISM: Homo sapiens

<400> SEQUENCE: 33
aagcttaaaa tggagccctt tgtcgtgttg gtactttgct tgagcttcat gttgttgttt      60
tccttatgga gacagtcgtg tcgtaggaga aaactaccac cgggtcctac tccactccca     120
ataattggta acatgctgca gatcgatgtt aaagacatct gtaaatcatt cacaaacttc     180
tcgaaggtat atggtcccgt ctttactgtc tacttcggta tgaacccgat cgtggtcttc     240
cacggttacg aggccgtgaa ggaagcattg atagataatg ggaagaatt ctcagggcgc     300 ggcaacagtc ccattagtca gaggatcacc aaggggttgg gaataatctc ttcgaatggt     360
aagagatgga aggagatccg aagattcagc cttaccactc tcagaaattt cggcatggga     420
aaacgcagta tagaggaccg tgtccaagag gaagctcact gcttagtaga ggagttgagg     480
aagacgaaag catctccatg tgatcctacc ttcatcttag gttgcgctcc atgcaatgtt     540
atatgctcag tggtattcca aaagagattc gactataaag accagaactt cctaactttg     600
atgaagcgct ttaatgagaa tttccgtatc cttaactcac cgtggatcca ggtctgcaac     660
aactttccac ttctgattga ttgtttcccg ggcactcaca caaagtgct taagaacgtt     720 gctctcactc gtagttacat ccgtgaaaag gttaaagagc accaagctag tctggacgtt     780
aacaacccac gtgacttcat agactgcttc ctaatcaaga tggaacaaga aaaggataac     840
cagaaatctg agtttaacat agaaaacctg gtaggtacgg tggctgatct gttcgtcgct     900
ggcactgaga caactagcac taccttgagg tacgggctac ttctgttgtt gaagcaccca     960
gaggtaactg ctaaagtaca agaggaaatt gatcatgtaa tcggtcgtca ccgtagtccg    1020
tgcatgcagg atagatccca catgccctac acagacgcag tggtccacga aatccagaga    1080
tactctgacc tagtgccaac tggcgtccca cacgcagtca caaccgacac gaagtttaga    1140 aattaccttta ttccgaaagg tacgactatc atggctttgc taacatcagt gctacatgat    1200
gacaaggagt tccccaaccc taatatctttt gatcctggcc attttcttga taagaacggc    1260
aacttcaaga aatcggacta ctttatgccg ttttcggctg gaagaggat ctgcgctgga    1320 gaaggattag ctagaatgga gttgttctta tttctgacga ctattctaca gaacttcaat    1380
ttaaagtcgg ttgacgattt gaagaacctg aacacaactg cagttacaaa gggcatagtt    1440
agtctaccgc catcttatca aatatgcttt atcccggtat agaagactcc gcgg         1494

<210> SEQ ID NO 34
<211> LENGTH: 490
<212> TYPE: PRT
<213> ORGANISM: Pan troglodytes

```
<400> SEQUENCE: 34

Met Glu Pro Phe Val Val Leu Val Leu Cys Leu Ser Phe Met Leu Leu
1               5                   10                  15

Phe Ser Leu Trp Arg Gln Ser Ser Gly Arg Arg Lys Leu Pro Pro Gly
            20                  25                  30

Pro Thr Pro Leu Pro Ile Ile Gly Asn Met Leu Gln Ile Asp Val Lys
        35                  40                  45

Asp Ile Cys Lys Ser Phe Ser Asn Phe Ser Lys Val Tyr Gly Pro Val
    50                  55                  60

Phe Thr Val Tyr Phe Gly Met Asn Pro Ile Val Val Leu His Gly Tyr
65                  70                  75                  80

Glu Ala Val Lys Glu Ala Leu Ile Asp Asn Gly Glu Glu Phe Ser Gly
                85                  90                  95

Arg Gly Ser Ser Pro Ile Ser Gln Arg Ile Thr Lys Gly Leu Gly Ile
            100                 105                 110

Ile Ser Ser Asn Gly Lys Arg Trp Lys Glu Ile Arg Arg Phe Ser Leu
        115                 120                 125

Thr Thr Leu Arg Asn Phe Gly Met Gly Lys Arg Ser Ile Glu Asp Arg
130                 135                 140

Val Gln Glu Glu Ala His Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Val Val Phe Gln Lys Arg Phe Asp Tyr Lys Asp Gln
            180                 185                 190

Asn Phe Leu Thr Leu Met Lys Arg Phe Asn Glu Asn Phe Arg Ile Leu
        195                 200                 205

Asn Ser Pro Trp Ile Gln Val Cys Asn Asn Phe Pro Leu Leu Ile Asp
    210                 215                 220

Cys Phe Pro Gly Thr His Asn Lys Val Leu Thr Asn Val Ala Leu Thr
225                 230                 235                 240

Gln Ser Tyr Ile Arg Glu Lys Val Lys Glu His Gln Ala Ser Leu Asp
                245                 250                 255

Val Asn Asn Pro Arg Asp Phe Ile Asp Cys Phe Leu Ile Lys Met Glu
            260                 265                 270

Gln Glu Lys Asp Asn Gln Lys Ser Glu Phe Asn Ile Glu Asn Leu Val
        275                 280                 285

Gly Thr Val Ala Asp Leu Phe Val Ala Gly Thr Glu Thr Thr Ser Thr
    290                 295                 300

Thr Leu Arg Tyr Gly Leu Leu Leu Leu Met His Pro Glu Val Thr
305                 310                 315                 320

Ala Lys Val Gln Glu Glu Ile Asp His Val Ile Gly Arg His Arg Thr
                325                 330                 335

Pro Cys Met Gln Asp Arg Ser His Met Pro Tyr Thr Asp Ala Val Val
            340                 345                 350

His Glu Ile Gln Arg Tyr Ser Asp Leu Val Pro Thr Gly Val Pro His
        355                 360                 365

Ala Val Thr Thr Asp Thr Lys Phe Arg Asn Tyr Leu Ile Pro Lys Gly
    370                 375                 380

Thr Thr Ile Met Thr Leu Leu Thr Ser Val Leu His Asp Asp Lys Glu
385                 390                 395                 400

Phe Pro Asn Pro Asn Ile Phe Asp Pro Gly His Phe Leu Asp Lys Asn
                405                 410                 415
```

Gly Asn Phe Lys Lys Ser Asp Tyr Phe Met Pro Phe Ser Ala Gly Lys
            420                 425                 430

Arg Ile Cys Ala Gly Glu Gly Leu Ala Arg Met Glu Leu Phe Leu Phe
        435                 440                 445

Leu Thr Thr Ile Leu Gln Asn Phe Asn Leu Lys Ser Val Asp Asp Leu
450                 455                 460

Lys Asn Leu Asn Thr Thr Ala Val Thr Lys Gly Ile Val Ser Leu Pro
465                 470                 475                 480

Pro Ser Tyr Gln Ile Cys Phe Ile Pro Val
                485                 490

<210> SEQ ID NO 35
<211> LENGTH: 1494
<212> TYPE: DNA
<213> ORGANISM: Pan troglodytes

<400> SEQUENCE: 35

```
aagcttaaaa tggagccctt cgtcgtatta gttctctgcc tttcttttat gttgctattc      60
tcattgtggc gccagagttc cggacgacgt aaattaccac ctggaccaac accactccca     120
ataaggta acatgctaca gatagacgta aaagacatat gcaagtcctt ctcaaacttt     180
tctaaggtat atggacctgt attcacggta tattttggga tgaatccat cgtggttctg      240
cacgatacg aagccgttaa agaggctctt attgataatg cgaggaatt tagtggcagg      300
ggctcgtcgc cgatatctca gaggataact aaaggactag gaattattag ctccaatgga    360
aagcgctgga aggagatcag aaggttcagc ctgacgacac tacgtaactt cggaatgggt    420
aagcgatcaa tagaggatag ggttcaggaa gaggcacact gcctggtaga agaattacgc    480
aagactaaag catccccatg tgatccgaca ttcatcctcg gctgcgcacc atgcaacgta    540
atctgctcgg tcgttttcca gaagcgattt gattacaagg accagaactt tcttacgttg    600
atgaagcgct ttaatgagaa tttcaggatt ttgaatagcc cttggatcca ggtctgcaat    660
aacttcccgc ttctaataga ctgcttccct ggtacccata taaggtgtt aaccaacgtc    720
gcactgaccc aatcctacat tcgagagaaa gtcaaagagc atcaagcatc acttgacgtc    780
aataacccta gagacttcat tgactgcttc ttgatcaaaa tggagcagga aaggacaat    840
cagaagtcag aattcaacat cgaaaactta gtcggtactg tggctgatct gtttgtcgca    900
gggacggaaa ctacttccac gaccttaaga tacggattat tgctgttgct tatgcacccc    960
gaggttacga cgaaagtcca agaggagatc gaccatgtaa ttggccgtca ccgtacgccc   1020
tgtatgcaag accgttcgca catgccctac acagatgcgg ttgtacacga gatccagcga    1080
tactcagacc tggtgccaac tggggtgccc cacgctgtaa ctactgacac gaagtttcgt    1140
aattacttaa ttccaaaagg cacgaccatt atgacgctat aacgtctgt cctgcacgac    1200
gacaaggagt tccctaaccc taacatattc gacccaggcc atttctaga taagaacggg    1260
aacttcaaga aatcggatta ctttatgcct ttctcagctg ggaagaggat ctgcgcaggt    1320
gagggcttgg ccaggatgga gttattcttg ttcttgacta ctatattaca gaacttcaac    1380
ttgaagtcag ttgatgactt gaagaaccct aacactacag cagtcactaa gggtatagtc    1440
tcattacccc ctagttatca aatctgcttc attcctgttt agaagactcc gcgg           1494
```

<210> SEQ ID NO 36
<211> LENGTH: 490
<212> TYPE: PRT
<213> ORGANISM: Pongo abelii

<400> SEQUENCE: 36

```
Met Glu Pro Phe Val Val Leu Val Leu Cys Leu Ser Phe Met Leu Leu
1               5                   10                  15

Phe Ser Leu Trp Arg Gln Ser Ser Gly Arg Arg Lys Leu Pro Pro Gly
            20                  25                  30

Pro Thr Pro Leu Pro Ile Ile Gly Asn Met Leu Gln Ile Asp Ile Lys
        35                  40                  45

Asp Ile Cys Lys Ser Phe Ser Asn Phe Ser Lys Val Tyr Gly Pro Val
    50                  55                  60

Phe Thr Val Tyr Phe Gly Met Asn Pro Met Val Val Leu His Gly Tyr
65                  70                  75                  80

Glu Ala Val Lys Glu Ala Leu Ile Asp Asn Gly Glu Glu Phe Ser Gly
                85                  90                  95

Arg Gly Ser Ser Pro Ile Ser Gln Arg Ile Thr Lys Gly Leu Gly Ile
            100                 105                 110

Ile Ser Ser Asn Gly Asn Arg Trp Lys Glu Ile Arg Arg Phe Ser Leu
            115                 120                 125

Thr Thr Leu Arg Asn Phe Gly Met Gly Lys Arg Ser Ile Glu Asp Arg
130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Val Val Phe Gln Lys Arg Phe Asp Tyr Lys Asp Gln
            180                 185                 190

Asn Phe Leu Thr Leu Met Lys Arg Phe Asn Glu Asn Phe Arg Ile Leu
            195                 200                 205

Asn Ser Pro Trp Ile Gln Val Cys Asn Asn Phe Pro Leu Leu Ile Asp
210                 215                 220

Cys Phe Pro Gly Thr His Asn Lys Leu Leu Lys Asn Val Ala Leu Thr
225                 230                 235                 240

Arg Ser Tyr Ile Arg Glu Lys Val Lys Glu His Gln Thr Ser Leu Asp
                245                 250                 255

Val Thr Ser Pro Arg Asp Phe Ile Asp Cys Phe Leu Ile Lys Met Glu
            260                 265                 270

Gln Glu Lys Asp Asn Gln Lys Ser Glu Phe Asn Ile Glu Asn Leu Val
            275                 280                 285

Gly Thr Val Ala Asp Leu Phe Val Ala Gly Thr Glu Thr Thr Ser Thr
290                 295                 300

Thr Leu Arg Tyr Gly Leu Leu Leu Leu Lys His Pro Glu Val Thr
305                 310                 315                 320

Ala Lys Val Gln Glu Glu Ile Asp His Val Ile Gly Arg His Arg Ser
                325                 330                 335

Pro Cys Met Gln Asp Arg Ser His Met Pro Tyr Thr Asp Ala Val Val
            340                 345                 350

His Glu Ile Gln Arg Tyr Ile Asp Leu Val Pro Thr Gly Val Pro His
            355                 360                 365

Ala Val Thr Thr Asp Ile Gln Phe Arg Asn Tyr Leu Ile Pro Lys Gly
            370                 375                 380

Thr Thr Ile Met Thr Leu Leu Thr Ser Val Leu His Asp Asp Lys Glu
385                 390                 395                 400

Phe Pro Asn Pro Lys Ile Phe Asp Pro Gly His Phe Leu Asp Lys Asn
```

```
                    405                 410                 415
Gly Asn Phe Lys Lys Ser Asp Tyr Phe Met Pro Phe Ser Ala Gly Lys
            420                 425                 430

Arg Ile Cys Ala Gly Glu Gly Leu Ala Arg Met Glu Leu Phe Leu Phe
            435                 440                 445

Leu Thr Thr Ile Leu Gln Asn Phe Asn Leu Lys Ser Val Asp Asp Leu
    450                 455                 460

Lys Asn Leu Asn Thr Thr Ala Val Thr Lys Gly Ile Val Ser Leu Pro
465                 470                 475                 480

Pro Ser Tyr Gln Ile Cys Phe Ile Pro Val
            485                 490

<210> SEQ ID NO 37
<211> LENGTH: 1494
<212> TYPE: DNA
<213> ORGANISM: Pongo abelii

<400> SEQUENCE: 37
aagcttaaaa tggagccatt tgtggtactt gtactgtgtc ttagcttcat gcttctgttc      60
tccctatgga gacagtcatc tggacgacgt aagttgccgc cagggccaac ccctttaccc     120
atcattggga acatgcttca aatagatatt aaggacatat gcaagagctt ttcgaacttc     180
tcaaaggttt atgggcctgt gtttaccgta tatttcggaa tgaacccaat ggtcgtgttg     240
catggttacg aggctgttaa ggaagcactg atagacaacg gcgaggagtt ctcaggccgt     300
gggtcatctc ctatctcaca aaggattacc aagggattgg aataatatc gtcaaacggt      360 aaccgctgga aggagatcag aagattcagc ctcactacct gcgtaacttt ggtatgggg      420 aaaagaagta tcgaggaccg tgtacaggaa gaggcaaggt gtcttgtcga ggagctacgt     480
aagaccaagg cgtccccgtg cgacccaacc tttatcttgg gctgcgctcc gtgtaacgta     540
atctgctcag tcgtgttcca gaagaggttt gattacaagg accagaactt cttgacttta     600
atgaagcgtt ttaatgagaa ctttaggatt ctaaactccc cgtggattca ggtttgtaac     660
aatttcccgt tacttataga ctgttttcca ggtactcaca ataagctact caagaatgtg     720
gcactaaccc gtagctatat tcgcgagaaa gtcaaagagc accagacgtc cctagatgtg     780 acttcacccca gggacttcat agactgcttc ttaataaaga tggagcagga aaggataac     840 cagaagagtg aattcaatat tgagaattta gtcggtacgg ttgccgatct attcgttgcc     900
ggaacggaga ctacatcgac tacactgcgt tatggtttgt tattgttgtt aaagcaccct     960
gaggtcacag ctaaagtgca ggaagagatt gatcacgtca tcggtagaca cagaagtcca    1020
tgcatgcaag acagaagcca catgccatat actgacgcag ttgtccacga gatacagcgt    1080
tacatcgatt tggtcccaac agggtgccac acgctgtta ccacggatat tcagtttaga    1140
aactatctta taccaaaagg aacgacaatc atgaccctc tgacctctgt tctacatgac    1200
gacaaagagt tcccaaatcc taagatcttc gacccaggtc acttcttgga caagaatgga    1260
aacttcaaga agtccgatta cttcatgcct ttcagtgccg gtaagagaat ctgtgctggt    1320
gaaggactag cgaggatgga gcttttctta ttcctaacaa ccatattgca gaactttaat    1380
cttaaatcag ttgacgacct aaagaaccta aatacaactg ccgtgacgaa aggcatagtt    1440
agtctcccac cgtcctacca gatatgtttc attccagtat agaagactcc gcgg          1494

<210> SEQ ID NO 38
<211> LENGTH: 490
<212> TYPE: PRT
```

<213> ORGANISM: Chlorocebus aethiops

<400> SEQUENCE: 38

```
Met Glu Pro Phe Val Val Leu Val Leu Cys Leu Ser Phe Val Leu Leu
1               5                   10                  15

Phe Ser Leu Trp Arg Gln Ser Ser Gly Arg Arg Asn Leu Pro Pro Gly
            20                  25                  30

Pro Thr Pro Phe Pro Ile Ile Gly Asn Met Leu Gln Ile Asp Val Lys
        35                  40                  45

Asp Ile Cys Lys Ser Phe Ser Asn Phe Ser Lys Val Tyr Gly Pro Val
50                  55                  60

Phe Thr Val Tyr Leu Gly Met Asn Pro Val Val Leu His Gly Tyr
65                  70                  75                  80

Glu Ala Val Lys Glu Ala Leu Ile Asp Asn Ala Glu Glu Phe Ser Gly
                85                  90                  95

Arg Gly Ile Leu Pro Ile Ser Glu Arg Ile Thr Lys Gly Leu Gly Ile
            100                 105                 110

Ile Ser Ser Asn Gly Lys Arg Trp Lys Glu Thr Arg Arg Phe Ser Leu
        115                 120                 125

Thr Thr Leu Arg Asn Phe Gly Met Gly Lys Arg Ser Ile Glu Asp Arg
130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Val Val Phe Gln Lys Arg Phe Asp Tyr Lys Asp Glu
            180                 185                 190

Asn Phe Leu Thr Leu Met Lys Arg Phe Thr Glu Asn Phe Arg Ile Leu
        195                 200                 205

Thr Ser Pro Trp Ile Gln Val Cys Asn Asn Phe Pro Leu Leu Ile Asp
210                 215                 220

Cys Phe Pro Gly Thr His Asn Lys Leu Leu Lys Asn Val Ala Leu Thr
225                 230                 235                 240

Lys Ser Tyr Ile Arg Glu Lys Val Lys Glu His Gln Ala Thr Leu Asp
                245                 250                 255

Ile Asn Asn Pro Arg Asp Phe Ile Asp Cys Phe Leu Ile Lys Met Glu
            260                 265                 270

Lys Glu Lys Asp Asn Gln Gln Ser Glu Phe Thr Ile Glu Asn Leu Val
        275                 280                 285

Gly Thr Val Ala Asp Leu Phe Val Ala Gly Thr Glu Thr Thr Ser Thr
290                 295                 300

Thr Leu Arg Tyr Gly Leu Leu Leu Leu Lys His Pro Glu Val Thr
305                 310                 315                 320

Ala Lys Val Gln Glu Glu Ile Asp His Val Ile Gly Arg His Arg Ser
                325                 330                 335

Pro Cys Met Gln Asp Arg Ser His Met Pro Tyr Thr Asp Ala Val Val
            340                 345                 350

His Glu Ile Gln Arg Tyr Ile Asp Leu Val Pro Thr Gly Val Pro His
        355                 360                 365

Ala Val Thr Thr Asp Ile Lys Phe Arg Asn Tyr Leu Ile Pro Lys Gly
370                 375                 380

Thr Ile Ile Met Thr Leu Leu Thr Ser Val Leu His Asp Asp Lys Glu
385                 390                 395                 400
```

| | | | | | | | | | | | | |
|---|---|---|---|---|---|---|---|---|---|---|---|---|
|Phe|Pro|Asn|Pro|Lys|Ile|Phe|Asp|Pro|Gly|His|Phe|Leu|Asp|Glu|Asn|
| | | | |405| | | | |410| | | | |415| |

| | | | | | | | | | | | | | | | |
|---|---|---|---|---|---|---|---|---|---|---|---|---|---|---|---|
|Gly|Asn|Phe|Lys|Lys|Ser|Asp|Tyr|Phe|Met|Pro|Phe|Ser|Ala|Gly|Lys|
| | | |420| | | | |425| | | | |430| | |

| | | | | | | | | | | | | | | | |
|---|---|---|---|---|---|---|---|---|---|---|---|---|---|---|---|
|Arg|Ile|Cys|Ala|Gly|Glu|Gly|Leu|Ala|Arg|Met|Glu|Leu|Phe|Leu|Phe|
| | |435| | | | |440| | | | |445| | | |

| | | | | | | | | | | | | | | | |
|---|---|---|---|---|---|---|---|---|---|---|---|---|---|---|---|
|Leu|Thr|Thr|Ile|Leu|Gln|Asn|Phe|Asn|Leu|Lys|Ser|Val|Ala|Asp|Leu|
| |450| | | | |455| | | | |460| | | | |

| | | | | | | | | | | | | | | | |
|---|---|---|---|---|---|---|---|---|---|---|---|---|---|---|---|
|Lys|Asn|Leu|Asn|Thr|Thr|Ser|Ala|Thr|Arg|Gly|Ile|Ile|Ser|Leu|Pro|
|465| | | | |470| | | | |475| | | | |480|

| | | | | | | | |
|---|---|---|---|---|---|---|---|
|Pro|Ser|Tyr|Gln|Ile|Cys|Phe|Ile|Pro|Val|
| | | | |485| | | | |490|

<210> SEQ ID NO 39
<211> LENGTH: 1494
<212> TYPE: DNA
<213> ORGANISM: Chlorocebus aethiops

<400> SEQUENCE: 39

```
aagcttaaaa tggagccatt cgttgtttta gtcctgtgct tatctttgt tttactgttc      60
tctttatggc gacagtcgag cggtcgacga aacctaccac caggcccac tccgttcccg     120
atcataggta atatgcttca aatcgacgta aaggatatct gcaagtcctt ctccaatttc    180
agtaaagtct acggcccggt gtttacagta tatttgggta tgaacccggt agtcgtacta    240
cacggatacg aggcggttaa agaagcatta atcgataacg cagaggaatt ctcagggcgc    300
gggatattac ccatatctga gcgcatcaca aaggggcttg cattattttc agcaatggt    360
aaaagatgga aggagacacg aagatttttca ctaacaactt tgcgtaactt cggaatggga    420
aaacgttcga tcgaggaccg cgtacaagag gaagcacgat gtcttgtgga agagttgaga    480
aagaccaagg cttcgccatg tgatcctaca ttcattcttg gatgtgcacc ctgcaacgta    540
atctgcagtg tggtattcca gaagcgattt gactataagg acgagaactt cttaacttta    600
atgaaaagat tcacggagaa ctttaggatc ttgacttcac cttggatcca ggtatgcaat    660
aactttcctc ttctaatcga ctgcttccca ggaacacata caagttgtt gaagaacgta    720
gcactaacta agtcatacat acgtgagaag gtgaaagaac accaagcaac acttgatatt    780
aataatcctc gtgactttat tgactgcttt ctaatcaaga tggagaaaga gaaggacaac    840
cagcagtctg agttcactat agagaaccta gttgggactg tagctgactt gttttgtcgcc    900
ggtaccgaga caacatcaac aaccttgagg tatggtctat tattgttact gaagcatccc    960
gaagtgacgg caaaggtcca ggaagagata gaccacgtaa tcggccgaca ccgttcaccg   1020
tgcatgcagg atagatcaca tatgccatat accgatgcgg tcgtacatga gatccaaagg   1080
tacattgact tggttcctac aggcgttccc cacgccgtaa caactgacat aaaattccgc   1140
aactatctaa tacccaaggg cactatcatc atgacgctac tgacgtccgt cctgcatgat   1200
gacaaggagt ttccaaaccc taagatcttc gacccgggac acttcctaga cgagaatggt   1260
aacttcaaga aatcagatta cttcatgccc ttctcagctg gtaaacgaat ctgcgccgga   1320
gaaggcctcg ctcgtatgga gctttcttg ttcttaacga ccatattgca gaacttcaac   1380
ctaaagtcag ttgcagacct taagaattta aatacaacca gcgccactcg tggcatcatc   1440
tctttgccgc cgtcatatca gatatgcttt attcctgtat agaagactcc gcgg          1494
```

<210> SEQ ID NO 40
<211> LENGTH: 502

<212> TYPE: PRT
<213> ORGANISM: Homo sapiens

<400> SEQUENCE: 40

```
Met Asp Leu Ile Pro Asn Leu Ala Val Glu Thr Trp Leu Leu Leu Ala
1               5                   10                  15

Val Ser Leu Val Leu Leu Tyr Leu Tyr Gly Thr Arg Thr His Gly Leu
            20                  25                  30

Phe Lys Arg Leu Gly Ile Pro Gly Pro Thr Pro Leu Pro Leu Leu Gly
        35                  40                  45

Asn Val Leu Ser Tyr Arg Gln Gly Leu Trp Lys Phe Asp Thr Glu Cys
    50                  55                  60

Tyr Lys Lys Tyr Gly Lys Met Trp Gly Thr Tyr Glu Gly Gln Leu Pro
65                  70                  75                  80

Val Leu Ala Ile Thr Asp Pro Asp Val Ile Arg Thr Val Leu Val Lys
                85                  90                  95

Glu Cys Tyr Ser Val Phe Thr Asn Arg Arg Ser Leu Gly Pro Val Gly
            100                 105                 110

Phe Met Lys Ser Ala Ile Ser Leu Ala Glu Asp Glu Trp Lys Arg
        115                 120                 125

Ile Arg Ser Leu Leu Ser Pro Thr Phe Thr Ser Gly Lys Leu Lys Glu
    130                 135                 140

Met Phe Pro Ile Ile Ala Gln Tyr Gly Asp Val Leu Val Arg Asn Leu
145                 150                 155                 160

Arg Arg Glu Ala Glu Lys Gly Lys Pro Val Thr Leu Lys Asp Ile Phe
                165                 170                 175

Gly Ala Tyr Ser Met Asp Val Ile Thr Gly Thr Ser Phe Gly Val Asn
            180                 185                 190

Ile Asp Ser Leu Asn Asn Pro Gln Asp Pro Phe Val Glu Ser Thr Lys
    195                 200                 205

Lys Phe Leu Lys Phe Gly Phe Leu Asp Pro Leu Phe Leu Ser Ile Ile
210                 215                 220

Leu Phe Pro Phe Leu Thr Pro Val Phe Glu Ala Leu Asn Val Ser Leu
225                 230                 235                 240

Phe Pro Lys Asp Thr Ile Asn Phe Leu Ser Lys Ser Val Asn Arg Met
                245                 250                 255

Lys Lys Ser Arg Leu Asn Asp Lys Gln Lys His Arg Leu Asp Phe Leu
            260                 265                 270

Gln Leu Met Ile Asp Ser Gln Asn Ser Lys Glu Thr Glu Ser His Lys
    275                 280                 285

Ala Leu Ser Asp Leu Glu Leu Ala Ala Gln Ser Ile Ile Phe Ile Phe
290                 295                 300

Ala Gly Tyr Glu Thr Thr Ser Ser Val Leu Ser Phe Thr Leu Tyr Glu
305                 310                 315                 320

Leu Ala Thr His Pro Asp Val Gln Gln Lys Leu Gln Lys Glu Ile Asp
                325                 330                 335

Ala Val Leu Pro Asn Lys Ala Pro Pro Thr Tyr Asp Ala Val Val Gln
            340                 345                 350

Met Glu Tyr Leu Asp Met Val Val Asn Glu Thr Leu Arg Leu Phe Pro
    355                 360                 365

Val Ala Ile Arg Leu Glu Arg Thr Cys Lys Lys Asp Val Glu Ile Asn
370                 375                 380

Gly Val Phe Ile Pro Lys Gly Ser Met Val Val Ile Pro Thr Tyr Ala
385                 390                 395                 400
```

```
Leu His His Asp Pro Lys Tyr Trp Thr Glu Pro Glu Phe Arg Pro
            405                 410                 415

Glu Arg Phe Ser Lys Lys Lys Asp Ser Ile Asp Pro Tyr Ile Tyr Thr
                420                 425                 430

Pro Phe Gly Thr Gly Pro Arg Asn Cys Ile Gly Met Arg Phe Ala Leu
            435                 440                 445

Met Asn Met Lys Leu Ala Leu Ile Arg Val Leu Gln Asn Phe Ser Phe
        450                 455                 460

Lys Pro Cys Lys Glu Thr Gln Ile Pro Leu Lys Leu Asp Thr Gln Gly
465                 470                 475                 480

Leu Leu Gln Pro Glu Lys Pro Ile Val Leu Lys Val Asp Ser Arg Asp
                485                 490                 495

Gly Thr Leu Ser Gly Glu
            500

<210> SEQ ID NO 41
<211> LENGTH: 1530
<212> TYPE: DNA
<213> ORGANISM: Homo sapiens

<400> SEQUENCE: 41
```

| | | | | | |
|---|---|---|---|---|---|
| aagcttaaaa | tggacttgat | cccaaacttg | gctgttgaaa | cttggttgtt | attggccgtt | 60 |
| tctttggtct | tgttgtactt | gtatggtact | agaacccatg | gtttgttcaa | gagattgggt | 120 |
| attccaggtc | caactccatt | gccattattg | ggtaatgttt | tgtcctacag | acaaggcttg | 180 |
| tggaagtttg | atactgagtg | ctataagaaa | tacggtaaga | gtgggggtac | ttacgaaggt | 240 |
| caattgccag | ttttggctat | tactgatcca | gatgttatca | gaaccgtctt | ggtcaaagaa | 300 |
| tgctactctg | ttttcaccaa | cagaagatct | ttgggtccag | ttggttttat | gaagtccgct | 360 |
| atttctttgg | ccgaagatga | agaatggaag | agaatcagat | ctttgttgtc | tccaactttc | 420 |
| acctccggta | agttgaaaga | atgttcccca | attattgccc | aatacggtga | tgttttggtc | 480 |
| agaaacttga | gaagagaagc | tgaaaaaggt | aagccagtta | ccttgaagga | tattttcggt | 540 |
| gcttactcca | tggatgttat | taccggtact | tctttcggtg | tcaacatcga | ttcttttgaac | 600 |
| aatccacaag | atcccttcgt | tgaatctacc | aagaagtttt | tgaagttcgg | tttcttggac | 660 |
| cccttgttct | tgtccattat | tttgttccca | tttctgaccc | cagttttcga | agccttgaat | 720 |
| gtttctttgt | ttccaaagga | caccatcaat | ttcttgagca | agtccgttaa | caggatgaag | 780 |
| aagtctagat | tgaacgacaa | gcaaaagcac | aggttggatt | tcttgcaact | gatgatcgat | 840 |
| tcccagaact | ctaaagaaac | tgaatcccat | aaggctttgt | ccgatttgga | attggctgcc | 900 |
| caatctatca | ttttcatttt | cgctggttac | gaaaccacct | cctctgtttt | gtcttttacc | 960 |
| ttgtatgaat | tggccactca | tccagacgtt | caacaaaagt | tgcaaaaaga | aatcgatgcc | 1020 |
| gtcttgccaa | acaaagctcc | accaactttat | gatgctgttg | tccaaatgga | atacttggat | 1080 |
| atggttgtca | acgaaacctt | gaggttgttt | ccagttgcta | tcagattgga | aagaacctgc | 1140 |
| aaaaaggatg | tcgaaatcaa | cggtgttttc | atcccaaaag | gttccatggt | tgtgattcca | 1200 |
| acttacgcat | tgcatcatga | tccaaagtat | tggactgaac | cagaagaatt | cagaccagaa | 1260 |
| agattctcca | agaagaagga | ttccattgat | ccttacatct | acactccatt | tggtactggt | 1320 |
| cctagaaact | gtattggtat | gagattcgct | ctgatgaaca | tgaagttggc | cttgattaga | 1380 |
| gtgttgcaga | acttctcttt | caacccctgt | aaagaaacgc | agatcccatt | gaagttggat | 1440 |
| acacaaggtt | tattgcaacc | agaaaagcct | atcgttttga | aggtcgattc | tagagatggt | 1500 |

```
actttgtctg gtgagtgaaa gactccgcgg                                      1530
```

<210> SEQ ID NO 42
<211> LENGTH: 502
<212> TYPE: PRT
<213> ORGANISM: Pan troglodytes

<400> SEQUENCE: 42

| | | | | | | | | | | | | | | | |
|---|---|---|---|---|---|---|---|---|---|---|---|---|---|---|---|
| Met | Asp | Leu | Ile | Pro | Asn | Leu | Ala | Val | Glu | Thr | Trp | Leu | Leu | Ala | |
| 1 | | | | 5 | | | | | 10 | | | | | 15 | |
| Val | Ser | Leu | Val | Leu | Leu | Tyr | Leu | Tyr | Gly | Thr | Arg | Thr | His | Gly | Leu |
| | | | 20 | | | | | 25 | | | | | 30 | | |
| Phe | Lys | Arg | Leu | Gly | Ile | Pro | Gly | Pro | Thr | Pro | Leu | Pro | Leu | Leu | Gly |
| | | 35 | | | | | 40 | | | | | 45 | | | |
| Asn | Val | Leu | Ser | Tyr | Arg | Gln | Gly | Leu | Trp | Lys | Phe | Asp | Thr | Glu | Cys |
| | 50 | | | | | 55 | | | | | 60 | | | | |
| Tyr | Lys | Lys | Tyr | Gly | Lys | Met | Trp | Gly | Met | Tyr | Asp | Gly | Gln | Leu | Pro |
| 65 | | | | | 70 | | | | | 75 | | | | | 80 |
| Val | Leu | Ala | Ile | Thr | Asp | Pro | Asp | Met | Ile | Arg | Thr | Val | Leu | Val | Lys |
| | | | | 85 | | | | | 90 | | | | | 95 | |
| Glu | Cys | Tyr | Ser | Val | Phe | Thr | Asn | Arg | Arg | Ser | Leu | Gly | Pro | Val | Gly |
| | | | 100 | | | | | 105 | | | | | 110 | | |
| Phe | Met | Lys | Ser | Ala | Ile | Ser | Leu | Ala | Glu | Asp | Glu | Glu | Trp | Lys | Arg |
| | | 115 | | | | | 120 | | | | | 125 | | | |
| Ile | Arg | Ser | Leu | Leu | Ser | Pro | Thr | Phe | Thr | Ser | Gly | Lys | Leu | Lys | Glu |
| | 130 | | | | | 135 | | | | | 140 | | | | |
| Met | Phe | Pro | Ile | Ile | Ala | Gln | Tyr | Gly | Asp | Val | Leu | Val | Arg | Asn | Leu |
| 145 | | | | | 150 | | | | | 155 | | | | | 160 |
| Arg | Arg | Glu | Ala | Glu | Lys | Gly | Lys | Pro | Val | Thr | Leu | Lys | Asp | Ile | Phe |
| | | | | 165 | | | | | 170 | | | | | 175 | |
| Gly | Ala | Tyr | Ser | Met | Asp | Val | Ile | Thr | Gly | Thr | Ser | Phe | Gly | Val | Asn |
| | | | 180 | | | | | 185 | | | | | 190 | | |
| Ile | Asp | Ser | Leu | Asn | Asn | Pro | Gln | Asp | Pro | Phe | Val | Glu | Ser | Thr | Lys |
| | | 195 | | | | | 200 | | | | | 205 | | | |
| Lys | Phe | Leu | Lys | Phe | Gly | Phe | Leu | Asp | Pro | Leu | Phe | Leu | Ser | Ile | Ile |
| | 210 | | | | | 215 | | | | | 220 | | | | |
| Leu | Phe | Pro | Phe | Leu | Thr | Pro | Val | Phe | Glu | Ala | Leu | Asn | Val | Ser | Leu |
| 225 | | | | | 230 | | | | | 235 | | | | | 240 |
| Phe | Pro | Lys | Asp | Thr | Ile | Asn | Phe | Leu | Ser | Lys | Ser | Val | Asn | Arg | Met |
| | | | | 245 | | | | | 250 | | | | | 255 | |
| Lys | Lys | Ser | Arg | Leu | Asn | Asp | Lys | Gln | Lys | His | Arg | Leu | Asp | Phe | Leu |
| | | | 260 | | | | | 265 | | | | | 270 | | |
| Gln | Leu | Met | Ile | Asp | Ser | Gln | Asn | Ser | Lys | Glu | Thr | Glu | Ser | His | Lys |
| | | 275 | | | | | 280 | | | | | 285 | | | |
| Ala | Leu | Ser | Asp | Leu | Glu | Leu | Ala | Ala | Gln | Ser | Ile | Ile | Phe | Ile | Phe |
| | 290 | | | | | 295 | | | | | 300 | | | | |
| Ala | Gly | Tyr | Glu | Thr | Thr | Ser | Ser | Val | Leu | Ser | Phe | Thr | Leu | Tyr | Glu |
| 305 | | | | | 310 | | | | | 315 | | | | | 320 |
| Leu | Ala | Thr | His | Pro | Asp | Val | Gln | Gln | Lys | Leu | Gln | Lys | Glu | Ile | Asp |
| | | | | 325 | | | | | 330 | | | | | 335 | |
| Ala | Val | Leu | Pro | Asn | Lys | Ala | Pro | Pro | Thr | Tyr | Asp | Ala | Val | Val | Gln |
| | | | 340 | | | | | 345 | | | | | 350 | | |
| Met | Glu | Tyr | Leu | Asp | Met | Val | Val | Asn | Glu | Thr | Leu | Arg | Leu | Phe | Pro |
| | | 355 | | | | | 360 | | | | | 365 | | | |

```
Val Ala Ile Arg Leu Glu Arg Thr Cys Lys Lys Asp Val Glu Ile Asn
    370                 375                 380
Gly Val Phe Ile Pro Lys Gly Ser Met Val Val Ile Pro Thr Tyr Ala
385                 390                 395                 400
Leu His His Asp Pro Lys Tyr Trp Thr Glu Pro Glu Glu Phe Arg Pro
                405                 410                 415
Glu Arg Phe Ser Lys Lys Lys Asp Ser Ile Asp Pro Tyr Ile Tyr Thr
                420                 425                 430
Pro Phe Gly Thr Gly Pro Arg Asn Cys Ile Gly Met Arg Phe Ala Leu
            435                 440                 445
Met Asn Met Lys Leu Ala Leu Ile Arg Val Leu Gln Asn Phe Ser Phe
450                 455                 460
Lys Pro Cys Lys Glu Thr Gln Ile Pro Leu Lys Leu Asp Thr Gln Gly
465                 470                 475                 480
Leu Leu Gln Pro Glu Lys Pro Ile Val Leu Lys Val Asp Ser Arg Asp
                485                 490                 495
Gly Thr Leu Ser Gly Glu
            500

<210> SEQ ID NO 43
<211> LENGTH: 1530
<212> TYPE: DNA
<213> ORGANISM: Pan troglodytes

<400> SEQUENCE: 43
```

| | | | | | |
|---|---|---|---|---|---|
| aagcttaaaa | tggacttgat | cccaaacttg | gctgttgaaa | cttggttgtt | attggccgtt | 60 |
| tctttggtct | tgttgtactt | gtatggtact | agaacccatg | gtttgttcaa | gagattgggt | 120 |
| attccaggtc | caactccatt | gccattattg | ggtaatgttt | tgtcctacag | acaaggcttg | 180 |
| tggaagtttg | atactgagtg | ctataagaaa | tacggtaaga | tgtggggtat | gtacgatggt | 240 |
| caattgccag | ttttggctat | tactgatcca | gatatgatca | gaaccgtctt | ggtcaaagaa | 300 |
| tgctactctg | ttttcaccaa | cagaagatct | ttgggtccag | ttggttttat | gaagtccgct | 360 |
| atttctttgg | ccgaagatga | agaatggaag | agaatcagat | ctttgttgtc | tccaactttc | 420 |
| acctccggta | agttgaaaga | aatgttccca | attattgccc | aatacggtga | tgttttggtc | 480 |
| agaaacttga | agagagaagc | tgaaaaaggt | aagccagtta | ccttgaagga | tattttcggt | 540 |
| gcttactcca | tggatgttat | taccggtact | tctttcggtg | tcaacatcga | ttctttgaac | 600 |
| aatccacaag | atcccttcgt | tgaatctacc | aagaagtttt | tgaagttcgg | tttcttggac | 660 |
| ccccttgttct | tgtccattat | tttgttccca | tttctgaccc | cagttttcga | agccttgaat | 720 |
| gtttctttgt | ttccaaagga | caccatcaat | tccttgagca | agtccgttaa | caggatgaag | 780 |
| aagtctagat | tgaacgacaa | gcaaaagcac | aggttggatt | tcttgcaact | gatgatcgat | 840 |
| tcccagaact | ctaaagaaac | tgaatcccat | aaggctttgt | ccgatttgga | attggctgcc | 900 |
| caatctatca | tttttcatttt | cgctggttac | gaaaccacct | cctctgtttt | gtcttttacc | 960 |
| ttgtatgaat | tggccactca | tccagatgtt | caacagaagt | tgcaaaaaga | aatcgatgcc | 1020 |
| gttttgccaa | acaaagctcc | accaactatt | gatgctgttg | tccaaatgga | atacttggat | 1080 |
| atggttgtca | acgaaacctt | gaggttgttt | ccagttgcta | tcagattgga | agaacctgc | 1140 |
| aaaaaggatg | tcgaaatcaa | cggtgttttc | atcccaaaag | gttccatggt | tgtgattcca | 1200 |
| acttacgcat | tgcatcatga | tccaaagtat | tggactgaac | cagaagaatt | cagaccagaa | 1260 |
| agattctcca | agaagaagga | ttccattgat | ccttacatct | acactccatt | tggtactggt | 1320 |

```
cctagaaact gtattggtat gagattcgct ctgatgaaca tgaagttggc cttgattaga      1380
gtgttgcaga acttctcttt caaaccctgt aaagaaacgc agatcccatt gaagttggat      1440
acacaaggtt tattgcaacc agaaaagcct atcgttttga aggtcgattc tagagatggt      1500
actttgtctg gtgagtgaaa gactccgcgg                                      1530
```

<210> SEQ ID NO 44
<211> LENGTH: 503
<212> TYPE: PRT
<213> ORGANISM: Macaca fascicularis

<400> SEQUENCE: 44

```
Met Asp Leu Ile Pro Asn Leu Ala Met Glu Thr Trp Leu Leu Leu Ala
1               5                   10                  15

Val Ser Leu Val Leu Leu Tyr Leu Tyr Gly Thr Arg Ser Tyr Gly Leu
            20                  25                  30

Phe Lys Arg Gln Gly Ile Pro Gly Pro Thr Pro Leu Pro Phe Leu Gly
        35                  40                  45

Asn Ile Leu Ser Tyr Arg Gln Gly Leu Trp Lys Phe Asp Thr Glu Cys
    50                  55                  60

Tyr Lys Lys Tyr Gly Lys Met Trp Arg Thr Gln Asp Gly Gln Leu Pro
65                  70                  75                  80

Val Leu Thr Ile Thr Asp Pro Asp Met Ile Lys Thr Val Leu Val Lys
                85                  90                  95

Glu Cys Tyr Ser Val Phe Thr Asn Arg Arg Pro Leu Gly Pro Val Gly
            100                 105                 110

Leu Met Lys Ser Ala Ile Ser Ile Ala Glu Asp Glu Glu Trp Lys Arg
        115                 120                 125

Ile Arg Ser Leu Leu Ser Pro Thr Phe Thr Ser Gly Lys Leu Lys Glu
    130                 135                 140

Met Phe Pro Ile Ile Ala Gln Tyr Gly Asp Met Leu Val Arg Asn Leu
145                 150                 155                 160

Arg Arg Glu Ala Glu Lys Gly Lys Pro Val Thr Leu Lys Asp Ile Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Lys Asp Pro Phe Val Glu Ser Val Lys
        195                 200                 205

Lys Phe Leu Lys Phe Asp Phe Leu Asp Pro Leu Phe Leu Leu Thr Ile
    210                 215                 220

Leu Phe Pro Phe Leu Ile Pro Ala Phe Glu Ala Leu Asn Val Ser Leu
225                 230                 235                 240

Phe Pro Lys Asp Ala Ile Asn Phe Leu Asn Lys Ser Val Asn Ser Met
                245                 250                 255

Lys Lys Ser Arg Leu Asn Asp Lys Gln Lys His Arg Val Asp Phe Leu
            260                 265                 270

Gln Leu Met Ile Asp Ser Gln Asn Ser Lys Glu Thr Glu Ser His Lys
        275                 280                 285

Ala Leu Ser Asp Gln Glu Leu Val Ala Gln Ser Ile Ile Phe Ile Phe
    290                 295                 300

Ala Gly Tyr Glu Thr Thr Ser Ser Val Leu Ser Phe Ile Ile Tyr Glu
305                 310                 315                 320

Leu Ala Thr His Pro Asp Val Gln Gln Lys Leu Gln Lys Glu Ile Asp
                325                 330                 335
```

```
Ala Val Leu Pro Asn Lys Ala Pro Thr Tyr Asp Ala Met Val Gln
            340                 345                 350

Met Glu Tyr Leu Asp Met Val Asn Glu Thr Leu Arg Leu Phe Pro
            355                 360                 365

Ile Ala Ile Arg Leu Glu Arg Ala Cys Lys Lys Asp Val Glu Ile Asn
370                 375                 380

Gly Val Phe Ile Pro Lys Gly Ala Met Val Val Ile Pro Thr Tyr Ala
385                 390                 395                 400

Leu His His Asp Pro Lys Tyr Trp Thr Glu Pro Glu Phe Arg Pro
            405                 410                 415

Glu Arg Phe Ser Lys Lys Asn Lys Asp Ser Ile Asp Pro Tyr Ile Tyr
            420                 425                 430

Thr Pro Phe Gly Ser Gly Pro Arg Asn Cys Ile Gly Met Arg Phe Ala
            435                 440                 445

Leu Met Asn Met Lys Leu Ala Ile Ile Lys Val Leu Gln Asn Phe Ser
450                 455                 460

Phe Lys Pro Cys Lys Glu Thr Gln Ile Pro Leu Lys Leu Gly Asn Gln
465                 470                 475                 480

Gly Leu Leu Gln Ser Glu Lys Pro Ile Val Leu Lys Val Glu Ser Arg
                485                 490                 495

Asp Gly Thr Leu Ser Gly Glu
            500

<210> SEQ ID NO 45
<211> LENGTH: 1533
<212> TYPE: DNA
<213> ORGANISM: Macaca fascicularis

<400> SEQUENCE: 45
aagcttaaaa tggacttgat cccaaacttg ctatggaaaa cttggttgtt gttggctgtt     60
tctttggtct tgttgtactt gtacggtact agatcttacg gtttgttcaa gagacaaggt    120
attccaggtc aactccatt gccatttttg ggtaacattt tgtcctacag acaaggcttg     180
tggaagttcg atactgaatg ctataagaaa tacggcaaga tgtggcgtac tcaagatggt    240
caattgccag ttttgactat taccgatcca gatatgatca agaccgtctt ggtcaaagaa    300
tgctactctg ttttcactaa cagaaggcca ttgggtccag ttggtttgat gaagtctgct    360
atttctattg ccgaagatga agaatggaag aggatcagat ctttgttgtc tccaactttc    420
acttccggca aattgaaaga atgttcccca attattgccc agtacggtga tatgttggtt    480
agaaacttga agagaagcc gaaaaaggt aagccagtta ccttgaagga tattttcggt    540
gcttactcca tggacgttat tacttctact tctttcggtg tcaacatcga cagttttgaac    600 aatccaaagg atccattcgt tgagagcgtt aagaagtttt tgaagttcga cttttttggac    660 cccttgttct tgttgactat tctgttccca tttttgattc cagctttcga agccttgaac    720
gtttctttgt ttccaaagga cgctatcaac ttcctgaaca agtctgttaa ctccatgaag    780
aagtctaggt tgaacgataa gcaaaagcac agggttgatt tcttgcagtt gatgatcgat    840
tcccagaact ctaaagaaac cgaatctcat aaggctttgt ccgatcaaga attggttgcc    900
caatccatca ttttcatttt cgctggttac gaaaccacct cctctgtttt gtctttcatc    960
atctatgaat ggctaccca tccagatgtc aacaaaagt tgcaaaaaga aatcgatgcc   1020
gtcttgccaa acaagctcc agctactat gatgctatgg tccaaatgga atacttggat   1080
atggttgtca acgaaacctt gaggttgttc cctattgcta tcagattgga aagggcttgc   1140
```

```
aaaaaagatg tcgaaatcaa cggtgttttc attccaaaag gtgccatggt tgttattcca    1200
acttacgcat tgcatcacga tccaaagtat tggactgaac cagaagaatt cagaccagaa    1260
agattctcca agaaaaacaa ggattccatc gatccttaca tctacactcc atttggttct    1320
ggtccaagaa actgtatcgg tatgagattt gctctgatga acatgaagtt ggccattatt    1380
aaggtcctgc agaacttctc tttcaaacca tgcaagaaa  cccagattcc attgaagttg    1440
ggtaatcaag gtctgttgca atctgaaaag ccaatcgttt tgaaggttga atccagagat    1500
ggtactttgt ctggtgagta aaagactccg cgg                                 1533
```

<210> SEQ ID NO 46
<211> LENGTH: 503
<212> TYPE: PRT
<213> ORGANISM: Callithrix jacchus

<400> SEQUENCE: 46

```
Met Asp Leu Ile Pro Asn Leu Ala Val Glu Thr Trp Leu Leu Leu Ala
1               5                   10                  15

Leu Ser Leu Val Leu Leu Tyr Leu Tyr Gly Thr Arg Ser His Gly Ile
            20                  25                  30

Phe Lys Lys Leu Gly Ile Pro Gly Pro Ala Pro Leu Pro Phe Val Gly
        35                  40                  45

Asn Ile Leu Ser Tyr Arg Gln Gly Ile Trp Lys Phe Asp Ser Glu Cys
    50                  55                  60

His Lys Lys Tyr Gly Lys Met Trp Gly Ser Tyr Asp Gly Gln Leu Pro
65                  70                  75                  80

Val Leu Ala Ile Thr Asp Pro Asp Ile Lys Ala Val Leu Val Lys
                85                  90                  95

Glu Cys Tyr Ser Ile Phe Thr Asn Arg Arg Pro Leu Gly Pro Val Gly
            100                 105                 110

Phe Met Lys Ser Ala Ile Thr Val Ala Gln Asp Asp Glu Trp Lys Arg
        115                 120                 125

Ile Arg Ser Leu Leu Ser Pro Thr Phe Thr Ser Gly Lys Leu Lys Glu
    130                 135                 140

Met Phe Pro Ile Ile Ala Gln Tyr Gly Asp Val Leu Val Arg Asn Leu
145                 150                 155                 160

Arg Arg Glu Ala Gly Lys Gly Lys Pro Val Thr Met Lys Asp Ile Phe
                165                 170                 175

Gly Ala Tyr Ser Met Asp Val Ile Thr Gly Thr Ser Phe Gly Val Asn
            180                 185                 190

Ile Asp Ser Leu Asn Asn Pro Lys Asp Pro Phe Val Glu Ser Val Lys
    195                 200                 205

Lys Phe Leu Lys Phe Asp Phe Leu Asp Pro Leu Phe Leu Ser Thr Ile
    210                 215                 220

Phe Phe Pro Phe Leu Thr Pro Val Phe Glu Ala Leu Asn Phe Ser Leu
225                 230                 235                 240

Phe Pro Lys Asp Ala Ile Asn Phe Leu Lys Gln Ser Val Asn Arg Met
                245                 250                 255

Lys Lys Ser Arg Leu Asn Asp Lys Gln Lys His Arg Val Asp Phe Leu
            260                 265                 270

Gln Leu Met Ile Asp Ser Gln Asn Ser Asn Glu Thr Ala Ser His Lys
    275                 280                 285

Ala Leu Ser Asp Leu Glu Leu Leu Ala Gln Ser Ile Ile Phe Ile Phe
    290                 295                 300
```

Ala Gly Tyr Glu Thr Thr Ser Ser Val Leu Ser Phe Thr Ile Tyr Glu
305                 310                 315                 320

Leu Ala Thr Asn Pro Asp Val Gln Gln Lys Leu Gln Glu Glu Ile Asp
            325                 330                 335

Val Val Leu Pro Asn Lys Ala Pro Ala Thr Tyr Asp Ala Val Val Gln
            340                 345                 350

Met Glu Tyr Leu Asp Met Val Val Asn Glu Thr Leu Arg Leu Tyr Pro
        355                 360                 365

Ile Ala Val Arg Leu Glu Arg Val Cys Lys Lys Asp Val Glu Ile Asn
370                 375                 380

Gly Val Phe Ile Pro Lys Gly Ala Leu Val Val Ile Pro Thr Tyr Ala
385                 390                 395                 400

Leu His His Asp Pro Lys Tyr Trp Thr Glu Pro Lys Glu Phe Arg Pro
                405                 410                 415

Glu Arg Phe Ser Lys Lys Asn Lys Asp Ser Ile Asp Pro Tyr Ile Tyr
            420                 425                 430

Thr Pro Phe Gly Thr Gly Pro Arg Asn Cys Ile Gly Met Arg Phe Ala
        435                 440                 445

Leu Met Asn Met Lys Leu Ala Leu Ile Arg Val Leu Gln Asn Phe Ser
    450                 455                 460

Phe Lys Pro Cys Lys Glu Thr Gln Ile Pro Leu Lys Leu Gly Val Gln
465                 470                 475                 480

Gly Leu Leu Gln Ala Glu Lys Pro Ile Ile Leu Lys Val Glu Ser Arg
                485                 490                 495

Asp Gly Thr Leu Ser Gly Glu
            500

<210> SEQ ID NO 47
<211> LENGTH: 1514
<212> TYPE: DNA
<213> ORGANISM: Callithrix jacchus

<400> SEQUENCE: 47

```
aagcttaaaa tggacttgat cccaaacttg gctgttgaaa cttggttgtt attggccttg      60
tctttggtct tgttgtactt gtatggtact agatcccatg gcatctttaa gaagttgggt     120
attccaggtc cagctccatt gccatttgtt ggtaacattt tgtcttacag caaggcatt     180
tggaagttcg attctgaatg ccataagaaa tacggtaaga tgtggggttc ttacgatggt     240
caattgccag ttttggctat tactgatcca gatattatca aggccgtctt ggtcaaagaa     300
tgctactctg tttttaccaa cagaaggcca tttggtccag ttggtttgat gaagtctgct     360
atttctttgg cccaagatga tgaatggaag agaatcagat ctttgttgtc tccaactttc     420
acctccggta agttgaaaga aatgttccca attattgccc aatacggtga tgttttggtc     480
agaaacttga agagaagc tggtaaaggt aagccagtta ccatgaagga tattttcggt     540
gcttactcca tggatgttat taccggtact tctttcggtg tcaacatcga ttctttgaac     600
aatccaaagg atcccttcgt tgaatctgtc aagaagtttt tgaagtttga cttcttggac     660
cccttgttct tgtctactat tttctttcca ttcttgacgc cagttttcga agccttgaat     720
tttagcttgt tcccaaagga tgctatcaac ttcctgaagc aatccgttaa caggatgaag     780
aagtctagat tgaacgacaa gcaaaagcac agggttgatt tcttgcaact gatgatcgat     840
tcccagaact ctaacgaaac tgcttctcat aaggctttgt ctgatttgga attgctggcc     900
caatccatta ttttcatttt cgctggttac gaaaccacct cctctgtttt gtcttttacc     960
```

```
atctatgaat tggccaccaa tccagatgtt caacagaaat tgcaagaaga aatcgacgtt    1020
gtcttgccaa acaaagctcc agctacttat gatgctgttg tccaaatgga atacttggat    1080
atggttgtca acgaaacctt gaggttgtat ccaattgctg tcagattgga aagggtctgc    1140
aaaaaggatg ttgaaatcaa cggtgttttc attccaaagg gtgctttagt tgttattcca    1200
acttacgcct tgcatcacga tcctaaatat tggactgaac ccaaagaatt cagaccagaa    1260
agattctcca agaaaaacaa ggattccatc gatccttaca tctacactcc atttggtact    1320
ggtcctagaa actgtattgg tatgagattc gctctgatga acatgaagtt ggccttgatt    1380
agagtgttgc agaacttctc tttcaaaccc tgtaaagaaa cccagattcc attgaaattg    1440
ggtgtccaag gtttgttgca agctgaaaaa cctatcatct tgaaggttga atccagagat    1500
ggtactttgt ctgg                                                      1514
```

<210> SEQ ID NO 48
<211> LENGTH: 134
<212> TYPE: PRT
<213> ORGANISM: Homo sapiens

<400> SEQUENCE: 48

```
Met Ala Glu Gln Ser Asp Glu Ala Val Lys Tyr Tyr Thr Leu Glu Glu
1               5                   10                  15

Ile Gln Lys His Asn His Ser Lys Ser Thr Trp Leu Ile Leu His His
            20                  25                  30

Lys Val Tyr Asp Leu Thr Lys Phe Leu Glu Glu His Pro Gly Gly Glu
        35                  40                  45

Glu Val Leu Arg Glu Gln Ala Gly Gly Asp Ala Thr Glu Asn Phe Glu
    50                  55                  60

Asp Val Gly His Ser Thr Asp Ala Arg Glu Met Ser Lys Thr Phe Ile
65                  70                  75                  80

Ile Gly Glu Leu His Pro Asp Asp Arg Pro Lys Leu Asn Lys Pro Pro
                85                  90                  95

Glu Thr Leu Ile Thr Thr Ile Asp Ser Ser Ser Ser Trp Trp Thr Asn
            100                 105                 110

Trp Val Ile Pro Ala Ile Ser Ala Val Ala Val Ala Leu Met Tyr Arg
        115                 120                 125

Leu Tyr Met Ala Glu Asp
        130
```

<210> SEQ ID NO 49
<211> LENGTH: 419
<212> TYPE: DNA
<213> ORGANISM: Homo sapiens

<400> SEQUENCE: 49

```
aagcttaaaa tggccgagca atctgatgaa gcagtgaagt actacacatt agaagagata     60
caaaaacaca accattcaaa aagcacttgg ctcattctac accataaagt ttatgatttg    120
actaagtttt tggaggaaca tccaggaggt gaagaggtcc ttagagaaca ggcaggcggt    180
gacgctactg aaaactttga agatgttggg cattcaaccg acgctagaga aatgagtaaa    240
actttcatta ttggtgaact tcacccagat gacagaccaa aactgaataa gcctcctgaa    300
acactaataa cgacaatcga ttcttcctct tcatggtgga caaattgggt tatcccagcg    360
atctctgccg tcgctgtagc attaatgtat aggttgtaca tggctgaaga ttaaccgcg     419
```

```
<210> SEQ ID NO 50
<211> LENGTH: 677
<212> TYPE: PRT
<213> ORGANISM: homo sapiens

<400> SEQUENCE: 50

Met Gly Asp Ser His Val Asp Thr Ser Ser Val Ser Glu Ala Val
1               5                   10                  15

Ala Glu Val Ser Leu Phe Ser Met Thr Asp Met Ile Leu Phe Ser
            20                  25                  30

Leu Ile Val Gly Leu Leu Thr Tyr Trp Phe Leu Phe Arg Lys Lys
        35                  40                  45

Glu Glu Val Pro Glu Phe Thr Lys Ile Gln Thr Leu Thr Ser Ser Val
50                  55                  60

Arg Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Asn Ala Leu Val Val Phe Cys Met Ala Thr Tyr Gly Glu Gly Asp
130                 135                 140

Pro Thr Asp Asn Ala Gln Asp Phe Tyr Asp Trp Leu Gln Glu Thr Asp
145                 150                 155                 160

Val Asp Leu Ser Gly Val Lys Phe Ala Val Phe Gly Leu Gly Asn Lys
                165                 170                 175

Thr Tyr Glu His Phe Asn Ala Met Gly Lys Tyr Val Asp Lys Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
210                 215                 220

Pro Ala Val Cys Glu His Phe Gly Val Glu Ala Thr Gly Glu Glu Ser
225                 230                 235                 240

Ser Ile Arg Gln Tyr Glu Leu Val Val His Thr Asp Ile Asp Ala Ala
                245                 250                 255

Lys Val Tyr Met Gly Glu Met Gly Arg Leu Lys Ser Tyr Glu Asn Gln
            260                 265                 270

Lys Pro Pro Phe Asp Ala Lys Asn Pro Phe Leu Ala Ala Val Thr Thr
        275                 280                 285

Asn Arg Lys Leu Asn Gln Gly Thr Glu Arg His Leu Met His Leu Glu
290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Ala Leu Val Asn Gln Leu Gly Lys
                325                 330                 335

Ile Leu Gly Ala Asp Leu Asp Val Val Met Ser Leu Asn Asn Leu Asp
            340                 345                 350

Glu Glu Ser Asn Lys Lys His Pro Phe Pro Cys Pro Thr Ser Tyr Arg
        355                 360                 365

Thr Ala Leu Thr Tyr Tyr Leu Asp Ile Thr Asn Pro Pro Arg Thr Asn
370                 375                 380
```

```
Val Leu Tyr Glu Leu Ala Gln Tyr Ala Ser Glu Pro Ser Glu Gln Glu
385                 390                 395                 400

Leu Leu Arg Lys Met Ala Ser Ser Gly Glu Gly Lys Glu Leu Tyr
            405                 410                 415

Leu Ser Trp Val Val Glu Ala Arg Arg His Ile Leu Ala Ile Leu Gln
            420                 425                 430

Asp Cys Pro Ser Leu Arg Pro Pro Ile Asp His Leu Cys Glu Leu Leu
            435                 440                 445

Pro Arg Leu Gln Ala Arg Tyr Tyr Ser Ile Ala Ser Ser Lys Val
        450                 455                 460

His Pro Asn Ser Val His Ile Cys Ala Val Val Glu Tyr Glu Thr
465                 470                 475                 480

Lys Ala Gly Arg Ile Asn Lys Gly Val Ala Thr Asn Trp Leu Arg Ala
                485                 490                 495

Lys Glu Pro Ala Gly Glu Asn Gly Gly Arg Ala Leu Val Pro Met Phe
            500                 505                 510

Val Arg Lys Ser Gln Phe Arg Leu Pro Phe Lys Ala Thr Thr Pro Val
        515                 520                 525

Ile Met Val Gly Pro Gly Thr Gly Val Ala Pro Phe Ile Gly Phe Ile
        530                 535                 540

Gln Glu Arg Ala Trp Leu Arg Gln Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Gln Phe His Arg Asp Gly Ala Leu Thr Gln Leu Asn
            580                 585                 590

Val Ala Phe Ser Arg Glu Gln Ser His Lys Val Tyr Val Gln His Leu
        595                 600                 605

Leu Lys Gln Asp Arg Glu His Leu Trp Lys Leu Ile Glu Gly Gly Ala
        610                 615                 620

His Ile Tyr Val Cys Gly Asp Ala Arg Asn Met Ala Arg Asp Val Gln
625                 630                 635                 640

Asn Thr Phe Tyr Asp Ile Val Ala Glu Leu Gly Ala Met Glu His Ala
                645                 650                 655

Gln Ala Val Asp Tyr Ile Lys Lys Leu Met Thr Lys Gly Arg Tyr Ser
            660                 665                 670

Leu Asp Val Trp Ser
        675

<210> SEQ ID NO 51
<211> LENGTH: 2040
<212> TYPE: DNA
<213> ORGANISM: homo sapiens

<400> SEQUENCE: 51
taaaatgggt gattcacatg ttgatacatc ttctacagtt tcagaagctg ttgctgaaga      60
agtttcttta ttttcaatga ctgatatgat tttgttttca ttaattgttg gtttgttgac     120
atattggttc ttgtttagaa agaagaagga agaagttcca gaattactaa gattcaaac     180 cttgacatct tcagttagag aatcatcttt tgttgaaaag atgaagaaga ctggtagaaa     240
tattattgtt ttctacggtt ctcaaactgg tactgctgaa gaatttgcta acagattgtc     300
aaaggatgca catagatatg gtatgagagg tatgtctgct gatcctgaag aatatgattt     360
agcagattta tcttcattgc ctgaaattga taatgcttta gttgtttcct gtatggctac     420
```

| | |
|---|---|
| ttatggtgaa ggtgatccta ctgataacgc tcaagatttt tatgattggt tgcaagaaac | 480 |
| tgatgttgat ttatctggtg ttaagttcgc tgttttcggt ttgggtaata agacttatga | 540 |
| acatttcaac gctatgggta aatacgttga taaaagattg aacaattggg gtgctcaaag | 600 |
| aattttgaa ttaggtttgg gtgatgatga tggtaactta aagaagatt ttattacatg | 660 |
| gagagaacaa ttttggcctg cagtttgtga acatttcggt gttgaagcta ccggtgaaga | 720 |
| atcatctatt agacaatatg aattggttgt tcatacagat attgatgctg ctaaagttta | 780 |
| catgggtgaa atgggtagat tgaaatcata tgaaaatcaa aagccacctt tcgatgctaa | 840 |
| gaatcctttc ttagctgcag ttacaacaaa cagaaagttg aatcaaggta cagaaagaca | 900 |
| tttgatgcat ttggaattgg atatttctga ttcaaaaatt agatacgaat ctggtgatca | 960 |
| tgttgctgtt tatccagcta atgattctgc tttagttaac caattaggta aaattttggg | 1020 |
| tgctgattta gatgttgtta tgtctttaaa taacttagat gaagaatcta caagaaaaca | 1080 |
| tccattccca tgtcctactt catacagaac agctttaact tattatttag atattacaaa | 1140 |
| ccctccaaga actaatgttt tgtatgaatt ggctcaatat gcatctgaac cttctgaaca | 1200 |
| agaattgtta agaaaaatgg cttcttcatc tggtgaaggt aaagaattat acttgtcatg | 1260 |
| ggttgttgaa gctagaagac atattttagc aattttacaa gattgtccat cattgagacc | 1320 |
| accaattgat catttgtgtg aattgttgcc tagattacaa gctagatatt attctattgc | 1380 |
| atcatcttct aaagttcatc caaattcagt tcatatttgt gctgttgttg ttgaatatga | 1440 |
| aactaaggct ggtagaatta acaaaggtgt tgcaactaat tggttgagag ctaaggaacc | 1500 |
| tgctggtgaa atggtggta gagcattagt tccaatgttc gttagaaagt ctcaatttag | 1560 |
| attgccattt aaagctacta caccagttat tatggttggt cctggtacag gtgttgctcc | 1620 |
| ttttattggt ttcattcaag aaagagcatg gttaagacaa caaggtaagg aagttggtga | 1680 |
| aacattatta tattacggtt gtagaagatc agatgaagat tatttgtaca gagaagaatt | 1740 |
| agcacaattc catagagatg gtgctttgac acaattgaat gttgcttttt caagagaaca | 1800 |
| atctcataaa gtttatgttc aacatttgtt gaaacaagat agagaacatt tatggaagtt | 1860 |
| gattgaaggt ggtgcacata tttatgtttg tggtgatgct agaacatgg caagagatgt | 1920 |
| tcaaaataca ttctatgata ttgttgctga attaggtgct atggaacatg cacaagcagt | 1980 |
| tgattacatt aagaaattga tgacaaaagg tagatattct ttggatgttt ggtcttaacc | 2040 |

<210> SEQ ID NO 52
<211> LENGTH: 1572
<212> TYPE: DNA
<213> ORGANISM: Mucor circinelloides

<400> SEQUENCE: 52

| | |
|---|---|
| atgactttga ttgcttctta taatcaaact ttgttggaaa gagttatttc tgttgttaga | 60 |
| aaaaataaaa cttcttatat tggtatggct attttgtgtg ttgttttgca acaagtttat | 120 |
| gcttctttta ctgttccacc aaaatatttg agaagatacc caactgtttc ttttttttgaa | 180 |
| atgatgaaat cttttttatag aaaagaatct gttttgaata gaaataaaag attggttact | 240 |
| ccattgacta tgctggtca tggtttttat gtttgtagaa taccattgga ttggactatt | 300 |
| tatgttactg atccaattgc tgctaaaact tgttgttga aaactgataa ttttccaaaa | 360 |
| tctcatgcta ttttttggtgc tttgggtgaa tcttctccag cagttaaatt tatgggttct | 420 |
| gaaaatgttt ctgtttctaa tggtgaaatg tggaaaaaac aaagaaaaat tatgaatcca | 480 |
| gcttttcata gatctcaacc agttaaattg tttggtggtg ttatgccaga tttgtttgct | 540 |

-continued

```
ttgattgatc aagatccaga acatgttttt gttgctccaa gaatgaaatc ttttgctttg      600
gatgctttgg gtttgtctgc ttttggtttt gattttcaat ctttgaaagg tgatccagaa      660
ggttggactt ctaaatataa tactgttatt tctactttgt ttaatccatt tattaatttg      720
tttgctaaat atgattttt gattaaatat atttctccag aaagaagaag agttattaaa       780
gctactgatg aatttaatgt tatgttgtct aatttggctg ataaaagaag acaagaaatt      840
ttggatggtg aaaaaaaga tatggctgaa atgaaaaag atttgttgac tttgatgatt       900
gaagctgata ttagagaagg tgttgaaact actactactg aattgagaca taatatggct      960 atttttttt tggctggtca tgatactact gctaatactt tggctttgtg tttgtatcaa      1020
ttggctaaac ataaacatgt tcaaaaaaaa gctagacaag aagttttgga tattttgggt     1080
gatgatccat gtgatgttac tccaactttg gaagatttga aaaaattgaa ttatgttaat     1140
atggttatta agaaaatttt gagaagaaat tctccagttg ataatttgat ggctagagat     1200
actcatcaag atattgattt gaatggtact tttattccaa aaggttctaa agttactgtt     1260
aatgttgctt ctattcattt gaatccaaaa atttggcatg atccagaatc ttttattcca     1320
gaaagatttg aaccaggtgg tgaatatgat ggtcatgatg gttttacttg gattccattt     1380
tctaatggtt ctagacaatg tttgggtttg aattttcttt tgactgaaca aagagttgtt      1440
ttgtgtatgt tgttgaaaag atatgaaatt gaaattccaa aagattctat tcattataat    1500
gaaattgttt ttgataaacc atttacttttt gctccacaat ctttggaatt gtcttttaaa  1560
aaaagatatt ag                                                          1572
```

<210> SEQ ID NO 53
<211> LENGTH: 523
<212> TYPE: PRT
<213> ORGANISM: Mucor Circinelloides

<400> SEQUENCE: 53

```
Met Thr Leu Ile Ala Ser Tyr Asn Gln Thr Leu Leu Glu Arg Val Ile
1               5                   10                  15

Ser Val Arg Lys Asn Lys Thr Ser Tyr Ile Gly Met Ala Ile Leu
            20                  25                  30

Cys Val Val Leu Gln Gln Val Tyr Ala Ser Phe Thr Val Pro Pro Lys
        35                  40                  45

Tyr Leu Arg Arg Tyr Pro Thr Val Ser Phe Phe Glu Met Met Lys Ser
    50                  55                  60

Phe Tyr Arg Lys Glu Ser Val Leu Asn Arg Asn Lys Arg Leu Val Thr
65                  70                  75                  80

Pro Leu Thr Asn Ala Gly His Gly Phe Tyr Val Cys Arg Ile Pro Leu
                85                  90                  95

Asp Trp Thr Ile Tyr Val Thr Asp Pro Ile Ala Ala Lys Thr Leu Leu
            100                 105                 110

Leu Lys Thr Asp Asn Phe Pro Lys Ser His Ala Ile Phe Gly Ala Leu
        115                 120                 125

Gly Glu Ser Ser Pro Ala Val Lys Phe Met Gly Ser Glu Asn Val Ala
    130                 135                 140

Val Ser Asn Gly Glu Met Trp Lys Lys Gln Arg Lys Ile Met Asn Pro
145                 150                 155                 160

Ala Phe His Arg Ser Gln Pro Val Lys Leu Phe Gly Gly Val Met Pro
                165                 170                 175

Asp Leu Phe Ala Leu Ile Asp Gln Asp Pro Glu His Val Phe Val Ala
```

```
              180                 185                 190
Pro Arg Met Lys Ser Phe Ala Leu Asp Ala Leu Gly Leu Ser Ala Phe
            195                 200                 205

Gly Phe Asp Phe Gln Ser Leu Lys Gly Asp Pro Glu Gly Trp Thr Ser
        210                 215                 220

Lys Tyr Asn Thr Val Ile Ser Thr Leu Phe Asn Pro Phe Ile Asn Leu
225                 230                 235                 240

Phe Ala Lys Tyr Asp Phe Leu Ile Lys Tyr Ile Ser Pro Glu Arg Arg
                245                 250                 255

Arg Val Ile Lys Ala Thr Asp Glu Phe Asn Val Met Leu Ser Asn Leu
            260                 265                 270

Ala Asp Lys Arg Arg Gln Glu Ile Leu Asp Gly Glu Lys Lys Asp Met
        275                 280                 285

Ala Glu Asn Glu Lys Asp Leu Leu Thr Leu Met Ile Glu Ala Asp Ile
    290                 295                 300

Arg Glu Gly Val Glu Thr Thr Thr Thr Glu Leu Arg His Asn Met Ala
305                 310                 315                 320

Ile Phe Phe Leu Ala Gly His Asp Thr Thr Ala Asn Thr Leu Ala Leu
                325                 330                 335

Cys Leu Tyr Gln Leu Ala Lys His Lys His Val Gln Lys Lys Ala Arg
            340                 345                 350

Gln Glu Val Leu Asp Ile Leu Gly Asp Asp Pro Cys Asp Val Thr Pro
        355                 360                 365

Thr Leu Glu Asp Leu Lys Lys Leu Asn Tyr Val Asn Met Val Ile Lys
    370                 375                 380

Glu Asn Leu Arg Arg Asn Ser Pro Val Asp Asn Leu Met Ala Arg Asp
385                 390                 395                 400

Thr His Gln Asp Ile Asp Leu Asn Gly Thr Phe Ile Pro Lys Gly Ser
                405                 410                 415

Lys Val Thr Val Asn Val Ala Ser Ile His Leu Asn Pro Lys Ile Trp
            420                 425                 430

His Asp Pro Glu Ser Phe Ile Pro Glu Arg Phe Glu Pro Gly Gly Glu
        435                 440                 445

Tyr Asp Gly His Asp Gly Phe Thr Trp Ile Pro Phe Ser Asn Gly Ser
    450                 455                 460

Arg Gln Cys Leu Gly Leu Asn Phe Ser Leu Thr Glu Gln Arg Val Val
465                 470                 475                 480

Leu Cys Met Leu Leu Lys Arg Tyr Glu Ile Glu Ile Pro Lys Asp Ser
                485                 490                 495

Ile His Tyr Asn Glu Ile Val Phe Asp Lys Pro Phe Thr Phe Ala Pro
            500                 505                 510

Gln Ser Leu Glu Leu Ser Phe Lys Lys Arg Tyr
        515                 520

<210> SEQ ID NO 54
<211> LENGTH: 1542
<212> TYPE: DNA
<213> ORGANISM: Lichtheimia corymbifera

<400> SEQUENCE: 54
atgactgaaa ttaaagatca tatttataga tatagacatt atattggtgt tgctgctgct      60
gttttgttgg tttgtcaaca agtttatcat agaattttta gaataccaaa aaatttgaga     120
catttgccag ctattccata cggtaaacaa ttgaaagcat tgcaatctca agaaaatttg     180
```

```
atttctagaa ctcaaagatt ggttttccca ttgttgccaa aagctcatgg tgtttatttg    240
aatagaatgc catttcaatg gactatttat gttgctgatc cagaaattgc tagaattgtt    300
ttttttaaac cagaatttgc taataaaact tcttctgttt tggattctat tgatcaaaat    360
actactttga ttgaatttgt tggtaatgat aatgtttcta ttgttaatgg tcatcattgg    420
aaagatcaaa gaaaaattat gaatccagct tttcatagag ctactccagt tggtatgttt    480
ggttctttga tgccaaaagt ttttagattg gttgaagaac aaccaactgt tccagttttg    540
gaattgatgc aaaaattgac tttggatgct ttgggtaaat ctgtttttgg ttttgatttt    600
ggtggtttgg atgatccaga ttctgtttgg gttaaaactt atagattgtt gtttgatggt    660
tttactaatg ttattccatt ggttttccca agattggatg gtttgtatag atattttttct   720 gctaaaagaa gagcacaaca tgatgctgtt tataaattga ttgatttgtt ggatggtgtt    780
gctgataaaa aaagatctat gttgcaagat gattctaatt ctcataatga tgttccagaa    840
catgaaaaag atttgttgca attgatgttg gaagctgaat tgagaggtga aggtaattgg    900
actaaaaaag aattgagaca taatatggct attttttttg ttgctggtca tgatactact    960
tctcatgctt tgacttttg tttgtatttg ttggctatga atcaagatat tcaaaaaaaa  1020
gctagagaag aaatttgag agttttggt gatgaaccaa agatgtttt tccaactttg  1080 gaagattgta aaaaattgga ttatttggat atggttatta agaatctat gagaatttat    1140 ccaccagcta atgatatttt ggctagagat gttcatgaag atttgaatgt taaaggtatt    1200
tttattccaa aaggtgctat ggtttctgtt gatattcaag cattgcatca tagaccagat    1260
ttgtggcatg aaccagaaaa atttaatcca gatagatttt tgccaggtgg tgaacatgat    1320
tctcatgaag gtattgctta tgctccattt tcttctggtg ctagacaatg tattgctttg    1380
aaattttcta ttatgcaaca aagagttgtt ttggctatgt tgttgagaaa atttgaatgg    1440
gaattgccaa agaatctaa acataaagat ggtattcaat ttgaaattcc atttaatttg    1500
gctccaaaag atttggaatt gattttcat aaaagatatt ag                       1542
```

<210> SEQ ID NO 55
<211> LENGTH: 513
<212> TYPE: PRT
<213> ORGANISM: Lichtheimia corymbifera

<400> SEQUENCE: 55

Met Thr Glu Ile Lys Asp His Ile Tyr Arg Tyr Arg His Tyr Ile Gly
1               5                   10                  15

Val Ala Ala Val Leu Leu Val Cys Gln Gln Val Tyr His Arg Ile
            20                  25                  30

Phe Arg Ile Pro Lys Asn Leu Arg His Leu Pro Ala Ile Pro Tyr Gly
        35                  40                  45

Lys Gln Leu Lys Ala Leu Gln Ser Gln Glu Asn Leu Ile Ser Arg Thr
    50                  55                  60

Gln Arg Leu Val Phe Pro Leu Leu Pro Lys Ala His Gly Val Tyr Leu
65                  70                  75                  80

Asn Arg Met Pro Phe Gln Trp Thr Ile Tyr Val Ala Asp Pro Glu Ile
                85                  90                  95

Ala Arg Ile Val Phe Phe Lys Pro Glu Phe Ala Asn Lys Thr Ser Ser
            100                 105                 110

Val Leu Asp Ser Ile Asp Gln Asn Thr Thr Leu Ile Glu Phe Val Gly
        115                 120                 125

Asn Asp Asn Val Ser Ile Val Asn Gly His His Trp Lys Asp Gln Arg

```
            130                 135                 140
Lys Ile Met Asn Pro Ala Phe His Arg Ala Thr Pro Val Gly Met Phe
145                 150                 155                 160

Gly Ser Leu Met Pro Lys Val Phe Arg Leu Val Glu Glu Gln Pro Thr
                165                 170                 175

Val Pro Val Leu Glu Leu Met Gln Lys Leu Thr Leu Asp Ala Leu Gly
                180                 185                 190

Lys Ser Val Phe Gly Phe Asp Phe Gly Gly Leu Asp Asp Pro Asp Ser
                195                 200                 205

Val Trp Val Lys Thr Tyr Arg Leu Leu Phe Asp Gly Phe Thr Asn Val
210                 215                 220

Ile Pro Leu Val Phe Pro Arg Leu Asp Gly Leu Tyr Arg Tyr Phe Ser
225                 230                 235                 240

Ala Lys Arg Arg Ala Gln His Asp Ala Val Tyr Lys Leu Ile Asp Leu
                245                 250                 255

Leu Asp Gly Val Ala Asp Lys Lys Arg Ser Met Leu Gln Asp Asp Ser
                260                 265                 270

Asn Ser His Asn Asp Val Pro Glu His Glu Lys Asp Leu Leu Gln Leu
                275                 280                 285

Met Leu Glu Ala Glu Leu Arg Gly Glu Gly Asn Trp Thr Lys Lys Glu
                290                 295                 300

Leu Arg His Asn Met Ala Ile Phe Phe Val Ala Gly His Asp Thr Thr
305                 310                 315                 320

Ser His Ala Leu Thr Phe Cys Leu Tyr Leu Leu Ala Met Asn Gln Asp
                325                 330                 335

Ile Gln Lys Lys Ala Arg Glu Glu Ile Leu Arg Val Leu Gly Asp Glu
                340                 345                 350

Pro Lys Asp Val Phe Pro Thr Leu Glu Asp Cys Lys Lys Leu Asp Tyr
                355                 360                 365

Leu Asp Met Val Ile Lys Glu Ser Met Arg Ile Tyr Pro Pro Ala Asn
                370                 375                 380

Asp Ile Leu Ala Arg Asp Val His Glu Asp Leu Asn Val Lys Gly Ile
385                 390                 395                 400

Phe Ile Pro Lys Gly Ala Met Val Ser Val Asp Ile Gln Ala Leu His
                405                 410                 415

His Arg Pro Asp Leu Trp His Glu Pro Glu Lys Phe Asn Pro Asp Arg
                420                 425                 430

Phe Leu Pro Gly Gly Glu His Asp Ser His Glu Gly Ile Ala Tyr Ala
                435                 440                 445

Pro Phe Ser Ser Gly Ala Arg Gln Cys Ile Ala Leu Lys Phe Ser Ile
                450                 455                 460

Met Gln Gln Arg Val Val Leu Ala Met Leu Leu Arg Lys Phe Glu Trp
465                 470                 475                 480

Glu Leu Pro Lys Glu Ser Lys His Lys Asp Gly Ile Gln Phe Glu Ile
                485                 490                 495

Pro Phe Asn Leu Ala Pro Lys Asp Leu Glu Leu Ile Phe His Lys Arg
                500                 505                 510

Tyr

<210> SEQ ID NO 56
<211> LENGTH: 1593
<212> TYPE: DNA
<213> ORGANISM: Lichtheimia corymbifera
```

<400> SEQUENCE: 56

```
atgtcttctt tgaatatttt gtctttgttg gataataaac atattaatgc ttttttttgat      60
aatccatcta gagcacaatc tggtattatt gctggttctg ttgctattgt ttctttgtgt     120
gctgcttatt ctttgggttc tagattgaga ggttctaata atggtgttcc attggttcca     180
tatactttc caattattgg ttctactaaa gaatatcaag ctgatccaca agcatttatt      240
gaaaaatgga ctgctaaatt gggtccagtt tttagagttc atttgtttgg tagaatacat     300
actgttgttt ctgatagata tgttagagaa gttttttga ataatgattt tgatttttttg    360
aaaggtactg gtaaaagatt tgatactttg ttgttgactg atactacttt ggaagatgtt     420
gatattgaag ttttttagaac tgttgttatg aaacatttga ctaaagaaat gaaacattat    480
actccaagag ttgttgaaca tttgactgct ggtggtgatg aaaaattggg tgatgctact     540
gaaccaaaag aattggttca tttgtttcca ttgttgcaac acatggttgc taaagcatct    600
gcttctattt tgttggtac tgaattggct gctgatgatg ctgttgttga aacttgtaaa     660
aatattgcta ttgatattgg ttctgaattg ggtccatctt cttatattat ggatgctttt    720
ccatctttgg ctagattgag aatgtggtat attggtaaat atggtaaagc tattaataaa    780
catagacaac atttgttgca cgctttgggt ccagttattg ataaaagatt ggctgctgct    840
gaaaaaggtg gtgattggga tagaccacaa gatatttttgc aagatattat tgaaactatt    900
aatttgactt tggataatcc aaaaagacat attttgccag ttaaatggtt gttggctttg    960
ttttttgctt ctattcatac tacttctgaa aattctacta ttgttttgta tagaattatg   1020
caaaatccag aaattattga tgttttgttg gaagaacaaa atgaaatttt ggaaaaacat   1080
tatggtacta atattgatta ttctgatact actaaattgt ttactggtga agttattaaa   1140
gaaatggtta aattggattc tgtttgtaga aagctatga gatctagaaa ttcttatttg    1200
gaattgccac atacttatgt tggtaaatct agaattactt tgtcttgtgg tgctgttatt   1260
gaaccaggtc atgatgtttt gattaatatg tggggtaatc atagagatgc taaaattcaa   1320
agagatacta ttggtgatca tcatgatttt aaaccattta gatttgttgg tttggataga   1380
caatctacta aaattggtga tgatttttttg atgtttggtc aaggtagaca tgcttgtcca   1440
ggtagatggt ttgctattca agaaattaaa actattgttt ctgttttgat tagatattat   1500
aaattgactc aaaaggtcc aattactttt ccaactcatc aagaatgcc aatgccaact    1560
ggtgaagtta ttattcaaag aagacaagaa tag                                 1593
```

<210> SEQ ID NO 57
<211> LENGTH: 530
<212> TYPE: PRT
<213> ORGANISM: Lichtheimia corymbifera

<400> SEQUENCE: 57

```
Met Ser Ser Leu Asn Ile Leu Ser Leu Leu Asp Asn Lys His Ile Asn
1               5                   10                  15

Ala Phe Phe Asp Asn Pro Ser Arg Ala Gln Ser Gly Ile Ile Ala Gly
            20                  25                  30

Ser Val Ala Ile Val Ser Leu Cys Ala Ala Tyr Ser Leu Gly Ser Arg
        35                  40                  45

Leu Arg Gly Ser Asn Asn Gly Val Pro Leu Val Pro Tyr Thr Phe Pro
    50                  55                  60

Ile Ile Gly Ser Thr Lys Glu Tyr Gln Ala Asp Pro Gln Ala Phe Ile
65                  70                  75                  80
```

```
Glu Lys Trp Thr Ala Lys Leu Gly Pro Val Phe Arg Val His Leu Phe
                 85                  90                  95
Gly Arg Ile His Thr Val Val Ser Asp Arg Tyr Val Arg Glu Val Phe
            100                 105                 110
Leu Asn Asn Asp Phe Asp Phe Leu Lys Gly Thr Gly Lys Arg Phe Asp
        115                 120                 125
Thr Leu Leu Leu Thr Asp Thr Leu Glu Asp Val Asp Ile Glu Val
    130                 135                 140
Phe Arg Thr Val Val Met Lys His Leu Thr Lys Glu Met Lys His Tyr
145                 150                 155                 160
Thr Pro Arg Val Val Glu His Leu Thr Ala Gly Gly Asp Glu Lys Leu
                165                 170                 175
Gly Asp Ala Thr Glu Pro Lys Glu Leu Val His Leu Phe Pro Leu Leu
            180                 185                 190
Gln His Met Val Ala Lys Ala Ser Ala Ser Ile Phe Val Gly Thr Glu
        195                 200                 205
Leu Ala Ala Asp Asp Ala Val Val Glu Thr Cys Lys Asn Ile Ala Ile
    210                 215                 220
Asp Ile Gly Ser Glu Leu Gly Pro Ser Ser Tyr Ile Met Asp Ala Phe
225                 230                 235                 240
Pro Ser Leu Ala Arg Leu Arg Met Trp Tyr Ile Gly Lys Tyr Gly Lys
                245                 250                 255
Ala Ile Asn Lys His Arg Gln His Leu Leu His Ala Leu Gly Pro Val
            260                 265                 270
Ile Asp Lys Arg Leu Ala Ala Ala Glu Lys Gly Gly Asp Trp Asp Arg
        275                 280                 285
Pro Gln Asp Ile Leu Gln Asp Ile Ile Glu Thr Ile Asn Leu Thr Leu
    290                 295                 300
Asp Asn Pro Lys Arg His Ile Leu Pro Val Lys Trp Leu Leu Ala Leu
305                 310                 315                 320
Phe Phe Ala Ser Ile His Thr Thr Ser Glu Asn Ser Thr Ile Val Leu
                325                 330                 335
Tyr Arg Ile Met Gln Asn Pro Glu Ile Ile Asp Val Leu Leu Glu Glu
            340                 345                 350
Gln Asn Glu Ile Leu Glu Lys His Tyr Gly Thr Asn Ile Asp Tyr Ser
        355                 360                 365
Asp Thr Thr Lys Leu Phe Thr Gly Glu Val Ile Lys Glu Met Val Lys
    370                 375                 380
Leu Asp Ser Val Cys Arg Glu Ala Met Arg Ser Arg Asn Ser Tyr Leu
385                 390                 395                 400
Glu Leu Pro His Thr Tyr Val Gly Lys Ser Arg Ile Thr Leu Ser Cys
                405                 410                 415
Gly Ala Val Ile Glu Pro Gly His Asp Val Leu Ile Asn Met Trp Gly
            420                 425                 430
Asn His Arg Asp Ala Lys Ile Gln Arg Asp Thr Ile Gly Asp His His
        435                 440                 445
Asp Phe Lys Pro Phe Arg Phe Val Gly Leu Asp Arg Gln Ser Thr Lys
    450                 455                 460
Ile Gly Asp Asp Phe Leu Met Phe Gly Gln Gly Arg His Ala Cys Pro
465                 470                 475                 480
Gly Arg Trp Phe Ala Ile Gln Glu Ile Lys Thr Ile Val Ser Val Leu
                485                 490                 495
Ile Arg Tyr Tyr Lys Leu Thr Pro Lys Gly Pro Ile Thr Phe Pro Thr
```

500             505             510
His Pro Arg Met Pro Met Pro Thr Gly Glu Val Ile Ile Gln Arg Arg
        515                 520                 525

Gln Glu
    530

<210> SEQ ID NO 58
<211> LENGTH: 1548
<212> TYPE: DNA
<213> ORGANISM: Absidia repens

<400> SEQUENCE: 58

| | | | | | |
|---|---|---|---|---|---|
| atgaataaat | tgtttccagt | tggtacttct | aataaaaaaa | agctgttttt | gttgtctttg | 60 |
| ggtgctactg | ttgctttgat | ttgtagagct | atttatagaa | tttattatgt | tccaagatct | 120 |
| ttgagacata | ttccatctgt | tggttatttt | agattgatta | gatctatttt | gagaagagaa | 180 |
| gatgctacta | ctagagctag | aactgtttat | ggtccagcta | ttaaaaaagg | taatggtatt | 240 |
| tatttggcta | attttccaat | tacttggtct | gttttttgttt | cttctccaat | tgctgctaaa | 300 |
| tctgttttga | tgaaaactga | taattttcca | aaatctatgg | aaattttca | tgctttgggt | 360 |
| aaagaaaatc | cagttgttag | atttttttggt | attgataatg | ttgctattgt | taatggtgaa | 420 |
| aaatggaaaa | acaaagaaa | agttatgaat | ccagcttttc | atagagctat | gccagttcaa | 480 |
| atgtttggta | gattgatgtt | gaaggttttt | aaaatattg | aaaacaaga | ttatcaagtt | 540 |
| ccaattttgg | atttttttca | aagattgact | ttggatgctt | tgggtattgc | tggttttggt | 600 |
| tttgattttc | attctgttga | tgatccagaa | tctatttgga | ctaaaactta | tgaaaatgtt | 660 |
| agattgggtt | tgagatctcc | atttctcttt | ttgtttccat | ctatggattg | ttgttgaaa | 720 |
| tatattattc | caggtagaaa | agaattggat | aaatctgttg | ataaattgaa | tgctttgttg | 780 |
| atgtctatgg | ctcaagaaag | aagattgcaa | gttagagctt | ctattgatga | taatgttcca | 840 |
| gattctgaaa | aagatttgtt | gactttgatg | ttggaagctg | aattgagagg | tgaaggtact | 900 |
| gcttctgatg | aacaattgag | atctaatttg | gctgttttt | ttttggctgg | tcatgaaact | 960 |
| actgctaata | ctatgtcttt | tgtttgtat | aatttggcta | tgaataaaga | agttcaatct | 1020 |
| aaagctagac | aagaagtttt | gactgttttg | ggtgatgaac | cagttgatat | tttgccacaa | 1080 |
| attgatgaat | tgagacaaat | gccatatatt | gatatggttt | tgaaagaaaa | tttgagaaga | 1140 |
| tttggtccag | cttctatgtt | gattgctaga | aaatctcaag | aagattttga | tttgaatggt | 1200 |
| gttttattc | caaaaaatac | tccagttgtt | gttgaaactc | atgctttgca | tcataatcca | 1260 |
| gatgtttgga | aaaatccaga | acaatttgat | ccagaaagat | ttgctccagg | tggtgaacat | 1320 |
| gaaacttgtc | atgaaggtat | ggcttggttg | ccattttctt | ctggttctag | aggttgtttg | 1380 |
| ggtatgaatt | tttctttggc | tgaacaaaga | acttttttgg | ttatgttgtt | gagaaaatat | 1440 |
| gaatgggaat | tgccagaaga | ttctattcat | agaaatggtg | ttaaaattca | aaattttcaa | 1500 |
| aatgctgctc | cagaatcttt | ggaaattaaa | ttttcttcta | gatattag | | 1548 |

<210> SEQ ID NO 59
<211> LENGTH: 515
<212> TYPE: PRT
<213> ORGANISM: Absidia repens

<400> SEQUENCE: 59

Met Asn Lys Leu Phe Pro Val Gly Thr Ser Asn Lys Lys Lys Ala Val
1               5                   10                  15

-continued

Leu Leu Ser Leu Gly Ala Thr Val Ala Leu Ile Cys Arg Ala Ile Tyr
            20                  25                  30

Arg Ile Tyr Tyr Val Pro Arg Ser Leu Arg His Ile Pro Ser Val Gly
            35                  40                  45

Tyr Phe Arg Leu Ile Arg Ser Ile Leu Arg Arg Glu Asp Ala Thr Thr
 50                  55                  60

Arg Ala Arg Thr Val Tyr Gly Pro Ala Ile Lys Lys Gly Asn Gly Ile
 65                  70                  75                  80

Tyr Leu Ala Asn Phe Pro Ile Thr Trp Ser Val Phe Ser Ser Pro
                85                  90                  95

Ile Ala Ala Lys Ser Val Leu Met Lys Thr Asp Asn Phe Pro Lys Ser
            100                 105                 110

Met Glu Ile Phe His Ala Leu Gly Lys Glu Asn Pro Val Val Arg Phe
            115                 120                 125

Phe Gly Ile Asp Asn Val Ala Ile Val Asn Gly Glu Lys Trp Lys Lys
            130                 135                 140

Gln Arg Lys Val Met Asn Pro Ala Phe His Arg Ala Met Pro Val Gln
145                 150                 155                 160

Met Phe Gly Arg Leu Met Leu Lys Gly Phe Lys Asn Ile Glu Lys Gln
            165                 170                 175

Asp Tyr Gln Val Pro Ile Leu Asp Phe Phe Gln Arg Leu Thr Leu Asp
            180                 185                 190

Ala Leu Gly Ile Ala Gly Phe Gly Phe Asp Phe His Ser Val Asp Asp
            195                 200                 205

Pro Glu Ser Ile Trp Thr Lys Thr Tyr Glu Asn Val Arg Leu Gly Leu
210                 215                 220

Arg Ser Pro Phe Ser Phe Leu Phe Pro Ser Met Asp Trp Leu Leu Lys
225                 230                 235                 240

Tyr Ile Ile Pro Gly Arg Lys Glu Leu Asp Lys Ser Val Asp Lys Leu
            245                 250                 255

Asn Ala Leu Leu Met Ser Met Ala Gln Glu Arg Arg Leu Gln Val Arg
            260                 265                 270

Ala Ser Ile Asp Asp Asn Val Pro Asp Ser Glu Lys Asp Leu Leu Thr
            275                 280                 285

Leu Met Leu Glu Ala Glu Leu Arg Gly Glu Gly Thr Ala Ser Asp Glu
290                 295                 300

Gln Leu Arg Ser Asn Leu Ala Val Phe Phe Leu Ala Gly His Glu Thr
305                 310                 315                 320

Thr Ala Asn Thr Met Ser Phe Cys Leu Tyr Asn Leu Ala Met Asn Lys
            325                 330                 335

Glu Val Gln Ser Lys Ala Arg Gln Glu Val Leu Thr Val Leu Gly Asp
            340                 345                 350

Glu Pro Val Asp Ile Leu Pro Gln Ile Asp Glu Leu Arg Gln Met Pro
            355                 360                 365

Tyr Ile Asp Met Val Leu Lys Glu Asn Leu Arg Arg Phe Gly Pro Ala
370                 375                 380

Ser Met Leu Ile Ala Arg Lys Ser Gln Glu Asp Phe Asp Leu Asn Gly
385                 390                 395                 400

Val Phe Ile Pro Lys Asn Thr Pro Val Val Glu Thr His Ala Leu
            405                 410                 415

His His Asn Pro Asp Val Trp Lys Asn Pro Glu Gln Phe Asp Pro Glu
            420                 425                 430

Arg Phe Ala Pro Gly Gly Glu His Glu Thr Cys His Glu Gly Met Ala

```
            435                 440                 445
Trp Leu Pro Phe Ser Ser Gly Ser Arg Gly Cys Leu Gly Met Asn Phe
    450                 455                 460

Ser Leu Ala Glu Gln Arg Thr Phe Leu Val Met Leu Leu Arg Lys Tyr
465                 470                 475                 480

Glu Trp Glu Leu Pro Glu Asp Ser Ile His Arg Asn Gly Val Lys Ile
                    485                 490                 495

Gln Asn Phe Gln Asn Ala Ala Pro Glu Ser Leu Glu Ile Lys Phe Ser
                500                 505                 510

Ser Arg Tyr
        515

<210> SEQ ID NO 60
<211> LENGTH: 1560
<212> TYPE: DNA
<213> ORGANISM: Thamnostylum piriforme

<400> SEQUENCE: 60
atgatttctt atccagttgt tagagataga ttgtctagat ataaatatta tattgttatt      60
ggtgctttgt tttctattgc ttggcaacaa atttattata gattttttag agttccaaga    120
aatttgagac atattccatc tattgcttat gctcaacaat tgttggcttt gttgagaggt    180
gaaccaatta ctttgagaac tcaaagattg gtttttccat tgttgtctaa agctaatggt    240
atttatttga atagagcacc atttttgtgg actattttg ttgctaatcc agttttggct    300
aaagaagttt tgtttaaatc tgaattggct aataaaaata ctattttgga tgcttttcca    360
aaagattctg cttttgttga atttgttggt aaagataatg ttgctttttc taatggtgaa    420
aaatggaaaa gacaaagaaa aattatgaat ccaattttc atagagctac tactgctgct    480
gcttttgctt ctgttacttt gaaattgttt agagttattg atgatactca agctgctggt    540
tctcatgttg ctgttccaat ttgatgaaa agattggctt ggaagcattg ggtagaact     600
atgtttggtt ttgattttgg tggtttggaa gatgaaggtt ctgaatgggt tgctgcttgt    660
aatgaagttt ttacttcttt ttctgatttt acttctttgt ctgctagagc tgatgctatg    720
ttgagagttt tttctagatc tagacaagaa aaatataaag ctagatttag attgattaat    780
atgtttgatg atatgattga acaaagaaga gttactttgt tggatactaa agaaacttct    840
tctactaatg ttccagataa tgaaaaagat tgttgacttt tgttgttgga agctgaaatg    900
agaggtgaag gtacttggag aaaaaatgaa ttgagatata atattgctac tttgtttttt    960
gctggtcatg tactactgc ttctacttg tcttttgctt tgtattcttt ggctgttaat   1020
aaagaagttc aatctaaagc tagagaagaa gttaatgatt tgttgggtaa taatcataat   1080
gatgttgctc aactttgga acaatgtaaa caattgccat atattgatat gattattaaa   1140
gaaactttga aatgtattc tccatctgat catttgtttg ctagagttgc ttctgatgat   1200
ttggaattgg gtggtgtttt gattccaaaa ggtgctaaag tttctgttga ttttcatgct   1260
ttgcattatc atccagattt gtgggaagct ccagaaagat ttattccaga aagatttct    1320
gattctggtg aacattctaa acatgaaggt attacttggg ctccattttc tggtggttct   1380
agacaatgta ttggtttgaa ttttctatg actgaacaaa gagttgcttt gtctatgttg   1440
ttgagaaaat atgaatggga attgccagca ggttctattc atgaaaaagg tttggttatg   1500
gatcaaccat ataattttgc tccaatgtct ttggaattga gatttaaaaa aatttattag   1560

<210> SEQ ID NO 61
```

<211> LENGTH: 519
<212> TYPE: PRT
<213> ORGANISM: Thamnostylum piriforme

<400> SEQUENCE: 61

```
Met Ile Ser Tyr Pro Val Val Arg Asp Arg Leu Ser Arg Tyr Lys Tyr
1               5                   10                  15

Tyr Ile Val Ile Gly Ala Leu Phe Ser Ile Ala Trp Gln Gln Ile Tyr
            20                  25                  30

Tyr Arg Phe Phe Arg Val Pro Arg Asn Leu Arg His Ile Pro Ser Ile
        35                  40                  45

Ala Tyr Ala Gln Gln Leu Leu Ala Leu Leu Arg Gly Glu Pro Ile Thr
    50                  55                  60

Leu Arg Thr Gln Arg Leu Val Phe Pro Leu Leu Ser Lys Ala Asn Gly
65                  70                  75                  80

Ile Tyr Leu Asn Arg Ala Pro Phe Leu Trp Thr Ile Phe Val Ala Asn
                85                  90                  95

Pro Val Leu Ala Lys Glu Val Leu Phe Lys Ser Glu Leu Ala Asn Lys
            100                 105                 110

Asn Thr Ile Leu Asp Ala Phe Pro Lys Asp Ser Ala Phe Val Glu Phe
        115                 120                 125

Val Gly Lys Asp Asn Val Ala Phe Ser Asn Gly Glu Lys Trp Lys Arg
    130                 135                 140

Gln Arg Lys Ile Met Asn Pro Ile Phe His Arg Ala Thr Thr Ala Ala
145                 150                 155                 160

Ala Phe Ala Ser Val Thr Leu Lys Leu Phe Arg Val Ile Asp Asp Thr
                165                 170                 175

Gln Ala Ala Gly Ser His Val Ala Val Pro Ile Leu Met Lys Arg Leu
            180                 185                 190

Ala Leu Glu Ala Leu Gly Arg Thr Met Phe Gly Phe Asp Phe Gly Gly
        195                 200                 205

Leu Glu Asp Glu Gly Ser Glu Trp Val Ala Ala Cys Asn Glu Val Phe
    210                 215                 220

Thr Ser Phe Ser Asp Phe Thr Ser Leu Ser Ala Arg Ala Asp Ala Met
225                 230                 235                 240

Leu Arg Val Phe Ser Arg Ser Arg Gln Glu Lys Tyr Lys Ala Arg Phe
                245                 250                 255

Arg Leu Ile Asn Met Phe Asp Asp Met Ile Glu Gln Arg Arg Val Thr
            260                 265                 270

Leu Leu Asp Thr Lys Glu Thr Ser Ser Thr Asn Val Pro Asp Asn Glu
        275                 280                 285

Lys Asp Leu Leu Thr Leu Leu Leu Glu Ala Glu Met Arg Gly Glu Gly
    290                 295                 300

Thr Trp Arg Lys Asn Glu Leu Arg Tyr Asn Ile Ala Thr Leu Phe Phe
305                 310                 315                 320

Ala Gly His Asp Thr Thr Ala Ser Thr Leu Ser Phe Ala Leu Tyr Ser
                325                 330                 335

Leu Ala Val Asn Lys Glu Val Gln Ser Lys Ala Arg Glu Glu Val Asn
            340                 345                 350

Asp Leu Leu Gly Asn Asn His Asn Asp Val Ala Pro Thr Leu Glu Gln
        355                 360                 365

Cys Lys Gln Leu Pro Tyr Ile Asp Met Ile Ile Lys Glu Thr Leu Arg
    370                 375                 380

Met Tyr Ser Pro Ser Asp His Leu Phe Ala Arg Val Ala Ser Asp Asp
```

```
                 385               390                395              400
Leu Glu Leu Gly Gly Val Leu Ile Pro Lys Gly Ala Lys Val Ser Val
                     405                 410                415

Asp Phe His Ala Leu His Tyr His Pro Asp Leu Trp Glu Ala Pro Glu
                 420                 425                430

Arg Phe Ile Pro Glu Arg Phe Ser Asp Ser Gly Glu His Ser Lys His
             435                 440                 445

Glu Gly Ile Thr Trp Ala Pro Phe Ser Gly Ser Arg Gln Cys Ile
         450                 455                 460

Gly Leu Asn Phe Ser Met Thr Glu Gln Arg Val Ala Leu Ser Met Leu
465                 470                 475                 480

Leu Arg Lys Tyr Glu Trp Glu Leu Pro Ala Gly Ser Ile His Glu Lys
                 485                 490                 495

Gly Leu Val Met Asp Gln Pro Tyr Asn Phe Ala Pro Met Ser Leu Glu
             500                 505                 510

Leu Arg Phe Lys Lys Ile Tyr
         515

<210> SEQ ID NO 62
<211> LENGTH: 1650
<212> TYPE: DNA
<213> ORGANISM: Cunninghamella echinulata

<400> SEQUENCE: 62
atgtctcaat ttatttctac tatttctcaa tattgggatg ttaataattt tattgatcaa       60
caagcatggt ctagatttta tgaaacttat ttgttgaaat atactgattc taaagctaaa      120
agattgacta ttggtgtttc tgtttctttg ttgttgttgg ttatggtat taaaagattg       180 ttgactccac caaacatttt gagacatatt aaacatgctt cttttttgag atttacttat      240
aattttgtta ttaaaggtgt tactccaaaa gaaatgcata ctactgtttc taaaaaaatt     300
gttgaagaaa ataatggttt ttatttgcaa ttggaaagaa ctggttgggt tgtttatgtt     360
gctaatccag aagctgttaa acaagttttg ttgaaatctg atattttcc aaaaatggat      420 tttttctaaa tggcttctga agaaggttct tattttgaaa aatttattgg ttttaaaaat     480
attttgatga ctactggttc tgaatggttg aaacatagaa aattgactaa tccagctttt     540
catagatctt tgccagctaa attgtttggt gaaactgctc aaggtttgtt taaaatttgg     600
gataatgaat ataatgataa accatttgaa gttaatattc ataatatgaa tgaaagaatt     660
actttggata ttattggtaa agctggtttt gcttttgatt ttaatgctgt tgctgatgaa    720
aaatctcctt ggaaaaaaac ttatgatatt attaatactg ctgcttctga tccattgttt    780
tttatgtttc caattttgga aaataaaattg ttgtggttgt ttccaaaaag acaagaatct    840
tttaaaaaat tggatgaatg aaagctatg ttgacttctg ttattgaaaa taaaagaaga    900
ttgttgaaag ataatattga tcaaggtgtt gaagaagctg aaaaagattt gttgactttg    960
atgattgaat ctgaatttag aggtgaaggt gttttgacta agaagaatt gattggtaat    1020 ttgactgttt ttttttttggc tggtcatgat actacttctt ttgctttgac ttctgctatt    1080
tattatatgg ctagatacccc agaaattcaa gaaaaagcta gacaagaagt taattctatt    1140
ttgtgtccaa atggtgaacc aaatgaaggt attttgccaa ctattgaaga tactaaaaaa    1200
ttggtttatt tgaatcaaat tatgaaagaa tctatgagaa ttggtaatcc agttttgttt    1260
ttgttgtctc aagacaagc tactaaagat tttaatttga atggtacttt tattccaaaa    1320
ggtactcaag ttaatattaa tattcatgat ttgcatcatt cttctaatgt ttgggatgat    1380
```

-continued

```
ccagatactt ttaatccaga tagatttgct ccaggtggtg aagctgataa aaaaactggt    1440
attgcttggg ttccattttc taatggttct agacaatgtt tgggtatgaa ttttctttg    1500 ttggaacaaa gagttatttt gtcttgtttg ttgagaaaat atgaatggac tttgccagaa    1560
aattctattc ataaaaatga tatgattct aaatttgatt tgattccatc tccaattgat    1620
atgaaaatta gatttgaaag aagatattaa                                    1650
```

<210> SEQ ID NO 63
<211> LENGTH: 549
<212> TYPE: PRT
<213> ORGANISM: Cunninghamella echinulata

<400> SEQUENCE: 63

```
Met Ser Gln Phe Ile Ser Thr Ile Ser Gln Tyr Trp Asp Val Asn Asn
1               5                   10                  15

Phe Ile Asp Gln Gln Ala Trp Ser Arg Phe Tyr Glu Thr Tyr Leu Leu
            20                  25                  30

Lys Tyr Thr Asp Ser Lys Ala Lys Arg Leu Thr Ile Gly Val Ser Val
        35                  40                  45

Ser Leu Leu Leu Gly Tyr Gly Ile Lys Arg Leu Leu Thr Pro Pro
    50                  55                  60

Lys His Leu Arg His Ile Lys His Ala Ser Phe Leu Arg Phe Thr Tyr
65                  70                  75                  80

Asn Phe Val Ile Lys Gly Val Thr Pro Lys Glu Met His Thr Thr Val
                85                  90                  95

Ser Lys Lys Ile Val Glu Glu Asn Asn Gly Phe Tyr Leu Gln Leu Glu
            100                 105                 110

Arg Thr Gly Trp Val Val Tyr Val Ala Asn Pro Glu Ala Val Lys Gln
        115                 120                 125

Val Leu Leu Lys Ser Asp Ile Phe Pro Lys Met Asp Phe Ser Lys Leu
    130                 135                 140

Ala Ser Glu Glu Gly Ser Tyr Phe Glu Lys Phe Ile Gly Phe Lys Asn
145                 150                 155                 160

Ile Leu Met Thr Thr Gly Ser Glu Trp Leu Lys His Arg Lys Leu Thr
                165                 170                 175

Asn Pro Ala Phe His Arg Ser Leu Pro Ala Lys Leu Phe Gly Glu Thr
            180                 185                 190

Ala Gln Gly Leu Phe Lys Ile Trp Asp Asn Glu Tyr Asn Asp Lys Pro
        195                 200                 205

Phe Glu Val Asn Ile His Asn Met Asn Glu Arg Ile Thr Leu Asp Ile
    210                 215                 220

Ile Gly Lys Ala Gly Phe Ala Phe Asp Phe Asn Ala Val Ala Asp Glu
225                 230                 235                 240

Lys Ser Pro Trp Lys Lys Thr Tyr Asp Ile Ile Asn Thr Ala Ala Ser
                245                 250                 255

Asp Pro Leu Phe Phe Met Phe Pro Ile Leu Glu Asn Lys Leu Leu Trp
            260                 265                 270

Leu Phe Pro Lys Arg Gln Glu Ser Phe Lys Lys Leu Asp Glu Trp Lys
        275                 280                 285

Ala Met Leu Thr Ser Val Ile Glu Asn Lys Arg Arg Leu Leu Lys Asp
    290                 295                 300

Asn Ile Asp Gln Gly Val Glu Glu Ala Glu Lys Asp Leu Leu Thr Leu
305                 310                 315                 320
```

Met Ile Glu Ser Glu Phe Arg Gly Glu Gly Val Leu Thr Lys Glu Glu
            325                 330                 335

Leu Ile Gly Asn Leu Thr Val Phe Phe Leu Ala Gly His Asp Thr Thr
        340                 345                 350

Ser Phe Ala Leu Thr Ser Ala Ile Tyr Tyr Met Ala Arg Tyr Pro Glu
        355                 360                 365

Ile Gln Glu Lys Ala Arg Gln Glu Val Asn Ser Ile Leu Cys Pro Asn
    370                 375                 380

Gly Glu Pro Asn Glu Gly Ile Leu Pro Thr Ile Glu Asp Thr Lys Lys
385                 390                 395                 400

Leu Val Tyr Leu Asn Gln Ile Met Lys Glu Ser Met Arg Ile Gly Asn
            405                 410                 415

Pro Val Leu Phe Leu Leu Ser Pro Arg Gln Ala Thr Lys Asp Phe Asn
        420                 425                 430

Leu Asn Gly Thr Phe Ile Pro Lys Gly Thr Gln Val Asn Ile Asn Ile
        435                 440                 445

His Asp Leu His His Ser Ser Asn Val Trp Asp Pro Asp Thr Phe
    450                 455                 460

Asn Pro Asp Arg Phe Ala Pro Gly Gly Glu Ala Asp Lys Lys Thr Gly
465                 470                 475                 480

Ile Ala Trp Val Pro Phe Ser Asn Gly Ser Arg Gln Cys Leu Gly Met
            485                 490                 495

Asn Phe Ser Leu Leu Glu Gln Arg Val Ile Leu Ser Cys Leu Leu Arg
        500                 505                 510

Lys Tyr Glu Trp Thr Leu Pro Glu Asn Ser Ile His Lys Asn Asp Met
    515                 520                 525

Ile Ser Lys Phe Asp Leu Ile Pro Ser Pro Ile Asp Met Lys Ile Arg
    530                 535                 540

Phe Glu Arg Arg Tyr
545

<210> SEQ ID NO 64
<211> LENGTH: 1392
<212> TYPE: DNA
<213> ORGANISM: Rhizopus delemar

<400> SEQUENCE: 64
atggtcaagt ccttcttgaa ggctgaatct ccaactgata gatacaagag aatcattcat      60
ccagtcgcct ctaaaggtaa tggtttctac gtttctaagg tcccattttt gtgggctgtt    120
tacgttacta atccagttgt tgctaagcag gtcttgttga agtctgatat tttcccaaag    180
aaccatgccg ttttccatca aattggtaag gattctccat tcactcagtt cttgggttta    240
gataacgttg ctttgtctaa cggtgatgtc tggaaaaagc aaagaaaggt tatgaaccca    300
gccttccata gatctttgcc aatcaaaact atggcctctg ttgttaacac cttgttctcc    360
gttattgata ctctgatgg tccagttttg atcacttctg ctatgcaaaa cttcaccttg    420
gatgttttag gtttggccat tttcggtttc gaattcaagg ctttacaagg tgatccagat    480
aactggacta agacttacaa gaccgttatc gaatctttgt tcgatccagt catgaacgtt    540
ttcgctactt tcgatacttt gttgacatgg gtttacccca agagaagaga atgttctgtt    600
gccatttcta gatgaacttt gaagttcgat gaactggcca acaaaaaag agccgaagtt    660 aagtctggtg cttatgctaa tgttccagat cacgataagg atctgttgac cttgatgttg    720
gaagctatgg aaaaaggtga agccttgact tctcaagacg aattgagaca taacattgcc    780

```
gttttttttct tggctggtca tggtactact gctcatactt tgtctttctg cttttaccat    840
ctggctaaga acaagcacat ccagagaaaa ttgagggaag aaatcatctc cgttttgggt    900
gatgaaccag ttgatatagt tccatccttg aacaaatga agcacatgaa gtatatgaac     960
ctggtcatca agaaaaacct gagaatgaat actccagccg ataccttgtt tactagagat   1020
actgttgagg atattaactt ggccggtcat atcattccaa aggataccgc tatttccatc   1080
gatattaacg ccattcatca cgatccaaag tactggcata atccagaaca tttcatccca   1140
gaaagatttg ctgaaggtgg tgaacaagaa tctcatgaag gtttgacttg gttgccattc   1200
tcaaatggtt ctagacaatg tatcggcatg aacttctcat ggctgaaca gagattggtt    1260
ttggctatgt tggttaggaa gtacgaaatc gatatcccaa aggattccat ccactacgaa   1320
agaatcttgt ttgacagacc aggtaacatt gctccattgt ctttgggttt gaccttcacc   1380
aagagatatt aa                                                        1392
```

<210> SEQ ID NO 65
<211> LENGTH: 463
<212> TYPE: PRT
<213> ORGANISM: Rhizopus delemar

<400> SEQUENCE: 65

```
Met Val Lys Ser Phe Leu Lys Ala Glu Ser Pro Thr Asp Arg Tyr Lys
1               5                   10                  15

Arg Ile Ile His Pro Val Ala Ser Lys Gly Asn Gly Phe Tyr Val Ser
                20                  25                  30

Lys Val Pro Phe Leu Trp Ala Val Tyr Val Thr Asn Pro Val Val Ala
            35                  40                  45

Lys Gln Val Leu Leu Lys Ser Asp Ile Phe Pro Lys Asn His Ala Val
        50                  55                  60

Phe His Gln Ile Gly Lys Asp Ser Pro Phe Thr Gln Phe Leu Gly Leu
65                  70                  75                  80

Asp Asn Val Ala Leu Ser Asn Gly Asp Val Trp Lys Lys Gln Arg Lys
                85                  90                  95

Val Met Asn Pro Ala Phe His Arg Ser Leu Pro Ile Lys Thr Met Ala
                100                 105                 110

Ser Val Val Asn Thr Leu Phe Ser Val Ile Asp Asn Ser Asp Gly Pro
            115                 120                 125

Val Leu Ile Thr Ser Ala Met Gln Asn Phe Thr Leu Asp Val Leu Gly
        130                 135                 140

Leu Ala Ile Phe Gly Phe Glu Phe Lys Ala Leu Gln Gly Asp Pro Asp
145                 150                 155                 160

Asn Trp Thr Lys Thr Tyr Lys Thr Val Ile Glu Ser Leu Phe Asp Pro
                165                 170                 175

Val Met Asn Val Phe Ala Thr Phe Asp Thr Leu Leu Thr Trp Val Tyr
                180                 185                 190

Pro Lys Arg Arg Glu Cys Ser Val Ala Ile Ser Lys Met Asn Leu Lys
            195                 200                 205

Phe Asp Glu Leu Ala Lys Gln Lys Arg Ala Glu Val Lys Ser Gly Ala
        210                 215                 220

Tyr Ala Asn Val Pro Asp His Asp Lys Asp Leu Leu Thr Leu Met Leu
225                 230                 235                 240

Glu Ala Met Glu Lys Gly Glu Ala Leu Thr Ser Gln Asp Glu Leu Arg
                245                 250                 255

His Asn Ile Ala Val Phe Phe Leu Ala Gly His Gly Thr Thr Ala His
```

|       |       |       |       |       | 260   |       |       |       |       | 265   |       |       |       |       | 270   |       |       |       |
|-------|-------|-------|-------|-------|-------|-------|-------|-------|-------|-------|-------|-------|-------|-------|-------|-------|-------|-------|

Thr Leu Ser Phe Cys Phe Tyr His Leu Ala Lys Asn Lys His Ile Gln
            275             280             285

Arg Lys Leu Arg Glu Glu Ile Ile Ser Val Leu Gly Asp Glu Pro Val
        290             295             300

Asp Ile Val Pro Ser Leu Glu Gln Met Lys His Met Lys Tyr Met Asn
305             310             315             320

Leu Val Ile Lys Glu Asn Leu Arg Met Asn Thr Pro Ala Asp Thr Leu
                325             330             335

Phe Thr Arg Asp Thr Val Glu Asp Ile Asn Leu Ala Gly His Ile Ile
            340             345             350

Pro Lys Asp Thr Ala Ile Ser Ile Asp Ile Asn Ala Ile His His Asp
        355             360             365

Pro Lys Tyr Trp His Asn Pro Glu His Phe Ile Pro Glu Arg Phe Ala
    370             375             380

Glu Gly Gly Glu Gln Glu Ser His Glu Gly Leu Thr Trp Leu Pro Phe
385             390             395             400

Ser Asn Gly Ser Arg Gln Cys Ile Gly Met Asn Phe Ser Leu Ala Glu
                405             410             415

Gln Arg Leu Val Leu Ala Met Leu Val Arg Lys Tyr Glu Ile Asp Ile
            420             425             430

Pro Lys Asp Ser Ile His Tyr Glu Arg Ile Leu Phe Asp Arg Pro Gly
        435             440             445

Asn Ile Ala Pro Leu Ser Leu Gly Leu Thr Phe Thr Lys Arg Tyr
    450             455             460

<210> SEQ ID NO 66
<211> LENGTH: 1584
<212> TYPE: DNA
<213> ORGANISM: Rhizopus microsporus

<400> SEQUENCE: 66

```
atggaattga ccgaaatcgc catcgaaact tatcatagag ctttggataa gctggtccca      60
atcttgcaaa aaagatccaa gagatcctac attggtgttg ctgttgcttt ggttgttttg     120
gaaagaatct acagcttctt cagagtccca aagtccatta gacatattcc agctgttcca     180
tactttgcta tggctaagtc tttcttgact tctgaagctc catcttccag acatcaaaga     240
atagttttgc cagtcatcga aaaggtaat ggtatctacg ttaacaagtt gccattggaa      300
tggactgtta atgttgctac tccaacctct gctaaacacg ttttgttgaa gtctgaaatc     360
taccccaagt ccgaatcctt tttgaaatta ttgggtccac aatctccagc cgttttgttt     420
ttaggtggta agaatgttgg tttcgttaac ggtgatgctt ggagaaagca agaaagatt      480
atgaacccag ccttccatag atccatgcca attcaaacta tggcttctgt tatgccagat     540
ttcttctcag ccattgataa gtatggtgat gaaggtattc caatctccac catcatgaga     600
gatttcacct tggatgtttt gggtcatact gcttttggtt tcgatttcaa ggcttttgaa     660
ggtgatccag ataactggac tagaacctac catatcatta caacgctttt gttcaaccca     720
accgctaata tgttgacttc tttgaacccc atcctgtcca ttatctctcc agaaagaaga     780
agaattttgg aggccatcaa aaagttgaac ggtatgttgg aagccatgat caagcaaaag     840
agacaagaag ttcaatccaa cgctcaagct catgctccag aaaacgaaaa agatttgttg     900
accttgatgt tggaggctca acaaagaggt gaaggttttgg ctactgatga agaattgaag     960
cacaatgtct ctggtttttt cttggctggt catgatacaa cctctgaaac tttgtctttc    1020
```

```
tacttctaca acattgccaa gaacaaggac gtccaaagaa agttgagaga agagttgaat    1080
gctgtcttgg gtgataagcc agttgatgtt attccaacct tggagcaatt gaagtccatg    1140
gaatatttga actgcaccat caaagaaaac ttgaggttga atggtccagc cgataatgtt    1200
ttgccaagag ttgctactga agatatggtt gttgatggta ctccaattcc aaagggtact    1260
gttgtgaacg ttgatattca tgccattcat cacgatacca gatactggaa agatccatac    1320
aagtttgtcc cagaaagatt tttgccaggt ggtgaacatg attctcattc tggtatgact    1380
tggttgcctt ttggtaatgg tgctagacaa tgtttgggta tgaatttctc attggccgaa    1440
cagagattgg ttattgctat gactgttagg aagtacgata tcgaagttcc aaaggattcc    1500
atccattacg atcatccaat cctggaatct tctaaaacaa aagctccagc ctccttgaag    1560
ttgatcttca gaaagagata ctga                                          1584
```

<210> SEQ ID NO 67
<211> LENGTH: 527
<212> TYPE: PRT
<213> ORGANISM: Rhizopus microsporus

<400> SEQUENCE: 67

```
Met Glu Leu Thr Glu Ile Ala Ile Glu Thr Tyr His Arg Ala Leu Asp
1               5                   10                  15

Lys Leu Val Pro Ile Leu Gln Lys Arg Ser Lys Arg Ser Tyr Ile Gly
            20                  25                  30

Val Ala Val Ala Leu Val Val Leu Glu Arg Ile Tyr Ser Phe Phe Arg
        35                  40                  45

Val Pro Lys Ser Ile Arg His Ile Pro Ala Val Pro Tyr Phe Ala Met
    50                  55                  60

Ala Lys Ser Phe Leu Thr Ser Glu Ala Pro Ser Ser Arg His Gln Arg
65                  70                  75                  80

Ile Val Leu Pro Val Ile Glu Lys Gly Asn Gly Ile Tyr Val Asn Lys
                85                  90                  95

Leu Pro Leu Glu Trp Thr Val Asn Val Ala Thr Pro Thr Ser Ala Lys
            100                 105                 110

His Val Leu Leu Lys Ser Glu Ile Tyr Pro Lys Ser Glu Ser Phe Leu
        115                 120                 125

Lys Leu Leu Gly Pro Gln Ser Pro Ala Val Leu Phe Leu Gly Gly Lys
    130                 135                 140

Asn Val Gly Phe Val Asn Gly Asp Ala Trp Arg Lys Gln Arg Lys Ile
145                 150                 155                 160

Met Asn Pro Ala Phe His Arg Ser Met Pro Ile Gln Thr Met Ala Ser
                165                 170                 175

Val Met Pro Asp Phe Phe Ser Ala Ile Asp Lys Tyr Gly Asp Glu Gly
            180                 185                 190

Ile Pro Ile Ser Thr Ile Met Arg Asp Phe Thr Leu Asp Val Leu Gly
        195                 200                 205

His Thr Ala Phe Gly Phe Asp Phe Lys Ala Leu Lys Gly Asp Pro Asp
    210                 215                 220

Asn Trp Thr Arg Thr Tyr His Ile Ile Asn Asn Ala Leu Phe Asn Pro
225                 230                 235                 240

Thr Ala Asn Met Leu Thr Ser Leu Asn Pro Ile Leu Ser Ile Ile Ser
                245                 250                 255

Pro Glu Arg Arg Arg Ile Leu Glu Ala Ile Lys Lys Leu Asn Gly Met
            260                 265                 270
```

```
Leu Glu Ala Met Ile Lys Gln Lys Arg Gln Glu Val Gln Ser Asn Ala
            275                 280                 285
Gln Ala His Ala Pro Glu Asn Glu Lys Asp Leu Leu Thr Leu Met Leu
    290                 295                 300
Glu Ala Gln Gln Arg Gly Glu Gly Leu Ala Thr Asp Glu Glu Leu Lys
305                 310                 315                 320
His Asn Val Ser Gly Phe Phe Leu Ala Gly His Asp Thr Thr Ser Glu
                325                 330                 335
Thr Leu Ser Phe Tyr Phe Tyr Asn Ile Ala Lys Asn Lys Asp Val Gln
            340                 345                 350
Arg Lys Leu Arg Glu Glu Leu Asn Ala Val Leu Gly Asp Lys Pro Val
                355                 360                 365
Asp Val Ile Pro Thr Leu Glu Gln Leu Lys Ser Met Glu Tyr Leu Asn
    370                 375                 380
Cys Thr Ile Lys Glu Asn Leu Arg Leu Asn Gly Pro Ala Asp Asn Val
385                 390                 395                 400
Leu Pro Arg Val Ala Thr Glu Asp Met Val Val Asp Gly Thr Pro Ile
                405                 410                 415
Pro Lys Gly Thr Val Val Asn Val Asp Ile His Ala Ile His His Asp
            420                 425                 430
Thr Arg Tyr Trp Lys Asp Pro Tyr Lys Phe Val Pro Glu Arg Phe Leu
                435                 440                 445
Pro Gly Gly Glu His Asp Ser His Ser Gly Met Thr Trp Leu Pro Phe
    450                 455                 460
Gly Asn Gly Ala Arg Gln Cys Leu Gly Met Asn Phe Ser Leu Ala Glu
465                 470                 475                 480
Gln Arg Leu Val Ile Ala Met Thr Val Arg Lys Tyr Asp Ile Glu Val
                485                 490                 495
Pro Lys Asp Ser Ile His Tyr Asp His Pro Ile Leu Glu Ser Ser Lys
            500                 505                 510
Thr Lys Ala Pro Ala Ser Leu Lys Leu Ile Phe Arg Lys Arg Tyr
            515                 520                 525

<210> SEQ ID NO 68
<211> LENGTH: 1488
<212> TYPE: DNA
<213> ORGANISM: Parasitella parasitica

<400> SEQUENCE: 68
atggccgttt tgtgcttggt cttggaaaga atctatgctt cttatgctgt tccaccatcc      60
tacttgagac attacccaaa ggtttctttg ttcgacatgc tgaagtcctt ctacatcaaa     120
gaatctgttg cctccagaaa caagagattg attgctccat tgactaatgc tggtcatggt     180
ttttacgtct gcagaattcc attgaactgg actatctatg ttaccgatcc attggctgct     240
aagactttgt tgttgaagtc tgaaaacttc ccaaagaaca aggctatttt cactgctttg     300
ggtgattctt caccagtcat taagttcatg ggtaaagaaa acgttgccat gtctaatggt     360
gaagagtgga aaaagcaacg taagattatg aacccagcct tccatagatc tcaaccagtt     420 aagactttg gtaacgttat gccagatttg ttcgccttga ttgatcaaga tccagaaaga     480
gttttcatca cgccaaagat gaagtctttt gctttggatg ctttaggttt gtctgctttc     540
ggtttcgatt ccaatctttt gaaggtgat ccagaaggtt ggactagaaa gtacaatgtt     600
gttatctcca ccttgttcaa ccccttcgtt aatatctttg cctccttgga tttcctggtc     660
```

| | | |
|---|---|---|
| aagtatattt caccagaaag aagaagagtt atcaaggcca ctgatgagtt caattctatg | 720 | |
| ttgggtgaat tggcagataa agagaaggcaa gaaattttgg acggtgagaa aaagaacatc | 780 | |
| ccagaaaacg aaaaggacct gttgaccttg atgattgaag ccgatattag agacaacatt | 840 | |
| aagactacta ccaccgaatt gagacataac atggccattt tcttttttggc cggtcatgat | 900 | |
| tctacagcta acactttgtc tctgtgcttg tacaatttgg ctaaacacaa gcacgttcaa | 960 | |
| aagaaggcta gacaagaagt tttggctatc ttgggtgatg aaccattgga tgttattcca | 1020 | |
| actgctgagg acttgaagaa gttggattac gttaacatgg tcatcaaaga aaacctgaga | 1080 | |
| agaaatggtc cagccgataa tttgatgtct agagatactc aacaggacat gaacttgaac | 1140 | |
| ggtactatta ttccaaaggg ctccaaggtt tctgttaacg ttgctgctat tcatctgaac | 1200 | |
| ccaaagattt ggcatgaccc agaaaatttc attccagaac gttttgagca aggtggtgaa | 1260 | |
| ttcgaacaac atgatggttt tacttggatc ccattctcta acggttctag acaatgtttg | 1320 | |
| ggtctgaact tctcattgac tgaacaaagg gttgttctgt gcatgatctt gaagagatac | 1380 | |
| gaaatcgata tccccaagga ttccatccat acaacgaaa tcgttttcga tggtgctttt | 1440 | |
| actttcgctc cacaatcttt ggaactgtcc ttcaagagaa gatactga | 1488 | |

<210> SEQ ID NO 69
<211> LENGTH: 495
<212> TYPE: PRT
<213> ORGANISM: Parasitella parasitica

<400> SEQUENCE: 69

```
Met Ala Val Leu Cys Leu Val Leu Glu Arg Ile Tyr Ala Ser Tyr Ala
1               5                   10                  15

Val Pro Pro Ser Tyr Leu Arg His Tyr Pro Lys Val Ser Leu Phe Asp
            20                  25                  30

Met Leu Lys Ser Phe Tyr Ile Lys Glu Ser Val Ala Ser Arg Asn Lys
        35                  40                  45

Arg Leu Ile Ala Pro Leu Thr Asn Ala Gly His Gly Phe Tyr Val Cys
    50                  55                  60

Arg Ile Pro Leu Asn Trp Thr Ile Tyr Val Thr Asp Pro Leu Ala Ala
65                  70                  75                  80

Lys Thr Leu Leu Leu Lys Ser Glu Asn Phe Pro Lys Asn Lys Ala Ile
                85                  90                  95

Phe Thr Ala Leu Gly Asp Ser Ser Pro Val Ile Lys Phe Met Gly Lys
            100                 105                 110

Glu Asn Val Ala Met Ser Asn Gly Glu Glu Trp Lys Lys Gln Arg Lys
        115                 120                 125

Ile Met Asn Pro Ala Phe His Arg Ser Gln Pro Val Lys Thr Phe Gly
    130                 135                 140

Asn Val Met Pro Asp Leu Phe Ala Leu Ile Asp Gln Asp Pro Glu Arg
145                 150                 155                 160

Val Phe Ile Thr Pro Lys Met Lys Ser Phe Ala Leu Asp Ala Leu Gly
                165                 170                 175

Leu Ser Ala Phe Gly Phe Asp Phe Gln Ser Leu Lys Gly Asp Pro Glu
            180                 185                 190

Gly Trp Thr Arg Lys Tyr Asn Val Val Ile Ser Thr Leu Phe Asn Pro
        195                 200                 205

Phe Val Asn Ile Phe Ala Ser Leu Asp Phe Leu Val Lys Tyr Ile Ser
    210                 215                 220

Pro Glu Arg Arg Arg Val Ile Lys Ala Thr Asp Glu Phe Asn Ser Met
```

```
             225                 230                 235                 240
Leu Gly Glu Leu Ala Asp Lys Arg Arg Gln Glu Ile Leu Asp Gly Glu
                245                 250                 255
Lys Lys Asn Ile Pro Glu Asn Glu Lys Asp Leu Leu Thr Leu Met Ile
                260                 265                 270
Glu Ala Asp Ile Arg Asp Asn Ile Lys Thr Thr Thr Glu Leu Arg
                275                 280                 285
His Asn Met Ala Ile Phe Phe Leu Ala Gly His Asp Ser Thr Ala Asn
                290                 295                 300
Thr Leu Ser Leu Cys Leu Tyr Asn Leu Ala Lys His Lys His Val Gln
305                 310                 315                 320
Lys Lys Ala Arg Gln Glu Val Leu Ala Ile Leu Gly Asp Glu Pro Leu
                325                 330                 335
Asp Val Ile Pro Thr Ala Glu Asp Leu Lys Lys Leu Asp Tyr Val Asn
                340                 345                 350
Met Val Ile Lys Glu Asn Leu Arg Arg Asn Gly Pro Ala Asp Asn Leu
                355                 360                 365
Met Ser Arg Asp Thr Gln Gln Asp Met Asn Leu Asn Gly Thr Ile Ile
                370                 375                 380
Pro Lys Gly Ser Lys Val Ser Val Asn Val Ala Ala Ile His Leu Asn
385                 390                 395                 400
Pro Lys Ile Trp His Asp Pro Glu Asn Phe Ile Pro Glu Arg Phe Glu
                405                 410                 415
Gln Gly Gly Glu Phe Glu Gln His Asp Gly Phe Thr Trp Ile Pro Phe
                420                 425                 430
Ser Asn Gly Ser Arg Gln Cys Leu Gly Leu Asn Phe Ser Leu Thr Glu
                435                 440                 445
Gln Arg Val Val Leu Cys Met Ile Leu Lys Arg Tyr Glu Ile Asp Ile
                450                 455                 460
Pro Lys Asp Ser Ile His Tyr Asn Glu Ile Val Phe Asp Gly Ala Phe
465                 470                 475                 480
Thr Phe Ala Pro Gln Ser Leu Glu Leu Ser Phe Lys Arg Arg Tyr
                485                 490                 495

<210> SEQ ID NO 70
<211> LENGTH: 1545
<212> TYPE: DNA
<213> ORGANISM: Rhizopus delemar

<400> SEQUENCE: 70
atggctttgg aaggtgcttt gcctttgttc caaaagagat ccaaatcctc ttatatcgtt      60
gccgccattt tgttgattac cgtcaaacaa atctacagct tcttcagagt tcctaccaac     120
ttgagacatt tgccatgtgt ttcttttttc gccatggcca atctttgtt gacttgtgaa      180 ccaccataca acagattcaa gagaattact ttcccagcca tccaagaagg taacggtttt    240
tacgtttcta agattccaac tggttggacc gtttatgttg ctaatccagt tgctgctaaa    300
cagctgctat tgaagtctaa caatttcccc aaatctcact acggtttgga taccattggt    360
gaaaaatcta ccgctgttca attcgttggt agagataacg ttgttttgtc aacggtgaa     420 atctggaaaa agcagagaaa gatcatgaac ccagttttcc atagatccat gccaatcaaa    480
actgttgctt ctttggttcc cttgttgttc tctgcaattg aagaagcaaa cggcagaatt    540
atgattacgc caaagatgaa ggatttcact ttggatgctt tgggtttgac catcttcgat    600 tttgattta aagccttgca gggtgatcca gataattgga cttctatcta cagattgatc    660
```

```
accaggtcta tcttcgatcc aatctcttac gttttctgtg ctttggaacc tttgttggtt    720
tacgtttacc caaagcgtag aagatctgtt gatgctgttg ctaagattaa cgccaagttc    780
gatcaagtca tctccaaaaa aagggaagaa ttgcagaacg gcatcttctc taacaaacca    840
gataacgaaa aggacttggt caccttgatg ttggaagctg gtatgcaaga agatgtttct    900
atcaccaacg aagaattgag acataacatg gccgttttgt ttttggctgg tcatgattct    960
acttccaaca ctttgtcttt ctgcttgtac catttggcta aaaacaagag agcccaacag   1020
aagttgagag aggaaattat caacatcttg ggtgatgatg atatcgacat cgttccatcc   1080
ttggaagagt tgaaacaaat gaagtacatg aacatggtca tcaaagaaac cttgagattg   1140
ggtatgccat tggatttgtt gaccccaaga aaaacagttg aagataccct tgtcgccgat   1200
acctttattc aaaggatac cgttattgct gttgacgctg gtgcattgca tagagatcct   1260
agatcttgga aagatccaga cgaatttgtc ccagaaagat cgaagatga tggtgaacaa   1320 aactcccatg aaggtttgac ttgggttcca ttttctaacg gtactagaca atgtatcggc   1380
atgaacttct cattgatgga acagagattg accctgacta tgttgttgag aaagtacgaa   1440
gttgatctgc caaggattc catccattac gatcatatca tctacgaaca accatcctac   1500
gtttgtccag aatctttgga attgatcttc accaagaggt actaa              1545

<210> SEQ ID NO 71
<211> LENGTH: 514
<212> TYPE: PRT
<213> ORGANISM: Rhizopus delemar

<400> SEQUENCE: 71

Met Ala Leu Glu Gly Ala Leu Pro Leu Phe Gln Lys Arg Ser Lys Ser
1               5                   10                  15

Ser Tyr Ile Val Ala Ala Ile Leu Leu Ile Thr Val Lys Gln Ile Tyr
            20                  25                  30

Ser Phe Phe Arg Val Pro Thr Asn Leu Arg His Leu Pro Cys Val Ser
        35                  40                  45

Phe Phe Ala Met Ala Lys Ser Leu Leu Thr Cys Glu Pro Pro Tyr Asn
    50                  55                  60

Arg Phe Lys Arg Ile Thr Phe Pro Ala Ile Gln Glu Gly Asn Gly Phe
65                  70                  75                  80

Tyr Val Ser Lys Ile Pro Thr Gly Trp Thr Val Tyr Val Ala Asn Pro
                85                  90                  95

Val Ala Ala Lys Gln Leu Leu Leu Lys Ser Asn Asn Phe Pro Lys Ser
            100                 105                 110

His Tyr Gly Leu Asp Thr Ile Gly Glu Lys Ser Thr Ala Val Gln Phe
        115                 120                 125

Val Gly Arg Asp Asn Val Val Leu Ser Asn Gly Glu Ile Trp Lys Lys
    130                 135                 140

Gln Arg Lys Ile Met Asn Pro Val Phe His Arg Ser Met Pro Ile Lys
145                 150                 155                 160

Thr Val Ala Ser Leu Val Pro Leu Leu Phe Ser Ala Ile Glu Glu Ala
                165                 170                 175

Asn Gly Arg Ile Met Ile Thr Pro Lys Met Lys Asp Phe Thr Leu Asp
            180                 185                 190

Ala Leu Gly Leu Thr Ile Phe Asp Phe Asp Phe Lys Ala Leu Gln Gly
        195                 200                 205

Asp Pro Asp Asn Trp Thr Ser Ile Tyr Arg Leu Ile Thr Arg Ser Ile
```

```
            210                 215                 220
Phe Asp Pro Ile Ser Tyr Val Phe Cys Ala Leu Glu Pro Leu Leu Val
225                 230                 235                 240

Tyr Val Tyr Pro Lys Arg Arg Ser Val Asp Ala Val Ala Lys Ile
                245                 250                 255

Asn Ala Lys Phe Asp Gln Val Ile Ser Lys Lys Arg Glu Glu Leu Gln
                260                 265                 270

Asn Gly Ile Phe Ser Asn Lys Pro Asp Asn Glu Lys Asp Leu Val Thr
                275                 280                 285

Leu Met Leu Glu Ala Gly Met Gln Glu Asp Val Ser Ile Thr Asn Glu
        290                 295                 300

Glu Leu Arg His Asn Met Ala Val Leu Phe Leu Ala Gly His Asp Ser
305                 310                 315                 320

Thr Ser Asn Thr Leu Ser Phe Cys Leu Tyr His Leu Ala Lys Asn Lys
                325                 330                 335

Arg Ala Gln Gln Lys Leu Arg Glu Glu Ile Asn Ile Leu Gly Asp
                340                 345                 350

Asp Asp Ile Asp Ile Val Pro Ser Leu Glu Glu Leu Lys Gln Met Lys
        355                 360                 365

Tyr Met Asn Met Val Ile Lys Glu Thr Leu Arg Leu Gly Met Pro Leu
                370                 375                 380

Asp Leu Leu Thr Pro Arg Lys Thr Val Glu Asp Thr Phe Val Ala Asp
385                 390                 395                 400

Thr Phe Ile Pro Lys Asp Thr Val Ile Ala Val Asp Ala Gly Ala Leu
                405                 410                 415

His Arg Asp Pro Arg Ser Trp Lys Asp Pro Asp Glu Phe Val Pro Glu
                420                 425                 430

Arg Phe Glu Asp Asp Gly Glu Gln Asn Ser His Glu Gly Leu Thr Trp
                435                 440                 445

Val Pro Phe Ser Asn Gly Thr Arg Gln Cys Ile Gly Met Asn Phe Ser
                450                 455                 460

Leu Met Glu Gln Arg Leu Thr Leu Thr Met Leu Leu Arg Lys Tyr Glu
465                 470                 475                 480

Val Asp Leu Pro Lys Asp Ser Ile His Tyr Asp His Ile Ile Tyr Glu
                485                 490                 495

Gln Pro Ser Tyr Val Cys Pro Gly Ser Leu Glu Leu Ile Phe Thr Lys
                500                 505                 510

Arg Tyr

<210> SEQ ID NO 72
<211> LENGTH: 1569
<212> TYPE: DNA
<213> ORGANISM: Rhizopus microsporus

<400> SEQUENCE: 72
atggaccact tgatccaggt ctacaactct tctactcaag ttttgattcc agtcttgcag       60
aagagatcta aggcttctta tattaccgct gccattgctt tgattattgc ccaaagactg      120
tactcctact tcagagttcc aaaacatttg agaggtttcc caaagttgcc atactttggt      180
attgctaagt cattcttcgc caaagaatct ccaagagaaa gagtcaagaa gtacatcttg      240
ccaatcatca cgaaagaga tggcttctac attagcaaca ttccatttgg ttggatgctg      300
tacgttacca atccaattgc tgctaagcaa atcctgttga agtctaacgg ttttccaaaa      360
aaccacggtt tgctagaaga tatgggtgag aatttgttca tcgagttcat cggtaaggat      420
```

```
aacgttgttt tgactaacgg tgatacctgg aagagacaaa gaaaggttat gaatccagcc    480
ttccatcatt ccttgcctat taagactatg tccaacgtcg ttttctcctt gatctccgtt    540
attgatcaag ctaatggtac tgttccagtt gcttctacta tgcaaaactt caccttggat    600
actttgggtt tagccatttt cggttttgac tttaaggcat gcaaggtga tggtgatgaa    660
tggactaaga cttacagatt ggtttccgat tgcttgttcg acccaattat caacgttttc    720
agctcctact ccttcatctt cgatagaatc tacccaagac gtagaagagg tgctatggct    780
actagaaaat tgggtgaaaa gttcttggaa atcgcccagc aaaaaaggat ggaaatcaaa    840
tctggtgctt tcgctgatgt tccagataac gaaaaagatc tgttgacctt gatgttggaa    900
gctgaagaaa aggtgatgt ctggacttct gaagatgaat tgagacataa cattgccgtt    960
ttgttcttgg ctggtcatga tacaactgct catgctttgt ctttctgctt ttaccatttg   1020
gctaagaaca aggacatcca gcagaagttg agaaaagaag ttttggattt gttgggtgat   1080
gaaccagttg atgttgttcc aactgttgaa caattgaagg acatgcagta cttgaacatg   1140
gtcatcaaag aaaacctgag gatgaattct ccagccgata tgttgttttc cagagatgtt   1200
caagaggata tcgttttggc taacaccttt attccaaagg gtactgtcat ctccattaac   1260
attgaagcct tgcattgcaa tccaaagttg tggcataatc cagatcaatt cgatccagaa   1320
agatttgctc caggtggtga acatgaacaa catgaaggta tgacttggtt gccattttct   1380
aacggtacta gacaatgtct gggtatgaac ttcagcttgt ttgaacagag attggttatc   1440
gccatgatct tgaagaagta cgaaatctcc attccagagg attccatcca tagaaaccac   1500
atcattaacg acatgccatt caatgttgct cccaagtctt tggaattgac tttcactaag   1560
aggtactaa                                                           1569
```

<210> SEQ ID NO 73
<211> LENGTH: 522
<212> TYPE: PRT
<213> ORGANISM: Rhizopus microsporus

<400> SEQUENCE: 73

```
Met Asp His Leu Ile Gln Val Tyr Asn Ser Ser Thr Gln Val Leu Ile
1               5                   10                  15

Pro Val Leu Gln Lys Arg Ser Lys Ala Ser Tyr Ile Thr Ala Ala Ile
            20                  25                  30

Ala Leu Ile Ile Ala Gln Arg Leu Tyr Ser Tyr Phe Arg Val Pro Lys
        35                  40                  45

His Leu Arg Gly Phe Pro Lys Leu Pro Tyr Phe Gly Ile Ala Lys Ser
    50                  55                  60

Phe Phe Ala Lys Glu Ser Pro Arg Glu Arg Val Lys Lys Tyr Ile Leu
65                  70                  75                  80

Pro Ile Ile Asn Glu Arg Asp Gly Phe Tyr Ile Ser Asn Ile Pro Phe
                85                  90                  95

Gly Trp Met Leu Tyr Val Thr Asn Pro Ile Ala Ala Lys Gln Ile Leu
            100                 105                 110

Leu Lys Ser Asn Gly Phe Pro Lys Asn His Gly Leu Leu Glu Asp Met
        115                 120                 125

Gly Glu Asn Leu Phe Ile Glu Phe Ile Gly Lys Asp Asn Val Val Leu
    130                 135                 140

Thr Asn Gly Asp Thr Trp Lys Arg Gln Arg Lys Val Met Asn Pro Ala
145                 150                 155                 160
```

Phe His His Ser Leu Pro Ile Lys Thr Met Ser Asn Val Val Phe Ser
                 165                 170                 175

Leu Ile Ser Val Ile Asp Gln Ala Asn Gly Thr Val Pro Val Ala Ser
             180                 185                 190

Thr Met Gln Asn Phe Thr Leu Asp Thr Leu Gly Leu Ala Ile Phe Gly
         195                 200                 205

Phe Asp Phe Lys Ala Leu Gln Gly Asp Gly Asp Glu Trp Thr Lys Thr
 210                 215                 220

Tyr Arg Leu Val Ser Asp Cys Leu Phe Asp Pro Ile Ile Asn Val Phe
225                 230                 235                 240

Ser Ser Tyr Ser Phe Ile Phe Asp Arg Ile Tyr Pro Arg Arg Arg Arg
                 245                 250                 255

Gly Ala Met Ala Thr Arg Lys Leu Gly Glu Lys Phe Leu Glu Ile Ala
             260                 265                 270

Gln Gln Lys Arg Met Glu Ile Lys Ser Gly Ala Phe Ala Asp Val Pro
         275                 280                 285

Asp Asn Glu Lys Asp Leu Leu Thr Leu Met Leu Glu Ala Glu Glu Lys
     290                 295                 300

Gly Asp Val Trp Thr Ser Glu Asp Glu Leu Arg His Asn Ile Ala Val
305                 310                 315                 320

Leu Phe Leu Ala Gly His Asp Thr Thr Ala His Ala Leu Ser Phe Cys
                 325                 330                 335

Phe Tyr His Leu Ala Lys Asn Lys Asp Ile Gln Gln Lys Leu Arg Lys
             340                 345                 350

Glu Val Leu Asp Leu Leu Gly Asp Glu Pro Val Asp Val Pro Thr
         355                 360                 365

Val Glu Gln Leu Lys Asp Met Gln Tyr Leu Asn Met Val Ile Lys Glu
     370                 375                 380

Asn Leu Arg Met Asn Ser Pro Ala Asp Met Leu Phe Ser Arg Asp Val
385                 390                 395                 400

Gln Glu Asp Ile Val Leu Ala Asn Thr Phe Ile Pro Lys Gly Thr Val
                 405                 410                 415

Ile Ser Ile Asn Ile Glu Ala Leu His Cys Asn Pro Lys Leu Trp His
             420                 425                 430

Asn Pro Asp Gln Phe Asp Pro Glu Arg Phe Ala Pro Gly Gly Glu His
         435                 440                 445

Glu Gln His Glu Gly Met Thr Trp Leu Pro Phe Ser Asn Gly Thr Arg
     450                 455                 460

Gln Cys Leu Gly Met Asn Phe Ser Leu Phe Glu Gln Arg Leu Val Ile
465                 470                 475                 480

Ala Met Ile Leu Lys Lys Tyr Glu Ile Ser Ile Pro Glu Asp Ser Ile
                 485                 490                 495

His Arg Asn His Ile Ile Asn Asp Met Pro Phe Asn Val Ala Pro Lys
             500                 505                 510

Ser Leu Glu Leu Thr Phe Thr Lys Arg Tyr
         515                 520

<210> SEQ ID NO 74
<211> LENGTH: 1452
<212> TYPE: DNA
<213> ORGANISM: Syncephalastrum racemosum

<400> SEQUENCE: 74
atgttcagac caccagcagg tttgccaaaa ttgccaatta tcaattactt caggttgctg        60

| | |
|---|---|
| tgggccttgt acagaaaaga atctccaact agaagatccc agagattgat tttgccagcc | 120 |
| ttgcaaaaac ataacgctaa agcttacttg gctaaggttc catatacttg gactgtttac | 180 |
| ttggttgatc cagttgctgt aagaccttc ttgatgagaa atggtacttt cccaaagacc | 240 |
| atggaatcca ttgatgcttt cgatcaatct cacccaaatg ttcaattttg gggtagagaa | 300 |
| aacttgggtt tctctgttgg tgattcttgg aagagacaac gtaagattat ctttccagct | 360 |
| tttagaaggg ctatgccagt tcaattattc ggtgaattgg ttccaaagat gttcgacttg | 420 |
| atcgacaaag aacattccac cattgccatc gatttgatgc aaagattcac cttggatgct | 480 |
| ttgggtttag ctgcttttc tttcgatttc catgccttgg ataaccacaa caatgaatgg | 540 |
| gaagttgcct acgagatgat cagaaaagag ttggtttctc cactgactaa catgttggct | 600 |
| agatacgatt acatcctgaa gtacattatt ccaggtagag ctgaaaaaca agctgccgtt | 660 |
| tctaagatca accacttgtt gtctgatatt gccaacgaga aagaaagat gattaagagg | 720 |
| aatcccgata tgttgaaggt tccagattct gaaaaggact tgttgacctt gatgttggaa | 780 |
| tccgatttgg aaaactctga tgatccagct tccgaagaat tgattagagc taatttggct | 840 |
| accttcttct tggctggtca tgatacaact gctaacactt tgtctttctg gttgtaccat | 900 |
| ttggccatgt acaaggatat tcaaaagaag gctagagaag aggtcattga aactatgggt | 960 |
| ggtgctccag aagatatagt tccaactgct gaacagctga agaaaatgaa gtacatggac | 1020 |
| tgcatcatca agaaaaacct gagattcatg ggtccagctt ggaattatt ccaaggatt | 1080 |
| gccaaagagg actacaactt gaacggtatt ttcatcccaa agggtactag agtttctgtt | 1140 |
| gacttgcata ccttacatca tcatccagat gttttggaaag aaccagagag atttgatcca | 1200 |
| ttgagattcg ttgaaaacgg cgaacattct aaacacgaag gtttgtcttg gattgctttt | 1260 |
| tcatctggtg ctagagtatg catcggtcaa aatttctcat tggttgaaca aagggtcgtc | 1320 |
| atgtctatgt tgttgagaag atacgaatgg gacatcccag aagattccat tcatagagaa | 1380 |
| ggcttgcaat tgaaggacac caacaatcaa gctccaagat cattggaaat cgtgttcaag | 1440 |
| aagaggtact aa | 1452 |

<210> SEQ ID NO 75
<211> LENGTH: 483
<212> TYPE: PRT
<213> ORGANISM: Syncephalastrum racemosum

<400> SEQUENCE: 75

Met Phe Arg Pro Pro Ala Gly Leu Pro Lys Leu Pro Ile Ile Asn Tyr
1               5                   10                  15

Phe Arg Leu Leu Trp Ala Leu Tyr Arg Lys Glu Ser Pro Thr Arg Arg
            20                  25                  30

Ser Gln Arg Leu Ile Leu Pro Ala Leu Gln Lys His Asn Ala Lys Ala
        35                  40                  45

Tyr Leu Ala Lys Val Pro Tyr Thr Trp Thr Val Tyr Leu Val Asp Pro
    50                  55                  60

Val Ala Val Lys Thr Phe Leu Met Arg Asn Gly Thr Phe Pro Lys Thr
65                  70                  75                  80

Met Glu Ser Ile Asp Ala Phe Asp Gln Ser His Pro Asn Val Gln Phe
                85                  90                  95

Trp Gly Arg Glu Asn Leu Gly Phe Ser Val Gly Asp Ser Trp Lys Arg
            100                 105                 110

Gln Arg Lys Ile Ile Phe Pro Ala Phe Arg Arg Ala Met Pro Val Gln
        115                 120                 125

```
Leu Phe Gly Glu Leu Val Pro Lys Met Phe Asp Leu Ile Asp Lys Glu
            130                 135                 140

His Ser Thr Ile Ala Ile Asp Leu Met Gln Arg Phe Thr Leu Asp Ala
145                 150                 155                 160

Leu Gly Leu Ala Ala Phe Ser Phe Asp Phe His Ala Leu Asp Asn His
                    165                 170                 175

Asn Asn Glu Trp Glu Val Ala Tyr Glu Met Ile Arg Lys Glu Leu Val
                180                 185                 190

Ser Pro Leu Thr Asn Met Leu Ala Arg Tyr Asp Tyr Ile Leu Lys Tyr
                195                 200                 205

Ile Ile Pro Gly Arg Ala Glu Lys Gln Ala Ala Val Ser Lys Ile Asn
210                 215                 220

His Leu Leu Ser Asp Ile Ala Asn Glu Arg Arg Lys Met Ile Lys Arg
225                 230                 235                 240

Asn Pro Asp Met Leu Lys Val Pro Asp Ser Glu Lys Asp Leu Leu Thr
                245                 250                 255

Leu Met Leu Glu Ser Asp Leu Glu Asn Ser Asp Asp Pro Ala Ser Glu
                260                 265                 270

Glu Leu Ile Arg Ala Asn Leu Ala Thr Phe Phe Leu Ala Gly His Asp
                275                 280                 285

Thr Thr Ala Asn Thr Leu Ser Phe Trp Leu Tyr His Leu Ala Met Tyr
290                 295                 300

Lys Asp Ile Gln Lys Lys Ala Arg Glu Glu Val Ile Glu Thr Met Gly
305                 310                 315                 320

Gly Ala Pro Glu Asp Ile Val Pro Thr Ala Glu Gln Leu Lys Lys Met
                325                 330                 335

Lys Tyr Met Asp Cys Ile Ile Lys Glu Asn Leu Arg Phe Met Gly Pro
                340                 345                 350

Ala Leu Glu Leu Phe Pro Arg Ile Ala Lys Glu Asp Tyr Asn Leu Asn
                355                 360                 365

Gly Ile Phe Ile Pro Lys Gly Thr Arg Val Ser Val Asp Leu His Thr
370                 375                 380

Leu His His His Pro Asp Val Trp Lys Glu Pro Glu Arg Phe Asp Pro
385                 390                 395                 400

Leu Arg Phe Val Glu Asn Gly Glu His Ser Lys His Glu Gly Leu Ser
                405                 410                 415

Trp Ile Ala Phe Ser Ser Gly Ala Arg Val Cys Ile Gly Gln Asn Phe
                420                 425                 430

Ser Leu Val Glu Gln Arg Val Val Met Ser Met Leu Leu Arg Arg Tyr
                435                 440                 445

Glu Trp Asp Ile Pro Glu Asp Ser Ile His Arg Glu Gly Leu Gln Leu
450                 455                 460

Lys Asp Thr Asn Asn Gln Ala Pro Arg Ser Leu Glu Ile Val Phe Lys
465                 470                 475                 480

Lys Arg Tyr

<210> SEQ ID NO 76
<211> LENGTH: 1485
<212> TYPE: DNA
<213> ORGANISM: Parasitella parasitica

<400> SEQUENCE: 76
atggccatcg aaaacttcat gcagtcttac aacagagcca ttgaaaacgt cttgccaatc      60
```

```
ttgagaaaaa ggtctaaggc ttcctatatt ggtatggcca ttatgtgcat cgttatcaag    120
caagtttact ccgcttactc tgttccaaaa cacttgcaaa gattcccaa ggtttcattc     180
ttgtccatga tcagatccta cttgatcaaa gaagccgttg tcgaaagaac taagagattg    240
gttactccat tgactgatgc tggtcatggt ttttacgtct gtaaaattcc attgacctgg    300
accgttttg ttaccgatcc aattgctgct aagaccttgt tgttgaaaac tgagttttc     360
ccaaagtctc acgctttctt tgatgctttg ggtgataatt ctccagccgt tcaattttg    420
ggtagagaaa atgttgctgc ctccaatggt gaaatctgga aaaagcaacg taaattcatg   480
aaccccgctt tcttgagatc ttctccagtt aagactttct cctctgttac ccacaacttg   540
attaaggtta tcgaaaccca atctgatgct gttccaattg caaactgtat gaaggctttc   600
actattgacg ctttaggttt gtctgctttc ggtttcgatt ccaatctttt gaatggtgat   660
ccagaaggtt ggactgaaac ttacaatatt gctattgccg gtttgttcga cccattcatt   720
aacatctttg ttaaggtcga cttcatgatg aactacatct cttctaagag aaagagaatc   780
aacaaggcca ttaccagatt caactccatg ttggaagatt tggctaacaa gagaaggcaa   840
gaaatcttga cggtgaaac tttgggtgtt ccagaaaacg aaaaggattt gttgaccttg    900
atgatcgaag ccgatattag agaaggttcc agaactactc taccgaattg agacataac    960
attgccttgt ttttcttggc cggtcatgat acaactgctc atactttggc ttttgcttg  1020
tacaacctgg ctaaaaacaa acacgttcaa gctaaagcta gagccgaagt tttggatatt  1080
ttaggtgatg aacctaagga tgttgaccca actatggaag atctgaagag aatggattac  1140
ctgaacatgt ttatcaaaga aaacttgaga agatgcggtc cagttgacaa gttgttgtct  1200
agagatactg ccgaagatat cgatttgaac ggtactttga ttccaaaggg ccaaaagatc  1260
tccatcgatt tcaactctat ccacatgaat ccaaagttgt ggcataaccc agaagaattt  1320
gtcccagaaa gatttgaacc aggtggtgaa tttgatcaac atactggttt tacttggctg  1380
ccattttctc atggttctag acaatgtatc ggcatgaact tttcattgac cgagcaaaaa  1440
gtcctgttgt ctatgatctg taagagagcc atcgaagaga tctga                 1485
```

<210> SEQ ID NO 77
<211> LENGTH: 494
<212> TYPE: PRT
<213> ORGANISM: Parasitella parasitica

<400> SEQUENCE: 77

```
Met Ala Ile Glu Asn Phe Met Gln Ser Tyr Asn Arg Ala Ile Glu Asn
1               5                   10                  15

Val Leu Pro Ile Leu Arg Lys Arg Ser Lys Ala Ser Tyr Ile Gly Met
            20                  25                  30

Ala Ile Met Cys Ile Val Ile Lys Gln Val Tyr Ser Ala Tyr Ser Val
        35                  40                  45

Pro Lys His Leu Gln Arg Phe Pro Lys Val Ser Phe Leu Ser Met Ile
    50                  55                  60

Arg Ser Tyr Leu Ile Lys Glu Ala Val Val Glu Arg Thr Lys Arg Leu
65                  70                  75                  80

Val Thr Pro Leu Thr Asp Ala Gly His Gly Phe Tyr Val Cys Lys Ile
                85                  90                  95

Pro Leu Thr Trp Thr Val Phe Val Thr Asp Pro Ile Ala Ala Lys Thr
            100                 105                 110

Leu Leu Leu Lys Thr Glu Phe Phe Pro Lys Ser His Ala Phe Phe Asp
        115                 120                 125
```

Ala Leu Gly Asp Asn Ser Pro Ala Val Gln Phe Leu Gly Arg Glu Asn
            130                 135                 140

Val Ala Ala Ser Asn Gly Glu Ile Trp Lys Lys Gln Arg Lys Phe Met
145                 150                 155                 160

Asn Pro Ala Phe Leu Arg Ser Ser Pro Val Lys Thr Phe Ser Ser Val
                165                 170                 175

Thr His Asn Leu Ile Lys Val Ile Glu Thr Gln Ser Asp Ala Val Pro
            180                 185                 190

Ile Ala Asn Cys Met Lys Ala Phe Thr Ile Asp Ala Leu Gly Leu Ser
            195                 200                 205

Ala Phe Gly Phe Asp Phe Gln Ser Leu Asn Gly Asp Pro Glu Gly Trp
        210                 215                 220

Thr Glu Thr Tyr Asn Ile Ala Ile Ala Gly Leu Phe Asp Pro Phe Ile
225                 230                 235                 240

Asn Ile Phe Val Lys Val Asp Phe Met Met Asn Tyr Ile Ser Ser Lys
                245                 250                 255

Arg Lys Arg Ile Asn Lys Ala Ile Thr Arg Phe Asn Ser Met Leu Glu
            260                 265                 270

Asp Leu Ala Asn Lys Arg Arg Gln Glu Ile Leu Asn Gly Glu Thr Leu
        275                 280                 285

Gly Val Pro Glu Asn Glu Lys Asp Leu Leu Thr Leu Met Ile Glu Ala
    290                 295                 300

Asp Ile Arg Glu Gly Ser Arg Thr Thr Ser Thr Glu Leu Arg His Asn
305                 310                 315                 320

Ile Ala Leu Phe Phe Leu Ala Gly His Asp Thr Thr Ala His Thr Leu
                325                 330                 335

Ala Phe Cys Leu Tyr Asn Leu Ala Lys Asn Lys His Val Gln Ala Lys
            340                 345                 350

Ala Arg Ala Glu Val Leu Asp Ile Leu Gly Asp Glu Pro Lys Asp Val
        355                 360                 365

Asp Pro Thr Met Glu Asp Leu Lys Arg Met Asp Tyr Leu Asn Met Val
    370                 375                 380

Ile Lys Glu Asn Leu Arg Arg Cys Gly Pro Val Asp Lys Leu Leu Ser
385                 390                 395                 400

Arg Asp Thr Ala Glu Asp Ile Asp Leu Asn Gly Thr Leu Ile Pro Lys
                405                 410                 415

Gly Gln Lys Ile Ser Ile Asp Phe Asn Ser Ile His Met Asn Pro Lys
            420                 425                 430

Leu Trp His Asn Pro Glu Glu Phe Val Pro Glu Arg Phe Glu Pro Gly
        435                 440                 445

Gly Glu Phe Asp Gln His Thr Gly Phe Thr Trp Leu Pro Phe Ser His
    450                 455                 460

Gly Ser Arg Gln Cys Ile Gly Met Asn Phe Ser Leu Thr Glu Gln Lys
465                 470                 475                 480

Val Leu Leu Ser Met Ile Cys Lys Arg Ala Ile Glu Glu Ile
                485                 490

<210> SEQ ID NO 78
<211> LENGTH: 1626
<212> TYPE: DNA
<213> ORGANISM: Lichtheimia corymbifera

<400> SEQUENCE: 78
atggctgttg cttctccaca gatcaagaac atggttacta tggatagatt gcaggacatc        60

```
tactctaccg tttctcaaca cgttgttgct catgcttcag ctgttacttc tagacaaaga    120
aagatttcca tttccgctgc tgttgcattg gttgcttttt acactgttta caaggttgtt    180
actccaccag ctaacttgag acatattcca tctatgggtt tcttctctta cttgaacgct    240
ttcttgagag gtaagcaatt gcacgatatc tccaagaatg ttgttttgcc acatgccgtt    300
aatgttgata acgtgtttta cttgagattc gacattttag gttggaccgt tcatattgct    360
agaccagaag ctgctaagag attcttgttg aagtctgata ttttcccaaa ggccgacatg    420
atttctgaaa gaggtaatac tttgttcggc aagttcgtgt caacagaaa catcgttatg     480 ttgaacggtg atgattggaa ggctcaaaga aaagttgcta atccagcttt ccatagagct    540
atgccagttg aattattcgg tagattgact caaaagaccc tgaaaagat ggaagaagaa     600 atggacggcg gtactttgaa cttccatgat attacagaaa ggtacacctt ggaagttatt    660
ggtttggctg gttttgaatt tgaattcggt gctatcgaaa acccaaagtc tgaatgggtt    720
gatagatacc agagattgat tgaagctact ttcaacccat ggttcattgc ttttccaaac    780
ttggacatga gatacaggtt tttgttccca tctaggaaga gattgcacag agaaatggat    840
gctttcttgg acaagatgtc ccaagttatt actcacaaga gagagttgtt gaaccaccaa    900
aaaactaccg ttccagaatc cgaaagagat atcttgacct tgatgatcga agctgaaaag    960
aatggtgaag gttctatgac caatgaagag ttgcagaaca acctgctggt tttttcatt    1020 gctggtcatg atacaacatc cttggctttg tcttatgctg cttattactt ggctgttaac    1080
ccagatgttc aaagaaaggc tagagaagaa gccattagag ttttgggtga tgctcctgaa    1140
gatgttatgc caacagttga acaaactaga cagttgacct acatcaacat ggtcatcaaa    1200
gaaaccttga atgtctcc accattggct actattccag ttagagaagc tagtgaagat     1260
accgaattgt gtggtacttt tatcccaaag ggtacaagaa ccttcttgga tatctacgaa    1320
atccaacata cccaaccgt ttggaaagat ccagaaactt ttaagcccga agattcaaa     1380 ccaggtggtg aagctgaaga attagctggt tctggtatgt cttggttgcc attttctaat    1440
ggttccagac aatgtatcgg cctgaatttc tcattggtag aacaaagggt tttcctgcca    1500
atgttgctga gaaagtatga atggcatttg ccagaagatt ccatccacaa agaacgtatt    1560
caaacaatgg gtttagccgt cattaagcca aaggatttga agttgacttt caagaagagg    1620
tactaa                                                               1626
```

<210> SEQ ID NO 79
<211> LENGTH: 541
<212> TYPE: PRT
<213> ORGANISM: Lichtheimia corymbifera

<400> SEQUENCE: 79

Met Ala Val Ala Ser Pro Gln Ile Lys Asn Met Val Thr Met Asp Arg
1               5                   10                  15

Leu Gln Asp Ile Tyr Ser Thr Val Ser Gln His Val Val Ala His Ala
            20                  25                  30

Ser Ala Val Thr Ser Arg Gln Arg Lys Ile Ser Ile Ser Ala Ala Val
        35                  40                  45

Ala Leu Val Ala Phe Tyr Thr Val Tyr Lys Val Thr Pro Pro Ala
    50                  55                  60

Asn Leu Arg His Ile Pro Ser Met Gly Phe Phe Ser Tyr Leu Asn Ala
65                  70                  75                  80

Phe Leu Arg Gly Lys Gln Leu His Asp Ile Ser Lys Asn Val Val Leu

```
            85                  90                  95
Pro His Ala Val Asn Val Asp Asn Gly Val Tyr Leu Arg Phe Asp Ile
            100                 105                 110

Leu Gly Trp Thr Val His Ile Ala Arg Pro Glu Ala Ala Lys Arg Phe
            115                 120                 125

Leu Leu Lys Ser Asp Ile Phe Pro Lys Ala Asp Met Ile Ser Glu Arg
130                 135                 140

Gly Asn Thr Leu Phe Gly Lys Phe Val Phe Asn Arg Asn Ile Val Met
145                 150                 155                 160

Leu Asn Gly Asp Asp Trp Lys Ala Gln Arg Lys Val Ala Asn Pro Ala
                165                 170                 175

Phe His Arg Ala Met Pro Val Glu Leu Phe Gly Arg Leu Thr Gln Lys
                180                 185                 190

Thr Leu Lys Lys Met Glu Glu Met Asp Gly Thr Leu Asn Phe
                195                 200                 205

His Asp Ile Thr Glu Arg Tyr Thr Leu Glu Val Ile Gly Leu Ala Gly
210                 215                 220

Phe Glu Phe Glu Phe Gly Ala Ile Glu Asn Pro Lys Ser Glu Trp Val
225                 230                 235                 240

Asp Arg Tyr Gln Arg Leu Ile Glu Ala Thr Phe Asn Pro Trp Phe Ile
                245                 250                 255

Ala Phe Pro Asn Leu Asp Met Arg Tyr Arg Phe Leu Phe Pro Ser Arg
                260                 265                 270

Lys Arg Leu His Arg Glu Met Asp Ala Phe Leu Asp Lys Met Ser Gln
                275                 280                 285

Val Ile Thr His Lys Arg Glu Leu Leu Asn His Gln Lys Thr Thr Val
                290                 295                 300

Pro Glu Ser Glu Arg Asp Ile Leu Thr Leu Met Ile Glu Ala Glu Lys
305                 310                 315                 320

Asn Gly Glu Gly Ser Met Thr Asn Glu Glu Leu Gln Asn Asn Leu Leu
                325                 330                 335

Val Phe Phe Ile Ala Gly His Asp Thr Thr Ser Leu Ala Leu Ser Tyr
                340                 345                 350

Ala Ala Tyr Tyr Leu Ala Val Asn Pro Asp Val Gln Arg Lys Ala Arg
                355                 360                 365

Glu Glu Ala Ile Arg Val Leu Gly Asp Ala Pro Glu Asp Val Met Pro
370                 375                 380

Thr Val Glu Gln Thr Arg Gln Leu Thr Tyr Ile Asn Met Val Ile Lys
385                 390                 395                 400

Glu Thr Leu Arg Met Ser Pro Pro Leu Ala Thr Ile Pro Val Arg Glu
                405                 410                 415

Ala Ser Glu Asp Thr Glu Leu Cys Gly Thr Phe Ile Pro Lys Gly Thr
                420                 425                 430

Arg Thr Phe Leu Asp Ile Tyr Glu Ile Gln His Asn Pro Thr Val Trp
                435                 440                 445

Lys Asp Pro Glu Thr Phe Lys Pro Glu Arg Phe Lys Pro Gly Gly Glu
                450                 455                 460

Ala Glu Glu Leu Ala Gly Ser Gly Met Ser Trp Leu Pro Phe Ser Asn
465                 470                 475                 480

Gly Ser Arg Gln Cys Ile Gly Leu Asn Phe Ser Leu Val Glu Gln Arg
                485                 490                 495

Val Phe Leu Pro Met Leu Leu Arg Lys Tyr Glu Trp His Leu Pro Glu
                500                 505                 510
```

Asp Ser Ile His Lys Glu Arg Ile Gln Thr Met Gly Leu Ala Val Ile
        515                 520                 525

Lys Pro Lys Asp Leu Lys Leu Thr Phe Lys Lys Arg Tyr
        530                 535                 540

<210> SEQ ID NO 80
<211> LENGTH: 1578
<212> TYPE: DNA
<213> ORGANISM: Choanephora cucurbitarum

<400> SEQUENCE: 80

| | | | | | |
|---|---|---|---|---|---|
| atgttcactg | aaaccgcctt | gcaaatctac | catcaaatgg | ctgaaaaggt | cttgccaatt | 60 |
| ttgaagagac | agccaaagtc | atcttatatt | ggtgctgctt | tggttttctt | gttggttgct | 120 |
| gaaattagaa | ggcaactgtc | cgttccaaaa | cacttgaaaa | agttcccaac | cattggtgtg | 180 |
| ttcaccttga | tgaagtcttt | catgagaaac | gactccgtta | tcgaaagaca | caatagattg | 240 |
| gttgctccaa | tcgttaagca | aggtcataag | ttttacgctg | ccaagattcc | atttgactgg | 300 |
| tctttgtcta | tagtcgatcc | agaaattgcc | aagatcatgt | tgatgaagag | tgatgctttt | 360 |
| ccaaagtctc | aaggtttcac | tagaaagttg | ggtgactctt | cattgatcgt | tagattcact | 420 |
| ggtagagaca | acgtgtctat | ttctaatggt | catgtctgga | gaggcagag | aaagtttatg | 480 |
| aatccagctt | tcagaagaag | cactccaatc | aagactttg | gtgaattgac | cttgaagttc | 540 |
| ttcgattgcg | ttgatgaaca | accacaagat | tttccagctg | ccattaagtt | gaagaactac | 600 |
| actttggatg | ctttgggtat | tgctgctttt | gatttcgact | tcaagtcttt | gtcaggtgat | 660 |
| ccagaaggtt | ggactgaaat | ctacaacgtt | attatgaagg | gtatgttcga | cccttgggtt | 720 |
| tttttgtttg | gtaagatgga | attcatcctg | cagtacatca | ttccatctaa | gagagaatgc | 780 |
| attaagtccg | tcgttaagtt | caacaagatg | ttggttgaaa | tggccgataa | gagaaggcaa | 840 |
| gaaattcaaa | acggtaagaa | gttgaacacc | ccaaactctg | aaaaggatct | gttgactttg | 900 |
| atgatcgaag | ctgaaatgga | agagggtatt | atgactacca | acgaagaact | gagagaaaac | 960 |
| attgccttgt | ttttcttggc | tggtcaagat | tctacaggca | actctttgtc | ttttgcttg | 1020 |
| taccatttgg | ccaagaacaa | gcacgttcaa | gataagttga | aagggaaat | catgtccgtt | 1080 |
| atgggtgata | gagatttgga | tgcaattcca | accgtcgaag | attttaagga | tatgccctac | 1140 |
| ttgaacatgg | tcatcaaaga | aaacttgagg | ttgtctggtc | cagctgatag | attttttggat | 1200 |
| agagttgttg | ccgaagatat | cgtcttaggt | ggtgaactaa | ttccaaaggg | tactttgatt | 1260 |
| accgttgatg | ttgcctccat | tcattacaat | ccagaatatt | ggcatgaccc | cgaagtttc | 1320 |
| attccagaaa | gatttgaacc | taacggtgaa | ttcgatcaac | atgctggtgt | gcttggttg | 1380 |
| ccattttcaa | atggtgctag | acaatgtatc | ggcatgaatt | tctcattggc | tgaacaaagg | 1440 |
| gtctttctga | ctatgttgtt | gagaagatac | gaagtcggta | tctccaagga | ttctatccat | 1500 |
| tacgattcca | tcgtctacga | acaatctttt | actttcgctc | catctagcct | gacttttgaac | 1560 |
| tttactaagc | tgaactaa | | | | | 1578 |

<210> SEQ ID NO 81
<211> LENGTH: 525
<212> TYPE: PRT
<213> ORGANISM: Choanephora cucurbitarum

<400> SEQUENCE: 81

Met Phe Thr Glu Thr Ala Leu Gln Ile Tyr His Gln Met Ala Glu Lys
1               5                   10                  15

```
Val Leu Pro Ile Leu Lys Arg Gln Pro Lys Ser Ser Tyr Ile Gly Ala
            20                  25                  30

Ala Leu Val Phe Leu Val Ala Glu Ile Arg Arg Gln Leu Ser Val
        35                  40                  45

Pro Lys His Leu Lys Lys Phe Pro Thr Ile Gly Val Phe Thr Leu Met
 50                  55                  60

Lys Ser Phe Met Arg Asn Asp Ser Val Ile Glu Arg His Asn Arg Leu
 65                  70                  75                  80

Val Ala Pro Ile Val Lys Gln Gly His Lys Phe Tyr Ala Ala Lys Ile
                85                  90                  95

Pro Phe Asp Trp Ser Leu Ser Ile Val Asp Pro Glu Ile Ala Lys Ile
                100                 105                 110

Met Leu Met Lys Ser Asp Ala Phe Pro Lys Ser Gln Gly Phe Thr Arg
            115                 120                 125

Lys Leu Gly Asp Ser Ser Leu Ile Val Arg Phe Thr Gly Arg Asp Asn
130                 135                 140

Val Ser Ile Ser Asn Gly His Val Trp Lys Arg Gln Arg Lys Phe Met
145                 150                 155                 160

Asn Pro Ala Phe Arg Arg Ser Thr Pro Ile Lys Thr Phe Gly Glu Leu
                165                 170                 175

Thr Leu Lys Phe Phe Asp Cys Val Asp Glu Gln Pro Gln Asp Phe Pro
            180                 185                 190

Ala Ala Ile Lys Leu Lys Asn Tyr Thr Leu Asp Ala Leu Gly Ile Ala
            195                 200                 205

Ala Phe Asp Phe Asp Phe Lys Ser Leu Ser Gly Asp Pro Glu Gly Trp
            210                 215                 220

Thr Glu Ile Tyr Asn Val Ile Met Lys Gly Met Phe Asp Pro Trp Val
225                 230                 235                 240

Phe Leu Phe Gly Lys Met Glu Phe Ile Leu Gln Tyr Ile Ile Pro Ser
                245                 250                 255

Lys Arg Glu Cys Ile Lys Ser Val Val Lys Phe Asn Lys Met Leu Val
            260                 265                 270

Glu Met Ala Asp Lys Arg Arg Gln Glu Ile Gln Asn Gly Lys Lys Leu
            275                 280                 285

Asn Thr Pro Asn Ser Glu Lys Asp Leu Leu Thr Leu Met Ile Glu Ala
            290                 295                 300

Glu Met Glu Glu Gly Ile Met Thr Thr Asn Glu Glu Leu Arg Glu Asn
305                 310                 315                 320

Ile Ala Leu Phe Phe Leu Ala Gly Gln Asp Ser Thr Gly Asn Ser Leu
                325                 330                 335

Ser Phe Cys Leu Tyr His Leu Ala Lys Asn Lys His Val Gln Asp Lys
            340                 345                 350

Leu Arg Arg Glu Ile Met Ser Val Met Gly Asp Arg Asp Leu Asp Ala
            355                 360                 365

Ile Pro Thr Val Glu Asp Phe Lys Asp Met Pro Tyr Leu Asn Met Val
            370                 375                 380

Ile Lys Glu Asn Leu Arg Leu Ser Gly Pro Ala Asp Arg Phe Leu Asp
385                 390                 395                 400

Arg Val Val Ala Glu Asp Ile Val Leu Gly Glu Leu Ile Pro Lys
                405                 410                 415

Gly Thr Leu Ile Thr Val Asp Val Ala Ser Ile His Tyr Asn Pro Glu
            420                 425                 430
```

```
Tyr Trp His Asp Pro Glu Val Phe Ile Pro Glu Arg Phe Glu Pro Asn
            435                 440                 445

Gly Glu Phe Asp Gln His Ala Gly Val Ala Trp Leu Pro Phe Ser Asn
        450                 455                 460

Gly Ala Arg Gln Cys Ile Gly Met Asn Phe Ser Leu Ala Glu Gln Arg
465                 470                 475                 480

Val Phe Leu Thr Met Leu Leu Arg Arg Tyr Glu Val Gly Ile Ser Lys
                485                 490                 495

Asp Ser Ile His Tyr Asp Ser Ile Val Tyr Glu Gln Ser Phe Thr Phe
            500                 505                 510

Ala Pro Ser Ser Leu Thr Leu Asn Phe Thr Lys Leu Asn
        515                 520                 525

<210> SEQ ID NO 82
<211> LENGTH: 1530
<212> TYPE: DNA
<213> ORGANISM: Absidia repens

<400> SEQUENCE: 82
```

| | | |
|---|---|---|
| atgggcacct cttacaaaag aaaggctgct tatgttacta ttggtgctgc tgttgttttg | 60 |
| ctgttcagat ctatctacgg tttctactac gttccaaagt ccttgagaca tttgccatgt | 120 |
| gttggttata gagaattggc ctactctatc atgaagaggg aagatgctgc tactagagct | 180 |
| agatctgttt tgggtcaagc tatcaaagaa agaacggtg cttttgttgc taagttccca | 240 |
| atggaatgga ctgttttttt gacttcccca agaaccattc aagccgtttt gttgaagtct | 300 |
| gacaagtttc aaagaccta cgatatgttt catgccttgg gtgaatcttc tccattcgtt | 360 |
| aagttttttgg gtatcaagaa cgtcggtttc tctaatggtg atgattggaa gagacaacgt | 420 |
| aaggttatga atccagcctt ccaaagatct gttccagttg aaatgttcgg taagttgatg | 480 |
| caaaagggta ttttggccat gaaaagcaa ggttacgaag ttagagcttt ggacttcttc | 540 |
| gaaagaatca ccttggattc catcggtatt ttcttgttct ctttcgactt cggttctttg | 600 |
| gataacccaa attctgtttg gtctttgacc tacgacacta ttagaagggg tattaagaat | 660 |
| ccagctttga ccgtttttcc acaattggat tgcttgttga atacgttac tccaggtaga | 720 |
| aggcatttgg atcaatgtgt tactaagctg aacaacctgt tgatggaagt cgctaaagaa | 780 |
| aaaagaaggc aagtccaatc tccatccgat aagttgattc cagattccga aaaggatctg | 840 |
| ttgaccttga ttttggaagc tgaattgaga ggtgatggtt ctgcttctga tgaagaacta | 900 |
| agaggtaatt tggccttgtt ttttttggct ggtcacgaaa ctactgcttc cgctatgtgt | 960 |
| ttttgcttgt acaatttggc catgaacaag gacattcaag agaaggctag aaaagaagtg | 1020 |
| ttggaagttt tgggtgatga accagttgat gttagaccag atatccaaga cttgaagcaa | 1080 |
| ttcaggtaca tggatatgat cttgcacgaa aacttgagaa gatttggtcc agctgctatg | 1140 |
| ttgttgccaa gaaatctga agaggatttc gttgccgatg gtattttgat tccaaagaat | 1200 |
| acccccagttg tcatcgattt gaacaccatg catcataatc cacaagtttg gaaggatcca | 1260 |
| gaaatctttg acccagaaag atttgctcct ggtggtgaat atgaagctaa cggtgaaaaa | 1320 |
| atggcttggt tgccattttc ttcaggttct agagtctgca tcggtaagtc ttttttctatg | 1380 |
| gctgaacaaa gggtgttcct gtcaatgttg ttgaaaaagt acgaatggga tttcccagat | 1440 |
| gactccattc atagagatgg cattaagatg gaaaacttcg aaaacaacgc tcccgaatct | 1500 |
| ttgtcttttta gatttcatcc aaggtactaa | 1530 |

```
<210> SEQ ID NO 83
<211> LENGTH: 509
<212> TYPE: PRT
<213> ORGANISM: Absidia repens

<400> SEQUENCE: 83

Met Gly Thr Ser Tyr Lys Arg Lys Ala Ala Tyr Val Thr Ile Gly Ala
1               5                   10                  15

Ala Val Val Leu Leu Phe Arg Ser Ile Tyr Gly Phe Tyr Tyr Val Pro
                20                  25                  30

Lys Ser Leu Arg His Leu Pro Cys Val Gly Tyr Arg Glu Leu Ala Tyr
            35                  40                  45

Ser Ile Met Lys Arg Glu Asp Ala Ala Thr Arg Ala Arg Ser Val Leu
50                  55                  60

Gly Gln Ala Ile Lys Glu Lys Asn Gly Ala Phe Val Ala Lys Phe Pro
65                  70                  75                  80

Met Glu Trp Thr Val Phe Leu Thr Ser Pro Arg Thr Ile Gln Ala Val
                85                  90                  95

Leu Leu Lys Ser Asp Lys Phe Pro Lys Thr Tyr Asp Met Phe His Ala
                100                 105                 110

Leu Gly Glu Ser Ser Pro Phe Val Lys Phe Leu Gly Ile Lys Asn Val
            115                 120                 125

Gly Phe Ser Asn Gly Asp Asp Trp Lys Arg Gln Arg Lys Val Met Asn
130                 135                 140

Pro Ala Phe Gln Arg Ser Val Pro Val Glu Met Phe Gly Lys Leu Met
145                 150                 155                 160

Gln Lys Gly Ile Leu Ala Ile Glu Lys Gln Gly Tyr Glu Val Arg Ala
                165                 170                 175

Leu Asp Phe Phe Glu Arg Ile Thr Leu Asp Ser Ile Gly Ile Phe Leu
            180                 185                 190

Phe Ser Phe Asp Phe Gly Ser Leu Asp Asn Pro Asn Ser Val Trp Ser
        195                 200                 205

Leu Thr Tyr Asp Thr Ile Arg Arg Gly Ile Lys Asn Pro Ala Leu Thr
210                 215                 220

Val Phe Pro Gln Leu Asp Cys Leu Leu Lys Tyr Val Thr Pro Gly Arg
225                 230                 235                 240

Arg His Leu Asp Gln Cys Val Thr Lys Leu Asn Asn Leu Leu Met Glu
                245                 250                 255

Val Ala Lys Glu Lys Arg Arg Gln Val Gln Ser Pro Ser Asp Lys Leu
            260                 265                 270

Ile Pro Asp Ser Glu Lys Asp Leu Leu Thr Leu Ile Leu Glu Ala Glu
        275                 280                 285

Leu Arg Gly Asp Gly Ser Ala Ser Asp Glu Glu Leu Arg Gly Asn Leu
290                 295                 300

Ala Leu Phe Phe Leu Ala Gly His Glu Thr Thr Ala Ser Ala Met Cys
305                 310                 315                 320

Phe Cys Leu Tyr Asn Leu Ala Met Asn Lys Asp Ile Gln Glu Lys Ala
                325                 330                 335

Arg Lys Glu Val Leu Glu Val Leu Gly Asp Glu Pro Val Asp Val Arg
            340                 345                 350

Pro Asp Ile Gln Asp Leu Lys Gln Phe Arg Tyr Met Asp Met Ile Leu
        355                 360                 365

His Glu Asn Leu Arg Arg Phe Gly Pro Ala Ala Met Leu Leu Pro Arg
370                 375                 380
```

```
Lys Ser Glu Glu Asp Phe Val Ala Asp Gly Ile Leu Ile Pro Lys Asn
385                 390                 395                 400

Thr Pro Val Val Ile Asp Leu Asn Thr Met His His Asn Pro Gln Val
                405                 410                 415

Trp Lys Asp Pro Glu Ile Phe Asp Pro Glu Arg Phe Ala Pro Gly Gly
            420                 425                 430

Glu Tyr Glu Ala Asn Gly Glu Lys Met Ala Trp Leu Pro Phe Ser Ser
        435                 440                 445

Gly Ser Arg Val Cys Ile Gly Lys Ser Phe Ser Met Ala Glu Gln Arg
    450                 455                 460

Val Phe Leu Ser Met Leu Leu Lys Lys Tyr Glu Trp Asp Phe Pro Asp
465                 470                 475                 480

Asp Ser Ile His Arg Asp Gly Ile Lys Met Glu Asn Phe Glu Asn Asn
                485                 490                 495

Ala Pro Glu Ser Leu Ser Phe Arg Phe His Pro Arg Tyr
        500                 505
```

<210> SEQ ID NO 84
<211> LENGTH: 1620
<212> TYPE: DNA
<213> ORGANISM: Absidia glauca

<400> SEQUENCE: 84

```
atgccaatcg ttaacgcctt gcaaacctat tcttatgaag aacctatcaa cttcttgaag      60
gacgtttggt tgaacagatt atttccagct ggtacgtcta acagaaaaaa ggctgctttg     120
ttgactttgg gtgctactat tgctttggta tgtagaactg tttacaggtt gtacagagtc     180
ccaagatcct tgagacatat tccagctgtt ggttatgttg ccatgttgag atctattttg     240
aagagggaag atgctactac tagagccatg actattttc aaccagccat gaagaaaggt     300
aacggtgttt ttttggttaa cttcccattg gagtggtcta tctatgttgc tgaaccattg     360
gctgctaaag ctgttttgat gaagtctgac aatttcccca gtccatcga tttcattcat     420
gccttgggta agaaaaccc agttgttaag ttttcggta ctgataacgt tgccttggtt     480
aatggtgaac aatggaagag acaacgtaag gttatgaatc cagctttcca tagagctatg     540
ccagttcaaa tgttcggtag gttgttgcaa aagggtttca gaacattga gaacaaggt      600
catcaagttg ctgccttgga ttttttccaa agattgacat tggatgcttt gggtcatgct     660
gttttttggtt ttgattttgg tgccttgaac gatagagaag ctgtttggac tgttacctac     720
gaatccatta gattgaactt gagaaaccca ttggctttcg cttttccatc tatggattgg     780
ttgttgaagt acgttattcc aggtagattg caaatggctg cttcagttga aagttgaac      840
ggtttgatga tggacatgat caaagagaag aggatcaagt tgttgaatc ccaagctcaa     900
gatgatactc cagaaaacga aaggatctg ttgaccttga tgttggaagc tgaacaaaga     960
ggtgaaggta ctaccaatga tgaagaattg agatccaata tggccgtttt tttcttggct    1020
ggtcacgaaa ctactgctaa cactatgtct ttttgcttgt acaacttggc catggataag    1080
tccgttcaag aaaaagctag acaagaggtt atcaaggttt tgggtgatga accagaagat    1140
gttttgccaa gaacgaaga gttgagacaa atcccatacc tggatatgat cctgaaagaa    1200
aacttgcgta gatttggtcc agcttctatg ttgaatgcta gaaagactgt tgaggacttc    1260
gatatgaacg gtacttttat cccaaagaac acctccgtta tcgttgaaac taatgccttg    1320
catcataacc cagaagtttg gaagaatcca gaacaattcg atccagaaag atttgctcca    1380
ggtggtgaac acgaaacttc tcatgaaggt atggcttggt tgccattttc ttcaggttct    1440
```

```
agaggttgtt tgggcatgaa tttttcaatg gcagaacaga gggttttcct ggctatgttg   1500
ttgagaaagt atgaatggga cttgccaaag gattccatcc ataagaacgg tattcaaatc   1560
ggtaacttcc aaaacgcttg tccagattct ttgaagattc aattcacccc aaggtactaa   1620
```

<210> SEQ ID NO 85
<211> LENGTH: 539
<212> TYPE: PRT
<213> ORGANISM: Absidia glauca

<400> SEQUENCE: 85

```
Met Pro Ile Val Asn Ala Leu Gln Thr Tyr Ser Tyr Glu Glu Pro Ile
1               5                   10                  15

Asn Phe Leu Lys Asp Val Trp Leu Asn Arg Leu Phe Pro Ala Gly Thr
            20                  25                  30

Ser Asn Arg Lys Lys Ala Ala Leu Leu Thr Leu Gly Ala Thr Ile Ala
        35                  40                  45

Leu Val Cys Arg Thr Val Tyr Arg Leu Tyr Arg Val Pro Arg Ser Leu
    50                  55                  60

Arg His Ile Pro Ala Val Gly Tyr Val Ala Met Leu Arg Ser Ile Leu
65                  70                  75                  80

Lys Arg Glu Asp Ala Thr Thr Arg Ala Met Thr Ile Phe Gln Pro Ala
                85                  90                  95

Met Lys Lys Gly Asn Gly Val Phe Leu Val Asn Phe Pro Leu Glu Trp
            100                 105                 110

Ser Ile Tyr Val Ala Glu Pro Leu Ala Ala Lys Ala Val Leu Met Lys
        115                 120                 125

Ser Asp Asn Phe Pro Lys Ser Ile Asp Phe Ile His Ala Leu Gly Lys
    130                 135                 140

Glu Asn Pro Val Val Lys Phe Phe Gly Thr Asp Asn Val Ala Leu Val
145                 150                 155                 160

Asn Gly Glu Gln Trp Lys Arg Gln Arg Lys Val Met Asn Pro Ala Phe
                165                 170                 175

His Arg Ala Met Pro Val Gln Met Phe Gly Arg Leu Leu Gln Lys Gly
            180                 185                 190

Phe Lys Asn Ile Glu Glu Gln Gly His Gln Val Ala Ala Leu Asp Phe
        195                 200                 205

Phe Gln Arg Leu Thr Leu Asp Ala Leu Gly His Ala Val Phe Gly Phe
    210                 215                 220

Asp Phe Gly Ala Leu Asn Asp Arg Glu Ala Val Trp Thr Val Thr Tyr
225                 230                 235                 240

Glu Ser Ile Arg Leu Asn Leu Arg Asn Pro Leu Ala Phe Ala Phe Pro
                245                 250                 255

Ser Met Asp Trp Leu Leu Lys Tyr Val Ile Pro Gly Arg Leu Gln Met
            260                 265                 270

Ala Ala Ser Val Asp Lys Leu Asn Gly Leu Met Met Asp Met Ile Lys
        275                 280                 285

Glu Lys Arg Ile Lys Leu Leu Glu Ser Gln Ala Gln Asp Asp Thr Pro
    290                 295                 300

Glu Asn Glu Lys Asp Leu Leu Thr Leu Met Leu Glu Ala Glu Gln Arg
305                 310                 315                 320

Gly Glu Gly Thr Thr Asn Asp Glu Glu Leu Arg Ser Asn Met Ala Val
                325                 330                 335

Phe Phe Leu Ala Gly His Glu Thr Thr Ala Asn Thr Met Ser Phe Cys
```

```
                  340                 345                 350
Leu Tyr Asn Leu Ala Met Asp Lys Ser Val Gln Glu Lys Ala Arg Gln
            355                 360                 365

Glu Val Ile Lys Val Leu Gly Asp Glu Pro Glu Asp Val Leu Pro Arg
        370                 375                 380

Asn Glu Glu Leu Arg Gln Ile Pro Tyr Leu Asp Met Ile Leu Lys Glu
385                 390                 395                 400

Asn Leu Arg Arg Phe Gly Pro Ala Ser Met Leu Asn Ala Arg Lys Thr
                405                 410                 415

Val Glu Asp Phe Asp Met Asn Gly Thr Phe Ile Pro Lys Asn Thr Ser
            420                 425                 430

Val Ile Val Glu Thr Asn Ala Leu His His Asn Pro Glu Val Trp Lys
        435                 440                 445

Asn Pro Glu Gln Phe Asp Pro Gly Arg Phe Ala Pro Gly Gly Glu His
                455                 460
            450

Glu Thr Ser His Glu Gly Met Ala Trp Leu Pro Phe Ser Ser Gly Ser
465                 470                 475                 480

Arg Gly Cys Leu Gly Met Asn Phe Ser Met Ala Glu Gln Arg Val Phe
                485                 490                 495

Leu Ala Met Leu Leu Arg Lys Tyr Glu Trp Asp Leu Pro Lys Asp Ser
            500                 505                 510

Ile His Lys Asn Gly Ile Gln Ile Gly Asn Phe Gln Asn Ala Cys Pro
        515                 520                 525

Asp Ser Leu Lys Ile Gln Phe Thr Pro Arg Tyr
530                 535

<210> SEQ ID NO 86
<211> LENGTH: 1584
<212> TYPE: DNA
<213> ORGANISM: Rhizopus microsporus

<400> SEQUENCE: 86
atggccttga ccgaaattgc cattgaaact tatcatagag ccttggataa gctggttcca      60
atcttgcaaa agagatctaa gcactcctat attggtgttg ctgttgtttt ggttgtcttg     120
gaaagaatct acagcttctt cagagttcca aagtccatta gacatattcc agccgtttct     180
tactttgcta tggctaagtc tttgttgact gctgaagctc catcttctag atacaagaga     240
atagttttgc ccgtcgtcaa aaaggtaat ggcttgtacg tttctaagtt gccattggaa      300
tggactgttc atgttgctac tccaatgtct gctaaacacg ttttgttgaa gtctgagatc     360
tacccaaagt ccgaatcttt cttgaaattg ctaggtccac aatctccagc tgtttttgttt     420 ttgggtgctt ctaatgttgg tttcgttaac ggtcatattt ggaagaacca gcgtaagatt     480
atgaacccag cttttcatag atccatgcca attcaaacta tggcctctgt tatgccagat     540
ttcttttccg ctattgacaa acatggtact gatggtacac aatttctgc cgttatgaga     600 gatttcacct tggatgtttt gggtcatact gcttttggtt tcgatttcaa ggcttttgaaa     660 ggtgatccag atcattggac tagaacctac atattatca acaacgcttt gttcaaccca      720
accgctaata tgttgacttc tttgaaccca atcctgtcca ttatctctcc agaaagaaga     780
agaattttgg aggccatcaa aaagttgaac ggtatgttgg aagccatgat caaacagaaa     840
agacaagaag ttcaaaacaa cgcccaagcc aatattccag aaaacgaaaa agatctgctg     900
accttgatgt tagaagccca acaaagaggt gaaggttttg gctactgatga agaattgaag     960 cacaatgtct ctggtttttt cttggctggt catgatacaa cctctgaaac tttgtctttc     1020
```

-continued

```
tacttctaca acattgccaa gaacaaggat gcccaaagaa agttgagaga agaattgtct    1080
actatcttgg gtgataagcc agttgatgtt attccaacct tggagcaatt gaagtccatg    1140
gaatatttga actgcaccat caaagaaaac ttgagattga atggtccagc cgataacatt    1200
ttgcctagaa ttgctactga agatatggtt gttgacggta ctccaattcc aaaaggtact    1260
gttgttaacg ttgatatcca cgccattcat catgatacca gatattggca agatccctac    1320
aagtttgtcc ctgaaagatt tttgccaggt ggtgaacatg aatctcattc tggtatgact    1380
tggttgcctt ttggtaatgg tgctagacaa tgtttgggta tgaatttctc attggccgaa    1440
cagagattgg ttattgctat gactgttagg aagtacgaca tcgaaattcc aaaggattcc    1500
atccattacg atcacccaat tctggaatct tcatctacaa aagctccagc ctctttgaag    1560 ttggtttttta gaaagaggta ctaa                                          1584
```

<210> SEQ ID NO 87
<211> LENGTH: 527
<212> TYPE: PRT
<213> ORGANISM: Rhizopus microsporus

<400> SEQUENCE: 87

```
Met Ala Leu Thr Glu Ile Ala Ile Glu Thr Tyr His Arg Ala Leu Asp
1               5                   10                  15

Lys Leu Val Pro Ile Leu Gln Lys Arg Ser Lys His Ser Tyr Ile Gly
            20                  25                  30

Val Ala Val Val Leu Val Val Leu Glu Arg Ile Tyr Ser Phe Phe Arg
        35                  40                  45

Val Pro Lys Ser Ile Arg His Ile Pro Ala Val Ser Tyr Phe Ala Met
    50                  55                  60

Ala Lys Ser Leu Leu Thr Ala Glu Ala Pro Ser Ser Arg Tyr Lys Arg
65                  70                  75                  80

Ile Val Leu Pro Val Val Lys Lys Gly Asn Gly Leu Tyr Val Ser Lys
                85                  90                  95

Leu Pro Leu Glu Trp Thr Val His Val Ala Thr Pro Met Ser Ala Lys
            100                 105                 110

His Val Leu Leu Lys Ser Glu Ile Tyr Pro Lys Ser Glu Ser Phe Leu
        115                 120                 125

Lys Leu Leu Gly Pro Gln Ser Pro Ala Val Leu Phe Leu Gly Ala Ser
    130                 135                 140

Asn Val Gly Phe Val Asn Gly His Ile Trp Lys Asn Gln Arg Lys Ile
145                 150                 155                 160

Met Asn Pro Ala Phe His Arg Ser Met Pro Ile Gln Thr Met Ala Ser
                165                 170                 175

Val Met Pro Asp Phe Phe Ser Ala Ile Asp Lys His Gly Thr Asp Gly
            180                 185                 190

Thr Pro Ile Ser Ala Val Met Arg Asp Phe Thr Leu Asp Val Leu Gly
        195                 200                 205

His Thr Ala Phe Gly Phe Asp Phe Lys Ala Leu Lys Gly Asp Pro Asp
    210                 215                 220

His Trp Thr Arg Thr Tyr His Ile Ile Asn Asn Ala Leu Phe Asn Pro
225                 230                 235                 240

Thr Ala Asn Met Leu Thr Ser Leu Asn Pro Ile Leu Ser Ile Ile Ser
                245                 250                 255

Pro Glu Arg Arg Arg Ile Leu Glu Ala Ile Lys Lys Leu Asn Gly Met
            260                 265                 270
```

Leu Glu Ala Met Ile Lys Gln Lys Arg Gln Glu Val Gln Asn Asn Ala
            275                 280                 285

Gln Ala Asn Ile Pro Glu Asn Glu Lys Asp Leu Leu Thr Leu Met Leu
    290                 295                 300

Glu Ala Gln Gln Arg Gly Glu Gly Leu Ala Thr Asp Glu Glu Leu Lys
305                 310                 315                 320

His Asn Val Ser Gly Phe Phe Leu Ala Gly His Asp Thr Thr Ser Glu
                325                 330                 335

Thr Leu Ser Phe Tyr Phe Tyr Asn Ile Ala Lys Asn Lys Asp Ala Gln
            340                 345                 350

Arg Lys Leu Arg Glu Glu Leu Ser Thr Ile Leu Gly Asp Lys Pro Val
            355                 360                 365

Asp Val Ile Pro Thr Leu Glu Gln Leu Lys Ser Met Glu Tyr Leu Asn
    370                 375                 380

Cys Thr Ile Lys Glu Asn Leu Arg Leu Asn Gly Pro Ala Asp Asn Ile
385                 390                 395                 400

Leu Pro Arg Ile Ala Thr Glu Asp Met Val Val Asp Gly Thr Pro Ile
                405                 410                 415

Pro Lys Gly Thr Val Val Asn Val Asp Ile His Ala Ile His His Asp
            420                 425                 430

Thr Arg Tyr Trp Gln Asp Pro Tyr Lys Phe Val Pro Glu Arg Phe Leu
            435                 440                 445

Pro Gly Gly Glu His Glu Ser His Ser Gly Met Thr Trp Leu Pro Phe
        450                 455                 460

Gly Asn Gly Ala Arg Gln Cys Leu Gly Met Asn Phe Ser Leu Ala Glu
465                 470                 475                 480

Gln Arg Leu Val Ile Ala Met Thr Val Arg Lys Tyr Asp Ile Glu Ile
                485                 490                 495

Pro Lys Asp Ser Ile His Tyr Asp His Pro Ile Leu Glu Ser Ser Ser
            500                 505                 510

Thr Lys Ala Pro Ala Ser Leu Lys Leu Val Phe Arg Lys Arg Tyr
            515                 520                 525

<210> SEQ ID NO 88
<211> LENGTH: 1590
<212> TYPE: DNA
<213> ORGANISM: Syncephalastrum racemosum

<400> SEQUENCE: 88
atgacccaat tgactacccc agatacctta ggtaagttgt tggctatcta tagacaaact      60
ccagcttcaa gaagggcttc ttggattggt tgggctgttg ctgctactgt tattgcttct     120
caactgtaca aaactttggt cccaccatct aatttgccaa acttgccaac tattaactac     180
ttcaggctgc tgtcatcttt cttgagaaga gattctccaa ccatcagatc caagaaatt      240 ttgattccag ctttggaaaa gcacgaacaa agaaagctt acttggctaa gttgccattg      300
acttggactg ttttttttggt tgatccaatt gccgccaaga tcttcttgat gaagatggat     360
attttcccca agatcaaaga aaccatcgat gccttggatt ctcaacatcc aatcgttgaa     420
tttttcggta gagaaaacgt tgccatctct gttggtgaag cttggagaaa tcagagaaag     480
gttatgaatc cagctttcag acgtgctatg ccaatttcta ttttcggcaa cttgatgttc     540
aaggtgttca agaacatcga agaaaacaag ccagttatcg ccatcgattt gatgcaagct     600
tttactttgg atgctttggg tagagctgct ttctctttg attttcacgc tttggatgac     660

```
caacactcca tttgggttga aacctacgaa atcatcagac agtctttgag aaatccagct    720
aatgctgttt tggccagata caacttcatc acgaaatatt tgatgccagg tagagctaaa    780
caaaaggctg ctactcataa gctgaacagc ttgttgttgg aaatggcttc tagaaagaga    840
gccgaattgg aaaaacatcc agaattgaga gaattgccag actccgaaaa agatttgttg    900
accttgatgg ttgaagccga tatggaatct ggtgatgatc aacttctgc cgaattattg    960
agagctaact tgtccgtttt tttcttggct ggtcatgata ccactgctaa cactttgtca   1020
ttttggttgt accatatggc cgttaacaaa gatgtacaag ctaaggctag agaagaggtc   1080
atcaagattt taggtgatgg tcctgaagat gttatgccaa ctgctgatca atgtaagcaa   1140
atgacttacc tggactgcat catcaaagag aatttgagat tattgggtcc agcctctcaa   1200
ttgattccaa gaatggctac cgaagatgtt gatttgaacg tatttcat cccaaagggt   1260
actagagtta ctgttgatat gcataccatg cactactctc caatgttgtg aaagatcca   1320
ggtgttttta agccagatag attcttggat gaaggtgaac actctcaaca tagaggtttg   1380
gcttggttgc cattttcttc aggtggtaga caatgtttgg gtatgaactt ctcattgacc   1440
gaacaaaggg ttgtcatgtc tatgatgtta agaaagtaca cctgggaatt gcctgccgat   1500
tctattcata gagatggtgt taagttgaac gaagttaaca ctgttgctcc aagaaccttg   1560
tccattatct tccaacaaag ataccactaa                                    1590
```

<210> SEQ ID NO 89
<211> LENGTH: 529
<212> TYPE: PRT
<213> ORGANISM: Syncephalastrum racemosum

<400> SEQUENCE: 89

```
Met Thr Gln Leu Thr Thr Pro Asp Thr Leu Gly Lys Leu Leu Ala Ile
1               5                   10                  15

Tyr Arg Gln Thr Pro Ala Ser Arg Arg Ala Ser Trp Ile Gly Trp Ala
            20                  25                  30

Val Ala Ala Thr Val Ile Ala Ser Gln Leu Tyr Lys Thr Leu Val Pro
        35                  40                  45

Pro Ser Asn Leu Pro Asn Leu Pro Thr Ile Asn Tyr Phe Arg Leu Leu
    50                  55                  60

Ser Ser Phe Leu Arg Arg Asp Ser Pro Thr Ile Arg Ser Gln Glu Ile
65                  70                  75                  80

Leu Ile Pro Ala Leu Glu Lys His Glu Gln Lys Lys Ala Tyr Leu Ala
                85                  90                  95

Lys Leu Pro Leu Thr Trp Thr Val Phe Leu Val Asp Pro Ile Ala Ala
            100                 105                 110

Lys Ile Phe Leu Met Lys Met Asp Ile Phe Pro Lys Ile Lys Glu Thr
        115                 120                 125

Ile Asp Ala Leu Asp Ser Gln His Pro Ile Val Glu Phe Phe Gly Arg
    130                 135                 140

Glu Asn Val Ala Ile Ser Val Gly Glu Ala Trp Arg Asn Gln Arg Lys
145                 150                 155                 160

Val Met Asn Pro Ala Phe Arg Arg Ala Met Pro Ile Ser Ile Phe Gly
                165                 170                 175

Asn Leu Met Phe Lys Val Phe Lys Asn Ile Glu Glu Asn Lys Pro Val
            180                 185                 190

Ile Ala Ile Asp Leu Met Gln Ala Phe Thr Leu Asp Ala Leu Gly Arg
        195                 200                 205
```

```
Ala Ala Phe Ser Phe Asp Phe His Ala Leu Asp Asp Gln His Ser Ile
    210                 215                 220
Trp Val Glu Thr Tyr Glu Ile Ile Arg Gln Ser Leu Arg Asn Pro Ala
225                 230                 235                 240
Asn Ala Val Leu Ala Arg Tyr Asn Phe Ile Thr Lys Tyr Leu Met Pro
                245                 250                 255
Gly Arg Ala Lys Gln Lys Ala Ala Thr His Lys Leu Asn Ser Leu Leu
            260                 265                 270
Leu Glu Met Ala Ser Arg Lys Arg Ala Glu Leu Glu Lys His Pro Glu
        275                 280                 285
Leu Arg Glu Leu Pro Asp Ser Glu Lys Asp Leu Leu Thr Leu Met Val
    290                 295                 300
Glu Ala Asp Met Glu Ser Gly Asp Pro Thr Ser Ala Glu Leu Leu
305                 310                 315                 320
Arg Ala Asn Leu Ser Val Phe Phe Leu Ala Gly His Asp Thr Thr Ala
                325                 330                 335
Asn Thr Leu Ser Phe Trp Leu Tyr His Met Ala Val Asn Lys Asp Val
            340                 345                 350
Gln Ala Lys Ala Arg Glu Glu Val Ile Lys Ile Leu Gly Asp Gly Pro
        355                 360                 365
Glu Asp Val Met Pro Thr Ala Asp Gln Cys Lys Gln Met Thr Tyr Leu
370                 375                 380
Asp Cys Ile Ile Lys Glu Asn Leu Arg Leu Leu Gly Pro Ala Ser Gln
385                 390                 395                 400
Leu Ile Pro Arg Met Ala Thr Glu Asp Val Asp Leu Asn Gly Ile Phe
                405                 410                 415
Ile Pro Lys Gly Thr Arg Val Thr Val Asp Met His Thr Met His Tyr
            420                 425                 430
Ser Pro Met Leu Trp Lys Asp Pro Gly Val Phe Lys Pro Asp Arg Phe
        435                 440                 445
Leu Asp Glu Gly Glu His Ser Gln His Arg Gly Leu Ala Trp Leu Pro
    450                 455                 460
Phe Ser Ser Gly Gly Arg Gln Cys Leu Gly Met Asn Phe Ser Leu Thr
465                 470                 475                 480
Glu Gln Arg Val Val Met Ser Met Met Leu Arg Lys Tyr Thr Trp Glu
                485                 490                 495
Leu Pro Ala Asp Ser Ile His Arg Asp Gly Val Lys Leu Asn Glu Val
            500                 505                 510
Asn Thr Val Ala Pro Arg Thr Leu Ser Ile Ile Phe Gln Gln Arg Tyr
        515                 520                 525
His

<210> SEQ ID NO 90
<211> LENGTH: 1569
<212> TYPE: DNA
<213> ORGANISM: Rhizopus microsporus

<400> SEQUENCE: 90
atggaccact tgatccaggt ctacaactct tctactcaag ttttgattcc agtcttgcag      60
aagagatcta aggcttctta tattaccgct gccattgctt tgattattgc ccaaagactg     120
tactcctact tcagagttcc aaaacatttg agaggtttcc caaagttgcc atactttggt     180
attgctaagt ctttgttgac cagagaatct ccaagagaaa gagttaagaa gtacgtcttg     240
ccaatcatcg acgaaaatga tggtttctac atcagcaaga ttccattcgg ttggatgttg     300
```

```
tacattgcta atccagttgc tgctaagcag ttgttgttga aatcttctgg ttttccaaag    360
aaccacggtt tgttggataa tatgggtgaa aacttgttcg tcgagttcat cggtaaagat    420
aacgttgctt tgtctaacgg tgatacctgg aaaagacaaa gaaaggttat gaacccagcc    480
ttccatcatt ctttgcctat taagactatg tccaaggtcg tgttctcttt gatttccgct    540
attgaacaag ccaacggtac tattccagtt gcatctgcta tgcaaaactt caccttggat    600
actttgggtt tagccatttt cggttttgac tttaaggcat gcaaggtga tccagatgaa     660 tggactaaga cttacagatt cgtttccgat tgcatcttcg atccagttat caacgttttc    720
tcctcctact ccttcatcat cgatagaatc tatccaagac gtagaagagg tgctattgct    780
accaaaaagt tgtccgaaaa gttcttgaag atcgcccaac aaaagcgtaa agaaatcaaa    840
tctggtgctt acgctgatgt tccagataac gaaaaagact tgttgacctt gatgttggaa    900
gctgaagaaa aaggtgatac ttggacctca gaagatgaat tgagacataa cattgccatc    960
ttgttcgttg ctggtcatga tacaactgct catgctttgt ccttttgctt ttaccatttg    1020
gccaagaaca aggatgtgca acagaagttg agaaagagg tcttgtctat cttgggtgat     1080
aagccagttg atgttgttcc aactgttgag caattgaaga acatgcagta cttgaacatg    1140
gtcatcaaag aaaacctgag gattaactct ccagccgata tgttgttttc cagggatgta    1200
aaagaagata ccatcttggc taacaccttg attccaaaag gtactgttgt taccattaac    1260
atcgaagcct tgcattacaa tccaagattg tggcataatc cagatcaatt cgacccagaa    1320
agatttgctc caggtggtga acacgaaaaa catgaaggta tgacttggtt gccattctct    1380
aatggtacta gacaatgtct gggtatgaac ttcagcttgt ttgaacagag attggttatc    1440
gccatgatcc tgaaaaagta cgaaatctcc attccagagg attccatcca tagagatcat    1500
atcgtttctg acattccatt caatggtgct ccaaagtctt tgaagttgac tttcactaag    1560
aggcactaa                                                            1569
```

<210> SEQ ID NO 91
<211> LENGTH: 522
<212> TYPE: PRT
<213> ORGANISM: Rhizopus microsporus

<400> SEQUENCE: 91

```
Met Asp His Leu Ile Gln Val Tyr Asn Ser Ser Thr Gln Val Leu Ile
1               5                   10                  15

Pro Val Leu Gln Lys Arg Ser Lys Ala Ser Tyr Ile Thr Ala Ala Ile
            20                  25                  30

Ala Leu Ile Ile Ala Gln Arg Leu Tyr Ser Tyr Phe Arg Val Pro Lys
        35                  40                  45

His Leu Arg Gly Phe Pro Lys Leu Pro Tyr Phe Gly Ile Ala Lys Ser
    50                  55                  60

Leu Leu Thr Arg Glu Ser Pro Arg Glu Arg Val Lys Lys Tyr Val Leu
65                  70                  75                  80

Pro Ile Ile Asp Glu Asn Asp Gly Phe Tyr Ile Ser Lys Ile Pro Phe
                85                  90                  95

Gly Trp Met Leu Tyr Ile Ala Asn Pro Val Ala Ala Lys Gln Leu Leu
            100                 105                 110

Leu Lys Ser Ser Gly Phe Pro Lys Asn His Gly Leu Leu Asp Asn Met
        115                 120                 125

Gly Glu Asn Leu Phe Val Glu Phe Ile Gly Lys Asp Asn Val Ala Leu
    130                 135                 140
```

```
Ser Asn Gly Asp Thr Trp Lys Arg Gln Arg Lys Val Met Asn Pro Ala
145                 150                 155                 160

Phe His His Ser Leu Pro Ile Lys Thr Met Ser Lys Val Val Phe Ser
            165                 170                 175

Leu Ile Ser Ala Ile Glu Gln Ala Asn Gly Thr Ile Pro Val Ala Ser
        180                 185                 190

Ala Met Gln Asn Phe Thr Leu Asp Thr Leu Gly Leu Ala Ile Phe Gly
    195                 200                 205

Phe Asp Phe Lys Ala Leu Gln Gly Asp Pro Asp Glu Trp Thr Lys Thr
210                 215                 220

Tyr Arg Phe Val Ser Asp Cys Ile Phe Asp Pro Val Ile Asn Val Phe
225                 230                 235                 240

Ser Ser Tyr Ser Phe Ile Ile Asp Arg Ile Tyr Pro Arg Arg Arg Arg
            245                 250                 255

Gly Ala Ile Ala Thr Lys Lys Leu Ser Glu Lys Phe Leu Lys Ile Ala
        260                 265                 270

Gln Gln Lys Arg Lys Glu Ile Lys Ser Gly Ala Tyr Ala Asp Val Pro
    275                 280                 285

Asp Asn Glu Lys Asp Leu Leu Thr Leu Met Leu Glu Ala Glu Lys
290                 295                 300

Gly Asp Thr Trp Thr Ser Glu Asp Glu Leu Arg His Asn Ile Ala Ile
305                 310                 315                 320

Leu Phe Val Ala Gly His Asp Thr Thr Ala His Ala Leu Ser Phe Cys
            325                 330                 335

Phe Tyr His Leu Ala Lys Asn Lys Asp Val Gln Gln Lys Leu Arg Lys
        340                 345                 350

Glu Val Leu Ser Ile Leu Gly Asp Lys Pro Val Asp Val Val Pro Thr
    355                 360                 365

Val Glu Gln Leu Lys Asn Met Gln Tyr Leu Asn Met Val Ile Lys Glu
370                 375                 380

Asn Leu Arg Ile Asn Ser Pro Ala Asp Met Leu Phe Ser Arg Asp Val
385                 390                 395                 400

Lys Glu Asp Thr Ile Leu Ala Asn Thr Leu Ile Pro Lys Gly Thr Val
            405                 410                 415

Val Thr Ile Asn Ile Glu Ala Leu His Tyr Asn Pro Arg Leu Trp His
        420                 425                 430

Asn Pro Asp Gln Phe Asp Pro Glu Arg Phe Ala Pro Gly Gly Glu His
    435                 440                 445

Glu Lys His Glu Gly Met Thr Trp Leu Pro Phe Ser Asn Gly Thr Arg
450                 455                 460

Gln Cys Leu Gly Met Asn Phe Ser Leu Phe Glu Gln Arg Leu Val Ile
465                 470                 475                 480

Ala Met Ile Leu Lys Lys Tyr Glu Ile Ser Ile Pro Glu Asp Ser Ile
            485                 490                 495

His Arg Asp His Ile Val Ser Asp Ile Pro Phe Asn Gly Ala Pro Lys
        500                 505                 510

Ser Leu Lys Leu Thr Phe Thr Lys Arg His
    515                 520

<210> SEQ ID NO 92
<211> LENGTH: 1569
<212> TYPE: DNA
<213> ORGANISM: Mucor ambiguus
```

<400> SEQUENCE: 92

```
atgtactcca ccgcctctta caatcaaacc ttggaaagag ttgtttccgt cgtcagaaaa      60
aacaagacct cttatattgg tatggccatc ttgtgtgttg tcttgcaaca aatctactcc     120
tcttttgctg ttccaccaaa acacttgaga agattcccaa aggtttcctt catggaactg     180
atgaagtcct tctacaagaa agaatccgtc atgaacagaa acaagagatt ggttactcca     240
ttgactaatg ctggtcatgg tttctacatt tccagaattc cattggattg gaccatctac     300
gttactgatc caattgctgc taagaccttg ttgttgaaaa ctgacaattt cccaaagtct     360
catgctattt ttggtgcctt gggtgaatct tcaccagttg ttaagtttat gggtaacgaa     420
aacgttgccg tttccaacga tattctttgg agaaagcaac gtaagattat gaacccagct     480
ttccatagat ctcaaccagt taaggttttt ggtggtgtta tgccagattt gttcgccttg     540
attgatcaag atccagaaca tgttttcatc acgccaaaga ttaagtcctt tgctttggat     600
gctttgggtt tgtctgcttt tggtttcgat ttccagtctt tgaagaatga tccagaaggt     660
tggacttcta agtacaatac cgttgtctct tctctgttca acccattcgt taacttgttc     720
gctaagtgcg acttcctgat taagtacatt tctgccgaaa gaagaagagt catcaaggtt     780
actgatgaat tcaacgccat tgttgtctaa cttggctgata gagaaggca agaaatcatg     840
aacggtgaga aaagaacat tgccgaaaac gaaaaggacc tgttgacttt gatgattgaa     900
gctgatacaa gagaaggtgt tgaaactact actaccgaat tgagacataa catggccatt     960
tttttcttgg ccggtcatga tacaactgct aatactttgg ctttgtgctt gtaccaattg    1020
gccaaacata agcacgttca aagaaggct agacaagaag ttttggatat cttgggtgat    1080
gatccatggg atgttgctcc atctttggaa gatttgaaga agctgaacta cctgaacatg    1140
gtcatcaaag aaaacctgag aagaaacggt ccagttgaca atttgatgtc tagagatacc    1200
caacaggaca tcaatttgaa cggtactttt atcccaaagg gttctaaggt tgttatcaac    1260
gttgcctcca ttcatttgaa cccaaagatt tggcataacc ccgaatcttt cattccagaa    1320
aggtttgaac aaggtggtga attcgattct catgatggtt ttacttggct gccatttfct    1380
aacggttcta gacaatgttt gggcctgaat ttctcattga ctgaacaaag ggttgctctg    1440
tgcatgttat tgaagagata cgaaattgac atccccaagg attctatcca ttacgacgaa    1500
atcgttttcg ataaggcttt tactttcgcc ccacaatcat tggaattgtc cttcaaaaag    1560
aggtactaa                                                             1569
```

<210> SEQ ID NO 93
<211> LENGTH: 522
<212> TYPE: PRT
<213> ORGANISM: Mucor ambiguus

<400> SEQUENCE: 93

```
Met Tyr Ser Thr Ala Ser Tyr Asn Gln Thr Leu Glu Arg Val Val Ser
1               5                   10                  15

Val Val Arg Lys Asn Lys Thr Ser Tyr Ile Gly Met Ala Ile Leu Cys
            20                  25                  30

Val Val Leu Gln Gln Ile Tyr Ser Ser Phe Ala Val Pro Pro Lys His
        35                  40                  45

Leu Arg Arg Phe Pro Lys Val Ser Phe Met Glu Leu Met Lys Ser Phe
    50                  55                  60

Tyr Lys Lys Glu Ser Val Met Asn Arg Asn Lys Arg Leu Val Thr Pro
65                  70                  75                  80
```

```
Leu Thr Asn Ala Gly His Gly Phe Tyr Ile Ser Arg Ile Pro Leu Asp
                85                  90                  95

Trp Thr Ile Tyr Val Thr Asp Pro Ile Ala Ala Lys Thr Leu Leu Leu
            100                 105                 110

Lys Thr Asp Asn Phe Pro Lys Ser His Ala Ile Phe Gly Ala Leu Gly
            115                 120                 125

Glu Ser Ser Pro Val Val Lys Phe Met Gly Asn Glu Asn Val Ala Val
            130                 135                 140

Ser Asn Asp Ile Leu Trp Arg Lys Gln Arg Lys Ile Met Asn Pro Ala
145                 150                 155                 160

Phe His Arg Ser Gln Pro Val Lys Val Phe Gly Gly Val Met Pro Asp
                165                 170                 175

Leu Phe Ala Leu Ile Asp Gln Asp Pro Glu His Val Phe Ile Thr Pro
                180                 185                 190

Lys Ile Lys Ser Phe Ala Leu Asp Ala Leu Gly Leu Ser Ala Phe Gly
                195                 200                 205

Phe Asp Phe Gln Ser Leu Lys Asn Asp Pro Glu Gly Trp Thr Ser Lys
                210                 215                 220

Tyr Asn Thr Val Val Ser Ser Leu Phe Asn Pro Phe Val Asn Leu Phe
225                 230                 235                 240

Ala Lys Cys Asp Phe Leu Ile Lys Tyr Ile Ser Ala Glu Arg Arg Arg
                245                 250                 255

Val Ile Lys Val Thr Asp Glu Phe Asn Ala Met Leu Ser Asn Leu Ala
                260                 265                 270

Asp Lys Arg Arg Gln Glu Ile Met Asn Gly Lys Lys Asn Ile Ala
                275                 280                 285

Glu Asn Glu Lys Asp Leu Leu Thr Leu Met Ile Glu Ala Asp Thr Arg
290                 295                 300

Glu Gly Val Glu Thr Thr Thr Glu Leu Arg His Asn Met Ala Ile
305                 310                 315                 320

Phe Phe Leu Ala Gly His Asp Thr Thr Ala Asn Thr Leu Ala Leu Cys
                325                 330                 335

Leu Tyr Gln Leu Ala Lys His Lys His Val Gln Lys Lys Ala Arg Gln
                340                 345                 350

Glu Val Leu Asp Ile Leu Gly Asp Asp Pro Trp Asp Val Ala Pro Ser
                355                 360                 365

Leu Glu Asp Leu Lys Lys Leu Asn Tyr Leu Asn Met Val Ile Lys Glu
                370                 375                 380

Asn Leu Arg Arg Asn Gly Pro Val Asp Asn Leu Met Ser Arg Asp Thr
385                 390                 395                 400

Gln Gln Asp Ile Asn Leu Asn Gly Thr Phe Ile Pro Lys Gly Ser Lys
                405                 410                 415

Val Val Ile Asn Val Ala Ser Ile His Leu Asn Pro Lys Ile Trp His
                420                 425                 430

Asn Pro Glu Ser Phe Ile Pro Glu Arg Phe Glu Gln Gly Gly Glu Phe
                435                 440                 445

Asp Ser His Asp Gly Phe Thr Trp Leu Pro Phe Ser Asn Gly Ser Arg
                450                 455                 460

Gln Cys Leu Gly Leu Asn Phe Ser Leu Thr Glu Gln Arg Val Ala Leu
465                 470                 475                 480

Cys Met Leu Leu Lys Arg Tyr Glu Ile Asp Ile Pro Lys Asp Ser Ile
                485                 490                 495

His Tyr Asp Glu Ile Val Phe Asp Lys Ala Phe Thr Phe Ala Pro Gln
```

```
                   500                 505                 510
Ser Leu Glu Leu Ser Phe Lys Lys Arg Tyr
        515                 520
```

<210> SEQ ID NO 94
<211> LENGTH: 1572
<212> TYPE: DNA
<213> ORGANISM: Phycomyces biakesleeanus

<400> SEQUENCE: 94

```
atggacacca tcaaccacat ctctccatct ttcgaatctt acattaccgt tttcgctaag      60
atcgttccaa agggttttta tgttgttgct gctgttgctc tgttcctgtg taaaaaggtt     120
tacgatttta ccgctgctcc atacaagttg agacattttc caaggtttc tttcttcgcc     180
ttctccaaat ctattttctc cgctgaatct gttaacaca gaactaagag attgatctct     240
ccactgttgc ataagtacaa gggtttctac attgctaagt cccattata ctggactgtt     300
ttcgttactg aacccatgc tgttcaatac gttttgatga agggtgaaat cttcccaaaa     360
aagaccagat tcatgaacac cttgaacaag gactcattga tgattaggtt gttcggctcc     420
tctaatattg cttttgcttc tggtgaaatt tggaagcacc aacgtaagat tatgaaccca     480
gcttttcata gaactgcccc aattgaatta ttcggtagaa tgatcccaga catgttcaga     540
ttgatcgata agtccaacgg taacattatg ttggccgatt tgttgcatag aattacccttt     600
gatgctatgg gcaaagcctt gtttggtttc gatttcaaaa ctgccagaga gaaaactct      660
gaatggactt ctgcttacaa cgatgctatg tctggtattt ctgctccaat tttgaacatc     720
acccccatcct tggaacatat cactagatac ttgtatccag attacgctaa ggccaaaaag     780
ggtattgata agttgactga attgaccttg gaaatggtca acgagaggaa agaaaagatt     840
caagaagcta tcggtcaacc agatgatggt agagaaaagg atttcttgac cttgattatc     900
gaagccgaaa tgaaggaaga taaggcttct ggttctggtg gttttgagaga aaatttgaag     960
gctttttgg ttgctggtca tgcttctact gctagctcta tttctttctg catctaccat    1020
ttggccatga caaagatgt ccaaaacaag gcaagaaaag aagccttgga tatcttgggt    1080
gatgatgcta atatttctac cccaaccgtt aacgaatgta agcacattac ctacatcaac    1140
atgatcatca agaaacgtt gagattgaac gctccattcg gtactttgtt cgaaagaatt    1200
gctactgaag atgtcacctt gtccggtgtt tttattccaa aaggtactat catctccgtc    1260
gacattgaaa ccattcataa gaatccagcc atttggaagt ctccaactgt ttttgatcca    1320
gagagatttt ctaaaggcgg tgaacatgac caacatgaag gtattacttg ggctccatt   1380
tctgatggta acagaaaatg cttgggcatc aatttctcta tggctgaaca caagtcatc    1440
ctgctgatgt tgttgaaaca ttacgaatgg gacttgtccg aaaactccat tcacaaaaat    1500
ggtatcgttt acgacggcat ctctttgttt actccaagat ccttgtacat caagttcaac    1560
aagagacact aa                                                        1572
```

<210> SEQ ID NO 95
<211> LENGTH: 523
<212> TYPE: PRT
<213> ORGANISM: Phycomyces biakesleeanus

<400> SEQUENCE: 95

```
Met Asp Thr Ile Asn His Ile Ser Pro Ser Phe Glu Ser Tyr Ile Thr
1               5                   10                  15

Val Phe Ala Lys Ile Val Pro Lys Gly Phe Tyr Val Val Ala Ala Val
```

```
            20                  25                  30
Ala Leu Phe Leu Cys Lys Lys Val Tyr Asp Phe Thr Ala Ala Pro Tyr
            35                  40                  45
Lys Leu Arg His Phe Pro Lys Val Ser Phe Ala Phe Ser Lys Ser
            50                  55                  60
Ile Phe Ser Ala Glu Ser Val Glu His Arg Thr Lys Arg Leu Ile Ser
 65                  70                  75                  80
Pro Leu Leu His Lys Tyr Lys Gly Phe Tyr Ile Ala Lys Phe Pro Leu
                    85                  90                  95
Tyr Trp Thr Val Phe Val Thr Glu Pro His Ala Val Gln Tyr Val Leu
                    100                 105                 110
Met Lys Gly Glu Ile Phe Pro Lys Lys Thr Arg Phe Met Asn Thr Leu
                    115                 120                 125
Asn Lys Asp Ser Leu Met Ile Arg Leu Phe Gly Ser Ser Asn Ile Ala
                    130                 135                 140
Phe Ala Ser Gly Glu Ile Trp Lys His Gln Arg Lys Ile Met Asn Pro
145                 150                 155                 160
Ala Phe His Arg Thr Ala Pro Ile Glu Leu Phe Gly Arg Met Ile Pro
                    165                 170                 175
Asp Met Phe Arg Leu Ile Asp Lys Ser Asn Gly Asn Ile Met Leu Ala
                    180                 185                 190
Asp Leu His Arg Ile Thr Phe Asp Ala Met Gly Lys Ala Leu Phe
                    195                 200                 205
Gly Phe Asp Phe Lys Thr Ala Arg Glu Glu Asn Ser Glu Trp Thr Ser
                    210                 215                 220
Ala Tyr Asn Asp Ala Met Ser Gly Ile Ser Ala Pro Ile Leu Asn Ile
225                 230                 235                 240
Thr Pro Ser Leu Glu His Ile Thr Arg Tyr Leu Tyr Pro Asp Tyr Ala
                    245                 250                 255
Lys Ala Lys Lys Gly Ile Asp Lys Leu Thr Glu Leu Thr Leu Glu Met
                    260                 265                 270
Val Asn Glu Arg Lys Glu Lys Ile Gln Glu Ala Ile Gly Gln Pro Asp
                    275                 280                 285
Asp Gly Arg Glu Lys Asp Phe Leu Thr Leu Ile Ile Glu Ala Glu Met
                    290                 295                 300
Lys Glu Asp Lys Ala Ser Gly Ser Gly Gly Leu Arg Glu Asn Leu Lys
305                 310                 315                 320
Ala Phe Leu Val Ala Gly His Ala Ser Thr Ala Ser Ser Ile Ser Phe
                    325                 330                 335
Cys Ile Tyr His Leu Ala Met Asn Lys Asp Val Gln Asn Lys Ala Arg
                    340                 345                 350
Lys Glu Ala Leu Asp Ile Leu Gly Asp Asp Ala Asn Ile Ser Thr Pro
                    355                 360                 365
Thr Val Asn Glu Cys Lys His Ile Thr Tyr Ile Asn Met Ile Ile Lys
                    370                 375                 380
Glu Thr Leu Arg Leu Asn Ala Pro Phe Gly Thr Leu Phe Glu Arg Ile
385                 390                 395                 400
Ala Thr Glu Asp Val Thr Leu Ser Gly Val Phe Ile Pro Lys Gly Thr
                    405                 410                 415
Ile Ile Ser Val Asp Ile Glu Thr Ile His Lys Asn Pro Ala Ile Trp
                    420                 425                 430
Lys Ser Pro Thr Val Phe Asp Pro Glu Arg Phe Ser Lys Gly Gly Glu
                    435                 440                 445
```

```
His Asp Gln His Glu Gly Ile Thr Trp Ala Pro Phe Ser Asp Gly Asn
    450                 455                 460

Arg Lys Cys Leu Gly Ile Asn Phe Ser Met Ala Glu Gln Gln Val Ile
465                 470                 475                 480

Leu Leu Met Leu Leu Lys His Tyr Glu Trp Asp Leu Ser Glu Asn Ser
                485                 490                 495

Ile His Lys Asn Gly Ile Val Tyr Asp Gly Ile Ser Leu Phe Thr Pro
            500                 505                 510

Arg Ser Leu Tyr Ile Lys Phe Asn Lys Arg His
            515                 520

<210> SEQ ID NO 96
<211> LENGTH: 1515
<212> TYPE: DNA
<213> ORGANISM: Phycomyces biakesleeanus

<400> SEQUENCE: 96
atgtgcctgt tcttctgcaa gaaggtttac gattttactg ccgttccata cgagttgaag      60
aagtttccaa atatcccctt cttctacttc gtcaaatcca tcttgtctgt tgaatccgtc     120
gaaaacagaa ctaagagatt ggttttgcct ctgttgcata gaacaacgg tttctacgtt      180 tctaggtttc cattctactg gactgttttc actactgatc agatgctgt tcagtacttg      240 ttgatgaagg gtgaaatttt cccaaaggat accagattca cttccgctgt ttctaaggat    300
tccttgatta ttaggctgtt cggttcttct aacgttgcct ttatttctgg tgaaccattg    360
aagcaccaat gcagaactat gaatccagct ttcagaagaa ctgccccagt taacattttc   420
ggtagattga ttccagacat gttcaggttg atcgataagt ccgatggtga tatcttgatc   480
gtcaacttgt tgcaaagaat gacctttgat gctttgggta agctttgtt cggtttcgat    540 ttcaagacca tgaaggaaga taattctgct tggatgactg cttactctga tgctatgtct   600
ggtgttactg ctccagtttt gaacattatt ccatccttgg agtacatcct gagatacttc   660 tatccaaaact acaccaaggc taagaacggt gttgataagt tgaacagatt gatcttggag   720
ctggtcaaca agaagaagca agaattggaa gaatccatgc cacaatcttg ctctaacaac   780
aacaatggtg atactgatgg tgatgcttac gaccaagaaa aggatttgtt gaccttgatt   840
ttggaagccg aaatgaagga caacaagtca tctggttctg atgatttgag agctaacatg    900
gctactttca ttatggctgg tcacgaaact actgcttcat ctgtttcttt ctgcatctac   960
cacatggtta tcaacaagga tgttagagat aaggctagaa gagaagcctt ggatattttg   1020
ggttacgatg atttcatttc cccaccaact ttcgatgaat gcaagagagt taactacatc  1080
aacatggttg tcaaagaggc tttgagattg tgtactccag gtggtttgtt gttcgaaaga   1140
attgctactg aggacgtttt cttgtccggt gtttttattc aaagggcac cagaatttcc   1200 gttgatattg aagccttgca caagaatcca gcaatttgga aaaacccatc cgttttcgat   1260
ccagagagat ttctcaaagg cggtgaacat gaacaacata gaggtattac ttgggctcca   1320
ttttctgatg gtaacagaaa atgcttgggc atcaacttct ctatgactga caacaggtc    1380 atcctgctga tgttgttgaa acattatgaa tgggacctgt ccgaaaactc catccataac   1440
aatggtatgg tttacgacaa cgtttttctcc ttcgctccaa aaaccttgtc tatcaagttc  1500
cataagaggc actga                                                     1515

<210> SEQ ID NO 97
<211> LENGTH: 504
```

<212> TYPE: PRT
<213> ORGANISM: Phycomyces biakesleeanus

<400> SEQUENCE: 97

```
Met Cys Leu Phe Phe Cys Lys Lys Val Tyr Asp Phe Thr Ala Val Pro
1               5                   10                  15

Tyr Glu Leu Lys Lys Phe Pro Asn Ile Pro Phe Phe Tyr Phe Val Lys
            20                  25                  30

Ser Ile Leu Ser Val Glu Ser Val Glu Asn Arg Thr Lys Arg Leu Val
        35                  40                  45

Leu Pro Leu Leu His Lys Asn Asn Gly Phe Tyr Val Ser Arg Phe Pro
    50                  55                  60

Phe Tyr Trp Thr Val Phe Thr Thr Asp Pro Asp Ala Val Gln Tyr Leu
65                  70                  75                  80

Leu Met Lys Gly Glu Ile Phe Pro Lys Asp Thr Arg Phe Thr Ser Ala
                85                  90                  95

Val Ser Lys Asp Ser Leu Ile Ile Arg Leu Phe Gly Ser Ser Asn Val
            100                 105                 110

Ala Phe Ile Ser Gly Glu Pro Leu Lys His Gln Cys Arg Thr Met Asn
        115                 120                 125

Pro Ala Phe Arg Arg Thr Ala Pro Val Asn Ile Phe Gly Arg Leu Ile
    130                 135                 140

Pro Asp Met Phe Arg Leu Ile Asp Lys Ser Asp Gly Asp Ile Leu Ile
145                 150                 155                 160

Val Asn Leu Leu Gln Arg Met Thr Phe Asp Ala Leu Gly Lys Ala Leu
                165                 170                 175

Phe Gly Phe Asp Phe Lys Thr Met Lys Glu Asp Asn Ser Ala Trp Met
            180                 185                 190

Thr Ala Tyr Ser Asp Ala Met Ser Gly Val Thr Ala Pro Val Leu Asn
        195                 200                 205

Ile Ile Pro Ser Leu Glu Tyr Ile Leu Arg Tyr Phe Tyr Pro Asn Tyr
    210                 215                 220

Thr Lys Ala Lys Asn Gly Val Asp Lys Leu Asn Arg Leu Ile Leu Glu
225                 230                 235                 240

Leu Val Asn Lys Lys Gln Glu Leu Glu Ser Met Pro Gln Ser
                245                 250                 255

Cys Ser Asn Asn Asn Gly Asp Thr Asp Gly Asp Ala Tyr Asp Gln
            260                 265                 270

Glu Lys Asp Leu Leu Thr Leu Ile Leu Glu Ala Glu Met Lys Asp Asn
            275                 280                 285

Lys Ser Ser Gly Ser Asp Asp Leu Arg Ala Asn Met Ala Thr Phe Ile
    290                 295                 300

Met Ala Gly His Glu Thr Thr Ala Ser Ser Val Ser Phe Cys Ile Tyr
305                 310                 315                 320

His Met Val Ile Asn Lys Asp Val Arg Asp Lys Ala Arg Arg Glu Ala
                325                 330                 335

Leu Asp Ile Leu Gly Tyr Asp Asp Phe Ile Ser Pro Pro Thr Phe Asp
            340                 345                 350

Glu Cys Lys Arg Val Asn Tyr Ile Asn Met Val Val Lys Glu Ala Leu
        355                 360                 365

Arg Leu Cys Thr Pro Gly Gly Leu Leu Phe Glu Arg Ile Ala Thr Glu
    370                 375                 380

Asp Val Phe Leu Ser Gly Val Phe Ile Pro Lys Gly Thr Arg Ile Ser
385                 390                 395                 400
```

Val Asp Ile Glu Ala Leu His Lys Asn Pro Ala Ile Trp Lys Asn Pro
            405                 410                 415

Ser Val Phe Asp Pro Glu Arg Phe Ser Lys Gly Gly Glu His Glu Gln
        420                 425                 430

His Arg Gly Ile Thr Trp Ala Pro Phe Ser Asp Gly Asn Arg Lys Cys
            435                 440                 445

Leu Gly Ile Asn Phe Ser Met Thr Glu Gln Gln Val Ile Leu Leu Met
        450                 455                 460

Leu Leu Lys His Tyr Glu Trp Asp Leu Ser Glu Asn Ser Ile His Asn
465                 470                 475                 480

Asn Gly Met Val Tyr Asp Asn Val Phe Ser Phe Ala Pro Lys Thr Leu
                485                 490                 495

Ser Ile Lys Phe His Lys Arg His
            500

<210> SEQ ID NO 98
<211> LENGTH: 1536
<212> TYPE: DNA
<213> ORGANISM: Phycomyces biakesleeanus

<400> SEQUENCE: 98

```
atgctggcca aaaggttaa tggttacgct ggttttacct tggatgctat tcaaaccatc      60
tacttcaaca gagccatcaa gttggttaga ccaccaaaag ctttgtccca tattccacat    120
gttccatact tcagctacat gtcctcattg atcaagaaag agaacaccat ctccagaaac    180
aagagattcg ctaacaagtt gttcgaagat ccagaatcta acggcttgta cttaagacca    240
aatgtcaaag gttgggaagt tgttgttact agaccagaag atgccaagaa gctgttgttc    300
aagtctgata ttttttccaaa ggccgatttc acctctggta ttgatggtac tattctgtcc    360
aagttttcta ggggtccaaa cttgttgttt actactggtg ctcattggaa ggctcaaaga    420
atggttgcta atccagcttt tcatagatct gctccagtta agttgtttgg tgaattgacc    480
caaaagctgt tcagagttat ggataacaga gctaacaaga ccgttgatat caccagattg    540
atggaagctt gggctttaga tgctattggt ttggctggtt ttgatttcga tttcaacgct    600
atcgaaaacc ccaattcttc ttgggttaga atctacgaaa gagtcgataa ggctttggtt    660
catccattct actcattttt cccaaaaagca gacaagtacc tgttgtgggt tttgccaaat    720
agaaagcaag ctcataccga tttggacatc ttcttgaaga tgatcgacaa cgttattatc    780
gccaagaaaa aagccttgca cgagaacaag tctaacaagc acttggaaaa ctccgaaaag    840
gatttgttga ccttgatgtt ggaatctgaa gctaagggtt ctactttgtc cgctaaagaa    900
ttgagatcta acatgtgcgt tttttttcgct gctggtcacg aaactactgc taattctttg    960
gcttacgcca tctatttcat ggctgttaat ccagatgttc aatgcaaggc tagagaagaa   1020
gcttttaagg ttttgggtga tgcccaagag gatattatgc caactattga acagaccaag   1080
agcatggatt acattaacgc cgttatcaaa gaaaccttga tcacattc tccagctttg    1140
ggtacttttg ctagaaaagc tactaaggac actgaattag gtggtgtttt gattccaaag   1200
gacaccatga tttccatgga tatcttcaac ttgcatcaca atccaaacgt ctggaacaac   1260
ccagatgaat tgatccatc tagatttttg ccaggtggtg aagctgaaaa gcaaatcaac   1320
aatggtttct cctggattcc atttggtaca ggtgctagac aatgtatcgg catgaatttc   1380
agcttgatcg aacaagggt tatgctgtct atgatgttga aaagtttgc ttggtctttg   1440
ccagaagatt ccatccataa ggattacttg cataccacca acttggttat tcttccgct   1500
```
aaggatctga acatcaactt cgaaaagctg tactaa          1536

<210> SEQ ID NO 99
<211> LENGTH: 511
<212> TYPE: PRT
<213> ORGANISM: Phycomyces blakesleeanus

<400> SEQUENCE: 99

```
Met Leu Ala Lys Lys Val Asn Gly Tyr Ala Gly Phe Thr Leu Asp Ala
1               5                   10                  15

Ile Gln Thr Ile Tyr Phe Asn Arg Ala Ile Lys Leu Val Arg Pro Pro
            20                  25                  30

Lys Ala Leu Ser His Ile Pro His Val Pro Tyr Phe Ser Tyr Met Ser
        35                  40                  45

Ser Leu Ile Lys Lys Glu Asn Thr Ile Ser Arg Asn Lys Arg Phe Ala
    50                  55                  60

Asn Lys Leu Phe Glu Asp Pro Glu Ser Asn Gly Leu Tyr Leu Arg Pro
65                  70                  75                  80

Asn Val Lys Gly Trp Glu Val Val Thr Arg Pro Glu Asp Ala Lys
                85                  90                  95

Lys Leu Leu Phe Lys Ser Asp Ile Phe Pro Lys Ala Asp Phe Thr Ser
            100                 105                 110

Gly Ile Asp Gly Thr Ile Leu Ser Lys Phe Ser Arg Gly Pro Asn Leu
        115                 120                 125

Leu Phe Thr Thr Gly Ala His Trp Lys Ala Gln Arg Met Val Ala Asn
    130                 135                 140

Pro Ala Phe His Arg Ser Ala Pro Val Lys Leu Phe Gly Glu Leu Thr
145                 150                 155                 160

Gln Lys Leu Phe Arg Val Met Asp Asn Arg Ala Asn Lys Thr Val Asp
                165                 170                 175

Ile Thr Arg Leu Met Glu Ala Trp Ala Leu Asp Ala Ile Gly Leu Ala
            180                 185                 190

Gly Phe Asp Phe Asp Phe Asn Ala Ile Glu Asn Pro Asn Ser Ser Trp
        195                 200                 205

Val Arg Ile Tyr Glu Arg Val Asp Lys Ala Leu Val His Pro Phe Tyr
    210                 215                 220

Ser Phe Phe Pro Lys Ala Asp Lys Tyr Leu Leu Trp Val Leu Pro Asn
225                 230                 235                 240

Arg Lys Gln Ala His Thr Asp Leu Asp Ile Phe Leu Lys Met Ile Asp
                245                 250                 255

Asn Val Ile Ile Ala Lys Lys Ala Leu His Glu Asn Lys Ser Asn
            260                 265                 270

Lys His Leu Glu Asn Ser Glu Lys Asp Leu Leu Thr Leu Met Leu Glu
        275                 280                 285

Ser Glu Ala Lys Gly Ser Thr Leu Ser Ala Lys Glu Leu Arg Ser Asn
    290                 295                 300

Met Cys Val Phe Phe Ala Ala Gly His Glu Thr Thr Ala Asn Ser Leu
305                 310                 315                 320

Ala Tyr Ala Ile Tyr Phe Met Ala Val Asn Pro Asp Val Gln Cys Lys
                325                 330                 335

Ala Arg Glu Glu Ala Phe Lys Val Leu Gly Asp Ala Gln Glu Asp Ile
            340                 345                 350

Met Pro Thr Ile Glu Gln Thr Lys Ser Met Asp Tyr Ile Asn Ala Val
        355                 360                 365
```

```
Ile Lys Glu Thr Leu Arg Ser His Ser Pro Ala Leu Gly Thr Phe Ala
    370                 375                 380

Arg Lys Ala Thr Lys Asp Thr Glu Leu Gly Gly Val Leu Ile Pro Lys
385                 390                 395                 400

Asp Thr Met Ile Ser Met Asp Ile Phe Asn Leu His His Asn Pro Asn
                405                 410                 415

Val Trp Asn Asn Pro Asp Glu Phe Asp Pro Ser Arg Phe Leu Pro Gly
            420                 425                 430

Gly Glu Ala Glu Lys Gln Ile Asn Asn Gly Phe Ser Trp Ile Pro Phe
        435                 440                 445

Gly Thr Gly Ala Arg Gln Cys Ile Gly Met Asn Phe Ser Leu Ile Glu
    450                 455                 460

Gln Arg Val Met Leu Ser Met Met Leu Arg Lys Phe Ala Trp Ser Leu
465                 470                 475                 480

Pro Glu Asp Ser Ile His Lys Asp Tyr Leu His Thr Thr Asn Leu Val
                485                 490                 495

Ile Ser Ser Ala Lys Asp Leu Asn Ile Asn Phe Glu Lys Leu Tyr
            500                 505                 510
```

<210> SEQ ID NO 100
<211> LENGTH: 1380
<212> TYPE: DNA
<213> ORGANISM: Rhizopus microsporus

<400> SEQUENCE: 100

```
atggccatct cgttcttgta tagagaaggt ccagctgaaa gattgaagag gttgaaattg      60
ccagctatga gaaaaggtaa cggcttctat ttgtctagag ttccatttg ttggaccgtt     120
tacgttgcta atccaattgc tgctaaacag ttgttgttga aggctgaaaa tttccccaag     180
tctcactttt tgatggttgg taaggattcc ccattcgttc aatttttggg tccagataac     240
gttgtcaact ctaatggtga aaactggaaa aagcagcgta aggttatgaa tccagctttc     300
catagatcaa tgccagttaa gactattgcc ggtgttgttt tgactttgtt cgccgttatt     360
gataagtaca aggtaaggt tccagtcacc tctactatgc aagaattcac cttggatgtt     420
ttgggtttag ccatcttcaa tttcgacttc ggttctttga aggtgatgc taaaaaatgg     480
cgtgctgagt acaaattggt tatgttgttt gatccagtga ccaacgtttt cactggtttc     540
gatttttgc tgaggtacat ctaccctaag agaatcaaag gtgctaacgc tgttaacaac     600
ctgaacaagt tgttcgatca attggtcaag cagaagagat tggaagttca atctggtgtt     660
catgctaaca agccacaaaa cgaaaaggat tgttgacct tgatgttgga agctgaacaa     720
aggggtgaag ctatgactac tgatatgaa atgagacata cgtcgccgt ttttttcttg     780
gctggtcatg aatctactgc ccatgttttg tctttcacct tgtactttt ggccaagaac     840
aagtacgtgc aacagaagtt gagagaagag gtttctagag ttatgggtag aaagtctgtt     900
gatgttgctc aactttgga agaattgaga cagatggaat acttgtacgc cgtcatcaaa     960
gaatccttga gattgtgctc tatcttcgac gttttgattt tgagagatgc cgtggaagat    1020
atgtacttgg atgatacttt tattcccaag ggcaccagaa ttaccattga tgtttctgcc    1080
attcagagag atccaaaggt tggaacaat ccagatgatt catcccaga aagattcatg    1140
gaaggtggtg aagccgaagg tcatgaaggt atgacttggt tgccatttgg tggtggtgct    1200
agacaatgta ttggtatgaa tttctccctg accgaacaaa aagttgcttt ggctatgttg    1260
gttcagagat acgatattga tgttcccaag gactccatcc attacgaaga tattgcttac    1320
```
gaaaggccat tttacttggc tccacaatct ttggaattga ccttcactaa gttgcactaa    1380

<210> SEQ ID NO 101
<211> LENGTH: 459
<212> TYPE: PRT
<213> ORGANISM: Rhizopus microsporus

<400> SEQUENCE: 101

```
Met Ala Ile Ser Phe Leu Tyr Arg Glu Gly Pro Ala Glu Arg Leu Lys
1               5                   10                  15

Arg Leu Lys Leu Pro Ala Met Arg Lys Gly Asn Gly Phe Tyr Leu Ser
            20                  25                  30

Arg Val Pro Phe Cys Trp Thr Val Tyr Val Ala Asn Pro Ile Ala Ala
        35                  40                  45

Lys Gln Leu Leu Leu Lys Ala Glu Asn Phe Pro Lys Ser His Phe Leu
    50                  55                  60

Met Val Gly Lys Asp Ser Pro Phe Val Gln Phe Leu Gly Pro Asp Asn
65                  70                  75                  80

Val Val Asn Ser Asn Gly Glu Asn Trp Lys Lys Gln Arg Lys Val Met
                85                  90                  95

Asn Pro Ala Phe His Arg Ser Met Pro Val Lys Thr Ile Ala Gly Val
            100                 105                 110

Val Leu Thr Leu Phe Ala Val Ile Asp Lys Tyr Lys Gly Lys Val Pro
        115                 120                 125

Val Thr Ser Thr Met Gln Glu Phe Thr Leu Asp Val Leu Gly Leu Ala
    130                 135                 140

Ile Phe Asn Phe Asp Phe Gly Ser Leu Lys Gly Asp Ala Lys Lys Trp
145                 150                 155                 160

Arg Ala Glu Tyr Lys Leu Val Met Leu Phe Asp Pro Val Thr Asn Val
                165                 170                 175

Phe Thr Gly Phe Asp Phe Leu Leu Arg Tyr Ile Tyr Pro Lys Arg Ile
            180                 185                 190

Lys Gly Ala Asn Ala Val Asn Asn Leu Asn Lys Leu Phe Asp Gln Leu
        195                 200                 205

Val Lys Gln Lys Arg Leu Glu Val Gln Ser Gly Val His Ala Asn Lys
    210                 215                 220

Pro Gln Asn Glu Lys Asp Leu Leu Thr Leu Met Leu Glu Ala Glu Gln
225                 230                 235                 240

Arg Gly Glu Ala Met Thr Thr Asp Met Glu Met Arg His Asn Val Ala
                245                 250                 255

Val Phe Phe Leu Ala Gly His Glu Ser Thr Ala His Val Leu Ser Phe
            260                 265                 270

Thr Leu Tyr Phe Leu Ala Lys Asn Lys Tyr Val Gln Gln Lys Leu Arg
        275                 280                 285

Glu Glu Val Ser Arg Val Met Gly Arg Lys Ser Val Asp Val Ala Pro
    290                 295                 300

Thr Leu Glu Glu Leu Arg Gln Met Glu Tyr Leu Tyr Ala Val Ile Lys
305                 310                 315                 320

Glu Ser Leu Arg Leu Cys Ser Ile Phe Asp Val Leu Ile Leu Arg Asp
                325                 330                 335

Ala Val Glu Asp Met Tyr Leu Asp Asp Thr Phe Ile Pro Lys Gly Thr
            340                 345                 350

Arg Ile Thr Ile Asp Val Ser Ala Ile Gln Arg Asp Pro Lys Val Trp
        355                 360                 365
```

```
Asn Asn Pro Asp Asp Phe Ile Pro Glu Arg Phe Met Glu Gly Gly Glu
        370                 375                 380

Ala Glu Gly His Glu Gly Met Thr Trp Leu Pro Phe Gly Gly Gly Ala
385                 390                 395                 400

Arg Gln Cys Ile Gly Met Asn Phe Ser Leu Thr Glu Gln Lys Val Ala
                405                 410                 415

Leu Ala Met Leu Val Gln Arg Tyr Asp Ile Asp Val Pro Lys Asp Ser
                420                 425                 430

Ile His Tyr Glu Asp Ile Ala Tyr Glu Arg Pro Phe Tyr Leu Ala Pro
            435                 440                 445

Gln Ser Leu Glu Leu Thr Phe Thr Lys Leu His
    450                 455

<210> SEQ ID NO 102
<211> LENGTH: 1581
<212> TYPE: DNA
<213> ORGANISM: Phycomyces blakesleenanus

<400> SEQUENCE: 102
atggccaact cctctttcga aaacctgcaa tctttgttcg ttgatttcgt ccaaccacaa      60
ttggtccaaa gaaaaaaaca agccggtgtt attttctccg ccgttgtttt ggttttgtgt     120
tacaacacca tcaacaagat catctaccca ccaaagtcct tgagacatat tccacacgtt     180
aactacattg cctacaccag atcacaattg agaaaacaac cagcttctga acaagctaga     240
gaactgttgt tgccattatt ggctgaaaac aatggtttct acgccattcc atttctaggt     300
aagtggtctg ttcaagttgc taacccaatt gccattaaga ccatcctgtt gaagtttgac     360
atgttcccaa aggctaactc cttgtctaaa tctcaaggta cattggccca tagattcatt     420
ggtggtccaa atgttttttt gttggagggt aaaaagtggc gtaagcagag aatgatttct     480
aacccagctt tctctagatc catgccagtt gatatgtttg gtaggattac catcaacctg     540
tttaagtact tggataacat cgatccaacc atcgatgttt tggataccat gaagaaatgg     600
accttggata ctttgggttc tgctgttttt gatttcgact tcgaatcttt gaccaagcca     660
aacaatgaat ggacctctat ctactacgag attaacgcct ctttgtttgt cccaatcttc     720
aacattttgc cagtcttgga aaagtccttc ttgtggatgt ttcctaagag aaaaagggtt     780
cacgataaga tgaccaagtt gaaggatatg atgagacaag tcatcatcca aaagcaggct     840
aggttgaaag aaaacaaacc caatccaaac ttgaaggaca ccgaaaagga tttgttgacc     900
ttgttgttgg aatccgaaaa tgaaggtcat gagccaatgt ctgaagatga ttgatgtct      960
aatttgtgcg cttttttctt cgctggtcat gatacaactg ctaacgcttt atcttctgcc    1020
ttgtatcatt tggctgttca acaagacgtt caaagaaag caagagaaga agtcatcaac    1080
gttttgggtg atgaaccaga agatgtcatt ccatctattg aagataccag acagttggac    1140
tacctgaact tgatcatcaa agaaacatg aggatcaacc caccagttgg tggaccatta    1200
gatagattgg ttactgaaga tatcgttttg gacggtgttt tgttgccaaa aggtacttct    1260
gttaaggttg ccgtttactc cttgcataga aatccattat tgtgggattc cccagaagaa    1320
ttcagaccag aaaagatttt tgccaggtggt gaagctgata agattgaagg tatgggttac    1380
atcccatttt ctgatggtgg tagacaatgt atcggtatga acttctcatt ggttgaacaa    1440
agggttttgt tggctatgat gttgagaaag tacacctgga agttgtctga aaacactatt    1500
aacaaggacg aattgcaagt ttcgcccttt aacattatgg ccccattcga tttgaagatc    1560
```
actttggaaa agaggtacta a                                           1581

<210> SEQ ID NO 103
<211> LENGTH: 526
<212> TYPE: PRT
<213> ORGANISM: Phycomyces blakesleeanus

<400> SEQUENCE: 103

Met Ala Asn Ser Ser Phe Glu Asn Leu Gln Ser Leu Phe Val Asp Phe
1               5                   10                  15

Val Gln Pro Gln Leu Val Gln Arg Lys Lys Gln Ala Gly Val Ile Phe
            20                  25                  30

Ser Ala Val Val Leu Val Leu Cys Tyr Asn Thr Ile Asn Lys Ile Ile
        35                  40                  45

Tyr Pro Pro Lys Ser Leu Arg His Ile Pro His Val Asn Tyr Ile Ala
    50                  55                  60

Tyr Thr Arg Ser Gln Leu Arg Lys Gln Pro Ala Ser Glu Gln Ala Arg
65                  70                  75                  80

Glu Leu Leu Leu Pro Leu Leu Ala Glu Asn Asn Gly Phe Tyr Ala Ile
                85                  90                  95

Pro Phe Leu Gly Lys Trp Ser Val Gln Val Ala Asn Pro Ile Ala Ile
            100                 105                 110

Lys Thr Ile Leu Leu Lys Phe Asp Met Phe Pro Lys Ala Asn Ser Leu
        115                 120                 125

Ser Lys Ser Gln Gly Thr Leu Ala His Arg Phe Ile Gly Gly Pro Asn
    130                 135                 140

Val Phe Leu Leu Glu Gly Lys Lys Trp Arg Lys Gln Arg Met Ile Ser
145                 150                 155                 160

Asn Pro Ala Phe Ser Arg Ser Met Pro Val Asp Met Phe Gly Arg Ile
                165                 170                 175

Thr Ile Asn Leu Phe Lys Tyr Leu Asp Asn Ile Asp Pro Thr Ile Asp
            180                 185                 190

Val Leu Asp Thr Met Lys Lys Trp Thr Leu Asp Thr Leu Gly Ser Ala
        195                 200                 205

Val Phe Asp Phe Asp Phe Glu Ser Leu Thr Lys Pro Asn Asn Glu Trp
    210                 215                 220

Thr Ser Ile Tyr Tyr Glu Ile Asn Ala Ser Leu Phe Val Pro Ile Phe
225                 230                 235                 240

Asn Ile Leu Pro Val Leu Glu Lys Ser Phe Leu Trp Met Phe Pro Lys
                245                 250                 255

Arg Lys Arg Val His Asp Lys Met Thr Lys Leu Lys Asp Met Met Arg
            260                 265                 270

Gln Val Ile Ile Gln Lys Gln Ala Arg Leu Lys Glu Asn Lys Pro Asn
        275                 280                 285

Pro Asn Leu Lys Asp Thr Glu Lys Asp Leu Leu Thr Leu Leu Leu Glu
    290                 295                 300

Ser Glu Asn Glu Gly His Glu Pro Met Ser Glu Asp Glu Leu Met Ser
305                 310                 315                 320

Asn Leu Cys Ala Phe Phe Phe Ala Gly His Asp Thr Thr Ala Asn Ala
                325                 330                 335

Leu Ser Ser Ala Leu Tyr His Leu Ala Val Gln Gln Asp Val Gln Lys
            340                 345                 350

Lys Ala Arg Glu Glu Val Ile Asn Val Leu Gly Asp Glu Pro Glu Asp
        355                 360                 365

```
Val Ile Pro Ser Ile Glu Asp Thr Arg Gln Leu Asp Tyr Leu Asn Leu
370                 375                 380
Ile Ile Lys Glu Asn Met Arg Ile Asn Pro Pro Val Gly Gly Pro Leu
385                 390                 395                 400
Asp Arg Leu Val Thr Glu Asp Ile Val Leu Asp Gly Val Leu Leu Pro
                405                 410                 415
Lys Gly Thr Ser Val Lys Val Ala Val Tyr Ser Leu His Arg Asn Pro
                420                 425                 430
Leu Leu Trp Asp Ser Pro Glu Glu Phe Arg Pro Glu Arg Phe Leu Pro
                435                 440                 445
Gly Gly Glu Ala Asp Lys Ile Glu Gly Met Gly Tyr Ile Pro Phe Ser
450                 455                 460
Asp Gly Gly Arg Gln Cys Ile Gly Met Asn Phe Ser Leu Val Glu Gln
465                 470                 475                 480
Arg Val Leu Leu Ala Met Met Leu Arg Lys Tyr Thr Trp Lys Leu Ser
                485                 490                 495
Glu Asn Thr Ile Asn Lys Asp Glu Leu Gln Val Tyr Ala Phe Asn Ile
                500                 505                 510
Met Ala Pro Phe Asp Leu Lys Ile Thr Leu Glu Lys Arg Tyr
                515                 520                 525

<210> SEQ ID NO 104
<211> LENGTH: 1341
<212> TYPE: DNA
<213> ORGANISM: Lichtheimia ramosa

<400> SEQUENCE: 104
atggataacc agacctggtc tagtgttcca ggtgcttcat tttggaaagg caaattggtt      60
tctggtcact acgttaggga agtgtttttg aacaacgatt tcgacttctt gaaaggcact     120
ggtaagagat tcgatacttt gttgttgact gataccacca ctcaagatgt tgacatcgaa     180
gttttcagaa ccgttgttat gaagcacttg accaaagaaa tgaaggctta cactccaaga     240
gttgttcaac atttgactgc tggtggtgac gaaaaattgg gtgatgctaa gaaccacaa      300
gaattggttc atctgttccc tttgttacaa catatggttg ctaaagcctc cgcctctatt     360
tttgttggta ctgaattggc ttccgatgat gatgttgttg aaacctgtaa gaacattgcc     420
atcgacattg ttctgaatt aggtccaggt tcctatatca tggatgcttt tccatctttg      480
gccagattga aatgtggta cattggtaaa tttggcaagg ccattaacaa gcacagacaa      540
catttgttga gctttggg tccagttatt gataagagat tggctgctgc tgaaaaaggt       600
ggtgattggg atagaccaca agatatattg caagacatca tcgaaaccat caacttgact     660
ttggataacc aaagagaca tatcttgcca gttaagtggt tgttggcttt gttctttgct     720
tctattcata ccacctccga aaactctact atcgtcttgt acagaatcat gcagaaccca     780
gaaatcatcg atgtcttgtt ggaagaacaa aaccaggtct tggaaaaaca ctacggttcc     840
aacattgatt actccgatac cactaagttg ttcactggtg aagtcatcaa agagttggtt     900
aagttggatt ccttgtgcag agaagctatg agagctagaa attcctattt ggaattgcca     960
catacttacg tcggtaagtc cagaattact ttgtcatgcg gtgctattat gaaccaggt     1020
catgatgttt tgatcaacat gtgggtaat catagagatg ccaaaattca aagggatacc    1080
atcggtgatc atcacgattt taagccattc agattcgttg gtttggacag acaatctacc    1140
aagattggtg atgactttt gatgttcggt caaggtagac atgcttgtcc aggtagatgg    1200
tttgctattc aagaaatcaa gaccatcgtg tccgttttga ttaggtacta caagttgact    1260
```

```
ccaaacggtc caattacttt tccaactcat ccaagaatgc caatgcctat gggtcaagtt    1320
ataattcaga gaaggcagta a                                              1341
```

<210> SEQ ID NO 105
<211> LENGTH: 446
<212> TYPE: PRT
<213> ORGANISM: Lichtheimia ramosa

<400> SEQUENCE: 105

```
Met Asp Asn Gln Thr Trp Ser Ser Val Pro Gly Ala Ser Phe Trp Lys
1               5                   10                  15

Gly Lys Leu Val Ser Gly His Tyr Val Arg Glu Val Phe Leu Asn Asn
                20                  25                  30

Asp Phe Asp Phe Leu Lys Gly Thr Gly Lys Arg Phe Asp Thr Leu Leu
            35                  40                  45

Leu Thr Asp Thr Thr Thr Gln Asp Val Asp Ile Glu Val Phe Arg Thr
        50                  55                  60

Val Val Met Lys His Leu Thr Lys Glu Met Lys Ala Tyr Thr Pro Arg
65                  70                  75                  80

Val Val Gln His Leu Thr Ala Gly Gly Asp Glu Lys Leu Gly Asp Ala
                85                  90                  95

Lys Glu Pro Gln Glu Leu Val His Leu Phe Pro Leu Leu Gln His Met
            100                 105                 110

Val Ala Lys Ala Ser Ala Ser Ile Phe Val Gly Thr Glu Leu Ala Ser
        115                 120                 125

Asp Asp Asp Val Val Glu Thr Cys Lys Asn Ile Ala Ile Asp Ile Gly
130                 135                 140

Ser Glu Leu Gly Pro Gly Ser Tyr Ile Met Asp Ala Phe Pro Ser Leu
145                 150                 155                 160

Ala Arg Leu Arg Met Trp Tyr Ile Gly Lys Phe Gly Lys Ala Ile Asn
                165                 170                 175

Lys His Arg Gln His Leu Leu Arg Ala Leu Gly Pro Val Ile Asp Lys
            180                 185                 190

Arg Leu Ala Ala Ala Glu Lys Gly Gly Asp Trp Asp Arg Pro Gln Asp
        195                 200                 205

Ile Leu Gln Asp Ile Ile Glu Thr Ile Asn Leu Thr Leu Asp Asn Pro
    210                 215                 220

Lys Arg His Ile Leu Pro Val Lys Trp Leu Leu Ala Leu Phe Phe Ala
225                 230                 235                 240

Ser Ile His Thr Thr Ser Glu Asn Ser Thr Ile Val Leu Tyr Arg Ile
                245                 250                 255

Met Gln Asn Pro Glu Ile Ile Asp Val Leu Leu Glu Glu Gln Asn Gln
            260                 265                 270

Val Leu Glu Lys His Tyr Gly Ser Asn Ile Asp Tyr Ser Asp Thr Thr
        275                 280                 285

Lys Leu Phe Thr Gly Glu Val Ile Lys Glu Leu Val Lys Leu Asp Ser
    290                 295                 300

Leu Cys Arg Glu Ala Met Arg Ala Arg Asn Ser Tyr Leu Glu Leu Pro
305                 310                 315                 320

His Thr Tyr Val Gly Lys Ser Arg Ile Thr Leu Ser Cys Gly Ala Ile
                325                 330                 335

Ile Glu Pro Gly His Asp Val Leu Ile Asn Met Trp Gly Asn His Arg
            340                 345                 350
```

| | | | | | | | | | | | | | | |
|---|---|---|---|---|---|---|---|---|---|---|---|---|---|---|
| Asp | Ala | Lys | Ile | Gln | Arg | Asp | Thr | Ile | Gly | Asp | His | His | Asp | Phe | Lys |
| | | | 355 | | | | 360 | | | | 365 | | | | |
| Pro | Phe | Arg | Phe | Val | Gly | Leu | Asp | Arg | Gln | Ser | Thr | Lys | Ile | Gly | Asp |
| | 370 | | | | | 375 | | | | | 380 | | | | |
| Asp | Phe | Leu | Met | Phe | Gly | Gln | Gly | Arg | His | Ala | Cys | Pro | Gly | Arg | Trp |
| 385 | | | | | 390 | | | | | 395 | | | | | 400 |
| Phe | Ala | Ile | Gln | Glu | Ile | Lys | Thr | Ile | Val | Ser | Val | Leu | Ile | Arg | Tyr |
| | | | | 405 | | | | | 410 | | | | | 415 | |
| Tyr | Lys | Leu | Thr | Pro | Asn | Gly | Pro | Ile | Thr | Phe | Pro | Thr | His | Pro | Arg |
| | | | 420 | | | | 425 | | | | | 430 | | | |
| Met | Pro | Met | Pro | Met | Gly | Gln | Val | Ile | Ile | Gln | Arg | Arg | Gln | | |
| | | | 435 | | | | 440 | | | | 445 | | | | |

<210> SEQ ID NO 106
<211> LENGTH: 1593
<212> TYPE: DNA
<213> ORGANISM: Hesseltinella vesiculosa

<400> SEQUENCE: 106

| | |
|---|---|
| atgctgttcc agtacatcca tcatttggcc gaaagattcg atcacaaaaa gaccttggat | 60 |
| caattgcaaa ctttcgcttc tactccagaa ggtgctgttg gtattactgc tgctgttgct | 120 |
| ttggttgctg gtgcttctta tttgaagaac aagaacaacg atagaggttg cccaaaagtt | 180 |
| ccaggttctt ctgtttgggg tacttctact gaagagtata gagctgatcc aaaggctttt | 240 |
| atcgttaagt ggcaaaatga attgggtcca gtttaccatg ctgagttgtt tggtcatact | 300 |
| gctacagttg tttctggttc ttacgtcaga gaaatcttct tgaacgataa gttcgatttc | 360 |
| atggctggct tgcatagaac tttcgataac atgttgttga ccaactgtgg tccatacgaa | 420 |
| gatttgtctg ctgctcatac ttctgaagtt gtcaagaagt ttttgtcgcc acatttgaaa | 480 |
| catttcaccc caagagttat cgaacacttg caacaaggtt gaaagctca aaccggtgaa | 540 |
| atttctgctg aaggtaaaca attcccacac gtttatggtt tggttcaaca tccagttgct | 600 |
| ttagcttcag cttctgtttt tgttggtcca gagttgtcta agaacgagtt gttgattgac | 660 |
| tccttcaaga acatggttat tgatgtcggt tccgagttgt taccaaatcc atggttggaa | 720 |
| ccatttccaa gattgaacag attgagaatg tggtgggttg gtaagacttc ttctactgtt | 780 |
| aagagacaca gaggtcaatt ggctactgct ttgaaaccag aattggatag aagattgaag | 840 |
| gctatggctt ccaatgattc taattgggaa agaccagatg acatcttgca gaacttgttg | 900 |
| gaacattaca ctccaccaaa aggtatggat accttgaact acatggttaa ttggatgact | 960 |
| caattgactt cgctgctat tcatacaacc tctgaaggtt ctacttgggt cttgtacaga | 1020 |
| ttattacaaa ctccaggttt gtgggaagag ttgtaccaag aacaaaacga agttttggaa | 1080 |
| gcctccggta ttgattcttc agctggtgct gaagttttca ccagagaaat tttgaacaag | 1140 |
| ttcgttaaga tggactccgt cattagaaa actatgagag ctagaactgc ctacattact | 1200 |
| ttgccacata tcaacaagtc caacgaagtc gttactttgt ctaatggtgc taaaatctac | 1260 |
| ccaggtgaat ccgcttatat caacgtttgg tctaatcaca atgacccctc attgcaaaat | 1320 |
| tccatgaagg acttacaaca gttcaagcca ttgagatttt tggacgctga aaagaactct | 1380 |
| accaagatcg gtgaagattt cctgttttc ggtatgggta acatgcttg tccaggtaga | 1440 |
| tggtttgctg ttcaagaaat caaaaccatc gttgccttgt tgttgagaga gtacaaattg | 1500 |
| gaagctgttg gcgatttgtt tttcccagaa gttgaatcca ttcctttttcc aatgggtgaa | 1560 |
| ttcaagatct acccaagaaa gcaagttgcc tga | 1593 |

<210> SEQ ID NO 107
<211> LENGTH: 530
<212> TYPE: PRT
<213> ORGANISM: Hesseltinella vesiculosa

<400> SEQUENCE: 107

```
Met Leu Phe Gln Tyr Ile His His Leu Ala Glu Arg Phe Asp His Lys
1               5                   10                  15

Lys Thr Leu Asp Gln Leu Gln Thr Phe Ala Ser Thr Pro Glu Gly Ala
            20                  25                  30

Val Gly Ile Thr Ala Ala Val Ala Leu Val Ala Gly Ala Ser Tyr Leu
        35                  40                  45

Lys Asn Lys Asn Asn Asp Arg Gly Cys Pro Lys Val Pro Gly Ser Ser
50                  55                  60

Val Trp Gly Thr Ser Thr Glu Glu Tyr Arg Ala Asp Pro Lys Ala Phe
65                  70                  75                  80

Ile Val Lys Trp Gln Asn Glu Leu Gly Pro Val Tyr His Ala Glu Leu
                85                  90                  95

Phe Gly His Thr Ala Thr Val Val Ser Gly Ser Tyr Val Arg Glu Ile
            100                 105                 110

Phe Leu Asn Asp Lys Phe Asp Phe Met Ala Gly Leu His Arg Thr Phe
        115                 120                 125

Asp Asn Met Leu Leu Thr Asn Cys Gly Pro Tyr Glu Asp Leu Ser Ala
130                 135                 140

Ala His Thr Ser Glu Val Val Lys Lys Phe Leu Ser Pro His Leu Lys
145                 150                 155                 160

His Phe Thr Pro Arg Val Ile Glu His Leu Gln Gln Gly Leu Lys Ala
                165                 170                 175

Gln Thr Gly Glu Ile Ser Ala Glu Gly Lys Gln Phe Pro His Val Tyr
            180                 185                 190

Gly Leu Val Gln His Pro Val Ala Leu Ala Ser Ala Ser Val Phe Val
        195                 200                 205

Gly Pro Glu Leu Ser Lys Asn Glu Leu Leu Ile Asp Ser Phe Lys Asn
210                 215                 220

Met Val Ile Asp Val Gly Ser Glu Leu Leu Pro Asn Pro Trp Leu Glu
225                 230                 235                 240

Pro Phe Pro Arg Leu Asn Arg Leu Arg Met Trp Val Gly Lys Thr
                245                 250                 255

Ser Ser Thr Val Lys Arg His Arg Gly Gln Leu Ala Thr Ala Leu Lys
            260                 265                 270

Pro Glu Leu Asp Arg Arg Leu Lys Ala Met Ala Ser Asn Asp Ser Asn
        275                 280                 285

Trp Glu Arg Pro Asp Asp Ile Leu Gln Asn Leu Leu Glu His Tyr Thr
290                 295                 300

Pro Pro Lys Gly Met Asp Thr Leu Asn Tyr Met Val Asn Trp Met Thr
305                 310                 315                 320

Gln Leu Thr Phe Ala Ala Ile His Thr Thr Ser Glu Gly Ser Thr Trp
                325                 330                 335

Val Leu Tyr Arg Leu Leu Gln Thr Pro Gly Leu Trp Glu Glu Leu Tyr
            340                 345                 350

Gln Glu Gln Asn Glu Val Leu Glu Ala Ser Gly Ile Asp Ser Ser Ala
        355                 360                 365

Gly Ala Glu Val Phe Thr Arg Glu Ile Leu Asn Lys Phe Val Lys Met
```

```
                   370                 375                 380
Asp Ser Val Ile Arg Glu Thr Met Arg Ala Arg Thr Ala Tyr Ile Thr
385                 390                 395                 400

Leu Pro His Ile Asn Lys Ser Asn Glu Val Val Thr Leu Ser Asn Gly
                405                 410                 415

Ala Lys Ile Tyr Pro Gly Glu Ser Ala Tyr Ile Asn Val Trp Ser Asn
                420                 425                 430

His Asn Asp Pro Ser Leu Gln Asn Ser Met Lys Asp Leu Gln Gln Phe
                435                 440                 445

Lys Pro Leu Arg Phe Leu Asp Ala Glu Lys Asn Ser Thr Lys Ile Gly
                450                 455                 460

Glu Asp Phe Leu Phe Phe Gly Met Gly Lys His Ala Cys Pro Gly Arg
465                 470                 475                 480

Trp Phe Ala Val Gln Glu Ile Lys Thr Ile Val Ala Leu Leu Leu Arg
                485                 490                 495

Glu Tyr Lys Leu Glu Ala Val Gly Asp Leu Phe Phe Pro Glu Val Glu
                500                 505                 510

Ser Ile Pro Phe Pro Met Gly Glu Phe Lys Ile Tyr Pro Arg Lys Gln
                515                 520                 525

Val Ala
    530

<210> SEQ ID NO 108
<211> LENGTH: 1572
<212> TYPE: DNA
<213> ORGANISM: Phycomyces blakesleeanus

<400> SEQUENCE: 108
atgatcgagt acctgaaaga attcgtcgac aggattgatt ctaagacctt ggaaaacgtt      60
aagtccttgg ccttttctaa agaaggtgcc attggtattt ctaccgccat tatttttgtcc    120 tccgcttaca attatcacaa gtggtcctct agaaccattt ctaatggttg tccaagagtt     180
ccacatacct tgccatttgt tggtttgact agagtttacc gtaaggactc taaggctttt     240
tgtgaagaat ggcatgctaa attgggtcca gttttttagag cacacttgtt cggtaaagaa    300
gttaccgttg tttctggtca ctacgtcaga gaagtttttt tgaacaagca cttcgatttc     360
gttaagggtg ttgctaaggt ttttgatacc aggttgttga ctgattccgg ttccagagaa     420 gatttttactc cagaagattt gagggaaatc atcacgaaat acttgacccc aaagttgaac     480
ttctacacca agagagttat caagagattg aagcaaggtg tcgaatcttc tttgggtgat     540
aaggattcca tcgaattgga taacttgtac ccattcgttc aacacttggt tgttaatgcc     600
tctgcctcta ttttttgtcgg tgaagaattg tcccaaaaca agttgttgat cgactccttc     660
aagaacatgg ttagagatgt gggtaaagag atcaagcaaa atccatggtt tgaaccctttt    720 ccaaccatca acaagtttag gatgtggttg attggtaaga cctctccagt tattaagaac     780
cacaaagagc aactgttgaa cgccattaag ccagaagttg agtatagatt gtctcaggct     840
agatctaatc cagactggaa aaaacctacc gatatgttgc aagacttgtt ggaaaattct     900
aagccaccag ctcatttgga tttgatggat catttggttc acatcatcac gttcttgatt     960
tttgttgcct tgcataccac ctctgaaaac actactgttt tgttgtacag gatgttggag    1020
aatccagcta tcgttgatga attggtcatc gaacaacaag aagtcttgga caagaaggt     1080 ttggacgcta ttgtggttc cgaagttttt ccaagagata tcttgaagaa gttcgtcaag     1140
ttggattctg tctgtagaga aaccttcaga atgaagaacc agtacatctc tttgccacat    1200
```

-continued

```
gaatacgatg gtaaggttcc attgactttg tctaatggtg ctgttattaa cccaggtgaa    1260
gatgttttga ttgatgtttg gactaaccac cagtacactg aagatgctaa tgatgttgaa    1320
gatgccgatc aattcaaggc ctttagattt gttgatcagg acaagcaatc taccaaggtt    1380
ggtgaagatt acttgttttt tggtatgggt agacgtgctt gtccaggtag atggtttgct    1440
attcaagaag tccaaaccat tttggccatg ttggttcgtg agtataagtt tatgccaaag    1500
ggtccaatcg ttttcccaac tgaagaaaga tctccaattc caaccggtaa gtgtattatc    1560
cagagaaagt ga                                                        1572
```

<210> SEQ ID NO 109
<211> LENGTH: 523
<212> TYPE: PRT
<213> ORGANISM: Phycomyces blakesleeanus

<400> SEQUENCE: 109

```
Met Ile Glu Tyr Leu Lys Glu Phe Val Asp Arg Ile Asp Ser Lys Thr
1               5                   10                  15

Leu Glu Asn Val Lys Ser Leu Ala Phe Ser Lys Glu Gly Ala Ile Gly
            20                  25                  30

Ile Ser Thr Ala Ile Ile Leu Ser Ser Ala Tyr Asn Tyr His Lys Trp
        35                  40                  45

Ser Ser Arg Thr Ile Ser Asn Gly Cys Pro Arg Val Pro His Thr Leu
    50                  55                  60

Pro Phe Val Gly Leu Thr Arg Val Tyr Arg Lys Asp Ser Lys Ala Phe
65                  70                  75                  80

Cys Glu Glu Trp His Ala Lys Leu Gly Pro Val Phe Arg Ala His Leu
                85                  90                  95

Phe Gly Lys Glu Val Thr Val Val Ser Gly His Tyr Val Arg Glu Val
            100                 105                 110

Phe Leu Asn Lys His Phe Asp Phe Val Lys Gly Val Ala Lys Val Phe
        115                 120                 125

Asp Thr Arg Leu Leu Thr Asp Ser Gly Ser Arg Glu Asp Phe Thr Pro
    130                 135                 140

Glu Asp Leu Arg Glu Ile Ile Thr Lys Tyr Leu Thr Pro Lys Leu Asn
145                 150                 155                 160

Phe Tyr Thr Lys Arg Val Ile Lys Arg Leu Lys Gln Gly Val Glu Ser
                165                 170                 175

Ser Leu Gly Asp Lys Asp Ser Ile Glu Leu Asp Asn Leu Tyr Pro Phe
            180                 185                 190

Val Gln His Leu Val Val Asn Ala Ser Ala Ser Ile Phe Val Gly Glu
        195                 200                 205

Glu Leu Ser Gln Asn Lys Leu Leu Ile Asp Ser Phe Lys Asn Met Val
    210                 215                 220

Arg Asp Val Gly Lys Glu Ile Lys Gln Asn Pro Trp Phe Glu Pro Phe
225                 230                 235                 240

Pro Thr Ile Asn Lys Phe Arg Met Trp Leu Ile Gly Lys Thr Ser Pro
                245                 250                 255

Val Ile Lys Asn His Lys Glu Gln Leu Leu Asn Ala Ile Lys Pro Glu
            260                 265                 270

Val Glu Tyr Arg Leu Ser Gln Ala Arg Ser Asn Pro Asp Trp Lys Lys
        275                 280                 285

Pro Thr Asp Met Leu Gln Asp Leu Leu Glu Asn Ser Lys Pro Pro Ala
    290                 295                 300
```

```
His Leu Asp Leu Met Asp His Leu Val His Ile Ile Thr Phe Leu Ile
305                 310                 315                 320

Phe Val Ala Leu His Thr Thr Ser Glu Asn Thr Thr Val Leu Leu Tyr
                325                 330                 335

Arg Met Leu Glu Asn Pro Ala Ile Val Asp Glu Leu Val Ile Glu Gln
            340                 345                 350

Gln Glu Val Leu Glu Gln Glu Gly Leu Asp Ala Asn Cys Gly Ser Glu
        355                 360                 365

Val Phe Thr Arg Asp Ile Leu Lys Lys Phe Val Lys Leu Asp Ser Val
370                 375                 380

Cys Arg Glu Thr Phe Arg Met Lys Asn Gln Tyr Ile Ser Leu Pro His
385                 390                 395                 400

Glu Tyr Asp Gly Lys Val Pro Leu Thr Leu Ser Asn Gly Ala Val Ile
                405                 410                 415

Asn Pro Gly Glu Asp Val Leu Ile Asp Val Trp Thr Asn His Gln Tyr
            420                 425                 430

Thr Glu Asp Ala Asn Asp Val Glu Asp Ala Asp Gln Phe Lys Ala Phe
        435                 440                 445

Arg Phe Val Asp Gln Asp Lys Gln Ser Thr Lys Val Gly Glu Asp Tyr
450                 455                 460

Leu Phe Phe Gly Met Gly Arg Arg Ala Cys Pro Gly Arg Trp Phe Ala
465                 470                 475                 480

Ile Gln Glu Val Gln Thr Ile Leu Ala Met Leu Val Arg Glu Tyr Lys
                485                 490                 495

Phe Met Pro Lys Gly Pro Ile Val Phe Pro Thr Glu Glu Arg Ser Pro
            500                 505                 510

Ile Pro Thr Gly Lys Cys Ile Ile Gln Arg Lys
        515                 520

<210> SEQ ID NO 110
<211> LENGTH: 1587
<212> TYPE: DNA
<213> ORGANISM: Licthheimia ramosa

<400> SEQUENCE: 110
atgccaagct tgattccaaa gaacgcttcc gatgctattg aacagtacat ctctagactg      60
aaaaccatgg atagaaggca catgggtatt attgctggtt ctgttgctgt tgtttccttg     120
tacactttct acagacattt gaccagatcc agagatgata ttccattggt tccatatacc     180
tggccattga ttggttctac tccatctttt aacagagatc cagttgcctt tgttgagaag     240
tggtcacaag aatatggtcc agttttttaga gcacacttgc aaggtagaat ccaaactatt     300
attgccgccg aatacgttag agacatcttc atgaattccg acttcgattt tttgttcgcc     360
gtcaacaaaa gattcgatcc acatttgttg gccgatatcg atgataacac tttcactacc     420
gaaatgttga aaggtcgtt tatgaagttg actacccagt tgaaatctta cactccaaga     480
gctgttgaat tcttggatgt tggtagaaac gaattcttgt ctcattttcc agctggtcct     540
gttcatttgc cacacttgta tccattgatc aacatatgg ttggtaaagc ctctgctgct     600
atttttgctg gtacaaagtt ggcttctaac ccagaagttg ttgagtcctt caagaacatt     660
actttggaag ttggtgctga atcgccgtt gattctgttt ttttggaaag atactggggc     720
ttgaacagat tcagaatgtg gttgatgggt aaattctcca gtccatgaa gagacatcac     780 agagttttga agatgccct aagaccagaa atcaaggata gaattgaagc ctcttctgac     840
```

```
ccatctagag aaagaccaga tgatatgttg cagatcatca tcgagtctta ctacactgaa    900
agaagaggtg aatccgttga tgatttgact gaagatttgg tcaagtggct gatctctttg    960
attttcgctg ctattcatac cacctctgaa aactctactg ttgtcttgta caggatcttg   1020
tctaagcctg atgttgttga agagttgttg gaagaacaaa gagaagtttt ggttaggcat   1080
ggtatttctc cagacgaaaa agatccatct aagatgttta ctggtgccgt tattaaggac   1140
ttggttaagt tggattctgc ttgcagagaa ggtatgagaa tgagaaacga ttacttgact   1200
ttgggtcata cctacttggg taaaaagcca attacattgt cttgcggtgc tgttatcaaa   1260
ccaggtgaag atgttattat caacacctgg tacaaccacc gtaacaacaa gatccaaaaa   1320
atccaaggtg acgactactc taactacaac ccattcagat tgttggttc cgatagacaa    1380
gctgctagaa ttggtgatga tttcttgatc ttcggtgaag gtaaacatgc ttgtccaggt   1440
agatggtttg ctctgcaaga aatgaagacc atcatctcgt ttttgatcag ggattacaaa   1500
atggctccag aaggtccaat tactttccca aagaatccta agatgacttt gccaatgggt   1560
caagtgattt tggaatccag acattaa                                       1587
```

<210> SEQ ID NO 111
<211> LENGTH: 528
<212> TYPE: PRT
<213> ORGANISM: Lichtheimia ramosa

<400> SEQUENCE: 111

```
Met Pro Ser Leu Ile Pro Lys Asn Ala Ser Asp Ala Ile Glu Gln Tyr
1               5                   10                  15

Ile Ser Arg Leu Lys Thr Met Asp Arg Arg His Met Gly Ile Ile Ala
            20                  25                  30

Gly Ser Val Ala Val Val Ser Leu Tyr Thr Phe Tyr Arg His Leu Thr
        35                  40                  45

Arg Ser Arg Asp Asp Ile Pro Leu Val Pro Tyr Thr Trp Pro Leu Ile
    50                  55                  60

Gly Ser Thr Pro Ser Phe Asn Arg Asp Pro Val Ala Phe Val Glu Lys
65                  70                  75                  80

Trp Ser Gln Glu Tyr Gly Pro Val Phe Arg Ala His Leu Gln Gly Arg
                85                  90                  95

Ile Gln Thr Ile Ile Ala Ala Glu Tyr Val Arg Asp Ile Phe Met Asn
            100                 105                 110

Ser Asp Phe Asp Phe Leu Phe Ala Val Asn Lys Arg Phe Asp Pro His
        115                 120                 125

Leu Leu Ala Asp Ile Asp Asp Asn Thr Phe Thr Thr Glu Met Leu Arg
    130                 135                 140

Lys Val Val Met Lys Leu Thr Thr Gln Leu Lys Ser Tyr Thr Pro Arg
145                 150                 155                 160

Ala Val Glu Phe Leu Asp Val Gly Arg Asn Glu Phe Leu Ser His Phe
                165                 170                 175

Pro Ala Gly Pro Val His Leu Pro His Leu Tyr Pro Leu Ile Gln His
            180                 185                 190

Met Val Gly Lys Ala Ser Ala Ala Ile Phe Ala Gly Thr Lys Leu Ala
        195                 200                 205

Ser Asn Pro Glu Val Val Glu Ser Phe Lys Asn Ile Thr Leu Glu Val
    210                 215                 220

Gly Ala Glu Ile Ala Val Asp Ser Val Phe Leu Glu Arg Tyr Trp Gly
225                 230                 235                 240
```

```
Leu Asn Arg Phe Arg Met Trp Leu Met Gly Lys Phe Ser Lys Ser Met
                245                 250                 255

Lys Arg His His Arg Val Leu Lys Asp Ala Leu Arg Pro Glu Ile Lys
            260                 265                 270

Asp Arg Ile Glu Ala Ser Ser Asp Pro Ser Arg Glu Arg Pro Asp Asp
        275                 280                 285

Met Leu Gln Ile Ile Ile Glu Ser Tyr Tyr Thr Glu Arg Arg Gly Glu
    290                 295                 300

Ser Val Asp Asp Leu Thr Glu Asp Leu Val Lys Trp Leu Ile Ser Leu
305                 310                 315                 320

Ile Phe Ala Ala Ile His Thr Thr Ser Glu Asn Ser Thr Val Val Leu
                325                 330                 335

Tyr Arg Ile Leu Ser Lys Pro Asp Val Val Glu Glu Leu Leu Glu Glu
            340                 345                 350

Gln Arg Glu Val Leu Val Arg His Gly Ile Ser Pro Asp Glu Lys Asp
        355                 360                 365

Pro Ser Lys Met Phe Thr Gly Ala Val Ile Lys Asp Leu Val Lys Leu
    370                 375                 380

Asp Ser Ala Cys Arg Glu Gly Met Arg Met Arg Asn Asp Tyr Leu Thr
385                 390                 395                 400

Leu Gly His Thr Tyr Leu Gly Lys Lys Pro Ile Thr Leu Ser Cys Gly
                405                 410                 415

Ala Val Ile Lys Pro Gly Glu Asp Val Ile Ile Asn Thr Trp Tyr Asn
            420                 425                 430

His Arg Asn Asn Lys Ile Gln Lys Ile Gln Gly Asp Asp Tyr Ser Asn
        435                 440                 445

Tyr Asn Pro Phe Arg Phe Val Gly Ser Asp Arg Gln Ala Ala Arg Ile
    450                 455                 460

Gly Asp Asp Phe Leu Ile Phe Gly Glu Gly Lys His Ala Cys Pro Gly
465                 470                 475                 480

Arg Trp Phe Ala Leu Gln Glu Met Lys Thr Ile Ile Ser Phe Leu Ile
                485                 490                 495

Arg Asp Tyr Lys Met Ala Pro Glu Gly Pro Ile Thr Phe Pro Lys Asn
            500                 505                 510

Pro Lys Met Thr Leu Pro Met Gly Gln Val Ile Leu Glu Ser Arg His
        515                 520                 525

<210> SEQ ID NO 112
<211> LENGTH: 1584
<212> TYPE: DNA
<213> ORGANISM: Absidia repens

<400> SEQUENCE: 112
atgctgaccc agtacatcca ccaattcttc aacaatttcg accagaaaaa gaccatggac    60
caattgcaat ctgttgcctc ttctaaggat ggtgttattg gtattgctac cgccttgatt   120
ttgatttctg gtgttgctgc ttacaagtcc tctactgttg aaagaggttg tccacaagtt   180
ccatgtggta cttttctctt cggttctact tctgagtaca gagaaaatcc agttgccttt   240
gttaagaagt gggaagaaaa attgggtcca gttttcggtg tcaattatt ggtcaatac     300 gctactatag tctctggtcc tcaagttaga gaaatcttct ccaacgaaaa cttctctttc   360
atggccggta ttcaaagaga tttcgatact tacttgttgg ctaacggtgg ttccattcat   420
gatttgccac acacatgttgt ttctggtggt attaagaaga acctgtctcc aaagttgcca   480
ttctacacct ctagagttat cgaacatttg aagatcggct tgtacgaaca atgtggtgtt   540
```

-continued

```
gttccagatg agggtaaaga attcgatcat gtttacccat tcgttcaaca tatggttgct      600
aaagcttccg cttctgtttt tgttggtcca gaattggcta aggatttgaa cttggttgac      660
tccttcaaga acatggtttt ggaagttggt tctgatatgg gtccaaagcc atacttggaa      720
cattttccac atttgatgag actgaggatg tggtacattg gtaagacttc tacaaacgtc      780
aagagacaca gagatcaatt attcgctgct ttggttccac aaatcgactc tagattgaaa      840
gccatgaagg aaaaggattc caattgggat agaccaaacg atttcttgca ggatattttg      900
gaaaccgatg attgtccacc tcacatggat atctattctt actgtgttga ttggatgacc      960
caaattatct tgctgccttt gcataccaca tctgaaaatg gtactattgt cctgtaccgt     1020
ttgttggata atccaaaagt cttggaagag ttgtacgaag aacaaaacgc tgtattggaa     1080
gaagctggtt acgacgatac tgttggtcct gaagttttca ccagagagat tttgaacaag     1140
ttcgtcaaga tggactccgt cattagagaa tcttgtagat tgagaaacga ctacattggt     1200
ttgccacata ccaatgttgg taagaaaacc atcgttttgt ctggtggtgc tatgattaga     1260
ccaggtgaaa atgctttcgt caacttctac tcaaaccata gggatgagaa gttgcaaaag     1320
tctggtatga atgccaacaa cttcgaacca tacagattcg ttgatcaggg taagaactct     1380
accaagattg gtgatgattt catgttcttc ggtatgttca acatgcttg tccaggtaga     1440 tggtttgcta tccaagaaat caagaccatt tggccatgc tgatcagatc ttacaagatg     1500
tctgctatcg attccgttgt tttcccaact tctgattaca ctagaattcc aaccggtaga     1560
ttcaaaatcg tcccaagaaa gtga                                            1584
```

<210> SEQ ID NO 113
<211> LENGTH: 527
<212> TYPE: PRT
<213> ORGANISM: Absidia repens

<400> SEQUENCE: 113

```
Met Leu Thr Gln Tyr Ile His Gln Phe Phe Asn Asn Phe Asp Gln Lys
1               5                   10                  15

Lys Thr Met Asp Gln Leu Gln Ser Val Ala Ser Ser Lys Asp Gly Val
            20                  25                  30

Ile Gly Ile Ala Thr Ala Leu Ile Leu Ile Ser Gly Val Ala Ala Tyr
        35                  40                  45

Lys Ser Ser Thr Val Glu Arg Gly Cys Pro Gln Val Pro Cys Gly Thr
    50                  55                  60

Phe Ser Phe Gly Ser Thr Ser Glu Tyr Arg Glu Asn Pro Val Ala Phe
65                  70                  75                  80

Val Lys Lys Trp Glu Glu Lys Leu Gly Pro Val Phe Gly Ala Gln Leu
                85                  90                  95

Phe Gly Gln Tyr Ala Thr Ile Val Ser Gly Pro Gln Val Arg Glu Ile
            100                 105                 110

Phe Ser Asn Glu Asn Phe Ser Phe Met Ala Gly Ile Gln Arg Asp Phe
        115                 120                 125

Asp Thr Tyr Leu Leu Ala Asn Gly Gly Ser Ile His Asp Leu Pro Pro
    130                 135                 140

His Val Val Ser Gly Gly Ile Lys Lys Asn Leu Ser Pro Lys Leu Pro
145                 150                 155                 160

Phe Tyr Thr Ser Arg Val Ile Glu His Leu Lys Ile Gly Leu Tyr Glu
                165                 170                 175

Gln Cys Gly Val Val Pro Asp Glu Gly Lys Glu Phe Asp His Val Tyr
```

```
                180                 185                 190
Pro Phe Val Gln His Met Val Ala Lys Ala Ser Ala Ser Val Phe Val
            195                 200                 205
Gly Pro Glu Leu Ala Lys Asp Leu Asn Leu Val Asp Ser Phe Lys Asn
            210                 215                 220
Met Val Leu Glu Val Gly Ser Asp Met Gly Pro Lys Pro Tyr Leu Glu
225                 230                 235                 240
His Phe Pro His Leu Met Arg Leu Arg Met Trp Tyr Ile Gly Lys Thr
                245                 250                 255
Ser Thr Asn Val Lys Arg His Arg Asp Gln Leu Phe Ala Ala Leu Val
            260                 265                 270
Pro Gln Ile Asp Ser Arg Leu Lys Ala Met Lys Glu Lys Asp Ser Asn
            275                 280                 285
Trp Asp Arg Pro Asn Asp Phe Leu Gln Asp Ile Leu Glu Thr Asp Asp
            290                 295                 300
Cys Pro Pro His Met Asp Ile Tyr Ser Tyr Cys Val Asp Trp Met Thr
305                 310                 315                 320
Gln Ile Ile Phe Ala Ala Leu His Thr Thr Ser Glu Asn Gly Thr Ile
                325                 330                 335
Val Leu Tyr Arg Leu Leu Asp Asn Pro Lys Val Leu Glu Glu Leu Tyr
            340                 345                 350
Glu Glu Gln Asn Ala Val Leu Glu Glu Ala Gly Tyr Asp Asp Thr Val
            355                 360                 365
Gly Pro Glu Val Phe Thr Arg Glu Ile Leu Asn Lys Phe Val Lys Met
            370                 375                 380
Asp Ser Val Ile Arg Glu Ser Cys Arg Leu Arg Asn Asp Tyr Ile Gly
385                 390                 395                 400
Leu Pro His Thr Asn Val Gly Lys Lys Thr Ile Val Leu Ser Gly Gly
                405                 410                 415
Ala Met Ile Arg Pro Gly Glu Asn Ala Phe Val Asn Phe Tyr Ser Asn
            420                 425                 430
His Arg Asp Glu Lys Leu Gln Lys Ser Gly Met Asn Ala Asn Asn Phe
            435                 440                 445
Glu Pro Tyr Arg Phe Val Asp Gln Gly Lys Asn Ser Thr Lys Ile Gly
            450                 455                 460
Asp Asp Phe Met Phe Phe Gly Met Phe Lys His Ala Cys Pro Gly Arg
465                 470                 475                 480
Trp Phe Ala Ile Gln Glu Ile Lys Thr Ile Leu Ala Met Leu Ile Arg
                485                 490                 495
Ser Tyr Lys Met Ser Ala Ile Asp Ser Val Val Phe Pro Thr Ser Asp
            500                 505                 510
Tyr Thr Arg Ile Pro Thr Gly Arg Phe Lys Ile Val Pro Arg Lys
            515                 520                 525

<210> SEQ ID NO 114
<211> LENGTH: 1605
<212> TYPE: DNA
<213> ORGANISM: Lichtheimia corymbifera

<400> SEQUENCE: 114
atgtacaccc tggtgtctttt cttgaaggac caaaacatta ttgccgtttt gaagaacgct      60
attcacgctc aacaacaagg tactactgct tcctctatta ccattttgtc tttggctgtt     120
gctattacca ctttcgccgt tcatagaatt aggctgtatt ccgtaaaaga acacggtgtt     180
```

```
ccattggttc catatgtttt gcctttcatt ggttcttcac cagagtacag aaaagatcca      240 aaggctttt  tggaaaagtg gactgctaaa ttcggtccag ttttagagc  ccatattttc      300 ggtagagttt acaccattat ctccggtcat tacgtcagag aagttttctt gaacgaggac      360
ttctcattcg aagttggtat gggtaaaact ttcgatggtt ggttgattac cgataccaaa      420
aagtctgagt tgttctctac accattggtc agatctatgg ttatgaagca cttagccgtt      480
gatgttaaga actatactcc aagagctgtt gagcatttga ctattgctgc tagaaaatg       540 ttgggtgata tcggtgaatc taaagaattg ccacacttgt acccattgat ccaacatatg      600
gtttctaccg ctattgcctc tatttggtt  ggtttgaaaa tctgcaagga caaggatttg      660
ttggagactt ttaagaacgt tgccgtcgat attggttctg aattgaatcc agattcctac      720
ttgtacgaag ctttcccaac tatctctaga ttgagacaat ggtacttggg taaatacggt      780
aaggctatta acaagcacca agagcatatg ttgagagttt gggtccaga  aattgacgaa      840 agattggctg ctatggaacg tggtgatggt ggatgggaaa gaccagaaga tattttacaa      900
ggtattctgg aaaccgccaa gttgacttct gatcatccac aaagatatat ggtcccaatc      960
aagtggttcc tgattttggt ttttgcttcc attcatacca cctctcaaaa cactacagtt     1020
gctatgtata ggttgttgca gcatccagaa gttattgacg aactgttgga agaacaaaac     1080
caggtctttg aaaaacacca cggttctaac tacgatgatc atgatattac caagttgttg     1140
accggtgaag ttattaagga tttggtcaag ttggattccg tctgtagaga agctatgaga     1200
atctcttctt tctacgctga attgcctcat acttacatcg gtaaatctcc attgactatg     1260
tccaacggta ctattatcaa tccaggtgat gatgtcttga tcaacggtta cactaaccat     1320
catgatccag atatccaaat tgatggtggt ggtgattatg ctgaattcaa gccattcaga     1380
ttcgtcgaaa aaggtagaca atctaccaga atcggtgatg actacttgat tttcggtcaa     1440
ggtaaacatg cttgtccagg tagatggttt gctatgcaag aaatgaagac caccatctcg     1500
tttttgatca gacagtacat tattaccgcc aagggtgaca ttatgttttt gaagggtcat     1560
agacaaaaga tccctatggg tcaagttatc ttccagaaga gatga                     1605
```

<210> SEQ ID NO 115
<211> LENGTH: 534
<212> TYPE: PRT
<213> ORGANISM: Lichtheimia corymbifera

<400> SEQUENCE: 115

```
Met Tyr Thr Leu Val Ser Phe Leu Lys Asp Gln Asn Ile Ile Ala Val
1               5                   10                  15

Leu Lys Asn Ala Ile His Ala Gln Gln Gln Gly Thr Thr Ala Ser Ser
            20                  25                  30

Ile Thr Ile Leu Ser Leu Ala Val Ala Ile Thr Thr Phe Ala Val His
        35                  40                  45

Arg Ile Arg Leu Tyr Ser Val Lys Glu His Gly Val Pro Leu Val Pro
    50                  55                  60

Tyr Val Leu Pro Phe Ile Gly Ser Ser Pro Glu Tyr Arg Lys Asp Pro
65                  70                  75                  80

Lys Ala Phe Leu Glu Lys Trp Thr Ala Lys Phe Gly Pro Val Phe Arg
                85                  90                  95

Ala His Ile Phe Gly Arg Val Tyr Thr Ile Ile Ser Gly His Tyr Val
            100                 105                 110

Arg Glu Val Phe Leu Asn Glu Asp Phe Ser Phe Glu Val Gly Met Gly
        115                 120                 125
```

```
Lys Thr Phe Asp Gly Trp Leu Ile Thr Asp Thr Lys Lys Ser Glu Leu
130                 135                 140

Phe Ser Thr Pro Leu Val Arg Ser Met Val Met Lys His Leu Ala Val
145                 150                 155                 160

Asp Val Lys Asn Tyr Thr Pro Arg Ala Val Glu His Leu Thr Ile Ala
                165                 170                 175

Ala Arg Glu Met Leu Gly Asp Ile Gly Glu Ser Lys Glu Leu Pro His
            180                 185                 190

Leu Tyr Pro Leu Ile Gln His Met Val Ser Thr Ala Ile Ala Ser Ile
        195                 200                 205

Leu Val Gly Leu Lys Ile Cys Lys Asp Lys Asp Leu Leu Glu Thr Phe
210                 215                 220

Lys Asn Val Ala Val Asp Ile Gly Ser Glu Leu Asn Pro Asp Ser Tyr
225                 230                 235                 240

Leu Tyr Glu Ala Phe Pro Thr Ile Ser Arg Leu Arg Gln Trp Tyr Leu
                245                 250                 255

Gly Lys Tyr Gly Lys Ala Ile Asn Lys His Gln Glu His Met Leu Arg
            260                 265                 270

Val Leu Gly Pro Glu Ile Asp Glu Arg Leu Ala Ala Met Glu Arg Gly
        275                 280                 285

Asp Gly Gly Trp Glu Arg Pro Glu Asp Ile Leu Gln Gly Ile Leu Glu
290                 295                 300

Thr Ala Lys Leu Thr Ser Asp His Pro Gln Arg Tyr Met Val Pro Ile
305                 310                 315                 320

Lys Trp Phe Leu Ile Leu Val Phe Ala Ser Ile His Thr Thr Ser Gln
                325                 330                 335

Asn Thr Thr Val Ala Met Tyr Arg Leu Leu Gln His Pro Glu Val Ile
            340                 345                 350

Asp Glu Leu Leu Glu Glu Gln Asn Gln Val Phe Glu Lys His His Gly
        355                 360                 365

Ser Asn Tyr Asp Asp His Asp Ile Thr Lys Leu Leu Thr Gly Glu Val
370                 375                 380

Ile Lys Asp Leu Val Lys Leu Asp Ser Val Cys Arg Glu Ala Met Arg
385                 390                 395                 400

Ile Ser Ser Phe Tyr Ala Glu Leu Pro His Thr Tyr Ile Gly Lys Ser
                405                 410                 415

Pro Leu Thr Met Ser Asn Gly Thr Ile Ile Asn Pro Gly Asp Asp Val
            420                 425                 430

Leu Ile Asn Gly Tyr Thr Asn His Asp Pro Asp Ile Gln Ile Asp
        435                 440                 445

Gly Gly Gly Asp Tyr Ala Glu Phe Lys Pro Phe Arg Phe Val Glu Lys
450                 455                 460

Gly Arg Gln Ser Thr Arg Ile Gly Asp Asp Tyr Leu Ile Phe Gly Gln
465                 470                 475                 480

Gly Lys His Ala Cys Pro Gly Arg Trp Phe Ala Met Gln Glu Met Lys
                485                 490                 495

Thr Thr Ile Ser Phe Leu Ile Arg Gln Tyr Ile Ile Thr Ala Lys Gly
            500                 505                 510

Asp Ile Met Phe Leu Lys Gly His Arg Gln Lys Ile Pro Met Gly Gln
        515                 520                 525

Val Ile Phe Gln Lys Arg
        530
```

<210> SEQ ID NO 116
<211> LENGTH: 1563
<212> TYPE: DNA
<213> ORGANISM: Syncephalastrum racemosum

<400> SEQUENCE: 116

| | | | | | |
|---|---|---|---|---|---|
| atgaacgcct | tgttgcaaag | acaggataag | atgagagatt | tcctgaacac | tagagaaggt | 60 |
| gtttacggta | ttactgctgc | tgttgctgtt | gttttgattt | ccgcttattc | tttgagaaga | 120 |
| accgtctaca | cctctagaag | aaaagacgaa | attgctaccg | ttccatacaa | gttgccattg | 180 |
| aaaggttcta | ctgaagagta | tagagctgat | ccaagagctt | tcgttgaaaa | gtacgctaaa | 240 |
| atgtacggtc | cagtttacag | agcttacttg | tttggtgaaa | tgatgaccat | cgtttccgat | 300 |
| tcttacgtca | gagaaatctt | cttgaacgac | aacttcaact | tcttccaagc | cgttaaggat | 360 |
| agattcgata | tggttaagtt | gtgcaactgc | gctaatgatg | aaggtcatgg | tattgctgat | 420 |
| atcgtcaaga | gatgtttgaa | cccaagattg | gatatgtaca | ccgaaagagt | caacgaacaa | 480 |
| ttagaggaag | cctccaaaga | aatcttgact | gaagttgata | ccaagggctc | tcaagaattg | 540 |
| atgcacatgt | acattttggt | ccaacatatg | gttgctagag | cttccgctac | tgttttttgtt | 600 |
| ggtccagaat | tggctaagaa | ctccgaattg | attgactcct | tcaagaacat | ggttatccaa | 660 |
| gtcggttctc | aactaagacc | aaatccatgg | ttggaaccat | tccaagatt | gaactcattg | 720 |
| aggatgtggt | acattggtaa | gacttctcca | gttgttagaa | agcacagatt | gcaattgaga | 780 |
| tctgctgtta | agccatccat | cgatgataga | ttggctagac | aaaagtctca | aggtaacgct | 840 |
| tttcaaagac | cagacgattt | gttgcaggat | atcattgaaa | acatccaga | agccaagacc | 900 |
| aagtctgata | tctatgatta | cgttgttgat | accttgaccg | ctttgatttt | tgctgcattg | 960 |
| cataccacct | ctgaaaactc | tactgttgtc | ttgtataggt | tgttgcagca | tcctgaattg | 1020 |
| atggaagaat | tggttgctga | acaagatgcc | gttttgttgg | aacacggttt | gccaaaagat | 1080 |
| tcttctgcta | gagttatgac | cagacagatg | atcaagaagt | tcgaaaagtt | ggattctgtc | 1140 |
| tgcagggaat | ctttcagatt | gagaaatgat | tacttgggtt | tgccacatac | ctacgaaggt | 1200 |
| aaaaaggata | tcgttttgtc | taacggtgcc | attattaagc | caggtgaaaa | ggctattatc | 1260 |
| aacttgtggg | gtaatcatca | ttctggtaac | actccacaat | ctacctctca | agattatttc | 1320 |
| ggtttcgacc | catacagatt | cgttaagcaa | gataagcaag | ctaccaagat | ctctgaggat | 1380 |
| ttttttgtttt | tcggtttggg | taaacatgct | tgcccaggta | gatttttttgc | tgtccaagaa | 1440 |
| gctaaggttc | tgatctctgt | tttgttgagg | aactacaagt | tgtcaccagt | tgatccacca | 1500 |
| tactttgcta | ctgatgatac | catgaagatt | ccagccggta | gaattagaat | cgaaagaagg | 1560 |
| taa | | | | | | 1563 |

<210> SEQ ID NO 117
<211> LENGTH: 520
<212> TYPE: PRT
<213> ORGANISM: Syncephalastrum racemosum

<400> SEQUENCE: 117

Met Asn Ala Leu Leu Gln Arg Gln Asp Lys Met Arg Asp Phe Leu Asn
1               5                   10                  15

Thr Arg Glu Gly Val Tyr Gly Ile Thr Ala Ala Val Ala Val Val Leu
            20                  25                  30

Ile Ser Ala Tyr Ser Leu Arg Arg Thr Val Tyr Thr Ser Arg Arg Lys
        35                  40                  45

```
Asp Glu Ile Ala Thr Val Pro Tyr Lys Leu Pro Leu Lys Gly Ser Thr
    50                  55                  60

Glu Glu Tyr Arg Ala Asp Pro Arg Ala Phe Val Glu Lys Tyr Ala Lys
65                  70                  75                  80

Met Tyr Gly Pro Val Tyr Arg Ala Tyr Leu Phe Gly Glu Met Met Thr
                85                  90                  95

Ile Val Ser Asp Ser Tyr Val Arg Glu Ile Phe Leu Asn Asp Asn Phe
                100                 105                 110

Asn Phe Phe Gln Ala Val Lys Asp Arg Phe Asp Met Val Lys Leu Cys
        115                 120                 125

Asn Cys Ala Asn Asp Glu Gly His Gly Ile Ala Asp Ile Val Lys Arg
130                 135                 140

Cys Leu Asn Pro Arg Leu Asp Met Tyr Thr Glu Arg Val Asn Glu Gln
145                 150                 155                 160

Leu Glu Glu Ala Ser Lys Glu Ile Leu Thr Glu Val Asp Thr Lys Gly
                165                 170                 175

Ser Gln Glu Leu Met His Met Tyr Ile Leu Val Gln His Met Val Ala
            180                 185                 190

Arg Ala Ser Ala Thr Val Phe Val Gly Pro Glu Leu Ala Lys Asn Ser
        195                 200                 205

Glu Leu Ile Asp Ser Phe Lys Asn Met Val Ile Gln Val Gly Ser Gln
    210                 215                 220

Leu Arg Pro Asn Pro Trp Leu Glu Pro Phe Pro Arg Leu Asn Ser Leu
225                 230                 235                 240

Arg Met Trp Tyr Ile Gly Lys Thr Ser Pro Val Val Arg Lys His Arg
                245                 250                 255

Leu Gln Leu Arg Ser Ala Val Lys Pro Ser Ile Asp Asp Arg Leu Ala
                260                 265                 270

Arg Gln Lys Ser Gln Gly Asn Ala Phe Gln Arg Pro Asp Asp Leu Leu
            275                 280                 285

Gln Asp Ile Ile Glu Arg His Pro Glu Ala Lys Thr Lys Ser Asp Ile
    290                 295                 300

Tyr Asp Tyr Val Val Asp Thr Leu Thr Ala Leu Ile Phe Ala Ala Leu
305                 310                 315                 320

His Thr Thr Ser Glu Asn Ser Thr Val Val Leu Tyr Arg Leu Leu Gln
                325                 330                 335

His Pro Glu Leu Met Glu Glu Leu Val Ala Glu Gln Asp Ala Val Leu
            340                 345                 350

Leu Glu His Gly Leu Pro Lys Asp Ser Ser Ala Arg Val Met Thr Arg
        355                 360                 365

Gln Met Ile Lys Lys Phe Glu Lys Leu Asp Ser Val Cys Arg Glu Ser
    370                 375                 380

Phe Arg Leu Arg Asn Asp Tyr Leu Gly Leu Pro His Thr Tyr Glu Gly
385                 390                 395                 400

Lys Lys Asp Ile Val Leu Ser Asn Gly Ala Ile Lys Pro Gly Glu
                405                 410                 415

Lys Ala Ile Ile Asn Leu Trp Gly Asn His His Ser Gly Asn Thr Pro
                420                 425                 430

Gln Ser Thr Ser Gln Asp Tyr Phe Gly Phe Asp Pro Tyr Arg Phe Val
            435                 440                 445

Lys Gln Asp Lys Gln Ala Thr Lys Ile Ser Glu Asp Phe Leu Phe Phe
450                 455                 460

Gly Leu Gly Lys His Ala Cys Pro Gly Arg Phe Phe Ala Val Gln Glu
```

Ala Lys Val Leu Ile Ser Val Leu Leu Arg Asn Tyr Lys Leu Ser Pro
                         485                 490                 495

Val Asp Pro Pro Tyr Phe Ala Thr Asp Asp Thr Met Lys Ile Pro Ala
            500                 505                 510

Gly Arg Ile Arg Ile Glu Arg Arg
            515                 520

<210> SEQ ID NO 118
<211> LENGTH: 1584
<212> TYPE: DNA
<213> ORGANISM: Absidia caerulea

<400> SEQUENCE: 118

| | | | | | |
|---|---|---|---|---|---|
| atgctgaccg | agtacatcca | tcacttcatc | aacaatttcg | accagaaaaa | gaccatggac | 60 |
| caattgcaaa | ctatggtgtc | atctaaagaa | ggtatgattg | gtttggctac | tgctgctgtt | 120 |
| ttgatgtctg | gtgctgcagt | ttacaagtct | accagaattg | aaagaggttg | tccacaagtc | 180 |
| ccaaatcagt | cttactttat | gggttctacc | aaagagtaca | gaaacaatcc | agctgccttt | 240 |
| atcgaaaagt | gggaaaaaga | attgggtcca | gtttatggtg | cttacttgtt | tggtcagtac | 300 |
| actactgttg | tttctggtcc | tcaagttagg | gaagttttct | tgaacgatga | cttcgatttc | 360 |
| attgccggta | tcagaagaga | tttcgatacc | aacttgttgt | ctaacggtgg | tgatttgaga | 420 |
| gatttgccag | ttcataagtt | tgccggttcc | attaagaaga | acttgtctcc | aaaattgccc | 480 |
| ttctacacct | ccagagttat | tgaacatttg | aagatcggcc | tgaaagaatt | ctgtggtgtt | 540 |
| gttccagatg | agggtaaaga | attcgatcat | gtttacccat | ggttcaaca | tatggttgct | 600 |
| aaagcttccg | cttctgtttt | tgttggtcca | gaattggcta | gaacgaaca | attgattgac | 660 |
| tccttcaaga | acatggtttt | ggaagtcggt | tctgaattgg | ctccaaaacc | ttacttggaa | 720 |
| ttcttcccaa | atttgatgag | actgaggatg | tggttcattg | gtaagacttc | tcaaaaggtc | 780 |
| aagagacaca | gagatcaatt | gagagctgct | ttggctccac | aagttgagta | tagattgaaa | 840 |
| gccatgaagg | aaaacgattc | caattgggat | agaccaaacg | atttcttgca | ggacattttg | 900 |
| gaatctggtg | atattccagc | tcatgttgat | gttactgatc | attgctgtga | ttggatgacc | 960 |
| caaattatct | tgctgccctt | gcataccaca | tctgaaaatg | gtactttgtc | cttctacagg | 1020 |
| ttgttggata | tccaaaggt | cttggaagat | tgttggaag | aacaaaacca | ggtgttagaa | 1080 |
| gatgctggtt | acgattcttc | tgttggtcct | gaagttttca | ccagagaaat | cttgaacaag | 1140 |
| ttcgtcaaga | tggactccgt | tattagagaa | acctctagat | tgagaaacga | ctacattggt | 1200 |
| ttgccacaca | gaacatttc | ttctaagacc | attacttgt | ctggtggtgc | tatgattaga | 1260 |
| ccaggtgaaa | gagcttacgt | taacgcttat | tctaaccaca | gagatggtac | tatccaaaag | 1320 |
| gttaccgata | acttgaagtc | cttcgaacca | tacagattcg | ttaaccagga | tagaaactct | 1380 |
| accaagatcg | tgaagatttt | catctttttc | ggtatgggta | agcacgcttg | tccaggtaga | 1440 |
| tggtttgcta | ttcaagaaat | caagaccatc | attgccatga | tgatcagatc | ctatcaattg | 1500 |
| tctgctttgg | gtcctgttac | tttcccaact | gatgattact | ctagaattcc | catgggtaga | 1560 |
| ttcaaaatcg | tgccaagaaa | gtaa | | | | 1584 |

<210> SEQ ID NO 119
<211> LENGTH: 527
<212> TYPE: PRT
<213> ORGANISM: Absidia caerulea

```
<400> SEQUENCE: 119

Met Leu Thr Glu Tyr Ile His His Phe Ile Asn Asn Phe Asp Gln Lys
1               5                   10                  15

Lys Thr Met Asp Gln Leu Gln Thr Met Val Ser Ser Lys Glu Gly Met
            20                  25                  30

Ile Gly Leu Ala Thr Ala Val Leu Met Ser Gly Ala Ala Val Tyr
        35                  40                  45

Lys Ser Thr Arg Ile Glu Arg Gly Cys Pro Gln Val Pro Asn Gln Ser
    50                  55                  60

Tyr Phe Met Gly Ser Thr Lys Glu Tyr Arg Asn Asn Pro Ala Ala Phe
65                  70                  75                  80

Ile Glu Lys Trp Glu Lys Glu Leu Gly Pro Val Tyr Gly Ala Tyr Leu
                85                  90                  95

Phe Gly Gln Tyr Thr Thr Val Val Ser Gly Pro Gln Val Arg Glu Val
                100                 105                 110

Phe Leu Asn Asp Asp Phe Asp Phe Ile Ala Gly Ile Arg Arg Asp Phe
            115                 120                 125

Asp Thr Asn Leu Leu Ser Asn Gly Gly Asp Leu Arg Asp Leu Pro Val
    130                 135                 140

His Lys Phe Ala Gly Ser Ile Lys Lys Asn Leu Ser Pro Lys Leu Pro
145                 150                 155                 160

Phe Tyr Thr Ser Arg Val Ile Glu His Leu Lys Ile Gly Leu Lys Glu
                165                 170                 175

Phe Cys Gly Val Val Pro Asp Glu Gly Lys Glu Phe Asp His Val Tyr
            180                 185                 190

Pro Leu Val Gln His Met Val Ala Lys Ala Ser Ala Ser Val Phe Val
        195                 200                 205

Gly Pro Glu Leu Ala Lys Asn Glu Gln Leu Ile Asp Ser Phe Lys Asn
    210                 215                 220

Met Val Leu Glu Val Gly Ser Glu Leu Ala Pro Lys Pro Tyr Leu Glu
225                 230                 235                 240

Phe Phe Pro Asn Leu Met Arg Leu Arg Met Trp Phe Ile Gly Lys Thr
                245                 250                 255

Ser Gln Lys Val Lys Arg His Arg Asp Gln Leu Arg Ala Ala Leu Ala
            260                 265                 270

Pro Gln Val Glu Tyr Arg Leu Lys Ala Met Lys Glu Asn Asp Ser Asn
        275                 280                 285

Trp Asp Arg Pro Asn Asp Phe Leu Gln Asp Ile Leu Glu Ser Gly Asp
    290                 295                 300

Ile Pro Ala His Val Asp Val Thr Asp His Cys Cys Asp Trp Met Thr
305                 310                 315                 320

Gln Ile Ile Phe Ala Ala Leu His Thr Thr Ser Glu Asn Gly Thr Leu
                325                 330                 335

Ser Phe Tyr Arg Leu Leu Asp Asn Pro Lys Val Leu Glu Asp Leu Leu
            340                 345                 350

Glu Glu Gln Asn Gln Val Leu Glu Asp Ala Gly Tyr Asp Ser Ser Val
        355                 360                 365

Gly Pro Glu Val Phe Thr Arg Glu Ile Leu Asn Lys Phe Val Lys Met
    370                 375                 380

Asp Ser Val Ile Arg Glu Thr Ser Arg Leu Arg Asn Asp Tyr Ile Gly
385                 390                 395                 400

Leu Pro His Lys Asn Ile Ser Ser Lys Thr Ile Thr Leu Ser Gly Gly
                405                 410                 415
```

```
Ala Met Ile Arg Pro Gly Glu Arg Ala Tyr Val Asn Ala Tyr Ser Asn
            420                 425                 430

His Arg Asp Gly Thr Ile Gln Lys Val Thr Asp Asn Leu Lys Ser Phe
        435                 440                 445

Glu Pro Tyr Arg Phe Val Asn Gln Asp Arg Asn Ser Thr Lys Ile Gly
    450                 455                 460

Glu Asp Phe Ile Phe Phe Gly Met Gly Lys His Ala Cys Pro Gly Arg
465                 470                 475                 480

Trp Phe Ala Ile Gln Glu Ile Lys Thr Ile Ile Ala Met Met Ile Arg
                485                 490                 495

Ser Tyr Gln Leu Ser Ala Leu Gly Pro Val Thr Phe Pro Thr Asp Asp
            500                 505                 510

Tyr Ser Arg Ile Pro Met Gly Arg Phe Lys Ile Val Pro Arg Lys
        515                 520                 525

<210> SEQ ID NO 120
<211> LENGTH: 1584
<212> TYPE: DNA
<213> ORGANISM: Absidia caerulea

<400> SEQUENCE: 120
atgttcaccc aatacctgca tcagttgttc actaacttcg accaaaaaaa gaccatggac      60
cacttgcatt ctctggtttc ttctaaagaa ggtgctattg gtttggctac tgctgctgtt     120
ttgatgtctg gtgctgcagt ttacagatct tctatgatgg atagaggttg tccagttgtt     180
ccatctggtt tgtttacttt gtcatctact gctgagtaca acaagatcc agcttctttc      240 attaagaagt ggcagaaaga attgggtcca gtttatggtg cttacttgtt tggtcaatac     300
gttaccgttg tttccggttc tcaagttaga gaaattttcc tgaacgagaa cttctccttc     360
atcgatggta tttccagaga tttcgatacc tacttgttgg ctaatgctgg tacttatcat     420
gatttgccaa cttccactat tgccgacatg attaagaaga acttgtctcc aaagttgcag     480
ttctacaccg gtagagttat tgaacatttg aagatggcct tgcatgaaca atgtggtgtt     540
gttccagctg aaggtaaaga attcaatcac gtttacccat tcgttcaaca tatggttgct     600
aaagcttccg cttctgtttt tgttggtgtt gaattggcta agaacgaagc cttggttgat     660
tctttcacta acatggtttt agaagttggt ggtgctttgg gtccaaaacc ttatatggaa     720
tacttcccca acttgatgaa gttgcatatg tggtacattg gcaagacttc caagaacgtt     780
aagagacacc aagaccaatt gagatctgct ttgaaaccag aaatcgacac tagattgaag     840
gccatgaagg aaaaagattc ctcttgggtt agaccaaacg atttcttaca agacttgttg     900
gaaaccgatg aatgcccaga tcatattgac atctactcca gagttatcta ctggatcacc     960
caaattatct tgctgccctt gcataccaca tctgaaaatg gtactttggc cttgtatagg    1020
ttgttggata tccagaatt attcgaggac ttgtacgaag aacaaaacca ggtcttggaa    1080
caagctggtt atgatagatc tgttggtcca gaagttttca ccagagaaat cttgaacaag    1140
ttcgtcaaga tggactcctt gattagagaa acctctagat tgaggaacga gttcatttct    1200
ttgccacata tgaacacctc caacaagact attactttat caggtggtgc catgattaga    1260
ccaggtgaaa atgttttcat taacttctac gccaaccacc acgacgaaaa attgcaaaaa    1320
gttgctgaca atttgggcaa gttcgaacca tacagattcg ttaatcaaga caagaactct    1380
accaaggtcg gtgaagattt tgttttttc ggtatgggta agcacgcttg tccaggtaga    1440
tggtttgcta ttcaagaaat caagaccatc atctccatgt tgatcagaga ctacaaaatc    1500
```

```
tctccattgg gtcctgttgt tttcccagtt tctgattaca ctagaattcc aaccggtaga    1560
ttcaaaatcg tcccaagaaa gtga                                           1584
```

<210> SEQ ID NO 121
<211> LENGTH: 527
<212> TYPE: PRT
<213> ORGANISM: Absidia caerulea

<400> SEQUENCE: 121

```
Met Phe Thr Gln Tyr Leu His Gln Leu Phe Thr Asn Phe Asp Gln Lys
1               5                   10                  15

Lys Thr Met Asp His Leu His Ser Leu Val Ser Ser Lys Glu Gly Ala
            20                  25                  30

Ile Gly Leu Ala Thr Ala Ala Val Leu Met Ser Gly Ala Ala Val Tyr
        35                  40                  45

Arg Ser Ser Met Met Asp Arg Gly Cys Pro Val Val Pro Ser Gly Leu
    50                  55                  60

Phe Thr Leu Ser Ser Thr Ala Glu Tyr Arg Gln Asp Pro Ala Ser Phe
65                  70                  75                  80

Ile Lys Lys Trp Gln Lys Glu Leu Gly Pro Val Tyr Gly Ala Tyr Leu
                85                  90                  95

Phe Gly Gln Tyr Val Thr Val Val Ser Gly Ser Gln Val Arg Glu Ile
            100                 105                 110

Phe Leu Asn Glu Asn Phe Ser Phe Ile Asp Gly Ile Ser Arg Asp Phe
        115                 120                 125

Asp Thr Tyr Leu Leu Ala Asn Ala Gly Thr Tyr His Asp Leu Pro Thr
    130                 135                 140

Ser Thr Ile Ala Asp Met Ile Lys Lys Asn Leu Ser Pro Lys Leu Gln
145                 150                 155                 160

Phe Tyr Thr Gly Arg Val Ile Glu His Leu Lys Met Ala Leu His Glu
                165                 170                 175

Gln Cys Gly Val Val Pro Ala Glu Gly Lys Glu Phe Asn His Val Tyr
            180                 185                 190

Pro Phe Val Gln His Met Val Ala Lys Ala Ser Ala Ser Val Phe Val
        195                 200                 205

Gly Val Glu Leu Ala Lys Asn Glu Ala Leu Val Asp Ser Phe Thr Asn
    210                 215                 220

Met Val Leu Glu Val Gly Gly Ala Leu Gly Pro Lys Pro Tyr Met Glu
225                 230                 235                 240

Tyr Phe Pro Asn Leu Met Lys Leu His Met Trp Tyr Ile Gly Lys Thr
                245                 250                 255

Ser Lys Asn Val Lys Arg His Gln Asp Gln Leu Arg Ser Ala Leu Lys
            260                 265                 270

Pro Glu Ile Asp Thr Arg Leu Lys Ala Met Lys Glu Lys Asp Ser Ser
        275                 280                 285

Trp Val Arg Pro Asn Asp Phe Leu Gln Asp Leu Leu Glu Thr Asp Glu
    290                 295                 300

Cys Pro Asp His Ile Asp Ile Tyr Ser Arg Val Ile Tyr Trp Ile Thr
305                 310                 315                 320

Gln Ile Ile Phe Ala Ala Leu His Thr Thr Ser Glu Asn Gly Thr Leu
                325                 330                 335

Ala Leu Tyr Arg Leu Leu Asp Asn Pro Glu Leu Phe Gly Asp Leu Tyr
            340                 345                 350
```

Glu Glu Gln Asn Gln Val Leu Glu Gln Ala Gly Tyr Asp Arg Ser Val
        355                 360                 365

Gly Pro Glu Val Phe Thr Arg Glu Ile Leu Asn Lys Phe Val Lys Met
    370                 375                 380

Asp Ser Leu Ile Arg Glu Thr Ser Arg Leu Arg Asn Glu Phe Ile Ser
385                 390                 395                 400

Leu Pro His Met Asn Thr Ser Asn Lys Thr Ile Thr Leu Ser Gly Gly
                405                 410                 415

Ala Met Ile Arg Pro Gly Glu Asn Val Phe Ile Asn Phe Tyr Ala Asn
            420                 425                 430

His His Asp Glu Lys Leu Gln Lys Val Ala Asp Asn Leu Gly Lys Phe
        435                 440                 445

Glu Pro Tyr Arg Phe Val Asn Gln Asp Lys Asn Ser Thr Lys Val Gly
    450                 455                 460

Glu Asp Phe Val Phe Phe Gly Met Gly Lys His Ala Cys Pro Gly Arg
465                 470                 475                 480

Trp Phe Ala Ile Gln Glu Ile Lys Thr Ile Ile Ser Met Leu Ile Arg
                485                 490                 495

Asp Tyr Lys Ile Ser Pro Leu Gly Pro Val Val Phe Pro Val Ser Asp
            500                 505                 510

Tyr Thr Arg Ile Pro Thr Gly Arg Phe Lys Ile Val Pro Arg Lys
        515                 520                 525

<210> SEQ ID NO 122
<211> LENGTH: 1461
<212> TYPE: DNA
<213> ORGANISM: Phycomyces blakesleeanus

<400> SEQUENCE: 122

```
atggccatca tcttgtcctc tgtttacaac tatcataagt ggtcctccag aaccatttct      60
aatggttgtc caagagttcc acataccttg ccatttttg gtttgaccaa ggtttaccgt     120
aaggattcta aggcttttg cgaagaatgg catgctaaat gggtccagt tttagagca      180
cacttgttcg gtaaagaagt taccgttgtt tctggtcact acgtcagaga agttttttg     240
aacaagcact tcgacttcat caagggtatc gttaaggttt ttgataccag gttgttgacc     300
gataacggtt ctagagaaga ttttccacca gaagatttga gggaaatcat cactaagtac     360
ttgaccccaa agttgaacat ctacactaga agattgatca agcagttgaa gcaagacgtc     420
gaaacatttt gggtttgat cgagttcgat aacttgtacc cattcgttca cacttgatc      480
gttaatgctt ccgcctctat tttcttgggt gaagaaaatt cccagaacaa gttgttgatc     540
gacagcatca agaacatggt tagattggtt ggttccgaag ttaagcaaaa cccatggatt     600
gaaccattca gcccaatcaa aaagatcaga atgtgggtta ttggtaagac ctctccagtt     660
atcaggtcct acaaagaaca attgattaac gccatcaagc cagttgttga gtacagattg     720
tctgaagcta aagaaatcc agactggaaa aacctactg atgtgttgca agacttgttg     780
gaaaattcta aaccaccagc tcacatggat ttgatggatt acttggtctg cattatcacc     840
atcttgattt tcgttgcctt gcattccact attgaaaaca ctaccgttct gttgtacagg     900
atcttggaaa acccagaaat catggatgaa ttggacttgg aacaaaggga agtcattgaa     960
caagaaggtt tggataccaa ttgtggctct gaattattca ccagagacat cttgaagaag    1020
ttcaccaaat ggattctgt ctgcagagaa accttcagaa tgaagaacca gtacatcact    1080
ttgccacatg aatacgatgg taaggttcca ttgactttgt ctaatggtgc tgttattaac    1140
```

```
ccaggtgatg atgttttgat tgatgtttgg accaaccaca ggtacaagaa agaaactact    1200
tctgttaagg atgccgacga attcagacca ttcagatttg ttaatcagaa caagcagtct    1260
accaaggtcg gtgaagatta cttgtttttt ggtatgggta gacatgcctg tccaggtaga    1320
tggtttgcta tgcaagaaat tcaagctatt accgccatct tggttagaga atgcaagttt    1380
attccaaagg gcccaattat ctttccaacc gctgaaagat ctccaattcc aactggtaga    1440
tgtatcatcc agagaaagtg a                                              1461
```

<210> SEQ ID NO 123
<211> LENGTH: 486
<212> TYPE: PRT
<213> ORGANISM: Phycomyces blakesleeanus

<400> SEQUENCE: 123

```
Met Ala Ile Ile Leu Ser Ser Val Tyr Asn Tyr His Lys Trp Ser Ser
1               5                   10                  15

Arg Thr Ile Ser Asn Gly Cys Pro Arg Val Pro His Thr Leu Pro Phe
            20                  25                  30

Phe Gly Leu Thr Lys Val Tyr Arg Lys Asp Ser Lys Ala Phe Cys Glu
        35                  40                  45

Glu Trp His Ala Lys Leu Gly Pro Val Phe Arg Ala His Leu Phe Gly
    50                  55                  60

Lys Glu Val Thr Val Val Ser Gly His Tyr Val Arg Glu Val Phe Leu
65                  70                  75                  80

Asn Lys His Phe Asp Phe Ile Lys Gly Ile Val Lys Val Phe Asp Thr
                85                  90                  95

Arg Leu Leu Thr Asp Asn Gly Ser Arg Glu Asp Phe Pro Pro Glu Asp
            100                 105                 110

Leu Arg Glu Ile Ile Thr Lys Tyr Leu Thr Pro Lys Leu Asn Ile Tyr
        115                 120                 125

Thr Arg Arg Leu Ile Lys Gln Leu Lys Gln Asp Val Glu Asn Ile Leu
    130                 135                 140

Gly Leu Ile Glu Phe Asp Asn Leu Tyr Pro Phe Val Gln His Leu Ile
145                 150                 155                 160

Val Asn Ala Ser Ala Ser Ile Phe Leu Gly Glu Asn Ser Gln Asn
                165                 170                 175

Lys Leu Leu Ile Asp Ser Ile Lys Asn Met Val Arg Leu Val Gly Ser
            180                 185                 190

Glu Val Lys Gln Asn Pro Trp Ile Glu Pro Phe Ser Pro Ile Lys Lys
        195                 200                 205

Ile Arg Met Trp Val Ile Gly Lys Thr Ser Pro Val Ile Arg Ser Tyr
    210                 215                 220

Lys Glu Gln Leu Ile Asn Ala Ile Lys Pro Val Glu Tyr Arg Leu
225                 230                 235                 240

Ser Glu Ala Arg Arg Asn Pro Asp Trp Lys Lys Pro Thr Asp Val Leu
                245                 250                 255

Gln Asp Leu Leu Glu Asn Ser Lys Pro Pro Ala His Met Asp Leu Met
            260                 265                 270

Asp Tyr Leu Val Cys Ile Thr Ile Leu Ile Phe Val Ala Leu His
        275                 280                 285

Ser Thr Ile Glu Asn Thr Thr Val Leu Leu Tyr Arg Ile Leu Glu Asn
    290                 295                 300

Pro Glu Ile Met Asp Glu Leu Asp Leu Glu Gln Arg Glu Val Ile Glu
305                 310                 315                 320
```

```
Gln Glu Gly Leu Asp Thr Asn Cys Gly Ser Glu Leu Phe Thr Arg Asp
                325                 330                 335

Ile Leu Lys Lys Phe Thr Lys Leu Asp Ser Val Cys Arg Glu Thr Phe
            340                 345                 350

Arg Met Lys Asn Gln Tyr Ile Thr Leu Pro His Glu Tyr Asp Gly Lys
        355                 360                 365

Val Pro Leu Thr Leu Ser Asn Gly Ala Val Ile Asn Pro Gly Asp Asp
    370                 375                 380

Val Leu Ile Asp Val Trp Thr Asn His Arg Tyr Lys Lys Glu Thr Thr
385                 390                 395                 400

Ser Val Lys Asp Ala Asp Glu Phe Arg Pro Phe Arg Phe Val Asn Gln
                405                 410                 415

Asn Lys Gln Ser Thr Lys Val Gly Glu Asp Tyr Leu Phe Phe Gly Met
            420                 425                 430

Gly Arg His Ala Cys Pro Gly Arg Trp Phe Ala Met Gln Glu Ile Gln
        435                 440                 445

Ala Ile Thr Ala Ile Leu Val Arg Glu Cys Lys Phe Ile Pro Lys Gly
    450                 455                 460

Pro Ile Ile Phe Pro Thr Ala Glu Arg Ser Pro Ile Pro Thr Gly Arg
465                 470                 475                 480

Cys Ile Ile Gln Arg Lys
            485
```

```
<210> SEQ ID NO 124
<211> LENGTH: 1608
<212> TYPE: DNA
<213> ORGANISM: Lichtheimia corymbifera

<400> SEQUENCE: 124
atgtacaagg ccttcttgga caacggtatc gtttcctcta ttatctctac cttggataac      60
aaggacatct ccgttttttt gaacgatcca aaccatgcta agaccagatc tgttgctttg     120
gtttctttct gtactgttat tgctgcttac gccttgtcta gatcaagatc tcattctaag     180
gataaggata ccccaatggt tccatatact tggccattga ttggttcttc tagagaatac     240
cgtaaagatc ctgaagcctt tatcaagaag tggtcatctg aattgggtga tgtttacaag     300
gttcacttgt tcggtagaat ccaaactgtt gtttccggta acacgtttta ctgcttgcaa     360
aaggatttcg actttcaaca gggtatgtct aagaccttcg atatctggtt gttgttggat     420
gctccattag tggtagatt cactttggat aagattagac atgccaccat caagttcacc     480
agaactaaga tgttgactaa cactccatgc gttgtcaagc aattgattgc tgctgaacac     540
gaaatgattg gtgatgctca aactccatct gaaattgcta acttgtaccc attgatggaa     600
cacttggttg ctattgcttc cgctactaat tttgttggtc aggtttgac caaagataag     660
gatttggttg aaacctacaa gcacttggct gttgatgttg gttcagaatt aggtgatggt     720
aacgaattct ggaagctttt ccatggatt tccagattga aatgtggta cttgggtaaa     780
tacggtaact ctgttgataa gcacagaaag cgtttgttga gagctatgaa gccaattatc     840
gacgaaagat ggctgctgc agaaaacggt attgaaaatc acaagatttt catccaggac     900
atcatcgaag aatccgaaat tacttctggt gatccagaca agtacatttt ggcagttaga     960
tggatcttgg ttatgattgc ttctgctggt cataccacta ctgaaaacac taccattatc    1020
ctgtacagaa tcttgcaaca cccagaagtc attgacgaac tattggaaga acaaagacag    1080
gtcttggaaa acatcatgg tccagatgtt aaggataacg aagatttggc tactttgttc    1140
```

```
actggtgaag ttattaagga cttggtcaag ttggattctg tctgtagaga aaccatgaga   1200
ttgaggtcct tctacattga tttgccacat acctacgttg gtaaatctcc attggctttg   1260
actaatacct gtaccattaa gccaggtgaa gatgtcttgt tgaatatgtg gttgaaccat   1320
aacagaaccg ccatgcaata tgatggtttg ggtgattaca atgagttcaa gccattcaga   1380
tttgtcggtt tggatagatc ctctactaag ttaggtggtg actttttgtt gttcggtttg   1440
ggtactcatg cttgtccagg tagatggttt gctatgcatc aaactaagac catcctgtcc   1500
atgttgttga gaagatacca aattactccc caagaaacca tcgttttccc aattggtaat   1560
agatcccatg ttccatctgg taaggttacc tttcaaaaga gacagtaa              1608
```

<210> SEQ ID NO 125
<211> LENGTH: 535
<212> TYPE: PRT
<213> ORGANISM: Lichtheimia corymbifera

<400> SEQUENCE: 125

```
Met Tyr Lys Ala Phe Leu Asp Asn Gly Ile Val Ser Ile Ile Ser
1               5                  10                  15

Thr Leu Asp Asn Lys Asp Ile Ser Val Phe Leu Asn Asp Pro Asn His
            20                  25                  30

Ala Lys Thr Arg Ser Val Ala Leu Val Ser Phe Cys Thr Val Ile Ala
        35                  40                  45

Ala Tyr Ala Leu Ser Arg Ser Arg Ser His Ser Lys Asp Lys Asp Thr
    50                  55                  60

Pro Met Val Pro Tyr Thr Trp Pro Leu Ile Gly Ser Ser Arg Glu Tyr
65                  70                  75                  80

Arg Lys Asp Pro Glu Ala Phe Ile Lys Lys Trp Ser Ser Glu Leu Gly
                85                  90                  95

Asp Val Tyr Lys Val His Leu Phe Gly Arg Ile Gln Thr Val Val Ser
            100                 105                 110

Gly Lys His Val Tyr Cys Leu Gln Lys Asp Phe Asp Phe Gln Gln Gly
        115                 120                 125

Met Ser Lys Thr Phe Asp Ile Trp Leu Leu Asp Ala Pro Leu Gly
    130                 135                 140

Gly Arg Phe Thr Leu Asp Lys Ile Arg His Ala Thr Ile Lys Phe Thr
145                 150                 155                 160

Arg Thr Lys Met Leu Thr Asn Thr Pro Cys Val Val Lys Gln Leu Ile
                165                 170                 175

Ala Ala Glu His Glu Met Ile Gly Asp Ala Gln Thr Pro Ser Glu Ile
            180                 185                 190

Ala Asn Leu Tyr Pro Leu Met Glu His Leu Val Ala Ile Ala Ser Ala
        195                 200                 205

Thr Asn Phe Val Gly Pro Gly Leu Thr Lys Asp Lys Asp Leu Val Glu
    210                 215                 220

Thr Tyr Lys His Leu Ala Val Asp Val Gly Ser Glu Leu Gly Asp Gly
225                 230                 235                 240

Asn Glu Phe Leu Glu Ala Phe Pro Trp Ile Ser Arg Leu Arg Met Trp
                245                 250                 255

Tyr Leu Gly Lys Tyr Gly Asn Ser Val Asp Lys His Arg Lys Arg Leu
            260                 265                 270

Leu Arg Ala Met Lys Pro Ile Ile Asp Glu Arg Leu Ala Ala Ala Glu
        275                 280                 285
```

```
Asn Gly Ile Glu Asn Pro Gln Asp Phe Ile Gln Asp Ile Ile Glu Glu
    290                 295                 300

Ser Glu Ile Thr Ser Gly Asp Pro Asp Lys Tyr Ile Leu Ala Val Arg
305                 310                 315                 320

Trp Ile Leu Val Met Ile Ala Ser Ala Gly His Thr Thr Thr Glu Asn
                325                 330                 335

Thr Thr Ile Ile Leu Tyr Arg Ile Leu Gln His Pro Glu Val Ile Asp
            340                 345                 350

Glu Leu Leu Glu Glu Gln Arg Gln Val Leu Glu Lys His His Gly Pro
        355                 360                 365

Asp Val Lys Asp Asn Glu Asp Leu Ala Thr Leu Phe Thr Gly Glu Val
    370                 375                 380

Ile Lys Asp Leu Val Lys Leu Asp Ser Val Cys Arg Glu Thr Met Arg
385                 390                 395                 400

Leu Arg Ser Phe Tyr Ile Asp Leu Pro His Thr Tyr Val Gly Lys Ser
                405                 410                 415

Pro Leu Ala Leu Thr Asn Thr Cys Thr Ile Lys Pro Gly Glu Asp Val
            420                 425                 430

Leu Leu Asn Met Trp Leu Asn His Asn Arg Thr Ala Met Gln Tyr Asp
        435                 440                 445

Gly Leu Gly Asp Tyr Asn Glu Phe Lys Pro Phe Arg Phe Val Gly Leu
    450                 455                 460

Asp Arg Ser Ser Thr Lys Leu Gly Gly Asp Phe Leu Leu Phe Gly Leu
465                 470                 475                 480

Gly Thr His Ala Cys Pro Gly Arg Trp Phe Ala Met Gln Thr Lys
                485                 490                 495

Thr Ile Leu Ser Met Leu Leu Arg Arg Tyr Gln Ile Thr Pro Gln Glu
            500                 505                 510

Thr Ile Val Phe Pro Ile Gly Asn Arg Ser His Val Pro Ser Gly Lys
        515                 520                 525

Val Thr Phe Gln Lys Arg Gln
    530                 535

<210> SEQ ID NO 126
<211> LENGTH: 1596
<212> TYPE: DNA
<213> ORGANISM: Hesseltinella vesiculosa

<400> SEQUENCE: 126
atgctgaccc aatacttgca attcgctgct gatagattgg gtcaaaaaaa gaccttggat      60
caattgcaag ctgttgtcac ttctaagcaa ggtgttgttg gtattactac tgctgttgct     120
ttgattgctt tggccaatca ttttagatcc ccaaagattg atagaggttg cccacaagtt     180
gaaggtaaag gttggtttgg ttatgctacc gaagaattca gagaaaaccc aggtaagttt     240
ttgtctgaat ggcacgaaaa attgggtcca gtttacggtg ttaagatctt tggtcattac     300
gctactgttg tttctggtcc atatgtcaga gaagttttct ggatgacag gttctctttc     360 attgctgcta ttaccaagtt gttcgaccca aacttgatga ctgattctgg tcattcttct     420
gaacaaactg ctaagaatgc tgccgattcc attaagagat ttctgtctcc aaatctgaag     480
cactacaccc caagagttat tgaacatttg aacttgggta tcgaagattg tgtggtgaa      540 gttccagctg aagtattgaa attgaaaac gctttcccat tcttgcaaca tttggttgct     600
agagcttcag cttctgtttt cgttggtatt gaattggcca agaacgaaga attggttgac     660
tctttccaaa acatggtgtc caacatttct ctggtttga aacctaaacc ttggttggaa     720
```

```
tactttccct ccttgaccaa attgggtatg tacatgattg gtaagactaa cccagctgtt    780
aagagacata gaactcaaat ggctaacgcc ttaagaccag aagttgatag aagattgaaa    840
gccatggcct ctaatgatac caattgggat agaccagatg atatgttgca gcacattttg    900
gaatcttatc cagctcctga aggtttggat gttattacct atttgatcaa ctggatgacg    960
cagttgattt tgctgcatt gcataccaca tctgaaaacg gtaaagttgt cttgtacaga    1020
ttgctacaac acccagaagt catggaagaa ttatacgctg aacaaaacga agttttggct    1080
gctgctggtt atgatgaatc tgctggtcca gaagttttg acagagagat gttgaacaag    1140
ttcgtcaagt tggattctgc tgttagaaa gcttgtaggt tgaagaatga attcgttggt    1200
ttgccacacg aaaacactac tgataagact ttgactttgt ccaacggtgc tgttattttg    1260
ccaggtgaat tgtttacat caaccagttc gttaaccaca gggatccaga attacaagct    1320
gctattgatg atgtccatca gttcaaacca ttcagattcg taggtactga tcataacgct    1380
gctaaagttt ccgaaggttt tgtctttttt ggtatgggta gacatgcttg tccaggtaga    1440
tggtttgcta ttcaagaaat caagaccatc gtgtccttgt tgttgagaaa gtacaaggtt    1500
gaacctatcg acccaatcgt gttctctaat caagaaagag atgcctttcc aattggtcca    1560
tgcagaatta gattgacacc aagaaaagcc ctgtaa                              1596
```

<210> SEQ ID NO 127
<211> LENGTH: 531
<212> TYPE: PRT
<213> ORGANISM: Hesseltinella vesiculosa

<400> SEQUENCE: 127

```
Met Leu Thr Gln Tyr Leu Gln Phe Ala Ala Asp Arg Leu Gly Gln Lys
1               5                   10                  15

Lys Thr Leu Asp Gln Leu Gln Ala Val Val Thr Ser Lys Gln Gly Val
            20                  25                  30

Val Gly Ile Thr Thr Ala Val Ala Leu Ile Ala Leu Ala Asn His Phe
        35                  40                  45

Arg Ser Pro Lys Ile Asp Arg Gly Cys Pro Gln Val Glu Gly Lys Gly
    50                  55                  60

Trp Phe Gly Tyr Ala Thr Glu Glu Phe Arg Glu Asn Pro Gly Lys Phe
65                  70                  75                  80

Leu Ser Glu Trp His Glu Lys Leu Gly Pro Val Tyr Gly Val Lys Ile
                85                  90                  95

Phe Gly His Tyr Ala Thr Val Val Ser Gly Pro Tyr Val Arg Glu Val
            100                 105                 110

Phe Leu Asp Asp Arg Phe Ser Phe Ile Ala Ala Ile Thr Lys Leu Phe
        115                 120                 125

Asp Pro Asn Leu Met Thr Asp Ser Gly His Ser Ser Glu Gln Thr Ala
    130                 135                 140

Lys Asn Ala Ala Asp Ser Ile Lys Arg Phe Leu Ser Pro Asn Leu Lys
145                 150                 155                 160

His Tyr Thr Pro Arg Val Ile Glu His Leu Asn Leu Gly Ile Glu Asp
                165                 170                 175

Trp Cys Gly Glu Val Pro Ala Glu Gly Ile Glu Ile Glu Asn Ala Phe
            180                 185                 190

Pro Phe Leu Gln His Leu Val Ala Arg Ala Ser Ala Ser Val Phe Val
        195                 200                 205

Gly Ile Glu Leu Ala Lys Asn Glu Glu Leu Val Asp Ser Phe Gln Asn
```

Met Val Ser Asn Ile Ser Ser Gly Leu Lys Pro Lys Pro Trp Leu Glu
225                 230                 235                 240

Tyr Phe Pro Ser Leu Thr Lys Leu Gly Met Tyr Met Ile Gly Lys Thr
            245                 250                 255

Asn Pro Ala Val Lys Arg His Arg Thr Gln Met Ala Asn Ala Leu Arg
                260                 265                 270

Pro Glu Val Asp Arg Arg Leu Lys Ala Met Ala Ser Asn Asp Thr Asn
            275                 280                 285

Trp Asp Arg Pro Asp Asp Met Leu Gln His Ile Leu Glu Ser Tyr Pro
290                 295                 300

Ala Pro Glu Gly Leu Asp Val Ile Thr Tyr Leu Ile Asn Trp Met Thr
305                 310                 315                 320

Gln Leu Ile Phe Ala Ala Leu His Thr Thr Ser Glu Asn Gly Lys Val
                325                 330                 335

Val Leu Tyr Arg Leu Leu Gln His Pro Glu Val Met Glu Glu Leu Tyr
                340                 345                 350

Ala Glu Gln Asn Glu Val Leu Ala Ala Gly Tyr Asp Glu Ser Ala
                355                 360                 365

Gly Pro Glu Val Phe Asp Arg Glu Met Leu Asn Lys Phe Val Lys Leu
370                 375                 380

Asp Ser Ala Val Arg Glu Ala Cys Arg Leu Lys Asn Glu Phe Val Gly
385                 390                 395                 400

Leu Pro His Glu Asn Thr Thr Asp Lys Thr Leu Thr Leu Ser Asn Gly
                405                 410                 415

Ala Val Ile Leu Pro Gly Glu Phe Val Tyr Ile Asn Gln Phe Val Asn
                420                 425                 430

His Arg Asp Pro Glu Leu Gln Ala Ala Ile Asp Asp Val His Gln Phe
                435                 440                 445

Lys Pro Phe Arg Phe Val Gly Thr Asp His Asn Ala Ala Lys Val Ser
                450                 455                 460

Glu Gly Phe Val Phe Phe Gly Met Gly Arg His Ala Cys Pro Gly Arg
465                 470                 475                 480

Trp Phe Ala Ile Gln Glu Ile Lys Thr Ile Val Ser Leu Leu Leu Arg
                485                 490                 495

Lys Tyr Lys Val Glu Pro Ile Asp Pro Ile Val Phe Ser Asn Gln Glu
                500                 505                 510

Arg Asp Ala Phe Pro Ile Gly Pro Cys Arg Ile Arg Leu Thr Pro Arg
                515                 520                 525

Lys Ala Leu
530

<210> SEQ ID NO 128
<211> LENGTH: 1554
<212> TYPE: DNA
<213> ORGANISM: Nicotiana sylvetris

<400> SEQUENCE: 128
atggtgtctc cagttgaagc tatcgttggt ttggttactt tggctttgtt gttctacttc      60
atcaggacca agaaatccca aaaccatct aaaccattgc caccaaaaat tccaggtggt     120
tggccagtta ttggtcactt gttttacttc gatgatgact ccgatgatag accattggct     180
agaaaattgg gtgatttggc tgataagtac ggtccagttt ttactttcag attgggtttg     240
ccattggtct tggttgtttc atcttacgaa gctatcaagg attgcttctc taccaacgat     300

```
gctatctttt ctaatagacc agctttcttg tacggtgagt atttgggtta taacaacgcc    360
atgttgttct tgactaagta tggtccatat tggaggaaga acagaaagtt ggttatccaa    420
gaggttttgt gcgcttctag attggaaaaa ttgaagcacg ttaggttcgg tgaaatccaa    480
acctctatta agaacttgta caccagaatc gacggtaact cttctactat taacttgacc    540
gattggctgg aagagttgaa ttttggtttg atcgttaaga tgatcgccgg taagaattac    600
gaatctggta aggtgatga acaggtcgaa agattcagaa aggctttcaa ggatttcatc     660
atcctgtcca tggaattcgt tttgtgggat gcttttccaa ttcctttgtt caagtgggtt    720
gatttccaag gtcatgttaa ggctatgaag agaaccttca aggatatcga ctctgttttc    780
caaaactggt tggaagaaca cgtcaaaaag aaagaaaga tggaagttaa cgccgaaggt     840
aacgaacaag atttcatcga tgttgtgctg tccaagatgt ctaacgaata tttggatgaa    900
ggttactcca gagataccgt tattaaggct actgttttct ccttggtttt ggatgctgct    960
gatactgttg cattgcatat gaattgggt atggccctgt tgattaacaa tcaacatgct     1020
ttgaagaagg cccaagaaga atcgacaaa aaggttggta agacagatg ggttgaagag      1080
tccgatatta aggatttggt ttacttgcag accatcgtca agaagttttt gagattatat    1140
ccaccaggtc ctttgttggt tccacacgaa atgttgaag attgcgttgt tccggttac     1200
catattccaa agggtactag attattcgcc aacgtcatga gttgcaaag ggatccaaaa    1260
ttgtggtcta acccagataa gttcgatcca gaaagatttt tcgctgccga tattgatttc    1320
agaggtcaac attacgaatt catcccattt ggttctggta aagatcttg tccaggtatg    1380
acttatgcta tgcaagttga acatttgact atcgcccatt tgatccaagg tttcaattac    1440
aagactccaa acgatgaacc actggatatg aaggaaggtg ctggtttgac aattagaaag    1500
gttaacccaa tcgaagttgt catcactcca agattgactc cagagttgta ctga          1554
```

<210> SEQ ID NO 129
<211> LENGTH: 517
<212> TYPE: PRT
<213> ORGANISM: Nicotiana sylvestris

<400> SEQUENCE: 129

```
Met Val Ser Pro Val Glu Ala Ile Val Gly Leu Val Thr Leu Ala Leu
1               5                   10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Asp Ser Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Tyr Glu Ala Ile Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
```

```
            145                 150                 155                 160
        Thr Ser Ile Lys Asn Leu Tyr Thr Arg Ile Asp Gly Asn Ser Ser Thr
                        165                 170                 175

Ile Asn Leu Thr Asp Trp Leu Glu Glu Leu Asn Phe Gly Leu Ile Val
                        180                 185                 190

Lys Met Ile Ala Gly Lys Asn Tyr Glu Ser Gly Lys Gly Asp Glu Gln
                        195                 200                 205

Val Glu Arg Phe Arg Lys Ala Phe Lys Asp Phe Ile Ile Leu Ser Met
        210                 215                 220

Glu Phe Val Leu Trp Asp Ala Phe Pro Ile Pro Leu Phe Lys Trp Val
        225                 230                 235                 240

Asp Phe Gln Gly His Val Lys Ala Met Lys Arg Thr Phe Lys Asp Ile
                        245                 250                 255

Asp Ser Val Phe Gln Asn Trp Leu Glu Glu His Val Lys Lys Lys Glu
                        260                 265                 270

Lys Met Glu Val Asn Ala Glu Gly Asn Glu Gln Asp Phe Ile Asp Val
                        275                 280                 285

Val Leu Ser Lys Met Ser Asn Glu Tyr Leu Asp Glu Gly Tyr Ser Arg
        290                 295                 300

Asp Thr Val Ile Lys Ala Thr Val Phe Ser Leu Val Leu Asp Ala Ala
        305                 310                 315                 320

Asp Thr Val Ala Leu His Met Asn Trp Gly Met Ala Leu Leu Ile Asn
                        325                 330                 335

Asn Gln His Ala Leu Lys Lys Ala Gln Glu Glu Ile Asp Lys Lys Val
                        340                 345                 350

Gly Lys Asp Arg Trp Val Glu Glu Ser Asp Ile Lys Asp Leu Val Tyr
                        355                 360                 365

Leu Gln Thr Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
        385                 390                 395                 400

His Ile Pro Lys Gly Thr Arg Leu Phe Ala Asn Val Met Lys Leu Gln
                        405                 410                 415

Arg Asp Pro Lys Leu Trp Ser Asn Pro Asp Lys Phe Asp Pro Glu Arg
                        420                 425                 430

Phe Phe Ala Ala Asp Ile Asp Phe Arg Gly Gln His Tyr Glu Phe Ile
                        435                 440                 445

Pro Phe Gly Ser Gly Arg Arg Ser Cys Pro Gly Met Thr Tyr Ala Met
                        450                 455                 460

Gln Val Glu His Leu Thr Ile Ala His Leu Ile Gln Gly Phe Asn Tyr
        465                 470                 475                 480

Lys Thr Pro Asn Asp Glu Pro Leu Asp Met Lys Glu Gly Ala Gly Leu
                        485                 490                 495

Thr Ile Arg Lys Val Asn Pro Ile Glu Val Val Ile Thr Pro Arg Leu
                        500                 505                 510

Thr Pro Glu Leu Tyr
                515

<210> SEQ ID NO 130
<211> LENGTH: 2121
<212> TYPE: DNA
<213> ORGANISM: Lictheimia ramosa

<400> SEQUENCE: 130
```

| | |
|---|---|
| atggctcaat ctccaccagc attggatact ttggatatcg ttttcttggg tactatcggt | 60 |
| ttgggtacaa ttgcttggtt tgctagaagg caaattgctg aaagattatt cggttccacc | 120 |
| tcttcctctg atgctaaatc taatggtcat gctactccag ctccaccaaa aagagaaaga | 180 |
| aacttcgtta agatcatgca agagcaaggt agaaaggtca ttttcttcta cggttctcaa | 240 |
| actggtactg ctgaagatta cgcttctaga ttggctaaag aatgctctca aaagtacggt | 300 |
| gttaactgta tgactgctga tttgagttg tacgacttgt cttacttgga tactgttcca | 360 |
| gaagattgcc tggttttttt cgttatggct acttatggtg aaggtgaacc tactgataat | 420 |
| gctgttgatt tctgggatgt cttgtctgaa gaagaaccac aattttctga agccgaaggt | 480 |
| gataagccat tgcaaaattt gagatacttg gttttcggct gggtaacaa gacttacgaa | 540 |
| cattataacg ctgttgccag aaacgttgac aagagattgg aagttttggg tgctcataga | 600 |
| attcatgaac gtggtgaggg tgatgatgat ggttctttgg aagaagattt tttggcctgg | 660 |
| caagaaaaca tgtggccagc ttttgtgaa gctttgggtg ttgatgaatc taacgctcat | 720 |
| tctggtccaa gacaagctac ttattctgtt gaagaattgg tcgatgtcaa catggatgat | 780 |
| gtttacttgg gtgaattggc cgaaaaacct aaagaaggtg ctagagttat ctacgatgct | 840 |
| aagaggcctt ttaatgctcc aattgccatt tctcaagact tgttcactaa caccgataga | 900 |
| cattgcttgc acatggaaat cgatatctcc gattccaact tgtcatacca aaccggtgat | 960 |
| catattgcta tttggccaac taactccgaa acgaagttg ctagactggc ttctattttg | 1020 |
| ggtttagctg ataagttgga taccgccatc aatgttaagg ctattgatcc agctgcttcc | 1080 |
| aaaaagtacc catttccttg tccagctact tacagagcta ttttcagaca ttacttggac | 1140 |
| atttgcgctg ccgtttctag acaatctttg atggcttttg ttgaatacgc tccaaccgaa | 1200 |
| gaatccaaag aaagattgag acaattggcc aaggataagg atgagtacag attgactgtt | 1260 |
| ggtgaagctg ttagaaattt gggtgaagta ttggaaatcg ttgctggtaa tgatgttaag | 1320 |
| ccaggttttct tttcttccgt tccattcgat ttggttgtcg aatctatttc cagattgcaa | 1380 |
| cctaggtact actccatttc ttcatctgca aaagagtccc caaaaaagat cgctgttact | 1440 |
| gctgttacat tgtcctatca accagatcca actccacaaa gaactgttta tggtgtcaac | 1500 |
| actaattact tgtggcgtat tcataccgcc tctaagcaac aatctactga agctgatttg | 1560 |
| ccaacctatg atttgtcagg tccaagaaat gctttacatg gtactaagtt gccagttcac | 1620 |
| gttagaagat ctcaattcaa gttgccaaga aacccaaccg ttccagttat tatggttggt | 1680 |
| ccaggtactg gtgttgctcc ttttagaggt tttgttagag aaagagcctt gcagaaatct | 1740 |
| gaaggtaaac cagttggtcc aactttgttt tttttcggtt gtagaaactc gaacaggac | 1800 |
| ttcttgtaca agatgaatg gcctgctttg tttgacacct taggtgaatc ctctagaatt | 1860 |
| attaccgcct tctcaagaga aaccgctcaa aaagtttacg tccagcatag attgcaagag | 1920 |
| aacggtcaag aagtttgggg tttgttgcaa aggggtgctt atatctatgt ttgtggtgat | 1980 |
| gcaaagaaca tggccagaga tgttcaacaa actttcgtta acttcggtat cgaattcggt | 2040 |
| ggtttgtctg atgataaggc tcatgatttt gtcaagaact tgagaaacac cggtagatac | 2100 |
| caagaagatg tttggtcttg a | 2121 |

<210> SEQ ID NO 131
<211> LENGTH: 706
<212> TYPE: PRT
<213> ORGANISM: Lichtheimia ramosa

<400> SEQUENCE: 131

```
Met Ala Gln Ser Pro Ala Leu Asp Thr Leu Asp Ile Val Phe Leu
1               5                   10                  15
Gly Thr Ile Gly Leu Gly Thr Ile Ala Trp Phe Ala Arg Arg Gln Ile
                20                  25                  30
Ala Glu Arg Leu Phe Gly Ser Thr Ser Ser Ser Asp Ala Lys Ser Asn
            35                  40                  45
Gly His Ala Thr Pro Ala Pro Pro Lys Arg Glu Arg Asn Phe Val Lys
        50                  55                  60
Ile Met Gln Glu Gln Gly Arg Lys Val Ile Phe Phe Tyr Gly Ser Gln
65                  70                  75                  80
Thr Gly Thr Ala Glu Asp Tyr Ala Ser Arg Leu Ala Lys Glu Cys Ser
                85                  90                  95
Gln Lys Tyr Gly Val Asn Cys Met Thr Ala Asp Leu Glu Leu Tyr Asp
            100                 105                 110
Leu Ser Tyr Leu Asp Thr Val Pro Glu Asp Cys Leu Val Phe Phe Val
        115                 120                 125
Met Ala Thr Tyr Gly Glu Gly Glu Pro Thr Asp Asn Ala Val Asp Phe
130                 135                 140
Trp Asp Val Leu Ser Glu Glu Pro Gln Phe Ser Glu Ala Glu Gly
145                 150                 155                 160
Asp Lys Pro Leu Gln Asn Leu Arg Tyr Leu Val Phe Gly Leu Gly Asn
                165                 170                 175
Lys Thr Tyr Glu His Tyr Asn Ala Val Ala Arg Asn Val Asp Lys Arg
            180                 185                 190
Leu Glu Val Leu Gly Ala His Arg Ile His Arg Gly Glu Gly Asp
        195                 200                 205
Asp Asp Gly Ser Leu Glu Glu Asp Phe Leu Ala Trp Gln Glu Asn Met
210                 215                 220
Trp Pro Ala Phe Cys Glu Ala Leu Gly Val Asp Glu Ser Asn Ala His
225                 230                 235                 240
Ser Gly Pro Arg Gln Ala Thr Tyr Ser Val Glu Leu Val Asp Val
                245                 250                 255
Asn Met Asp Asp Val Tyr Leu Gly Glu Leu Ala Glu Lys Pro Lys Glu
            260                 265                 270
Gly Ala Arg Val Ile Tyr Asp Ala Lys Arg Pro Phe Asn Ala Pro Ile
        275                 280                 285
Ala Ile Ser Gln Asp Leu Phe Thr Asn Thr Asp Arg His Cys Leu His
290                 295                 300
Met Glu Ile Asp Ile Ser Asp Ser Asn Leu Ser Tyr Gln Thr Gly Asp
305                 310                 315                 320
His Ile Ala Ile Trp Pro Thr Asn Ser Glu Asn Glu Val Ala Arg Leu
                325                 330                 335
Ala Ser Ile Leu Gly Leu Ala Asp Lys Leu Asp Thr Ala Ile Asn Val
            340                 345                 350
Lys Ala Ile Asp Pro Ala Ala Ser Lys Lys Tyr Pro Phe Pro Cys Pro
        355                 360                 365
Ala Thr Tyr Arg Ala Ile Phe Arg His Tyr Leu Asp Ile Cys Ala Ala
370                 375                 380
Val Ser Arg Gln Ser Leu Met Ala Phe Val Glu Tyr Ala Pro Thr Glu
385                 390                 395                 400
Glu Ser Lys Glu Arg Leu Arg Gln Leu Ala Lys Asp Lys Asp Glu Tyr
                405                 410                 415
```

```
Arg Leu Thr Val Gly Glu Ala Val Arg Asn Leu Gly Glu Val Leu Glu
                420                 425                 430
Ile Val Ala Gly Asn Asp Val Lys Pro Gly Phe Phe Ser Ser Val Pro
            435                 440                 445
Phe Asp Leu Val Val Glu Ser Ile Ser Arg Leu Gln Pro Arg Tyr Tyr
    450                 455                 460
Ser Ile Ser Ser Ala Lys Glu Ser Pro Lys Lys Ile Ala Val Thr
465                 470                 475                 480
Ala Val Thr Leu Ser Tyr Gln Pro Asp Pro Thr Pro Gln Arg Thr Val
                485                 490                 495
Tyr Gly Val Asn Thr Asn Tyr Leu Trp Arg Ile His Thr Ala Ser Lys
            500                 505                 510
Gln Gln Ser Thr Glu Ala Asp Leu Pro Thr Tyr Asp Leu Ser Gly Pro
    515                 520                 525
Arg Asn Ala Leu His Gly Thr Lys Leu Pro Val His Val Arg Arg Ser
530                 535                 540
Gln Phe Lys Leu Pro Arg Asn Pro Thr Val Pro Val Ile Met Val Gly
545                 550                 555                 560
Pro Gly Thr Gly Val Ala Pro Phe Arg Gly Phe Val Arg Glu Arg Ala
                565                 570                 575
Leu Gln Lys Ser Glu Gly Lys Pro Val Gly Pro Thr Leu Leu Phe Phe
            580                 585                 590
Gly Cys Arg Asn Ser Glu Gln Asp Phe Leu Tyr Lys Asp Glu Trp Pro
    595                 600                 605
Ala Leu Phe Asp Thr Leu Gly Glu Ser Ser Arg Ile Ile Thr Ala Phe
    610                 615                 620
Ser Arg Glu Thr Ala Gln Lys Val Tyr Val Gln His Arg Leu Gln Glu
625                 630                 635                 640
Asn Gly Gln Glu Val Trp Gly Leu Leu Gln Arg Gly Ala Tyr Ile Tyr
                645                 650                 655
Val Cys Gly Asp Ala Lys Asn Met Ala Arg Asp Val Gln Gln Thr Phe
            660                 665                 670
Val Asn Phe Gly Ile Glu Phe Gly Gly Leu Ser Asp Asp Lys Ala His
    675                 680                 685
Asp Phe Val Lys Asn Leu Arg Asn Thr Gly Arg Tyr Gln Glu Asp Val
690                 695                 700
Trp Ser
705

<210> SEQ ID NO 132
<211> LENGTH: 1083
<212> TYPE: DNA
<213> ORGANISM: Papaver somniferum

<400> SEQUENCE: 132
atggaaactc ctatactaat taagttggga acggtctaa gtattccttc agtgcaggag     60
ttagcaaaat taacattagc ggagatccca agccgataca cgtgcaccgg cgaatcccca    120
ttgaataaca tcggtgcttc agtcaccgat gacgagaccg ttcccgtcat cgacctacag    180
aacttgcttt ctccagagcc ggtagtagga agttggagt tagataagtt acacagcgca    240
tgcaaggagt ggggtttctt tcagctagta atcacggag tagatgcttt actaatggat    300
aatattaagt ccgagataaa gggcttcttt aatctgccaa tgaatgagaa gaccaaatac    360
ggacagcaag acggggattt cgagggcttc ggccaacctt acatcgagag cgaggaccag    420
```

-continued

```
cgtcttgact ggacagaggt attttccatg ctctcactgc cacttcacct gaggaagccg    480
catttattcc ctgaattgcc gctgcctttt agagaaactc tagaatctta tctatcgaaa    540
atgaagaagt tatcgacggt ggttttcgaa atgttagaga agagcctaca gctagtcgag    600
attaaaggaa tgacagactt attcgaggac ggccttcaga caatgcgtat gaactactat    660
ccaccatgtc ccagacctga gctagtttta ggtttgacgt ctcactcaga cttttcaggt    720
ctgaccatcc tgttacaact gaatgaggtc gaaggtctac agatacgcaa agaggagaga    780
tggatctcta taaagcccct acccgacgct ttcattgtga atgtgggaga tatattggag    840
ataatgacga acgggatata cagatccgtt gagcaccgcg ctgtcgtaaa ctcaaccaag    900
gaaaggttga gtatagctac gtttcacgat tcgaaattag agagcgagat aggccctatt    960
agttccttag tcactcccga accccggcc ttattcaaaa gagggcgtta cgaggatata   1020
cttaaagaaa acttaagtcg aaagctggat gggaaatcat ttcttgatta catgcgaatg   1080
tag                                                                1083
```

<210> SEQ ID NO 133
<211> LENGTH: 360
<212> TYPE: PRT
<213> ORGANISM: Papaver somniferum

<400> SEQUENCE: 133

```
Met Glu Thr Pro Ile Leu Ile Lys Leu Gly Asn Gly Leu Ser Ile Pro
1               5                   10                  15

Ser Val Gln Glu Leu Ala Lys Leu Thr Leu Ala Glu Ile Pro Ser Arg
            20                  25                  30

Tyr Thr Cys Thr Gly Glu Ser Pro Leu Asn Asn Ile Gly Ala Ser Val
        35                  40                  45

Thr Asp Asp Glu Thr Val Pro Val Ile Asp Leu Gln Asn Leu Leu Ser
    50                  55                  60

Pro Glu Pro Val Val Gly Lys Leu Glu Leu Asp Lys Leu His Ser Ala
65                  70                  75                  80

Cys Lys Glu Trp Gly Phe Phe Gln Leu Val Asn His Gly Val Asp Ala
                85                  90                  95

Leu Leu Met Asp Asn Ile Lys Ser Glu Ile Lys Gly Phe Phe Asn Leu
            100                 105                 110

Pro Met Asn Glu Lys Thr Lys Tyr Gly Gln Gln Asp Gly Asp Phe Glu
        115                 120                 125

Gly Phe Gly Gln Pro Tyr Ile Glu Ser Glu Asp Gln Arg Leu Asp Trp
    130                 135                 140

Thr Glu Val Phe Ser Met Leu Ser Leu Pro Leu His Leu Arg Lys Pro
145                 150                 155                 160

His Leu Phe Pro Glu Leu Pro Leu Pro Phe Arg Glu Thr Leu Glu Ser
                165                 170                 175

Tyr Leu Ser Lys Met Lys Lys Leu Ser Thr Val Val Phe Glu Met Leu
            180                 185                 190

Glu Lys Ser Leu Gln Leu Val Glu Ile Lys Gly Met Thr Asp Leu Phe
        195                 200                 205

Glu Asp Gly Leu Gln Thr Met Arg Met Asn Tyr Tyr Pro Pro Cys Pro
    210                 215                 220

Arg Pro Glu Leu Val Leu Gly Leu Thr Ser His Ser Asp Phe Ser Gly
225                 230                 235                 240

Leu Thr Ile Leu Leu Gln Leu Asn Glu Val Glu Gly Leu Gln Ile Arg
                245                 250                 255
```

```
Lys Glu Glu Arg Trp Ile Ser Ile Lys Pro Leu Pro Asp Ala Phe Ile
            260                 265                 270

Val Asn Val Gly Asp Ile Leu Glu Ile Met Thr Asn Gly Ile Tyr Arg
        275                 280                 285

Ser Val Glu His Arg Ala Val Val Asn Ser Thr Lys Glu Arg Leu Ser
    290                 295                 300

Ile Ala Thr Phe His Asp Ser Lys Leu Glu Ser Glu Ile Gly Pro Ile
305                 310                 315                 320

Ser Ser Leu Val Thr Pro Glu Thr Pro Ala Leu Phe Lys Arg Gly Arg
                325                 330                 335

Tyr Glu Asp Ile Leu Lys Glu Asn Leu Ser Arg Lys Leu Asp Gly Lys
            340                 345                 350

Ser Phe Leu Asp Tyr Met Arg Met
        355                 360
```